(12) United States Patent
Kong et al.

US008044100B2

(10) Patent No.: US 8,044,100 B2
(45) Date of Patent: Oct. 25, 2011

(54) METHODS AND COMPOSITIONS FOR TREATING AMYLOID-RELATED DISEASES

(75) Inventors: Xianqi Kong, Dollard-des-Ormeaux (CA); Xinfu Wu, Laval (CA); Abderrahim Bouzide, Laval (CA); Isabelle Valade, Laval (CA); David Migneault, Laval (CA); Francine Gervais, Ile Bizard (CA); Daniel Delorme, Saint-Lazare (CA); Benoit Bachand, Saint-Laurent (CA); Mohamed Atfani, Laval (CA); Sophie Levesque, Mirabel (CA); Bita Samim, Laval (CA)

(73) Assignee: Bellus Health Inc. (CA)

( * ) Notice: Subject to any disclaimer, the term of this patent is extended or adjusted under 35 U.S.C. 154(b) by 1519 days.

(21) Appl. No.: 11/316,693

(22) Filed: Dec. 21, 2005

(65) Prior Publication Data

US 2006/0223855 A1    Oct. 5, 2006

Related U.S. Application Data

(60) Provisional application No. 60/638,636, filed on Dec. 22, 2004.

(51) Int. Cl.
*A61K 31/185* (2006.01)
*C07C 309/14* (2006.01)
*A61P 25/28* (2006.01)

(52) U.S. Cl. ........... 514/578; 562/41; 562/100; 562/104
(58) Field of Classification Search .................. None
See application file for complete search history.

(56) References Cited

U.S. PATENT DOCUMENTS

| | | | |
|---|---|---|---|
| 2,531,468 A | 11/1950 | Reynolds et al. |
| 2,866,786 A | 12/1958 | Feichtinger et al. |
| 3,218,352 A | 11/1965 | Freifelder et al. |
| 3,236,881 A | 2/1966 | Distler et al. |
| 3,351,549 A * | 11/1967 | Bloch ........................ 210/686 |
| 3,658,966 A | 4/1972 | Tsunoo et al. |
| 3,872,125 A | 3/1975 | Houlihan et al. |
| 3,920,833 A | 11/1975 | Cook et al. |
| 4,199,601 A | 4/1980 | Durlach |
| 4,255,448 A | 3/1981 | Fariello |
| 4,267,194 A | 5/1981 | Durlach |
| 4,271,189 A | 6/1981 | Durlach |
| 4,355,043 A | 10/1982 | Durlach |
| 4,386,081 A | 5/1983 | Helgstrand et al. |
| 4,448,779 A | 5/1984 | Blanchard et al. |
| 4,522,811 A | 6/1985 | Eppstein et al. |
| 4,528,184 A | 7/1985 | Kurono et al. |
| 4,540,564 A | 9/1985 | Bodor |
| 4,563,470 A | 1/1986 | Durlach |
| 4,713,376 A | 12/1987 | Kuzuya et al. |
| 4,737,353 A | 4/1988 | Flanigen et al. |
| 4,737,357 A | 4/1988 | Lehmann et al. |
| 4,847,082 A | 7/1989 | Sabin |
| 4,956,347 A | 9/1990 | Ban et al. |
| 5,017,566 A | 5/1991 | Bodor |
| 5,023,252 A | 6/1991 | Hseih |
| 5,024,998 A | 6/1991 | Bodor |
| 5,039,794 A | 8/1991 | Wier et al. |
| 5,064,923 A | 11/1991 | Kashihara et al. |
| 5,112,863 A | 5/1992 | Hashimoto et al. |
| 5,124,146 A | 6/1992 | Neuwelt |
| 5,153,179 A | 10/1992 | Eibl |
| 5,164,295 A | 11/1992 | Kisilevsky et al. |
| 5,166,320 A | 11/1992 | Wu et al. |
| 5,177,064 A | 1/1993 | Bodor |
| 5,192,753 A | 3/1993 | McGeer et al. |
| 5,194,654 A | 3/1993 | Hostetler et al. |
| 5,242,932 A | 9/1993 | Gandy et al. |
| 5,254,342 A | 10/1993 | Shen et al. |
| 5,258,402 A | 11/1993 | Maryanoff |
| 5,270,312 A | 12/1993 | Glase et al. |
| 5,276,059 A | 1/1994 | Caughey et al. |
| 5,284,876 A | 2/1994 | Shashoua et al. |
| 5,318,958 A | 6/1994 | Kisilevsky |
| 5,342,977 A | 8/1994 | Baschang et al. |
| 5,374,548 A | 12/1994 | Caras |
| 5,383,988 A | 1/1995 | Herrmann et al. |
| 5,385,915 A | 1/1995 | Buxbaum et al. |
| 5,389,623 A | 2/1995 | Bodor |
| 5,399,331 A | 3/1995 | Loughrey et al. |
| 5,405,834 A | 4/1995 | Bundgaard et al. |
| 5,413,996 A | 5/1995 | Bodor |
| 5,416,016 A | 5/1995 | Low et al. |
| 5,430,052 A | 7/1995 | Higashiura et al. |
| 5,434,137 A | 7/1995 | Black |
| 5,442,043 A | 8/1995 | Fukuta et al. |

(Continued)

FOREIGN PATENT DOCUMENTS

CA        2031433        6/1991

(Continued)

OTHER PUBLICATIONS

Doctor's Guide Global Edition, "Alzhemed Showing Continued Positive Interim Results After 20 Months in Patients With Alzheimer's Disease", Jul. 19, 2004. http://pslgroup.com/dg/244952.htm.*
Thompson et al., Current Medicinal Chemistry, Oct. 2002, 9(19), pp. 1751-1762; and especially p. 1753, col. 2.*
Allen, C.F.H. et al., "Sultones as Reagents for Derivatizing Aliphatic Amines in Qualitative Organic Analysis," *Analytical Chemistry*, vol. 37(1):156-158 (1965).
Carretero, J.C. et al., "Synthesis of α,β-epoxysulphonic acids as potential inhibitors of bacterial D,D-peptidases," *Bulletin de la Societe Chimique de France*, vol. 6:835-842 (1990).
Chauvel, Eric N. et al., "Differential Inhibition of Aminopeptidase A and Aminopeptidase N by New β-Amino Thiols," *J. Med. Chem.*, vol. 37:2950-2957 (1994).
David, Christelle et al., "Investigation of Subsite Preferences in Aminopeptidase A (EC 3.4.11.7) Led to the Design of the First Highly Potent and Selective Inhibitors of This Enzyme," *J. Med. Chem.*, vol. 42:5197-5211 (1999).

(Continued)

*Primary Examiner* — Fiona T Powers
(74) *Attorney, Agent, or Firm* — McCarter & English LLP; Danielle Herritt

(57) ABSTRACT

Methods, compounds, pharmaceutical compositions and kits are described for treating or preventing amyloid-related disease.

11 Claims, No Drawings

U.S. PATENT DOCUMENTS

| | | | |
|---|---|---|---|
| 5,463,092 A | 10/1995 | Hostetler et al. |
| 5,466,683 A | 11/1995 | Sterling et al. |
| 5,525,727 A | 6/1996 | Bodor |
| 5,527,527 A | 6/1996 | Friden |
| 5,643,562 A | 7/1997 | Kisilevsky et al. |
| 5,668,117 A | 9/1997 | Shapiro |
| 5,672,683 A | 9/1997 | Friden et al. |
| 5,728,375 A | 3/1998 | Kisilevsky et al. |
| 5,780,510 A | 7/1998 | Carney |
| 5,840,294 A | 11/1998 | Kisilevsky et al. |
| 5,858,326 A | 1/1999 | Kisilevsky et al. |
| 5,869,469 A | 2/1999 | Szarek et al. |
| 5,952,389 A | 9/1999 | Fogel |
| 5,972,328 A | 10/1999 | Kisilevsky et al. |
| 5,977,307 A | 11/1999 | Friden et al. |
| 5,989,592 A | 11/1999 | Collin |
| 6,015,555 A | 1/2000 | Friden |
| 6,015,835 A | 1/2000 | Miyamoto et al. |
| 6,024,977 A | 2/2000 | Yatvin et al. |
| 6,037,327 A | 3/2000 | Castillo et al. |
| 6,265,437 B1 * | 7/2001 | Berthelon et al. ............ 514/474 |
| 6,294,583 B1 | 9/2001 | Fogel |
| 6,306,909 B1 | 10/2001 | Weaver et al. |
| 6,310,073 B1 | 10/2001 | Kisilevsky et al. |
| 6,316,501 B1 | 11/2001 | Miyamoto et al. |
| 6,329,356 B1 | 12/2001 | Szarek et al. |
| 6,376,557 B1 | 4/2002 | Zaveri |
| 6,440,952 B2 | 8/2002 | Szarek et al. |
| 6,562,836 B1 | 5/2003 | Szarek et al. |
| 6,670,399 B2 | 12/2003 | Green et al. |
| 6,930,112 B2 | 8/2005 | Weaver et al. |
| 7,244,764 B2 | 7/2007 | Kong et al. |
| 7,253,306 B2 | 8/2007 | Kong et al. |
| 7,262,223 B2 | 8/2007 | Kong et al. |
| 2001/0048941 A1 | 12/2001 | Kisilevsky et al. |
| 2002/0022657 A1 | 2/2002 | Gervais et al. |
| 2002/0115717 A1 | 8/2002 | Gervais et al. |
| 2002/0193395 A1 | 12/2002 | Kisilevsky et al. |
| 2003/0027796 A1 | 2/2003 | Szarek et al. |
| 2003/0077833 A1 | 4/2003 | Campbell et al. |
| 2003/0108595 A1 | 6/2003 | Kisilevsky et al. |
| 2003/0114441 A1 | 6/2003 | Weaver et al. |
| 2003/0153584 A1 | 8/2003 | Weaver et al. |
| 2003/0194375 A1 | 10/2003 | Weaver et al. |
| 2003/0229144 A1 | 12/2003 | Weaver et al. |
| 2004/0006092 A1 | 1/2004 | Chalifour et al. |
| 2004/0096453 A1 | 5/2004 | Kisilevsky et al. |
| 2004/0138178 A1 | 7/2004 | Szarek et al. |
| 2004/0208875 A1 | 10/2004 | Kisilevsky et al. |
| 2004/0220138 A1 | 11/2004 | Gervais et al. |
| 2004/0248876 A1 | 12/2004 | Szarek et al. |
| 2005/0031651 A1 | 2/2005 | Gervais et al. |
| 2005/0038000 A1 | 2/2005 | Kong et al. |
| 2005/0048000 A1 | 3/2005 | Gervais et al. |
| 2005/0096385 A1 | 5/2005 | Kong et al. |
| 2005/0142191 A1 | 6/2005 | Legore |
| 2005/0215562 A1 | 9/2005 | Tremblay et al. |
| 2006/0008917 A1 | 1/2006 | Campbell et al. |
| 2006/0014752 A1 | 1/2006 | Weaver et al. |
| 2006/0116347 A1 | 6/2006 | Kisilevsky et al. |
| 2006/0135479 A1 | 6/2006 | Szarek et al. |
| 2006/0167057 A1 | 7/2006 | Kong et al. |
| 2006/0167095 A1 | 7/2006 | Kisilevsky et al. |
| 2006/0183800 A1 | 8/2006 | Kong et al. |
| 2006/0252829 A1 | 11/2006 | Garceau et al. |
| 2007/0010573 A1 | 1/2007 | Kong et al. |
| 2007/0015737 A1 | 1/2007 | Clark et al. |
| 2007/0021483 A1 | 1/2007 | Chalifour et al. |
| 2007/0078082 A1 | 4/2007 | Kisilevsky et al. |
| 2009/0099100 A1 * | 4/2009 | Szarek et al. ............ 514/23 |

FOREIGN PATENT DOCUMENTS

| | | |
|---|---|---|
| CA | 2046037 | 1/1992 |
| DE | 927992 | 5/1955 |
| DE | 2140278 | 3/1972 |
| DE | 4004978 A1 | 8/1991 |
| DE | 4313118 A1 | 10/1994 |
| EP | 0003275 A1 | 8/1979 |
| EP | 0115657 B1 | 8/1984 |
| EP | 0236251 A2 | 9/1987 |
| EP | 0293974 B1 | 12/1988 |
| EP | 0309421 B1 | 3/1989 |
| EP | 0330353 B1 | 8/1989 |
| EP | 0387867 B1 | 9/1990 |
| EP | 0405834 A2 | 1/1991 |
| EP | 0434173 A2 | 6/1991 |
| EP | 0457295 B1 | 11/1991 |
| EP | 0464759 A2 | 1/1992 |
| EP | 0533352 A2 | 3/1993 |
| EP | 0797992 A2 | 10/1997 |
| FR | 2437834 | 6/1980 |
| JP | 1-151514 | 6/1989 |
| JP | 1-171638 | 7/1989 |
| JP | 2-78620 A | 3/1990 |
| JP | 2-149341 A | 6/1990 |
| JP | 3-83921 A | 4/1991 |
| JP | 5-17471 A | 1/1993 |
| WO | WO-85/02342 A1 | 6/1985 |
| WO | WO-88/09171 A1 | 12/1988 |
| WO | WO-89/05646 A1 | 6/1989 |
| WO | WO-89/11299 A1 | 11/1989 |
| WO | WO-90/09789 A2 | 9/1990 |
| WO | WO-91/04014 A1 | 4/1991 |
| WO | WO-91/04745 A1 | 4/1991 |
| WO | WO-91/14438 A1 | 10/1991 |
| WO | WO-92/02248 A1 | 2/1992 |
| WO | WO-92/14456 | 9/1992 |
| WO | WO-93/10459 A1 | 5/1993 |
| WO | WO-93/11762 A1 | 6/1993 |
| WO | WO-93/24118 A1 | 12/1993 |
| WO | WO-94/00135 A1 | 1/1994 |
| WO | WO-94/01116 A1 | 1/1994 |
| WO | WO-94/01131 A1 | 1/1994 |
| WO | WO-94/02178 A1 | 2/1994 |
| WO | WO-94/03424 A1 | 2/1994 |
| WO | WO-94/06450 A1 | 3/1994 |
| WO | WO-94/22437 A2 | 10/1994 |
| WO | WO-94/27602 A1 | 12/1994 |
| WO | WO-95/01096 A1 | 1/1995 |
| WO | WO-95/06477 | 3/1995 |
| WO | WO-95/07092 A1 | 3/1995 |
| WO | WO-96/00537 A1 | 1/1996 |
| WO | WO-96/04001 A1 | 2/1996 |
| WO | WO-96/04915 A1 | 2/1996 |
| WO | WO-96/22303 A1 | 7/1996 |
| WO | WO-96/28187 A1 | 9/1996 |
| WO | WO-97/07402 | 9/1996 |
| WO | WO-96/37612 | 11/1996 |
| WO | WO-96/39129 A1 | 12/1996 |
| WO | WO-97/09445 A1 | 3/1997 |
| WO | WO-97/09976 | 3/1997 |
| WO | WO-97/14306 A1 | 4/1997 |
| WO | WO-97/16191 | 5/1997 |
| WO | WO-98/11923 | 3/1998 |
| WO | WO-98/13046 | 4/1998 |
| WO | WO-98/25938 | 6/1998 |
| WO | WO-99/06545 A2 | 2/1999 |
| WO | WO-99/08685 A1 | 2/1999 |
| WO | WO-99/38498 A1 | 8/1999 |
| WO | WO-99/40909 A1 | 8/1999 |
| WO | WO-00/06133 | 2/2000 |
| WO | WO-00/56328 A1 | 9/2000 |
| WO | WO-00/57707 | 10/2000 |
| WO | WO-00/64420 | 11/2000 |
| WO | WO-00/71101 A2 | 11/2000 |
| WO | WO-01/03680 | 1/2001 |
| WO | WO-2004/113277 A2 | 12/2004 |
| WO | WO-2005/000406 A2 | 1/2005 |
| WO | WO-2006/059252 A2 | 6/2006 |
| WO | WO-2006/085149 A2 | 8/2006 |

OTHER PUBLICATIONS

Enders, D. et al., "A Highly Efficient Asymmetric Syntiesis of Homotaurine Derivatives via Diastereoselective Ring-Opening of γ-Sultones," *Synthesis*, vol. 17:2910-2918 (2004).

Helferich, Burckhardt et al., "Über Sultame, VIID, Sultame von Aminosauren," *Liebigs Annalen der Chemie*, vol. 651:33-42 (1962).
Lee, Albert W. M. et al., "Synthesis and Diels-Alder reactions of α,β-unsaturated γ-sultone," *Chemical Communications*, vol. 6:611-612 (1997).
Li, Chun-Sing at al., "Synthesis of (±)-3-Amino-2-(4-chlorophenyl)propanesulfonic acid (Saclofen)," *Synthesis*, vol. 3:244 (1991).
Truce, William E. et al., "The Chemistry of Sultones. I. Friedel-Crafts Reactions to Sultones," *Journal of the American Chemical Society*, vol. 76(21):5357-5360 (1954).
Willems, J. et al., "The aliphatic hydroxysulphonic acids and their internal esters: the sultones. Part II. The Sultones," *Bulletin des Societes Chimiques Beiges*, vol. 64:747-771 (1955).
International Search Report for Application No. PCT/IB2005/004166, dated Mar. 13, 2007.
Ancsin, John B. et al., "The Heparin/Heparan Sulfate-binding Site on Apo-serum Amyloid A: Implications for the Therapeutic Intervention of Amyloidosis," *The Journal of Biological Chemistry*. vol: 274(11):7172-7181 (1999).
Aprile, Carlo et al, "Cardiac and pleuropulmonary AL amyloid imaging with technetium-99m labeled aprotinin," *European Journal of Nuclear Medicine*, vol. 22(12):1393-1401 (1995).
Axelrad, M.A. et al., "Further Characterization of Amyloid-Enhancing Factor," *Laboratory Investigation*, vol. 47(2)139-146 (1982).
Baures, Paul W. et al, "Discovering Transthyretin Amyloid Fibril Inhibitors by Limited Screening," *Bioorganic & Medicinal Chemistry*, vol. 6:1389-1401 (1998).
Beilstein Registry No. 3388511, 2-dibenzylamino-ethanesulfonic acid, Feb. 15, 1990.
Beilstein Registry No. 4261672, 2-<<<3-hydroxy-5-(hydroxymethyl)-2-meth-4-pyridyl>methyl>amino<ethane sulphonic acid, Jul. 20, 1992: Iskander, MN et al, "Transition-state analogues as inhibitors for GABA-aminotransferase," *Eur. J. Med. Chem.*, vol. 26:129-136 (1991).
Beilstein Registry No. 7023352, N-(1'-aza-cyclopenten-2'yl)-2-aminoethane sulfonic acid, May 11, 1995: Campagna, Francesco et al, "Cyclic Amidine Analogues of Taurine and Homotaurine: Synthesis and Effects on Rat Skeletal Muscle," *Il Farmaco*, vol. 49(10):653-658 (1994).
Beilstein Registry No. 8919306, Microxine, Jan. 24, 2002: Killday, K Brian et al, "Microxine, a New cdc2 Kinase Inhibitor from the Australian Marine Sponge *Microxina* Species," *J. Nat. Prod.*, vol. 64:525-526 (2001).
Beilstein Registry No. 6023409. N,N-bis(2-sulfonylethyl)-1-octanamme disodium salt, Jul. 22, 1993: Tomson, R. et al, "Preparation and Properties of Surfactants of the Type of disodium Salts of N,N-Bis(2-Sulfoethyl)-1-Alkanamins," *Appl. Chem. USSR*, vol. 57(9):1885-1891 (1984).
Beilstein Registry No. 2272192, N-(2-Sulfo-ethyl)-benzamid, Jun. 29, 1989: Wood, J. Matthew et al, "Reactivity and the mechanisms of reactions of β-sultarns with nucleophiles," *J. Chem. Soc.*, vol. 2:938-946 (2002).
Beilstein Registry No. 3948718, N-(Butyl-sulfonsaeure-(4))-DL-alanin, Mar. 19, 1991: Helferich, von Burckhardt et al, "Sultame von Aminosäuren," *Liebigs Ann. Chem.*, vol. 651:33-42 (1962).
Beilstein Registry No. 1712477, 2-leucylamino-ethanesulfonic acid, Feb. 27, 1989: Abderhalden, Emil et al, "Weitere Studien über das Wesen von Ferment-wirkungen, ausgeführt mit Fermenten der Gruppe der Potypeptidasen," *Fermentforschung*, vol. 12:183-223 (1930).
Beilstein Registry No. 2972476, 3-Benzylamino-propan-1-sulfonsaeure, Jul. 11, 1989: Dom. Helmut et al, "Cyanäthylierung und Sulfopropylierung von Phenyl-, Benzyl- und Cyclohexyl-hydrazin," *Z. Chem.*, vol. 7:151-152 (1967).
Bellsteln Registry No. 2434022, 4-Aethylamino-butan-sutfonsaeure-(1), Jul. 5, 1989: Helferich, von Burckhardt et al, "Alkylamino- und Arylaminoalkansulfonsäuren Sowie Arylaminobutansultame," *Liebigs Ann. Chem.*, vol. 647:37-40 1961).
Beilstein Registry No. 5620601, H-α-Glu-Ser-Tau-OH, Feb. 12, 1993: Ienaga, Kazuharu et al, "Simple Peptides. Ill. Syntheses and Properties of Taurine-Oligopeptides Containing an Acidic α-Amino Acid," *Chem. Pharm, Bull.* vol, 36(8):2796-2801 (1988).

Beilstein Registry No. 2846394, β-Naphthylaminomethyl-sulfonsaeure, Jul. 11, 1989.
Beilstein Registry No. 3952462, 4-Azonia-6-phenyl-hexan-1-sulfonat, Mar. 19, 1991: Allen, C.F.H. et al, "Sultones as Reagents for Derivatizing Aliphatic Amines in Qualitative Organic Analysis," *Anal. Chem.*, vol. 37:156-158 (1965).
Beilstein Registry No. 5568774, L-phenylalanyltaurine, Feb. 12, 1993: Ienaga, Kazuharu et al, "Simple Peptides, II, Syntheses and Properties of Taurine-Dipeptides Containing Neutral α-Amino Acid," *Chem. Pharm. Bull.*, vol. 36(1):70-77 (1988).
Berge, Stephen M. et al, "Pharmaceutical Salts," *Journal Pharmaceutical Sciences*, vol. 66(1):1-19 (1977).
Bloemen, P.G.M. et al. "Adhesion molecules: a new target for immunoliposome-mediated drug delivery," *FEBS*, vol. 357:140-144 (1995).
Boismare, F. et al, "A Homotaurine Derivative Reduces the Voluntary of Ethanol by Rats: are Cerebral GABA Receptors Involved?" *Pharmacology Biochemist & Behavior*, vol. 21:787-789 (1984).
Briggs, Andrew D. et al, "Acyloxymethyl and 4-Acyloxybenzyl Diester Prodrugs of Phosphonoformate," *Tetrahedron*, vol. 52(47):14937-14950 (1996).
Briscoe, Page et al, "Delivery of superoxide dismutase pulmonary pithelium via pH-sensitive liposomes," *Am. J. Physiol.*, vol. 268:L374-L380 (1995).
Brissette, Louise et al, "Differential induction of the Serum Amyloid A Gene Family in Response to an Inflammatory Agent and to Amyloid-enhancing Factor," *The Journal of Biological Chemistry*, vol. 264(32):19327-19332 (1989).
Buèe, L. et al, "Alzheimer's disease: binding of vascular and neuroblastoma heparan sulfate proteoglycans to amytoid β protein A4," *Advances in the Biosciences*, vol. 87:217-218 (1993).
Cal, Xiao-Dan et al, "Release of Excess Amyloid β Protein from a Mutant Amyloid β Protein Precursor,"*Science*, vol. 259:514-516 (1993).
Campagna, Francesco et al, "Cyclic Amidine Analogues of Taurine Taurtne are Homotaurine: Synthesis and Effects on Rat Skeletal Muscle," *Il Farmaco*, vol. 49(10):653-658 (1994).
Caughey, Byron et al, "Sulfated Polyanion Inhibition of Scrapie-Associated PrP Accumulation in Cultured Cells," *Journal of Virology*, vol. 67(2):643-650 (1993).
Caughey, B., "Scrapie associated PrP accumulation and its prevention: insights from cell culture," *British Medical Bulletin*, vol. 49(4):860-872 (1993).
Caughey, B., "Protease-resistant PrP accumulation and scrapie agent replication: a role for sulphated glycosaminolycans?" *Biochemical Society Transactions, 648th Meeting* Belfast, vol. 22:163-167 (1994).
Caughey, Byron, "Scrapie-associated PrP accumulation and agent replication: effects on sulphated glycosaminoglycan analogues," *Phil. Trans. R. Soc. Lond. B.*, vol. 343:399-404 (1994).
Caughey, Bryon et al, "Binding of the Protease-Sensitive Form of Prion Protein PrP to Sulfated Glycosaminoglycan and Congo Red," *Virology*, vol. 68(4):2135-2141 (1994).
Chabenat, C. et al, "Physicochemical, Pharmacological and Pharmacokinetic Study of a New GABAergic Compound, Calcium Acetylhomotaurinate," *Meth and Find Expti Clin Pharmacol.*, vol. 10(5):311-317 (1988).
Chishli, M. Azhar et al, "Early-onset Amyloid Deposition and Cognitive Deficits in Transgenic Mice Expressing a Double Mutant Form of Amyloid Precursor Protein 695," *The Journal of Biological Chemistry*, vol. 276(24):21562-21570 (2001).
Colon, Wilfredo et al, "Partial Denaturation of Transthyretin is Sufficient for Amyloid Fibril Formation in Vitro," *Biochemistry*, vol. 31:8654-8660 (1992).
Copani, A. et al, "Activation of Metabotropic Glutamate Receptors Protects Cultured Neurons Against Apoptosis Induced by β-Amyloid Peptide," *Molecular Pharmacology*, vol. 47:890-897 (1995).
DeMattos, Ronald B. et al, "Brain to Plasma Amyloid-β Efflux: a Measure of Brain Amyloid Burden in a Mouse Model Alzheimer's Disease," *Science*, vol. 295:2264-2267 (2002).
De Strooper, Bart et al, "Deficiency of presenilin-1 inhibits the normal cleavage of amyloid precursor protein," *Nature*, vol. 394:387-390 (1998).

Dow, Kimberly E. et al, "Effects of 4-deoxy-L-*threo*-pentose, a novel carbohydrate, on neural cell proteoglycan synthesis and function," *Biochimica et Biophysica Acta*, vol. 1156:7-14 (1992).

Durbin, PH et al, "Evidence of Acamprosate Penetration into the Rat Brain," *Behavioural Pharmacology*, vol. 6:620 (1995).

Ehlers, Bernhard et al, "Dextran Sulphate 500 Delays and Prevents Mouse Scrapie by Impairment of Agent Replication in Spleen," *The Journal of General Virology*, vol. 65:1325-1330 (1984).

Eisai America, Inc., "Aricept." Copyright 1995-1996, Center Watch, Inc. http://www.centerwatch.com/patient/drugs/dru190.html.

Fraser, Paul E. et al, "Effects of Sulfate ions on Atzheimer β/A4 Peptide Assemblies: Implications for Amyloid Fibril-Proteoglycan Interactions," *Journal of Neurochemistry*, vol. 59:1531-1540 (1992).

Fraser, Paul E. et al, "Fibril Formation by Primate, Rodent, and Dutch-Hemorrhagic Analogues of Alzheimer Amyloid β-Protein," *Biochemistry*, vol. 31:10715-10723 (1992).

Fujil, Akira et al, "Probiotics. Antistaphylococcal and Antifibrinolytic Activities of ω-Amino- and ω-Guanidinoalkanesufonic Acids," *Journal of Medicinal Chemistry*, vol. 18(5):502-505 (1975).

Gervais, Francine. "Amyloid—Those Deadly Fibriis," *Eur. Biopharm. Review*, pp. 40-42 (2001).

Gervais, Francine et at, "Proteoglycans and Amyloidogenic Proteins in Peripheral Arnyloidosis," *Curr. Med. Chem.—Immun., Endoc. & Metab. Agents*, vol. 3:361-370 (2003).

Girault, J. et al. "Determination of calcium acetylhomotaurinate in human plasma and urine by combined gas chromatography-negative-ion chemical ionization mass spectrometry," *Journal of Chromatography*, vol. 530(2):295-305 (1990).

Gorin, Boris I. et al, "A Novel Esterification Procedure Applied to Synthesis of Biologically Active Esters of Foscamet," *Tetrahedron*, vol. 38(16):2791-2794 (1997).

Grant, K.A. et al, "Reinforcing and Discriminative Stimulus Effects of Ca-Acetyl Homotaurine in Animals," *Pharmacology, Biochemistry & Behavior*, vol. 32:607-611 (1989).

Hamazaki, Hideaki et al, "Calcium-dependent polymerization of human serum amyloid P component is inhibited by heparins and dextran sulfate," *Biochimica et Biophysica Acta*, vol. 998:231-235 (1989).

Hamazaki, Hideaki, "$Ca^{2+}$-mediated Association of Human Serum Amyloid P Component with Heparan Sulfate and Dermatan Sulfate," *The Journal of Biological Chemistry*, vol. 262(4):1456-1460 (1987).

Hamilton, Ronald L., "Lewy Bodies in Alzheimer's Disease: A Neuropathological Review of 145 Cases Using α-Synuclein Immunohistochemistry," *Brain Pathology*, vol. 10:378-384 (2000).

Han, Hogyu et al, "The core Alzheimer's peptide NAC forms amyloid fibrils which seed and are seeded by β-amyloid: Is NAC a common trigger or target in neurodegenerative disease?" *Chemistry & Biology*, vol. 2:163-169 (1995).

Hawkins, P.N., "Diagnosis and monitoring of amyloidosis," *Baillière's Clinical Rheumatology*, vol. 8(3):635-659 (1994).

Hutchings, R. et al, "The Effect of Excitotoxin Antagonists on Ibotenic Acid-Induced Alteration of APP MRNA Hippocampal Expression," *J. Pharmacy and Pharmacology*, vol. 47 (12B):1131 (1995).

Ismail, Ibrahim Imam, "Reactions with sultones II," *Afinidad L.*, vol. 446:256-258 (1993).

Ismail, Ibrahim Imam, "Reactions with sultones and sultams," *J. Serb. Chem. Soc.*, vol. 57(7):415-420 (1992).

Iwai, Aidhiko, "Properties of NACP/α-synuclein and its role in Alzheimer's disease," *Biochimica et Biophysica Acta*, vol. 1502:95-109 (2000).

Iwai, Akihiko et al, "Non-Aβ Component of Alzheimer's Disease Amyloid (NAC) Is Amyloidogenic," *Biochemistry*, vol. 34:10139-10145 (1995).

James, Guy L. et al, "Benzodiazepine Peptidomimetics: Potent inhibitors of Ras Famesylation in Animal Cells," *Science*, vol. 260:1937-1942 (1993).

Kagan, D.Z. et al, "Congo Red Inhibition of Amylogenesis in Experimental Amyloidosis," *Problemy Tuberkuleza*, vol. 40:72-74, 1974.

Keinänen, Kari at, "Biosynthetic lipid-tagging of antibodies," *FEBS*, vol. 346:123-126 (1994).

Killion, Jerald J. et al, "Systemic Targeting of Liposome-Encapsulated Immunomodulators to Macrophages for Treatment of Cancer Metastasis," *Immunomethods*, vol. 4:273-279 (1994).

Kisilevsky, R, "From arthritis to Alzheimer's disease: current concepts on the pathogenesis of amyloidosis," *Can. J. Physiol. Pharmacol.*, vol. 65:1805-1815 (1987) May 20, 2009.

Kisilevsky, R. et al, "The Potential Significance of Sulphated Glycosaminoglycans as a Common Constituent of all Amyloids: or, Perhaps Amyloid is not a Misnomer," *Medical Hypotheses*, vol. 26:231-236 (1988).

Kisilevsky, Robert, "Theme and Variations on a String of Amyloid," *Neurobiology of Aging*, vol, 10:499-500 (1989).

Kistievsky, Robert, "Heparan Sulfate Proteoglycans in Amyloidogenesis: An Epiphenomenon, A Unique Factor, or the Tip of a More Fundamental Process," *Laboratory Investigation*. vol. 63(5):589-591 (1990).

KIsilevsky, Robert, "A Critical Analysis of Postulated Pathogenetic Mechanisms in Amyloidogenesis," *Critical Reviews in Clinical Laboratory Sciences*, vol. 29(1):59-82 (1992).

Kisilevsky, Robert et al, "Arresting amyloidosis in vivo using small-molecule anionic sulphonates or sulphates: implications for Alzheimer's disease," *Nature Medicine*, vol. 1(2):143-148 (1995).

Krogsgaard-Larsen, P. et al, "Novel (Gamma-Aminobutyric Acid)A Agonists and Partial Agonists," *FIDIA Research Foundation Symposium Series* (1991).

Lacoste, Anne-Marie et al, "Inhibition of D-Alanyl-D-Alanine Ligase in Different Bacterial Species by Amino Phosphonic Acids," *Current Microbiology*, vol. 2:113-117 (1979).

Leveugle, B. et al, "Binding of heparan sutfate glycosaminoglycan to β-amyloid peptide: inhibition by potentially therapeutic polysulfated compounds," *NeuroReport*, vol. 5:1389-1392 (1994).

Lhuintre, Jean-Pierre et al, "Ability of Calcium Bis Acetyl Homotaurine, a Gaba Agonist, to Prevent REIapse in Weaned Alcoholics." *The Lancet*, vol. 1(8436):1014-1016 (1985).

Littleton, John, "Acamprosate in alcohol dependence: how does It work?" *Addiction*, vol. 90:1179-1188 (1995).

Lyon, A.W. et al, "Co-deposition of Basement Membrane Components during the Induction of Murine Splenic AA Amyloid," *Laboratory Investigation*, vol. 64(6):785-790 (1991).

Madamba, Samuel G. et al, "Acamprosate (Calcium Acetylhomotaurinate) Enhances the N-Methyl-D-Aspartate Component of Excitatory Neurotransmission in Rat Hippocampal CA1 Neurons in Vitro," *Alcoholism: Clinical and Experimental Research*, vol. 20(4):651-658 (1996).

Malmusi, Luca et al, "1,2,3,4-Tetrahydroisoquinollne and Related Analogs of the Phenylalkytamine Designer Drug MDMA," *Med. Chem. Res.*, vol. 6(6):412-426 (1996).

Masliah, Eliezer et al, "Altered Presynaptic Protein NACP Is Associated with Plaque Formas and Neurodegeneration in Alzheimer's Disease," *American Journal of Pathology*, vol. 14 201-210 (1996).

Masuda, Midori et al, "Effect of taurine on nonspecific protection against bacterial infection,"Database STN International, Chemical Abstracts Service, Accession No. 105:108004 (1985) (Abstract only).

May, Patrick C., "Current progress on new therapies for Alzheimer's disease," *Drug Discovery Today*, vol. 6(9):459-462 (2001).

McCubbin, William D. et al, "Circular-dichroism studies on two murine serum amyloid A proteins," *Biochem. J.*, vol. 256:775-783 (1998).

Merck Index, p. 883, Merck & Co. Inc., Rahway, N.J., USA.

Mimura, Testutaro et al, "A Novel Class of Enkephalinase inhibitors Containing a C-Terminal Sulfo Group," *J. Med. Chem.*, vol, 35:602-608 (1992).

Morgan, Barry A. et al, "Approaches to the Discovery of Non-Peptide Ligands for Peptide Receptors and Peptidases," *Ann. Rep. Med. Chem.*, Virick F.J. (Ed) pp. 243-253, Academic Press, San Diego, CA (1989).

Mukaetova-Ladinska, E.B. et al, "α-Synuclein Inclusions in Alzheimer and Lewy Body Diseases," *Journal of Neuropathology and Experimental Neurology*, vol. 59(5):408-417 (2000).

Nakada, Tsutomu et al, "Guanidinoethane sulfate: brain pH alkaline shifter," *NeuroReport*, vol. 4:1035-1038 (1993).

Narindrasorasak, Suree et al, "Characterization of High Affinity Binding between Laminin and Alzheimer's Disease Amyloid Precursor Proteins," *Laboratory Investigation*, vol. 67(5):643-652 (1992).

Narindrasorasak, Suree et al, "High Affinity Interactions between the Alzheimer's β-Amyloid Precursor Proteins and the Basement Membrane Form of Heparan Sulfate Proteoglycan," *The Journal of Biological Chemistry*, vol. 266 (20):12878-12883 (1991).

National Institute on Alcohol Abuse and Alcoholism No. 33 PH 366, Jul. 1996; "Alcohol Alerg," http://pubs.niaaa.nih.gov/publications/aa33.htm.

Norén, Jan O. et al, "Synthesis of Esters Phosphonoformic Acid and Their Antiherpes Activity," *Journal of Medicinal Chemistry*, vol. 26(2):264-270 (1982).

O'Brien, Timothy D. et al, "Human Islet Amyloid Polypeptide Expression in COS-1 Cells," *Amencan Journal of Pathology*, vol. 147(3):609-616 (1995).

Owais, Mohammad et al, "Chloroquine Encapsulated in Malaria-Infected Erythrocyte-Specific Antibody-Bearing Liposomes Effectively Controls Chloroquine-Resistant *Plasmodium berghei* Infections in Mice," *Antimicrobial Agents and Chemotherapy*, vol. 39(1):180-184 (1995).

Panula-Lehto, Elina et al, "Comparison of the Effects of Intraventricular Taurine, GABA and Homotaurine on Serum Prolactin Levels in Male Rats," *Pharmacology and Toxicology*, vol. 65:152-156 (1989).

Pollack, Scott J. et al, "Sulfonated dyes attenuate the toxic effects of β-amyiold in a structure-specific fashion," *Neuroscience Letters*, vol. 197:211-214 (1995).

Powell, D.S. et al, "Insulin and Polyionic Sulphonates Modify Human Islet Amyloid Polypeptide Fibril Aggregation in Vitro," *Diabetologia*, vol. 41 (Suppl. 1):656 (1998).

Puchtler, H. et al, "Application of Thiazole Dyes to Amyloid under Conditions of Direct Cotton Dyeing: Correlation of Histochemical and Chemical Data," *Histochemistry*, vol. 77:431-445 1983.

Ranade, Vasant V., "Drug Delivery Systems. 1. Site-Specific Drug Delivery Using Liposomes as Carriers," *J. Clin. Pharmacol.*, vol. 29:685-694 (1989).

Rodier, Par P. Toffoli et N. et al, "Bis(acétamido-3 propanesulfate-1) de Calcium ( N-Acétylhomotaurinate de Calcium," *Acta Cryst.*, vol. C44:1493-1494 (1988).

Sadler, Isobel I. J. et at, "Sulphated compounds attenuate β-amyloid toxicity by inhibiting its association with calls," *NeuroReport*, vol. 7:49-53 (1995).

St. Georgiev, Vassil et al, "Drug-Induced Modifications of the Immune Response. 1. Substituted 1- Phenylisoquinolines," *Journal of Medicinal Chemistry*, vol. 22(4):348-352 (1979).

Sass, Henning et al, "Relapse Prevention by Acamprosate," *Arch. Gen. Psychiatry*, vol. 53:673-680 (1996).

Schreier, Hans et at, "Targeting of Liposomes to Cells Expressing CD4 Using Glycosylphosphatidylinositol-anchored gp120," *The Journal of Biological Chemistry*, vol. 269(12):9090- 9098 (1994).

Shue, Ho-Jane et al, "A Study of 3-Amino-N-Hydroxypropanesulfonamide Derivatives as Potential $GABA_B$ Agonists and Their Fragmentation to 3-AMinopropanesulfinic Acid," *Bioorganic & Medicinal Chemistry Letters*, vol. 6(14):1709-1714 (1996).

Silverman, Richard B., "Prodrugs and Drug Delivery Systems," The Organic Chemistry of Drug Design and Drug Action, Academic Press, Inc, Chapter 8, pp. 352-401.

Small, D.H. et al, "Association and Release of the Amyloid Protein Precursor of Alzheimer's Disease from Chick Brain Extracellular Matrix," *The Journal of Neuroscience*, vol. 12(11):4143-4150 (1992).

Snow, Alan D. et al, "Sulfated Glycosaminoglycans: A Common Constituent of All Amyloids?" *Laboratory Investigation*, vol. 56(1):120-123 (1987).

Snow, Alan D. et al, "Temporal Relationship between Glycosaminoglycan Accumulation and Amyloid Deposition during Experimental Amyloidosis," *Laboratory Investigation*, vol, 53(1). 37-44 (1985).

Snow, Alan D. et al, "Sulfated Glycosaminoglycans in Alzheimer's Disease," *Human Pathology*, vol. 18(5):506-510 (1987).

Snow, Alan David et al, "Characterization of Tissue and Plasma Glycosaminoglycans during Experimental AA Amyloidosis and Acute Inflammation, Qualitative and Quantitative Analysis," *Laboratory Investigation*, vol. 56(6):665-675 (1987).

Snow, Alan David et al, "A Close Ultrastructural Relationship between Sulfated Proteoglycans and AA Amyloid Fibrils," *Laboratory Investigation*, vol. 57(6):687-698 (1987).

Snow, A. D. et al, "Sulfated glycosaminoglycans in amyloid plaques of prion diseases," *Acta Neuropathol.*, vol. 77:337-342 (1989).

Snow, Alan D. et al, "A Temporal and Ultrastructural Relationship Between Heparan Sulfate Proteoglycans and AA Amyloid in Experimental Amyloidosis," *The Journal of Histochernistry and Cytochemistry*, vol. 39(10):1321-1330 (1991).

Stregan, G.H. et al, "Suppression of Chronic-Relapsing Experimental Allergic Encephalomyelitis in Strain-13 Guinea Pigs by Administration of Liposorne-Associated Myelin Basic Protein," *Journal of Neuroimmunology*, vol. 7:27-41 (1984).

Tape, C. et al, "Direct Evidence for Circulating apoSAA as the Precursor of Tissue AA Amyloid Deposits," *Scand. J. Immunol.*, vol. 28:317-324 (1988).

Travis, John, "New Piece of Alzheimer's Puzzle," *Science*, vol. 261:828-829 (1993).

Uéda, Kenji et al, "Molecular cloning of cDNA encoding an unrecognized component of amyloid in Alzheimer disease," *Proc. Natl. Acad. Sci. USA*, vol. 90:11282-11286 (1993).

Umezawa, F. et al, "Liposome Targeting to Mouse Brain: Mannose as a Recognition Marker," *Biochemical and Biophysical Research Communications*, vol. 153(3):1038-1044 (1988).

Westennark, P., Islet Pathology of Non-Insulin-dependent Diabetes Mellitus (NIDDM), *Diabetic Medicine*, vol. 13:S46-S48 (1996).

Whitworth, A. et al, "Is Acamprosate an Effective Treatment for Alcohol Dependence?" *The Lancet*, vol. 347:1438-1442 (1996).

Wong, S. et al, "Influence of Sulphate Ions on the Structure of AA Amyloid Fibrils," *Scand. J. Immunol.*, vol. 32:225-232 (1990).

Wood, Stephen J. et al, "Selective Inhibition of Aβ Fibril Formation," *The Journal of Biological Chemistry*, vol. 271(8):4086-4092 (1996).

Yoshimoto, Makoto et al, "NACP, the precursor protein of the non-amyloid β/A4 (Aβ) component of Alzheimer disease amyloid, binds Aβ and stimulates Aβ aggregation," *Proc. Natl. Acad. Sci. USA*, vol. 92:9141-9145 (1995).

Young, I.D. et al, "The ultrastructural localization of sulfated proteoglycans is identical in the amyloids of Alzheimer's disease and AA, AL, senile cardiac and medullary carcinoma-associated amyloidosis,"*Acta Neuropathol.*, vol. 78:202-209 (1989).

Young, lain D. et al, "Localization of the Basement Membrane Heparan Sulfate Proteoglycan in Islet Amyloid Deposits in Type II Diabetes Mellitus," *Arch Pathol Lab Med.*, vol. 116:951-954 (1992).

International Search Report for Application No. PCT/IB2004/002375, dated Jul. 13, 2005.

* cited by examiner

METHODS AND COMPOSITIONS FOR TREATING AMYLOID-RELATED DISEASES

RELATED APPLICATIONS

This application claims priority to U.S. Provisional Patent Application No. 60/638,636, filed on Dec. 22, 2004. This application is related to U.S. patent application Ser. No. 10/871,514, filed Jun. 18, 2004, which claims priority to U.S. patent application Ser. No. 10/871,365 filed Jun. 18, 2004, U.S. Provisional Patent Application No. 60/512,047, filed Oct. 17, 2003, and U.S. Provisional Patent Application No. 60/480,906, filed Jun. 23, 2003, all entitled Methods and Compositions for Treating Amyloid-Related Diseases. This application is also related to U.S. Provisional Patent Application 60/638,819, entitled Methods and Compositions for Treating Amyloid-Related Diseases, filed Dec. 22, 2004 and U.S. application Ser. No. 11/316,694, filed concurrently herewith.

This application is also related to U.S. Provisional Patent Application No. 60/512,017, filed Oct. 17, 2003, U.S. Provisional Patent Application No. 60/480,918, filed Jun. 23, 2003, and U.S. patent application Ser. No. 10/871,613, filed Jun. 18, 2004, all entitled Methods for Treating Protein Aggregation Disorders.

This application is related to U.S. Provisional Patent Application No. 60/512,116, filed Oct. 17, 2003, U.S. Provisional Patent Application No. 60/480,984, filed Jun. 23, 2003, and U.S. application Ser. No. 10/871,549, filed Jun. 18, 2004, all entitled Pharmaceutical Formulations of Amyloid-Inhibiting Compounds.

This application is related to U.S. Provisional Patent Application No. 60/436,379, filed Dec. 24, 2002, U.S. Provisional Patent Application No. 60/482,214, filed Jun. 23, 2003, entitled Combination Therapy for the Treatment of Alzheimer's Disease, U.S. patent application Ser. No. 10/746,138, filed Dec. 24, 2003, International Patent Application No. PCT/CA2003/002011, filed Dec. 24, 2003, and U.S. patent application Ser. No. 10/871,537, filed Jun. 18, 2004, entitled Therapeutic Formulations for the Treatment of Beta-Amyloid Related Diseases.

This application is related to U.S. Provisional Patent Application No. 60/512,135, filed Oct. 17, 2003, U.S. Provisional Patent Application No. 60/482,058, filed Jun. 23, 2003, both entitled Synthetic Process for Preparing Compounds for Treating Amyloidosis, and U.S. patent application Ser. No. 10/871,543, filed Jun. 18, 2004, entitled Improved Pharmaceutical Drug Candidates and Method for Preparation Thereof.

This application is related to U.S. Provisional Patent Application Ser. No. 60/512,018, filed on Oct. 17, 2003 and U.S. Provisional Patent Application Ser. No. 60/480,928, filed on Jun. 23, 2003, and U.S. application Ser. No. 10/871,512, filed Jun. 18, 2004, all entitled Methods and Compositions for Treating Amyloid- and Epileptogenesis-Associated Diseases.

This application is also related to Method for Treating Amyloidosis, U.S. patent application Ser. No. 08/463,548, now U.S. Pat. No. 5,972,328.

The entire contents of each of these patent applications and patents are hereby expressly incorporated herein by reference including without limitation the specification, claims, and abstract, as well as any figures, tables, or drawings thereof.

BACKGROUND

Amyloidosis refers to a pathological condition characterized by the presence of amyloid fibrils. Amyloid is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Amyloid-related diseases can either be restricted to one organ or spread to several organs. The first instance is referred to as "localized amyloidosis" while the second is referred to as "systemic amyloidosis."

Some amyloid diseases can be idiopathic, but most of these diseases appear as a complication of a previously existing disorder. For example, primary amyloidosis (AL amyloid) can appear without any other pathology or can follow plasma cell dyscrasia or multiple myeloma.

Secondary amyloidosis is usually seen associated with chronic infection (such as tuberculosis) or chronic inflammation (such as rheumatoid arthritis). A familial form of secondary amyloidosis is also seen in other types of familial amyloidosis, e.g., Familial Mediterranean Fever (FMF). This familial type of amyloidosis is genetically inherited and is found in specific population groups. In both primary and secondary amyloidosis, deposits are found in several organs and are thus considered systemic amyloid diseases.

"Localized amyloidoses" are those that tend to involve a single organ system. Different amyloids are also characterized by the type of protein present in the deposit. For example, neurodegenerative diseases such as scrapie, bovine spongiform encephalitis, Creutzfeldt-Jakob disease, and the like are characterized by the appearance and accumulation of a protease-resistant form of a prion protein (referred to as AScr or PrP-27) in the central nervous system. Similarly, Alzheimer's disease, another neurodegenerative disorder, is characterized by neuritic plaques and neurofibrillary tangles. In this case, the amyloid plaques found in the parenchyma and the blood vessel is formed by the deposition of fibrillar Aβ amyloid protein. Other diseases such as adult-onset diabetes (type II diabetes) are characterized by the localized accumulation of amyloid fibrils in the pancreas.

Once these amyloids have formed, there is no known, widely accepted therapy or treatment which significantly dissolves amyloid deposits in situ, prevents further amyloid deposition or prevents the initiation of amyloid deposition.

Each amyloidogenic protein has the ability to undergo a conformational change and to organize into β-sheets and form insoluble fibrils which may be deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences which, although different, show similarities such as regions with the ability to bind to the glycosaminoglycan (GAG) portion of proteoglycan (referred to as the GAG binding site) as well as other regions which promote β-sheet formation. Proteoglycans are macromolecules of various sizes and structures that are distributed almost everywhere in the body. They can be found in the intracellular compartment, on the surface of cells, and as part of the extracellular matrix. The basic structure of all proteoglycans is comprised of a core protein and at least one, but frequently more, polysaccharide chains (GAGs) attached to the core protein. Many different GAGs have been discovered including chondroitin sulfate, dermatan sulfate, keratan sulfate, heparin, and hyaluronan.

In specific cases, amyloid fibrils, once deposited, can become toxic to the surrounding cells. For example, the Aβ fibrils organized as senile plaques have been shown to be associated with dead neuronal cells, dystrophic neurites, astrocytosis, and microgliosis in patients with Alzheimer's disease. When tested in vitro, oligomeric (soluble) as well as fibrillar Aβ peptide was shown to be capable of triggering an activation process of microglia (brain macrophages), which would explain the presence of microgliosis and brain inflammation found in the brain of patients with Alzheimer's disease. Both oligomeric and fibrillar Aβ peptide can also induce neuronal cell death in vitro. See, e.g., M P Lambert, et al., *Proc. Natl. Acad. Sci. USA* 95, 6448-53 (1998).

In another type of amyloidosis seen in patients with type II diabetes, the amyloidogenic protein IAPP, when organized in oligomeric forms or in fibrils, has been shown to induce β-islet cell toxicity in vitro. Hence, appearance of IAPP fibrils in the pancreas of type II diabetic patients contributes to the loss of the β islet cells (Langerhans) and organ dysfunction which can lead to insulinemia.

Another type of amyloidosis is related to $\beta_2$ microglobulin and is found in long-term hemodialysis patients. Patients undergoing long term hemodialysis will develop $\beta_2$-microglobulin fibrils in the carpal tunnel and in the collagen rich tissues in several joints. This causes severe pains, joint stiffness and swelling.

Amyloidosis is also characteristic of Alzheimer's disease. Alzheimer's disease is a devastating disease of the brain that results in progressive memory loss leading to dementia, physical disability, and death over a relatively long period of time. With the aging populations in developed countries, the number of Alzheimer's patients is reaching epidemic proportions.

People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals (dystrophic neurites) and activated microglia (microgliosis and astrocytosis). A main constituent of these amyloid plaques is the amyloid-β peptide (Aβ), a 39-43 amino-acid protein that is produced through cleavage of the β-amyloid precursor protein (APP). Extensive research has been conducted on the relevance of Aβ deposits in Alzheimer's disease, see, e.g., Selkoe, *Trends in Cell Biology* 8, 447-453 (1998). Aβ naturally arises from the metabolic processing of the amyloid precursor protein ("APP") in the endoplasmic reticulum ("ER"), the Golgi apparatus, or the endosomal-lysosomal pathway, and most is normally secreted as a 40 ("Aβ1-40") or 42 ("Aβ1-42") amino acid peptide (Selkoe, *Annu. Rev. Cell Biol.* 10, 373-403 (1994)). A role for Aβ as a primary cause for Alzheimer's disease is supported by the presence of extracellular Aβ deposits in senile plaques of Alzheimer's disease, the increased production of Aβ in cells harboring mutant Alzheimer's disease associated genes, e.g., amyloid precursor protein, presenilin I and presenilin II; and the toxicity of extracellular soluble (oligomeric) or fibrillar Aβ to cells in culture. See, e.g., Gervais, *Eur. Biopharm. Review*, 40-42 (Autumn 2001); May, *DDT* 6, 459-62 (2001). Although symptomatic treatments exist for Alzheimer's disease, this disease cannot be prevented or cured at this time.

Alzheimer's disease is characterized by diffuse and neuritic plaques, cerebral angiopathy, and neurofibrillary tangles. Plaque and blood vessel amyloid is believed to be formed by the deposition of insoluble Aβ amyloid protein, which may be described as diffuse or fibrillary. Both soluble oligomeric Aβ and fibrillar Aβ are also believed to be neurotoxic and inflammatory.

Another type of amyloidosis is cerebral amyloid angiopathy (CAA). CAA is the specific deposition of amyloid-β fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)).

Presently available therapies for treatment of β-amyloid diseases are almost entirely symptomatic, providing only temporary or partial clinical benefit. Although some pharmaceutical agents have been described that offer partial symptomatic relief, no comprehensive pharmacological therapy is currently available for the prevention or treatment of, for example, Alzheimer's disease.

SUMMARY OF THE INVENTION

The present invention relates to the use of certain compounds in the treatment of amyloid-related diseases. In particular, the invention relates to a method of treating or preventing an amyloid-related disease in a subject comprising administering to the subject a therapeutic amount of a compound of the invention. The invention also pertains to each of the novel compounds of the invention as described herein. Among the compounds for use in the invention are those according to the following Formulae, such that, when administered, amyloid fibril formation, organ specific dysfunction (e.g., neurodegeneration), or cellular toxicity is reduced or inhibited.

In one embodiment, the invention pertains, at least in part to compounds of Formula I:

(I)

wherein:

$R^1$ is a substituted or unsubstituted cycloalkyl, heterocyclic, aryl, arylcycloalkyl, bicyclic or tricyclic ring, a bicyclic or tricyclic fused ring group, or a substituted or unsubstituted $C_2$-$C_{10}$ alkyl group;

$R^2$ is selected from a group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

Y is $SO_3^-X^+$, $OSO_3^-X^+$, or $SSO_3^-X^+$;

$X^+$ is hydrogen, a cationic group, or an ester-forming group (i.e., as in a prodrug, which are described elsewhere herein); and each of $L^1$ and $L^2$ is independently a substituted or unsubstituted $C_1$-$C_5$ alkyl group or absent, or a pharmaceutically acceptable salt thereof, provided that when $R^1$ is alkyl, $L^1$ is absent.

In another embodiment, the invention pertains, at least in part to compounds of Formula II:

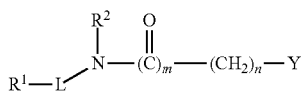

(II)

wherein:

$R^1$ is a substituted or unsubstituted cyclic, bicyclic, tricyclic, or benzoheterocyclic group or a substituted or unsubstituted $C_2$-$C_{10}$ alkyl group;

$R^2$ is hydrogen, alkyl, mercaptoalkyl, alkenyl, alkynyl, cycloalkyl, aryl, arylalkyl, thiazolyl, triazolyl, imidazolyl, benzothiazolyl, benzoimidazolyl, or linked to $R^1$ to form a heterocycle;

Y is $SO_3^-X^+$, $OSO_3^-X^+$, or $SSO_3^-X^+$;

$X^+$ is hydrogen, a cationic group, or an ester forming moiety;

m is 0 or 1;

n is 1, 2, 3, or 4;

L is substituted or unsubstituted $C_1$-$C_3$ alkyl group or absent, or a pharmaceutically acceptable salt thereof, provided that when $R^1$ is alkyl, L is absent.

In yet another embodiment, the invention pertains, at least in part to compounds of Formula III:

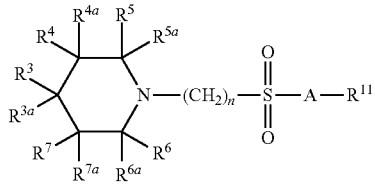

(III)

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

$R^3$, $R^{3a}$, $R^4$, $R^{4a}$, $R^5$, $R^{5a}$, $R^6$, $R^{6a}$, $R^7$ and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond, provided that one of $R^3$, $R^{3a}$, $R^4$, $R^{4a}$, $R^5$, $R^{5a}$, $R^6$, $R^{6a}$, $R^7$ and $R^{7a}$ is a moiety of Formula IIIa:

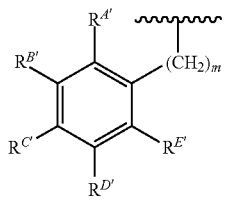

(IIIa)

wherein:

m is 0, 1, 2, 3, or 4;

$R^{A'}$, $R^{B'}$, $R^{C'}$, $R^{D'}$, and $R^{E'}$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; and pharmaceutically acceptable salts and esters thereof, provided that said compound is not 3-(4-phenyl-1,2,3,6-tetrahydro-1-pyridyl)-1-propanesulfonic acid.

In yet another embodiment, the invention pertains at least in part to compounds of Formula IV:

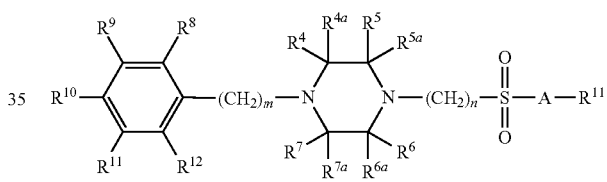

(IV)

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

$R^4$, $R^{4a}$, $R^5$, $R^{5a}$, $R^6$, $R^{6a}$, $R^7$, and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, $R^4$ and $R^5$ taken together, with the ring atoms they are attached to, form a double bond, or $R^6$ and $R^7$ taken together, with the ring atoms they are attached to, form a double bond;

m is 0, 1, 2, 3, or 4;

$R^8$, $R^9$, $R^{10}$, $R^{11}$, and $R^{12}$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl, and pharmaceutically acceptable salts and esters thereof.

In another embodiment, the invention includes compounds of Formula V:

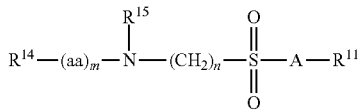

(V)

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

aa is a natural or unnatural amino acid residue;

m is 0, 1, 2, or 3;

$R^{14}$ is hydrogen or protecting group;

$R^{15}$ is hydrogen, alkyl or aryl, and pharmaceutically acceptable salts and prodrugs thereof.

In another embodiment, the invention includes compounds of the Formula VI:

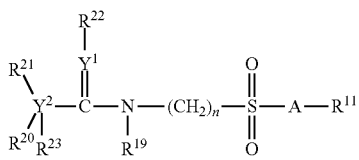

(VI)

wherein:

n is 1, 2, 3, 4, 5, 6, 7, 8, 9, or 10;

A is oxygen or nitrogen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

$R^{19}$ is hydrogen, alkyl or aryl;

$Y^1$ is oxygen, sulfur, or nitrogen;

$Y^2$ is carbon, nitrogen, or oxygen;

$R^{20}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl;

$R^{21}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl, or absent if $Y^2$ is oxygen;

$R^{22}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl; or $R^{22}$ is hydrogen, hydroxyl, alkoxy or aryloxy if $Y^1$ is nitrogen; or $R^{22}$ is absent if $Y^1$ is oxygen or sulfur; or $R^{22}$ and $R^{21}$ may be linked to form a cyclic moiety if $Y^1$ is nitrogen;

$R^{23}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl, or absent if $Y^2$ is nitrogen or oxygen;

or pharmaceutically acceptable salts thereof.

In another embodiment, the invention includes compounds of Formula VII:

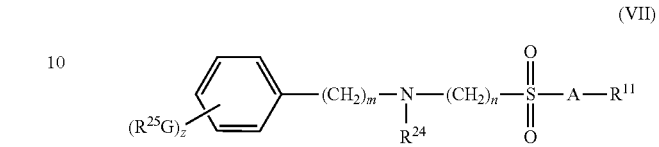

(VII)

wherein:

n is 2, 3, or 4;

A is oxygen or nitrogen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

G is a direct bond or oxygen, nitrogen, or sulfur;

z is 0, 1, 2, 3, 4, or 5;

m is 0 or 1;

$R^{24}$ is selected from a group consisting of hydrogen, alkyl, mercaptoalkyl, alkenyl, alkynyl, aroyl, alkylcarbonyl, aminoalkylcarbonyl, cycloalkyl, aryl, arylalkyl, thiazolyl, triazolyl, imidazolyl, benzothiazolyl, and benzoimidazolyl;

each $R^{25}$ is independently selected from hydrogen, halogen, cyano, hydroxyl, alkoxy, thiol, amino, nitro, alkyl, aryl, carbocyclic, or heterocyclic, and pharmaceutically acceptable salts thereof.

In a further embodiment, the compounds of the invention include compounds of the formula:

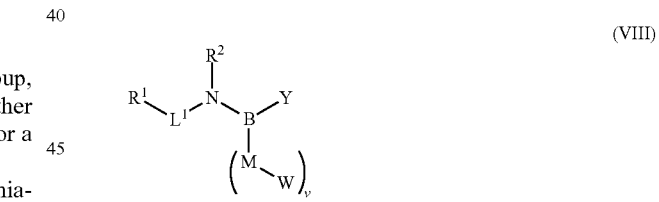

(VIII)

wherein:

$R^1$ is hydrogen, a substituted or unsubstituted cycloalkyl, heterocyclic, aryl, arylcycloalkyl, bicyclic or tricyclic ring, a bicyclic or tricyclic fused ring group, or a substituted or unsubstituted $C_2$-$C_{10}$ alkyl group;

$R^2$ is selected from a group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

Y is $SO_3^-X^+$, $OSO_3^-X^+$, or $SSO_3^-X^+$;

$X^+$ is hydrogen, a cationic group, or an ester-forming group;

$L^1$ is a substituted or unsubstituted $C_1$-$C_5$ alkyl group or absent, B is $C_1$-$C_5$ alkyl, alkenyl, or alkynyl group, optionally fused with W when M is absent;

M is a covalent bond, amino, $C_1$-$C_6$ alkyl, alkenyl, alkynyl, carboxyl, oxy, amide, ester, thioether, thioester or absent;

W is a substituted or unsubstituted alkyl, alkenyl, alkynyl, cycloalkyl, aryl, arylalkyl, bicyclic or tricyclic ring, a bicyclic or tricyclic fused ring group, heterocyclic, thiazolyl, triazolyl, imidazolyl, benzothiazolyl, or benzoimidazolyl; and v is 1, 2, 3, 4, 5, or 6; or a pharmaceutically acceptable salt, ester or prodrug thereof, provided that when Y is methyl, $R^1$ and $R^2$ are hydrogen, Y is $SO_3^-X^+$, M is a covalent bond, B is not $CH_2$—CH(M-W)—$CH_2$.

In another embodiment, the invention pertains, at least in part, to compounds of Formula IX:

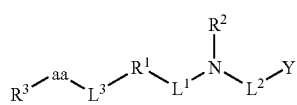

(IX)

wherein:

$R^1$ is a substituted or unsubstituted cycloalkyl, heterocyclic, aryl, arylcycloalkyl, bicyclic or tricyclic ring, a bicyclic or tricyclic fused ring group, or a substituted or unsubstituted $C_2$-$C_{10}$ alkyl group;

$R^2$ is selected from the group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

$R^3$ is hydrogen or a protecting group;

aa is a natural or unnatural amino acid residue;

$L^3$ is a covalent bond, amino, $C_1$-$C_6$ alkyl, alkenyl, alkynyl, carboxyl, amide, aminoalkyl, ether, ester, thioether, thioester or absent;

Y is $SO_3^-X^+$, $OSO_3^-X^+$, or $SSO_3^-X^+$;

$X^+$ is hydrogen, a cationic group, or ester-forming group; and each of $L^1$ and $L^2$ is independently a substituted or unsubstituted $C_1$-$C_5$ alkyl group or absent, or a pharmaceutically acceptable salt, ester or prodrug thereof.

In another embodiment, the invention pertains, at least in part, to compounds of the formula (X):

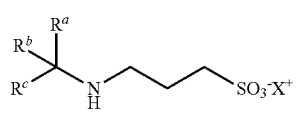

(X)

wherein:

$R^a$ is hydrogen, substituted or unsubstituted alkyl, aryl, heteroaryl, carboxyl, alkyloxycarbonyl, or aminocarbonyl;

$R^b$ and $R^c$ are each selected independently from hydrogen, substituted or unsubstituted alkyl, alkenyl, alkynyl, cycloalkyl, $CONH_2$, or $R^b$, $R^c$ and the carbon atom they are attached to can form a substituted or unsubstituted cyclic structure of 4 to 12-membered ring or a fused ring system; and $X^+$ is hydrogen, a cationic group, or an ester-forming group, or a pharmaceutically acceptable salt, ester, or prodrug thereof.

In another embodiment, the invention pertains, at least in part, to compounds of the formula (XI):

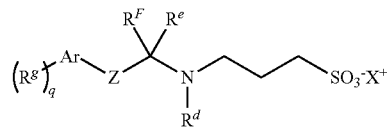

(XI)

wherein:

$R^d$ is H or alkyl;

$R^e$ and $R^f$ are each independently hydrogen, $C_1$-$C_6$ alkyl, or $R^e$ and $R^f$, taken together with the carbon they are attached to, form a 3 to 12-membered ring;

$R^g$ is independently selected for each occurence from the group consisting of: hydrogen, alkyl, alkoxy, halogen, $NO_2$, and alkyl-$SO_2$;

q is 1, 2, 3, 4, or 5;

$X^+$ is hydrogen, a cationic group, or an ester-forming group;

Ar is aryl or heteroaryl; and

Z is —$(CH_2)_{0-3}$—, —(CHOH)—, $(CH_2)_{1-3}O(CH_2)_{1-3}$, or a carbonyl group, or a pharmaceutically acceptable salt, ester, or prodrug thereof.

In another embodiment, the invention also pertains to compounds of the formula (XII):

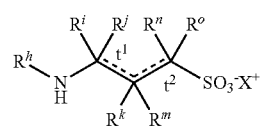

(XII)

wherein:

$R^h$ is hydrogen, benzyl, aryl-alkyl, aryl, or alkyl;

$R^i$, $R^j$, $R^k$, $R^m$, $R^n$, and $R^o$ are each independently hydrogen, substituted or unsubstituted aryl, substituted or unsubstituted benzyl, alkyl, alkenyl, carbocyclic, heterocyclic, absent or together may be linked to form a ring structure;

$X^+$ is hydrogen, a cationic group, or an ester-forming group; and $t^1$ and $t^2$ are each single or double bonds, provided that both $t^1$ and $t^2$ are not both double bonds, or a pharmaceutically acceptable salt, ester, or prodrug thereof.

In another embodiment, the invention also pertains to compounds of the formula (XIII):

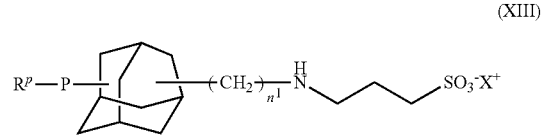

(XIII)

wherein:

$n^1$ is 0, 1, 2, or 3;

P is a covalent bond, alkyl, alkyloxy, amino, alkylamino, sulfur, or alkylthio;

$X^+$ is hydrogen, a cationic group, or an ester-forming group; and $R^p$ is a natural or unnatural amino acid residue, or a pharmaceutically acceptable salt, ester, or prodrug thereof.

In another embodiment, the invention includes compounds of the formula (XIV):

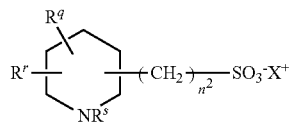

(XIV)

wherein:

$n^2$ is 0, 1, 2, or 3, selected such that three carbons are between the $SO_3^-X^+$ group and the nitrogen atom in the ring;

$X^+$ is hydrogen, a cationic group, or an ester-forming group;

$R^s$ is hydrogen or when $n^2$ is 3, $R^s$ is $(CH_2)_3$—$SO_3^-X^+$;

$R^q$ and $R^r$ are each selected independently from hydrogen or alkyl, or a pharmaceutically acceptable salt, ester, or prodrug thereof.

In yet another embodiment, the invention also pertains, at least in part, to compounds of the formula (XV):

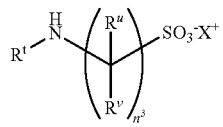

(XV)

wherein:

$R^t$ is hydrogen, alkyl, or aryl;

$R^u$ and $R^v$ are each independently for each occurence selected from hydrogen, aryl, benzyl, alkyl, alkenyl, carbocyclic, heterocyclic, or two $R^u$ or $R^v$ groups on adjacent carbon atoms may form a double bond, or together with the carbon atoms they are attached to form a carbocyclic or heterocyclic ring;

$n^3$ is 4, 5, 6, or 7; and $X^+$ is hydrogen, a cationic group, or an ester-forming group; or a pharmaceutically acceptable salt, ester, or prodrug thereof.

In one embodiment, the compounds disclosed herein prevent or inhibit amyloid protein assembly into insoluble fibrils which, in vivo, are deposited in various organs, or it favors clearance of pre-formed deposits or slows deposition in patients already having deposits. In another embodiment, the compound may also prevent the amyloid protein, in its soluble, oligomeric form or in its fibrillar form, from binding or adhering to a cell surface and causing cell damage or toxicity. In yet another embodiment, the compound may block amyloid-induced cellular toxicity or macrophage activation. In another embodiment, the compound may block amyloid-induced neurotoxicity or microglial activation. In another embodiment, the compound protects cells from amyloid induced cytotoxicity of B-islet cells. In another embodiment, the compound may enhance clearance from a specific organ, e.g., the brain or it decreases concentration of the amyloid protein in such a way that amyloid fibril formation is prevented in the targeted organ.

The compounds of the invention may be administered therapeutically or prophylactically to treat diseases associated with amyloid fibril formation, aggregation or deposition. The compounds of the invention may act to ameliorate the course of an amyloid related disease using any of the following mechanisms (this list is meant to be illustrative and not limiting): slowing the rate of amyloid fibril formation or deposition; lessening the degree of amyloid deposition; inhibiting, reducing, or preventing amyloid fibril formation; inhibiting neurodegeneration or cellular toxicity induced by amyloid; inhibiting amyloid induced inflammation; enhancing the clearance of amyloid; or favoring the degradation of amyloid protein prior to its organization in fibrils.

The compounds of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; enhancing the clearance of amyloid-β from the brain; or favoring the degradation of amyloid-β protein prior to its organization in fibrils.

Therapeutic compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. It may also increase the catabolism of neuronal Aβ and change the rate of exit from the brain. An increase in the exit of Aβ from the brain would result in a decrease in Aβ brain and cerebral spinal fluid (CSF) concentration and therefore favor a decrease in Aβ deposition. Alternatively, compounds that penetrate the brain could control deposition by acting directly on brain Aβ e.g., by maintaining it in a non-fibrillar form, favoring its clearance from the brain, or by slowing down APP processing. These compounds could also prevent Aβ in the brain from interacting with the cell surface and therefore prevent neurotoxicity, neurodegeneration or inflammation. They may also decrease Aβ production by activated microglia. The compounds may also increase degradation by macrophages or neuronal cells.

In one embodiment, the method is used to treat Alzheimer's disease (e.g., sporadic, familial, or early AD). The method can also be used prophylactically or therapeutically to treat other clinical occurrences of amyloid-D deposition, such as in Down's syndrome individuals and in patients with cerebral amyloid angiopathy ("CAA") or hereditary cerebral hemorrhage.

In another embodiment, the method is used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM)

(Askanas, et al., Proc. Natl. Acad. Sci. USA 93, 1314-1319 (1996); Askanas, et al., Current Opinion in Rheumatology 7, 486-496 (1995)). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (AMD). AMD is a cause of irreversible vision loss in older individuals. It is believed that Aβ deposition could be an important component of the local inflammatory events that contribute to atrophy of the retinal pigmented epithelium, drusen biogenesis, and the pathogenesis of AMD (Johnson, et al., Proc. Natl. Acad. Sci. USA 99(18), 11830-5 (2002)).

The present invention therefore relates to the use of compounds of Formulae I-XV or otherwise described herein in the prevention or treatment of amyloid-related diseases, including, inter alia, Alzheimer's disease, cerebral amyloid angiopathy, mild cognitive impairment, inclusion body myositis, Down's syndrome, macular degeneration, as well as other types of amyloidosis such as IAPP-related amyloidosis (e.g., diabetes), primary (AL) amyloidosis, secondary (AA) amyloidosis and β$_2$ microglobulin-related (dialysis-related) amyloidosis.

In Type II diabetes-related amyloidosis (IAPP), the amyloidogenic protein IAPP induces β-islet cell toxicity when organized in oligomeric forms or in fibrils. Hence, appearance of IAPP fibrils in the pancreas of type II diabetic patients contributes to the loss of the β islet cells (Langerhans) and organ dysfunction which leads to insulinemia.

Primary amyloidosis (AL amyloid) is usually found associated with plasma cell dyscrasia and multiple myeloma. It can also be found as an idiopathic disease.

Secondary (AA) amyloidosis is usually seen associated with chronic infection (such as tuberculosis) or chronic inflammation (such as rheumatoid arthritis). A familial form of secondary amyloidosis is also seen in Familial Mediterranean Fever (FMF).

β$_2$ microglobulin-related (dialysis-related) amyloidosis is found in long-term hemodialysis patients. Patients undergoing long term hemodialysis will develop β$_2$-microglobulin fibrils in the carpal tunnel and in the collagen rich tissues in several joints. This causes severe pains, joint stiffness and swelling. These deposits are due to the inability to maintain low levels of β$_2$M in plasma of dialyzed patients. Increased plasma concentrations of β$_2$M protein will induce structural changes and may lead to the deposition of modified β$_2$M as insoluble fibrils in the joints.

DETAILED DESCRIPTION OF THE INVENTION

The present invention relates to the use of compounds of Formulae I-XV or compounds otherwise described herein in the treatment of amyloid-related diseases. For convenience, some definitions of terms referred to herein are set forth below.

Amyloid-Related Diseases

AA (Reactive) Amyloidosis

Generally, AA amyloidosis is a manifestation of a number of diseases that provoke a sustained acute phase response. Such diseases include chronic inflammatory disorders, chronic local or systemic microbial infections, and malignant neoplasms. The most common form of reactive or secondary (AA) amyloidosis is seen as the result of long-standing inflammatory conditions. For example, patients with Rheumatoid Arthritis or Familial Mediterranean Fever (which is a genetic disease) can develop AA amyloidosis. The terms "AA amyloidosis" and "secondary (AA) amyloidosis" are used interchangeably.

AA fibrils are generally composed of 8,000 Dalton fragments (AA peptide or protein) formed by proteolytic cleavage of serum amyloid A protein (ApoSAA), a circulating apolipoprotein which is mainly synthesized in hepatocytes in response to such cytokines as IL-1, IL-6 and TNF. Once secreted, ApoSAA is complexed with HDL. Deposition of AA fibrils can be widespread in the body, with a preference for parenchymal organs. The kidneys are usually a deposition site, and the liver and the spleen may also be affected. Deposition is also seen in the heart, gastrointestinal tract, and the skin.

Underlying diseases which can lead to the development of AA amyloidosis include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia. Other underlying conditions that may be associated with AA amyloidosis are Castleman's disease and Schnitzler's syndrome.

AL Amyloidoses (Primary Amyloidosis)

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia. AL amyloidosis is also described in detail in *Current Drug Targets*, 2004, 5 159-171.

Fibrils of AL amyloid deposits are composed of monoclonal immunoglobulin light chains or fragments thereof. More specifically, the fragments are derived from the N-terminal region of the light chain (kappa or lambda) and contain all or part of the variable (V$_L$) domain thereof. Deposits generally occur in the mesenchymal tissues, causing peripheral and autonomic neuropathy, carpal tunnel syndrome, macroglossia, restrictive cardiomyopathy, arthropathy of large joints, immune dyscrasias, myelomas, as well as occult dyscrasias. However, it should be noted that almost any tissue, particularly visceral organs such as the kidney, liver, spleen and heart, may be involved.

Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 1 summarizes the fibril composition of exemplary forms of these disorders.

TABLE 1

Fibril Composition of Exemplary Amyloid-Related Diseases

| Fibril Peptide/Protein | Genetic Variant | Clinical Syndrome |
|---|---|---|
| ATTR protein from Transthyretin and fragments | Met30, many others | Familial amyloid polyneuropathy (FAP), (Mainly peripheral nerves) |
| ATTR protein from Transthyretin and fragments | Thr45, Ala60, Ser84, Met111, Ile 122 | Cardiac involvement predominant without neuropathy, familial amyloid polyneuropathy, senile systemic amyloidosis, Tenosynovium |
| N-terminal fragment of Apolipoprotein A1 (apoAI) | Arg26 | Familial amyloid polyneuropathy (FAP), (mainly peripheral nerves) |
| N-terminal fragment of Apoliproprotein A1 (AapoAI) | Arg26, Arg50, Arg 60, others | Ostertag-type, non-neuropathic (predominantly visceral involvement) |
| AapoAII from Apolipoprotein AII | | Familial amyloidosis |
| Lysozyme (Alys) | Thr56, His67 | Ostertag-type, non-neuropathic (predominantly visceral involvement) |
| Fibrogen alpha chain fragment | Leu554, Val 526 | Cranial neuropathy with lattic corneal dystrophy |
| Gelsolin fragment (Agel) | Asn187, Tyr187 | Cranial neuropathy with lattice corneal dystrophy |
| Cystatin C fragment (ACys) | Glu68 | Hereditary cerebral hemorrhage (cerebral amyloid angiopathy) - Icelandic type |
| β-amyloid protein (Aβ) derived from Amyloid Precursor Protein (APP) | Gln693 | Hereditary cerebral hemorrhage (cerebral amyloid angiopathy) - Dutch type |
| β-amyloid protein (Aβ) derived from Amyloid Precursor Protein (APP) | Ile717, Phe717, Gly717 | Familial Alzheimer's Disease |
| β-amyloid protein (Aβ) derived from Amyloid Precursor Protein (APP), e.g., bPP 695 | Gln 618 | Alzheimer's disease, Down's syndrome, hereditary cerebral hemorrhage with amyloidosis, Dutch type |
| β-amyloid protein (Aβ) derived from Amyloid Precursor Protein (APP) | Asn670, Leu671 | Familial Dementia - probably Alzheimer's Disease |
| Prion Protein (PrP, APrP$^{SC}$) derived from Prp precursor protein (51-91 insert) | Leu102, Val167, Asn178, Lys200 | Familial Creutzfeldt-Jakob disease; Gerstmann-Straussler-Scheinker syndrome (hereditary spongiform encephalopathies, prion diseases) |
| AA derived from Serum amyloid A protein (ApoSAA) | | Familial Mediterranean fever, predominant renal involvement (autosomal recessive) |
| AA derived from Serum amyloid A protein (ApoSAA) | | Muckle-Well's syndrome, nephropathy, deafness, urticaria, limb pain |
| Unknown | | Cardiomyopathy with persistent atrial standstill |
| Unknown | | Cutaneous deposits (bullous, papular, pustulodermal) |
| AH amyloid protein, derived from immunoglobulin heavy chain (gamma I) | AγI | Myeloma associated amyloidosis |
| ACal amyloid protein from (pro)calcitonin | (Pro) calcitonin | Medullary carcinomas of the thyroid |
| AANF amyloid protein from atrial natriuretic factor | | Isolated atrial amyloid |
| Apro from Prolactin | | Prolactinomas |
| Abri/ADan from ABri peptide | | British and Danish familial Dementia |

Data derived from Tan SY, Pepys MB. Amyloidosis. Histopathology, 25(5), 403-414 (Nov 1994), WHO/IUIS Nomenclature Subcommittee, Nomenclature of Amyloid and Amyloidosis. Bulletin of the World Health Organisation 1993; 71: 10508; and Merlini et al., Clin Chem Lab Med 2001; 39(11): 1065-75.

The data provided in Table 1 are exemplary and are not intended to limit the scope of the invention. For example, more than 40 separate point mutations in the transthyretin gene have been described, all of which give rise to clinically similar forms of familial amyloid polyneuropathy.

In general, any hereditary amyloid disorder can also occur sporadically, and both hereditary and sporadic forms of a disease present with the same characteristics with regard to amyloid. For example, the most prevalent form of secondary AA amyloidosis occurs sporadically, e.g. as a result of ongoing inflammation, and is not associated with Familial Mediterranean Fever. Thus general discussion relating to hereditary amyloid disorders below can also be applied to sporadic amyloidoses.

Transthyretin (TTR) is a 14 kiloDalton protein that is also sometimes referred to as prealbumin. It is produced by the liver and choroid plexus, and it functions in transporting thyroid hormones and vitamin A. At least 50 variant forms of the protein, each characterized by a single amino acid change, are responsible for various forms of familial amyloid polyneuropathy. For example, substitution of proline for leucine at position 55 results in a particularly progressive form of neuropathy; substitution of methionine for leucine at position 111 resulted in a severe cardiopathy in Danish patients.

Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known in the art (e.g., Gustavsson, A., et al., Laboratory Invest. 73: 703-708, 1995; Kametani, F., et al., Biochem. Biophys. Res. Commun. 125: 622-628, 1984; Pras, M., et al., PNAS 80: 539-42, 1983).

Persons having point mutations in the molecule apolipoprotein Al (e.g., Gly→Arg26; Trp→Arg50; Leu→Arg60) exhibit a form of amyloidosis ("Östertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form (Benson, M. D., et al. CIBA Fdn. Symp. 199: 104-131, 1996).

Immunoglobulin light chains tend to form aggregates in various morphologies, including fibrillar (e.g., AL amyloidosis and AH amyloidosis), granular (e.g., light chain deposition disease (LCDD), heavy chain deposition disease (HCDD), and light-heavy chain deposition disease (LH-CDD)), crystalline (e.g., Acquired Farconi's Syndome), and microtubular (e.g., Cryoglobulinemia). AL and AH amyloidosis is indicated by the formation of insoluble fibrils of immunoglobulin light chains and heavy chain, respectively, and/or their fragments. In AL fibrils, lambda ($\lambda$) chains such as $\lambda$ VI chains ($\lambda$6 chains), are found in greater concentrations than kappa ($\kappa$) chains. $\lambda$III chains are also slightly elevated. Merlini et al., CLIN CHEM LAB MED 39(11):1065-75 (2001). Heavy chain amyloidosis (AH) is generally characterized by aggregates of gamma chain amyloid proteins of the IgG1 subclass. Eulitz et al., PROC NATL ACAD SCI USA 87:6542-46 (1990).

Comparison of amyloidogenic to non-amyloidogenic light chains has revealed that the former can include replacements or substitutions that appear to destabilize the folding of the protein and promote aggregation. AL and LCDD have been distinguished from other amyloid diseases due to their relatively small population monoclonal light chains, which are manufactured by neoplastic expansion of an antibody-producing B cell. AL aggregates typically are well-ordered fibrils of lambda chains. LCDD aggregates are relatively amorphous aggregations of both kappa and lambda chains, with a majority being kappa, in some cases $\kappa$IV. Bellotti et al., JOURNAL OF STRUCTURAL BIOLOGY 13:280-89 (2000). Comparison of amyloidogenic and non-amyloidogenic heavy chains in patients having AH amyloidosis has revealed missing and/or altered components. Eulitz et al., PROC NATL ACAD SCI USA 87:6542-46 (1990) (pathogenic heavy chain characterized by significantly lower molecular mass than non-amyloidogenic heavy chains); and Solomon et al. AM J HEMAT 45(2) 171-6 (1994) (amyloidogenic heavy chain characterized as consisting solely of the VH-D portion of the non-amyloidogenic heavy chain).

Accordingly, potential methods of detecting and monitoring treatment of subjects having or at risk of having AL, LCDD, AH, and the like, include but are not limited to immunoassaying plasma or urine for the presence or depressed deposition of amyloidogenic light or heavy chains, e.g., amyloid $\lambda$, amyloid $\kappa$, amyloid $\kappa$IV, amyloid $\gamma$, or amyloid $\gamma$1.

Brain Amyloidosis

The most frequent type of amyloid in the brain is composed primarily of A$\beta$ peptide fibrils, resulting in dementia associated with sporadic (non-hereditary) Alzheimer's disease. In fact, the incidence of sporadic Alzheimer's disease greatly exceeds forms shown to be hereditary. Nevertheless, fibril peptides forming plaques are very similar in both types. Brain amyloidosis includes those diseases, conditions, pathologies, and other abnormalities of the structure or function of the brain, including components thereof, in which the causative agent is amyloid. The area of the brain affected in an amyloid-related disease may be the stroma including the vasculature or the parenchyma including functional or anatomical regions, or neurons themselves. A subject need not have received a definitive diagnosis of a specifically recognized amyloid-related disease. The term "amyloid related disease" includes brain amyloidosis.

Amyloid-$\beta$ peptide ("A$\beta$") is a 39-43 amino acid peptide derived by proteolysis from a large protein known as Beta Amyloid Precursor Protein ("$\beta$APP"). Mutations in $\beta$APP result in familial forms of Alzheimer's disease, Down's syndrome, cerebral amyloid angiopathy, and senile dementia, characterized by cerebral deposition of plaques composed of A$\beta$ fibrils and other components, which are described in further detail below. Known mutations in APP associated with Alzheimer's disease occur proximate to the cleavage sites of $\beta$ or $\gamma$-secretase, or within A$\beta$. For example, position 717 is proximate to the site of gamma-secretase cleavage of APP in its processing to A$\beta$, and positions 670/671 are proximate to the site of $\beta$-secretase cleavage. Mutations at any of these residues may result in Alzheimer's disease, presumably by causing an increase in the amount of the 42/43 amino acid form of A$\beta$ generated from APP. The familial form of Alzheimer's disease represents only 10% of the subject population. Most occurrences of Alzheimer's disease are sporadic cases where APP and A$\beta$ do not possess any mutation. The structure and sequence of A$\beta$ peptides of various lengths are well known in the art. Such peptides can be made according to methods known in the art, or extracted from the brain according to known methods (e.g., Glenner and Wong, Biochem. Biophys. Res. Comm. 129, 885-90 (1984); Glenner and Wong, Biochem. Biophys. Res. Comm. 122, 1131-35 (1984)). In addition, various forms of the peptides are commercially available. APP is expressed and constitutively catabolized in most cells. The dominant catabolic pathway appears to be cleavage of APP within the A$\beta$ sequence by an enzyme provisionally termed $\alpha$-secretase, leading to release of a soluble ectodomain fragment known as APPs$\alpha$. This cleavage precludes the formation of A$\beta$ peptide. In contrast to this non-amyloidogenic pathway, APP can also be cleaved by enzymes known as $\beta$- and $\gamma$-secretase at the N- and C-termini of the A$\beta$, respectively, followed by release of A$\beta$ into the extracellular space. To date, BACE has been identified as $\beta$-secretase (Vasser, et al., Science 286:735-741, 1999) and presenilins have been implicated in $\gamma$-secretase activity (De Strooper, et al., Nature 391, 387-90 (1998)). The 39-43 amino acid A$\beta$ peptide is produced by sequential proteolytic cleavage of the amyloid precursor protein (APP) by the $\beta$ and $\gamma$ secretases enzyme. Although A$\beta$40 is the predominant form produced, 5-7% of total A$\beta$ exists as A$\beta$42 (Cappai et al., Int. J. Biochem. Cell Biol. 31. 885-89 (1999)).

The length of the A$\beta$ peptide appears to dramatically alter its biochemical/biophysical properties. Specifically, the additional two amino acids at the C-terminus of A$\beta$42 are very hydrophobic, presumably increasing the propensity of A$\beta$42 to aggregate. For example, Jarrett, et al. demonstrated that A$\beta$42 aggregates very rapidly in vitro compared to A$\beta$40, suggesting that the longer forms of A$\beta$ may be the important pathological proteins that are involved in the initial seeding of the neuritic plaques in Alzheimer's disease (Jarrett, et al, Biochemistry 32, 4693-97 (1993); Jarrett, et al., Ann. N.Y. Acad. Sci. 695, 144-48 (1993)). This hypothesis has been further substantiated by the recent analysis of the contributions of specific forms of A$\beta$ in cases of genetic familial forms of Alzheimer's disease ("FAD"). For example, the "London" mutant form of APP (APPV7171) linked to FAD selectively increases the production of A$\beta$ 42/43 forms versus A$\beta$ 40

(Suzuki, et al., *Science* 264, 1336-40 (1994)) while the "Swedish" mutant form of APP (APPK670N/M671L) increases levels of both Aβ40 and Aβ42/43 (Citron, et al., *Nature* 360, 672-674 (1992); Cai, et al., *Science* 259, 514-16, (1993)). Also, it has been observed that FAD-linked mutations in the Presenilin-1 ("PS1") or Presenilin-2 ("PS2") genes will lead to a selective increase in Aβ42/43 production but not A040 (Borchelt, et al., *Neuron* 17, 1005-13 (1996)). This finding was corroborated in transgenic mouse models expressing PS mutants that demonstrate a selective increase in brain Aβ42 (Borchelt, op cit.; Duff, et al., *Neurodegeneration* 5(4), 293-98 (1996)). Thus the leading hypothesis regarding the etiology of Alzheimer's disease is that an increase in Aβ42 brain concentration due to an increased production and release of Aβ42 or a decrease in clearance (degradation or brain clearance) is a causative event in the disease pathology.

Multiple mutation sites in either Aβ or the APP gene have been identified and are clinically associated with either dementia or cerebral hemorrhage. Exemplary CAA disorders include, but are not limited to, hereditary cerebral hemorrhage with amyloidosis of Icelandic type (HCHWA-I); the Dutch variant of HCHWA (HCHWA-D; a mutation in Aβ); the Flemish mutation of Aβ; the Arctic mutation of Aβ; the Italian mutation of Aβ; the Iowa mutation of Aβ; familial British dementia; and familial Danish dementia. CAA may also be sporadic.

As used herein, the terms "β amyloid," "amyloid-β," and the like refer to amyloid β proteins or peptides, amyloid β precursor proteins or peptides, intermediates, and modifications and fragments thereof, unless otherwise specifically indicated. In particular, "Aβ" refers to any peptide produced by proteolytic processing of the APP gene product, especially peptides which are associated with amyloid pathologies, including Aβ1-39, Aβ1-40, Aβ1-41, Aβ1-42, and Aβ1-43. For convenience of nomenclature, "Aβ1-42" may be referred to herein as "Aβ(1-42)" or simply as "Aβ42" or "Aβ$_{42}$" (and likewise for any other amyloid peptides discussed herein). As used herein, the terms "β amyloid," "amyloid-β," and "Aβ" are synonymous.

Unless otherwise specified, the term "amyloid" refers to amyloidogenic proteins, peptides, or fragments thereof which can be soluble (e.g., monomeric or oligomeric) or insoluble (e.g., having fibrillary structure or in amyloid plaque). See, e.g., MP Lambert, et al., *Proc. Nat'l Acad. Sci. USA* 95, 6448-53 (1998). "Amyloidosis" or "amyloid disease" or "amyloid-related disease" refers to a pathological condition characterized by the presence of amyloid fibers. "Amyloid" is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Gelsolin is a calcium binding protein that binds to fragments and actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173-243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs. (Kangas, H., et al. Human Mol. Genet. 5(9): 1237-1243, 1996).

Other mutated proteins, such as mutant alpha chain of fibrinogen (AfibA) and mutant cystatin C (Acys) also form fibrils and produce characteristic hereditary disorders. AfibA fibrils form deposits characteristic of a nonneuropathic hereditary amyloid with renal disease; Acys deposits are characteristic of a hereditary cerebral amyloid angiopathy reported in Iceland (Isselbacher, Harrison's Principles of Internal Medicine, McGraw-Hill, San Francisco, 1995; Benson, et al.). In at least some cases, patients with cerebral amyloid angiopathy (CAA) have been shown to have amyloid fibrils containing a non-mutant form of cystatin C in conjunction with amyloid beta protein (Nagai, A., et al. Molec. Chem. Neuropathol. 33: 63-78, 1998).

Certain forms of prion disease are now considered to be heritable, accounting for up to 15% of cases, which were previously thought to be predominantly infectious in nature. (Baldwin, et al., in Research Advances in *Alzheimer's Disease and Related Disorders*, John Wiley and Sons, New York, 1995). In hereditary and sporadic prion disorders, patients develop plaques composed of abnormal isoforms of the normal prion protein (PrP$^{Sc}$).

A predominant mutant isoform, PrP$^{Sc}$, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jacob disease (CJD), Gerstmann-Straussler-Scheinker syndrome (GSS), and fatal familial insomnia (FFI). (Baldwin, supra) Methods for extracting fibril peptides from scrapie fibrils, determining sequences and making such peptides are known in the art (e.g., Beekes, M., et al. J. Gen. Virol. 76: 2567-76, 1995).

For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. The most common occurrences of cerebral amyloidosis are sporadic and not familial. For example, the incidence of sporadic Alzheimer's disease and sporadic CAA greatly exceeds the incidence of familial AD and CAA. Moreover, sporadic and familial forms of the disease cannot be distinguished from each other (they differ only in the presence or absence of an inherited genetic mutation); for example, the clinical symptoms and the amyloid plaques formed in both sporadic and familial AD are very similar, if not identical.

Cerebral amyloid angiopathy (CAA) refers to the specific deposition of amyloid fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)). CAA can occur sporadically or be hereditary.

Senile Systemic Amyloidosis

Amyloid deposition, either systemic or focal, increases with age. For example, fibrils of wild type transthyretin (TTR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate ($\beta_2$ microglobulin), joints and seminal vesicles.

Dialysis-Related Amyloidosis (DRA)

Plaques composed of $\beta_2$ microglobulin ($\beta_2$M) fibrils commonly develop in patients receiving long term hemodialysis or peritoneal dialysis. $\beta_2$ microglobulin is a 11.8 kiloDalton polypeptide and is the light chain of Class I MHC antigens, which are present on all nucleated cells. Under normal circumstances, $\beta_2$M is usually distributed in the extracellular space unless there is an impaired renal function, in which case $\beta_2$M is transported into tissues where it polymerizes to form amyloid fibrils. Failure of clearance such as in the case of impaired renal function, leads to deposition in the carpal tunnel and other sites (primarily in collagen-rich tissues of the joints). Unlike other fibril proteins, $\beta_2$M molecules are not produced by cleavage of a longer precursor protein and are generally present in unfragmented form in the fibrils. (Benson, supra). Retention and accumulation of this amyloid precursor has been shown to be the main pathogenic process underlying DRA. DRA is characterized by peripheral joint osteoarthropathy (e.g., joint stiffness, pain, swelling, etc.). Isoforms of $\beta_2$M, glycated $\beta_2$M, or polymers of $\beta_2$M in tissue are the most amyloidogenic form (as opposed to native $\beta_2$M). Unlike other types of amyloidosis, $\beta_2$M is confined largely to osteoarticular sites. Visceral depositions are rare. Occasionally, these deposits may involve blood vessels and other important anatomic sites.

Despite improved dialysis methods for removal of $\beta_2$M, the majority of patients have plasmatic $\beta_2$M concentrations that remain dramatically higher than normal. These elevated $\beta_2$M concentrations generally lead to Diabetes-Related Amyloidosis (DRA) and cormorbidities that contribute to mortality.

Islet Amyloid Polypeptide and Diabetes

Islet hyalinosis (amyloid deposition) was first described over a century ago as the presence of fibrous protein aggregates in the pancreas of patients with severe hyperglycemia (Opie, E L., *J Exp. Med.* 5: 397-428, 1901). Today, islet amyloid, composed predominantly of islet amyloid polypeptide (IAPP), or amylin, is a characteristic histopathological marker in over 90% of all cases of Type II diabetes (also known as Non-Insulin Dependent Diabetes, or NIDDM). These fibrillar accumulations result from the aggregation of the islet amyloid polypeptide (IAPP) or amylin, which is a 37 amino acid peptide, derived from a larger precursor peptide, called pro-IAPP.

IAPP is co-secreted with insulin in response to β-cell secretagogues. This pathological feature is not associated with insulin-dependent (Type I) diabetes and is a unifying characteristic for the heterogeneous clinical phenotypes diagnosed as NIDDM (Type II diabetes).

Longitudinal studies in cats and immunocytochemical investigations in monkeys have shown that a progressive increase in islet amyloid is associated with a dramatic decrease in the population of insulin-secreting β-cells and increased severity of the disease. More recently, transgenic studies have strengthened the relationship between IAPP plaque formation and β-cell apoptosis and dysfunction, indicating that amyloid deposition is a principal factor in increasing severity of Type II diabetes.

IAPP has also been shown to induce β-islet cell toxicity in vitro, indicating that appearance of IAPP fibrils in the pancreas of Type II or Type I diabetic patients (post-islet transplantation) could contribute to the loss of the β-cell islets (Langerhans) and organ dysfunction. In patients with Type II diabetes, the accumulation of pancreatic IAPP leads to formation of oligomeric IAPP, leading to a buildup of IAPP-amyloid as insoluble fibrous deposits which eventually destroys the insulin-producing β cells of the islet, resulting in β cell depletion and failure (Westermark, P., Grimelius, L., *Acta Path. Microbiol. Scand., sect. A.* 81: 291-300, 1973; de Koning, EJP., et al., *Diabetologia* 36: 378-384, 1993; and Lorenzo, A., et al., *Nature* 368: 756-760, 1994). Accumulation of IAPP as fibrous deposits can also have an impact on the ratio of pro-IAPP to IAPP normally found in plasma by increasing this ratio due to the trapping of IAPP in deposits. Reduction of β cell mass can be manifested by hyperglycemia and insulinemia. This β-cell mass loss can lead to a need for insulin therapy.

Diseases caused by the death or malfunctioning of a particular type or types of cells can be treated by transplanting into the patient healthy cells of the relevant type of cell. This approach has been used for Type I diabetes patients. Often pancreatic islet cells from a donor are cultured in vitro prior to transplantation, to allow them to recover after the isolation procedure or to reduce their immunogenicity. However, in many instances islet cell transplantation is unsuccessful, due to death of the transplanted cells. One reason for this poor success rate is IAPP, which organizes into toxic oligomers. Toxic effects may result from intracellular and extracellular accumulation of fibril oligomers. The IAPP oligomers can form fibrils and become toxic to the cells in vitro. In addition, IAPP fibrils are likely to continue to grow after the cells are transplanted and cause death or dysfunction of the cells. This may occur even when the cells are from a healthy donor and the patient receiving the transplant does not have a disease that is characterized by the presence of fibrils. For example, compounds of the present invention may also be used in preparing tissues or cells for transplantation according to the methods described in International Patent Application (PCT) number WO 01/003680.

The compounds of the invention may also stabilize the ratio of the concentrations of Pro-IAPP/IAPP, pro-Insulin/Insulin and C-peptide levels. In addition, as biological markers of efficacy, the results of the different tests, such as the arginine-insulin secretion test, the glucose tolerance test, insulin tolerance and sensitivity tests, could all be used as markers of reduced β-cell mass and/or accumulation of amyloid deposits. Such class of drugs could be used together with other drugs targeting insulin resistance, hepatic glucose production, and insulin secretion. Such compounds might prevent insulin therapy by preserving β-cell function and be applicable to preserving islet transplants.

Hormone-Derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), and atrial natriuretic peptide (isolated atrial amyloidosis). Sequences and structures of these proteins are well known in the art.

Miscellaneous Amyloidoses

There are a variety of other forms of amyloid disease that are normally manifest as localized deposits of amyloid. In general, these diseases are probably the result of the localized production or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid. Other amyloid related diseases include those described in Table 1, such as familial amyloid polyneuropathy (FAP), senile systemic amyloidosis, Tenosynovium, familial amyloidosis, Ostertag-type, non-neuropathic amyloidosis, cranial neuropathy, hereditary cerebral hemorrhage, familial dementia, chronic dialysis, familial Creutzfeldt-Jakob disease; Gerstmann-Sträussler-Scheinker syndrome, hereditary spongiform encephalopathies, prion diseases, familial Mediterranean fever, Muckle-Well's syndrome, nephropathy, deafness, urticaria, limb pain, cardiomyopathy, cutaneous deposits, multiple myeloma, benign monoclonal gammopathy, maccoglobulinaemia, myeloma associated amyloidosis, medullary carcinomas of the thyroid, isolated atrial amyloid, and diabetes.

The compounds of the invention may be administered therapeutically or prophylactically to treat diseases associated with amyloid fibril formation, aggregation or deposition, regardless of the clinical setting. The compounds of the invention may act to ameliorate the course of an amyloid related disease using any of the following mechanisms, such as, for example but not limited to: slowing the rate of amyloid fibril formation or deposition; lessening the degree of amyloid deposition; inhibiting, reducing, or preventing amyloid fibril formation; inhibiting amyloid induced inflammation; enhancing the clearance of amyloid from, for example, the brain; or protecting cells from amyloid induced (oligomers or fibrillar) toxicity.

In an embodiment, the compounds of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; enhancing the clearance of amyloid-β from the brain; or favoring greater catabolism of Aβ.

Compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. An increase in the exit of Aβ from the brain would result in a decrease in Aβ brain concentration and therefore favor a decrease in Aβ deposition. In addition, compounds that penetrate the brain may control deposition by acting directly on brain Aβ, e.g., by maintaining it in a non-fibrillar form or favoring its clearance from the brain. The compounds may slow down APP processing; may increase degradation of Aβ fibrils by macrophages or by neuronal cells; or may decrease Aβ production by activated microglia. These compounds could also prevent Aβ in the brain from interacting with the cell surface and therefore prevent neurotoxicity, neurodegeneration, or inflammation.

In a preferred embodiment, the method is used to treat Alzheimer's disease (e.g., sporadic or familial AD). The method can also be used prophylactically or therapeutically to treat other clinical occurrences of amyloid-β deposition, such as in Down's syndrome individuals and in patients with cerebral amyloid angiopathy ("CAA"), hereditary cerebral hemorrhage, or early Alzheimer's disease.

In another embodiment, the method is used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM) (Askanas, V., et al. (1996) *Proc. Natl. Acad. Sci. USA* 93: 1314-1319; Askanas, V. et al. (1995) *Current Opinion in Rheumatology* 7: 486-496). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al., Proc. Natl. Acad. Sci. USA 99(18), 11830-5 (2002)).

In another embodiment, the invention also relates to a method of treating or preventing an amyloid-related disease in a subject (preferably a human) comprising administering to the subject a therapeutic amount of a compound according to the following Formulae or otherwise described herein, such that amyloid fibril formation or deposition, neurodegeneration, or cellular toxicity is reduced or inhibited. In another embodiment, the invention relates to a method of treating or preventing an amyloid-related disease in a subject (preferably a human) comprising administering to the subject a therapeutic amount of a compound according to the following Formulae or otherwise described herein, such that cognitive function is improved or stabilized or further deterioration in cognitive function is prevented, slowed, or stopped in patients with brain amyloidosis, e.g., Alzheimer's disease, Down's syndrome or cerebral amyloid angiopathy. These compounds can also improve quality of daily living in these subjects.

The therapeutic compounds of the invention may treat amyloidosis related to type II diabetes by, for example, stabilizing glycemia, preventing or reducing the loss of β cell mass, reducing or preventing hyperglycemia due to loss of β cell mass, and modulating (e.g., increasing or stabilizing) insulin production. The compounds of the invention may also stabilize the ratio of the concentrations of pro-IAPP/IAPP.

The therapeutic compounds of the invention may treat AA (secondary) amyloidosis and/or AL (primary) amyloidosis, by stabilizing renal function, decreasing proteinuria, increasing creatinine clearance (e.g., by at least 50% or greater or by at least 100% or greater), by leading to remission of chronic diarrhea or weight gain (e.g., 10% or greater), or by reducing serum creatinine. Visceral amyloid content as determined, e.g., by SAP scintigraphy may also be reduced.

Compounds of the Invention

The present invention relates, at least in part, to the use of certain chemical compounds (and pharmaceutical formulations thereof) in the prevention or treatment of amyloid-related diseases, including, inter alia, Alzheimer's disease, cerebral amyloid angiopathy, inclusion body myositis, Down's syndrome, diabetes related amyloidosis, hemodialysis-related amyloidosis ($\beta_2$M), primary amyloidosis (e.g., $\lambda$ or $\kappa$ chain-related), familial amyloid polyneuropathy (FAP), senile systemic amyloidosis, familial amyloidosis, Ostertag-type non-neuropathic amyloidosis, cranial neuropathy, hereditary cerebral hemorrhage, familial dementia, chronic dialysis, familial Creutzfeldt-Jakob disease, Gerstmann-Sträussler-Scheinker syndrome, hereditary spongiform encephalopathies, prion diseases, familial Mediterranean fever, Muckle-Well's syndrome, nephropathy, deafness, urticaria, limb pain, cardiomyopathy, cutaneous deposits, multiple myeloma, benign monoclonal gammopathy, maccoglobulinaemia, myeloma associated amyloidosis, medullary carcinomas of the thyroid, and isolated atrial amyloid.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention.

A "small molecule" refers to a compound that is not itself the product of gene transcription or translation (e.g., protein, RNA, or DNA) and preferably has a low molecular weight, e.g., less than about 2500 amu.

In general, the term "nucleophile" is art-recognized to mean a chemical group having a reactive pair of electrons that reacts with a compound by displacing a leaving group (commonly another nucleophile), such as commonly occur in aliphatic chemistry as unimolecular (known as "$S_N1$") or bimolecular ("$S_N2$") reactions. Examples of nucleophiles include uncharged compounds such as amines, mercaptans, and alcohols, and charged groups such as alkoxides, thiolates, carbanions, and a variety of organic and inorganic anions. Illustrative anionic nucleophiles include, inter alia, simple anions such as azide, cyanide, thiocyanate, acetate, formate, or chloroformate, and bisulfite. Organometallic reagents such as organocuprates, organozincs, organolithiums, Grignard reagents, enolates, and acetylides, will under appropriate reaction conditions, be suitable nucleophiles.

Similarly, an "electrophile" means an atom, molecule, or ion able to accept an electron pair, particularly a pair of electrons from a nucleophile, such as typically occurs during an electrophilic substitution reaction. In an electrophilic substitution reaction, an electrophile binds to a substrate with the expulsion of another electrophile, e.g., the substitution of a proton by another electrophile such as a nitronium ion on an aromatic substrate (e.g., benzene). Electrophiles include cyclic compounds such as epoxides, aziridines, episulfides, cyclic sulfates, carbonates, lactones, and lactams; and non-cyclic electrophiles include sulfates, sulfonates (e.g., tosylates), chlorides, bromides, and iodides. Generally, an electrophile may be a saturated carbon atom (e.g., a methylene group) bonded to a leaving group; however, an electrophile may also be an unsaturated group, such as an aldehyde, ketone, ester, or conjugated ($\alpha,\beta$-unsaturated) analog thereof, which upon reaction with a nucleophile forms an adduct.

The term "leaving group" generally refers to a group that is readily displaced and substituted by a nucleophile (e.g., an amine, a thiol, an alcohol, or cyanide). Such leaving groups are well known and include carboxylates, N-hydroxysuccinimide ("NHS"), N-hydroxybenzotriazole, a halogen (fluorine, chlorine, bromine, or iodine), alkoxides, and thioalkoxides. A variety of sulfur-based leaving groups are routinely used in synthetic chemistry, including alkane sulfonyloxy groups (e.g., $C_1$-$C_4$ alkane such as methane sulfonyloxy, ethane sulfonyloxy, propane sulfonyloxy, and butane sulfonyloxy groups) and the halogenated analogs (e.g., halogeno ($C_1$-$C_4$ alkane)sulfonyloxy groups, such as trifluoromethane sulfonyloxy (i.e., triflate), 2,2,2-trichloroethane sulfonyloxy, 3,3,3-tribromopropane sulfonyloxy, and 4,4,4-trifluorobutane sulfonyloxy groups), as well as arylsulfonyloxy groups (e.g., $C_6$-$C_{10}$ aryl optionally substituted with 1 to 3 $C_1$-$C_4$ alkyl groups, such as benzene sulfonyloxy, $\alpha$-naphthylsulfonyloxy, $\beta$-naphthylsulfonyloxy, p-toluenesulfonyloxy (i.e., tosylates), 4-tert-butylbenzene sulfonyloxy, mesitylene sulfonyloxy, and 6-ethyl-$\alpha$-naphthylsulfonyloxy groups).

"Activated esters" may be represented by the formula —COL, where L is a leaving group, typical examples of which include N-hydroxysulfosuccinimidyl and N-hydroxysuccinimidyl groups; aryloxy groups substituted with electron-withdrawing groups (e.g., p-nitro, pentafluoro, pentachloro, p-cyano, or p-trifluoromethyl); and carboxylic acids activated by a carbodiimide to form an anhydride or mixed anhydride, e.g., —OCOR$^a$ or —OCNR$^a$NHR$^b$, where R$^a$ and R$^b$ are independently $C_1$-$C_6$ alkyl, $C_5$-$C_8$ alkyl (e.g., cyclohexyl), $C_1$-$C_6$ perfluoroalkyl, or $C_1$-$C_6$ alkoxy groups. An activated ester may be formed in situ or may be an isolable reagent. Sulfosuccinimidyl esters, pentafluorothiophenol esters, and sulfotetrafluorophenol are preferred activated esters. However, the ester leaving group may be, for example, substituted or unsubstituted $C_1$-$C_6$ alkyl (such as methyl, ethyl, propyl, isopropyl, butyl, isobutyl, sec-butyl, tert-butyl, pentyl, or hexyl), or substituted or unsubstituted $C_6$-$C_{14}$ aryl or heterocyclic groups, such as 2-fluoroethyl, 2-chloroethyl, 2-bromoethyl, 2,2-dibromoethyl, 2,2,2-trichloroethyl, 3-fluoropropyl, 4-chlorobutyl, methoxymethyl, 1,1-dimethyl-1-methoxymethyl, ethoxymethyl, N-propoxymethyl, isopropoxymethyl, N-butoxymethyl, tert-butoxymethyl, 1-ethoxyethyl, 1-methyl-1-methoxyethyl, 1-(isopropoxy)ethyl, 3-methoxypropyl-4-methoxybutyl, fluoromethoxymethyl, 2,2,2-trichloroethoxymethyl, bis(2-chloroethoxy)methyl, 3-fluoropropoxymethyl, 4-chlorobutoxyethyl, dibromomethoxyethyl, 2-chloroethoxypropyl, fluoromethoxybutyl, 2-methoxyethoxymethyl, ethoxymethoxyethyl, methoxyethoxypropyl, methoxyethoxybutyl, benzyl, phenethyl, 3-phenylpropyl, 4-phenylbutyl, $\alpha$-naphthylmethyl, $\beta$-naphthylmethyl, diphenylmethyl, triphenylmethyl, $\alpha$-naphthyldipheylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, or bis(2-nitrophenyl)methyl groups.

The term "electron-withdrawing group" is art-recognized and describes the ability of a substituent to attract valence electrons (e.g., pi-electrons) from neighboring atoms, e.g., the substituent is more electronegative than neighboring atoms, or it draws electrons to itself more than a hydrogen atom would at the same position. The Hammett sigma value (σ) is an accepted measure of a group's electron-donating and withdrawing ability, especially the sigma para value ($\sigma_p$). See, e.g., "Advanced Organic Chemistry" by J. March, 5$^{th}$ Ed., John Wiley & Sons, Inc., New York, pp. 368-75 (2001). The Hammett constant values are generally negative for electron-donating groups ($\sigma_p$=−0.66 for NH$_2$) and positive for electron-withdrawing groups ($\sigma_p$=0.78 for a nitro group), $\sigma_p$ indicating para substitution. Exemplary electron-withdrawing groups include nitro, acyl(ketone), formyl(aldehyde), sulfonyl, trifluoromethyl, halogeno (e.g., chloro and fluoro), and cyano groups, among others. Conversely, an "electron-donating group" designates a substituent that contributes electrons more than hydrogen would if it occupied the same position in the molecule. Examples include amino (including alkylamino and dialkylamino), aryl, alkoxy (including aralkoxy), aryloxy, mercapto and alkylthio, and hydroxyl groups, among others.

As used herein, "alkyl" groups include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). The term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups.

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more preferably 18 or fewer. Likewise, preferred cycloalkyl groups have from 4-10 carbon atoms in their ring structure, and more preferably have 4-7 carbon atoms in the ring structure. The term "lower alkyl" refers to alkyl groups having from 1 to 6 carbons in the chain, and to cycloalkyl groups having from 3 to 6 carbons in the ring structure.

Unless the number of carbons is otherwise specified, "lower" as in "lower aliphatic," "lower alkyl," "lower alkenyl," etc. as used herein means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_6$ for branched-chain), and more preferably 4 or fewer. Likewise, preferred cycloalkyl groups have from 3-8 carbon atoms in their ring structure, and more preferably have 5 or 6 carbons in the ring structure. The term "$C_1$-$C_6$" as in "$C_1$-$C_6$ alkyl" means alkyl groups containing 1 to 6 carbon atoms.

Moreover, unless otherwise specified the term alkyl includes both "unsubstituted alkyls" and "substituted alkyls," the latter of which refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, or aromatic (including heteroaromatic) groups.

An "arylalkyl" group is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight-chain (i.e., unbranched) unsubstituted alkyl group. An "alkylene" group is a divalent analog of the corresponding alkyl group. The terms "alkenyl" and "alkynyl" refer to unsaturated aliphatic groups analogous to alkyls, but which contain at least one double or triple carbon-carbon bond respectively. Suitable alkenyl and alkynyl groups include groups having 2 to about 12 carbon atoms, preferably from 2 to about 6 carbon atoms.

The term "aromatic group" or "aryl group" includes unsaturated and aromatic cyclic hydrocarbons as well as unsaturated and aromatic heterocycles containing one or more rings. Aryl groups may also be fused or bridged with alicyclic or heterocyclic rings that are not aromatic so as to form a polycycle (e.g., tetralin). An "arylene" group is a divalent analog of an aryl group. Aryl groups can also be fused or bridged with alicyclic or heterocyclic rings which are not aromatic so as to form a polycycle (e.g., tetralin).

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may have aromatic character, in which case they may be referred to as "heteroaryl" or "heteroaromatic" groups.

Unless otherwise stipulated, aryl and heterocyclic (including heteroaryl) groups may also be substituted at one or more constituent atoms. Examples of heteroaromatic and heteroalicyclic groups may have 1 to 3 separate or fused rings with 3 to about 8 members per ring and one or more N, O, or S heteroatoms. In general, the term "heteroatom" includes atoms of any element other than carbon or hydrogen, preferred examples of which include nitrogen, oxygen, sulfur, and phosphorus. Heterocyclic groups may be saturated or unsaturated or aromatic.

Examples of heterocycles include, but are not limited to, acridinyl; azocinyl; benzimidazolyl; benzofuranyl; benzothiofuranyl; benzothiophenyl; benzoxazolyl; benzthiazolyl; benztriazolyl; benztetrazolyl; benzisoxazolyl; benzisothiazolyl; benzimidazolinyl; carbazolyl; 4aH-carbazolyl; carbolinyl; chromanyl; chromenyl; cinnolinyl; decahydroquinolinyl; 2H,6H-1,5,2-dithiazinyl; dihydrofuro[2,3-b]tetrahydrofuran; furanyl; furazanyl; imidazolidinyl; imidazolinyl; imidazolyl; 1H-indazolyl; indolenyl; indolinyl; indolizinyl; indolyl; 3H-indolyl; isobenzofuranyl; isochromanyl; isoindazolyl; isoindolinyl; isoindolyl; isoquinolinyl; isothiazolyl; isoxazolyl; methylenedioxyphenyl; morpholinyl; naphthyridinyl; octahydroisoquinolinyl; oxadiazolyl; 1,2,3-oxadiazolyl; 1,2,4-oxadiazolyl; 1,2,5-oxadiazolyl; 1,3,4-oxadiazolyl; oxazolidinyl; oxazolyl; oxazolidinyl; pyrimidinyl; phenanthridinyl; phenanthrolinyl; phenazinyl; phenothiazinyl; phenoxathiinyl; phenoxazinyl; phthalazinyl; piperazinyl; piperidinyl; piperidonyl; 4-piperidonyl; piperonyl; pteridinyl; purinyl; pyranyl; pyrazinyl; pyrazolidinyl;

pyrazolinyl; pyrazolyl; pyridazinyl; pyridooxazole; pyridoimidazole; pyridothiazole; pyridinyl; pyridyl; pyrimidinyl; pyrrolidinyl; pyrrolinyl; 2H-pyrrolyl; pyrrolyl; quinazolinyl; quinolinyl; 4H-quinolizinyl; quinoxalinyl; quinuclidinyl; tetrahydrofuranyl; tetrahydroisoquinolinyl; tetrahydroquinolinyl; tetrazolyl; 6H-1,2,5-thiadiazinyl; 1,2,3-thiadiazolyl; 1,2,4-thiadiazolyl; 1,2,5-thiadiazolyl; 1,3,4-thiadiazolyl; thianthrenyl; thiazolyl; thienyl; thienothiazolyl; thienooxazolyl; thienoimidazolyl; thiophenyl; triazinyl; 1,2,3-triazolyl; 1,2,4-triazolyl; 1,2,5-triazolyl; 1,3,4-triazolyl; and xanthenyl. Preferred heterocycles include, but are not limited to, pyridinyl; furanyl; thienyl; pyrrolyl; pyrazolyl; pyrrolidinyl; imidazolyl; indolyl; benzimidazolyl; 1H-indazolyl; oxazolidinyl; benzotriazolyl; benzisoxazolyl; oxindolyl; benzoxazolinyl; and isatinoyl groups. Also included are fused ring and spiro compounds containing, for example, the above heterocycles.

A common hydrocarbon aryl group is a phenyl group having one ring. Two-ring hydrocarbon aryl groups include naphthyl, indenyl, benzocyclooctenyl, benzocycloheptenyl, pentalenyl, and azulenyl groups, as well as the partially hydrogenated analogs thereof such as indanyl and tetrahydronaphthyl. Exemplary three-ring hydrocarbon aryl groups include acephthylenyl, fluorenyl, phenalenyl, phenanthrenyl, and anthracenyl groups.

Aryl groups also include heteromonocyclic aryl groups, i.e., single-ring heteroaryl groups, such as thienyl, furyl, pyranyl, pyrrolyl, imidazolyl, pyrazolyl, pyridinyl, pyrazinyl, pyrimidinyl, and pyridazinyl groups; and oxidized analogs thereof such as pyridonyl, oxazolonyl, pyrazolonyl, isoxazolonyl, and thiazolonyl groups. The corresponding hydrogenated (i.e., non-aromatic) heteromonocylic groups include pyrrolidinyl, pyrrolinyl, imidazolidinyl, imidazolinyl, pyrazolidinyl, pyrazolinyl, piperidyl and piperidino, piperazinyl, and morpholino and morpholinyl groups.

Aryl groups also include fused two-ring heteroaryls such as indolyl, isoindolyl, indolizinyl, indazolyl, quinolinyl, isoquinolinyl, phthalazinyl, quinoxalinyl, quinazolinyl, cinnolinyl, chromenyl, isochromenyl, benzothienyl, benzimidazolyl, benzothiazolyl, purinyl, quinolizinyl, isoquinolonyl, quinolonyl, naphthyridinyl, and pteridinyl groups, as well as the partially hydrogenated analogs such as chromanyl, isochromanyl, indolinyl, isoindolinyl, and tetrahydroindolyl groups. Aryl groups also include fused three-ring groups such as phenoxathiinyl, carbazolyl, phenanthridinyl, acridinyl, perimidinyl, phenanthrolinyl, phenazinyl, phenothiazinyl, phenoxazinyl, and dibenzofuranyl groups.

Some typical aryl groups include substituted or unsubstituted 5- and 6-membered single-ring groups. In another aspect, each Ar group may be selected from the group consisting of substituted or unsubstituted phenyl, pyrrolyl, furyl, thienyl, thiazolyl, isothiaozolyl, imidazolyl, triazolyl, tetrazolyl, pyrazolyl, oxazolyl, isooxazolyl, pyridinyl, pyrazinyl, pyridazinyl, and pyrimidinyl groups. Further examples include substituted or unsubstituted phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl groups.

The term "amine" or "amino," as used herein, refers to an unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated. Thus, the term "alkylamino" as used herein means an alkyl group having an amino group attached thereto. Suitable alkylamino groups include groups having 1 to about 12 carbon atoms, preferably from 1 to about 6 carbon atoms. The term amino includes compounds or moieties in which a nitrogen atom is covalently bonded to at least one carbon or heteroatom. The term "dialkylamino" includes groups wherein the nitrogen atom is bound to at least two alkyl groups. The term "arylamino" and "diarylamino" include groups wherein the nitrogen is bound to at least one or two aryl groups, respectively. The term "alkylarylamino" refers to an amino group which is bound to at least one alkyl group and at least one aryl group. The term "alkaminoalkyl" refers to an alkyl, alkenyl, or alkynyl group substituted with an alkylamino group. The term "amide" or "aminocarbonyl" includes compounds or moieties which contain a nitrogen atom which is bound to the carbon of a carbonyl or a thiocarbonyl group.

The term "alkylthio" refers to an alkyl group, having a sulfhydryl group attached thereto. Suitable alkylthio groups include groups having 1 to about 12 carbon atoms, preferably from 1 to about 6 carbon atoms.

The term "alkylcarboxyl" as used herein means an alkyl group having a carboxyl group attached thereto.

The term "alkoxy" as used herein means an alkyl group having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. Examples of alkoxy groups include-methoxy, ethoxy, isopropyloxy, propoxy, butoxy, and pentoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc., as well as perhalogenated alkyloxy groups.

The term "acylamino" includes moieties wherein an amino moiety is bonded to an acyl group. For example, the acylamino group includes alkylcarbonylamino, arylcarbonylamino, carbamoyl and ureido groups.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "ether" or "ethereal" includes compounds or moieties which contain an oxygen bonded to two carbon atoms. For example, an ether or ethereal group includes "alkoxyalkyl" which refers to an alkyl, alkenyl, or alkynyl group substituted with an alkoxy group.

A "sulfonate" group is a —$SO_3H$ or —$SO_3^-X^+$ group bonded to a carbon atom, where $X^+$ is a cationic counter ion group. Similarly, a "sulfonic acid" compound has a —$SO_3H$ or —$SO_3^-X^+$ group bonded to a carbon atom, where $X^+$ is a cationic group. A "sulfate" as used herein is a —$OSO_3H$ or —$OSO_3^-X^+$ group bonded to a carbon atom, and a "sulfuric acid" compound has a —$SO_3H$ or —$OSO_3^-X^+$ group bonded to a carbon atom, where $X^+$ is a cationic group. According to the invention, a suitable cationic group may be a hydrogen atom. In certain cases, the cationic group may actually be another group on the therapeutic compound that is positively charged at physiological pH, for example an amino group.

A "counter ion" is required to maintain electroneutrality. Examples of anionic counter ions include halide, triflate, sulfate, nitrate, hydroxide, carbonate, bicarbonate, acetate, phosphate, oxalate, cyanide, alkylcarboxylate, N-hydroxysuccinimide, N-hydroxybenzotriazole, alkoxide, thioalkoxide, alkane sulfonyloxy, halogenated alkane sulfonyloxy, arylsulfonyloxy, bisulfate, oxalate, valerate, oleate, palmitate, stearate, laurate, borate, benzoate, lactate, citrate, maleate, fumarate, succinate, tartrate, naphthylate mesylate, glucoheptonate, or lactobionate. Compounds containing a cationic group covalently bonded to an anionic group may be referred to as an "internal salt."

The term "nitro" means —$NO_2$; the term "halogen" or "halogeno" or "halo" designates —F, —Cl, —Br or —I; the term "thiol," "thio," or "mercapto" means SH; and the term "hydroxyl" or "hydroxy" means —OH.

The term "acyl" refers to a carbonyl group that is attached through its carbon atom to a hydrogen (i.e., a formyl), an aliphatic group (e.g., acetyl), an aromatic group (e.g., benzoyl), and the like. The term "substituted acyl" includes acyl groups where one or more of the hydrogen atoms on one or more carbon atoms are replaced by, for example, an alkyl group, alkynyl group, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless otherwise specified, the chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen), which allow the molecule to perform its intended function. Examples of substituents include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, and heteroaryl groups, as well as $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$ (substituted or unsubstituted phenyl), $(CR'R'')_{0-3}$ ($C_3$-$C_8$ cycloalkyl), $(CR'R'')_{0-3}CO_2R'$ (e.g., —$CO_2H$), and $(CR'R'')_{0-3}OR'$ groups, wherein R' and R" are each independently hydrogen, a $C_1$-$C_5$ alkyl, $C_2$-$C_5$ alkenyl, $C_2$-$C_5$ alkynyl, or aryl group; or the side chain of any naturally occurring amino acid.

In another embodiment, a substituent may be selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-10}NR'R''$ (e.g., —$NH_2$), $(CR'R'')_{0-10}CN$ (e.g., —CN), $NO_2$, halogen (e.g., F, Cl, Br, or I), $(CR'R'')_{0-10}C(halogen)_3$ (e.g., —$CF_3$), $(CR'R'')_{0-10}CH(halogen)_2$, $(CR'R'')_{0-10}CH_2(halogen)$, $(CR'R'')_{0-10}CONR'R''$, $(CR'R'')_{0-10}(CNH)NR'R''$, $(CR'R'')_{0-10}S(O)_{1-2}NR'R''$, $(CR'R'')_{0-10}CHO$, $(CR'R'')_{0-10}O(CR'R'')_{0-10}H$, $(CR'R'')_{0-10}S(O)_{0-3}R'$ (e.g., —$SO_3H$), $(CR'R'')_{0-10}O(CR'R'')_{0-10}H$ (e.g., —$CH_2OCH_3$ and —$OCH_3$), $(CR'R'')_{0-10}S(CR'R'')_{0-3}H$ (e.g., —SH and —$SCH_3$), $(CR'R'')_{0-10}OH$ (e.g., —OH), $(CR'R'')_{0-10}COR'$, $(CR'R'')_{0-10}$ (substituted or unsubstituted phenyl), $(CR'R'')_{0-10}(C_3$-$C_8$ cycloalkyl), $(CR'R'')_{0-10}CO_2R'$ (e.g., —$CO_2H$), or $(CR'R'')_{0-10}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more.

In some embodiments, a "substituent" may be selected from the group consisting of, for example, halogeno, trifluoromethyl, nitro, cyano, $C_1$-$C_6$ alkyl, $C_2$-$C_6$ alkenyl, $C_2$-$C_6$ alkynyl, $C_1$-$C_6$ alkylcarbonyloxy, arylcarbonyloxy, $C_1$-$C_6$ alkoxycarbonyloxy, aryloxycarbonyloxy, $C_1$-$C_6$ alkylcarbonyl, $C_1$-$C_6$ alkoxycarbonyl, $C_1$-$C_6$ alkoxy, $C_1$-$C_6$ alkylthio, arylthio, heterocyclyl, aralkyl, and aryl (including heteroaryl) groups.

In one embodiment, the invention pertains to compounds of Formula I:

(I)

wherein:

R$^1$ is a substituted or unsubstituted cycloalkyl, heterocyclic, aryl, arylcycloalkyl, bicyclic or tricyclic ring, a bicyclic or tricyclic fused ring group, or a substituted or unsubstituted C$_2$-C$_{10}$ alkyl group;

R$^2$ is selected from a group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

Y is SO$_3^-$X$^+$, OSO$_3^-$X$^+$, or SSO$_3^-$X$^+$;

X$^+$ is hydrogen, a cationic group, or ester-forming group; and each of L$^1$ and L$^2$ is independently a substituted or unsubstituted C$_1$-C$_5$ alkyl group or absent, or a pharmaceutically acceptable salt thereof, provided that when R$_1$ is alkyl, L$^1$ is absent.

In a further embodiment, the invention pertains to compounds of Formula II:

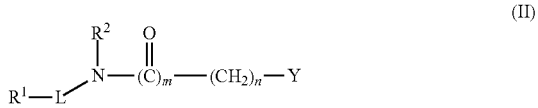

(II)

wherein:

R$^1$ is a substituted or unsubstituted cyclic, bicyclic, tricyclic, or benzoheterocyclic group or a substituted or unsubstituted C$_2$-C$_{10}$ alkyl group;

R$^2$ is hydrogen, alkyl, mercaptoalkyl, alkenyl, alkynyl, cycloalkyl, aryl, arylalkyl, thiazolyl, triazolyl, imidazolyl, benzothiazolyl, benzoimidazolyl, or linked to R$^1$ to form a heterocycle;

Y is SO$_3^-$X$^+$, OSO$_3^-$X$^+$, or SSO$_3^-$X$^+$;

X$^+$ is hydrogen, a cationic group, or an ester forming moiety;

m is 0 or 1;

n is 1, 2, 3, or 4;

L is substituted or unsubstituted C$_1$-C$_3$ alkyl group or absent, or a pharmaceutically acceptable salt thereof, provided that when R$^1$ is alkyl, L is absent.

In a further embodiment, R$^2$ is hydrogen. In another further embodiment, R$^1$ is straight chain alkyl, for example, ethyl, n-pentyl, n-heptyl, or n-octyl. In another embodiment, R$^1$ is t-butyl. In yet another alternate embodiment, R$^1$ is C$_7$-C$_{10}$ bicycloalkyl or tricycloalkyl, such as, for example, tricyclo[3.3.1.0$^{3,7}$]decyl (or adamantyl), bicyclo[2.1.2]heptyl, or indolyl. In another alternate embodiment, R$^1$ is tetrahydronaphthyl.

In one embodiment, L$^2$ is —(CH$_2$)$_3$—. In another further embodiment, L$^2$ is —(CH$_2$)$_4$— or —(CH$_2$)$_5$—. In yet another further embodiment, L$_2$ is —(CH$_2$)$_2$—. In yet another further embodiment, L$^2$ is substituted alkyl, e.g., —CH$_2$—(CHOH)—CH$_2$—.

In another embodiment, L$^1$ is CH$_2$CH$_2$ or absent.

In a further embodiment, R$^1$ is branched alkyl, e.g., t-butyl. In another embodiment, R$^1$ is adamanyl. In another embodiment, R$^1$ is cyclic alkyl, e.g., cyclopropyl, cyclohexyl, cycloheptyl, cyclo-octyl, etc. The cycloalkyl moieties may be substituted further, e.g., with additional alkyl groups or other groups which allow the molecule to perform its intended function. In another embodiment, R$^1$ is alkyl substituted with a propargyl moiety (e.g., HC≡C—). In another embodiment, R$^1$ is cyclohexyl substituted with one or more methyl or propargyl groups.

In other embodiments, L$^1$ is a C$_1$-C$_2$ alkyl linker group (e.g., —CH(CH$_3$)— or —(CH$_2$)$_2$—. In a further embodiment, R$^1$ is phenyl. In certain embodiments, R$^1$ is substituted with a methoxy group. In other embodiments, L$^1$ is C$_3$, e.g., —(CH$_2$)$_3$— or C(CH$_3$)$_2$—. In certain embodiments, L$^1$ is substituted, e.g., with an alkoxy, carboxylate (—COOH), benzyl, amido (—C=O—NH—), or ester (C=O—C—O) group. In certain embodiment, the ester group is a methyl, ethyl, propyl, butyl, cyclohexyl, or benzyl ester. In other embodiments, the ester group may be propenyl. In other embodiments, L$^1$ is substituted with a carboxylate group. In a further embodiment, R$^1$ is substituted with a subsituted amido group, wherein the amido group is substituted with an alkyl, e.g., methyl, ethyl, propyl, butyl, pentyl, or hexyl group. In another embodiment, the alkyl R$^1$ group is a substituted with a —C=O—NH—OH, C=O—NH$_2$, or an amido group. In certain embodiments, the amido group is substituted with an alkyl (e.g., methyl, ethyl, propyl, butyl, pentyl, hexyl, cyclohexyl, etc.), a benzyl or an aryl group. In another embodiment, the amido group is substituted with a —CH(CH$_2$)$_2$ group. R$^1$ itself may be substituted with a phenyl or may be branched or straight chain alkyl. In certain embodiments, R$^1$ may also be substituted with a thioether moiety. Examples of thioethers include S-Me, S-Et, etc. In certain embodiments, the alkyl R$^1$ moiety is substituted with both an aryl or a thioether moiety and an amido moiety. In other embodiments, the alkyl R$^1$ moiety may be substituted with both a thioether and a carboxylate moiety. In other embodiments, alkyl R$^1$ groups are substituted with hydroxyl. R$^1$ groups, e.g., alkyl R$^1$ groups, may also be substituted with both thioether and hydroxyl groups. In other embodiments, R$^1$ groups, e.g., alkyl R$^1$ groups are substituted with cyano groups. Examples of R$^1$ groups including —CN moieties include —C(CH$_3$)$_2$CN, cyclohexyl substituted with one or more cyano groups, etc.

In other embodiments, alkyl R$^1$ groups are substituted with aryl groups. The aryl groups may be substituted phenyl, for example. The substituted phenyl may be substituted with one or more substituents such as hydroxy, cyano and alkoxy. In other embodiments, alkyl R$^1$ groups are substituted with tetrazolyl or substituted or unsubstituted benzyl.

In a further embodiment, L$^1$ is —C(CH$_3$)$_2$—(CH$_2$)—. In another embodiment, L$^1$ is —(C(CH$_3$)$_2$—CHOH—. In yet another embodiment, L$^1$ is —(C(CH$_3$)$_2$CH(OMe)—. In another embodiment, R$^1$ is substituted or unsubstituted phenyl. In a further embodiment, R$^1$ is para-substituted phenyl. Examples of substitutuents include but are not limited to fluorine, chlorine, bromine, iodine, methyl, t-butyl, alkoxy, methoxy, etc. In other embodiment, R$^1$ is substituted at the meta position. Examples of substituents include methoxy, chloro, methyl, t-butyl, fluoro, alkyl, alkoxy, iodo, trifluoroalkyl, methoxy, etc. In another embodiment, R$^1$ is phenyl substituted in the ortho position, with similar substituents. In another embodiment, L$^1$ comprises a cycloalkyl moiety, e.g., cyclopentyl. In another embodiment, L$^1$ comprises an alkyenyl group and, optionally, a substituted aryl group, with substittuents similar to those described about.

In certain embodiments, R$^1$ is cyclopropyl or cyclohexyl. In certain embodiments, the cyclopropyl or cyclohexyl group is subsituted with an ether group or an alkyl group. In certain further embodiments, the ether group is a benzyl ether group.

In another embodiment, wherein R$^1$ is alkyl, it is substituted with groups such as phenyl, or hydroxy.

In other embodiments, the compound of the invention is selected from the group consisting of:
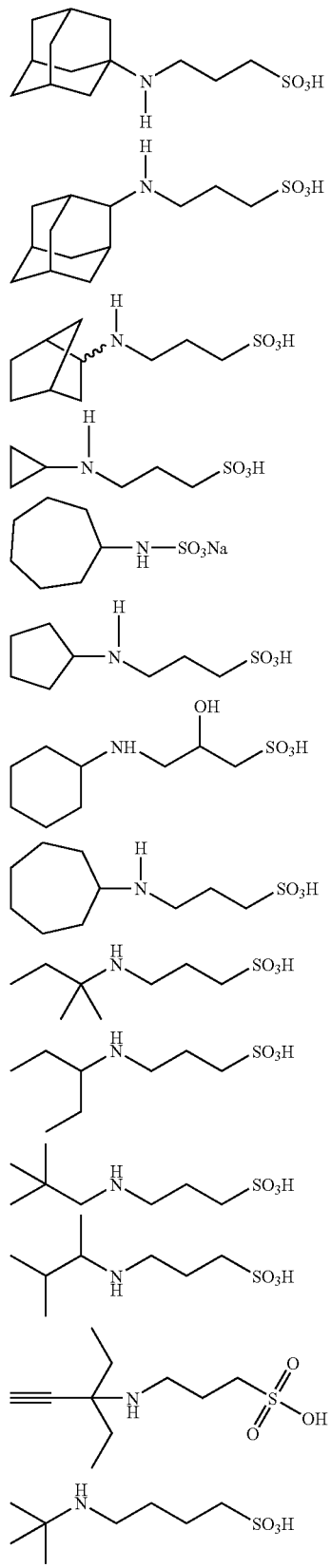
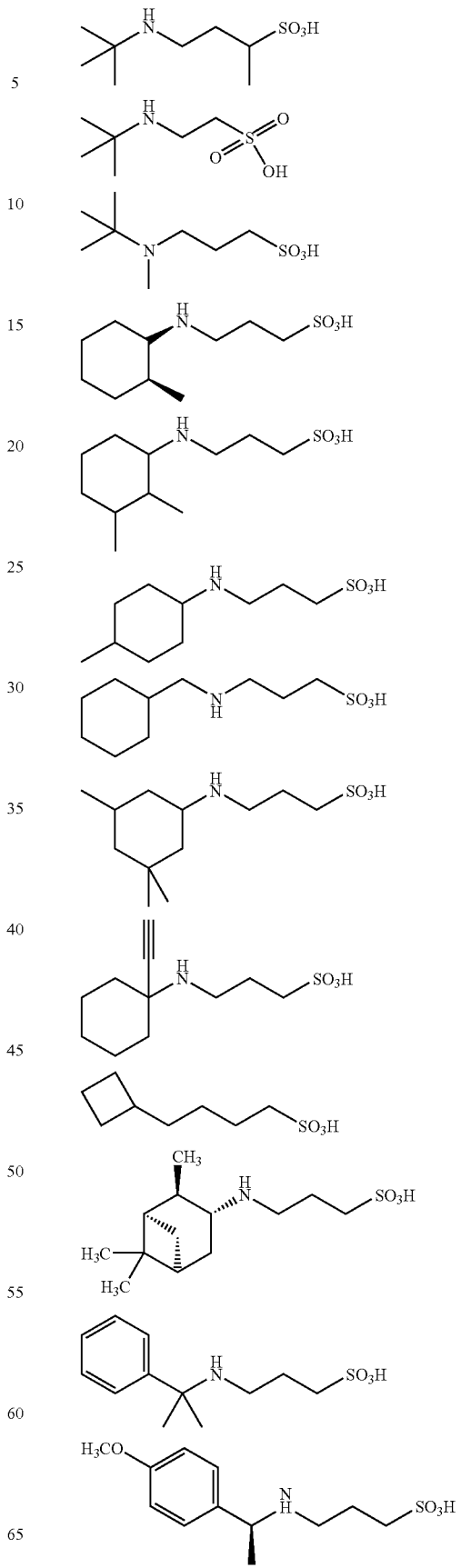

37
-continued
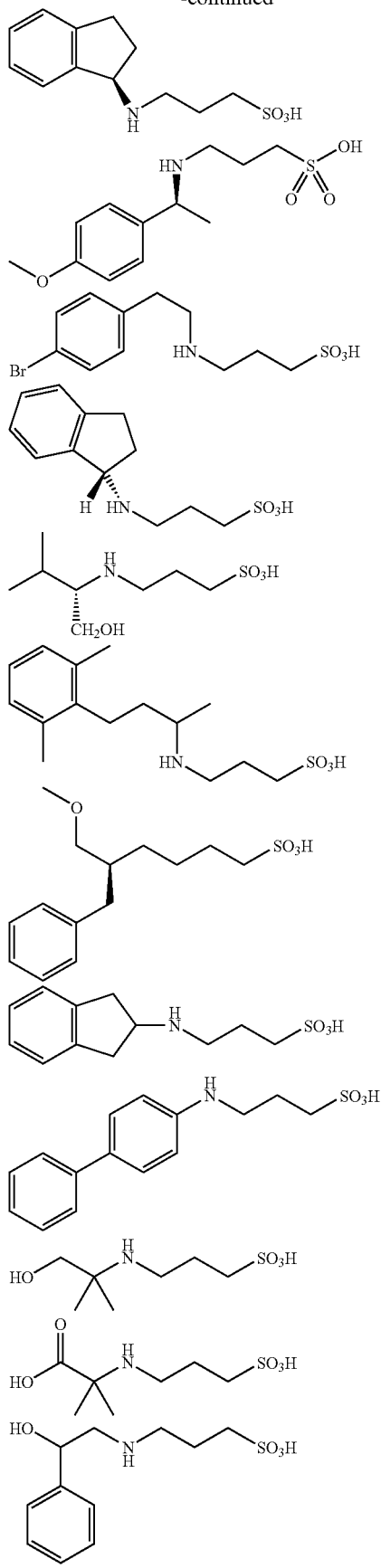
38
-continued
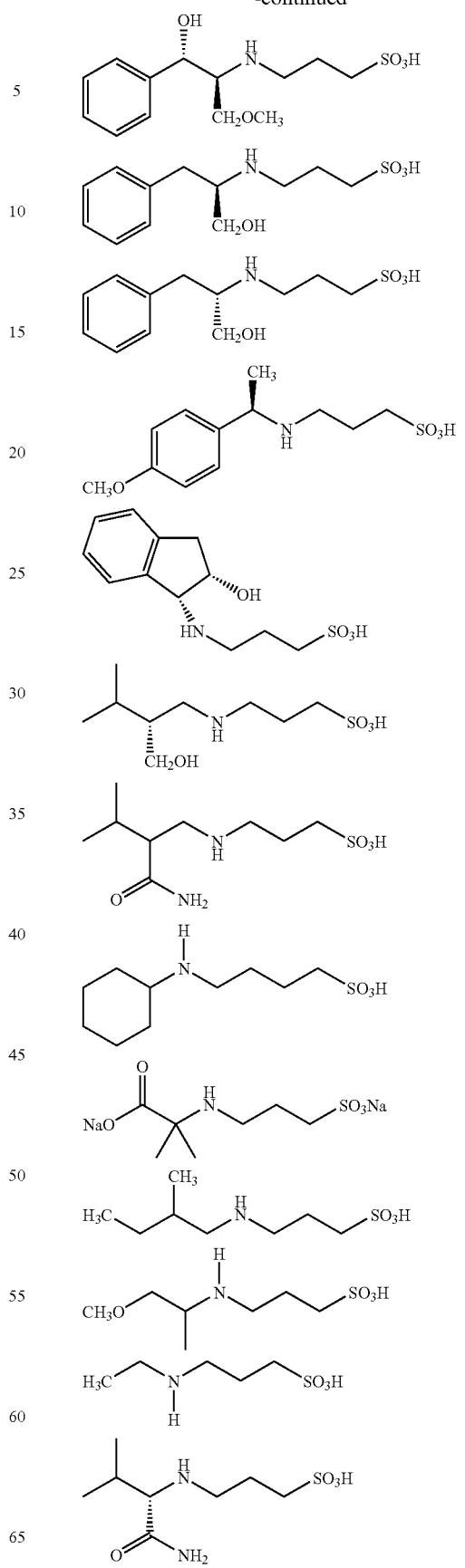

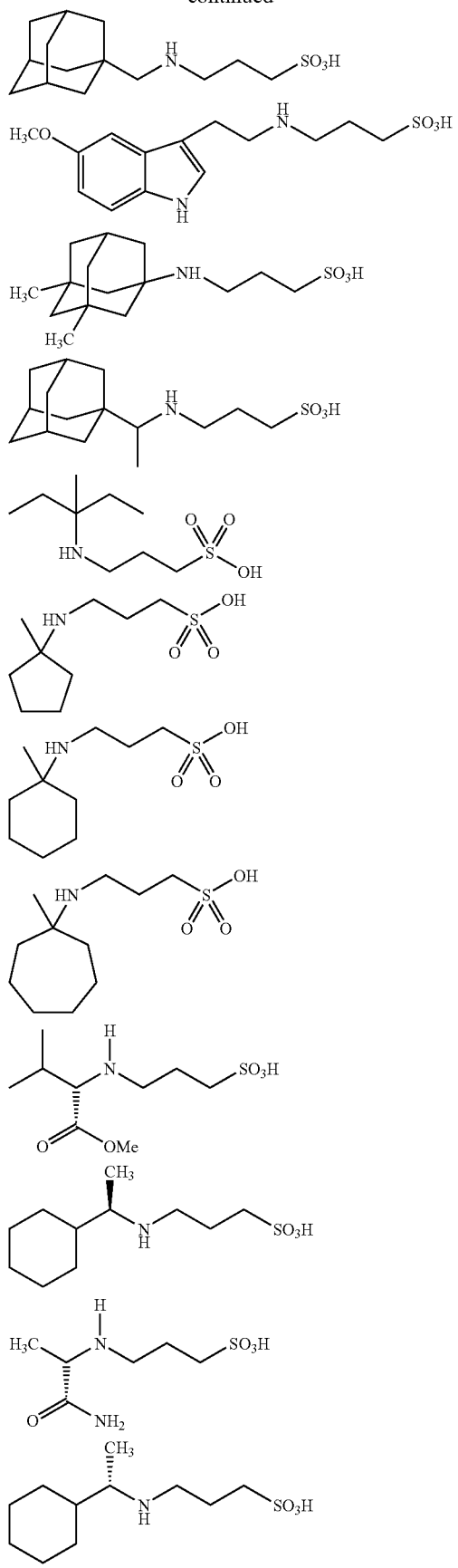
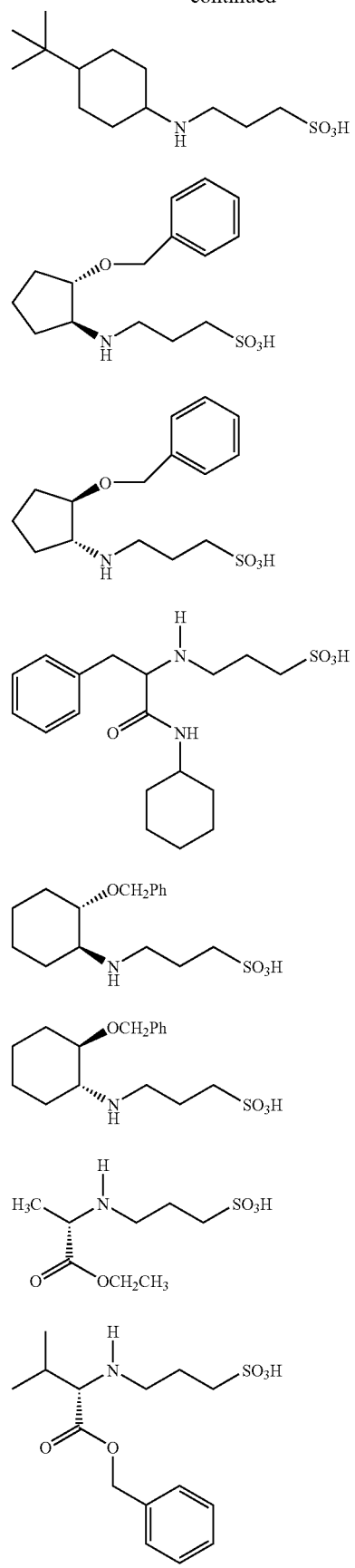

41
-continued
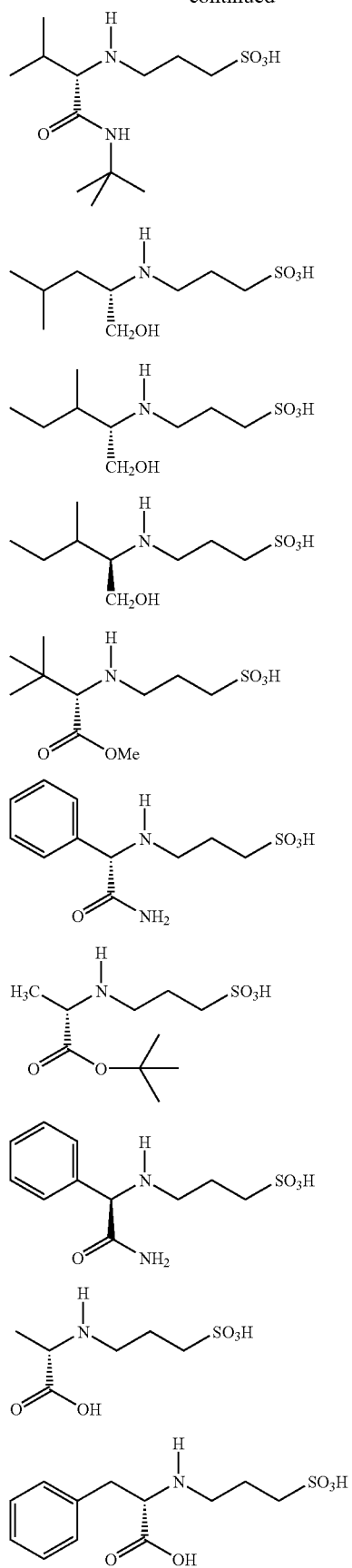
42
-continued
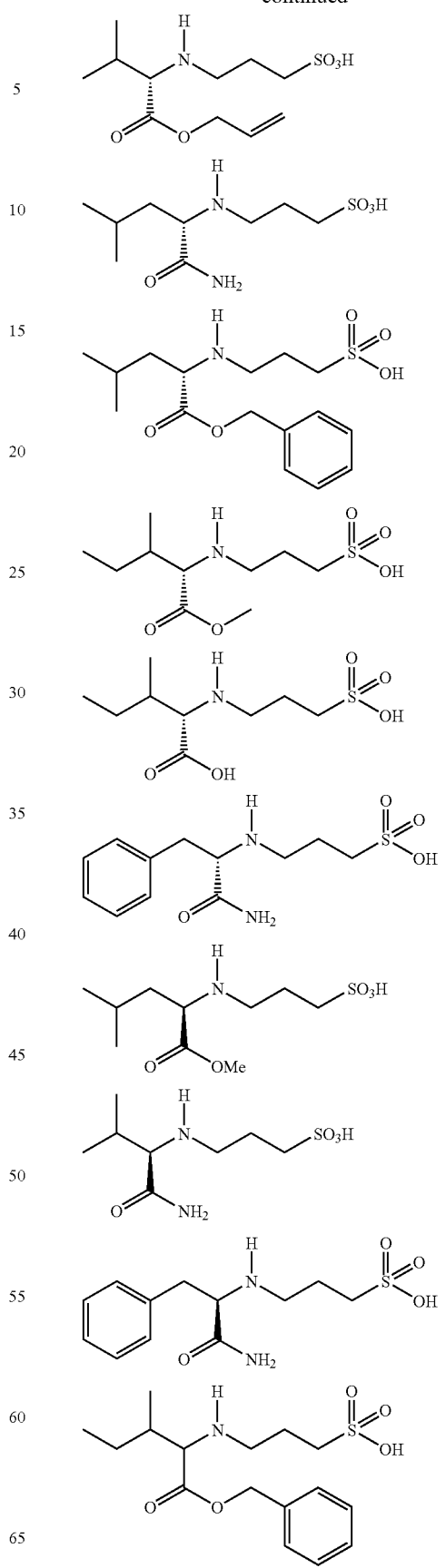

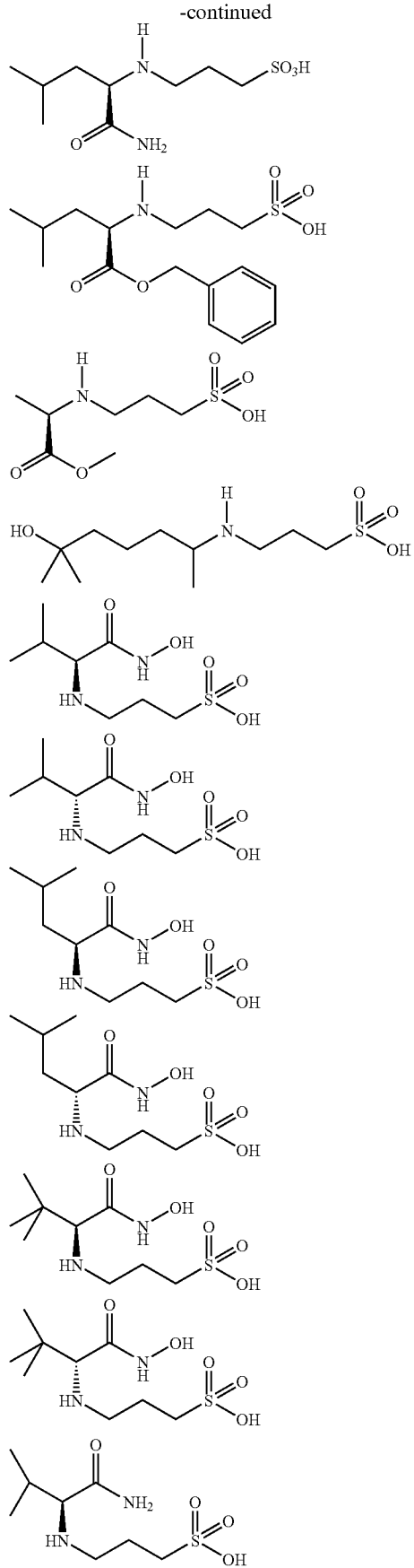
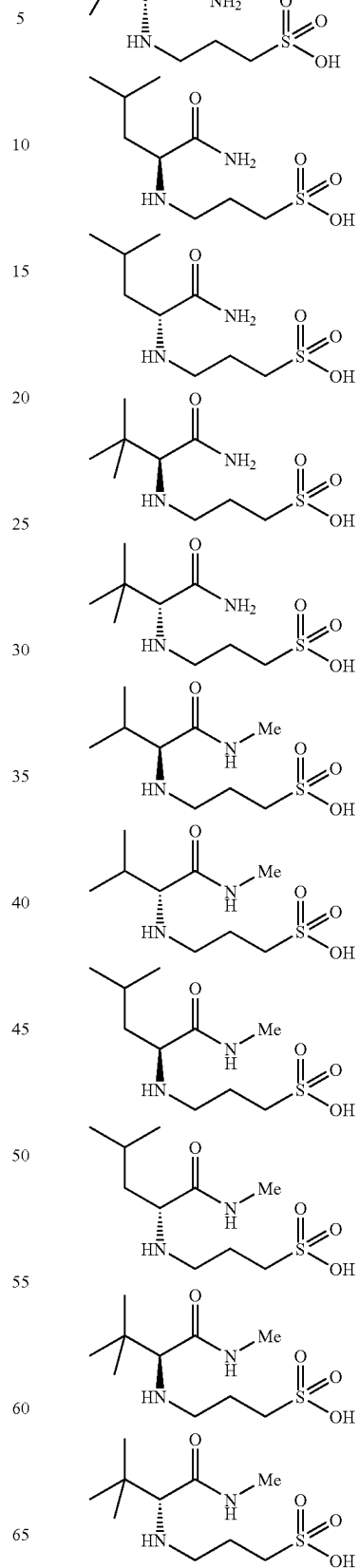

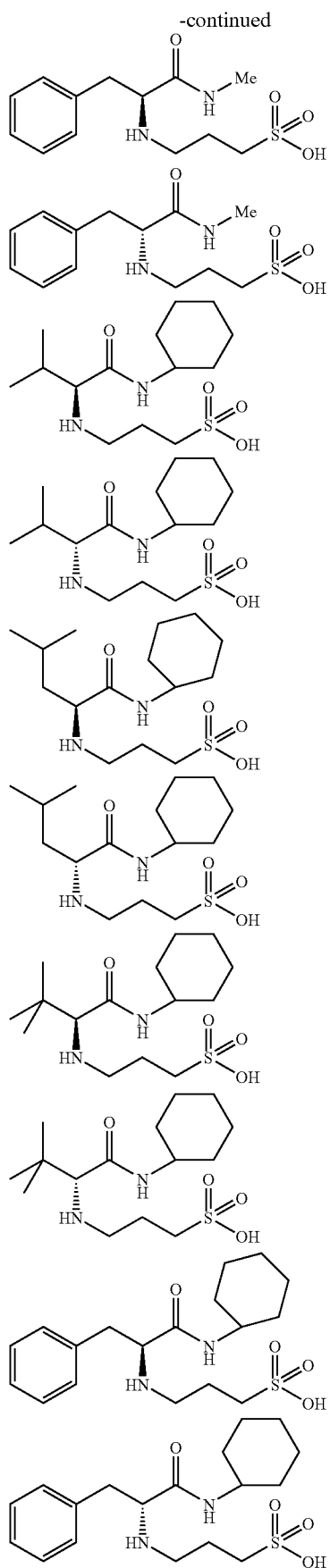
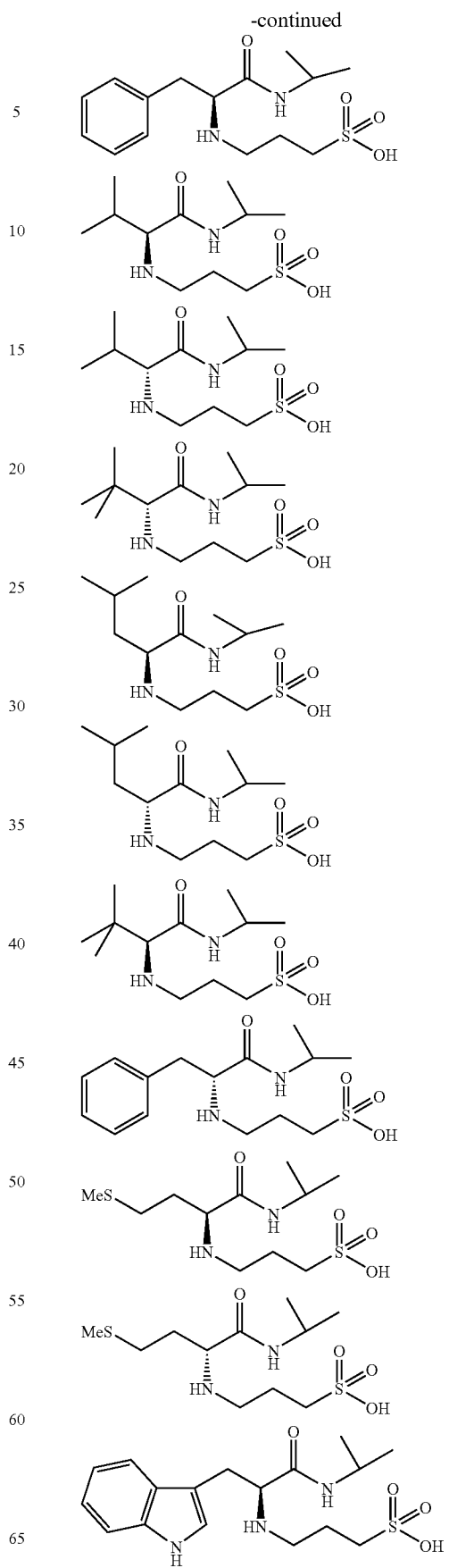

47
-continued
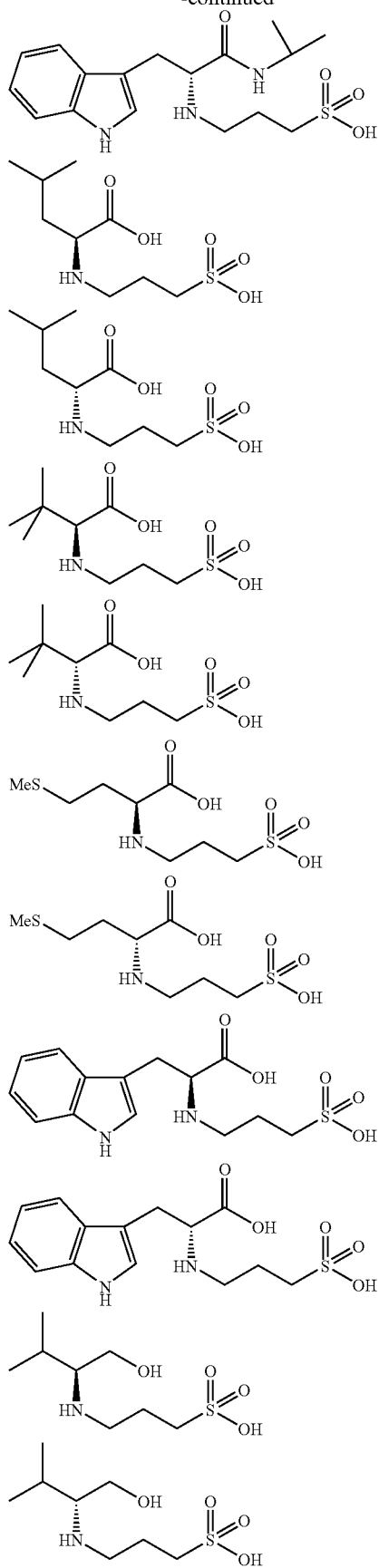
48
-continued
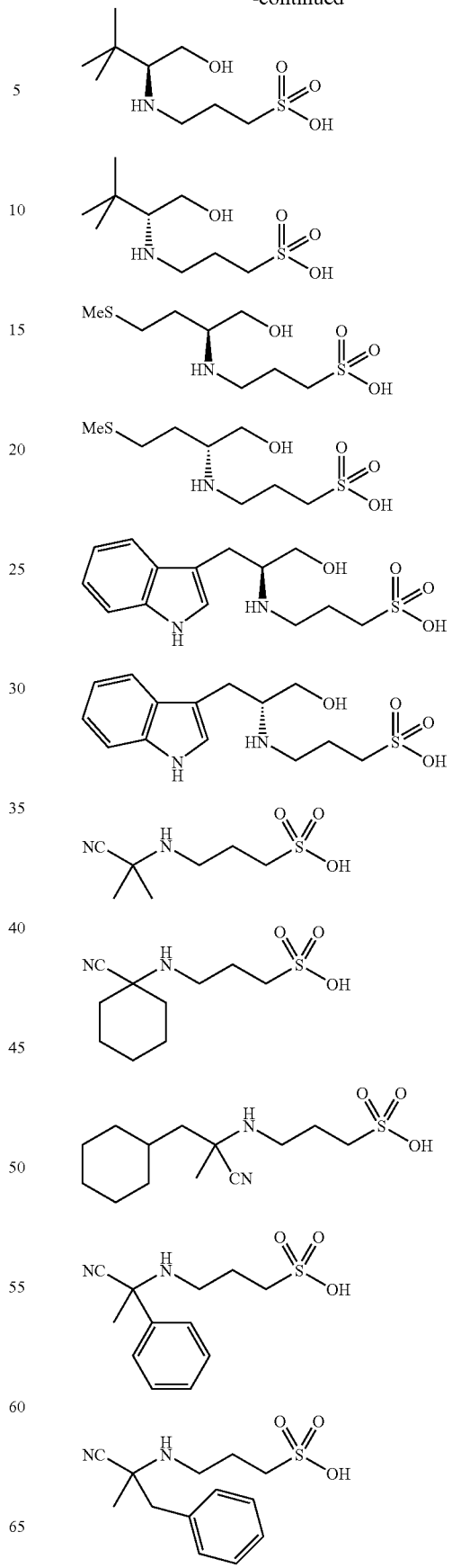

-continued
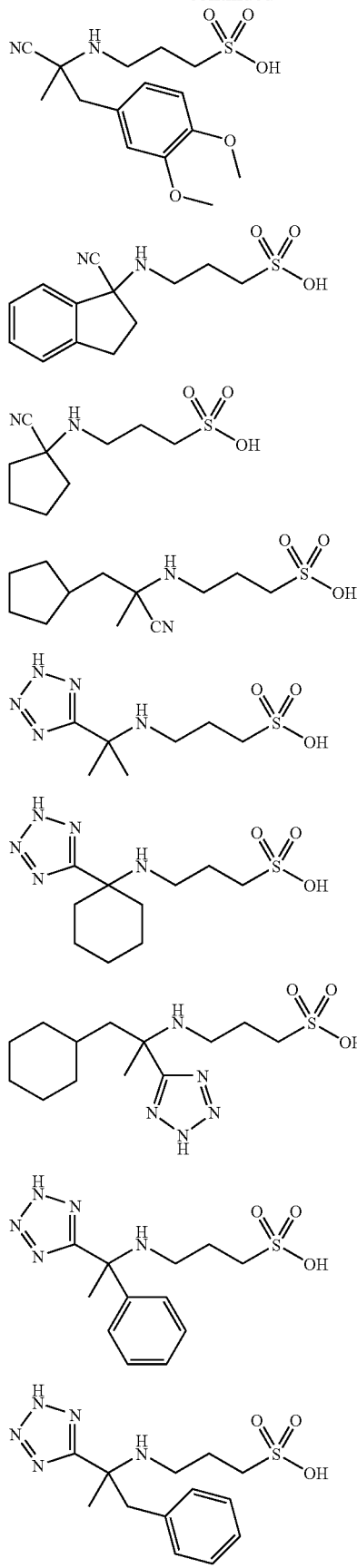
-continued
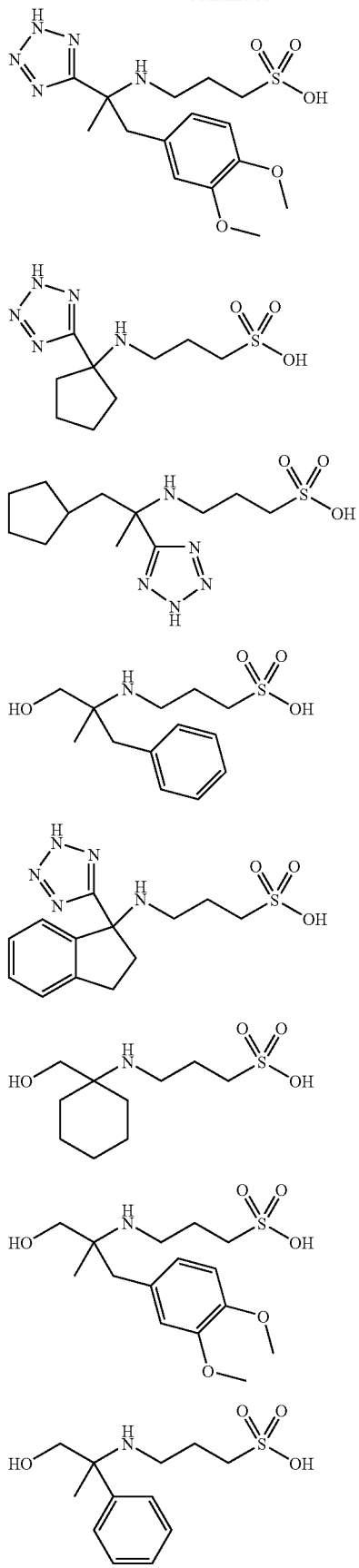

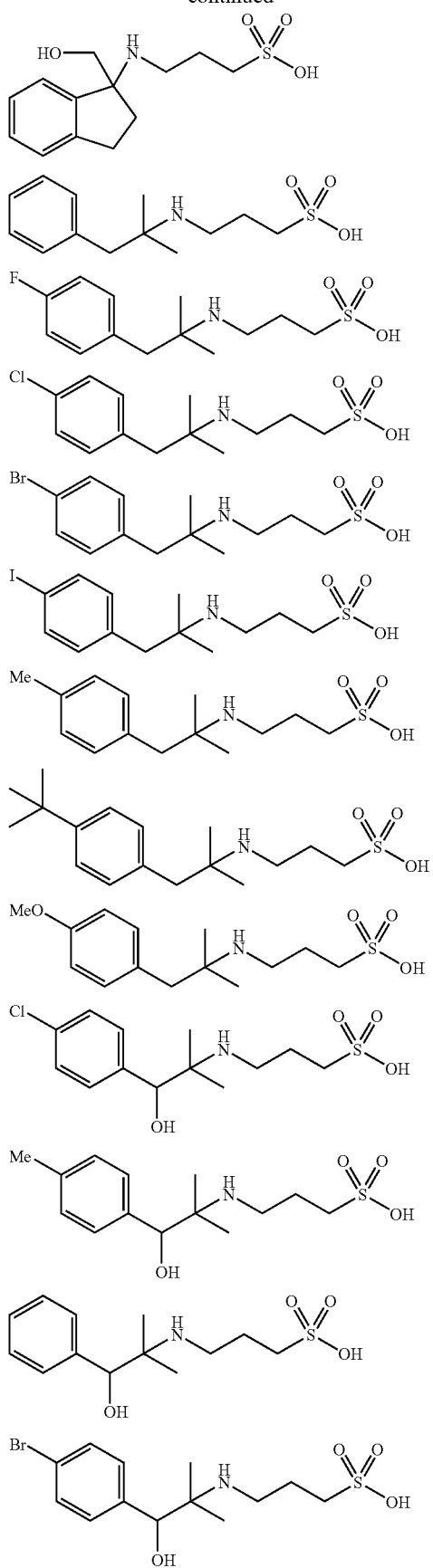
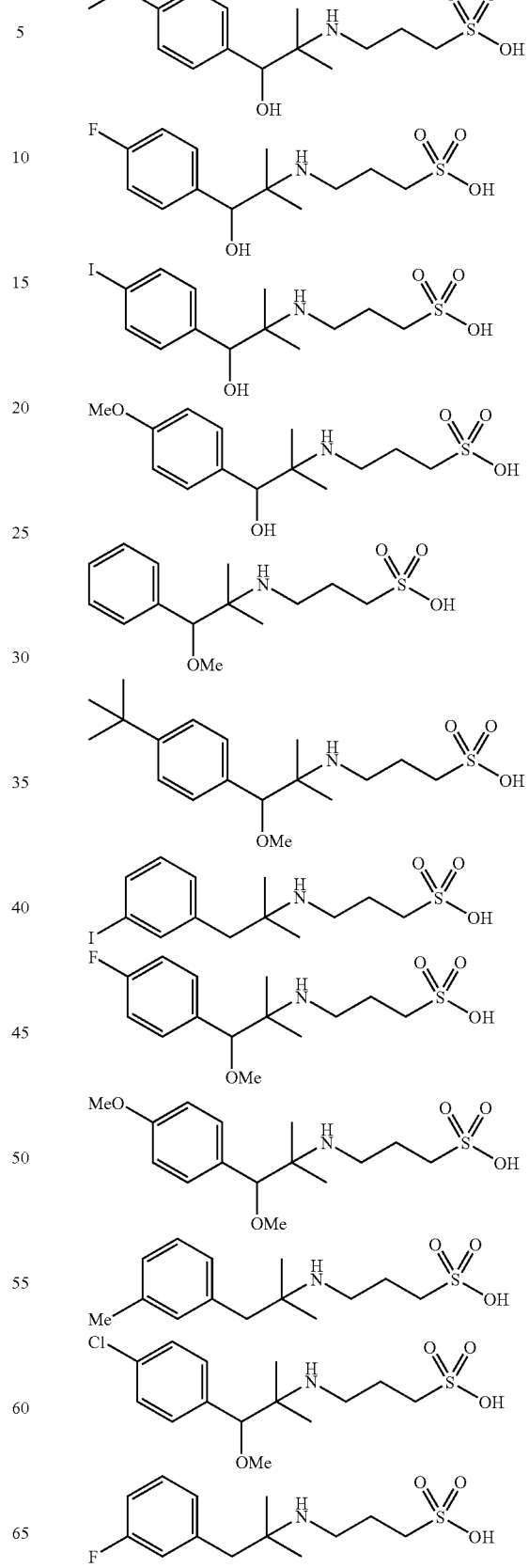

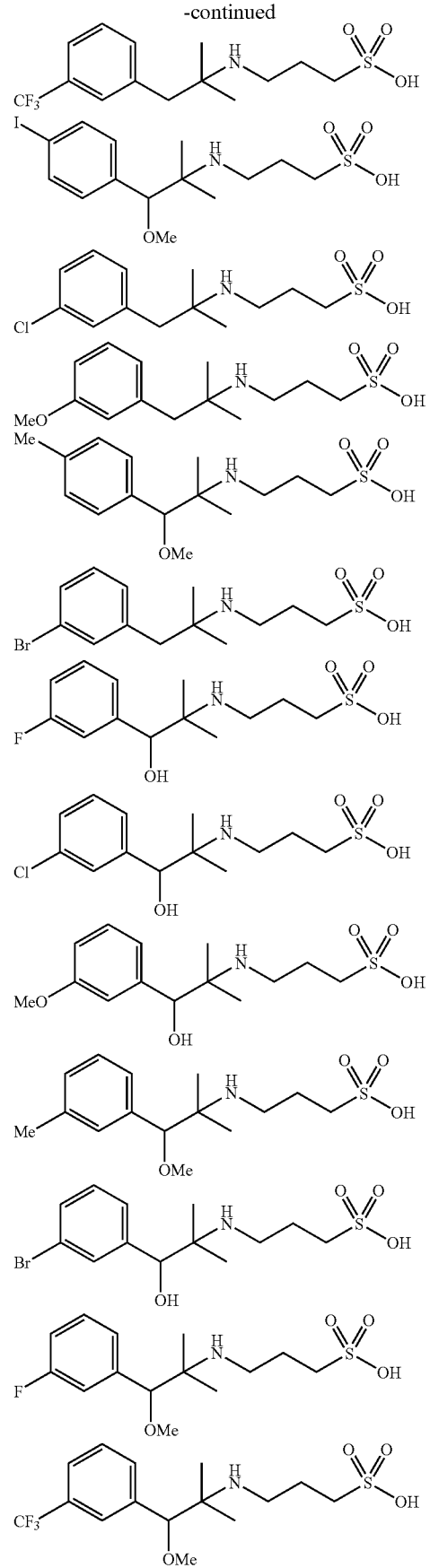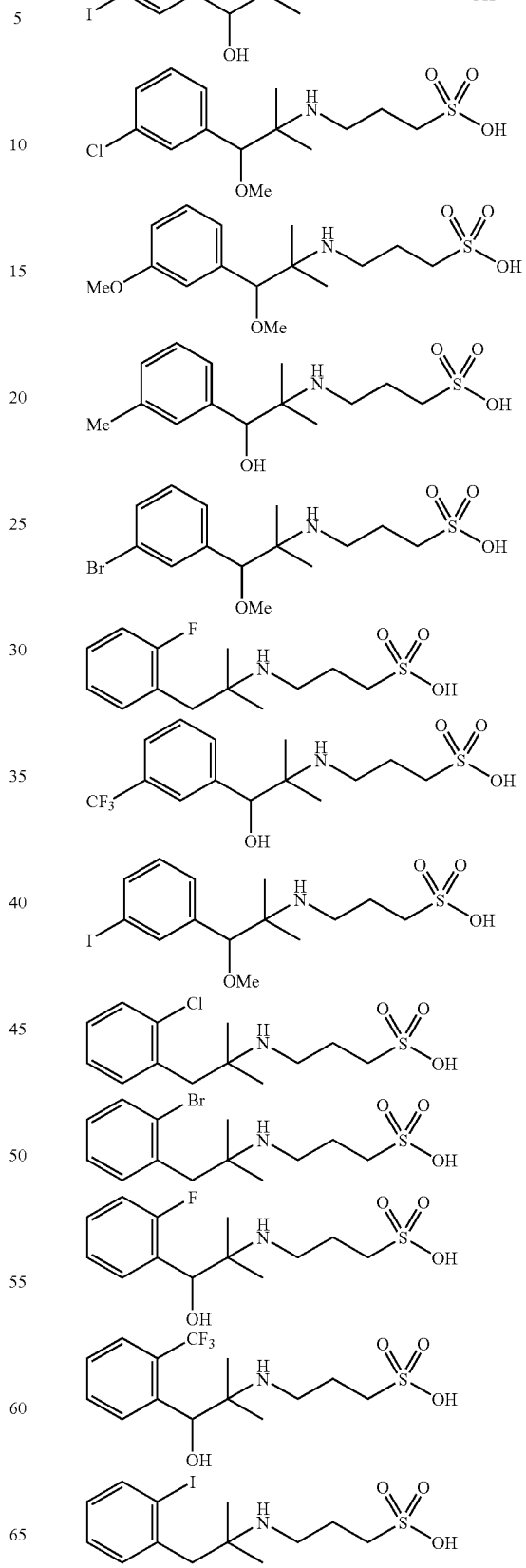

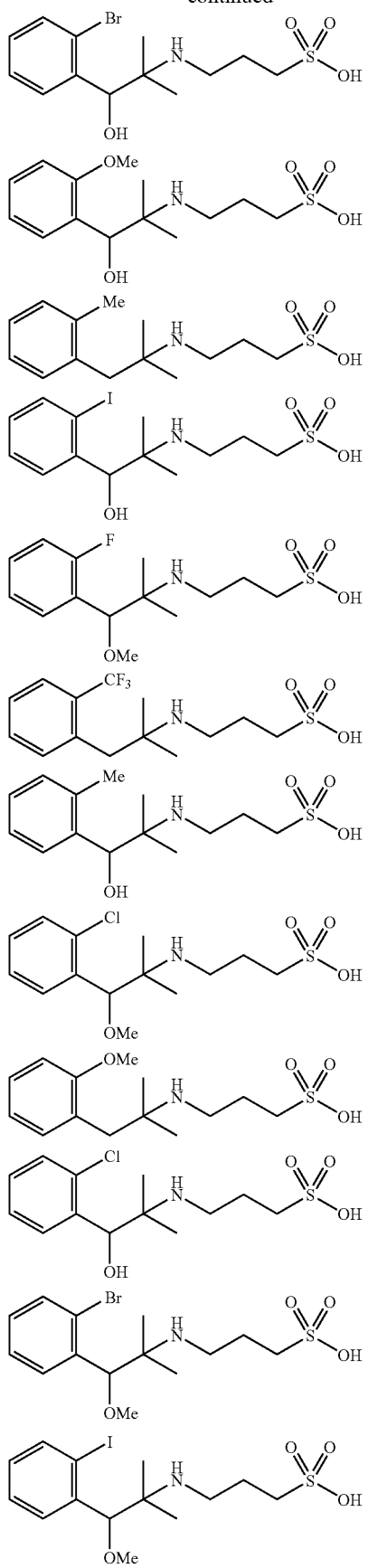
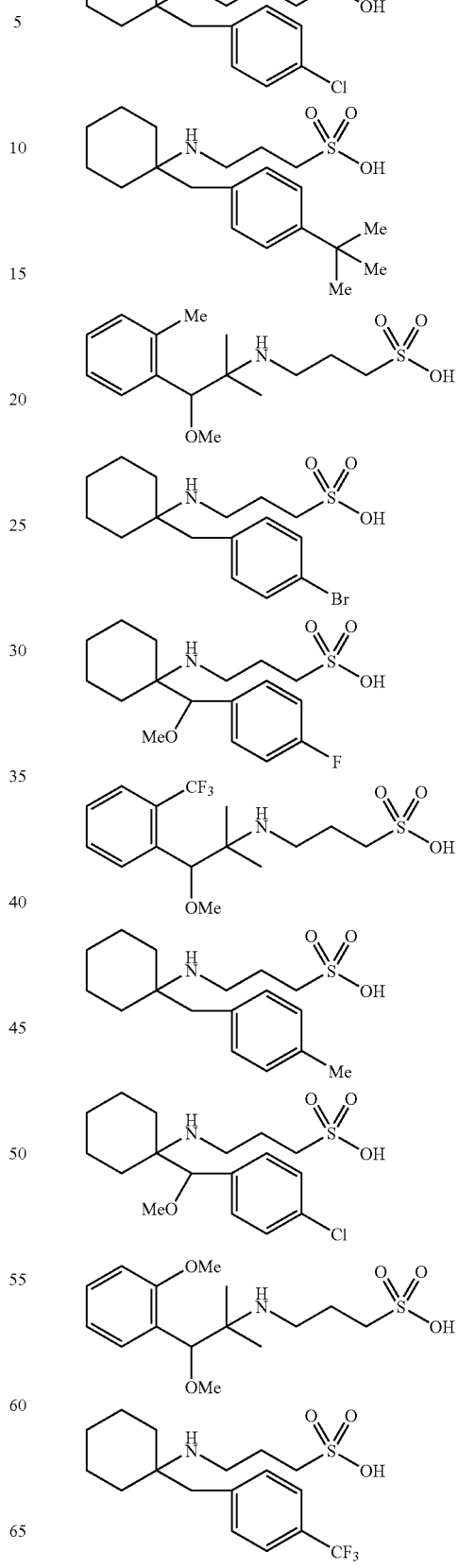

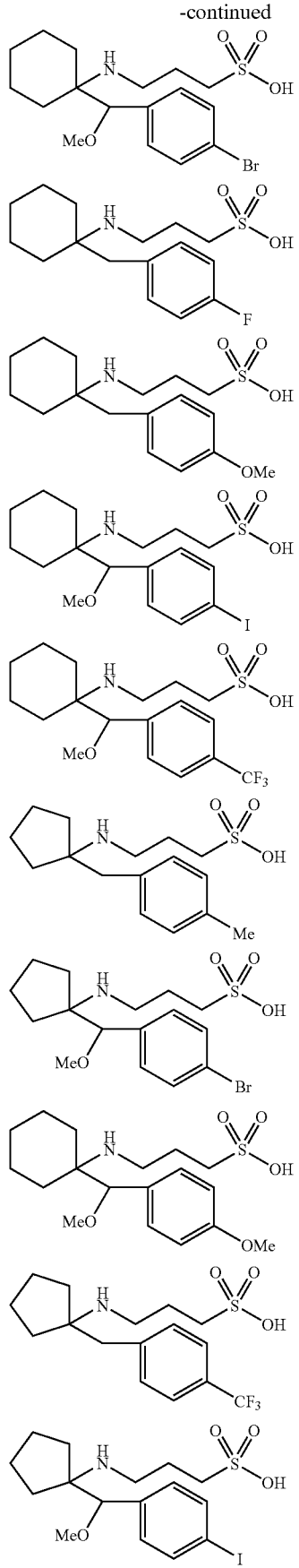
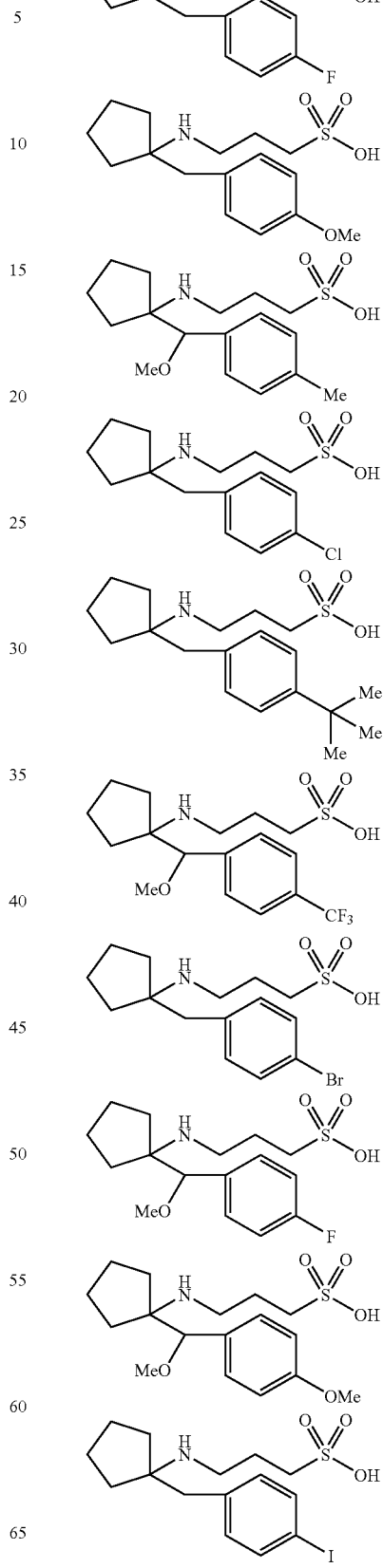

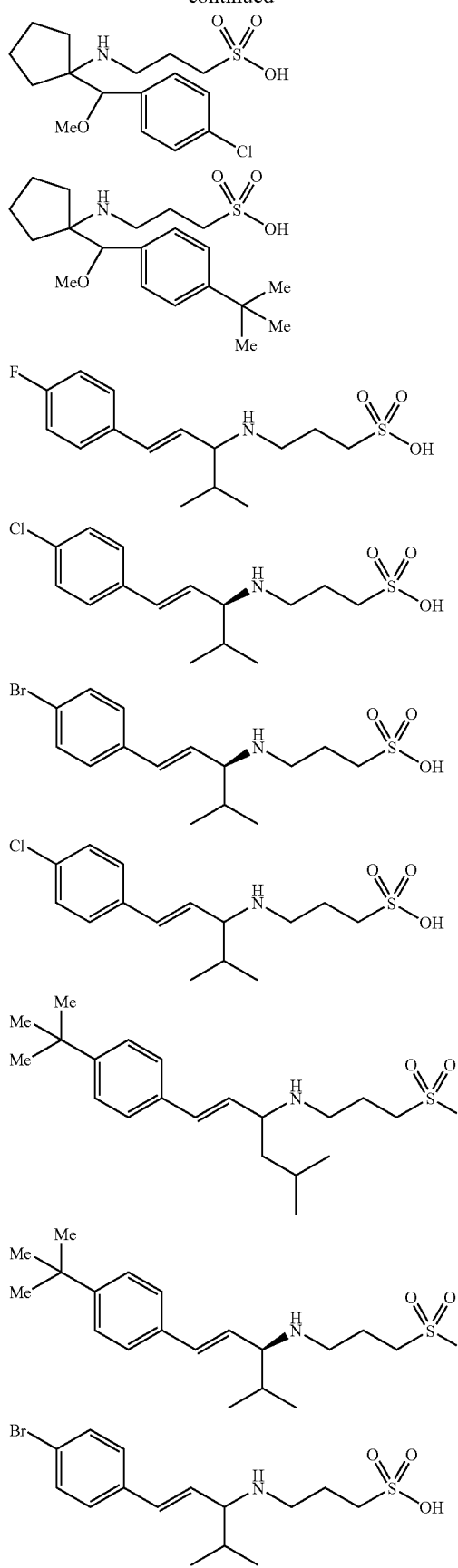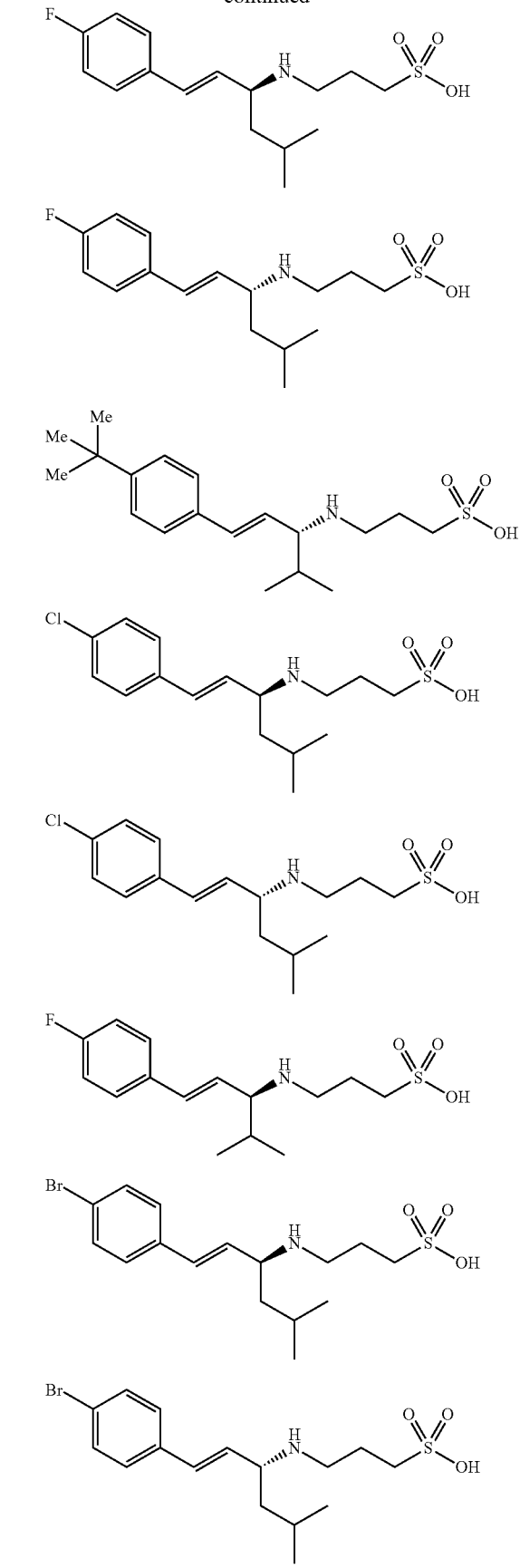

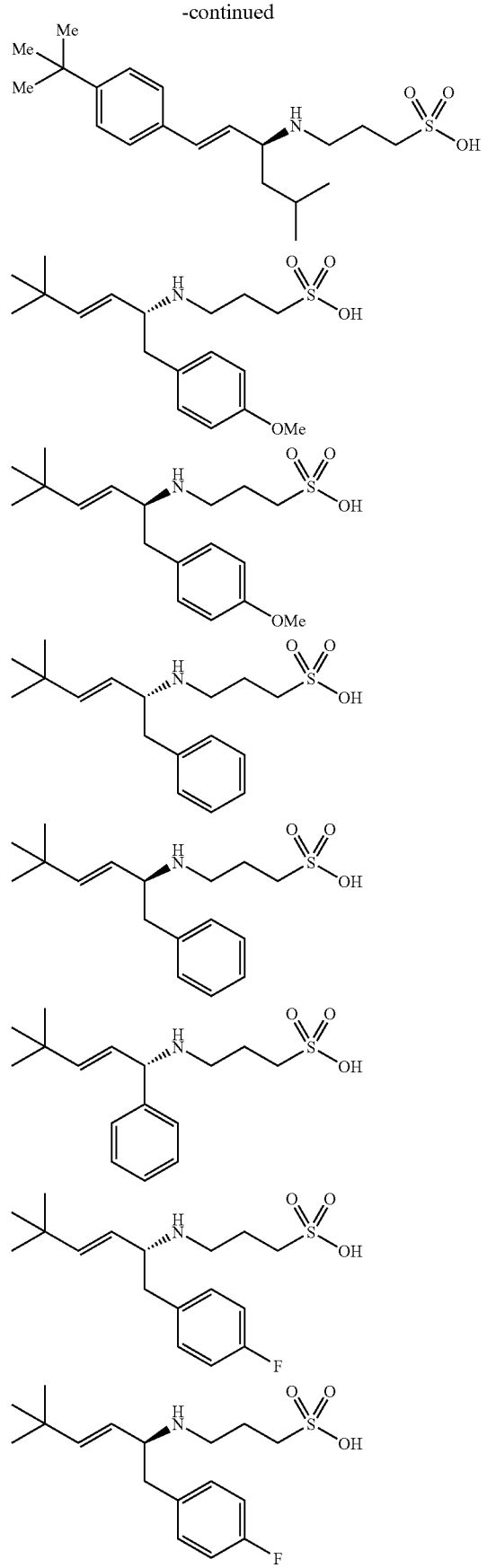
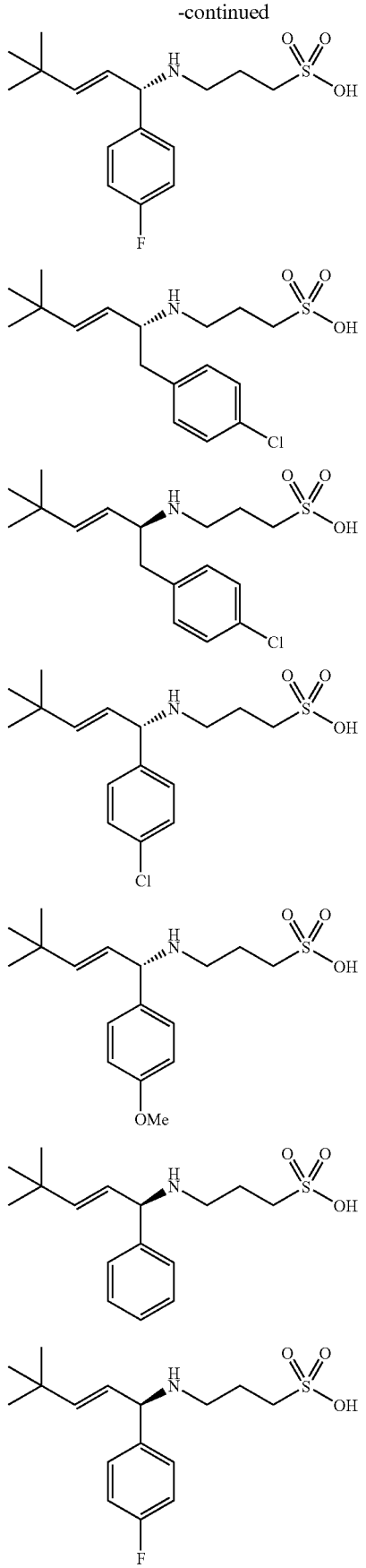

63
-continued
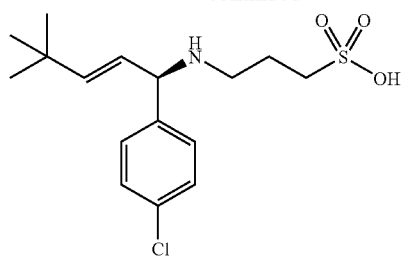
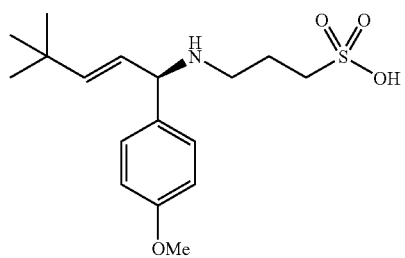
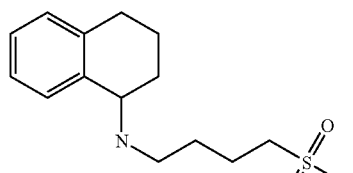
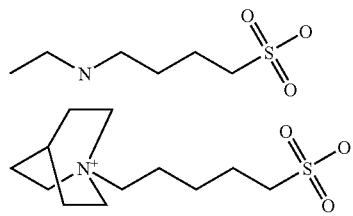
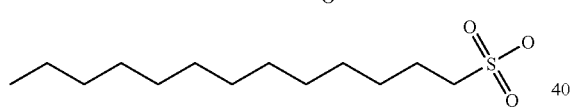
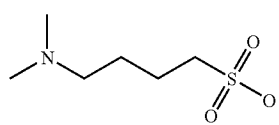
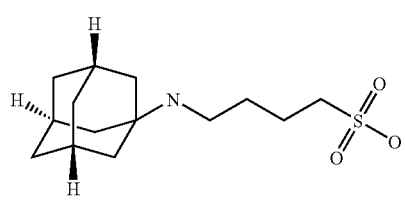
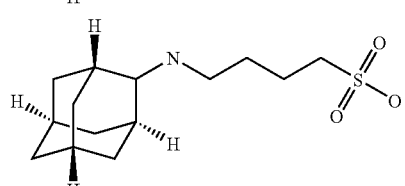
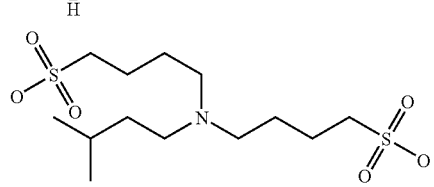
64
-continued
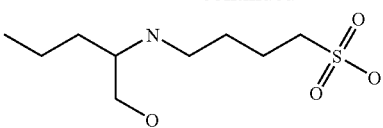
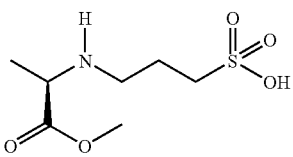
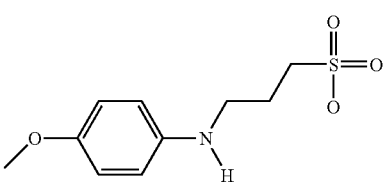
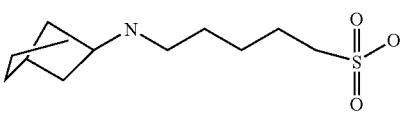
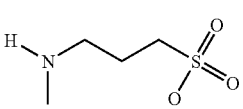
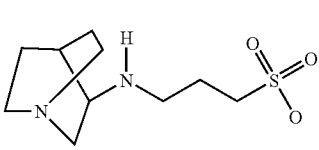
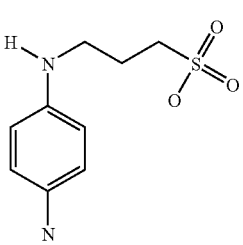
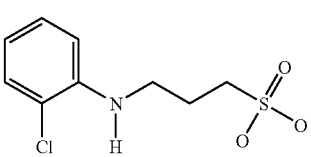
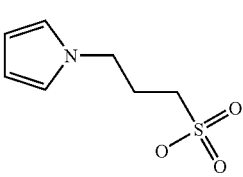
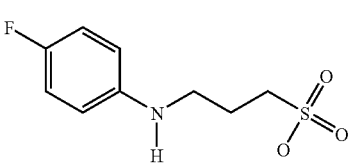

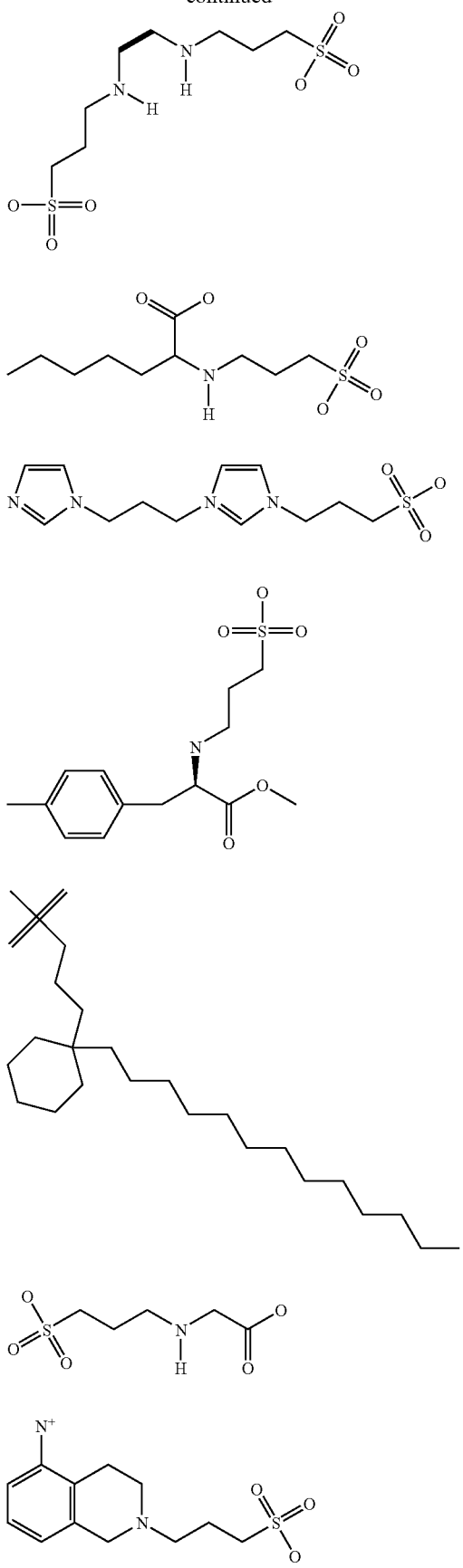

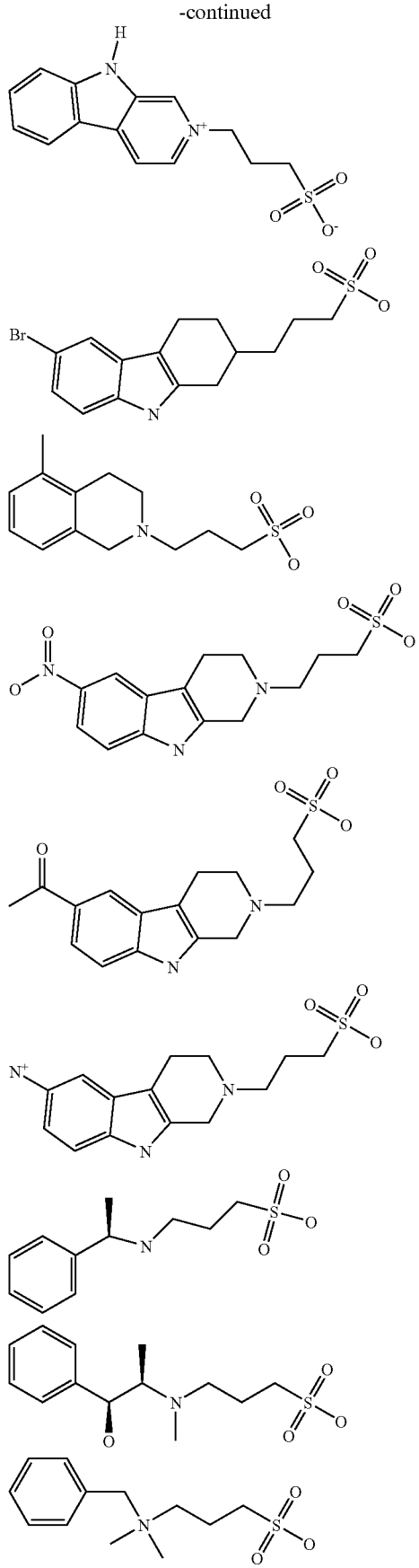
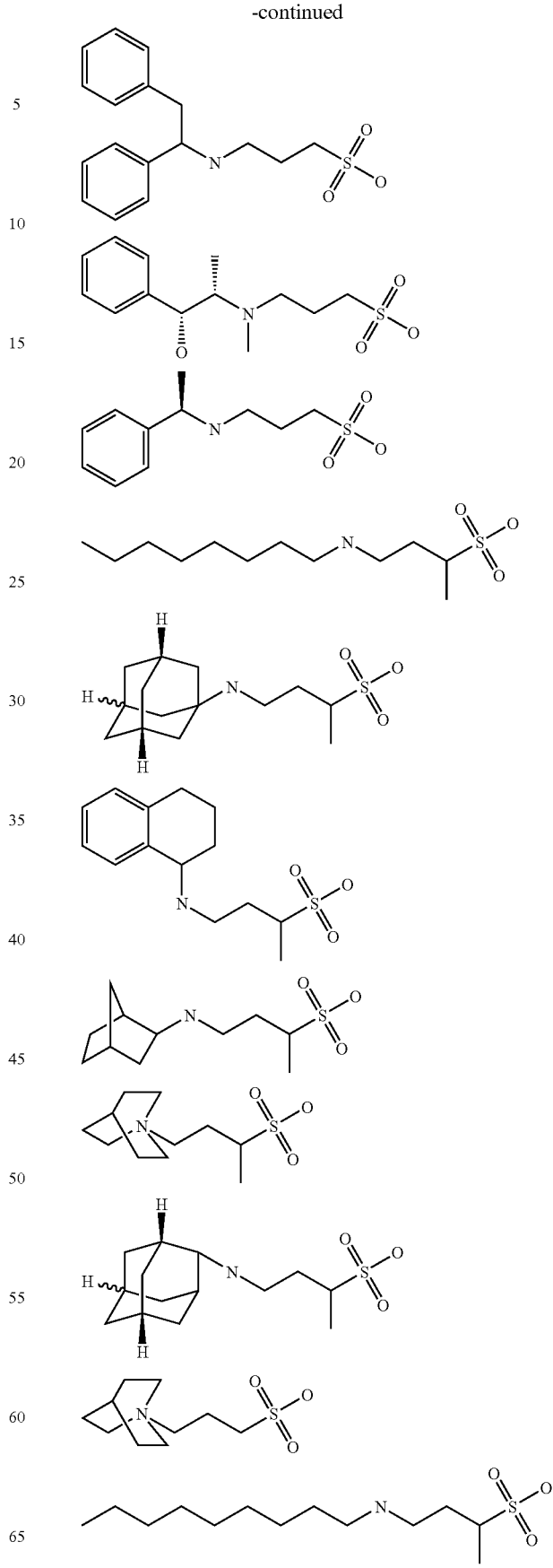

69
-continued
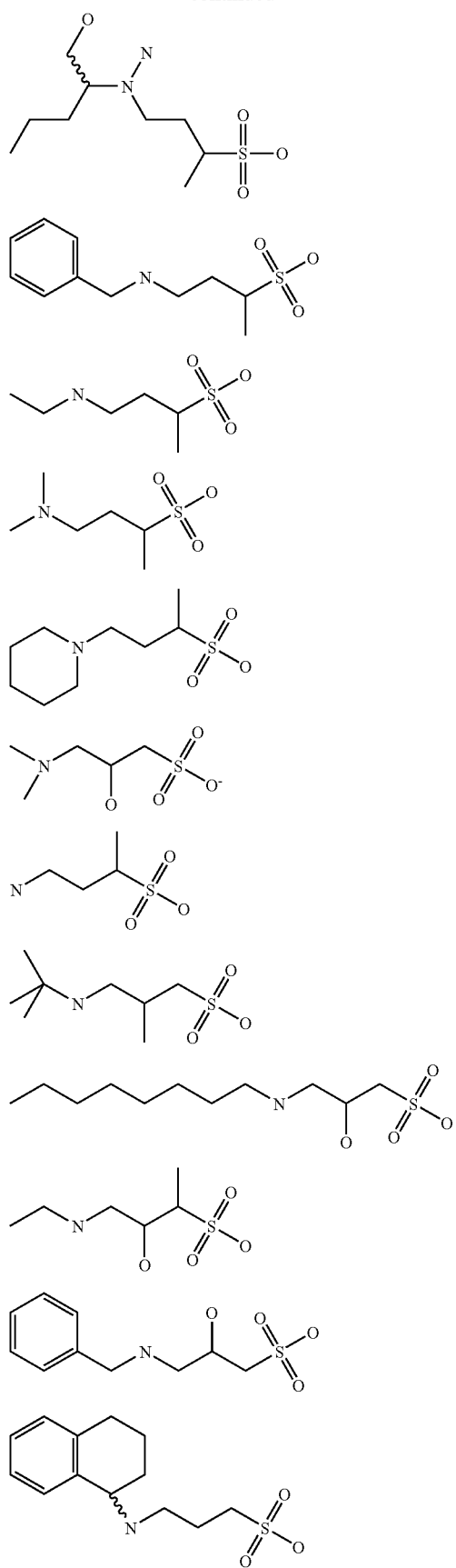
70
-continued
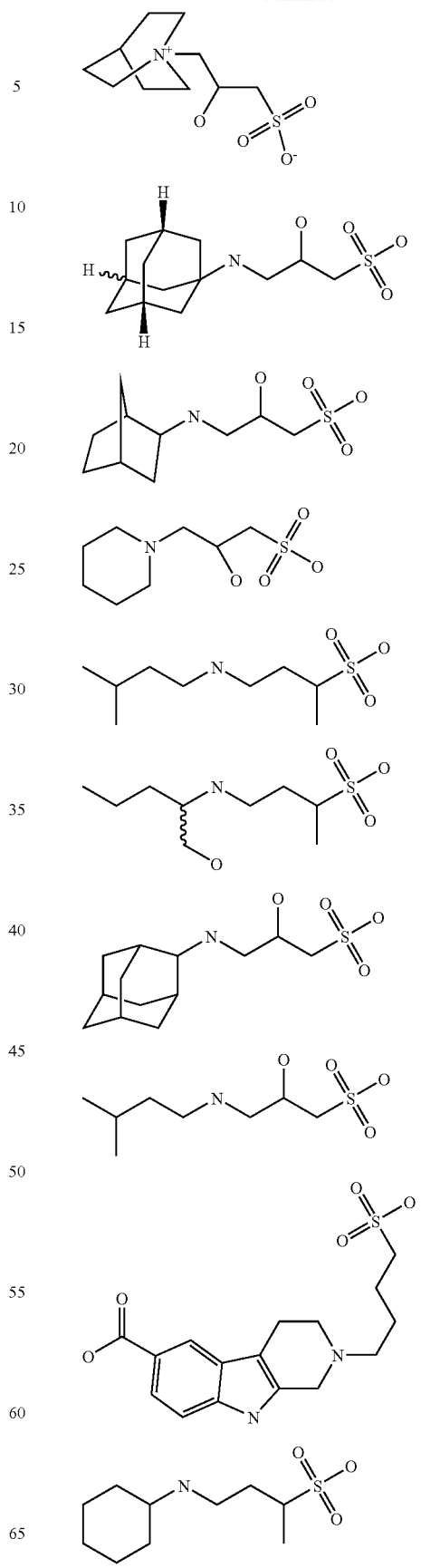

-continued

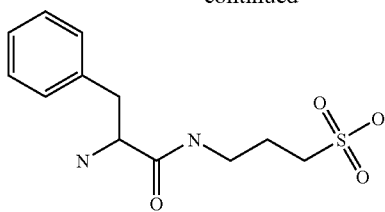

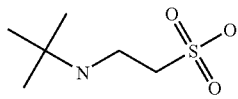

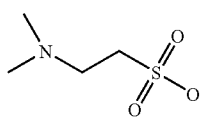

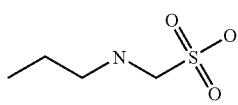

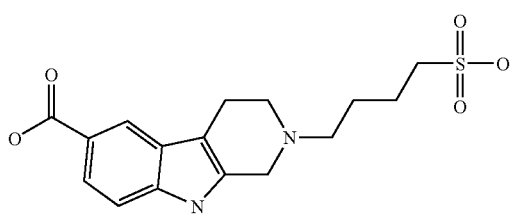

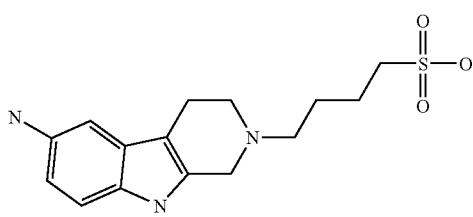

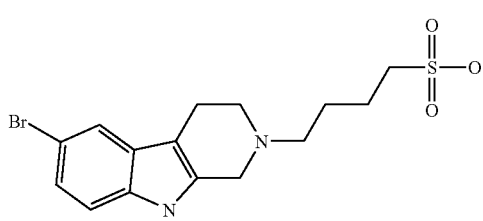

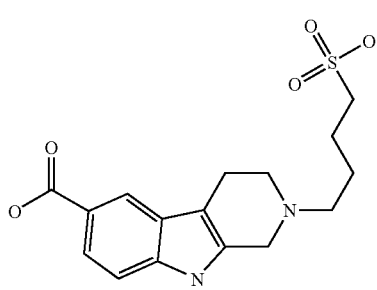

and pharmaceutically acceptable salts, esters, and prodrugs thereof.

In another embodiment, the invention pertains to compounds of Formula III:

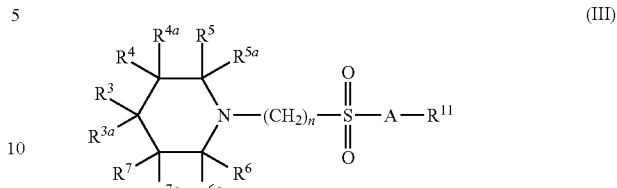

(III)

wherein:

A is nitrogen or oxygen;

$R^{11}$ is hydrogen, salt-forming cation, ester forming group, $-(CH_2)_x-Q$, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

$R^3 R^{3a}$, $R^4$, $R^{4a}$, $R^5$, $R^{5a}$, $R^6$, $R^{6a}$, $R^7$ and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond, provided that one of $R^3$, $R^{3a}$, $R^4$, $R^{4a}$, $R^5$, $R^{5a}$, $R^6$, $R^{6a}$, $R^7$ and $R^{7a}$ is a moiety of the Formula IIa:

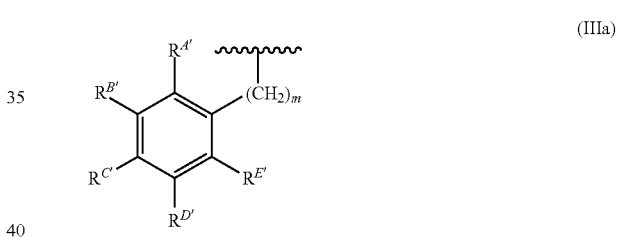

(IIIa)

wherein:

m is 0, 1, 2, 3, or 4;

$R^{A'}$, $R^{B'}$, $R^{C'}$, $R^{D'}$, and $R^{E'}$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; and pharmaceutically acceptable salts and esters thereof, provided that said compound is not 3-(4-phenyl-1,2,3,6-tetrahydro-1-pyridyl)-1-propanesulfonic acid.

In a further embodiment, n is 2, 3 or 4.

In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In another embodiment, $R^{11}$ is an ester-forming group. An ester-forming group includes groups which when bound form an ester. Examples of such groups include substituted or unsubstituted alkyl, aryl, alkenyl, alkynyl, or cycloalkyl. In another embodiment, A is oxygen.

In another embodiment, $R^3$ and $R^4$ are taken together with the carbon atoms to which they are attached to form a double bond. In another embodiment, $R^{A'}$, $R^{B'}$, $R^{C'}$, $R^{D'}$, and $R^{E'}$ are each hydrogen. $R^{A'}$, $R^{B'}$, $R^{D'}$, and $R^{E'}$ are each hydrogen and $R^{C'}$ is a halogen, such as fluorine, chlorine, iodine, or bromine.

In another embodiment, $R^3$ or $R^{5a}$ is a moiety of Formula IIIa.

In another embodiment, $R^4$, $R^5$, $R^6$, and $R^7$ are each hydrogen. In another further embodiment, $R^{4a}$, $R^{5a}$, $R^{6a}$ and $R^{7a}$ are each hydrogen.

In another, $R^{3a}$ is hydroxyl, cyano, acyl, or hydroxyl.

In another further embodiment, $R^{11}$ and A taken together are a natural or unnatural amino acid residue or a pharmaceutically acceptable salt or ester thereof. Examples of amino acid residues include esters and salts of phenylalanine and leucine.

In another embodiment, m is 0, 1, or 3.

Examples of compounds of Formula III include, but are not limited to:

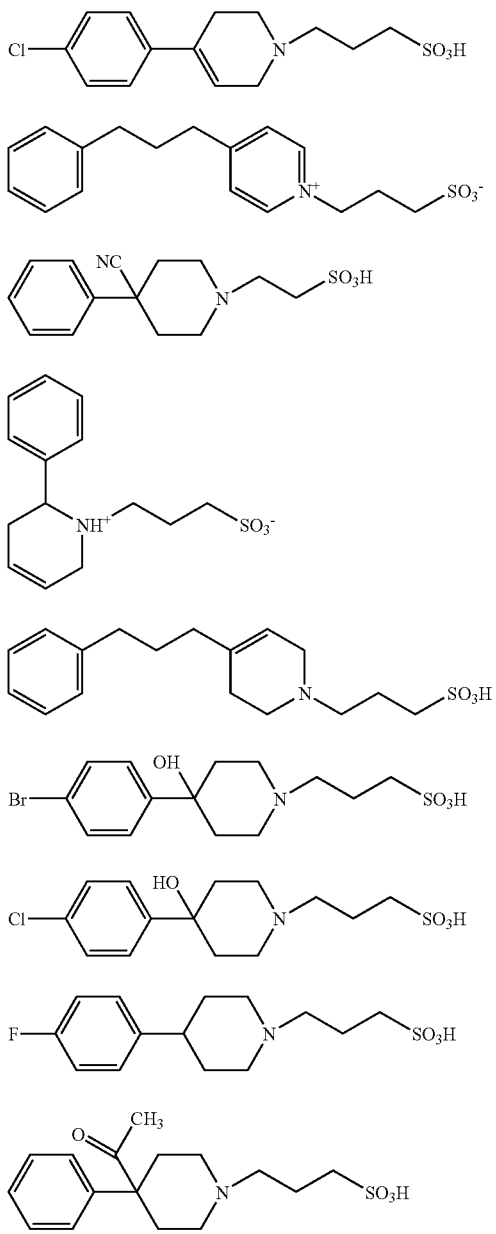

and pharmaceutically acceptable salts, esters, and prodrugs thereof.

In another embodiment, the invention pertains to compounds of Formula IV:

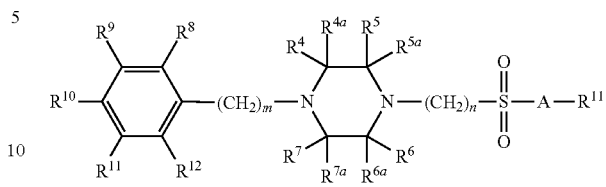

(IV)

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

$R^4$, $R^{4a}$, $R^5$, $R^{5a}$, $R^6$, $R^{6a}$, $R^7$, and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, $R^4$ and $R^5$ taken together, with the ring atoms they are attached to, form a double bond, or $R^6$ and $R^7$ taken together, with the ring atoms they are attached to, form a double bond;

m is 0, 1, 2, 3, or 4;

$R^8$, $R^9$, $R^{10}$, $R^{11}$, and $R^{12}$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl, and pharmaceutically acceptable salts and esters thereof.

In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In another embodiment, $R^{11}$ is an ester-forming group. An ester-forming group includes groups which when bound form an ester. Examples of such groups include substituted or unsubstituted alkyl, aryl, alkenyl, alkynyl, or cycloalkyl. In another embodiment, A is oxygen.

In another embodiment, m is 0 or 1. In another further embodiment, n is 2, 3, or 4. In another further embodiment, $R^4$, $R^5$, $R^6$ and $R^7$ are each hydrogen. $R^{4a}$, $R^{5a}$, $R^{6a}$, and $R^{7a}$ also may be hydrogen. Examples of $R^8$, $R^9$, $R^{10}$, $R^{11}$, and $R^{12}$ include hydrogen. In another embodiment $R^8$, $R^9$, $R^{11}$, $R^{12}$ are each hydrogen, and $R^{10}$ is a halogen, (e.g., fluorine, chlorine, bromine, or iodine), nitro, or alkyl (e.g., methyl, ethyl, butyl).

In another embodiment, A-$R^{11}$ may be the residue of an amino acid, e.g., a phenylalanine residue. In another embodiment, $R^9$, $R^{10}$, $R^{11}$ and $R^{12}$ are each hydrogen, and $R^8$ is not hydrogen, e.g., halogen, e.g., fluorine, bromine, chlorine, or iodine.

In another embodiment, the compound is:

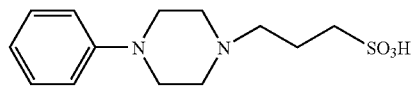

-continued

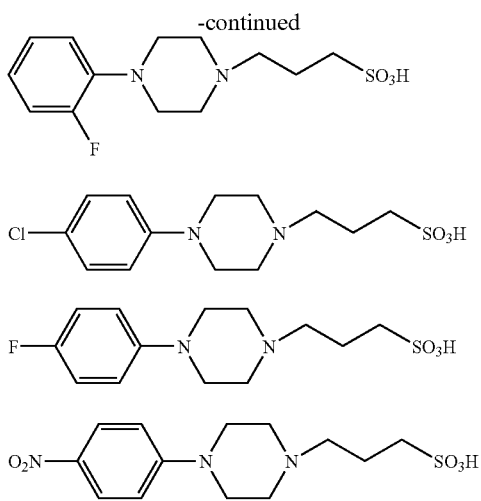

and pharmaceutically acceptable salts, esters, and prodrugs thereof.

In another embodiment, the invention pertains to compounds of Formula V:

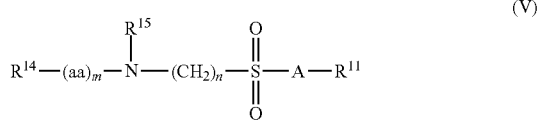

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

aa is a natural or unnatural amino acid residue;

m is 0, 1, 2, or 3;

$R^{14}$ is hydrogen or protecting group;

$R^{15}$ is hydrogen, alkyl or aryl, and pharmaceutically acceptable salts, esters and prodrugs thereof.

In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In another embodiment, $R^{11}$ is an ester-forming group. An ester-forming group includes groups which when bound form an ester. Examples of such groups include substituted or unsubstituted alkyl, aryl, alkenyl, alkynyl, or cycloalkyl. In another embodiment, A is oxygen.

In an embodiment, n is 2, 3 or 4. In certain embodiments, m is 0. In certain embodiments, A-$R^{11}$ is a residue of a natural amino acid, or a salt or ester thereof. Examples of amino acid residues, include, but are not limited to, leucine or phenylalanine residues, and pharmaceutically acceptable salts and esters thereof. Examples of possible esters include methyl, ethyl, and t-butyl.

In another embodiment, m is 1. Examples of aa include natural and unnatural amino acid residues such as phenylalanine, glycine, and leucine.

In another embodiment, $(aa)_m$ is a residue of phe-phe, or an ester thereof.

In certain embodiments, $R^{15}$ is hydrogen or substituted alkyl, e.g., arylalkyl.

The term "unnatural amino acid" refers to any derivative of a natural amino acid including D forms, and α- and β-amino acid derivatives. The terms "unnatural aminoacid" and "non-natural amino acid" are used interchangably herein and are meant to include the same moieties. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): β-alanine (β-ALA), γ-aminobutyric acid (GABA), 2-aminobutyric acid (2-Abu), α,β-dehydro-2-aminobutyric acid (8-AU), 1-aminocyclopropane-1-carboxylic acid (ACPC), aminoisobutyric acid (Aib), 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid(4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), biphenylalanine (Bip), para-bromophenylalanine (4-Br-Phe), ortho-chlorophenylalanine] (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-$C_{12}$-Phe), 3,4-diflurorphenylalanine (3,4-$F_2$-Phe), 3,5-diiodotyrosine (3,5-$I_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-I-Phe), 3-iodotyrosine (3-I-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th). Additionally, N-alkylated amino acids may be used, as well as amino acids having amine-containing side chains (such as Lys and Orn) in which the amine has been acylated or or alkylated.

Examples of compounds of the invention include, but are not limited to:

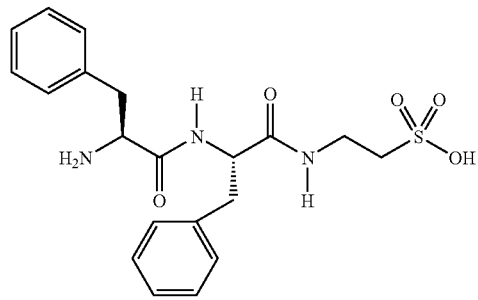

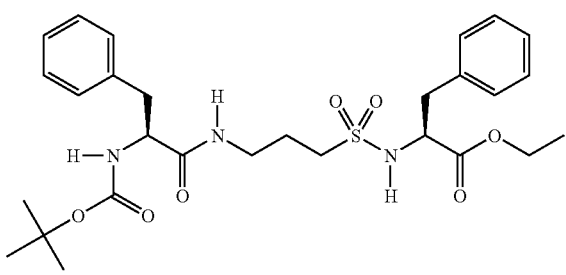

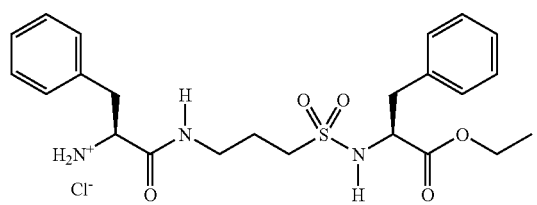

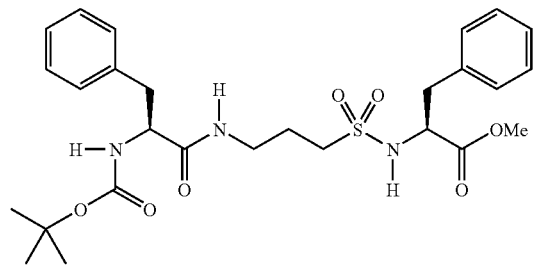

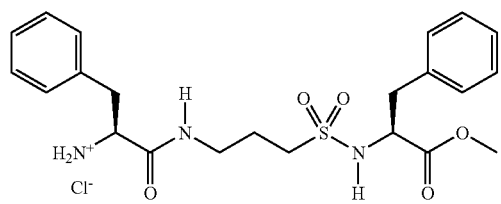

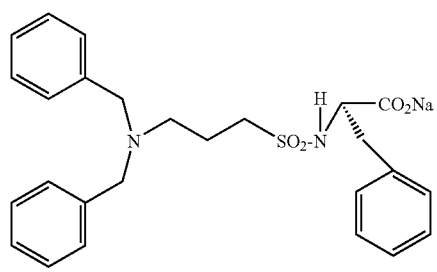

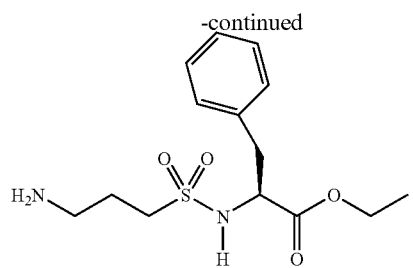

and pharmaceutically acceptable salts, esters, and prodrugs thereof.

In another embodiment, the invention pertains, at least in part, to compounds of Formula VI:

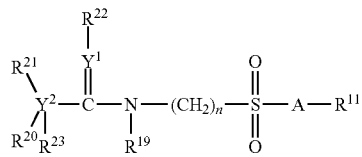

wherein:

n is 1, 2, 3, 4, 5, 6, 7, 8, 9, or 10;

A is oxygen or nitrogen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

$R^{19}$ is hydrogen, alkyl or aryl;

$Y^1$ is oxygen, sulfur, or nitrogen;

$Y^2$ is carbon, nitrogen, or oxygen;

$R^{20}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl;

$R^{21}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl, or absent if $Y^2$ is oxygen;

$R^{22}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl; or $R^{22}$ is hydrogen, hydroxyl, alkoxy or aryloxy if $Y^1$ is nitrogen; or $R^{22}$ is absent if $Y^1$ is oxygen or sulfur; or $R^{22}$ and $R^{21}$ may be linked to form a cyclic moiety if $Y^1$ is nitrogen;

$R^{23}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl, or absent if $Y^2$ is nitrogen or oxygen;

or pharmaceutically acceptable salts thereof.

In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In a further embodiment, the salt is a sodium salt. In a further, embodiment, A is oxygen.

In another embodiment, $Y^1$ is oxygen or sulfur, and $R^{22}$ is absent.

In another embodiment, $Y^2$ is oxygen and $R^{21}$ is absent. Examples of $R^{20}$ include benzyl, aryl (e.g., phenyl), alkyl, cycloalkyl (e.g., adamantyl), etc. In other embodiment, $Y^2$ is nitrogen and $R^{21}$ is hydrogen. In other embodiment, $R^{21}$ is benzyl. In another further embodiment, $R^{20}$ and $R^{21}$ are linked to form a pyridyl ring. In another embodiment, Y, is sulfur.

Examples of compounds of the invention, include

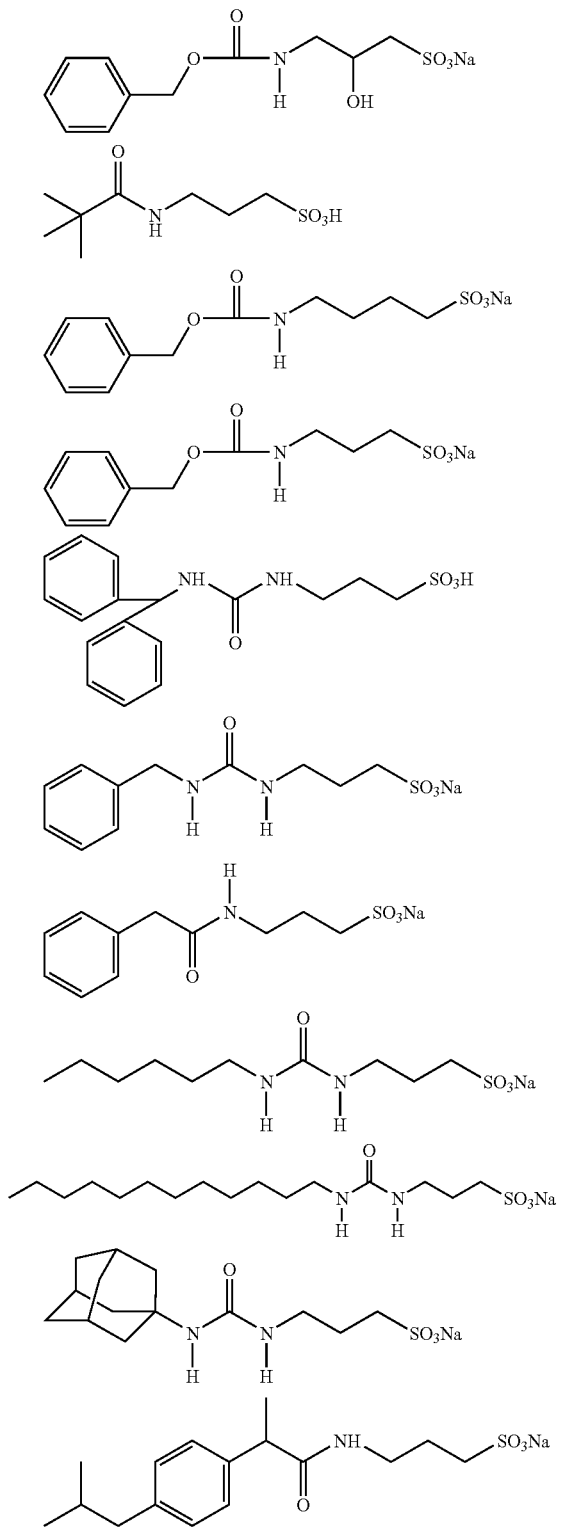

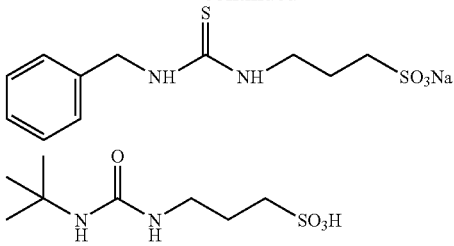

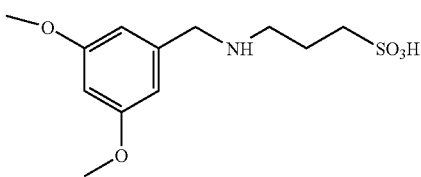

and pharmaceutically acceptable salts, esters, and prodrugs thereof.

In another embodiment, the invention pertains to compounds of Formula VII:

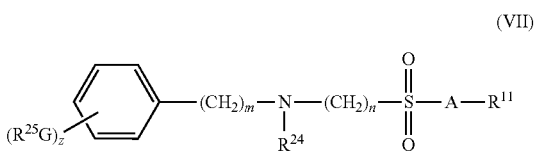

(VII)

wherein:

n is 2, 3, or 4;

A is oxygen or nitrogen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

G is a direct bond or oxygen, nitrogen, or sulfur;

z is 0, 1, 2, 3, 4, or 5;

m is 0 or 1;

$R^{24}$ is selected from a group consisting of hydrogen, alkyl, mercaptoalkyl, alkenyl, alkynyl, aroyl, alkylcarbonyl, aminoalkylcarbonyl, cycloalkyl, aryl, arylalkyl, thiazolyl, triazolyl, imidazolyl, benzothiazolyl, and benzoimidazolyl;

each $R^{25}$ is independently selected from hydrogen, halogen, cyano, hydroxyl, alkoxy, thiol, amino, nitro, alkyl, aryl, carbocyclic, or heterocyclic, and pharmaceutically acceptable salts, esters, and prodrugs thereof.

In one embodiment, $R^{11}$ is hydrogen. In another, A is oxygen. For example, n may be 3 and m may be 1. In other embodiments, $R^{24}$ is hydrogen or benzyl.

In certain embodiments, z is 0, 2, or 3. In others, $R^{25}$ is hydroxyl or alkoxy, e.g., methoxy, ethoxy, etc. In certain embodiments, two or more $R^{25}$ substituents can be linked to form a fused ring (e.g., to form a methylendioxyphenyl moiety).

Examples of compounds of the invention include:

-continued

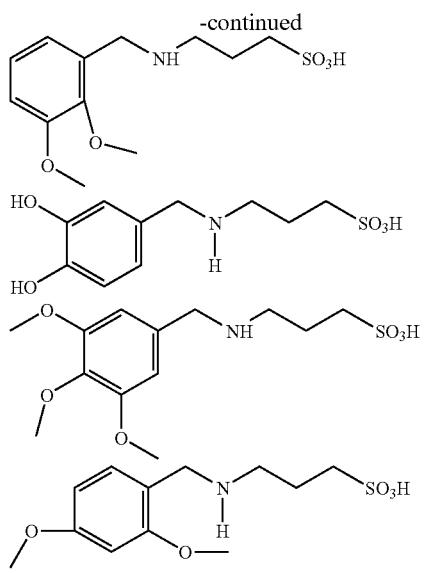

and pharmaceutically acceptable salts, esters, and prodrugs thereof.

In another embodiment, compounds of the invention include compound of the formula:

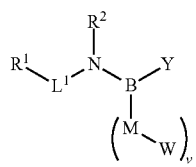

(VIII)

wherein:

$R^1$ is hydrogen, a substituted or unsubstituted cycloalkyl, heterocyclic, aryl, arylcycloalkyl, bicyclic or tricyclic ring, a bicyclic or tricyclic fused ring group, or a substituted or unsubstituted $C_2$-$C_{10}$ alkyl group;

$R^2$ is selected from a group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

Y is $SO_3^-X^+$, $OSO_3^-X^+$, or $SSO_3^-X^+$;

$X^+$ is hydrogen, a cationic group, or an ester-forming group;

$L^1$ is a substituted or unsubstituted $C_1$-$C_5$ alkyl group or absent,

B is $C_1$-$C_5$ alkyl, alkenyl, or alkynyl group, optionally fused with W when M is absent;

M is a covalent bond, amino, $C_1$-$C_6$ alkyl, alkenyl, alkynyl, carboxyl, oxy, amide, ester, thioether, thioester or absent;

W is a substituted or unsubstituted alkyl, alkenyl, alkynyl, cycloalkyl, aryl, arylalkyl, bicyclic or tricyclic ring, a bicyclic or tricyclic fused ring group, heterocyclic, thiazolyl, triazolyl, imidazolyl, benzothiazolyl, or benzoimidazolyl; and v is 1, 2, 3, 4, 5, or 6; or a pharmaceutically acceptable salt, ester or prodrug thereof, provided that when Y is methyl, $R^1$ and $R^2$ are hydrogen, Y is $SO_3^-X^+$, M is a covalent bond, B is not $CH_2$—CH(M-W)—$CH_2$.

In a further embodiment, $R^1$ and $R^2$ are each hydrogen and $L^1$ is a covalent bond. In another embodiment, $R^1$ is alkyl and $R^2$ is hydrogen. In another further embodiment, Y is $SO_3^-X^+$.

In another embodiment, v is 1. In another embodiment, M is a covalent bond or $C_1$-$C_3$ alkyl. In another embodiment, W is alkenyl. In another embodiment, W is aryl (e.g., substituted or unsubstituted phenyl) or heteroaryl. In another embodiment, W is substituted or unsubstituted alkyl (e.g., straight chain, branched or cyclic (e.g., adamanyl, etc.).

In another embodiment, B is $C_1$-$C_5$ alkyl. Examples of B include: —CH(M-W)—$CH_2$—$CH_2$—, —$CH_2$—CH(M-W)—$CH_2$—, and —($CH_2$)—$CH_2$—CH(M-W)—. In another embodiment B is alkenyl. In a further embodiment, the compound is selected from the group consisting of:

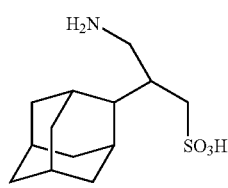

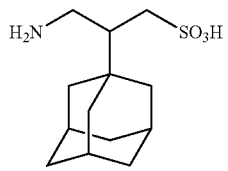

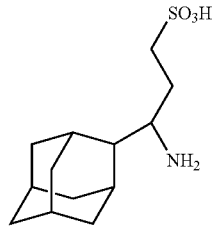

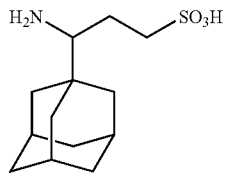

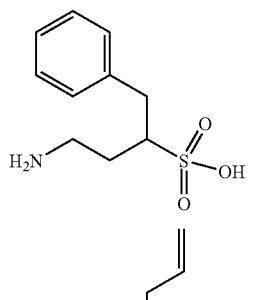

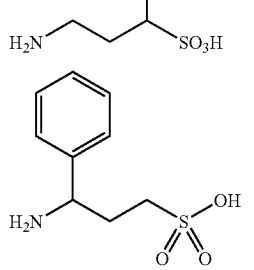

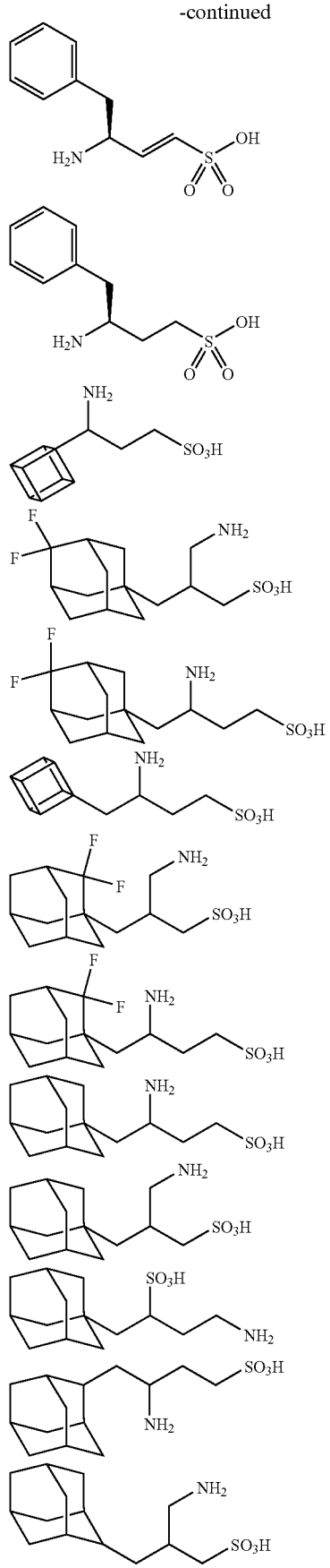
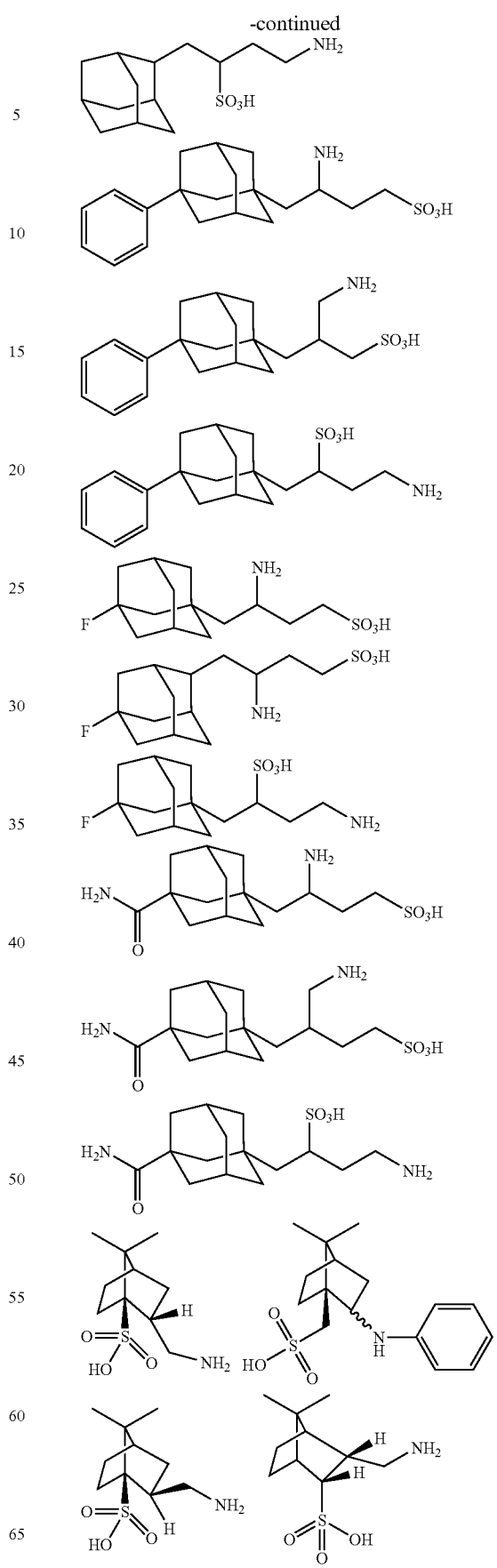

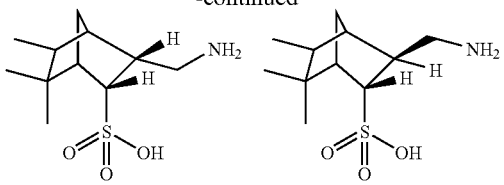

In one embodiment, the invention pertains to compounds of Formula IX:

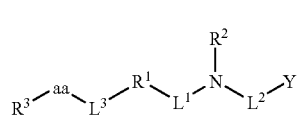

(IX)

wherein:

$R^1$ is a substituted or unsubstituted cycloalkyl, heterocyclic, aryl, arylcycloalkyl, bicyclic or tricyclic ring, a bicyclic or tricyclic fused ring group, or a substituted or unsubstituted $C_2$-$C_{10}$ alkyl group;

$R^2$ is selected from the group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

$R^3$ is hydrogen or a protecting group;

aa is a natural or unnatural amino acid residue;

$L^3$ is a covalent bond, amino, $C_1$-$C_6$ alkyl, alkenyl, alkynyl, carboxyl, amide, aminoalkyl, ether, ester, thioether, thioester or absent;

Y is $SO_3^-X^+$, $OSO_3^-X^+$, or $SSO_3^-X^+$;

$X^+$ is hydrogen, a cationic group, or ester-forming group; and each of $L^1$ and $L^2$ is independently a substituted or unsubstituted $C_1$-$C_5$ alkyl group or absent, or a pharmaceutically acceptable salt thereof.

In a further embodiment, $R^2$ is hydrogen, Y is $SO_3^-X^+$, and $L^2$ is —$(CH_2)_3$—. In another further embodiment, $R^1$ is carbocyclic or heterocyclic. In a further embodiment, $R^1$ is adamantyl. In a further embodiment, $L^3$ is a covalent bond, a thioether, amino, oxy, aminoalkyl, or ether. In a further embodiment, $R^3$ is hydrogen. In another further embodiment, aa is glycine, proline, alanine or phenylalanine. The $R^3$ moiety may be connected to the amino acid through any available atom, not necessarily through a peptide bond.

In a further embodiment, the compound of formula IX is selected from the group consisting of:

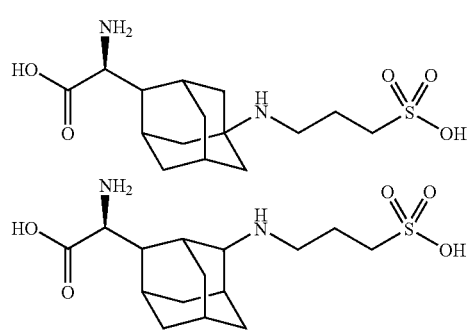

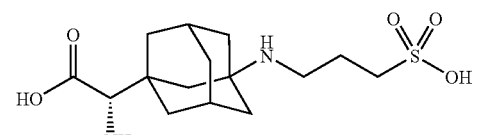

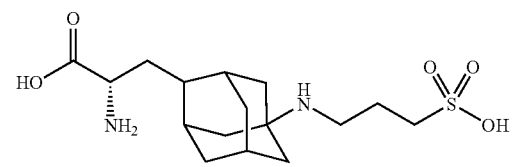

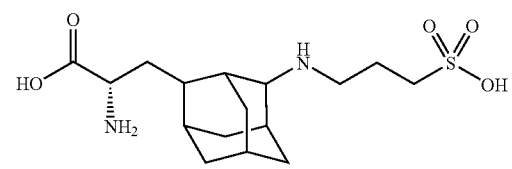

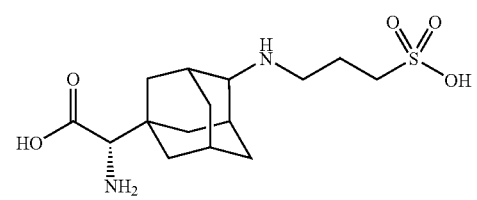

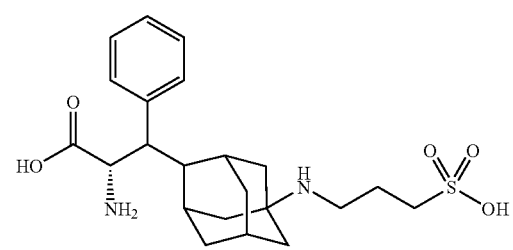

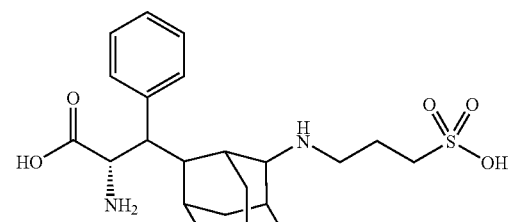

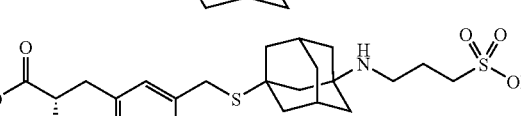

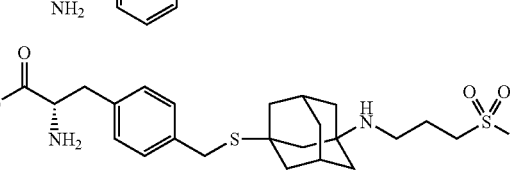

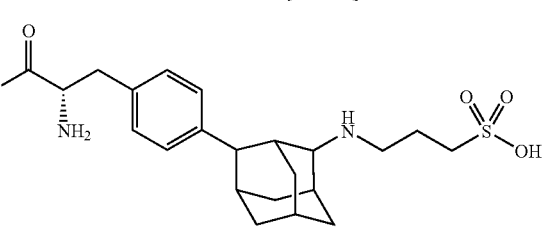

-continued

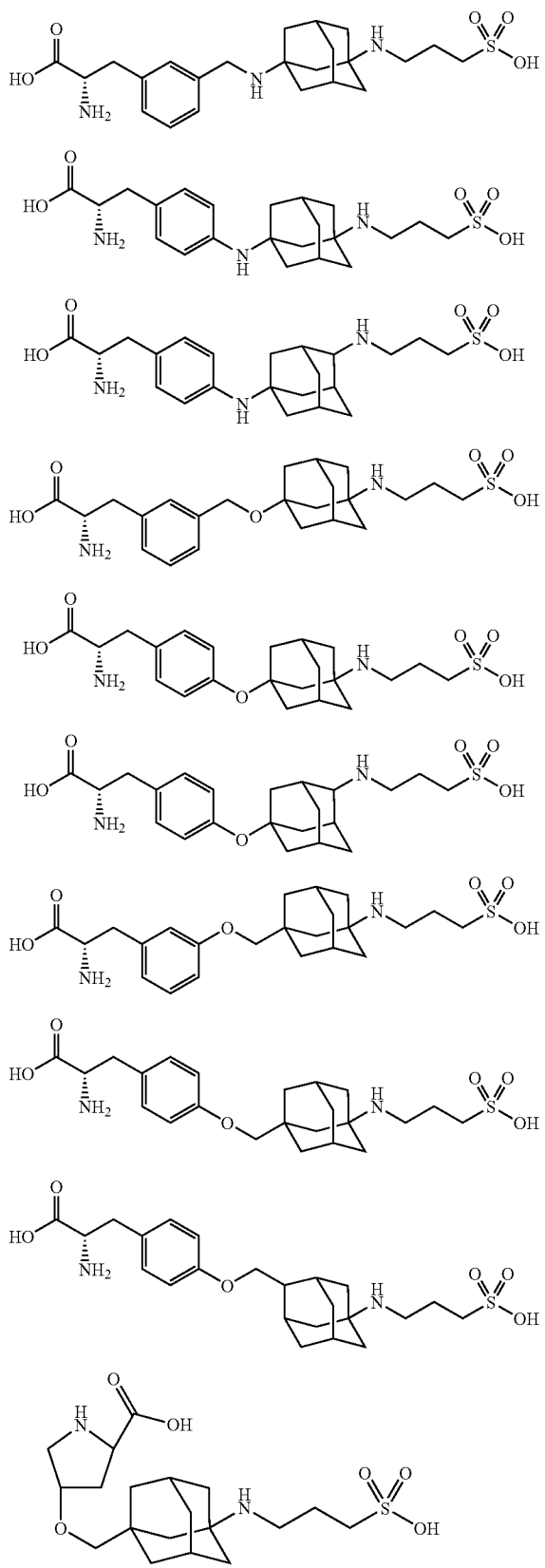

and pharmaceutically salts, esters and prodrugs thereof.

In another embodiment, the invention pertains to compounds of the formula (X):

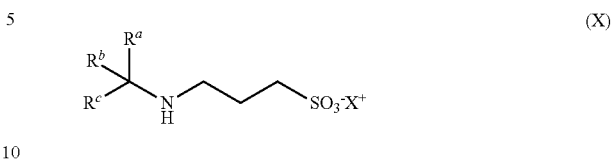

wherein:

$R^a$ is hydrogen, substituted or unsubstituted alkyl, aryl, heteroaryl, carboxyl, alkyloxycarbonyl, or aminocarbonyl;

$R^b$ and $R^c$ are each selected independently from hydrogen, substituted or unsubstituted alkyl, alkenyl, alkynyl, cycloalkyl, $CONH_2$, or $R^b$, $R^c$ and the carbon atom they are attached to can form a substituted or unsubstituted cyclic structure of 4 to 8-membered ring or a fused ring system; and $X^+$ is hydrogen, a cationic group, or an ester-forming group, or a pharmaceutically acceptable salt, ester, or prodrug thereof.

In a further embodiment, $X^+$ is hydrogen.

In another further embodiment, $R^a$ is substituted or unsubstituted alkyl. Examples of $R^a$ groups include methyl, ethyl, hydroxymethyl, or phenyl substituted alkyl (e.g., 1-(para-methyl-phenyl)-1-hydroxymethyl). In another embodiment, $R^a$ is hydrogen or aminocarbonyl (e.g., $NH_2$—C(=O)—).

In another embodiment, at least one of $R^b$ and $R^c$ are substituted or unsubstituted alkyl. In another further embodiment, $R^b$ and $R^c$ are each unsubstituted alkyl. Examples of $R^b$ and $R^c$ include methyl, ethyl, iso-propyl, propyl, iso-butyl, n-butyl, t-butyl, pentyl, hexyl, or heptyl. In another embodiment, at least one of $R^b$ and $R^c$ are hydroxyalkyl, alkoxyalkyl, alkylthioalkyl, aryloxyalkyl, alkylcarbonylalkyl, or arylalkyl.

In other embodiments, $R^b$ and $R^c$ are connected to form a ring. The ring may be cycloalkyl (e.g., cyclopropyl, cyclopentyl, cyclohexyl; or cycloheptyl) or cycloalkenyl. In other embodiments, $R^b$ and $R^c$ are connected to form a bridged or fused ring system, e.g., adamantyl, norborane, indanyl, fluorenyl, etc.

Examples of compounds of Formula (X) include, but are not limited to: Compound N1, N3, N7, N8, N18, N28, N29, N44, N47, N49, N50, N51, N53, N56, N58, N59, N61, N62, N68, N72, N77, N81, MJ, NN, NM, NO, NP, NQ, NR, NT, NW, NZ, OC, OF, OG, ON, OQ, OS, OT, OU, OV, OW, OX, OY, PH, PJ, PK, PL, PM, PN, PO, PP, PR, PS, PT, PU, PV, PW, PX, PY, QB, QE, QF, and QM.

In another embodiment, the invention pertains to compounds of the formula (XI):

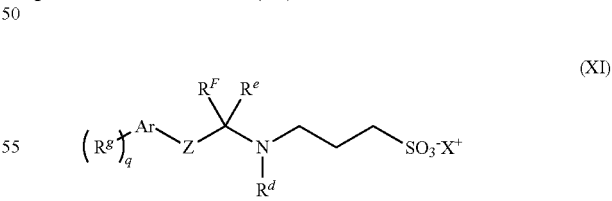

wherein:

$R^d$ is H or alkyl;

$R^e$ and $R^f$ are each independently hydrogen, $C_1$-$C_6$ alkyl, or $R^e$ and $R^f$ taken together with the carbon they are attached to form a 3 to 6-membered ring;

$R^g$ is independently selected for each occurence from the group consisting of: hydrogen, alkyl, alkoxy, halogen, $NO_2$, and alkyl-$SO_2$;

q is 1, 2, 3, 4, or 5;

X⁺ is hydrogen, a cationic group, or an ester-forming group;

Ar is aryl or heteroaryl; and

Z is —(CH$_2$)$_{0-3}$—, —(CHOH)—, (CH$_2$)$_{1-3}$O(CH$_2$)$_{1-3}$, or a carbonyl group, or a pharmaceutically acceptable salt, ester, or prodrug thereof.

In one embodiment, X⁺ is hydrogen. In another embodiment, R$^d$ is hydrogen. In yet another embodiment, R$^e$ and R$^f$ are each independently hydrogen, methyl, ethyl or are linked to form a ring, e.g., cyclohexyl ring. In another embodiment, Z is —CH$_2$—, —CHOH—, or a covalent bond. In another embodiment, Ar is phenyl, naphthyl, thiophenyl, furanyl, or benzothiophenyl. In yet another embodiment, q is 1 or 2. Examples of R$^g$ include methyl, ethyl, propyl, butyl, pentyl, hexyl, heptyl, hydroxy, bromine, chlorine, methoxy, ethoxy, propoxy, alkyl-SO$_2$—, and nitro.

Examples of compounds of Formula (XI) include, but are not limited to: Compound N37, N39, N43, N45, N46, N48, N52, N54, N55, N57, N60, N64, N65, N66, N67, NS, NU, NV, NX, NY, OA, OB, OD, OE, OH, OL, OM, OO, OP, OR, OZ, PA, PB, PD, PE, PF, PI, PQ, PZ, QA, QC, QD, QG, QH, QI, QJ, QK, QL and QW.

In another embodiment, the invention pertains to compounds of the formula (XII):

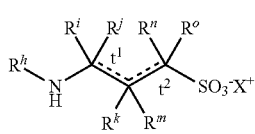

(XII)

wherein:

R$^h$ is hydrogen, benzyl, aryl-alkyl, aryl, or alkyl;

R$^i$, R$^j$, R$^k$, R$^m$, R$^n$, and R$^o$ are each independently hydrogen, substituted or unsubstituted aryl, substituted or unsubstituted benzyl, alkyl, alkenyl, carbocyclic, heterocyclic, absent or together may be linked to form a ring structure;

X⁺ is hydrogen, a cationic group, or an ester-forming group; and t$^1$ and t$^2$ are each single or double bonds, provided that both t$^1$ and t$^2$ are not both double bonds, or a pharmaceutically acceptable salt, ester, or prodrug thereof.

In one embodiment, R$^h$ is methyl, phenyl, indanyl, t-butyl, hydrogen, benzyl, or adamantyl. In a further embodiment, R$^i$, R$^j$, R$^k$, R$^m$, and R$^n$ are each hydrogen and t$^1$ and t$^2$ are both single bonds. In another further embodiment, R$^o$ is benzyl, phenyl, ethyl, butyl, thiophenyl-alkyl, or propylenyl.

In another embodiment, R$^j$, R$^m$, and R$^o$ are each hydrogen, R$^n$ and R$^k$ are each absent, t$^1$ is a single bond, and t$^2$ is a double bond.

In yet another embodiment, R$^j$, R$^k$, R$^m$, R$^n$ and R$^o$ are each hydrogen, and t$^1$ and t$^2$ are each single bonds.

In a further embodiment, R$^i$ is benzyl, adamantyl, methyl, ethyl, propyl, butyl, pentyl, hexyl, heptyl, cyclohexyl, hydroxyalkyl, cubanyl, cubanyl-methyl-, adamantyl-methyl-, phenyl-adamantyl-methyl, aminocarbonyl-adamantyl-methyl-, or heteroaryl-alkyl.

In another further embodiment, R$^i$, R$^j$, R$^m$, R$^n$ and R$^o$ are each hydrogen, and t$^1$ and t$^2$ are each single bonds. In yet a further embodiment, R$^k$ is benzyl, substituted phenyl, t-butyl, adamantyl, adamantyl-methyl, phenyl-adamantyl-methyl, aminocarbonyl-adamantyl-methyl-, or heteroaryl-alkyl.

In another embodiment, R$^i$, R$^j$, R$^k$, and R$^n$ are each hydrogen and R$^m$ and R$^o$ are linked to form a ring. In a further embodiment, the ring is unsubstituted or substituted cycloalkyl. In another embodiment, the ring is a fused or a bridged ring.

Examples of compounds of Formula (XII) include, but are not limited to: Compound N2, N4, N5, N6, N9, N10, N1, N12, N13, N14, N15, N16, N17, N19, N20, N21, N22, N23, N24, N25, N26, N30, N32, N33, N34, N35, N36, N38, N40, N41, N42, N63, N69, N70, N71, N73, N74, N75, N76, N78, N79, N80, N82, N83, N84, N85, N86, N87, N88, QN, QO, QQ, QR, QS, QT, QU, QV, QX, QY, QZ, RA, RB, RC, RD, RE, RF, RG, RH, RI, RJ, RK, RL, RM, RN, RO, RP, RQ, RR, RS, RT, RU, RV, RW, RX, RY, RZ, SA, SB, SX, SY, SZ, TA and TB.

In another embodiment, the invention also pertains to compounds of the formula (XIII):

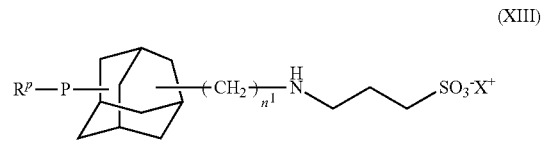

(XIII)

wherein:

n$^1$ is 0, 1, 2, or 3;

P is a covalent bond, alkyl, alkyloxy, amino, alkylamino, sulfur, or alkylthio;

X⁺ is hydrogen, a cationic group, or an ester-forming group; and

R$^p$ is a natural or unnatural amino acid residue, or a pharmaceutically acceptable salt, ester, or prodrug thereof.

In one embodiment, R$^p$ is connected to P through a non-peptidic bond. The non-peptidic bond may originate from any carbon atom of the amino acid resdue. In certain embodiments, R$^p$ may be connected to P through a heteroatom. Examples of R$^p$ include glycine (e.g., HO(C=O)—CHNH—), phenylalanine, and proline. In another embodiment, P is a covalent bond, CH$_2$, —NH—, —O—, alkylthio, or alkyloxy.

Examples of compounds of Formula (XIII) include, but are not limited to: Compound SC, SD, SE, SF, SG, SH, SI, SJ, SK, SL, SM, SN, SO, SP, SQ, SR, SS, ST, SU, SV and SW.

In another embodiment, compound of the formula (XIV):

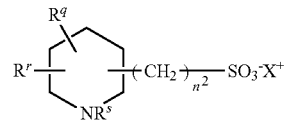

(XIV)

wherein:

n$^2$ is 0, 1, 2, or 3, selected such that three carbons are between the SO$_3$⁻X⁺ group and the nitrogen atom in the ring;

X⁺ is hydrogen, a cationic group, or an ester-forming group;

RS is hydrogen or when n$^2$ is 3, R$^s$ is (CH$_2$)$_3$—SO$_3$⁻X⁺;

R$^q$ and R$^r$ are each selected independently from hydrogen or alkyl, or a pharmaceutically acceptable salt, ester, or prodrug thereof.

In one embodiment, X⁺ is hydrogen.

In another embodiment, n$^2$ is 0 and the SO$_3$⁻X⁺ group is attached to at the 4-position of the piperazine ring. In another embodiment, n$^2$ is 1 and the SO$_3$⁻X⁺ group is attached to at the 3-position of the piperazine ring. In yet another embodiment, $n^2$ is 2 and the $SO_3^-X^+$ group is attached to at the 2-position of the piperazine ring. In another embodiment, $n^2$ is 3 and $R^s$ is $(CH_2)_3$—$SO_3^-X^+$.

Examples of compounds of Formula XIV include, but are not limited to: Compound OI, OJ, OK, PG and QP.

In yet another embodiment, the invention also pertains to compounds of the formula (XV):

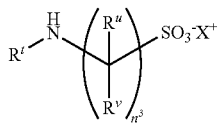
(XV)

wherein:
$R^t$ is hydrogen, alkyl, or aryl;
$R^u$ and $R^v$ are each independently for each occurence selected from hydrogen, aryl, benzyl, alkyl, alkenyl, carbocyclic, heterocyclic, or two $R^u$ or $R^v$ groups on adjacent carbon atoms may form a double bound, or together with the carbon atoms they are attached to forming a carbocyclic or heterocyclic ring;
$n^3$ is 4, 5, 6, or 7; and
$X^+$ is hydrogen, a cationic group, or an ester-forming group; or a pharmaceutically acceptable salt, ester, or prodrug thereof.

Examples of compounds of Formula XV include, but are not limited to: Compound N27 and N31.

Other compounds of the invention include:

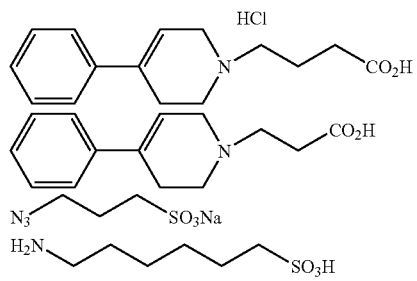

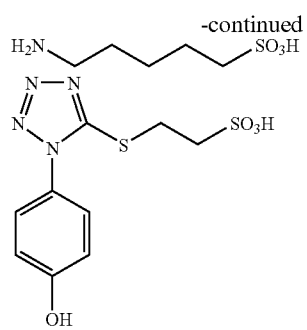

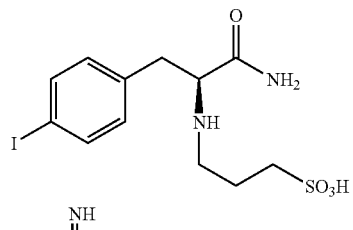

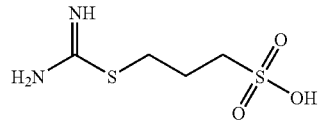

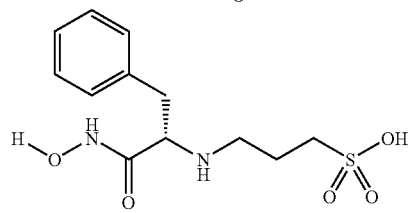

and pharmaceutically acceptable salts, esters, and prodrugs thereof.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein.

Compounds of the invention are also shown in Tables 2A, 2B, 3A, and 3B below.

TABLE 2A

| ID | STRUCTURE |
|---|---|
| B | (structure) |
| C | (structure) |
| D | (structure) |

TABLE 2A-continued
| ID | STRUCTURE |
|---|---|
| E | 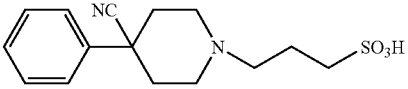 |
| F | 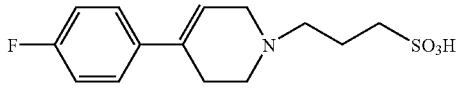 |
| G | 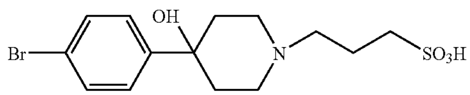 |
| H | 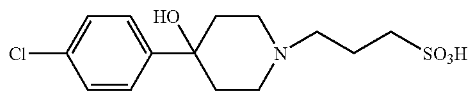 |
| I | 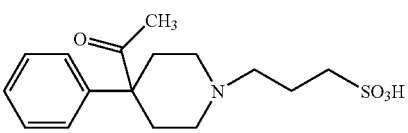 |
| J | 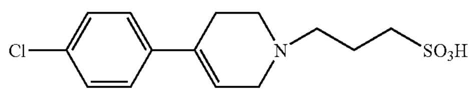 |
| K | 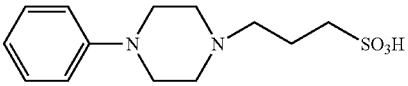 |
| L | 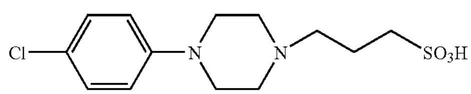 |
| M | 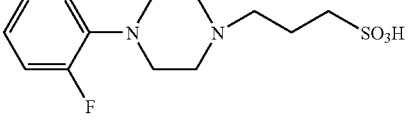 |
| N | 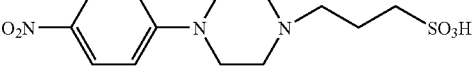 |
| P | 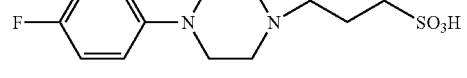 |
| Q | 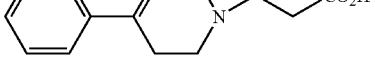 |
| R | 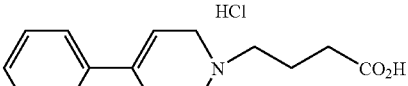 |
| S | 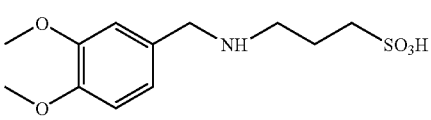 |

TABLE 2A-continued
| ID | STRUCTURE |
|---|---|
| X | 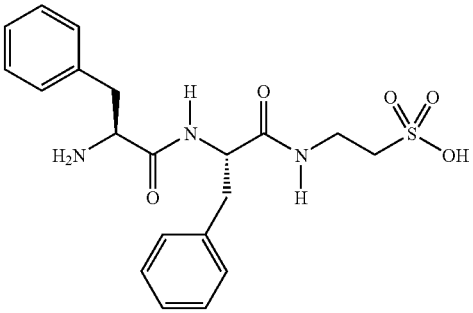 |
| Y | 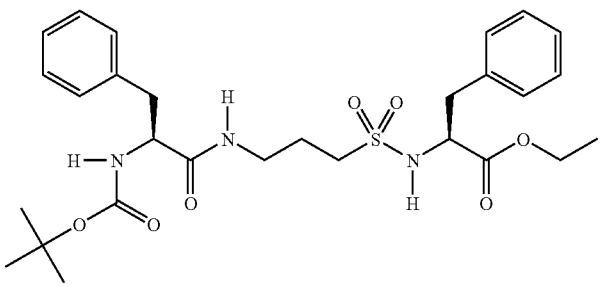 |
| Z | 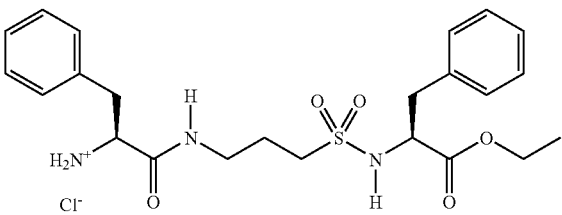 |
| AA | 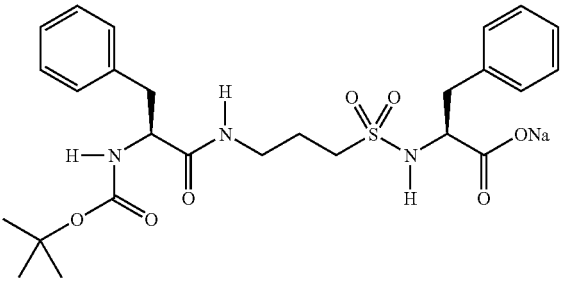 |
| AB | 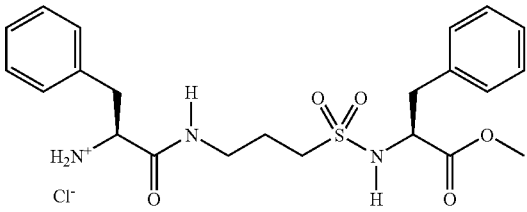 |
| AC | 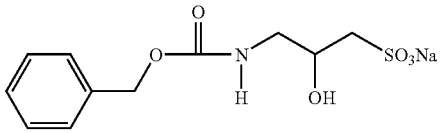 |

TABLE 2A-continued

| ID | STRUCTURE |
|---|---|
| AD | Benzyl N-(4-sulfonatobutyl)carbamate, sodium salt (benzyl carbamate linked to -(CH$_2$)$_4$-SO$_3$Na) |
| AE | Benzyl N-(3-sulfonatopropyl)carbamate, sodium salt (benzyl carbamate linked to -(CH$_2$)$_3$-SO$_3$Na) |
| AF | 1-(Diphenylmethyl)-3-(3-sulfopropyl)urea (Ph$_2$CH-NH-C(O)-NH-(CH$_2$)$_3$-SO$_3$H) |
| AG | N-(3-sulfonatopropyl)-2-phenylacetamide, sodium salt (PhCH$_2$-C(O)-NH-(CH$_2$)$_3$-SO$_3$Na) |
| AH | 1-Benzyl-3-(3-sulfonatopropyl)urea, sodium salt (PhCH$_2$-NH-C(O)-NH-(CH$_2$)$_3$-SO$_3$Na) |
| AI | 1-Hexyl-3-(3-sulfonatopropyl)urea, sodium salt (C$_6$H$_{13}$-NH-C(O)-NH-(CH$_2$)$_3$-SO$_3$Na) |
| AJ | 1-Dodecyl-3-(3-sulfonatopropyl)urea, sodium salt (long alkyl chain-NH-C(O)-NH-(CH$_2$)$_3$-SO$_3$Na) |
| AK | 1-(Adamantan-1-yl)-3-(3-sulfonatopropyl)urea, sodium salt (adamantyl-NH-C(O)-NH-(CH$_2$)$_3$-SO$_3$Na) |
| AL | N-(3-sulfonatopropyl)-2-(4-isobutylphenyl)propanamide, sodium salt (ibuprofen amide with -(CH$_2$)$_3$-SO$_3$Na) |
| AM | 1-Benzyl-3-(3-sulfonatopropyl)thiourea, sodium salt (PhCH$_2$-NH-C(S)-NH-(CH$_2$)$_3$-SO$_3$Na) |

TABLE 2A-continued

| ID | STRUCTURE |
|---|---|
| AU | Dibenzylamine-propyl-SO2-NH-CH(CH2Ph)-CO2Na |
| AV | Dibenzylamine-propyl-SO3H |
| AW | 3,4-methylenedioxybenzyl-NH-propyl-SO3H |
| AX | 3,4-dimethoxybenzyl-NH-propyl-SO3H |
| AY | 3,4,5-trimethoxybenzyl-NH-propyl-SO3H |
| AZ | 2,3-dimethoxybenzyl-NH-propyl-SO3H |
| BA | 3,5-dimethoxybenzyl-NH-propyl-SO3H |
| BB | 2,4-dimethoxybenzyl-NH-propyl-SO3H |
| BC | 3,4-dihydroxybenzyl-NH-propyl-SO3H |

TABLE 2A-continued

| ID | STRUCTURE |
|----|-----------|
| BW | 1-adamantyl-NH-(CH2)3-SO3H |
| BX | tert-butyl-NH-(CH2)3-SO3H |
| BY | 2-norbornyl-NH-(CH2)3-SO3H |
| BZ | 2-adamantyl-NH-(CH2)3-SO3H |
| CC | $H_2N-(CH_2)_4-SO_3H$ |
| CD | $H_2N-(CH_2)_5-SO_3H$ |
| CE | isobutyl-NH-(CH2)3-SO3H |
| CG | isopropyl-NH-(CH2)3-SO3H |
| CH | isoamyl-NH-(CH2)3-SO3H |
| CI | cyclopropyl-NH-(CH2)3-SO3H |
| CJ | cyclopentyl-NH-(CH2)3-SO3H |
| CK | cycloheptyl-NH-(CH2)3-SO3H |

TABLE 2A-continued

| ID | STRUCTURE |
|---|---|
| CL | 3-amino-propylsulfonyl-N-(ethoxycarbonyl-phenylmethyl)amide (H₂N-CH₂CH₂CH₂-SO₂-NH-CH(CH₂Ph)-C(O)-O-Et) |
| CM | Cyclopentyl-NH-SO₃Na |
| CN | Cycloheptyl-NH-SO₃Na |
| CO | (4-iodophenyl)-CH₂-CH(C(O)NH₂)-NH-CH₂CH₂CH₂-SO₃H |
| CV | Et-NH-CH₂CH₂CH₂-SO₃H |
| CY | (3,5-dimethyl-1-adamantyl)-NH-CH₂CH₂CH₂-SO₃H |
| DC | Cyclohexyl-NH-CH₂-CH(OH)-CH₂-SO₃H |
| DD | (Et)₂CH-NH-CH₂CH₂CH₂-SO₃H |
| DE | 1-(4-hydroxyphenyl)-5-(S-CH₂CH₂-SO₃H)-tetrazole |

TABLE 2A-continued
| ID | STRUCTURE |
|---|---|
| DG | 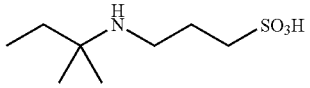 |
| DH | 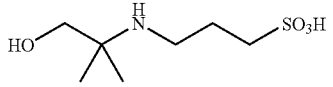 |
| DI | 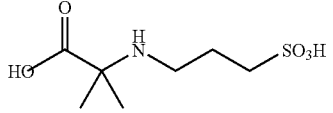 |
| DJ | 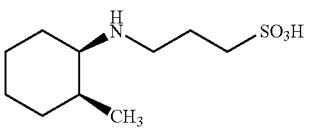 |
| DK | 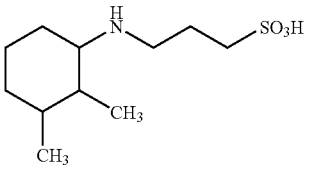 |
| DL | 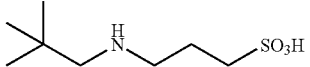 |
| DM | 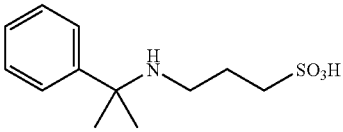 |
| DN | 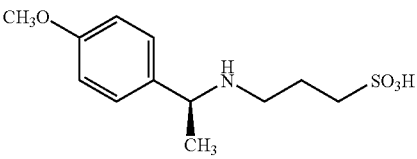 |
| DO | 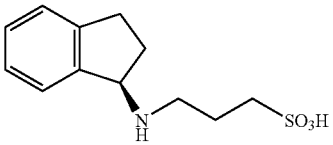 |
| DP | 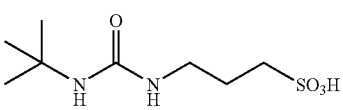 |
| DQ | 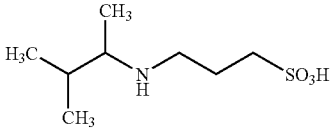 |

TABLE 2A-continued

| ID | STRUCTURE |
|---|---|
| DR | 4-methylcyclohexyl-NH-(CH$_2$)$_3$-SO$_3$H |
| DS | (2-methylbutyl)-NH-(CH$_2$)$_3$-SO$_3$H |
| DT | (CH$_3$)$_3$C-C(O)-NH-(CH$_2$)$_3$-SO$_3$H |
| DU | tert-butyl-NH-CH$_2$CH$_2$-SO$_3$H |
| DV | cyclohexyl-CH$_2$-NH-(CH$_2$)$_3$-SO$_3$H |
| DW | (3-ethylpent-1-yn-3-yl)-NH-(CH$_2$)$_3$-SO$_3$H |
| DX | (1-ethynylcyclohexyl)-NH-(CH$_2$)$_3$-SO$_3$H |
| DY | PhCH(OH)-CH$_2$-NH-(CH$_2$)$_3$-SO$_3$H |
| DZ | (S)-1-(4-methoxyphenyl)ethyl-NH-(CH$_2$)$_3$-SO$_3$H |
| EA | (4-bromophenyl)-CH$_2$CH$_2$-NH-(CH$_2$)$_3$-SO$_3$H |
| EB | (R)-2,3-dihydro-1H-inden-1-yl-NH-(CH$_2$)$_3$-SO$_3$H |

TABLE 2A-continued
| ID | STRUCTURE |
|---|---|
| EC | 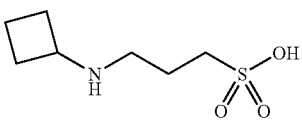 |
| ED | 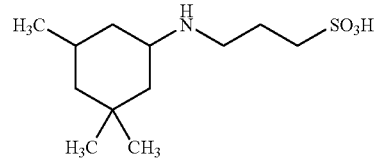 |
| EE | 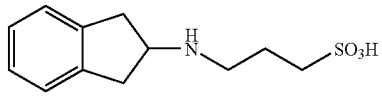 |
| EF | 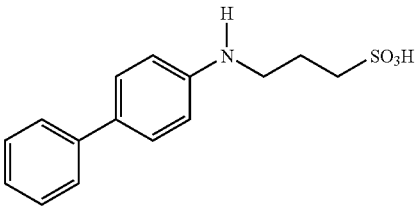 |
| EG | 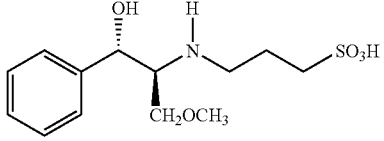 |
| EH | 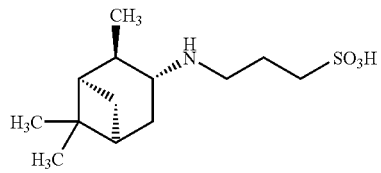 |
| EI | 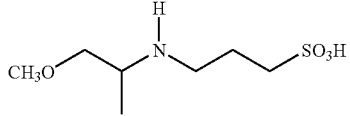 |
| EJ | 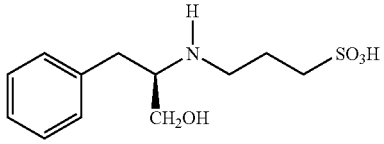 |
| EK | 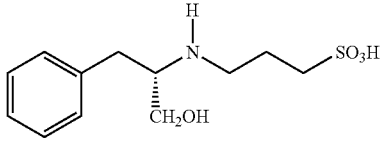 |
| EL | 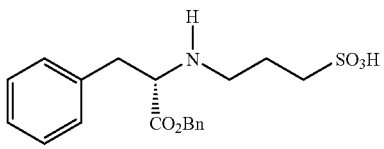 |

TABLE 2A-continued
| ID | STRUCTURE |
|---|---|
| EN | 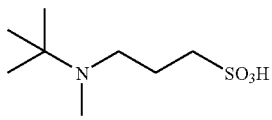 |
| EO | 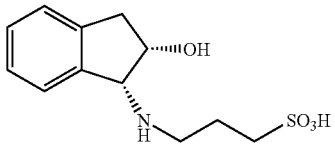 |
| EP | 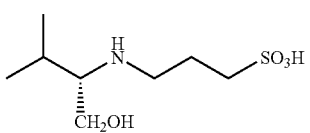 |
| EQ | 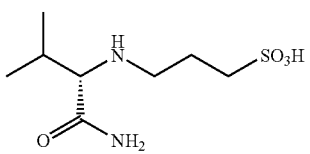 |
| ER | 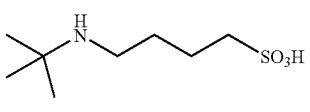 |
| ES | 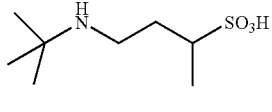 |
| ET | 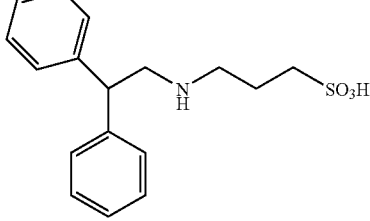 |
| EV | 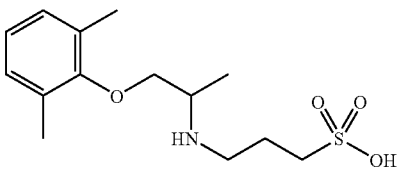 |
| EW | 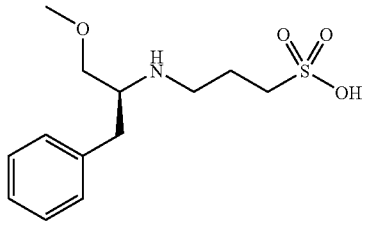 |
| EY | 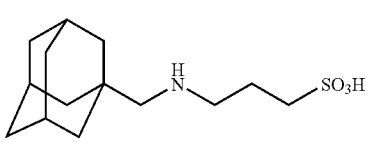 |

TABLE 2A-continued
| ID | STRUCTURE |
|---|---|
| EZ | 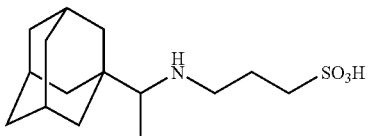 |
| FA | 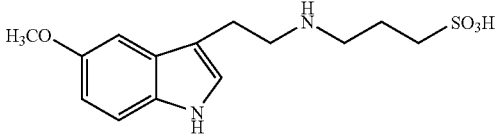 |
| FH | 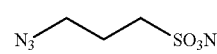 |
| FL | 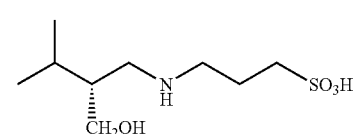 |
| FM | 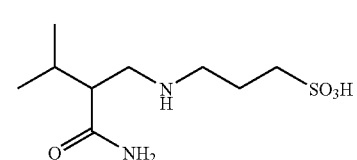 |
| FN | 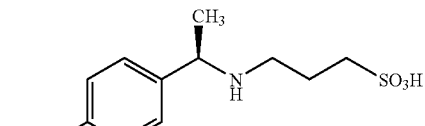 |
| FO | 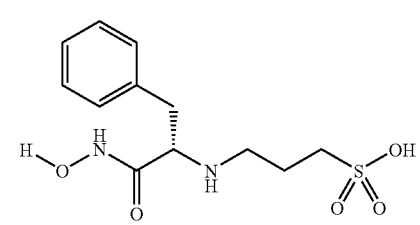 |
| FP | 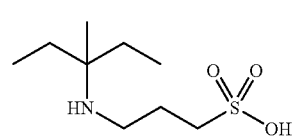 |
| FQ | 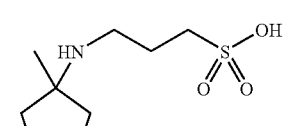 |
| FR | 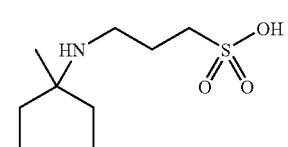 |

TABLE 2A-continued

| ID | STRUCTURE |
|---|---|
| FS | 1-methylcycloheptyl-NH-CH2CH2CH2-SO2-OH |
| FT | (S)-methyl 2-((3-sulfopropyl)amino)-3-methylbutanoate |
| FU | (R)-1-cyclohexylethyl-NH-CH2CH2CH2-SO3H |
| FV | (S)-2-((3-sulfopropyl)amino)propanamide |
| FW | (S)-1-cyclohexylethyl-NH-CH2CH2CH2-SO3H |
| FX | 4-tert-butylcyclohexyl-NH-CH2CH2CH2-SO3H |
| FY | (1S,2S)-2-(benzyloxy)cyclopentyl-NH-CH2CH2CH2-SO3H |
| FZ | (1R,2R)-2-(benzyloxy)cyclopentyl-NH-CH2CH2CH2-SO3H |

TABLE 2A-continued

| ID | STRUCTURE |
|---|---|
| GA | (S)-2-benzyl-N-cyclohexyl-2-((3-sulfopropyl)amino)acetamide; phenylalanine-derived with N-(3-sulfopropyl) and N-cyclohexyl amide |
| GB | trans-2-(benzyloxy)-N-(3-sulfopropyl)cyclohexan-1-amine |
| GC | (S)-3-methyl-2-((3-sulfopropyl)amino)butanoic acid (valine-N-sulfopropyl) |
| GD | trans-2-(benzyloxy)-N-(3-sulfopropyl)cyclohexan-1-amine (stereoisomer) |
| GE | benzyl (S)-3-methyl-2-((3-sulfopropyl)amino)butanoate |
| GF | ethyl (S)-2-((3-sulfopropyl)amino)propanoate |
| GH | methyl (S)-4-methyl-2-((3-sulfopropyl)amino)pentanoate |
| GI | (S)-N-tert-butyl-2-((3-sulfopropyl)amino)propanamide |

TABLE 2A-continued

| ID | STRUCTURE |
|---|---|
| GJ | (S)-3-((1-hydroxymethyl-3-methylbutyl)amino)propane-1-sulfonic acid derivative: isobutyl-CH(CH₂OH)-NH-CH₂CH₂CH₂-SO₃H |
| GK | sec-butyl-CH(CH₂OH)-NH-CH₂CH₂CH₂-SO₃H |
| GL | (R)-isobutyl-CH(CH₂OH)-NH-CH₂CH₂CH₂-SO₃H |
| GM | tert-butyl-CH(CO₂Me)-NH-CH₂CH₂CH₂-SO₃H |
| GN | Ph-CH(CONH₂)-NH-CH₂CH₂CH₂-SO₃H |
| GO | H₃C-CH(CO₂tBu)-NH-CH₂CH₂CH₂-SO₃H |
| GP | Ph-CH(CONH₂)-NH-CH₂CH₂CH₂-SO₃H |
| GQ | H₃C-CH(CO₂H)-NH-CH₂CH₂CH₂-SO₃H |
| GR | Bn-CH(CO₂H)-NH-CH₂CH₂CH₂-SO₃H |

TABLE 2A-continued

| ID | STRUCTURE |
|---|---|
| GS | Valine with N-propylsulfonic acid, allyl ester |
| GT | Leucine with N-propylsulfonic acid, amide |
| GU | Leucine with N-propylsulfonic acid, benzyl ester |
| GZ | Isoleucine with N-propylsulfonic acid, methyl ester |
| HA | Isoleucine with N-propylsulfonic acid, carboxylic acid |
| HB | Phenylalanine with N-propylsulfonic acid, amide |
| HC | Leucine with N-propylsulfonic acid, methyl ester |
| HD | Valine with N-propylsulfonic acid, amide |
| HE | Phenylalanine with N-propylsulfonic acid, amide |

TABLE 2A-continued

| ID | STRUCTURE |
|---|---|
| HF | *(structure: N-(benzyloxycarbonyl isoleucine) propanesulfonic acid derivative)* |
| HG | *(structure: leucine amide N-linked to propanesulfonic acid)* |
| HI | *(structure: N-(benzyloxycarbonyl leucine) propanesulfonic acid derivative)* |
| HJ | *(structure: 6-hydroxy-6-methylheptan-2-yl amino propanesulfonic acid)* |
| HK | *(structure: N-(methyl ester of alanine) propanesulfonic acid)* |
| HL | *(structure: 4-methoxyphenyl amino propanesulfonate)* |
| HM | *(structure: 4-aminophenyl amino propanesulfonate)* |
| HN | *(structure: 3-azidopropanesulfonate)* |
| HO | *(structure: N-methylamino propanesulfonate)* |

TABLE 2A-continued

| ID | STRUCTURE |
|---|---|
| HP | (imidazolium with two propylsulfonate groups, one as sulfonate anion) |
| HQ | (quinuclidine with NH-CH₂CH₂CH₂-SO₃⁻ substituent) |
| HR | (imidazole with N-propylsulfonate) |
| HS | (imidazolium chloride with two N-propyl-SO₃H groups) |
| HT | (4-fluorophenyl-NH-CH₂CH₂CH₂-SO₃⁻) |
| HU | (2-hydroxyphenyl-NH-CH₂CH₂CH₂-SO₃⁻) |
| HV | (pyrrole with N-propylsulfonate) |
| HW | (bis-imidazole linked by propyl, with terminal propylsulfonate) |

TABLE 2A-continued
| ID | STRUCTURE |
|----|-----------|
| HX | 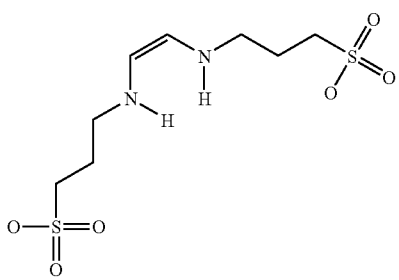 |
| HY | 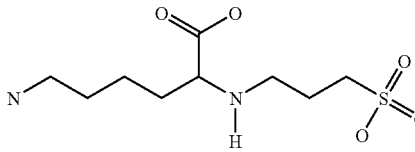 |
| HZ | 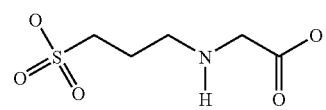 |
| IA | 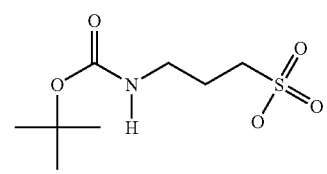 |
| IB | 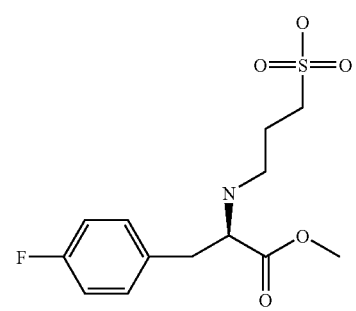 |
| IC | 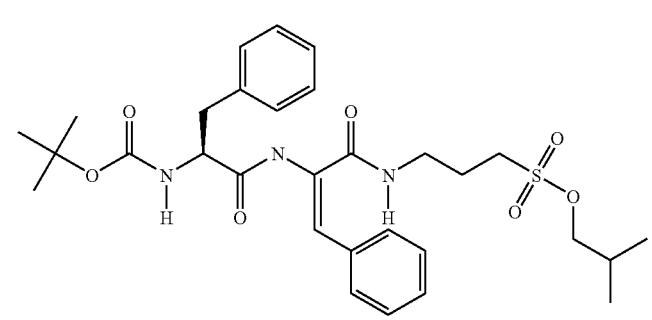 |

TABLE 2A-continued

| ID | STRUCTURE |
|---|---|
| ID | (structure) |
| IE | (structure) |
| IF | (structure) |
| IG | (structure) |
| IH | (structure) |

TABLE 2A-continued

| ID | STRUCTURE |
|---|---|
| II | (5-(N,N-diacetylamino)-2-(3-sulfopropyl)isoquinolinium) |
| IJ | (5-nitro-2-(3-sulfopropyl)isoquinolinium) |
| IK | (5-bromo-2-(3-sulfopropyl)-1,2,3,4-tetrahydroisoquinoline) |
| IL | (7-nitro-2-(3-sulfopropyl)-1,2,3,4-tetrahydroisoquinoline) |
| IM | (7-amino-2-(3-sulfopropyl)-1,2,3,4-tetrahydroisoquinoline) |
| IN | (7-bromo-2-(3-sulfopropyl)-1,2,3,4-tetrahydroisoquinoline) |
| IO | (5-methyl-2-(3-(isobutoxysulfonyl)propyl)-1,2,3,4-tetrahydroisoquinoline) |

TABLE 2A-continued
| ID | STRUCTURE |
|---|---|
| IP | 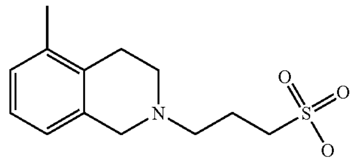 |
| IR | 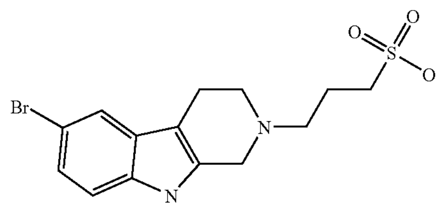 |
| IS | 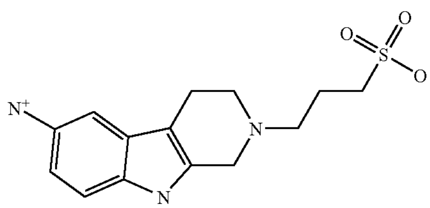 |
| IT | 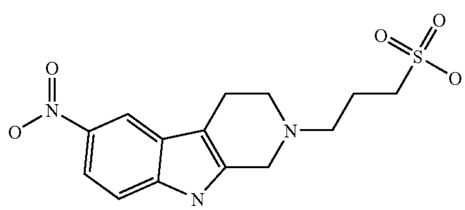 |
| IU | 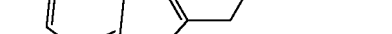 |
| IV | 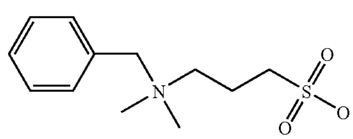 |
| IW | 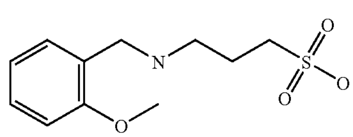 |
| IX | 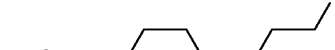 |

TABLE 2A-continued
| ID | STRUCTURE |
|---|---|
| IY | 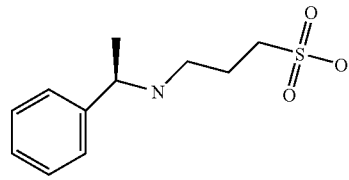 |
| IZ | 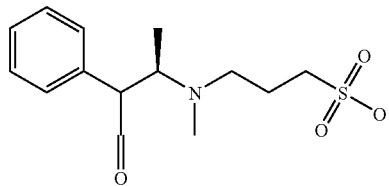 |
| JA | 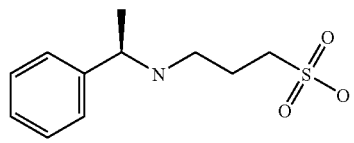 |
| JB | 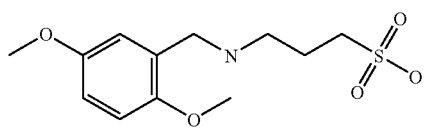 |
| JC | 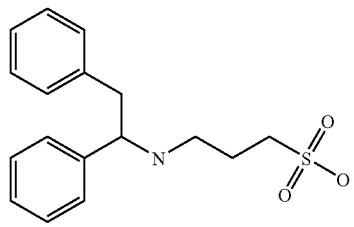 |
| JD | 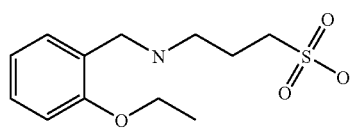 |
| JE | 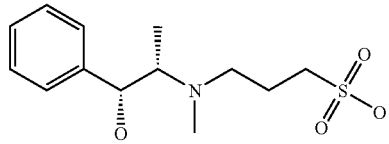 |
| JF | 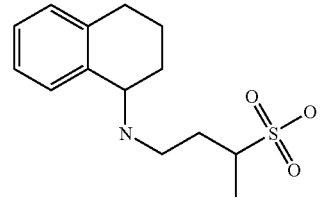 |
| JG | 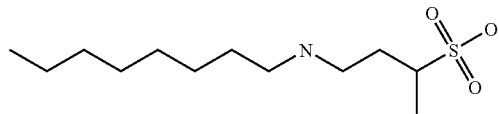 |

TABLE 2A-continued
| ID | STRUCTURE |
|---|---|
| JH | 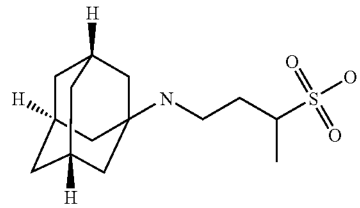 |
| JI | 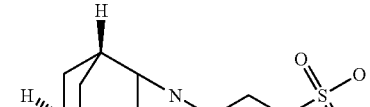 |
| JJ | 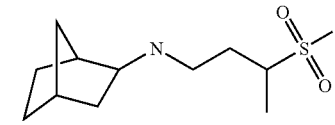 |
| JK | 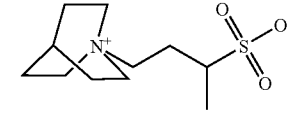 |
| JL | 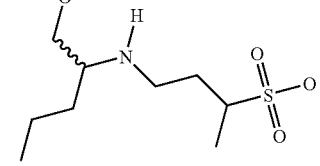 |
| JM | 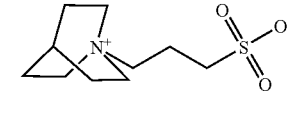 |
| JN | 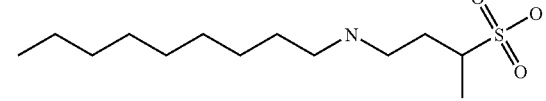 |
| JO | 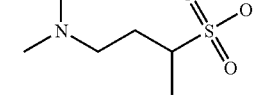 |
| JP | 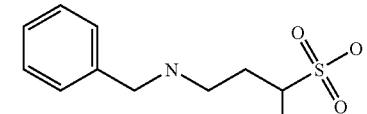 |
| JQ | 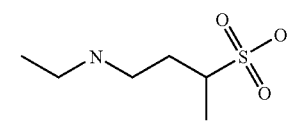 |

TABLE 2A-continued
| ID | STRUCTURE |
|---|---|
| JR | 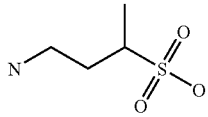 |
| JS | 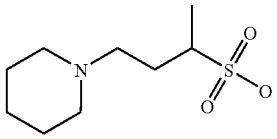 |
| JT | 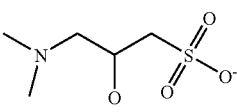 |
| JU | 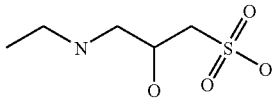 |
| JV | 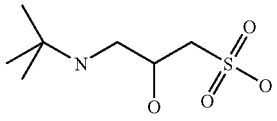 |
| JW | 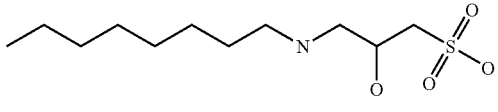 |
| JX | 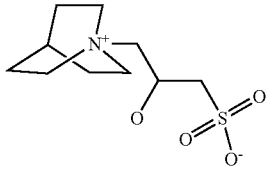 |
| JY | 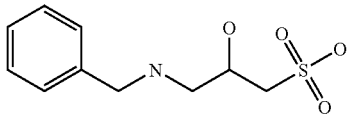 |
| JZ | 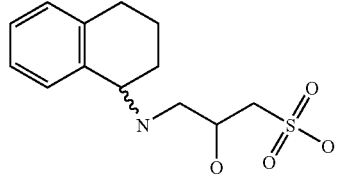 |
| KA | 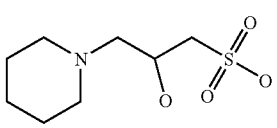 |

TABLE 2A-continued

| ID | STRUCTURE |
|---|---|
| KB | 1-adamantyl-NH-CH2-CH(OH)-CH2-SO3- |
| KH | isopentyl-NH-CH2-CH2-CH(CH3)-SO3- |
| KI | 2-norbornyl-NH-CH2-CH(OH)-CH2-SO3- |
| KJ | 2-adamantyl-NH-CH2-CH(OH)-CH2-SO3- |
| KK | isopentyl-NH-CH2-CH(OH)-CH2-SO3- |
| KL | CH3CH2CH2-CH(CH2OH)-NH-CH2-CH(OH)-CH2-SO3- |
| KM | cyclohexyl-NH-CH2-CH2-CH(CH3)-SO3- |
| KN | H2N-CH(CH2-Ph)-C(O)-NH-CH2CH2CH2-SO3- |

TABLE 2A-continued

| ID | STRUCTURE |
|---|---|
| KP | (structure) |
| KQ | (structure) |
| KR | (structure) |
| KS | (structure) |
| KT | (structure) |
| KV | (structure) |
| KW | (structure) |
| KX | (structure) |

TABLE 2A-continued
| ID | STRUCTURE |
|---|---|
| KY | 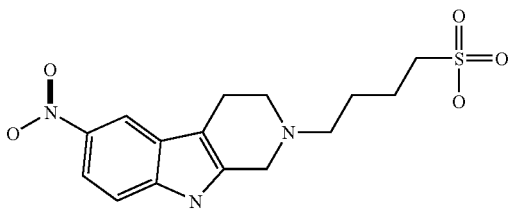 |
| LA | 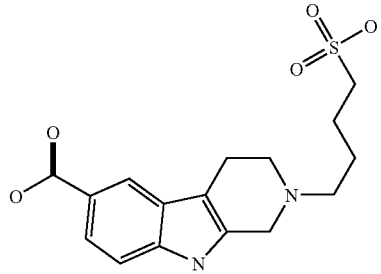 |
| LC | 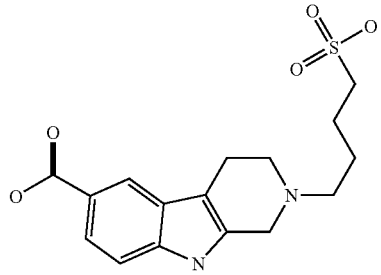 |
| LD | 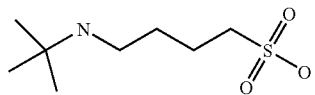 |
| LE | 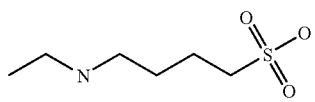 |
| LF | 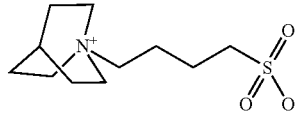 |
| LG | 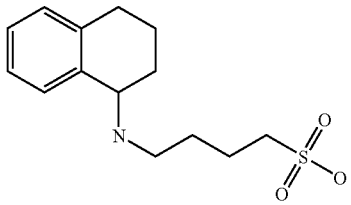 |
| LH | 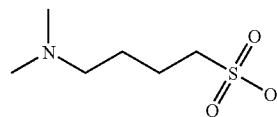 |

TABLE 2A-continued
| ID | STRUCTURE |
|---|---|
| LI | 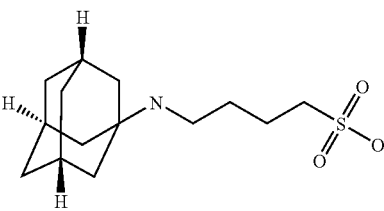 |
| LJ | 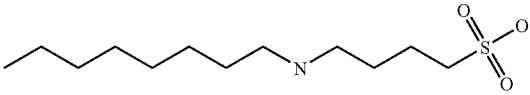 |
| LK | 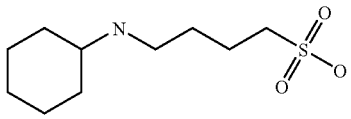 |
| LL | 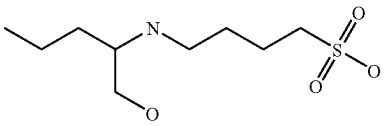 |
| LM | 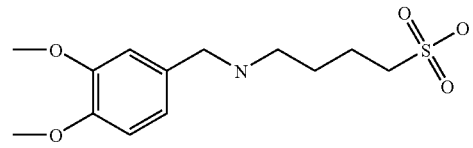 |
| LN | 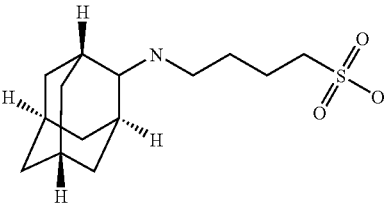 |
| LO | 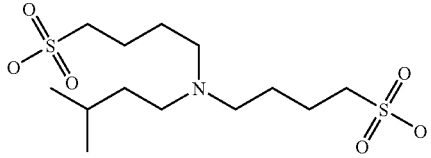 |
| LP | 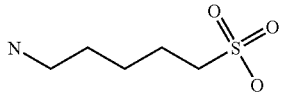 |
| LQ | 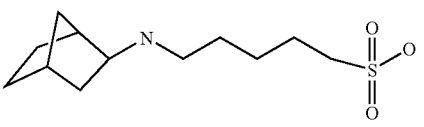 |
| NG | 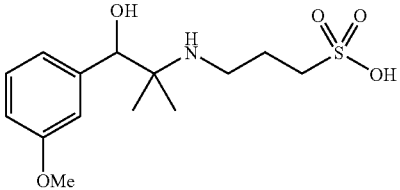 |

TABLE 2A-continued

| ID | STRUCTURE |
|---|---|
| NH | [cyclohexyl-CH2-(4-methylphenyl) with NH-CH2CH2CH2-SO3H substituent on cyclohexane] |
| NI | 4-MeO-C6H4-CH2-C(CH3)2-NH-CH2CH2CH2-SO3H |
| NJ | 4-Me-C6H4-CH(OH)-C(CH3)2-NH-CH2CH2CH2-SO3H |
| NK | 4-Me-C6H4-CH2-C(CH3)2-NH-CH2CH2CH2-SO3H |
| NL | 4-F-C6H4-CH(OH)-C(CH3)2-NH-CH2CH2CH2-SO3H |

TABLE 2B

| ID | STRUCTURE |
|---|---|
| P1 | benzo[d][1,2]oxathiole-3(2H)-one 1,1-dioxide |
| P2 | 1,2-oxathiolane 2,2-dioxide |
| P3 | 1,2-oxathiane 2,2-dioxide |

TABLE 2B-continued
P4 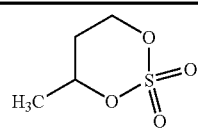
P5 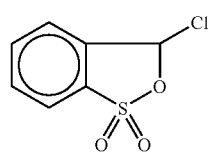
P6 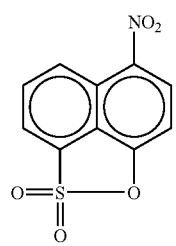
P7 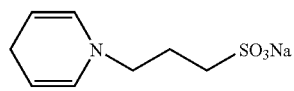
P8 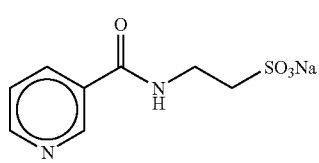
P9 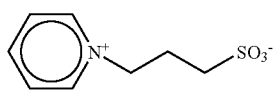
P10 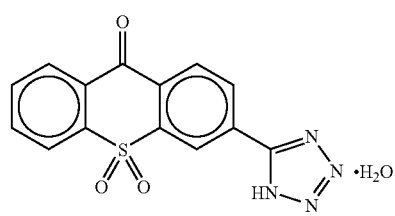
P11 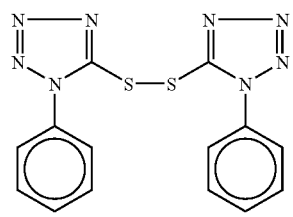
P12 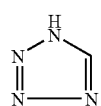
P13 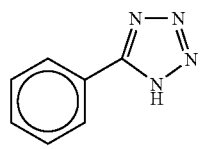

TABLE 2B-continued
P14 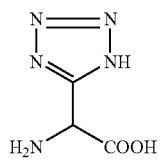
P15 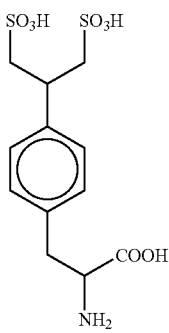
P16 NaO$_3$SOCH$_2$(CH$_2$)$_3$CH$_2$OSO$_3$Na
P17 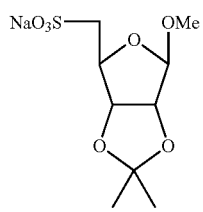
P178 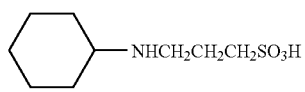
P19 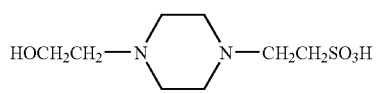
P20 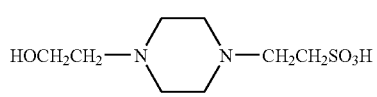
P21 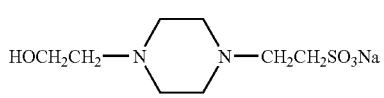
P22 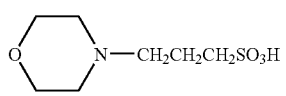
P23 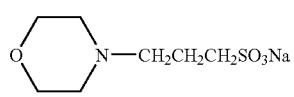
P24 HOCH$_2$CH$_2$CH$_2$CH$_2$SO$_3$Na
P25 (NaO$_3$SCH$_2$CH$_2$CH$_2$CH$_2$)$_2$O
P26 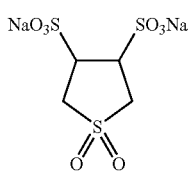

TABLE 2B-continued
P27 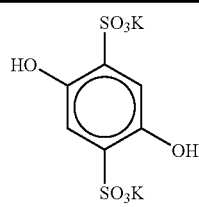
P28 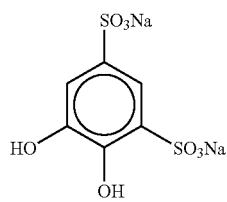
P29 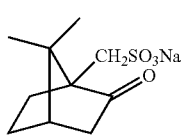
P30 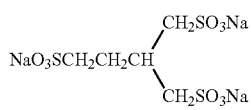
P31 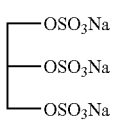
P32 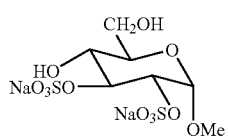
P33 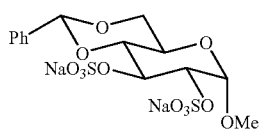
P34 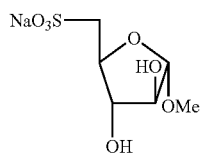
P35 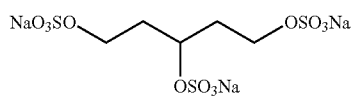
P36       $HC(CH_2OSO_3Na)_3$
P37       $CH_3C(CH_2OSO_3Na)_3$
P38       $NH_2CH_2CH_2CH_2SO_3Na$
P38 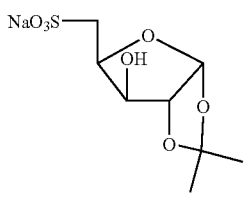

TABLE 2B-continued

| | |
|---|---|
| P40 | NH$_2$C(CH$_2$OSO$_3$Na)$_3$ |
| P41 | NH$_2$CH$_2$CH$_2$OSO$_3$H |

P42

[Structure: bis-indolinone with NaO$_3$S groups — indigo disulfonate disodium salt]

| | |
|---|---|
| P43 | NaO$_3$SNHCH$_2$CH$_2$OSO$_3$Na |
| P44 | H$_2$NCH$_2$CH$_2$CH$_2$OSO$_3$Na |

P45

[Structure: PhCH$_2$O—CH(CH$_2$OSO$_3$Na)—CH$_2$OSO$_3$Na]

| | |
|---|---|
| P46 | NaO$_3$SNHCH$_2$CH$_2$CH$_2$OSO$_3$Na |
| P47 | HN(CH$_2$CH$_2$OSO$_3$Na)$_2$ |
| P48 | NaO$_3$SN(CH$_2$CH$_2$OSO$_3$Na)$_2$ |

P49

[Structure: sucrose derivative with OR groups]

| | |
|---|---|
| P50 | H$_2$NCH$_2$CH$_2$SO$_3$H |
| P51 | H$_2$NCH$_2$CH$_2$SO$_3$H |
| P52 | NaO$_3$SOCH$_2$CH$_2$CH$_2$SO$_3$Na |

P53

[Structure: benzene-1,3-disulfonate disodium]

P54

[Structure: 2,5-dimethoxybenzene-1,4-disulfonate disodium]

P55

[Structure: 2,3-dimethoxybenzene-1,4-disulfonate disodium (alt. substitution)]

P56

[Structure: 2,5-dimethoxybenzene-1,4-disulfonate dipotassium]

TABLE 2B-continued
P57 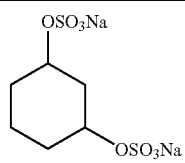
P58 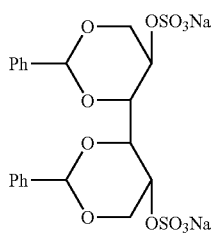
P59 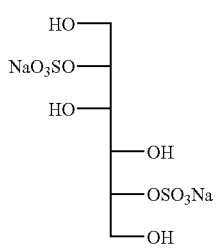
P60 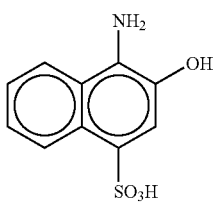
P61 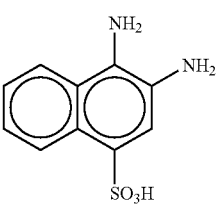
P62 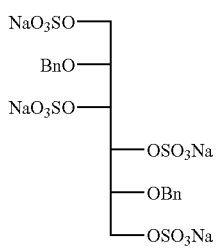
P63 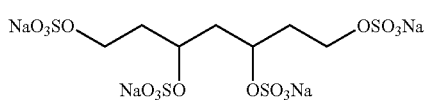
P64     CH$_3$CH$_2$CH$_2$CH$_2$SO$_3$Na
P65     CH$_3$(CH$_2$)$_8$CH$_2$SO$_3$Na
P66 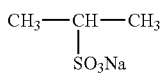

TABLE 2B-continued

| | |
|---|---|
| P67 | CH$_3$—CH$_2$—CH(SO$_3$Na)—CH$_2$—CH$_3$ |
| P68 | CH$_3$CH$_2$SO$_3$Na |
| P69 | CH$_3$CH$_2$CH$_2$SO$_3$Na |
| P70 | CH$_3$CH$_2$CH$_2$CH$_2$CH$_2$SO$_3$Na |
| P71 | (propyl)$_2$CH–SO$_3$Na |
| P71 | HO–(CH$_2$)$_3$–CH(SO$_3$Na)–(CH$_2$)$_3$–OH |
| P73 | N-(pyridin-4-yl)-3-sulfonatopropanamide, Na salt |
| P74 | NaO$_3$SO–(CH$_2$)$_3$–CH(OSO$_3$Na)–(CH$_2$)$_3$–OSO$_3$Na |
| P75 | 1-benzyl-4-(3-sulfonatopropanamido)piperidine, Na salt |
| P76 | NaO$_3$S–CH$_2$–CH(OH)–CH$_2$–SO$_3$Na |
| P77 | 4-(sulfonatooxy)pyrrolidine-2-carboxylate, Na$_2$ salt |
| P78 | 1,4-phenylene bis(sulfate), Na$_2$ salt |
| P79 | benzene-1,3,5-triyl tris(sulfate), Na$_3$ salt |
| P80 | N-(1-benzylpiperidin-4-yl)-2-sulfonatoacetamide, Na salt |

TABLE 2B-continued
| | |
|---|---|
| P81 | 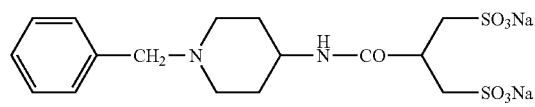 |
| P82 | 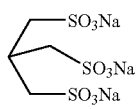 |
| P823 |  |
| P84 | 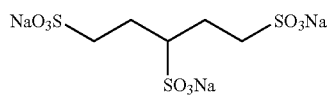 |
| P85 | 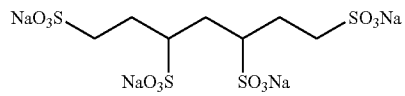 |
| P86 | 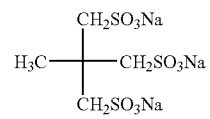 |
| P87 | 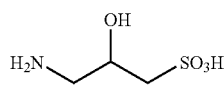 |
| P88 | 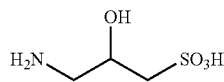 |
| P89 | 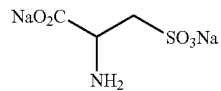 |
| P90 | 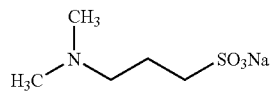 |
| P91 | 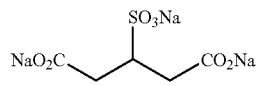 |
| P92 | 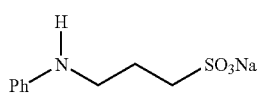 |
| P93 | 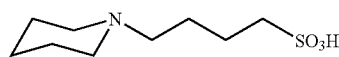 |
| P94 | 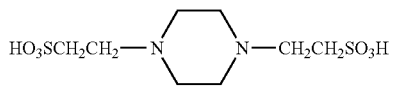 |
| P95 | 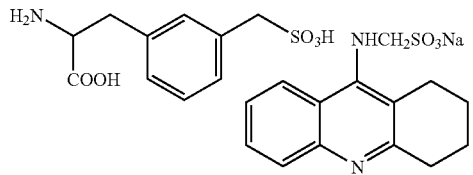 |

TABLE 2B-continued
P96 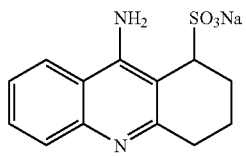
P97 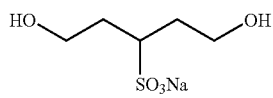
P98 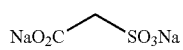
P99 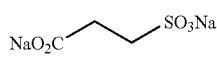
P100 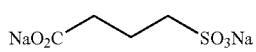
P101 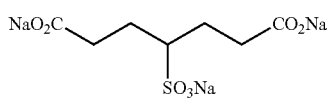
P102 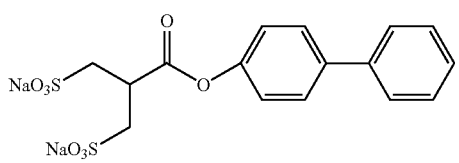
P103 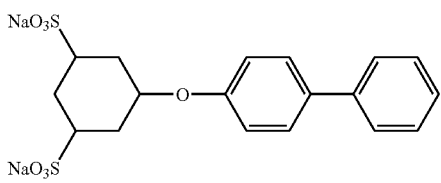
P104 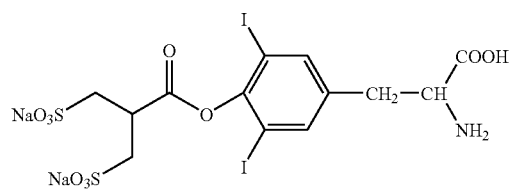
P105 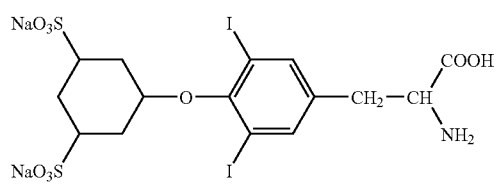
P106 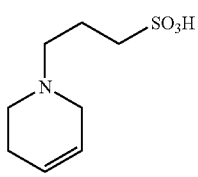

TABLE 2B-continued
P107 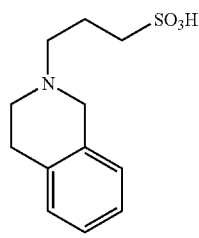
P108 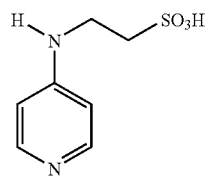
P109 $CH_3(CH_2)_{13}N^+(CH_3)_2[(CH_2)_3SO_3^-]$
P110 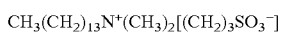
P111 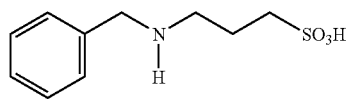
R = SO₃Na
P112 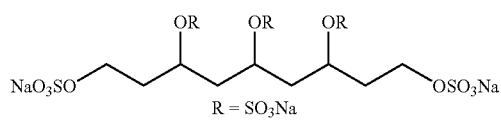
P113 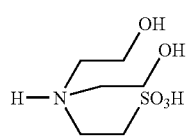
P114 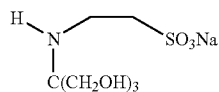
P115 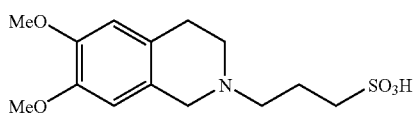
P116 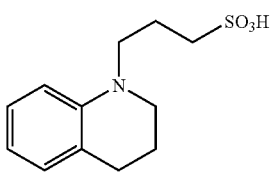
P117 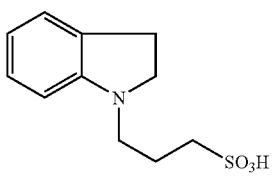

TABLE 2B-continued
P118 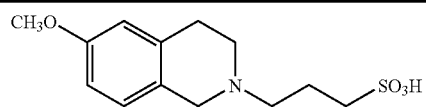
P119 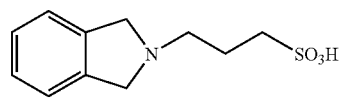
P120 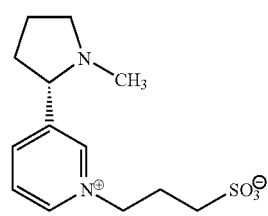
P121 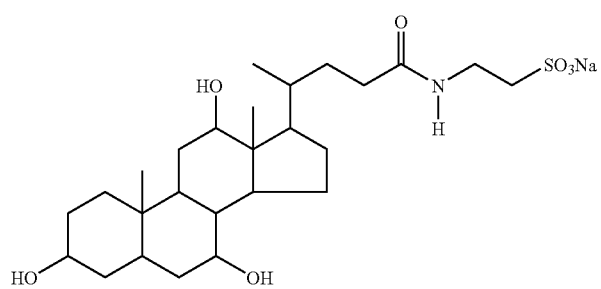
P122 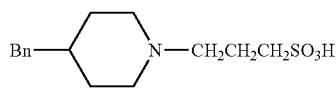
P123 AcNHCH$_2$CH$_2$CH$_2$SO$_3$Na
P124 BzNHCH$_2$CH$_2$CH$_2$SO$_3$Na
P125 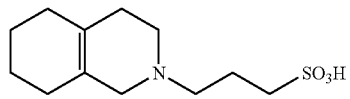
P126 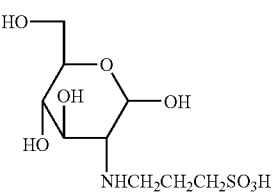
P127 HOCH$_2$CH$_2$CH$_2$NHCH$_2$CH$_2$CH$_2$SO$_3$H
P128 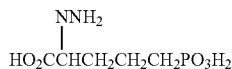
P129 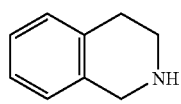
P130 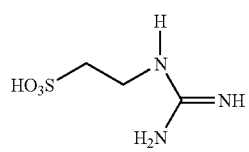

TABLE 2B-continued
P131 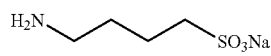
P132 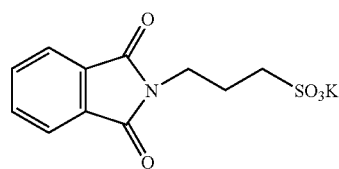
P134 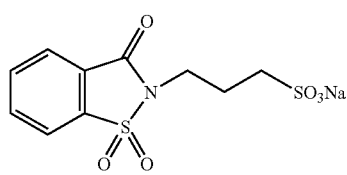
P135 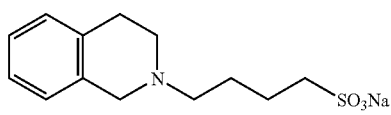
P136 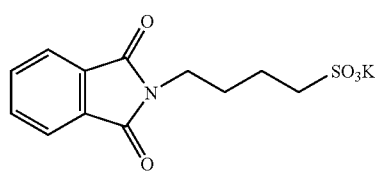
P137 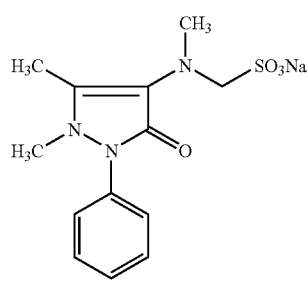
P138 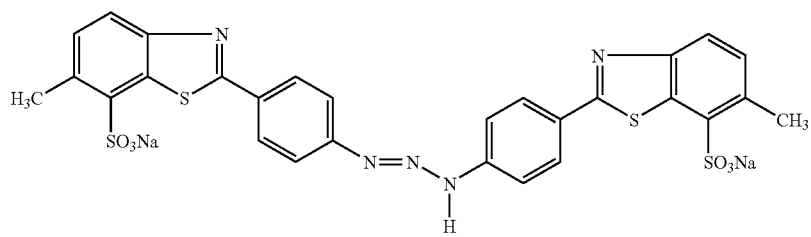
P139 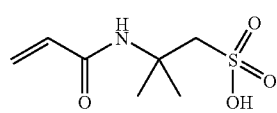
P140 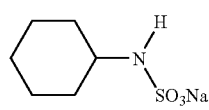

TABLE 2B-continued
P141 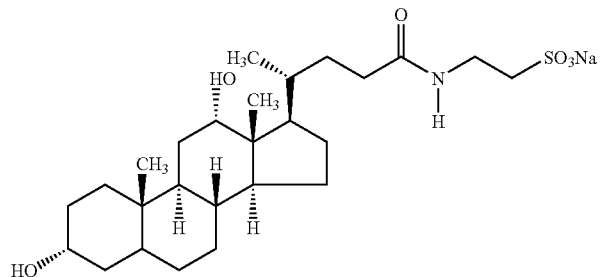
P142 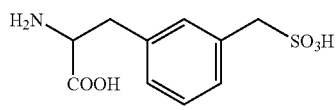
P143 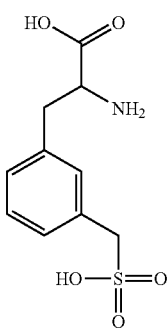
P144 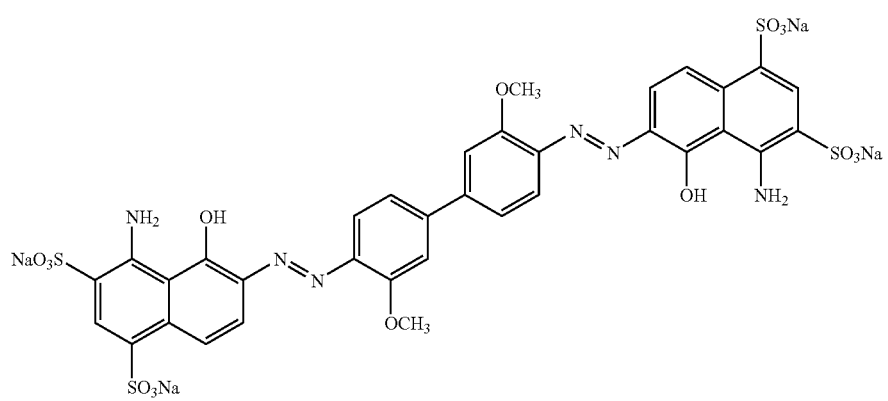
P145 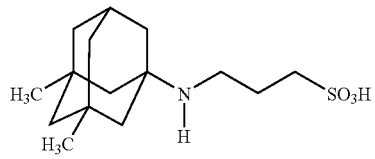
P146 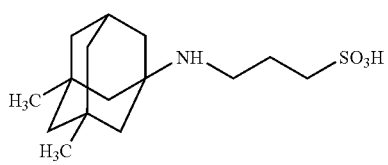
P147 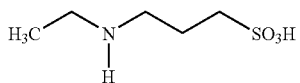

TABLE 2B-continued
| | |
|---|---|
| P148 | 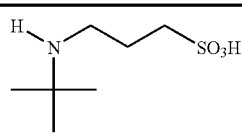 |
| P149 | 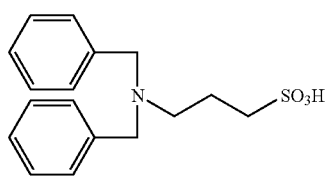 |
| P150 | 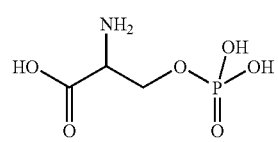 |
| P151 | 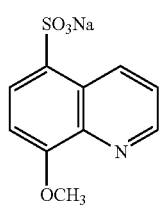 |
| P152 | 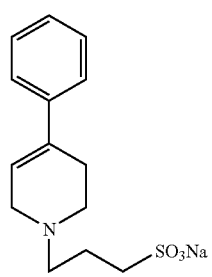 |
| P153 | 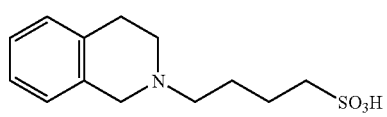 |
| P154 | 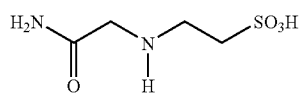 |
| P155 | 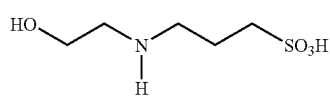 |
| P156 | 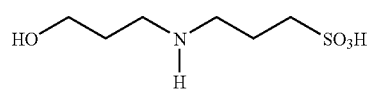 |
| P157 | 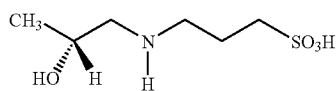 |
| P158 | 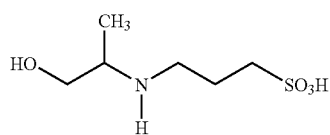 |

TABLE 2B-continued

| | |
|---|---|
| P159 | HO~~~N(H)~~~SO₃H |
| P160 | HO~~~~N(H)~~~SO₃H |
| P161 | HO~~~~~N(H)~~~SO₃H |
| P162 | HO-C₆H₄-N(H)-(CH₂)₃-SO₃H |
| P163 | CH₃-CH(OH)-CH₂-N(H)-(CH₂)₃-SO₃H |
| P164 | HOCH₂-C*(H)(CH₃)-N(H)-(CH₂)₃-SO₃H |
| P165 | HOCH₂-C*(H)(CH₃)-N(H)-(CH₂)₃-SO₃H |
| P166 | CH₃CH₂-C*(H)(CH₂OH)-N(H)-(CH₂)₃-SO₃H |
| P167 | CH₃CH₂-C*(H)(CH₂OH)-N(H)-(CH₂)₃-SO₃H |
| P168 | HO-(CH₂)₄-CH(CH₃)-N(H)-(CH₂)₃-SO₃H |
| P169 | cyclopentyl(CH₂OH)-N(H)-(CH₂)₃-SO₃H |
| P170 | CH₃(CH₂)₄-N(H)-(CH₂)₃-SO₃H |
| P171 | CH₃(CH₂)₅-N(H)-(CH₂)₃-SO₃H |

TABLE 2B-continued
| | |
|---|---|
| P172 | 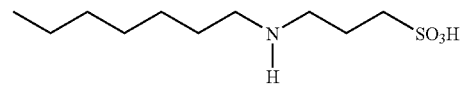 |
| P173 | 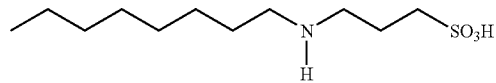 |
| P174 | CH$_3$(CH$_2$)$_8$NH(CH$_2$)$_3$SO$_3$H |
| P175 | CH$_3$(CH$_2$)$_9$NH(CH$_2$)$_3$SO$_3$H |
| P176 | CH$_3$(CH$_2$)$_{10}$NH(CH$_2$)$_3$SO$_3$H |
| P177 | CH$_3$(CH$_2$)$_{11}$NH(CH$_2$)$_3$SO$_3$H |
| P178 | CH$_3$(CH$_2$)$_{12}$NH(CH$_2$)$_3$SO$_3$H |
| P179 | CH$_3$(CH$_2$)$_{13}$NH(CH$_2$)$_3$SO$_3$H |
| P180 | CH$_3$(CH$_2$)$_{15}$NH(CH$_2$)$_3$SO$_3$H |
| P181 | CH$_3$(CH$_2$)$_{17}$NHCH$_2$CH$_2$CH$_2$SO$_3$H |
| P182 | 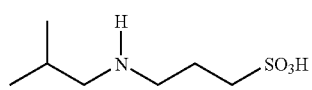 |
| P183 | 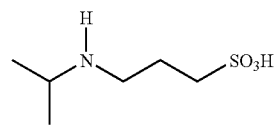 |
| P184 | 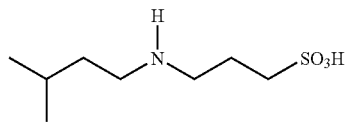 |
| P185 | 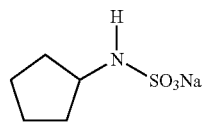 |
| P186 | 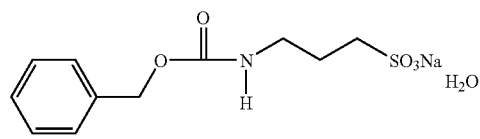 |
| P187 | 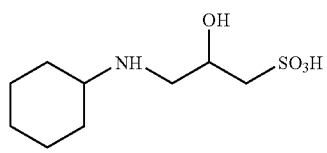 |
| P188 | 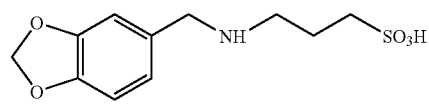 |
| P189 | 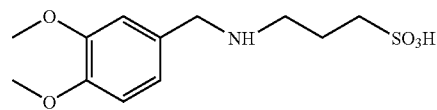 |

TABLE 2B-continued

| | |
|---|---|
| P190 | 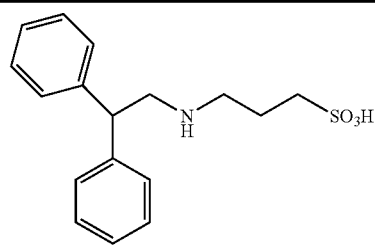 |
| P191 | 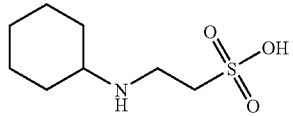 |
| P192 | 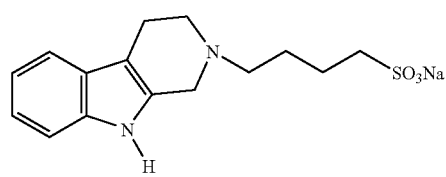 |

TABLE 3A

| ID | STRUCTURE |
|---|---|
| MJ | ethylamino-2-hydroxypropanesulfonic acid structure |
| NN | 1-ethylcyclopentylamino propanesulfonic acid structure |
| MX | norbornylamino butanesulfonic acid structure |
| NE | benzimidazol-2-ylthio methylpropanesulfonic acid structure |
| NM | 3-ethylpentan-3-ylamino propanesulfonic acid structure |
| NO | 1-ethylcycloheptylamino propanesulfonic acid structure |
| NP | 4-methylpentan-2-ylamino propanesulfonic acid structure |

TABLE 3A-continued
| ID | STRUCTURE |
|---|---|
| NQ | 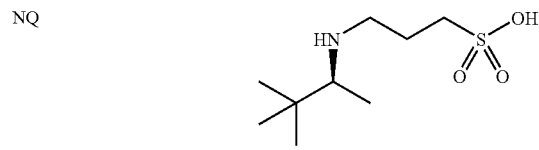 |
| NR | 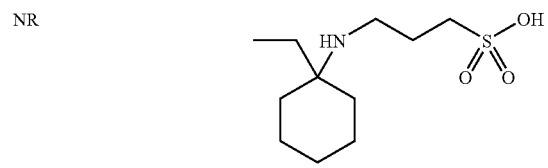 |
| NS | 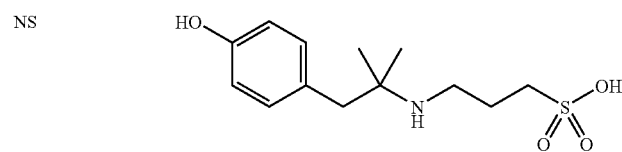 |
| NT | 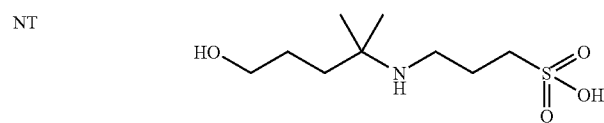 |
| NU | 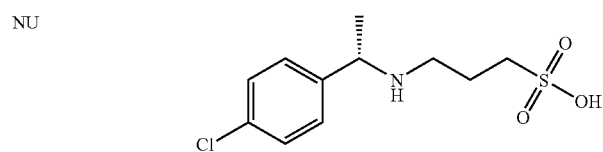 |
| NV | 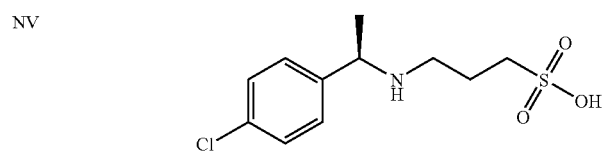 |
| NW | 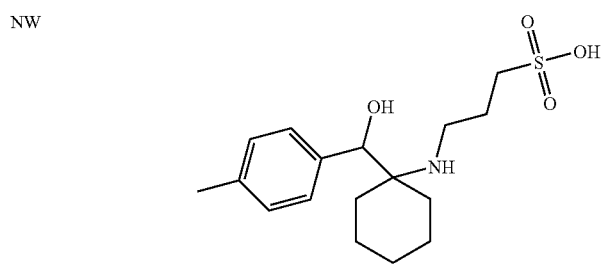 |
| NX | 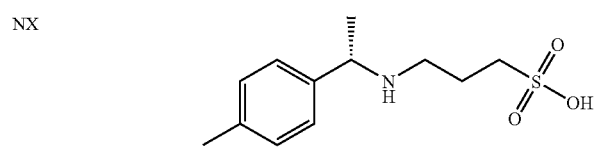 |
| NY | 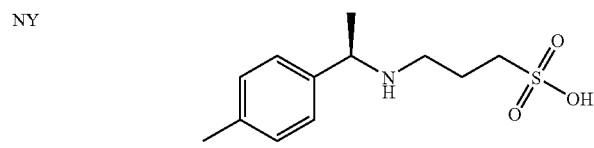 |

TABLE 3A-continued
| ID | STRUCTURE |
|---|---|
| NZ | 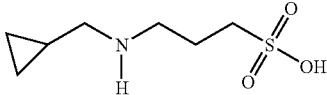 |
| OA | 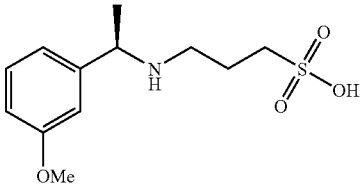 |
| OB | 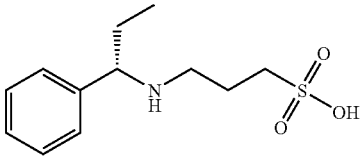 |
| OC | 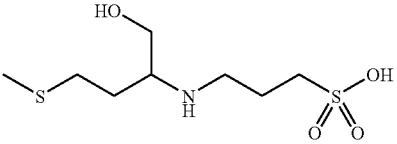 |
| OD | 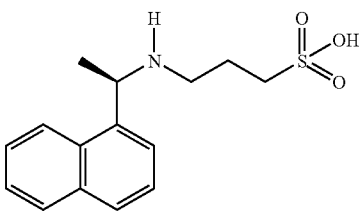 |
| OE | 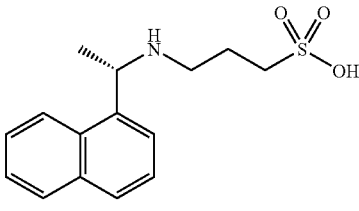 |
| OF | 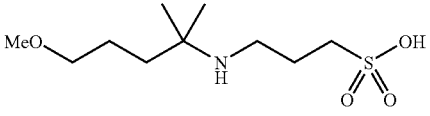 |
| OG | 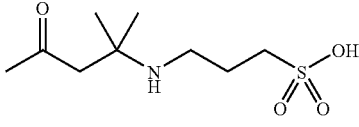 |
| OH | 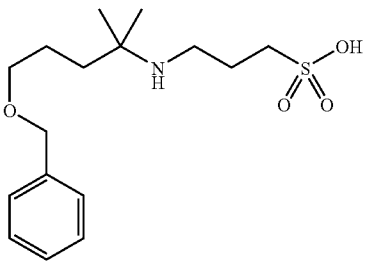 |

TABLE 3A-continued

| ID | STRUCTURE |
|---|---|
| OI | (piperidin-3-yl)methanesulfonic acid |
| OJ | 3-(3-(hydroxymethyl)piperidin-1-yl)propane-1-sulfonic acid |
| OK | 3-(2-(2-hydroxyethyl)piperidin-1-yl)propane-1-sulfonic acid |
| OL | 3-((1-(4-bromophenyl)ethyl)amino)propane-1-sulfonic acid |
| OM | 3-((1-(4-nitrophenyl)ethyl)amino)propane-1-sulfonic acid |
| ON | 3-((2-carbamoylcyclohexyl)amino)propane-1-sulfonic acid |
| OO | 4-((1-(naphthalen-2-yl)ethyl)amino)butane-1-sulfonic acid |
| OP | 3-((1-(naphthalen-2-yl)ethyl)amino)propane-1-sulfonic acid |

TABLE 3A-continued
| ID | STRUCTURE |
|----|-----------|
| OQ | 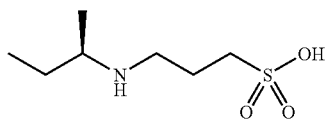 |
| OR | 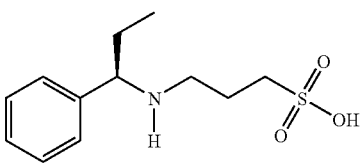 |
| OS | 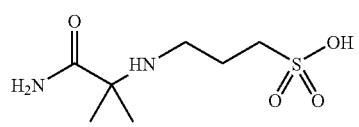 |
| OT | 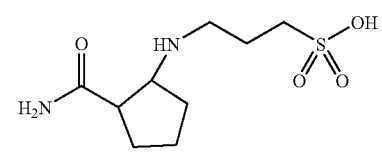 |
| OU | 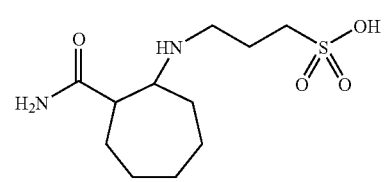 |
| OV | 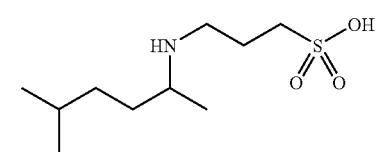 |
| OW | 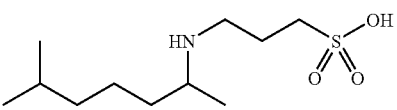 |
| OX | 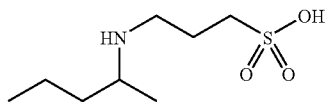 |
| OY | 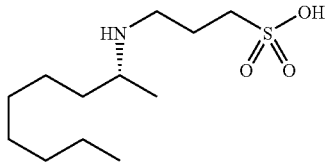 |

TABLE 3A-continued

| ID | STRUCTURE |
|---|---|
| OZ | 1-[(3,5-dimethoxyphenyl)methyl]cyclohexyl-NH-(CH₂)₃-SO₃H |
| PA | 1-[(2,4-dichlorophenyl)methyl]cyclohexyl-NH-(CH₂)₃-SO₃H |
| PB | (3,5-dimethoxybenzyl)-C(CH₃)₂-NH-(CH₂)₃-SO₃H |
| PD | (2,4-dichlorobenzyl)-C(CH₃)₂-NH-(CH₂)₃-SO₃H |
| PE | (4-methoxyphenyl)-CH₂CH₂-C(CH₃)₂-NH-(CH₂)₃-SO₃H |
| PF | (4-propoxyphenyl)-CH₂-C(CH₃)₂-NH-(CH₂)₃-SO₃H |
| PG | piperidin-2-yl-CH₂CH₂-SO₃H |

TABLE 3A-continued

| ID | STRUCTURE |
|---|---|
| PH | (structure) |
| PI | (structure) |
| PJ | (structure) |
| PK | (structure) |
| PL | (structure) |
| PM | (structure) |
| PN | (structure) |
| PO | (structure) |
| PP | (structure) |
| PQ | (structure) |

TABLE 3A-continued

| ID | STRUCTURE |
|---|---|
| PR | 3-methoxyphenyl-CH(OH)-C(cyclopentyl)(NH-CH2CH2CH2-SO2OH) |
| PS | (S)-CH3(CH2)4CH(CH3)-NH-CH2CH2CH2-SO2OH |
| PT | (S)-CH3(CH2)5CH(CH3)-NH-CH2CH2CH2-SO2OH |
| PU | CH3CH2CH2-NH-CH2CH2CH2-SO2OH |
| PV | (S)-CH3(CH2)4CH(CH3)-NH-CH2CH2CH2-SO2OH |
| PW | (S)-CH3(CH2)3CH(CH3)-NH-CH2CH2CH2-SO2OH |
| PX | 3-oxocyclohex-1-enyl-NH-CH2CH2CH2-SO2OH |
| PY | CH3CH2CH2CH2-NH-CH2CH2CH2-SO2OH |
| PZ | PhCH2-N(C(CH3)3)-CH2CH2CH2-SO2OH |
| QA | (S)-3-methoxyphenyl-CH(CH3)-NH-CH2CH2CH2-SO2OH |
| QB | CH2=CHCH2C(CH3)2-NH-CH2CH2CH2-SO2OH |

TABLE 3A-continued
| ID | STRUCTURE |
|---|---|
| QC | 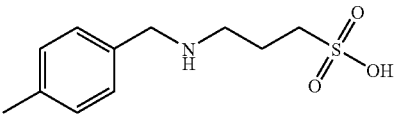 |
| QD | 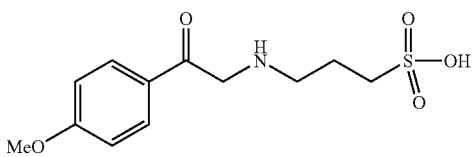 |
| QE | 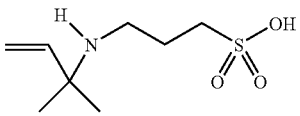 |
| QF | 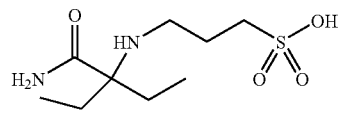 |
| QG | 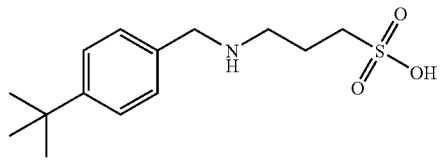 |
| QH | 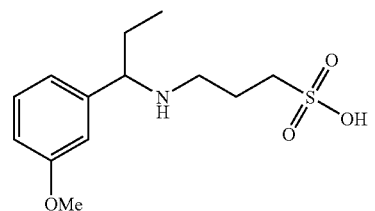 |
| QI | 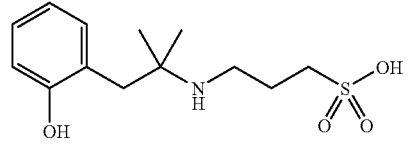 |
| QJ | 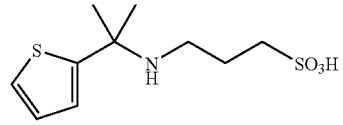 |
| QK | 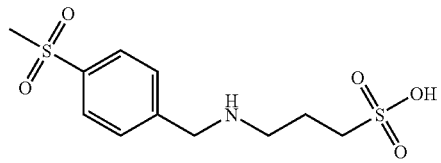 |

TABLE 3A-continued

| ID | STRUCTURE |
|---|---|
| QL | (S)-3-((1-(4-nitrophenyl)ethyl)amino)propane-1-sulfonic acid |
| QM | 3-((3-ethylpent-1-en-3-yl)amino)propane-1-sulfonic acid |
| QN | 4-(tert-butylamino)-1-phenylbutane-2-sulfonic acid |
| QO | 1-(tert-butylamino)hept-6-ene-3-sulfonic acid |
| QP | piperidine-4-sulfonic acid |
| QQ | 4-amino-1-phenylbutane-2-sulfonic acid |
| QR | 1-aminohex-5-ene-3-sulfonic acid |
| QS | 3-amino-3-phenylpropane-1-sulfonic acid |

TABLE 3A-continued

| ID | STRUCTURE |
|---|---|
| QT | (S)-3-amino-4-phenylbut-1-ene-1-sulfonic acid |
| QU | (S)-3-amino-4-phenylbutane-1-sulfonic acid |
| QV | 3-amino-2-methylpropane-1-sulfonic acid |
| QW | 3-((5-fluoro-2-methylbenzyl)amino)propane-1-sulfonic acid |
| QX | 3-amino-3-(adamantan-1-yl)propane-1-sulfonic acid |
| QY | 3-amino-3-(cubyl)propane-1-sulfonic acid |
| QZ | 3-amino-4-(cubyl)butane-1-sulfonic acid |
| RA | 3-amino-4-(adamantan-1-yl)butane-1-sulfonic acid |
| RB | 3-amino-4-(adamantan-2-yl)butane-1-sulfonic acid |
| RC | 3-amino-4-(3-phenyladamantan-1-yl)butane-1-sulfonic acid |

TABLE 3A-continued
| ID | STRUCTURE |
|----|-----------|
| RD | 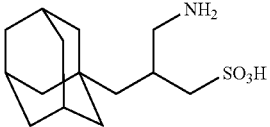 |
| RE | 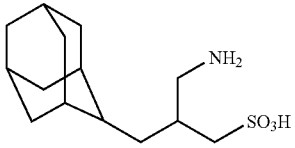 |
| RF | 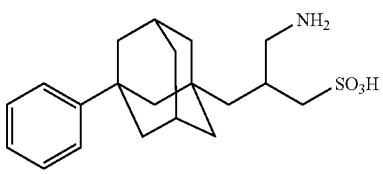 |
| RG | 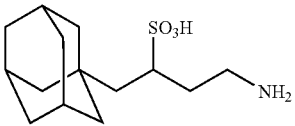 |
| RH | 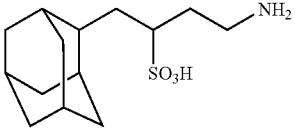 |
| RI | 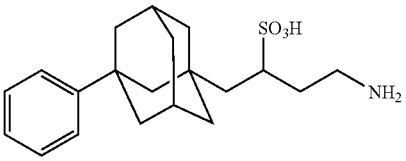 |
| RJ | 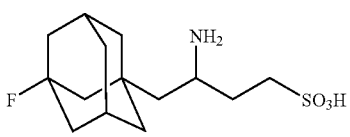 |
| RK | 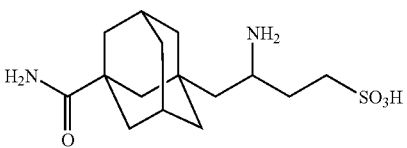 |
| RL | 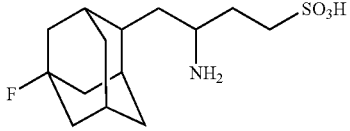 |
| RM | 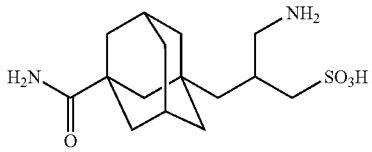 |

TABLE 3A-continued
| ID | STRUCTURE |
|---|---|
| RN | 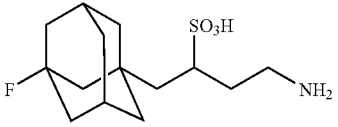 |
| RO | 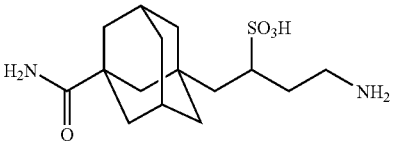 |
| RP | 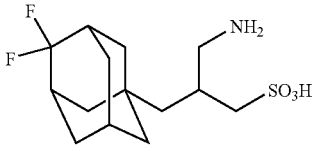 |
| RQ | 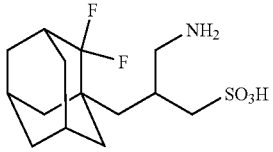 |
| RR | 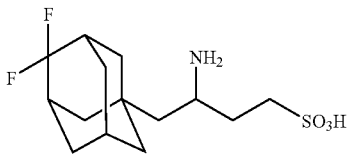 |
| RS | 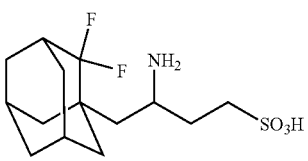 |
| RT | 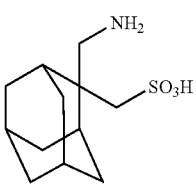 |
| RU | 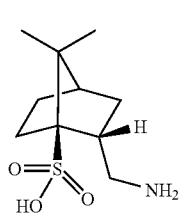 |
| RV | 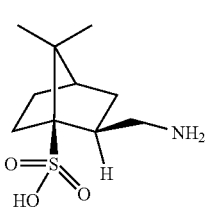 |

TABLE 3A-continued

| ID | STRUCTURE |
|---|---|
| RW | 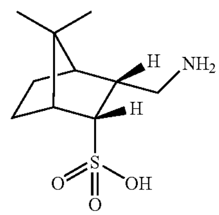 |
| RX | 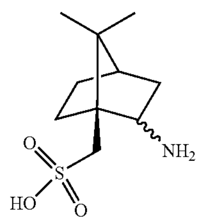 |
| RY | 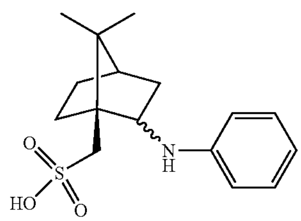 |
| RZ | 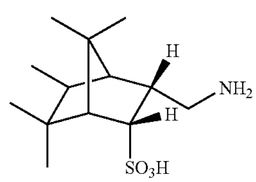 |
| SA | 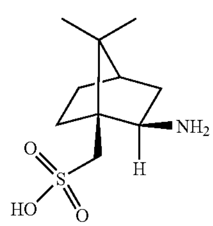 |
| SB | 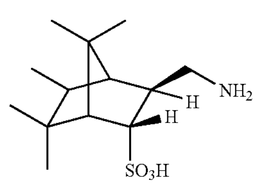 |
| SC | 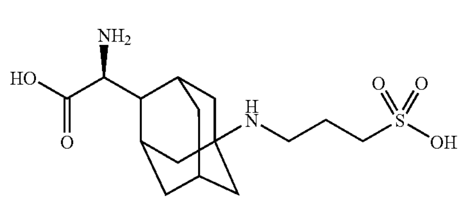 |

TABLE 3A-continued

| ID | STRUCTURE |
|---|---|
| SD | (structure) |
| SE | (structure) |
| SF | (structure) |
| SG | (structure) |
| SH | (structure) |
| SI | (structure) |
| SJ | (structure) |

TABLE 3A-continued

| ID | STRUCTURE |
|---|---|
| SK | 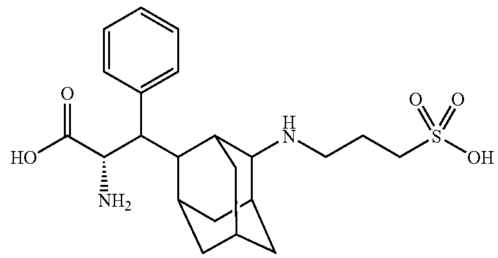 |
| SL | 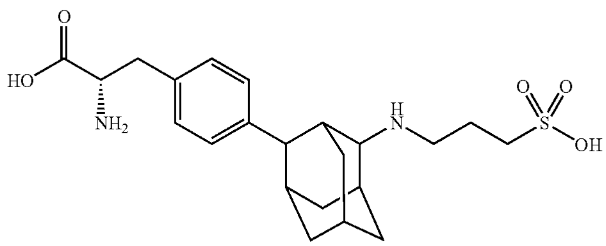 |
| SM | 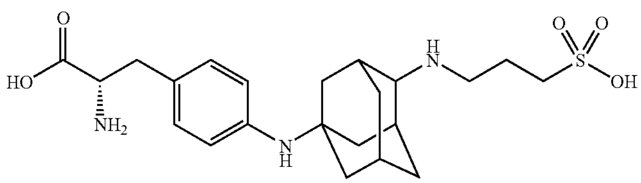 |
| SN | 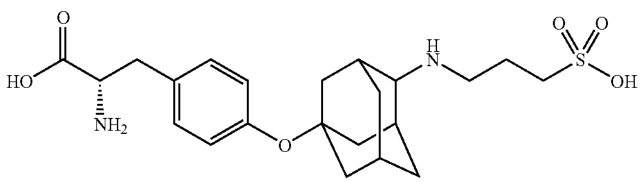 |
| SO | 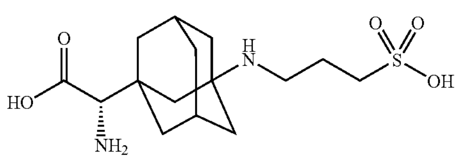 |
| SP | 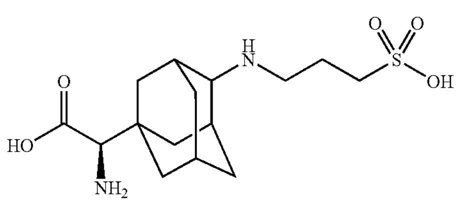 |
| SQ | 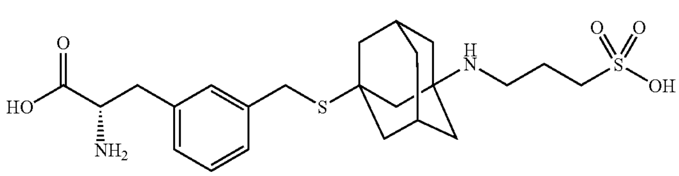 |
| SR | 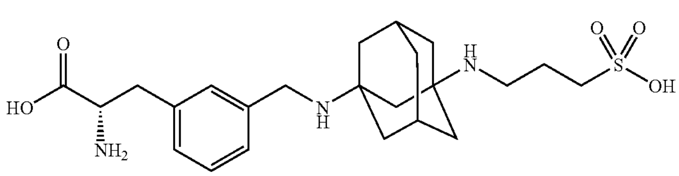 |

TABLE 3A-continued

| ID | STRUCTURE |
|---|---|
| SS | (structure) |
| ST | (structure) |
| SU | (structure) |
| SV | (structure) |
| SW | (structure) |
| SX | (structure) |
| SY | (structure) |

TABLE 3A-continued

| ID | STRUCTURE |
|---|---|
| SZ | H₂N–CH₂–CH(1-adamantyl)–CH₂–SO₃H |
| TA | (1S,2R,4S)-2-(aminomethyl)-5,6,6-trimethylbicyclo[2.2.1]heptane-1-sulfonic acid |
| TB | (1S,2R,3S,4R)-3-(aminomethyl)-5,5,6-trimethylbicyclo[2.2.1]heptane-2-sulfonic acid |

TABLE 3B

| ID | Structure |
|---|---|
| N1 | (S)-3-(nonan-2-ylamino)propane-1-sulfonic acid |
| N2 | 3-amino-1-allyl-1-(but-3-enyl)propane-1-sulfonic acid derivative |
| N3 | methyl 2-methyl-2-((3-sulfopropyl)amino)propanoate |
| N4 | 3-amino-2-benzylpropane-1-sulfonic acid |
| N5 | 3-aminopentane-... sulfonic acid |
| N6 | 3-aminobutane-1-sulfonic acid |
| N7 | 3-((cycloheptylmethyl)amino)propane-1-sulfonic acid |
| N8 | (R)-3-((1-(benzylthio)-3-hydroxypropan-2-yl)amino)propane-1-sulfonic acid |
| N9 | 1-amino-5-methylhexane-3-sulfonic acid |
| N10 | 3-amino-3-cyclohexylpropane-1-sulfonic acid |

TABLE 3B-continued

| ID | Structure |
|---|---|
| N11 | 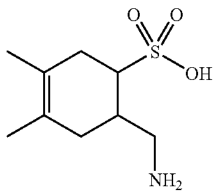 |
| N12 | 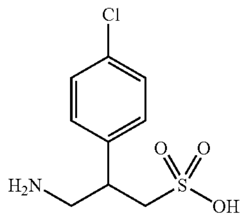 |
| N13 | 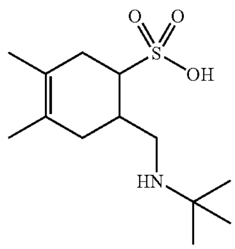 |
| N14 | 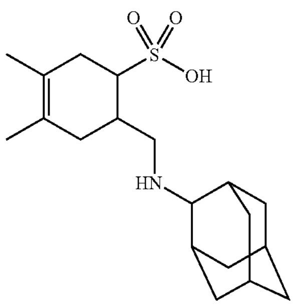 |
| N15 | 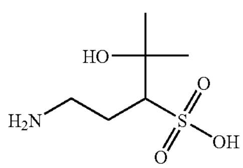 |
| N16 | 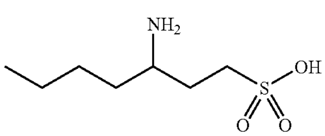 |
| N17 | 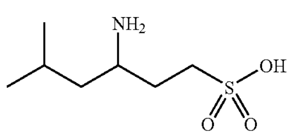 |
| N18 | 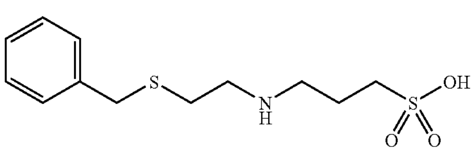 |
| N19 | |
| N20 | |
| N21 | |
| N22 | |
| N23 | |
| N24 | |

TABLE 3B-continued
| ID | Structure |
|---|---|
| N25 | 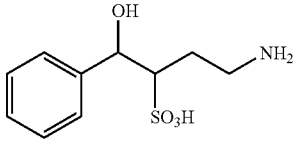 |
| N26 | 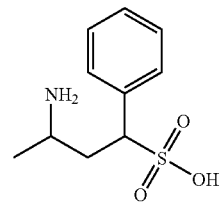 |
| N27 | 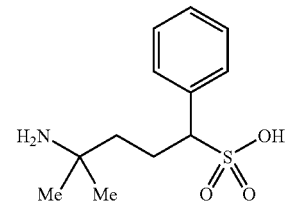 |
| N28 | 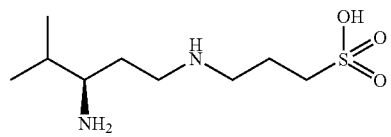 |
| N29 | 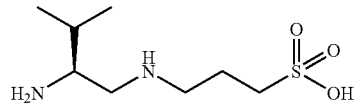 |
| N30 | 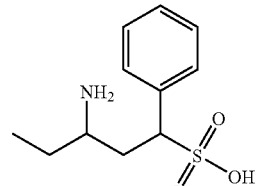 |
| N31 | 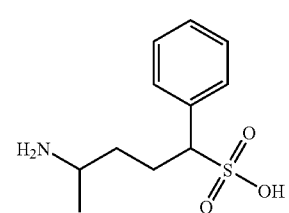 |
| N32 | 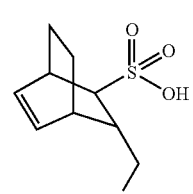 |
TABLE 3B-continued
| ID | Structure |
|---|---|
| N33 | 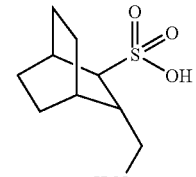 |
| N34 | 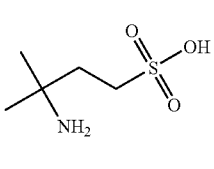 |
| N35 | 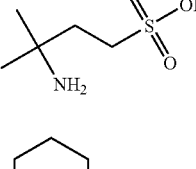 |
| N36 | 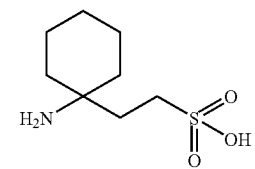 |
| N37 | 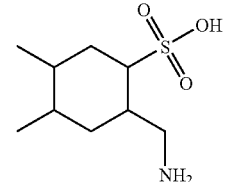 |
| N38 | 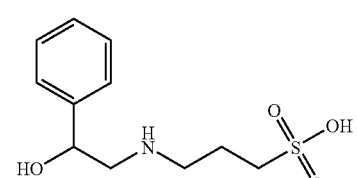 |
| N39 | 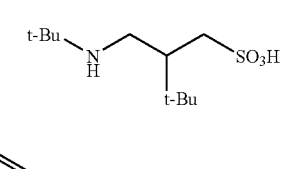 |
| N40 | 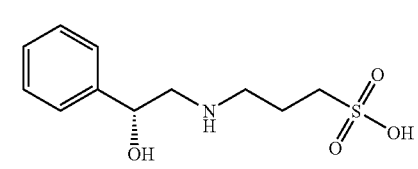 |
| N41 | 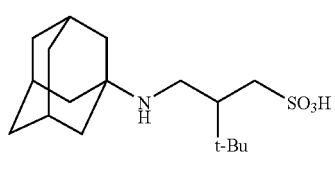 |

TABLE 3B-continued

| ID | Structure |
|---|---|
| N42 | 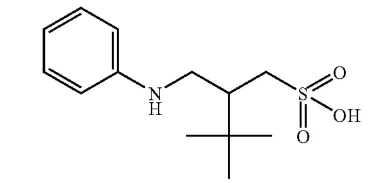 |
| N43 | 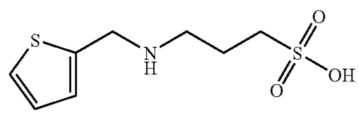 |
| N44 | 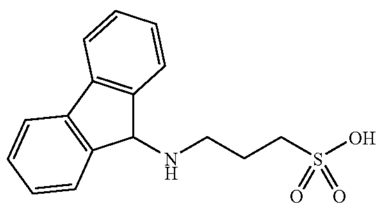 |
| N45 | 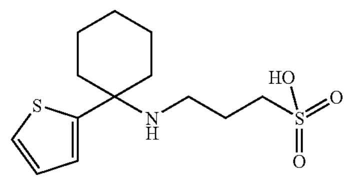 |
| N46 | 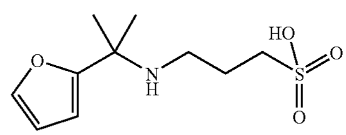 |
| N47 | 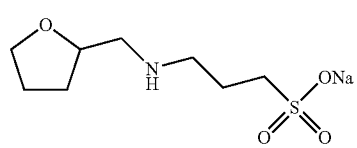 |
| N48 | 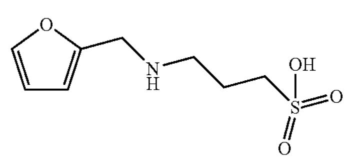 |
| N49 | 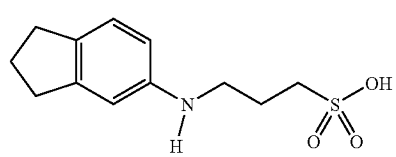 |
| N50 | 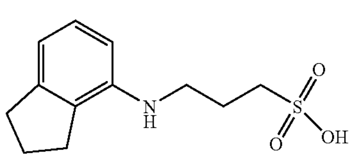 |

TABLE 3B-continued

| ID | Structure |
|---|---|
| N51 | 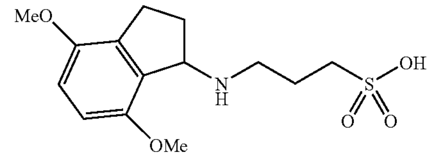 |
| N52 | 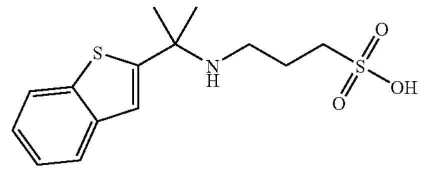 |
| N53 | 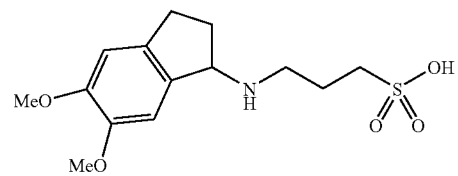 |
| N54 | 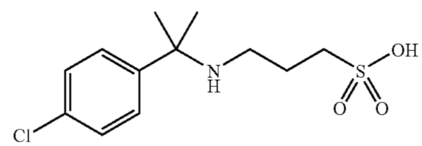 |
| N55 | 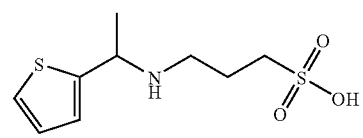 |
| N56 | 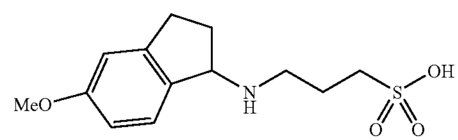 |
| N57 | 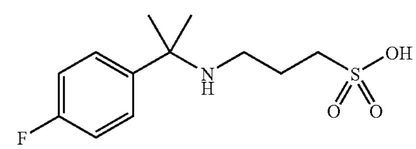 |
| N58 | 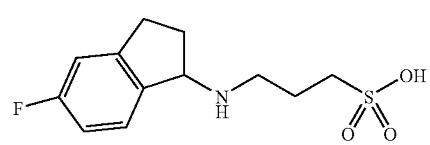 |
| N59 | 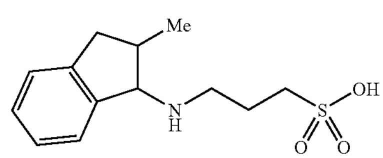 |
| N60 | 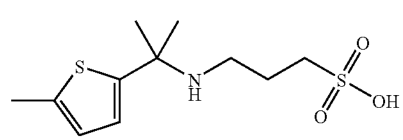 |

TABLE 3B-continued

| ID | Structure |
|----|-----------|
| N61 | 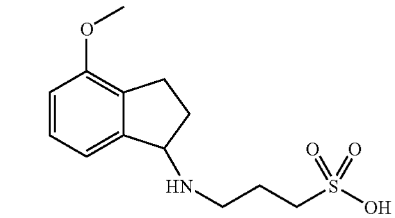 |
| N62 | 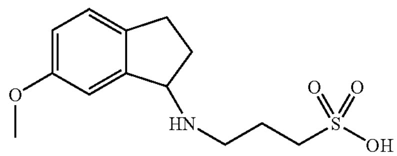 |
| N63 | 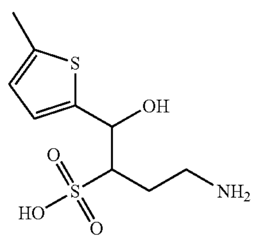 |
| N64 | 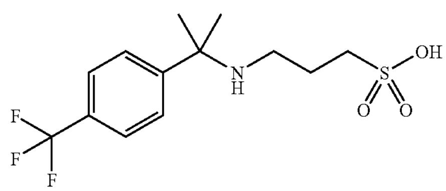 |
| N65 | 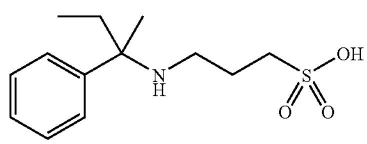 |
| N66 | 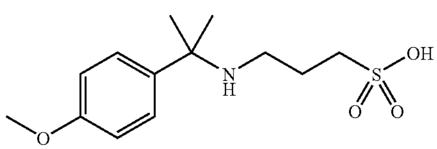 |
| N67 | 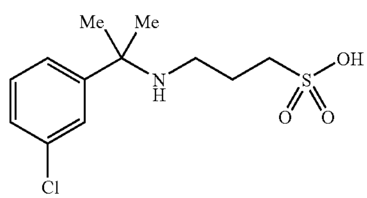 |
| N68 | 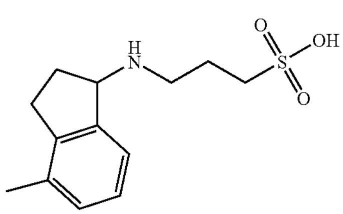 |
| N69 | 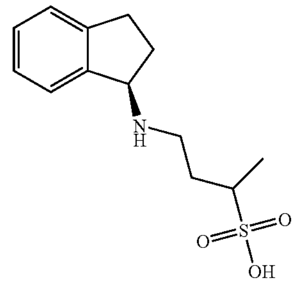 |
| N70 | 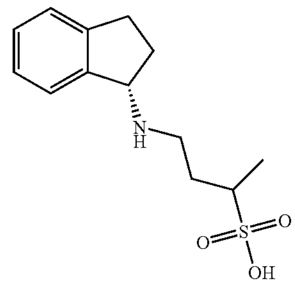 |
| N71 | 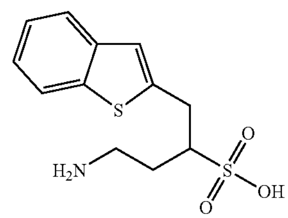 |
| N72 | 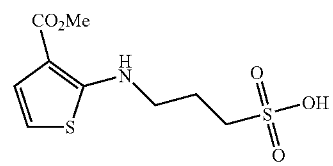 |
| N73 | 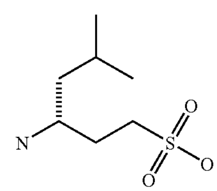 |
| N74 | 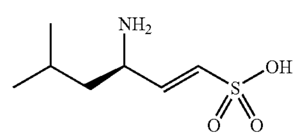 |
| N75 | 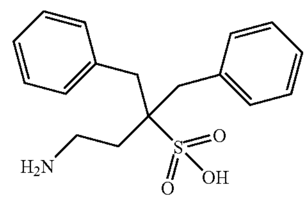 |

TABLE 3B-continued

| ID | Structure |
|----|-----------|
| N76 | 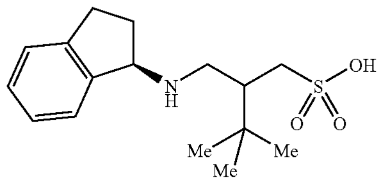 |
| N77 | 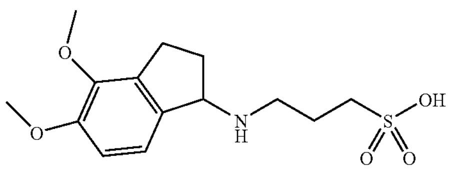 |
| N78 | 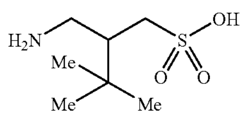 |
| N79 | 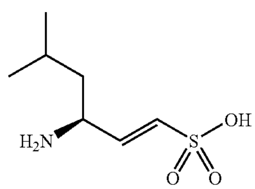 |
| N80 | 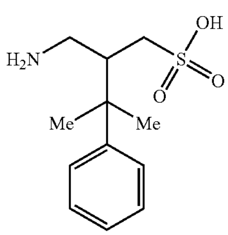 |
| N81 | 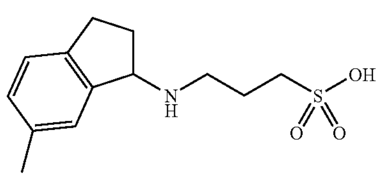 |
| N82 | 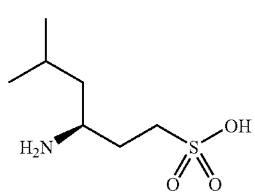 |
| N83 | 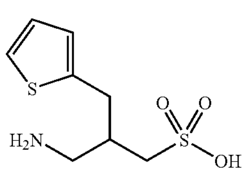 |
| N84 | |
| N85 | |
| N86 | |
| N87 | |
| N88 | |
| N89 | |
| N90 | |
| N91 | |

It should be noted that in the above table and throughout the application when an atom is shown without hydrogens, but hydrogens are required or chemically necessary to form a stable compound, hydrogens should be inferred to be part of the compound.

In one embodiment, the invention does not pertain to the compounds described in WO 00/64420 and WO 96/28187. In this embodiment, the invention does not pertain to methods of using the compounds described in WO 00/64420 and WO 96/28187 for the treatment of diseases or disorders described therein. In a further embodiment, the invention pertains to methods of using the compounds described in WO 00/64420 and WO 96/28187 for methods described in this application, which are not described in WO 00/64420 and WO 96/28187. Both of WO 00/64420 and WO 96/28187 are incorporated by reference herein in their entirety. In a further embodiment, this application does not pertain to the compounds described in U.S. application Ser. Nos. 10/871,512, 10/871,514, or 10/871,365, all filed on Jun. 18, 2004, and incorporated herein by reference. In a further embodiment, the invention does not pertain to the compounds of Tables 2A or 2B.

In another embodiment, the invention pertains to methods of the invention which use and pharmaceutical compositions comprising the compounds of Tables 2A, 2B, 3A or 3B. In another, the invention pertains to methods of the invention which use and pharmaceutical compositions comprising the compounds of Tables 2A, 2B, 3A, or 3B. In another embodiment, the compounds of the invention do not include the compounds of Table 2A or 2B. In another embodiment, the compounds of the invention do not include the compounds of Table 2A or 2B.

It should be understood that the use of any of the compounds described herein or in the applications identified in "The Related Applications" Section is within the scope of the present invention and is intended to be encompassed by the present invention and each of the applications are expressly incorporated herein at least for these purposes, and are furthermore expressly incorporated for all other purposes.

Subjects and Patient Populations

The term "subject" includes living organisms in which amyloidosis can occur, or which are susceptible to amyloid diseases, e.g., Alzheimer's disease, Down's syndrome, CAA, dialysis-related ($\beta_2$M) amyloidosis, secondary (AA) amyloidosis, primary (AL) amyloidosis, hereditary amyloidosis, diabetes, etc. Examples of subjects include humans, chickens, ducks, peking ducks, geese, monkeys, deer, cows, rabbits, sheep, goats, dogs, cats, mice, rats, and transgenic species thereof. Administration of the compositions of the present invention to a subject to be treated can be carried out using known procedures, at dosages and for periods of time effective to modulate amyloid aggregation or amyloid-induced toxicity in the subject as further described herein. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to modulate amyloid aggregation in the subject. Dosage regimens can be adjusted to provide the optimum therapeutic response. For example, several divided doses may be administered daily or the dose may be proportionally reduced as indicated by the exigencies of the therapeutic situation.

In certain embodiments of the invention, the subject is in need of treatment by the methods of the invention, and is selected for treatment based on this need. A subject in need of treatment is art-recognized, and includes subjects that have been identified as having a disease or disorder related to amyloid-deposition or amyloidosis, has a symptom of such a disease or disorder, or is at risk of such a disease or disorder, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

In an exemplary aspect of the invention, the subject is a human. For example, the subject may be a human over 30 years old, human over 40 years old, a human over 50 years old, a human over 60 years old, a human over 70 years old, a human over 80 years old, a human over 85 years old, a human over 90 years old, or a human over 95 years old. The subject may be a female human, including a postmenopausal female human, who may be on hormone (estrogen) replacement therapy. The subject may also be a male human. In another embodiment, the subject is under 40 years old.

A subject may be a human at risk for Alzheimer's disease, e.g., being over the age of 40 or having a predisposition for Alzheimer's disease. Alzheimer's disease predisposing factors identified or proposed in the scientific literature include, among others, a genotype predisposing a subject to Alzheimer's disease; environmental factors predisposing a subject to Alzheimer's disease; past history of infection by viral and bacterial agents predisposing a subject to Alzheimer's disease; and vascular factors predisposing a subject to Alzheimer's disease. A subject may also have one or more risk factors for cardiovascular disease (e.g., atherosclerosis of the coronary arteries, angina pectoris, and myocardial infarction) or cerebrovascular disease (e.g., atherosclerosis of the intracranial or extracranial arteries, stroke, syncope, and transient ischemic attacks), such as hypercholesterolemia, hypertension, diabetes, cigarette smoking, familial or previous history of coronary artery disease, cerebrovascular disease, and cardiovascular disease. Hypercholesterolemia typically is defined as a serum total cholesterol concentration of greater than about 5.2 mmol/L (about 200 mg/dL).

Several genotypes are believed to predispose a subject to Alzheimer's disease. These include the genotypes such as presenilin-1, presenilin-2, and amyloid precursor protein (APP) missense mutations associated with familial Alzheimer's disease, and α-2-macroglobulin and LRP-1 genotypes, which are thought to increase the risk of acquiring sporadic (late-onset) Alzheimer's disease. E. van Uden, et al., *J. Neurosci.* 22(21), 9298-304 (2002); J. J. Goto, et al., J. Mol. Neurosci. 19(1-2), 37-41 (2002). Another genetic risk factor for the development of Alzheimer's disease are variants of ApoE, the gene that encodes apolipoprotein E (particularly the apoE4 genotype), a constituent of the low-density lipoprotein particle. W J Strittmatter, et al., *Annu. Rev. Neurosci.* 19, 53-77 (1996). The molecular mechanisms by which the various ApoE alleles alter the likelihood of developing Alzheimer's disease are unknown, however the role of ApoE in cholesterol metabolism is consistent with the growing body of evidence linking cholesterol metabolism to Alzheimer's disease. For example, chronic use of cholesterol-lowering drugs such as statins has recently been associated with a lower incidence of Alzheimer's disease, and cholesterol-lowering drugs have been shown to reduce pathology in APP transgenic mice. These and other studies suggest that cholesterol may affect APP processing. ApoE4 has been suggested to alter Aβ trafficking (in and out of the brain), and favor retention of Aβ in the brain. ApoE4 has also been suggested to favor APP processing toward Aβ formation. Environmental factors have been proposed as predisposing a subject to Alzheimer's disease, including exposure to aluminum, although the epidemiological evidence is ambiguous. In addition, prior infection by certain viral or bacterial agents may predispose a subject to Alzheimer's disease, including the herpes simplex virus and *chlamydia pneumoniae*. Finally, other predisposing factors for Alzheimer's disease can include risk factors for cardiovascular or cerebrovascular disease, including cigarette smoking, hypertension and diabetes. "At risk for Alzheimer's disease" also encompasses any other predisposing factors not listed above or as yet identified and includes an increased risk for Alzheimer's disease caused by head injury, medications, diet, or lifestyle.

The methods of the present invention can be used for one or more of the following: to prevent Alzheimer's disease, to treat Alzheimer's disease, or ameliorate symptoms of Alzheimer's disease, or to regulate production of or levels of amyloid β (Aβ) peptides. In an embodiment, the human carries one or more mutations in the genes that encode β-amyloid precursor protein, presenilin-1 or presenilin-2. In another embodiment, the human carries the Apolipoprotein ε4 gene. In another embodiment, the human has a family history of Alzheimer's Disease or a dementia illness. In another embodiment, the human has trisomy 21 (Down's Syndrome). In another embodiment, the subject has a normal or low serum total blood cholesterol level. In another embodiment, the serum total blood cholesterol level is less than about 200 mg/dL, or less than about 180, and it can range from about 150 to about 200 mg/dL. In another embodiment, the total LDL cholesterol level is less than about 100 mg/dL, or less than about 90 mg/dL and can range from about 30 to about 100 mg/dL. Methods of measuring serum total blood cholesterol and total LDL cholesterol are well known to those skilled in the art and for example include those disclosed in WO 99/38498 at p. 11, incorporated by reference herein. Methods of determining levels of other sterols in serum are disclosed in H. Gylling, et al., "Serum Sterols During Stanol Ester Feeding in a Mildly Hypercholesterolemic Population", *J. Lipid Res.* 40: 593-600 (1999).

In another embodiment, the subject has an elevated serum total blood cholesterol level. In another embodiment, the serum total cholesterol level is at least about 200 mg/dL, or at least about 220 mg/dL and can range from about 200 to about 1000 mg/dL. In another embodiment, the subject has an elevated total LDL cholesterol level. In another embodiment, the total LDL cholesterol level is greater than about 100 mg/dL, or even greater than about 110 mg/dL and can range from about 100 to about 1000 mg/dL.

In another embodiment, the human is at least about 40 years of age. In another embodiment, the human is at least about 60 years of age. In another embodiment, the human is at least about 70 years of age. In another embodiment, the human is at least about 80 years of age. In another embodiment, the human is at least about 85 years of age. In one embodiment, the human is between about 60 and about 100 years of age.

In still a further embodiment, the subject is shown to be at risk by a diagnostic brain imaging technique, for example, one that measures brain activity, plaque deposition, or brain atrophy.

In still a further embodiment, the subject is shown to be at risk by a cognitive test such as Clinical Dementia Rating ("CDR"), Alzheimer's Disease Assessment Scale-Cognition ("ADAS-Cog"), Disability Assessment for Dementia ("DAD") or Mini-Mental State Examination ("MMSE"). The subject may exhibit a below average score on a cognitive test, as compared to a historical control of similar age and educational background. The subject may also exhibit a reduction in score as compared to previous scores of the subject on the same or similar cognition tests.

In determining the CDR, a subject is typically assessed and rated in each of six cognitive and behavioural categories: memory, orientation, judgement and problem solving, community affairs, home and hobbies, and personal care. The assessment may include historical information provided by the subject, or preferably, a corroborator who knows the subject well. The subject is assessed and rated in each of these areas and the overall rating, (0, 0.5, 1.0, 2.0 or 3.0) determined. A rating of 0 is considered normal. A rating of 1.0 is considered to correspond to mild dementia. A subject with a CDR of 0.5 is characterized by mild consistent forgetfulness, partial recollection of events and "benign" forgetfulness. In one embodiment the subject is assessed with a rating on the CDR of above 0, of above about 0.5, of above about 1.0, of above about 1.5, of above about 2.0, of above about 2.5, or at about 3.0.

Another test is the Mini-Mental State Examination (MMSE), as described by Folstein "Mini-mental state. A practical method for grading the cognitive state of patients for the clinician." J. Psychiatr. Res. 12:189-198, 1975. The MMSE evaluates the presence of global intellectual deterioration. See also Folstein "Differential diagnosis of dementia. The clinical process." Psychiatr Clin North Am. 20:45-57, 1997. The MMSE is a means to evaluate the onset of dementia and the presence of global intellectual deterioration, as seen in Alzheimer's disease and multi-infart dementia. The MMSE is scored from 1 to 30. The MMSE does not evaluate basic cognitive potential, as, for example, the so-called IQ test. Instead, it tests intellectual skills. A person of "normal" intellectual capabilities will score a "30" on the MMSE objective test (however, a person with a MMSE score of 30 could also score well below "normal" on an IQ test). See, e.g., Kaufer, J. Neuropsychiatry Clin. Neurosci. 10:55-63, 1998; Becke, Alzheimer Dis Assoc Disord. 12:54-57, 1998; Ellis, Arch. Neurol. 55:360-365, 1998; Magni, Int. Psychogeriatr. 8:127-134, 1996; Monsch, Acta Neurol. Scand. 92:145-150, 1995. In one embodiment, the subject scores below 30 at least once on the MMSE. In another embodiment, the subject scores below about 28, below about 26, below about 24, below about 22, below about 20, below about 18, below about 16, below about 14, below about 12, below about 10, below about 8, below about 6, below about 4, below about 2, or below about 1.

Another means to evaluate cognition, particularly Alzheimer's disease, is the Alzheimer's Disease Assessment Scale (ADAS-Cog), or a variation termed the Standardized Alzheimer's Disease Assessment Scale (SADAS). It is commonly used as an efficacy measure in clinical drug trials of Alzheimer's disease and related disorders characterized by cognitive decline. SADAS and ADAS-Cog were not designed to diagnose Alzheimer's disease; they are useful in characterizing symptoms of dementia and are a relatively sensitive indicator of dementia progression. (See, e.g., Doraiswamy, Neurology 48:1511-1517, 1997; and Standish, J. Am. Geriatr. Soc. 44:712-716, 1996.) Annual deterioration in untreated Alzheimer's disease patients is approximately 8 points per year (See, eg., Raskind, M Prim. Care Companion J Clin Psychiatry 2000 August; 2(4):134-138).

The Disability Assessment for Dementia ("DAD") scale has been developed to measure a patient's ability to perform the activities of daily living (Gélinas I et al. Development of a Functional Measure for Persons with Alzheimer's Disease: The Disability Assessment for Dementia *Am. J. Occupational Therapy*. 1999; 53: 471-481). Activities of daily living may be assessed according to self care (i.e., dressing and personal hygiene) and instrumental activities (e.g., housework, cooking, and using household devices). The objectives of the DAD scale include quantitatively measuring functional abilities in activities of daily living in individuals with cognitive impairments and to help delineate areas of cognitive deficits that may impair performance in activities of daily living. The DAD is administered through an interview with the caregiver. It measures actual performance in activities of daily living of the individual as observed over a 2 week period prior to the interview. The scale assesses the following domains of activities: hygiene, dressing, telephoning, continence, eating, meal preparation, outing activities, finance and correspondence, medication use, leisure and housework. A total score is obtained by adding the rating for each question and converting this total score out of 100. Higher scores represent less disability in ADL while lower scores indicate more dysfunction. In one embodiment, the subject scores below 100 at least once on the DAD. In another embodiment, the subject scores below about 95, below about 90, below about 85, below about 80, below about 75, below about 70, below about 65, below about 60, below about 55, below about 50, below about 45, below about 40, below about 30, below about 20, or below about 10.

The ADAS-cog is designed to measure, with the use of questionnaires, the progression and the severity of cognitive decline as seen in AD on a 70-point scale. The ADAS-cog scale quantifies the number of wrong answers. Consequently, a high score on the scale indicates a more severe case of cognitive decline. In one embodiment, a subject exhibits a score of greater than 0, greater than about 5, greater than about 10, greater than about 15, greater than about 20, greater than about 25, greater than about 30, greater than about 35, greater than about 40, greater than about 45, greater than about 50, greater than about 55, greater than about 60, greater than about 65, greater than about 68, or about 70.

In another embodiment, the subject exhibits no symptoms of Alzheimer's Disease. In another embodiment, the subject is a human who is at least 40 years of age and exhibits no symptoms of Alzheimer's Disease. In another embodiment, the subject is a human who is at least 40 years of age and exhibits one or more symptoms of Alzheimer's Disease.

In another embodiment, the subject has Mild Cognitive Impairment. In a further embodiment, the subject has a CDR rating of about 0.5. In another embodiment, the subject has early Alzheimer's disease. In another embodiment, the subject has cerebral amyloid angiopathy.

By using the methods of the present invention, the levels of amyloid β peptides in a subject's plasma or cerebrospinal fluid (CSF) can be reduced from levels prior to treatment from about 10 to about 100 percent, or even about 50 to about 100 percent.

In an alternative embodiment, the subject can have an elevated level of amyloid $A\beta_{40}$ and $A\beta_{42}$ peptide in the blood and CSF prior to treatment, according to the present methods, of greater than about 10 pg/mL, or greater than about 20 pg/mL, or greater than about 35 pg/mL, or even greater than about 40 pg/mL. In another embodiment, the elevated level of amyloid $A\beta_{42}$ peptide can range from about 30 pg/mL to about 200 pg/mL, or even to about 500 pg/mL. One skilled in the art would understand that as Alzheimer's disease progresses, the measurable levels of amyloid β peptide in the CSF may decrease from elevated levels present before onset of the disease. This effect is attributed to increased deposition, i.e., trapping of Aβ peptide in the brain instead of normal clearance from the brain into the CSF.

In an alternative embodiment, the subject can have an elevated level of amyloid $A\beta_{40}$ peptide in the blood and CSF prior to treatment, according to the present methods, of greater than about 5 pg $A\beta_{42}$/mL or greater than about 50 pg $A\beta_{40}$/mL, or greater than about 400 pg/mL. In another embodiment, the elevated level of amyloid $A\beta_{40}$ peptide can range from about 200 pg/mL to about 800 pg/mL, to even about 1000 pg/mL.

In another embodiment, the subject can have an elevated level of amyloid $A\beta_{42}$ peptide in the CSF prior to treatment, according to the present methods, of greater than about 5 pg/mL, or greater than about 10 pg/mL, or greater than about 200 pg/mL, or greater than about 500 pg/mL. In another embodiment, the level of amyloid β peptide can range from about 10 pg/mL to about 1,000 pg/mL, or even about 100 pg/mL to about 1,000 pg/mL.

In another embodiment, the subject can have an elevated level of amyloid $A\beta_{40}$ peptide in the CSF prior to treatment according to the present methods of greater than about 10 pg/mL, or greater than about 50 pg/mL, or even greater than about 100 pg/mL. In another embodiment, the level of amyloid β peptide can range from about 10 pg/mL to about 1,000 pg/mL.

The amount of amyloid f peptide in the brain, CSF, blood, or plasma of a subject can be evaluated by enzyme-linked immunosorbent assay ("ELISA") or quantitative immunoblotting test methods or by quantitative SELDI-TOF which are well known to those skilled in the art, such as is disclosed by Zhang, et al., *J. Biol. Chem.* 274, 8966-72 (1999) and Zhang, et al., *Biochemistry* 40, 5049-55 (2001). See also, A. K. Vehmas, et al., *DNA Cell Biol.* 20(11), 713-21 (2001), P. Lewczuk, et al., *Rapid Commun. Mass Spectrom.* 17(12), 1291-96 (2003); B. M. Austen, et al., *J. Peptide Sci.* 6, 459-69 (2000); and H. Davies, et al., *BioTechniques* 27, 1258-62 (1999). These tests are performed on samples of the brain or blood which have been prepared in a manner well known to one skilled in the art. Another example of a useful method for measuring levels of amyloid β peptides is by Europium immunoassay (EIA). See, e.g., WO 99/38498 at p. 11.

The methods of the invention may be applied as a therapy for a subject having Alzheimer's disease or a dementia, or the methods of the invention may be applied as a prophylaxis against Alzheimer's disease or dementia for subject with such a predisposition, as in a subject, e.g., with a genomic mutation in the APP gene, the ApoE gene, or a presenilin gene. The subject may have (or may be predisposed to developing or may be suspected of having) vascular dementia, or senile dementia, Mild Cognitive Impairment, or early Alzheimer's disease. In addition to Alzheimer's disease, the subject may have another amyloid-related disease such as cerebral amyloid angiopathy, or the subject may have amyloid deposits, especially amyloid-β amyloid deposits in the brain.

Treatment of Amyloid-Related Diseases

The present invention pertains to methods of using the compounds and pharmaceutical compositions thereof in the treatment and prevention of amyloid-related diseases. The pharmaceutical compositions of the invention may be administered therapeutically or prophylactically to treat diseases associated with amyloid (e.g., AL amyloid protein (λ or κ-chain related, e.g., amyloid λ, amyloid κ, amyloid κIV, amyloid λVI, amyloid γ, amyloid γ1), Aβ, IAPP, $\beta_2$M, AA, or AH amyloid protein) fibril formation, aggregation or deposition.

The pharmaceutical compositions of the invention may act to ameliorate the course of an amyloid-related disease using any of the following mechanisms (this list is meant to be illustrative and not limiting): slowing the rate of amyloid fibril formation or deposition; lessening the degree of amyloid deposition; inhibiting, reducing, or preventing amyloid fibril formation; inhibiting neurodegeneration or cellular toxicity induced by amyloid; inhibiting amyloid induced inflammation; enhancing the clearance of amyloid from the brain; enhancing degradation of Aβ in the brain; or favoring clearance of amyloid protein prior to its organization in fibrils.

"Modulation" of amyloid deposition includes both inhibition, as defined above, and enhancement of amyloid deposition or fibril formation. The term "modulating" is intended, therefore, to encompass prevention or stopping of amyloid formation or accumulation, inhibition or slowing down of further amyloid formation or accumulation in a subject with ongoing amyloidosis, e.g., already having amyloid deposition, and reducing or reversing of amyloid formation or accumulation in a subject with ongoing amyloidosis; and enhancing amyloid deposition, e.g., increasing the rate or amount of amyloid deposition in vivo or in vitro. Amyloid-enhancing compounds may be useful in animal models of amyloidosis, for example, to make possible the development of amyloid deposits in animals in a shorter period of time or to increase amyloid deposits over a selected period of time. Amyloid-enhancing compounds may be useful in screening assays for compounds which inhibit amyloidosis in vivo, for example, in animal models, cellular assays and in vitro assays for amyloidosis. Such compounds may be used, for example, to provide faster or more sensitive assays for compounds. Modulation of amyloid deposition is determined relative to an untreated subject or relative to the treated subject prior to treatment.

"Inhibition" of amyloid deposition includes preventing or stopping of amyloid formation, e.g., fibrillogenesis, clearance of amyloid, e.g., soluble Aβ from brain, inhibiting or slowing down of further amyloid deposition in a subject with amyloidosis, e.g., already having amyloid deposits, and reducing or reversing amyloid fibrillogenesis or deposits in a subject with ongoing amyloidosis. Inhibition of amyloid deposition is determined relative to an untreated subject, or relative to the treated subject prior to treatment, or, e.g., determined by clinically measurable improvement, e.g., or in the case of a subject with brain amyloidosis, e.g., an Alzheimer's or cerebral amyloid angiopathy subject, stabilization of cognitive function or prevention of a further decrease in cognitive function (i.e., preventing, slowing, or stopping disease progression), or improvement of parameters such as the concentration of Aβ or tau in the CSF.

As used herein, "treatment" of a subject includes the application or administration of a composition of the invention to a subject, or application or administration of a composition of the invention to a cell or tissue from a subject, who has an amyloid-related disease or condition, has a symptom of such a disease or condition, or is at risk of (or susceptible to) such a disease or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as CDR, MMSE, DAD, ADAS-Cog, or another test known in the art. For example, the methods of the invention successfully treat a subject's dementia by slowing the rate of or lessening the extent of cognitive decline.

In one embodiment, the term "treating" includes maintaining a subject's CDR rating at its base line rating or at 0. In another embodiment, the term treating includes decreasing a subject's CDR rating by about 0.25 or more, about 0.5 or more, about 1.0 or more, about 1.5 or more, about 2.0 or more, about 2.5 or more, or about 3.0 or more. In another embodiment, the term "treating" also includes reducing the rate of the increase of a subject's CDR rating as compared to historical controls. In another embodiment, the term includes reducing the rate of increase of a subject's CDR rating by about 5% or more, about 10% or more, about 20% or more, about 25% or more, about 30% or more, about 40% or more, about 50% or more, about 60% or more, about 70% or more, about 80% or more, about 90% or more, or about 100%, of the increase of the historical or untreated controls.

In another embodiment, the term "treating" also includes maintaining a subject's score on the MMSE. The term "treating" includes increasing a subject's MMSE score by about 1, about 2, about 3, about 4, about 5, about 7.5, about 10, about 12.5, about 15, about 17.5, about 20, or about 25 points. The term also includes reducing the rate of the decrease of a subject's MMSE score as compared to historical controls. In another embodiment, the term includes reducing the rate of decrease of a subject's MMSE score by about 5% or less, about 10% or less, about 20% or less, about 25% or less, about 30% or less, about 40% or less, about 50% or less, about 60% or less, about 70% or less, about 80% or less, about 90% or less or about 100% or less, of the decrease of the historical or untreated controls.

In another embodiment, the term "treating" also includes maintaining a subject's score on the DAD. The term "treating" includes increasing a subject's DAD score by about 1, about 5, about 10, about 15, about 20, about 30, about 35, about 40, about 50, about 60, about 70, or about 80 points. The term also includes reducing the rate of the decrease of a subject's DAD score as compared to historical controls. In another embodiment, the term includes reducing the rate of decrease of a subject's DAD score by about 5% or less, about 10% or less, about 20% or less, about 25% or less, about 30% or less, about 40% or less, about 50% or less, about 60% or less, about 70% or less, about 80% or less, about 90% or less or about 100% or less, of the decrease of the historical or untreated controls.

In yet another embodiment, the term "treating" includes maintaining a subject's score on the ADAS-Cog. The term "treating" includes decreasing a subject's ADAS-Cog score by about 1 point or greater, by about 2 points or greater, by about 3 points or greater, by about 4 points or greater, by about 5 points or greater, by about 7.5 points or greater, by about 10 points or greater, by about 12.5 points or greater, by about 15 points or greater, by about 17.5 points or greater, by about 20 points or greater, or by about 25 points or greater. The term also includes reducing the rate of the increase of a subject's ADAS-Cog score as compared to historical controls. In another embodiment, the term includes reducing the rate of increase of a subject's ADAS-Cog score by about 5% or more, about 10% or more, about 20% or more, about 25% or more, about 30% or more, about 40% or more, about 50% or more, about 60% or more, about 70% or more, about 80% or more, about 90% or more or about 100% of the increase of the historical or untreated controls.

In another embodiment, the term "treating" e.g., for AA or AL amyloidosis, includes an increase in serum creatinine, e.g., an increase of creatinine clearance of 10% or greater, 20% or greater, 50% or greater, 80% or greater, 90% or greater, 100% or greater, 150% or greater, 200% or greater. The term "treating" also may include remission of nephrotic syndrome (NS). It may also include remission of chronic diarrhea and/or a gain in body weight, e.g., by 10% or greater, 15% or greater, or 20% or greater.

Without wishing to be bound by theory, in some aspects the pharmaceutical compositions of the invention contain a compound that prevents or inhibits amyloid fibril formation, either in the brain or other organ of interest (acting locally) or throughout the entire body (acting systemically). Pharmaceutical compositions of the invention may be effective in controlling amyloid deposition either following their entry into the brain (following penetration of the blood brain barrier) or from the periphery. When acting from the periphery, a compound of a pharmaceutical composition may alter the equilibrium of amyloidogenic peptide between the brain and the plasma so as to favor the exit of amyloidogenic peptide from the brain. It may also favor clearance (or catabolism) of the amyloid protein (soluble), and then prevent amyloid fibril formation and deposition due to a reduction of the amyloid protein pool in a specific organ, e.g., liver, spleen, pancreas, kidney, joints, brain, etc. An increase in the exit of amyloidogenic peptide from the brain would result in a decrease in amyloidogenic peptide brain concentration and therefore favor a decrease in amyloidogenic peptide deposition. In particular, an agent may lower the levels of amyloid β peptides, e.g., both Aβ40 and Aβ42 in the CSF and the plasma, or the agent may lower the levels of amyloid β peptides, e.g., Aβ40 and Aβ42 in the CSF and increase it in the plasma. Alternatively, compounds that penetrate the brain could control deposition by acting directly on brain amyloidogenic peptide e.g., by maintaining it in a non-fibrillar form or favoring its clearance from the brain, by increasing its degradation in the brain, or protecting brain cells from the detrimental effect of amyloidogenic peptide. An agent can also cause a decrease of the concentration of the amyloid protein (i.e., in a specific organ so that the critical concentration needed to trigger amyloid fibril formation or deposition is not reached). Furthermore, the compounds described herein may inhibit or reduce an interaction between amyloid and a cell surface constituent, for example, a glycosaminoglycan or proteoglycan constituent of a basement membrane, whereby inhibiting or reducing this interaction produces the observed neuroprotective and cell-protective effects. For example, the compound may also prevent an amyloid peptide from binding or adhering to a cell surface, a process which is known to cause cell damage or toxicity. Similarly, the compound may block amyloid-induced cellular toxicity or microglial activation or amyloid-induced neurotoxicity, or inhibit amyloid induced inflammation. The compound may also reduce the rate or amount of amyloid aggregation, fibril formation, or deposition, or the compound lessens the degree of amyloid deposition. The foregoing mechanisms of action should not be construed as limiting the scope of the invention inasmuch as the invention may be practiced without such information.

The Aβ peptide has been shown by several groups to be highly toxic to neurons. Amyloid plaques are directly associated with reactive gliosis, dystrophic neurites and apoptotic cells, suggesting that plaques induce neurodegenerative changes. Neurotoxicity may eventually disrupt or even kill neurons. In vitro, Aβ has been shown to induce apoptosis in many different neuronal cell types, such as rat PC-12 cells, primary rat hippocampal and cortical cultures, and the predifferentiated human neurotype SH-SY5Y cell line (Dickson D W (2004) *J Clin Invest* 114:23-7; Canu et al. (2003) *Cerebellum* 2:270-278; Li et al. (1996) *Brain Research* 738:196-204). Numerous reports have shown that Aβ fibrils can induce neurodegeneration, and it has been shown that neuronal cells exposed in vitro to Aβ can become apoptotic (Morgan et al. (2004) *Prog. Neurobiol.* 74:323-349; Stefani et al. (2003) *J. Mol. Med.* 81:678-99; La Ferla et al. (1997) *J. Clin. Invest.* 100(2):310-320). In Alzheimer's disease, a progressive neuronal cell loss accompanies the deposition of Aβ amyloid fibrils in senile plaques.

In yet another aspect, the invention pertains to a method for inhibiting Aβ-induced neuronal cell death by administering an effective amount of a compound of the present invention.

Another aspect of the invention pertains to a method for providing neuroprotection to a subject having an Aβ-amyloid related disease, e.g. Alzheimer's disease, that includes administering an effective amount of a compound of the present invention to the subject, such that neuroprotection is provided.

In another aspect, methods for inhibiting Aβ-induced neuronal cell death are provided that include administration of an effective amount of a compound of the present invention to a subject such that neuronal cell death is inhibited.

In another aspect, methods for treating a disease state characterized by Aβ-induced neuronal cell death in a subject are provided, e.g., by administering an effective amount of a compound of the present invention. Non-limiting examples of such disease states include Alzheimer's disease and Aβ-amyloid related diseases.

The term "neuroprotection" includes protection of neuronal cells of a subject from Aβ-induced cell death, e.g., cell death induced directly or indirectly by an Aβ peptide. Aβ-induced cell death may result in initiation of processes such as, for example: the destabilization of the cytoskeleton; DNA fragmentation; the activation of hydrolytic enzymes, such as phospholipase A2; activation of caspases, calcium-activated proteases and/or calcium-activated endonucleases; inflammation mediated by macrophages; calcium influx into a cell; membrane potential changes in a cell; the disruption of cell junctions leading to decreased or absent cell-cell communication; and the activation of expression of genes involved in cell death, e.g., immediate-early genes.

The term "amyloid-β disease" (or "amyloid-β related disease," which terms as used herein are synonymous) may be used for mild cognitive impairment; vascular dementia; early Alzheimer's disease; Alzheimer's disease, including sporadic (non-hereditary) Alzheimer's disease and familial (hereditary) Alzheimer's disease; age-related cognitive decline; cerebral amyloid angiopathy ("CAA"); hereditary cerebral hemorrhage; senile dementia; Down's syndrome; inclusion body myositis ("IBM"); or age-related macular degeneration ("ARMD"). According to certain aspects of the invention, amyloid-β is a peptide having 39-43 amino-acids, or amyloid-β is an amyloidogenic peptide produced from βAPP.

Mild cognitive impairment ("MCI") is a condition characterized by a state of mild but measurable impairment in thinking skills, which is not necessarily associated with the presence of dementia. MCI frequently, but not necessarily, precedes Alzheimer's disease. It is a diagnosis that has most often been associated with mild memory problems, but it can also be characterized by mild impairments in other thinking skills, such as language or planning skills. However, in general, an individual with MCI will have more significant memory lapses than would be expected for someone of their age or educational background. As the condition progresses, a physician may change the diagnosis to "Mild-to-Moderate Cognitive Impairment," as is well understood in this art.

Cerebral amyloid angiopathy ("CAA") refers to the specific deposition of amyloid fibrils in the walls of leptomingeal and cortical arteries, arterioles and in capillaries and veins. It is commonly associated with Alzheimer's disease, Down's syndrome and normal aging, as well as with a variety of familial conditions related to stroke or dementia (see Frangione, et al., *Amyloid: J. Protein Folding Disord.* 8, Suppl. 1, 36-42 (2001)). CAA can occur sporadically or be hereditary. Multiple mutation sites in either Aβ or the APP gene have been identified and are clinically associated with either dementia or cerebral hemorrhage. Exemplary CAA disorders include, but are not limited to, hereditary cerebral hemorrhage with amyloidosis of Icelandic type (HCHWA-I); the Dutch variant of HCHWA (HCHWA-D; a mutation in Aβ); the Flemish mutation of Aβ; the Arctic mutation of Aβ; the Italian mutation of Aβ; the Iowa mutation of Aβ; familial British dementia; and familial Danish dementia. Cerebral amyloid angiopathy is known to be associated with cerebral hemorrhage (or hemorrhagic stroke).

Additionally, abnormal accumulation of APP and of amyloid-β protein in muscle fibers has been implicated in the pathology of sporadic inclusion body myositis ("IBM") (Askanas, et al., *Proc. Natl. Acad. Sci. USA* 93, 1314-19 (1996); Askanas, et al., *Current Opinion in Rheumatology* 7, 486-96 (1995)). Accordingly, the compounds of the invention can be used prophylactically or therapeutically in the treatment of disorders in which amyloid-β protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al., *Proc. Natl. Acad. Sci. USA* 99(18), 11830-5 (2002)). Therefore, the invention also relates to the treatment or prevention of age-related macular degeneration.

Also, the invention relates to a method for preventing or inhibiting amyloid deposition in a subject. For example, such a method comprises administering to a subject a therapeutically effective amount of a compound capable of reducing the concentration of amyloid (e.g., AL amyloid protein (λ or κ-chain related, e.g., amyloid λ, amyloid κ, amyloid κIV, amyloid λVI, amyloid γ, amyloid γ1), Aβ, IAPP, β$_2$M, AA, AH amyloid protein, or other amyloids), such that amyloid accumulation or deposition is prevented or inhibited.

In another aspect, the invention relates to a method for preventing, reducing, or inhibiting amyloid deposition in a subject. For example, such a method comprises administering to a subject a therapeutically effective amount of a compound capable of inhibiting amyloid (e.g., AL amyloid protein (λ or κ-chain related, e.g., amyloid λ, amyloid κ, amyloid κIV, amyloid λVI, amyloid γ, amyloid γ1), Aβ, IAPP, β$_2$M, AA, AH amyloid protein, or other amyloids), such that amyloid deposition is prevented, reduced, or inhibited.

The invention also relates to a method for modulating, e.g., minimizing, amyloid-associated damage to cells, comprising the step of administering a compound capable of reducing the concentration of amyloid (e.g., AL amyloid protein (λ or κ-chain related, e.g., amyloid λ, amyloid κ, amyloid κIV, amyloid λVI, amyloid γ, amyloid γ1), Aβ, IAPP, β$_2$M, AA, AH amyloid protein, or another amyloid), such that said amyloid-associated damage to cells is modulated. In certain aspects of the invention, the methods for modulating amyloid-associated damage to cells comprise a step of administering a compound capable of reducing the concentration of amyloid or reducing the interaction of an amyloid with a cell surface.

The invention also includes a method for directly or indirectly preventing cell death in a subject, the method comprising administering to a subject a therapeutically effective amount of a compound capable of preventing amyloid (e.g., AL amyloid protein (λ or κ-chain related, e.g., amyloid λ, amyloid κ, amyloid κIV, amyloid λVI, amyloid γ, amyloid γ1), Aβ, IAPP, β$_2$M, AA, AH amyloid protein, or other amyloid) mediated events that lead, directly or indirectly, to cell death.

In an embodiment, the method is used to treat Alzheimer's disease (e.g. sporadic or familial AD). The method can also be used prophylactically or therapeutically to treat other clinical occurrences of amyloid-β deposition, such as in Down's syndrome individuals and in patients with cerebral amyloid angiopathy ("CAA") or hereditary cerebral hemorrhage.

The compounds of the invention may be used prophylactically or therapeutically in the treatment of disorders in which amyloid-beta peptide is abnormally deposited at non-neurological locations, such as treatment of IBM by delivery of the compounds to muscle fibers, or treatment of macular degeneration by delivery of the compound(s) of the invention to the basal surface of the retinal pigmented epithelium.

The present invention also provides a method for modulating amyloid-associated damage to cells, comprising the step of administering a compound capable of reducing the concentration of Aβ, or capable of mimimizing the interaction of Aβ (soluble oligomeric or fibrillary) with the cell surface, such that said amyloid-associated damage to cells is modulated. In certain aspects of the invention, the methods for modulating amyloid-associated damage to cells comprise a step of administering a compound capable of reducing the concentration of Aβ or reducing the interaction of Aβ with a cell surface.

In accordance with the present invention, there is further provided a method for preventing cell death in a subject, said method comprising administering to a subject a therapeutically effective amount of a compound capable of preventing Aβ-mediated events that lead, directly or indirectly, to cell death.

The present invention also provides a method for modulating amyloid-associated damage to cells, comprising the step of administering a compound capable of reducing the concentration of IAPP, or capable of mimimizing the interaction of IAPP (soluble oligomeric or fibrillary) with the cell surface, such that said amyloid-associated damage to cells is modulated. In certain aspects of the invention, the methods for modulating amyloid-associated damage to cells comprise a step of administering a compound capable of reducing the concentration of IAPP or reducing the interaction of LAPP with a cell surface.

In accordance with the present invention, there is further provided a method for preventing cell death in a subject, said method comprising administering to a subject a therapeutically effective amount of a compound capable of preventing IAPP-mediated events that lead, directly or indirectly, to cell death.

This invention also provides methods and compositions which are useful in the treatment of amyloidosis. The methods of the invention involve administering to a subject a therapeutic compound which inhibits amyloid deposition. Accordingly, the compositions and methods of the invention are useful for inhibiting amyloidosis in disorders in which amyloid deposition occurs. The methods of the invention can be used therapeutically to treat amyloidosis or can be used prophylactically in a subject susceptible to (hereditary) amyloidosis or identified as being at risk to develop amyloidosis, e.g., hereditary, or identified as being at risk to develop amyloidosis. In certain embodiments, the invention includes a method of inhibiting an interaction between an amyloidogenic protein and a constituent of basement membrane to inhibit amyloid deposition. The constituent of basement membrane is a glycoprotein or proteoglycan, preferably heparan sulfate proteoglycan. A therapeutic compound used in this method may interfere with binding of a basement membrane constituent to a target binding site on an amyloidogenic protein, thereby inhibiting amyloid deposition.

In some aspects, the methods of the invention involve administering to a subject a therapeutic compound which inhibits amyloid deposition. "Inhibition of amyloid deposition," includes the prevention of amyloid formation, inhibition of further amyloid deposition in a subject with ongoing amyloidosis and reduction of amyloid deposits in a subject with ongoing amyloidosis. Inhibition of amyloid deposition is determined relative to an untreated subject or relative to the treated subject prior to treatment. In an embodiment, amyloid deposition is inhibited by inhibiting an interaction between an amyloidogenic protein and a constituent of basement membrane. "Basement membrane" refers to an extracellular matrix comprising glycoproteins and proteoglycans, including laminin, collagen type IV, fibronectin, perlecan, agrin, dermatan sulfate, and heparan sulfate proteoglycan (HSPG). In one embodiment, amyloid deposition is inhibited by interfering with an interaction between an amyloidogenic protein and a sulfated glycosaminoglycan such as HSPG, dermatan sulfate, perlecan or agrin sulfate. Sulfated glycosaminoglycans are known to be present in all types of amyloids (see Snow, et al. Lab. Invest. 56, 120-23 (1987)) and amyloid deposition and HSPG deposition occur coincidentally in animal models of amyloidosis (see Snow, et al. Lab. Invest. 56, 665-75 (1987) and Gervais, F. et al. *Curr. Med. Chem.*, 3, 361-370 (2003)). Consensus binding site motifs for HSPG in amyloidogenic proteins have been described (see, e.g., Cardin and Weintraub Arteriosclerosis 9, 21-32 (1989)).

The ability of a compound to prevent or block the formation or deposition of amyloid may reside in its ability to bind to non-fibrillar, soluble amyloid protein and to maintain its solubililty.

The ability of a therapeutic compound of the invention to inhibit an interaction between an amyloidogenic protein and a glycoprotein or proteoglycan constituent of a basement membrane can be assessed by an in vitro binding assay, such as that described in U.S. Pat. No. 5,164,295, the contents of which are hereby incorporated by reference. Alternatively, the ability of a compound to bind to an amyloidogenic protein or to inhibit the binding of a basement membrane constituent (e.g. HSPG) to an amyloidogenic protein (e.g. AP) can be measured using a mass spectrometry assay where soluble protein, e.g. Aβ, IAPP, β$_2$M is incubated with the compound. A compound which binds to, e.g. AP, will induce a change in the mass spectrum of the protein. Exemplary protocols for a mass spectrometry assay employing Aβ and IAPP can be found in the Examples, the results of which are provided in Table 3. The protocol can readily be modified to adjust the sensitivity of the data, e.g., by adjusting the amount of protein and/or compound employed. Thus, e.g., binding might be detected for test compounds noted as not having detectable binding employing less sensitive test protocols.

Alternative methods for screening compounds exist and can readily be employed by a skilled practitioner to provide an indication of the ability of test compounds to bind to, e.g., fibrillar Aβ. One such screening assay is an ultraviolet absorption assay. In an exemplary protocol, a test compound (20 μM) is incubated with 50 μM Aβ(1-40) fibers for 1 hour at 37° C. in Tris buffered saline (20 mM Tris, 150 mM NaCl, pH 7.4 containing 0.01 sodium azide). Following incubation, the solution is centrifuged for 20 minutes at 21,000 g to sediment the Aβ(1-40) fibers along with any bound test compound. The amount of test compound remaining in the supernatant can then be determined by reading the absorbance. The fraction of test compound bound can then be calculated by comparing the amount remaining in the supernatants of incubations with Aβ to the amount remaining in control incubations which do not contain Aβ fibers. Thioflavin T and Congo Red, both of which are known to bind to Aβ fibers, may be included in each assay run as positive controls. Before assaying, test compounds can be diluted to 40 μM, which would be twice the concentration in the final test, and then scanned using the Hewlett Packard 8453 UV/VIS spectrophotometer to determine if the absorbance is sufficient for detection.

In another embodiment, the invention pertains to a method for improving cognition in a subject suffering from an amyloid-related disease. The method includes administering an effective amount of a therapeutic compound of the invention, such that the subject's cognition is improved. The subject's cognition can be tested using methods known in the art such as the Clinical Dementia Rating ("CDR"), Mini-Mental State Examination ("MMSE"), Disability Assessment for Dementia ("DAD"), and the Alzheimer's Disease Assessment Scale-Cognition ("ADAS-Cog").

In another embodiment, the invention pertains to a method for treating a subject for an amyloid-related disease. The method includes administering a cognitive test to a subject prior to administration of a compound of the invention, administering an effective amount of a compound of the invention to the subject, and administering a cognitive test to the subject subsequent to administration of the compound, such that the subject is treated for the amyloid-related disease, wherein the subject's score on said cognitive test is improved.

"Improvement," "improved" or "improving" in cognition is present within the context of the present invention if there is a statistically significant difference in the direction of normality between the performance of subjects treated using the methods of the invention as compared to members of a placebo group, historical control, or between subsequent tests given to the same subject.

In one embodiment, a subject's CDR is maintained at 0. In another embodiment, a subject's CDR is decreased (e.g., improved) by about 0.25 or more, about 0.5 or more, about 1.0 or more, about 1.5 or more, about 2.0 or more, about 2.5 or more, or about 3.0 or more. In another embodiment, the rate of increase of a subject's CDR rating is reduced by about 5% or more, about 10% or more, about 20% or more, about 25% or more, about 30% or more, about 40% or more, about 50% or more, about 60% or more, about 70% or more, about 80% or more, about 90% or more, or about 100% or more of the increase of the historical or untreated controls.

In one embodiment, a subject's score on the MMSE is maintained. Alternatively, the subject's score on the MMSE may be increased by about 1, about 2, about 3, about 4, about 5, about 7.5, about 10, about 12.5, about 15, about 17.5, about 20, or about 25 points. In another alternative, the rate of the decrease of a subject's MMSE score as compared to historical controls is reduced. For example, the rate of the decrease of a subject's MMSE score may be reduced by about 5% or more, about 10% or more, about 20% or more, about 25% or more, about 30% or more, about 40% or more, about 50% or more, about 60% or more, about 70% or more, about 80% or more, about 90% or more, or about 100% or more of the decrease of the historical or untreated controls.

In one embodiment, a subject's score on the DAD is maintained. Alternatively, the subject's score on the DAD may be increased by about 1, about 2, about 3, about 4, about 5, about 7.5, about 10, about 15, about 20, about 30, about 40, or about 50 or more points. In another alternative, the rate of the decrease of a subject's DAD score as compared to historical controls is reduced. For example, the rate of the decrease of a subject's DAD score may be reduced by about 5% or more, about 10% or more, about 20% or more, about 25% or more, about 30% or more, about 40% or more, about 50% or more, about 60% or more, about 70% or more, about 80% or more, about 90% or more, or about 100% or more of the decrease of the historical or untreated controls.

In one embodiment, the invention pertains to a method for treating, slowing or stopping an amyloid-related disease associated with cognitve impairment, by administering to a subject an effective amount of a therapeutic compound of the invention, wherein the annual deterioration of the subject's cognition as measured by ADAS-Cog is less than 8 points per year, less the 6 points per year, less than 5 points per year, less than 4 points per year, or less than 3 points per year. In a further embodiment, the invention pertains to a method for treating, slowing or stopping an amyloid-related disease associated with cognition by administering an effective amount of a therapeutic compound of the invention such that the subject's cognition as measured by ADAS-Cog remains constant over a year. "Constant" includes fluctuations of no more than 2 points. Remaining constant includes fluctuations of two points or less in either direction. In a further embodiment, the subject's cognition improves by 2 points or greater per year, 3 points or greater per year, 4 point or greater per year, 5 points or greater per year, 6 points or greater per year, 7 points or greater per year, 8 points or greater per year, etc. as measured by the ADAS-Cog. In another alternative, the rate of the increase of a subject's ADAS-Cog score as compared to historical controls is reduced. For example, the rate of the increase of a subject's ADAS-Cog score may be reduced by about 5% or more, about 10% or more, about 20% or more, about 25% or more, about 30% or more, about 40% or more, about 50% or more, about 60% or more, about 70% or more, about 80% or more, about 90% or more or about 100% of the increase of the historical or untreated controls.

In another embodiment, the ratio of $A\beta42:A\beta40$ in the CSF or plasma of a subject decreases by about 15% or more, about 20% or more, about 25% or more, about 30% or more, about 35% or more, about 40% or more, about 45% or more, or about 50% or more. In another embodiment, the levels of $A\beta$ in the subject's cerebrospinal fluid decrease by about 15% or more, about 25% or more, about 35% or more, about 45% or more, about 55% or more, about 75% or more, or about 90% or more.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values in these values and ranges may also be the upper or lower limits of a range.

Furthermore, the invention pertains to any novel chemical compound described herein. That is, the invention relates to novel compounds, and novel methods of their use as described herein, which are within the scope of the Formulae disclosed herein, and which are not disclosed in the cited Patents and Patent Applications.

Synthesis of Compounds of the Invention

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here. Functional and structural equivalents of the compounds described herein and which have the same general properties, wherein one or more simple variations of substituents are made which do not adversely affect the essential nature or the utility of the compound are also included.

The compounds of the present invention may be readily prepared in accordance with the synthesis schemes and protocols described herein, as illustrated in the specific procedures provided. However, those skilled in the art will recognize that other synthetic pathways for forming the compounds of this invention may be used, and that the following is provided merely by way of example, and is not limiting to the present invention. See, e.g., "Comprehensive Organic Transformations" by R. Larock, VCH Publishers (1989). It will be further recognized that various protecting and deprotecting strategies will be employed that are standard in the art (See, e.g., "Protective Groups in Organic Synthesis" by Greene and Wuts). Those skilled in the relevant arts will recognize that the selection of any particular protecting group (e.g., amine and carboxyl protecting groups) will depend on the stability of the protected moiety with regards to the subsequent reaction conditions and will understand the appropriate selections.

Further illustrating the knowledge of those skilled in the art is the following sampling of the extensive chemical literature: "Chemistry of the Amino Acids" by J. P. Greenstein and M. Winitz, John Wiley & Sons, Inc., New York (1961); "Comprehensive Organic Transformations" by R. Larock, VCH Publishers (1989); T. D. Ocain, et al., J. Med. Chem. 31, 2193-99 (1988); E. M. Gordon, et al., J. Med. Chem. 31, 2199-10 (1988); "Practice of Peptide Synthesis" by M. Bodansky and A. Bodanszky, Springer-Verlag, New York (1984); "Protective Groups in Organic Synthesis" by T. Greene and P. Wuts (1991); "Asymmetric Synthesis: Construction of Chiral Molecules Using Amino Acids" by G. M. Coppola and H. F. Schuster, John Wiley & Sons, Inc., New York (1987); "The Chemical Synthesis of Peptides" by J. Jones, Oxford University Press, New York (1991); and "Introduction of Peptide Chemistry" by P. D. Bailey, John Wiley & Sons, Inc., New York (1992).

The synthesis of compounds of the invention is carried out in a solvent. Suitable solvents are liquids at ambient room temperature and pressure or remain in the liquid state under the temperature and pressure conditions used in the reaction. Useful solvents are not particularly restricted provided that they do not interfere with the reaction itself (that is, they preferably are inert solvents), and they dissolve a certain amount of the reactants. Depending on the circumstances, solvents may be distilled or degassed. Solvents may be, for example, aliphatic hydrocarbons (e.g., hexanes, heptanes, ligroin, petroleum ether, cyclohexane, or methylcyclohexane) and halogenated hydrocarbons (e.g., methylenechloride, chloroform, carbontetrachloride, dichloroethane, chlorobenzene, or dichlororbenzene); aromatic hydrocarbons (e.g., benzene, toluene, tetrahydronaphthalene, ethylbenzene, or xylene); ethers (e.g., diglyme, methyl-tert-butyl ether, methyl-tert-amyl ether, ethyl-tert-butyl ether, diethylether, diisopropylether, tetrahydrofuran or methyltetrahydrofurans, dioxane, dimethoxyethane, or diethyleneglycol dimethylether); nitrites (e.g., acetonitrile); ketones (e.g., acetone); esters (e.g., methyl acetate or ethyl acetate); and mixtures thereof.

In general, after completion of the reaction, the product is isolated from the reaction mixture according to standard techniques. For example, the solvent is removed by evaporation or filtration if the product is solid, optionally under reduced pressure. After the completion of the reaction, water may be added to the residue to make the aqueous layer acidic or basic and the precipitated compound filtered, although care should be exercised when handling water-sensitive compounds. Similarly, water may be added to the reaction mixture with a hydrophobic solvent to extract the target compound. The organic layer may be washed with water, dried over anhydrous magnesium sulphate or sodium sulphate, and the solvent is evaporated to obtain the target compound. The target compound thus obtained may be purified, if necessary, e.g., by recrystallization, reprecipitation, chromatography, or by converting it to a salt by addition of an acid or base.

The compounds of the invention may be supplied in a solution with an appropriate solvent or in a solvent-free form (e.g., lyophilized). In another aspect of the invention, the compounds and buffers necessary for carrying out the methods of the invention may be packaged as a kit, optionally including a container. The kit may be commercially used for treating or preventing amyloid-related disease according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The term "container" includes any receptacle for holding the therapeutic compound. For example, in one embodiment, the container is the packaging that contains the compound. In other embodiments, the container is not the packaging that contains the compound, i.e., the container is a receptacle, such as a box or vial that contains the packaged compound or unpackaged compound and the instructions for use of the compound. Moreover, packaging techniques are well known in the art. It should be understood that the instructions for use of the therapeutic compound may be contained on the packaging containing the therapeutic compound, and as such the instructions form an increased functional relationship to the packaged product.

Pharmaceutical Preparations

In another embodiment, the present invention relates to pharmaceutical compositions comprising agents according to any of the Formulae herein for the treatment of an amyloid-related disease, as well as methods of manufacturing such pharmaceutical compositions.

In general, the agents of the present invention may be prepared by the methods illustrated in the general reaction schemes as, for example, in the patents and patent applications refered to herein, or by modifications thereof, using readily available starting materials, reagents and conventional synthesis procedures. In these reactions, it is also possible to make use of variants which are in themselves known, but are not mentioned here. Functional and structural equivalents of the agents described herein and which have the same general properties, wherein one or more simple variations of substituents are made which do not adversely affect the essential nature or the utility of the agent are also included.

The agents of the invention may be supplied in a solution with an appropriate solvent or in a solvent-free form (e.g., lyophilized). In another aspect of the invention, the agents and buffers necessary for carrying out the methods of the invention may be packaged as a kit. The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The therapeutic agent may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

To administer the therapeutic agent by other than parenteral administration, it may be necessary to coat the agent with, or co-administer the agent with, a material to prevent its inactivation. For example, the therapeutic agent may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7, 27 (1984)).

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

The therapeutic agent can be orally administered, for example, with an inert diluent or an assimilable edible carrier. The therapeutic agent and other ingredients may also be enclosed in a hard or soft shell gelatin capsule, compressed into tablets, or incorporated directly into the subject's diet. For oral therapeutic administration, the therapeutic agent may be incorporated with excipients and used in the form of ingestible tablets, buccal tablets, troches, capsules, elixirs, suspensions, syrups, wafers, and the like. The percentage of the therapeutic agent in the compositions and preparations may, of course, be varied. The amount of the therapeutic agent in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic agent calculated to produce the desired therapeutic effect in association with the required pharmaceutical vehicle. The specification for the dosage unit forms of the invention are dictated by and directly dependent on (a) the unique characteristics of the therapeutic agent and the particular therapeutic effect to be achieved, and (b) the limitations inherent in the art of compounding such a therapeutic agent for the treatment of amyloid deposition in subjects.

The present invention therefore includes pharmaceutical formulations comprising the agents of the Formulae described herein, including pharmaceutically acceptable salts thereof, in pharmaceutically acceptable vehicles for aerosol, oral and parenteral administration. Also, the present invention includes such agents, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present invention, an agent of the Formulae described herein, and pharmaceutically acceptable salts thereof, may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical formulations are also provided which are suitable for administration as an aerosol, by inhalation. These formulations comprise a solution or suspension of the desired agent of any Formula herein, or a salt thereof, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

Peroral compositions also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emolients, emulsifiers, thickening agents, solvents and the like.

In one embodiment, active agents are administered at a therapeutically effective dosage sufficient to inhibit amyloid deposition in a subject. A "therapeutically effective" dosage inhibits amyloid deposition by, for example, at least about 20%, or by at least about 40%, or even by at least about 60%, or by at least about 80% relative to untreated subjects. In the case of an Alzheimer's subject, a "therapeutically effective" dosage stabilizes cognitive function or prevents a further decrease in cognitive function (i.e., preventing, slowing, or stopping disease progression). The present invention accordingly provides therapeutic drugs. By "therapeutic" or "drug" is meant an agent having a beneficial ameliorative or prophylactic effect on a specific disease or condition in a living human or non-human animal.

In the case of AA or AL amyloidosis, the agent may improve or stabilize specific organ function. As an example, renal function may be stabilized or improved by 10% or greater, 20% or greater, 30% or greater, 40% or greater, 50% or greater, 60% or greater, 70% or greater, 80% or greater, or by greater than 90%.

In the case of IAPP, the agent may maintain or increase β-islet cell function, as determined by insulin concentration or the Pro-IAPP/IAPP ratio. In a further embodiment, the Pro-IAPP/IAPP ratio is increased by about 10% or greater, about 20% or greater, about 30% or greater, about 40% or greater, or by about 50%. In a further embodiment, the ratio is increased up to 50%. In addition, a therapeutically effective amount of the agent may be effective to improve glycemia or insulin levels.

In another embodiment, the active agents are administered at a therapeutically effective dosage sufficient to treat AA (secondary) amyloidosis and/or AL (primary) amyloidosis, by stabilizing renal function, decreasing proteinuria, increasing creatinine clearance (e.g., by at least 50% or greater or by at least 100% or greater), remission of chronic diarrhea, or by weight gain (e.g., 10% or greater). In addition, the agents may be administered at a therapeutically effective dosage sufficient to improve nephrotic syndrome.

Furthermore, active agents may be administered at a therapeutically effective dosage sufficient to decrease deposition in a subject of amyloid protein, e.g., Aβ40 or Aβ42. A therapeutically effective dosage decreases amyloid deposition by, for example, at least about 15%, or by at least about 40%, or even by at least 60%, or at least by about 80% relative to untreated subjects.

In another embodiment, active agents are administered at a therapeutically effective dosage sufficient to increase or enhance amyloid protein, e.g., Aβ40 or Aβ42, in the blood, CSF, or plasma of a subject. A therapeutically effective dosage increases the concentration by, for example, at least about 15%, or by at least about 40%, or even by at least 60%, or at least by about 80% relative to untreated subjects.

In yet another embodiment, active agents are administered at a therapeutically effective dosage sufficient to maintain a subject's CDR rating at its base line rating or at 0. In another embodiment, the active agents are administered at a therapeutically effective dosage sufficient to decrease a subject's CDR rating by about 0.25 or more, about 0.5 or more, about 1.0 or more, about 1.5 or more, about 2.0 or more, about 2.5 or more, or about 3.0 or more. In another embodiment, the active agents are administered at a therapeutically effective dosage sufficient to reduce the rate of the increase of a subject's CDR rating as compared to historical or untreated controls. In another embodiment, the therapeutically effective dosage is sufficient to reduce the rate of increase of a subject's CDR rating (relative to untreated subjects) by about 5% or greater, about 10% or greater, about 20% or greater, about 25% or greater, about 30% or greater, about 40% or greater, about 50% or greater, about 60% or greater, about 70% or greater, about 80% or greater, about 90% or greater or about 100% or greater.

In yet another embodiment, active agents are administered at a therapeutically effective dosage sufficient to maintain a subject's score on the MMSE. In another embodiment, the active agents are administered at a therapeutically effective dosage sufficient to increase a subject's MMSE score by about 1, about 2, about 3, about 4, about 5, about 7.5, about 10, about 12.5, about 15, about 17.5, about 20, or about 25 points. In another embodiment, the active agents are administered at a therapeutically effective dosage sufficient to reduce the rate of the decrease of a subject's MMSE score as compared to historical controls. In another embodiment, the therapeutically effective dosage is sufficient to reduce the rate of decrease of a subject's MMSE score may be about 5% or less, about 10% or less, about 20% or less, about 25% or less, about 30% or less, about 40% or less, about 50% or less, about 60% or less, about 70% or less, about 80% or less, about 90% or less or about 100% or less, of the decrease of the historical or untreated controls.

In yet another embodiment, active agents are administered at a therapeutically effective dosage sufficient to maintain a subject's score on the ADAS-Cog. In another embodiment, the active agents are administered at a therapeutically effective dosage sufficient to decrease a subject's ADAS-Cog score by about 2 points or greater, by about 3 points or greater, by about 4 points or greater, by about 5 points or greater, by about 7.5 points or greater, by about 10 points or greater, by about 12.5 points or greater, by about 15 points or greater, by about 17.5 points or greater, by about 20 points or greater, or by about 25 points or greater. In another embodiment, the active agents are administered at a therapeutically effective dosage sufficient to reduce the rate of the increase of a subject's ADAS-Cog scores as compared to historical or untreated controls. In another embodiment, the therapeutically effective dosage is sufficient to reduce the rate of increase of a subject's ADAS-Cog scores (relative to untreated subjects) by about 5% or greater, about 10% or greater, about 20% or greater, about 25% or greater, about 30% or greater, about 40% or greater, about 50% or greater, about 60% or greater, about 70% or greater, about 80% or greater, about 90% or greater or about 100% or greater.

In another embodiment, active agents are administered at a therapeutically effective dosage sufficient to decrease the ratio of Aβ42:Aβ40 in the CSF or plasma of a subject by about 15% or more, about 20% or more, about 25% or more, about 30% or more, about 35% or more, about 40% or more, about 45% or more, or about 50% or more.

In another embodiment, active agents are administered at a therapeutically effective dosage sufficient to lower levels of Aβ in the CSF or plasma of a subject by about 15% or more, about 25% or more, about 35% or more, about 45% or more, about 55% or more, about 75% or more, or about 95% or more.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50, and usually a larger therapeutic index is more efficacious. While agents that exhibit toxic side effects may be used, care should be taken to design a delivery system that targets such agents to the site of affected tissue in order to minimize potential damage to unaffected cells and, thereby, reduce side effects.

It is understood that appropriate doses depend upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the subject. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses depend upon the potency. Such appropriate doses may be determined using the assays described herein. When one or more of these compounds is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, and any drug combination.

The ability of an agent to inhibit amyloid deposition can be evaluated in an animal model system that may be predictive of efficacy in inhibiting amyloid deposition in human diseases, such as a transgenic mouse expressing human APP or other relevant animal models where Aβ deposition is seen or for example in an animal model of AA amyloidosis. Likewise, the ability of an agent to prevent or reduce cognitive impairment in a model system may be indicative of efficacy in humans. Alternatively, the ability of an agent can be evaluated by examining the ability of the agent to inhibit amyloid fibril formation in vitro, e.g., using a fibrillogenesis assay such as that described herein, including a ThT, CD, or EM assay. Also the binding of an agent to amyloid fibrils may be measured using a MS assay as described herein. The ability of the agent to protect cells from amyloid induced toxicity is determined in vitro using biochemical assays to determine percent cell death induced by amyloid protein. The ability of an agent to modulate renal function may also be evaluated in an appropriate animal model system.

The therapeutic agent of the invention may be also be administered ex vivo to inhibit amyloid deposition or treat certain amyloid-related diseases, such as β₂M amyloidosis and other amyloidoses related to dialysis. Ex vivo administration of the therapeutic agents of the invention can be accomplished by contacting a body fluid (e.g., blood, plasma, etc.) with a therapeutic compound of the invention such that the therapeutic compound is capable of performing its intended function and administering the body fluid to the subject. The therapeutic compound of the invention may perform its function ex vivo (e.g., dialysis filter), in vivo (e.g., administered with the body fluid), or both. For example, a therapeutic compound of the invention may be used to reduce plasma β₂M levels and/or maintain β₂M in its soluble form ex vivo, in vivo, or both.

Prodrugs

The present invention is also related to prodrugs of the agents of the Formulae disclosed herein. Prodrugs are agents which are converted in vivo to active forms (see, e.g., R. B. Silverman, 1992, "The Organic Chemistry of Drug Design and Drug Action," Academic Press, Chp. 8). Prodrugs can be used to alter the biodistribution (e.g., to allow agents which would not typically enter the reactive site of the protease) or the pharmacokinetics for a particular agent. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate agent which subsequently decomposes to yield the active agent. The prodrug moieties may be metabolized in vivo by esterases or by other mechanisms to carboxylic acids.

Examples of prodrugs and their uses are well known in the art (see, e.g., Berge, et al., "Pharmaceutical Salts", *J. Pharm. Sci.* 66, 1-19 (1977)). The prodrugs can be prepared in situ during the final isolation and purification of the agents, or by separately reacting the purified agent in its free acid form with a suitable derivatizing agent. Carboxylic acids can be converted into esters via treatment with an alcohol in the presence of a catalyst.

Examples of cleavable carboxylic acid prodrug moieties include substituted and unsubstituted, branched or unbranched lower alkyl ester moieties, (e.g., ethyl esters, propyl esters, butyl esters, pentyl esters, cyclopentyl esters, hexyl esters, cyclohexyl esters), lower alkenyl esters, dilower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, dilower alkyl amides, and hydroxy amides.

Pharmaceutically Acceptable Salts

Certain embodiments of the present agents can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of agents of the present invention. These salts can be prepared in situ during the final isolation and purification of the agents of the invention, or by separately reacting a purified agent of the invention in its free base form with a suitable organic or inorganic acid, and isolating the salt thus formed.

Representative salts include the hydrohalide (including hydrobromide and hydrochloride), sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, 2-hydroxyethanesulfonate, and laurylsulphonate salts and the like. See, e.g., Berge et al., "Pharmaceutical Salts", *J. Pharm. Sci.* 66, 1-19 (1977).

In other cases, the agents of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of agents of the present invention.

These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Pharmaceutically acceptable salts" also includes, for example, derivatives of agents modified by making acid or base salts thereof, as described further below and elsewhere in the present application. Examples of pharmaceutically acceptable salts include mineral or organic acid salts of basic residues such as amines; and alkali or organic salts of acidic residues such as carboxylic acids. Pharmaceutically acceptable salts include the conventional non-toxic salts or the quaternary ammonium salts of the parent agent formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid. Pharmaceutically acceptable salts may be synthesized from the parent agent which contains a basic or acidic moiety by conventional chemical methods. Generally, such salts may be prepared by reacting the free acid or base forms of these agents with a stoichiometric amount of the appropriate base or acid in water or in an organic solvent, or in a mixture of the two.

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference. The invention is further illustrated by the following examples, which should not be construed as further limiting.

EXAMPLES

The Examples set forth herein below provide exemplary syntheses of certain representative compounds of the invention. Also provided are exemplary methods for assaying the compounds of the invention for Aβ binding affinity, in vivo efficacy, and neuroprotective activity.

Example 1

Synthesis of Representative Compounds of the Invention

The present invention also relates to novel compounds and the synthesis thereof. Accordingly, the following examples are presented to illustrate how some of those compounds may be prepared.

The synthetic protocols of compounds C; D; E; F; G; H; I; J; K; L; M; N; P; Q; R; S; X; Y; Z; AA; AB; AC; AD; AE; AF; AG; AH; AJ; AK; AL; AM; AV; AW; AY; AZ; BA; BB; BW; BY; BZ; CE; CG; CH; CI; CJ; CK; CL; CO; CV; DD; DG; DH; DI; DJ; DK; DL; DM; DO; DP; DQ; DR; DS; DT; DU; DV; DW; DX; DY; DZ; EA; EB; EC; ED; EE; EF; EG; EH; EI; EJ; EK; EN; EO; EP; EQ; ER; ES; ET; EV; EW; FN; FO are described at pages 155 to 201 of co-owned PCT publication No. WO 2004/113275, which is incorporated herein in its entirety.

Preparation of 3-{[(1S)-1-benzyl-2-(benzyloxy)-2-oxoethyl]amino}propane-1-sulfonic acid (Compound EL)

L-Phenylalanine benzylester hydrochloride (2.0 g, 6.9 mmol) was treated with a saturated aqueous solution of $K_2CO_3$ (50 mL) and EtOAc (3×50 mL) was added. The organic extracts were separated, combined, dried with $Na_2SO_4$, filtered, evaporated under reduced pressure and dried in vacuo.

To a solution of L-Phenylalanine benzylester (1.8 g, 6.8 mmol) in 1,4-dioxane (10 mL) was added 1,3-propanesultone (708 mg, 6.5 mmol). The solution was stirred at reflux. After 1 hour, 20 mL of 1,4-dioxane was added to allow for good stirring. The reaction was stirred at reflux for an additional 1 hour. It was cooled to room temperature. The solid was collected by filtration, washed with acetone (2×25 mL). The product was suspended 80% Acetone/EtOH. The suspension was stirred at reflux for 30 seconds. The solid was filtered and dried in the vacuum oven (50° C.) affording the title compound (1.14 g, 46%). $^1$H NMR (DMSO, 500 MHz) δ ppm 7.27 (m, 6H), 7.12 (m, 4H), 5.05 (dd, 2H, J=12.3 Hz), 4.49 (m, 1H) 3.29 (m, 1H), 3.00 (m, 1H), 2.98 (m, 1H), 2.61 (t, 2H, J=6.5 Hz), 1.97 (m, 2H). $^{13}$C (DMSO, 125 MHz) δ ppm 168.88, 135.21, 134.90, 130.00, 129.31, 129.07, 128.01, 67.98, 60.50, 49.77, 46.72, 35.87, 22.43. $[\alpha]_D$=+4.8° (c=0.00073 in water), ES-MS 378 (M+1).

Preparation of 3-{[(1S)-1-(methoxycarbonyl)-2-methylpropyl]amino}-1-propanesulfonic acid (Compound FT)

L-valine methylester hydrochloride (5.0 g, 29.8 mmol) was treated with a saturated solution of $K_2CO_3$ (75 mL) and EtOAc (3×75 mL) was added. The organic extracts were separated, combined, dried with $Na_2SO_4$, filtered, evaporated under reduced pressure and dried in vacuo.

To a solution of L-valine methylester in THF (25 mL) was slowly added 1,3-propanesultone (2.49 g, 19.9 mmol). The solution was stirred at reflux for 2 hours. The reaction was cooled to room temperature. The solid was collected by filtration, washed with acetone (2×30 mL). It was dried in the vacuum oven (50° C.) affording the title compound (2.52 g, 50%). $^1$H NMR ($D_2O$, 500 MHz) δ ppm 3.92 (m, 1H), 3.75 (s, 3H), 3.13 (t, 2H, J=6.8 Hz), 2.88 (t, 2H, J=6.8 Hz), 2.24 (m, 1H), 2.06 (m, 2H)), 0.96 (d, 3H, J=6.8 Hz), 0.88 (d, 3H, J=6.8 Hz). $^{13}$C ($D_2O$, 125 MHz) δ ppm 169.35, 65.85, 55.61, 48.14, 45.59, 29.48, 21.32, 18.25, 16.57. $[\alpha]_D$=+9.6° (c=0.0014 in water), ES-MS 254 (M+1).

Preparation of 3-{[(1R)-1-cyclohexylethyl]amino}-1-propanesulfonic acid (Compound FU)

To a solution of (R)-(−)-cyclohexylethylamine (2.5 g, 19.7 mmol) in tetrahydrofuran (25 mL) was slowly added 1,3-propanesultone (2.33 g, 18.7 mmol). The solution was stirred at reflux for 2 hours. The reaction was cooled to room temperature. The solid was collected by filtration, washed with acetone (2×25 mL) and dried in vacuo, affording the title compound (3.47 g, 74%). $^1$H NMR ($D_2O$, 500 MHz) δ ppm 3.09 (m, 3H), 2.88 (t, 2H, J=7.3 Hz), 2.00 (m, 2H), 1.58 (m, 6H), 1.13 (m, 5H), 1.03 (m, 3H). $^{13}$C ($D_2O$, 125 MHz) δ ppm 58.37, 48.17, 44.00, 39.84, 29.00, 26.01, 25.82, 25.73, 25.47, 21.51, 11.79. $[\alpha]_D$=+4.5° (c=0.0022 in water), ES-MS 250 (M−1).

Preparation of 3-{[(1S)-1-cyclohexylethyl]amino}-1-propanesulfonic acid (Compound FW)

To a solution of (S)-(+)-cyclohexylethylamine (5.0 g, 39.3 mmol) in tetrahydrofuran (50 mL) was slowly added 1,3-propanesultone (4.66 g, 37.4 mmol). The solution was stirred at reflux for 2 hours. The reaction was cooled to room temperature. The solid was collected by filtration and washed with acetone (2×25 mL). The solid was suspended in 80% acetone/EtOH (200 mL). The suspension was stirred at reflux for 30 seconds before the solid was filtered and dried in vacuo, affording the title compound (6.13 g, 66%). $^1$H NMR (D$_2$O, 500 MHz) δ ppm 3.09 (m, 3H), 2.88 (t, 2H, J=7.3 Hz), 2.00 (m, 2H), 1.55 (m, 6H), 1.13 (m, 5H), 1.03 (m, 3H). $^{13}$C (D$_2$O, 125 MHz) δ ppm 59.37, 48.17, 44.00, 39.84, 29.00, 26.01, 25.82, 25.73, 25.47, 21.51, 11.78. [α]$_D$=−2.8° (c=0.0014 in water), ES-MS 250 (M−1).

Preparation of 3-[(4-tert-butylcyclohexyl)amino]-1-propanesulfonic acid (Compound FX)

To a solution of 4-tert-butylcyclohexylethylamine (mixture of cis and trans isomers, 2.5 g, 16.1 mmol) in tetrahydrofuran (30 mL) was slowly added 1,3-propanesultone (1.84 g, 15.3 mmol). The solution was stirred at reflux for 2 hours. The reaction was cooled to room temperature. The solid was collected by filtration and washed with acetone (2×35 mL). The solid was suspended in 80% acetone/EtOH (200 mL). The suspension was stirred at reflux for 30 seconds before the solid was filtered and dried in vacuo, affording the title compound (3.07 g, 72%). $^1$H NMR (DMSO, 500 MHz) δ ppm 3.21 (m, 0.5H), 3.04 (m, 2H), 2.89 (m, 1H), 2.67 (m, 0.5H), 1.97 (m, 4H), 1.77 (m, 1H), 1.52 (m, 1H), 1.19 (m, 2H), 0.96 (m, 2H), 0.81 (s, 9H). $^{13}$C (DMSO, 125 MHz) δ ppm 56.47, 53.62, 50.44, 49.77, 47.56, 47.04, 46.28, 44.49, 32.98, 32.74, 29.61, 28.10, 28.03, 25.57, 22.68, 22.48, 21.01. ES-MS 276 (M−1).

Preparation of 3-{[(1S,2S)-2-(benzyloxy)cyclopentyl]amino}-1-propanesulfonic acid (Compound FY)

To a solution of (1S,2S)-2-benzyloxycyclopentylamine (1.0 g, 5.2 mmol) in tetrahydrofuran (12 mL) was slowly added 1,3-propanesultone (601 mg, 5.0 mmol). The solution was stirred at reflux for 2 hours. The reaction was cooled to room temperature. The solid was collected by filtration, washed with acetone (2×25 mL) and dried in vacuo, affording the title compound (1.36 g, 87%). $^1$H NMR (D$_2$O, 500 MHz) δ ppm 7.32 (m, 5H), 4.53 (d, 1H, J=11.2 Hz), 4.41 (d, 1H, J=11.2 Hz), 4.01 (m, 1H), 3.36 (m, 1H), 3.00 (t, 2H, J=7.8 Hz), 2.80 (t, 2H, J=7.8 Hz), 2.00 (m, 4H), 1.64 (m, 3H), 1.49 (m, 1H). $^{13}$C NMR (D$_2$O, 125 MHz) δ ppm 136.99, 129.06, 129.01, 128.77, 81.78, 71.81, 63.88, 48.01, 45.33, 29.91, 27.43, 21.60, 20.93. [α]$_D$=+31.1° (c=0.0064 in water). ES-MS 314 (M+1).

Preparation of 3-{[(1R,2R)-2-(benzyloxy)cyclopentyl]amino}-1-propanesulfonic acid (Compound FZ)

To a solution of (1R,2R)-2-benzyloxycyclopentylamine (1.0 g, 5.2 mmol) in tetrahydrofuran (12 mL) was slowly added 1,3-propanesultone (601 mg, 5.0 mmol). The solution was stirred at reflux for 2 hours. The reaction was cooled to room temperature. The solid was collected by filtration and washed with acetone (2×15 mL). The product was suspended in EtOH and the solvent was evaporated (to remove THF residue). The solid was dried in vacuo, affording the title compound (717 mg, 46%). $^1$H NMR (D$_2$O, 500 MHz) δ ppm 7.32 (m, 5H), 4.53 (d, 1H, J=11.2 Hz), 4.42 (d, 1H, J=11.2 Hz), 4.02 (m, 1H), 3.36 (m, 1H), 3.01 (t, 2H, J=7.8 Hz), 2.81 (t, 2H, J=7.8 Hz), 2.01 (m, 4H), 1.65 (m, 3H), 1.49 (m, 1H). $^{13}$C NMR (D$_2$O, 125 MHz) δ ppm 137.00, 129.07, 129.01, 128.77, 81.78, 71.81, 63.89, 48.02, 45.34, 29.93, 27.43, 21.61, 20.94. [α]$_D$=−38.8° (c=0.00122 in water). ES-MS 314 (M+1).

Preparation of 3-{[(1S)-1-benzyl-2-(cyclohexylamino)-2-oxoethyl]amino}-1-propanesulfonic acid (Compound GA)

To a solution of L-Phenylalanine cyclohexylamide (2.5 g, 10.1 mmol) in tetrahydrofuran (25 mL) was added 1,3-propanesultone (1.17 g, 9.7 mmol). The solution was stirred at reflux for 2 hours. It was cooled to room temperature. The solid was collected by filtration, washed with acetone (2×25 mL) and dried in the vacuum oven (50° C.), affording the title compound (1.39 g, 39%). $^1$H NMR (D$_2$O, 500 MHz) δ ppm 7.21 (m, 3H), 7.08 (m, 2H), 4.42 (m, 0.5H), 3.83 (m, 1H) 3.29 (m, 1H), 3.15 (m, 1H), 3.02 (m, 2H), 2.86 (m, 3H), 2.49 (m, 0.5H), 2.01 (m, 2H), 1.54 (m, 1H), 1.45 (m, 1H), 1.33 (m, 2H), 1.02 (m, 4H), 0.55 (m, 1H). $^{13}$C (D$_2$O, 125 MHz) δ ppm 133.71, 129.54, 129.18, 128.03, 62.08, 49.25, 47.97, 45.41, 36.29, 31.73, 31.46, 24.86, 24.28, 24.20, 21.39. [α]$_D$=+36.4° (c=0.0019 in water), ES-MS 369 (M+1).

Preparation of 3-{[(1S,2S)-2-(benzyloxy)cyclopentyl]amino}-1-propanesulfonic acid (Compound GB)

To a solution of (1S,2S)-2-benzyloxycyclohexylamine (1.0 g, 5.2 mmol) in tetrahydrofuran (12 mL) was slowly added 1,3-propanesultone (601 mg, 5.0 mmol). The solution was stirred at reflux for 2 hours. The reaction was cooled to room temperature. The solid was collected by filtration, washed with acetone (2×20 mL) and dried in the vacuum oven (50° C.), affording the title compound (1.15 g, 75%). $^1$H NMR (D$_2$O, 500 MHz) δ ppm 7.34 (m, 5H), 4.62 (d, 1H, J=11.2 Hz), 4.42 (d, 1H, J=11.2 Hz), 3.40 (m, 1H), 2.97 (m, 2H), 2.90 (m, 1H), 2.76 (t, 2H, J=6.5 Hz), 2.26 (m, 1H), 1.92 (m, 3H), 1.66 (m, 2H), 1.18 (m, 4H). $^{13}$C NMR (D$_2$O, 125 MHz)$_6$ ppm 137.22, 129.34, 129.11, 128.84, 76.74, 70.26, 60.84, 48.02, 42.74, 29.49, 26.43, 23.57, 23.02, 21.53. [α]$_D$=+74.8° (c=0.00207 in water). ES-MS 326 (M−1).

Preparation of 3-{[(1R,2R)-2-(benzyloxy)cyclopentyl]amino}-1-propanesulfonic acid (Compound GD)

To a solution of (1R,2R)-2-benzyloxycyclohexylamine (1.0 g, 5.2 mmol) in tetrahydrofuran (12 mL) was slowly added 1,3-propanesultone (601 mg, 5.0 mmol). The solution was stirred at reflux for 2 hours. The reaction was cooled to room temperature. The solid was collected by filtration and washed with acetone (2×35 mL). The solid was suspended in 80% acetone/EtOH (200 mL). The suspension was stirred at reflux for 30 seconds before the solid was filtered and dried in the vacuum oven (50° C.), affording the title compound (844 mg. 55%). $^1$H NMR (D$_2$O, 500 MHz) δ ppm 7.32 (m, 5H), 4.60 (d, 1H, J=11.2 Hz), 4.40 (d, 1H, J=11.2 Hz), 3.39 (m, 1H), 2.94 (m, 2H), 2.85 (m, 1H), 2.74 (t, 2H, J=6.5 Hz), 2.24 (m, 1H), 1.90 (m, 3H), 1.64 (m, 2H), 1.14 (m, 4H). $^{13}$C NMR (D$_2$O, 125 MHz) δ ppm 137.35, 129.28, 129.19, 128.90, 76.90, 70.35, 60.97, 48.12, 42.90, 29.59, 26.53, 23.64, 23.09, 21.63. [α]$_D$=−68.9° (c=0.0026 in water). ES-MS 326 (M−1).

Preparation of 3-({(1S)-1-[(benzyloxy)carbonyl]-2-methylpropyl}amino)-1-propanesulfonic acid (Compound GE)

L-valine benzylester p-tosylate (2.5 g, 6.6 mmol) was treated with a saturated solution of $K_2CO_3$ (50 mL) and EtOAc (3×50 mL). The organic extracts were separated, combined, dried with $Na_2SO_4$, filtered, evaporated under reduced pressure and dried in vacuo.

To a solution of L-valine benzylester in MeOH (12 mL) was slowly added 1,3-propanesultone (604 mg, 5.0 mmol). The solution was stirred at reflux for 2 hours. The reaction was cooled to room temperature. The solid was collected by filtration, washed with cold MeOH and acetone (2×25 mL). It was dried in the vacuum oven (50° C.), affording the title compound (649 mg, 39%). $^1$H NMR ($D_2O$, 500 MHz) δ ppm 7.47 (m, 5H), 5.41 (d, 1H, J=11.7 Hz), 5.31 (d, 3H, J=11.7 Hz), 4.04 (m, 1H), 3.19 (m, 2H), 2.95 (t, 2H, J=6.8 Hz), 2.35 (m, 1H), 2.14 (m, 2H), 1.04 (d, 3H, J=6.3 Hz), 0.95 (d, 3H, J=6.3 Hz). $^{13}$C ($D_2O$, 125 MHz) δ ppm 168.75, 134.81, 129.38, 129.31, 129.17, 69.00, 65.96, 48.24, 46.71, 29.67, 21.40, 18.39, 16.65. $[α]_D$=−7.2° (c=0.0015 in water), ES-MS 330 (M+1).

Preparation of 3-{[(1S)-2-ethoxy-1-methyl-2-oxoethyl]amino}-1-propanesulfonic acid (Compound GF)

L-alanine ethyl ester hydrochloride (2.5 g, 16.3 mmol) was treated with a saturated solution of $K_2CO_3$ (50 mL) and EtOAc (3×50 mL). The organic extracts were separated, combined, dried with $Na_2SO_4$, filtered, evaporated under reduced pressure and dried in vacuo.

To a solution of L-alanine ethyl ester (1.67 g, 14.3 mmol) in tetrahydrofuran (25 mL) was slowly added 1,3-propanesultone (1.42 g, 11.9 mmol). The solution was stirred at reflux for 2 hours. The reaction was cooled to room temperature. The solid was collected by filtration, washed with acetone (2×25 mL) and dried in vacuo, affording the title compound (1.19 g, 42%). $^1$H NMR ($D_2O$, 500 MHz) δ ppm 4.16 (m, 2H), 4.01 (m, 1H), 3.12 (m, 2H), 2.87 (t, 2H, J=7.3 Hz), 2.01 (m, 2H), 1.43 (d, 3H, J=7.3 Hz), 1.14 (t, 3H, J=6.8 Hz). $^{13}$C ($D_2O$, 125 MHz) δ ppm 170.22, 63.84, 55.69, 47.94, 44.73, 21.51, 14.05, 13.25. $[α]_D$=−2.4° (c=0.0022 in water), ES-MS 240 (M+1).

Preparation of (2S)-3-methyl-2-[(3-sulfopropyl)amino]butanoic acid (Compound GC)

L-valine methylester hydrochloride (5.0 g, 29.8 mmol) was treated with a saturated solution of $K_2CO_3$ (75 mL) and EtOAc (3×75 mL). The organic extracts were separated, combined, dried with $Na_2SO_4$, filtered, evaporated under reduced pressure and dried in vacuo.

To a solution of L-valine methylester in tetrahydrofuran (25 mL) was slowly added 1,3-propanesultone (2.49 g, 19.9 mmol). The solution was stirred at reflux for 2.5 hours. The reaction was cooled to room temperature. The solid was collected by filtration, washed with acetone (2×30 mL) and dried in vacuo affording the desired ester.

The ester (860 mg, 3.4 mmol) was dissolved in 2M NaOH (1.20 g of NaOH and 15 mL of water). The reaction was stirred at room temperature overnight. Dowex Marathon C ion exchange resin (strongly acidic) was added to the solution. The suspension was stirred for 15 minutes before the resin was removed by filtration. The filtrate was evaporated under reduced pressure and dried in vacuo, affording the title compound (645 mg, 79%). $^1$H NMR ($D_2O$, 500 MHz) δ ppm 3.66 (m, 1H), 3.09 (t, 2H, J=6.3 Hz), 2.86 (t, 2H, J=7.3 Hz), 2.17 (m, 1H), 2.07 (m, 2H)), 0.93 (d, 3H, J=6.8 Hz), 0.87 (d, 3H, J=6.8 Hz). $^{13}$C ($D_2O$, 125 MHz) δ ppm 171.24, 66.83, 48.28, 46.77, 29.33, 21.44, 18.30, 16.98. $[α]_D$=−16.5° (c=0.0020 in water), ES-MS 238 (M−1).

Preparation of 3-{[(1S)-1-(methoxycarbonyl)-3-methylbutyl]amino}-1-propanesulfonic acid (Compound GH)

L-Leucine methylester hydrochloride (5.0 g, 27.5 mmol) was treated with a saturated solution of $K_2CO_3$ (50 mL) and EtOAc (3×50 mL) was added. The organic extracts were separated, combined, dried with $Na_2SO_4$, filtered, evaporated under reduced pressure and dried in vacuo.

To a solution of L-valine methylester (3.74 g, 25.6 mmol) in tetrahydrofuran (35 mL) was slowly added 1,3-propanesultone (2.04 g, 17.2 mmol). The solution was stirred at reflux for 3 hours. The reaction was cooled to room temperature. The solid was collected by filtration. Dowex Marathon C ion exchange resin (strongly acidic) was added to the solution. The suspension was stirred for 15 minutes before the resin was removed by filtration. The filtrate was evaporated under reduced pressure. The solid was suspended in acetone (50 mL), filtered and dried in vacuo, affording the title compound (1.80 g, 39%). $^1$H NMR ($D_2O$, 500 MHz) δ ppm 3.99 (m, 1H), 3.72 (s, 3H), 3.12 (m, 2H), 2.87 (t, 2H, J=7.3 Hz), 2.02 (m, 2H), 1.74 (m, 1H), 1.60 (m, 2H), 0.81 (d, 3H, J=5.4 Hz), 0.87 (d, 3H, J=6.8 Hz). $^{13}$C ($D_2O$, 125 MHz) δ ppm 170.60, 58.91, 53.81, 48.08, 45.50, 38.17, 24.44, 22.15, 21.59, 20.93. $[α]_D$=+13.8° (c=0.0016 in water), ES-MS 268 (M+1).

Preparation of 3-({(1S)-1-[(tert-butylamino)carbonyl]-2-methylpropyl}amino)-1-propanesulfonic acid (Compound GI)

L-valine tert-butylamide hydrochloride (2.5 g, 12.0 mmol) was treated with a saturated solution of $K_2CO_3$ (50 mL) and EtOAc (3×50 mL) was added. The organic extracts were separated, combined, dried with $Na_2SO_4$, filtered, evaporated under reduced pressure and dried in vacuo.

To a solution of L-valine tert-butylamide (1.87 g, 11.0 mmol) in 1,4-dioxane (20 mL) was added 1,3-propanesultone (1.07 g, 9.0 mmol). The solution was stirred at reflux for 5 hours. The reaction was cooled to room temperature. The solid was collected by filtration, washed with acetone (2×30 mL) and dried in vacuo, affording the title compound (801 mg, 25%). $^1$H NMR ($D_2O$, 500 MHz) δ ppm 3.43 (m, 1H), 3.00 (m, 2H), 2.85 (m, 2H), 2.03 (m, 3H), 1.21 (m, 9H), 0.92 (d, 3H, J=6.3 Hz), 0.85 (d, 3H, J=6.8 Hz). $^{13}$C ($D_2O$, 125 MHz) δ ppm 166.47, 66.55, 52.56, 48.23, 46.11, 29.91, 27.81, 21.29, 18.30, 17.44. $[α]_D$=−11.6° (c=0.0023 in water), ES-MS 293 (M−1).

Preparation of 3-{[(1S)-1-(hydroxymethyl)-3-methylbutyl]amino}-1-propanesulfonic acid (Compound GJ)

To a solution of L-(+)-leucinol (5.0 g, 42.8 mmol) in THF (65 mL) was slowly added 1,3-propanesultone (4.85 g, 40.7 mmol in THF (10 mL)). The solution was stirred at reflux for 2 hours. The reaction was cooled to room temperature. The solid was collected by filtration and washed with acetone (2×50 mL). The solid was dissolved in 50% water/EtOH (400 mL). Dowex Marathon C ion exchange resin (strongly acidic) was added to the solution. The suspension was stirred for 15 minutes before the resin was removed by filtration. The filtrate was evaporated under reduced pressure. The solid was suspended in acetone (150 mL), filtered and dried in the vacuum oven (50° C.), affording the title compound (6.11 g, 63%). $^1$H NMR (D$_2$O, 500 MHz) δ ppm 3.77 (m, 1H), 3.59 (m, 1H), 3.23 (m, 1H), 3.13 (m, 2H), 2.90 (m, 2H), 2.02 (m, 2H), 1.53 (m, 2H), 1.35 (m, 1H), 0.81 (d, 3H, J=16.1 Hz). $^{13}$C (D$_2$O, 125 MHz) δ ppm 58.72, 58.00, 48.17, 43.54, 35.96, 24.34, 22.53, 21.62, 20.89. [α]$_D$=+16.6° (c=0.0022 in water), ES-MS 240 (M+1).

Preparation of 3-{[(1S)-1-(hydroxymethyl)-2-methylbutyl]amino}-1-propanesulfonic acid (Compound GK)

To a solution of L-(+)-isoleucinol (2.0 g, 17.1 mmol) in THF (30 mL) was slowly added 1,3-propanesultone (1.94 g, 16.3 mmol). The solution was stirred at reflux for 2 hours. The reaction was cooled to room temperature. The solid was collected by filtration and washed with acetone (2×20 mL). The solid was dissolved in 70% water/EtOH (240 mL). Dowex Marathon C ion exchange resin (strongly acidic, 15 g) was added to the solution. The suspension was stirred for 15 minutes before the resin was removed by filtration. The filtrate was evaporated under reduced pressure. The solid was suspended in acetone (60 mL), filtered and dried in the vacuum oven (50° C.), affording the title compound (1.70 g, 44%). $^1$H NMR (D$_2$O, 500 MHz) δ ppm 3.78 (d, 1H, J=13.1 Hz), 3.64 (m, 1H), 3.14 (m, 3H), 2.03 (m, 2H), 1.75 (m, 1H), 1.32 (m, 1H), 1.17 (m, 1H), 0.79 (m, 6H). $^{13}$C (D$_2$O, 125 MHz) δ ppm 63.42, 57.38, 48.27, 44.77, 33.64, 25.91, 21.52, 13.31, 10.94. [α]$_D$=+20.4° (c=0.00212 in water), ES-MS 240 (M+1).

Preparation of 3-{[(1R)-1-(hydroxymethyl)-3-methylbutyl]amino}-1-propanesulfonic acid (Compound GL)

To a solution of D-(−)-leucinol (2.0 g, 17.1 mmol) in THF (30 mL) was slowly added 1,3-propanesultone (1.94 g, 16.3 mmol). The solution was stirred at reflux for 2 hours. The reaction was cooled to room temperature. The solid was collected by filtration and washed with acetone (2×20 mL). The solid was dissolved in 50% water/EtOH (240 mL). Dowex Marathon C ion exchange resin (strongly acidic) was added to the solution. The suspension was stirred for 15 minutes before the resin was removed by filtration. The filtrate was evaporated under reduced pressure. The solid was suspended in acetone (50 mL), filtered and dried in the vacuum oven (50° C.), affording the title compound (2.55 g, 65%). $^1$H NMR (D$_2$O, 500 MHz) δ ppm 3.74 (d, 1H, J=12.7 Hz), 3.56 (d, 1H, J=12.7 Hz), 3.20 (m, 1H), 3.10 (t, 2H, J=7.3 Hz), 2.87 (t, 2H, J=7.3 Hz), 2.00 (m, 2H), 1.49 (m, 2H), 1.31 (m, 1H), 0.80 (d, 3H, J=6.3 Hz), 0.76 (d, 3H, J=6.3 Hz). $^{13}$C (D$_2$O, 125 MHz) δ ppm 58.74, 58.01, 48.19, 43.56, 35.98, 24.34, 22.54, 21.63, 20.90. [α]$_D$=−16.3° (c=0.0019 in water), ES-MS 238 (M−1).

Preparation of 3-{[(1S)-2-amino-2-oxo-1-phenylethyl]amino}-1-propanesulfonic acid (Compound GN)

L-Phenylglycine amide hydrochloride (1.0 g, 6.7 mmol) was treated with a solution of K$_2$CO$_3$ (20 mL). The resultant mixture was extracted with EtOAc (3×20 mL). The organic extracts were separated, combined, dried over Na$_2$SO$_4$. The solid material was removed by filtration, and the filtrate was concentrated to dryness under reduced pressure.

To a solution of L-Phenylglycine amide (670 mg, 5.9 mmol) in tetrahydrofuran (10 mL) and 1,4-dioxane (4 mL) was added 1,3-propanesultone (674 mg, 5.6 mmol). The solution stirred at reflux for 2 hours. The reaction was cooled to room temperature. The solid was collected by filtration and washed with acetone (2×20 mL). The solid was dissolved in 50% water/EtOH mL). Dowex Marathon C ion exchange resin (strongly acidic) was added to the solution. The suspension was stirred for 15 minutes before the resin was removed by filtration. The filtrate was evaporated under reduced pressure. The solid was suspended in acetone (50 mL), filtered and dried in the vacuum oven (50° C.), affording the title compound (743 mg, 50%). $^1$H NMR (D$_2$O, 500 MHz) δ ppm 7.38 (m, 5H), 4.92, (s, 1H), 3.01 (m, 1H), 2.91 (m, 1H), 2.78 (t, 2H, J=7.3 Hz), 2.0 (m, 2H). $^{13}$C (D$_2$O, 125 MHz) δ ppm 170.15, 130.95, 130.24, 129.94, 128.74, 63.40, 47.99, 44.92, 21.27. [α]$_D$=−124° (c=0.0041 in water), ES-MS 271 (M−1).

Preparation of 3-{[(1S)-2-tert-butoxy-1-methyl-2-oxoethyl]amino}-1-propanesulfonic acid (Compound GO)

L-Alanine tert-butylester hydrochloride (2.61 g, 14.4 mmol) was treated with a solution of K$_2$CO$_3$ (75 mL). The resultant mixture was extracted with EtOAc (3×75 mL). The organic extracts were separated, combined, dried over Na$_2$SO$_4$. The solid material was removed by filtration, and the filtrate was concentrated to dryness under reduced pressure.

To a solution of L-Alanine tert-butylester (1.53 g, 10.5 mmol) in tetrahydrofuran (20 mL) was added 1,3-propanesultone (1.16 g, 9.6 mmol). The solution stirred at reflux for 2 hours. The reaction was cooled to room temperature. The solid was collected by filtration and washed with acetone (2×20 mL). The solid was dissolved in water (80 mL). Dowex Marathon C ion exchange resin (strongly acidic) was added to the solution. The suspension was stirred for 15 minutes before the resin was removed by filtration. The filtrate was evaporated under reduced pressure. The solid was suspended in acetone (80 mL), filtered and dried in the vacuum oven (50° C.), affording the title compound (1.37 g, 54%). $^1$H NMR (D$_2$O, 500 MHz) δ ppm 3.88 (m, 1H), 3.09 (m, 2H), 2.86 (t, 2H, J=7.3 Hz), 2.00 (m, 2H), 1.39 (d, 3H, J=7.3 Hz), 1.35 (s, 9H). $^{13}$C (D$_2$O, 125 MHz) δ ppm 169.13, 86.12, 56.24, 47.94, 44.71, 27.11, 21.52, 14.17. [α]$_D$=−1.1° (c=0.0027 in water), ES-MS 266 (M−1).

Preparation of 3-{[(1S)-2-amino-2-oxo-1-phenylethyl]amino}-1-propanesulfonic acid (Compound GP)

D-Phenylglycine amide hydrochloride (1.0 g, 6.7 mmol) was treated with a solution of K$_2$CO$_3$ (20 mL). The resultant mixture was extracted with EtOAc (3×20 mL). The organic extracts were separated, combined, dried over Na$_2$SO$_4$. The solid material was removed by filtration, and the filtrate was concentrated to dryness under reduced pressure.

To a solution of D-Phenylglycine amide (850 mg, 7.5 mmol) in tetrahydrofuran (10 mL) and 1,4-dioxane (4 mL) was added 1,3-propanesultone (818 mg, 6.8 mmol). The solution stirred at reflux for 2 hours. The reaction was cooled to room temperature. The solid was collected by filtration and washed with acetone (2×20 mL). The solid was dissolved in 50% water/EtOH mL). Dowex Marathon C ion exchange resin (strongly acidic) was added to the solution. The suspension was stirred for 15 minutes before the resin was removed by filtration. The filtrate was evaporated under reduced pressure. The solid was suspended in acetone (50 mL), filtered and dried in the vacuum oven (50° C.), affording the title compound (720 mg, 34%). $^1$H NMR (D$_2$O, 500 MHz) δ ppm 7.38 (m, 5H), 4.92, (s, 1H), 3.00 (m, 1H), 2.90 (m, 1H), 2.78 (m, 2H), 1.97 (m, 2H). $^{13}$C (D$_2$O, 125 MHz) δ ppm 170.14, 130.95, 130.24, 129.94, 128.74, 63.40, 47.99, 44.92, 21.27. [α]$_D$=+106° (c=0.0016 in water), ES-MS 273 (M+1).

Preparation of (2S)-2-[(3-sulfopropyl)amino]propanoic acid (Compound GQ)

L-alanine methylester hydrochloride (5.0 g, 35.8 mmol) was treated with a saturated solution of K$_2$CO$_3$ (75 mL). The mixture was extracted with EtOAc (3×75 mL). The organic extracts were separated, combined, dried with Na$_2$SO$_4$, filtered, evaporated under reduced pressure and dried in vacuo.

To a solution of L-alanine methylester (2.37 g, 23.3 mmol) in tetrahydrofuran (35 mL) was added 1,3-propanesultone (2.41 g, 20.0 mmol). The solution was stirred at reflux for 2 hours. The reaction was cooled to room temperature. The solid was collected by filtration, washed with acetone (2×30 mL) and dried in vacuo.

The ester (2.21 g, 9.8 mmol) was dissolved in 2M NaOH (2.40 g of NaOH and 30 mL of water). The reaction was stirred at room temperature overnight. Dowex Marathon C ion exchange resin (strongly acidic) was added to the solution. The suspension was stirred for 15 minutes before the resin was removed by filtration. The filtrate was evaporated under reduced pressure and lyophilized, affording the title compound (1.81 g, 87%). $^1$H NMR (D$_2$O, 500 MHz) δ ppm 3.76 (m, 1H), 3.07 (m, 2H), 2.85 (t, 2H, J=7.3 Hz), 1.99 (m, 2H), 1.38 (d, 3H, J=7.3 Hz), 0.87 (d, 3H, J=6.8 Hz). $^{13}$C (D$_2$O, 125 MHz) δ ppm 173.31, 56.66, 47.97, 44.76, 21.56, 14.51. [α]$_D$=+3.5° (c=0.0023 in water), ES-MS 210 (M−1).

Preparation of (2S)-3-phenyl-2-[(3-sulfopropyl) amino]propanoic acid (Compound GR)

The N-(3-sulfo-propyl)-phenylalanine ethyl ester (DM-258-069, 860 mg, 2.7 mmol) was dissolved in 2N NaOH (1.2 g of NaOH and 15 mL of water). The reaction was stirred at room temperature overnight. Dowex Marathon C ion exchange resin (strongly acidic) was added to the solution. The suspension was stirred for 15 minutes before the resin was removed by filtration. The filtrate was evaporated under reduced pressure and lyophilized, affording the title compound (654 mg, 84%). $^1$H NMR (D$_2$O, 500 MHz) δ ppm 7.20 (m, 5H), 3.96 (t, 1H, J=6.3 Hz), 3.11 (m, 4H), 2.80 (t, 2H, J=7.3 Hz), 1.95 (m, 2H). $^{13}$C (D$_2$O, 125 MHz) δ ppm 171.46, 134.03, 129.50, 129.28, 128.10, 62.02, 47.97, 45.64, 35.23, 21.39. [α]$_D$=+14.9° (c=0.0013 in water), ES-MS 286 (M−1).

Preparation of 3-{[(1S)-1-isopropyl-2-oxopent-4-enyl]amino}-1-propanesulfonic acid (Compound GS)

L-Valine allylester p-tosylate (3.0 g, 9.1 mmol) was treated with a saturated solution of K$_2$CO$_3$ (30 mL). The mixture was extracted with EtOAc (3×30 mL). The organic extracts were separated, combined, dried with Na$_2$SO$_4$, filtered and evaporated under reduced pressure.

To a solution of L-valine allylester (1.30 g, 8.3 mmol) in tetrahydrofuran (6 mL), 1,4-dioxane (6 mL) and MeOH (0.5 mL) was added 1,3-propanesultone (910 mg, 7.5 mmol). The solution was stirred at reflux for 2 hours. The reaction was cooled to room temperature. The solvent was evaporated under reduced pressure. The sticky paste was suspended in 20% acetone/ether. The solid was filtered and dissolved EtOH (75 mL). Dowex Marathon C ion exchange resin (strongly acidic) was added to the solution. The suspension was stirred for 15 minutes before the resin was removed by filtration. The filtrate was evaporated to dryness under reduced pressure, affording the title compound (605 mg, 26%). $^1$H NMR (D$_2$O, 500 MHz) δ ppm 5.84 (m, 1H), 5.27 (d, 1H, J=17.1 Hz), 5.19 (m, 1H, J=10.3 Hz), 3.91 (d, 1H, J=3.9 Hz), 3.10 (t, 2H, J=7.3 Hz), 2.85 (t, 2H, J=7.3 Hz), 2.22 (m, 1H), 2.03 (m, 2H), 0.93 (d, 3H, J=6.8 Hz), 0.85 (d, 3H, J=6.8 Hz). $^{13}$C (D$_2$O, 125 MHz) δ ppm 168.55, 130.90, 120.31, 67.58, 65.82, 48.09, 46.57, 29.53, 21.29, 18.25, 16.57. [α]$_D$=+5.0° (c=0.0011 in water), ES-MS 278 (M−1).

Preparation of 3-{[(1S)-1-(aminocarbonyl)-3-methylbutyl]amino}-1-propanesulfonic acid (Compound GT)

L-Leucinamide hydrochloride (5.0 g, 30.0 mmol) was treated with a saturated solution of K$_2$CO$_3$ (100 mL). The mixture was extracted with EtOAc (3×100 mL). The organic extracts were separated, combined, dried with Na$_2$SO$_4$, filtered and evaporated under reduced pressure.

To a solution of L-Leucinamide (3.20 g, 24.5 mmol) in tetrahydrofuran (35 mL) was added 1,3-propanesultone (2.82 g, 23.3 mmol). The solution was stirred at reflux for 2 hours. The reaction mixture was cooled to room temperature. The solid was filtered and washed with acetone (2×25 mL). The solid was dissolved in 50% EtOH/water (200 mL). Dowex Marathon C ion exchange resin (strongly acidic, 25 g) was added to the solution. The suspension was stirred for 15 minutes before the resin was removed by filtration. The filtrate was evaporated to dryness under reduced pressure. The solid was suspended in acetone (75 mL), and it was then filtered and dried in vacuo, affording the title compound (3.13 g, 53%). $^1$H NMR (D$_2$O, 500 MHz) δ ppm 3.79 (m, 1H), 3.04 (m, 2H), 2.85 (m, 2H), 2.02 (m, 2H), 1.65 (m, 1H), 1.54 (m, 2H), 0.80 (m, 6H). $^{13}$C (D$_2$O, 125 MHz) δ ppm 171.46, 59.42, 48.04, 45.46, 39.04, 24.27, 22.24, 21.49, 21.17. [α]$_D$=+13.5° (c=0.0026 in water), ES-MS 251 (M−1).

Preparation of 3-{[(1S)-1-(benzyloxycarbonyl)-3-methylbutyl]amino}-1-propanesulfonic acid (Compound GU)

L-Leucine benzylester p-tosylate (5.0 g, 12.7 mmol) was treated with a saturated solution of K$_2$CO$_3$ (100 mL). The mixture was extracted with EtOAc (3×100 mL). The organic extracts were separated, combined, dried with Na$_2$SO$_4$, filtered and evaporated under reduced pressure.

To a solution of L-Leucine benzylester (2.81 g, 12.7 mmol) in tetrahydrofuran (6 mL), 1,4-dioxane (6 mL) and MeOH (6 mL) was added 1,3-propane sultone (1.40 g, 11.5 mmol). The solution was stirred at reflux for 2.5 hours. The reaction mixture was cooled to room temperature. The solid was filtered and washed with acetone (2×20 mL). The filtrate was evaporated under reduced pressure. The residue was dissolved in acetone (20 mL). The product was precipitated with Et$_2$O (200 mL). The solid material was filtered. Both solids were combined and dissolved in 50% EtOH/water (200 mL). Dowex Marathon C ion exchange resin (strongly acidic) was added to the solution. The suspension was stirred for 15 minutes before the resin was removed by filtration. The filtrate was evaporated under reduced pressure and lyophilized, affording the title compound (1.87 g, 47%). $^1$H NMR (DMSO, 500 MHz) δ ppm 9.34 (s (broad), 1H), 7.39 (m, 5H), 5.25 (s, 2H), 4.10 (m, 1H), 3.09 (m, 2H), 2.60 (m, 2H), 1.95

(m, 2H), 1.64 (m, 3H), 0.86 (m, 6H). $^{13}$C (DMSO, 125 MHz) δ ppm 168.90, 134.91, 128.53, 128.50, 128.41, 67.38, 57.37, 49.17, 45.79, 38.06, 24.07, 22.79, 21.78, 21.33. $[\alpha]_D$=+1.8° (c=0.0017 in water), ES-MS 344 (M+1).

Preparation of 3-{[(1S)-1-(methyloxycarbonyl)-3-methylbutyl]amino}-1-propanesulfonic acid (Compound GZ)

L-Isoleucine methylester hydrochloride (5.0 g, 27.5 mmol) was treated with a saturated solution of $K_2CO_3$ (100 mL). The mixture was extracted with EtOAc (3×100 mL). The organic layers were separated, combined, dried with $Na_2SO_4$, filtered and evaporated under reduced pressure.

To a solution of L-Isoleucine methlylester (3.43 g, 23.6 mmol) in acetone (30 mL) was added 1,3-propane sultone (2.62 g, 21.5 mmol). The solution was stirred at reflux for 2 h. The reaction mixture was cooled to room temperature. The solid was filtered and washed with acetone (2×20 mL). The filtrate was evaporated under reduced pressure. The residue was suspended in acetone (50 mL). The solid was filtered. The solid materials were combined and dissolved in water (100 mL). Dowex Marathon C ion exchange resin (strongly acidic) was added to the solution. The suspension was stirred for 15 minutes before the resin was removed by filtration. The filtrate was evaporated under reduced pressure. The solid product was suspended in acetone (100 mL), filtered and dried in vacuo, affording the title compound (3.23 g, 56%). $^1$H NMR ($D_2O$, 500 MHz) δ ppm 4.00 (m, 1H), 3.74 (s, 3H), 3.14 (t, 2H, J=7.8 Hz), 2.89 (t, 2H, J=7.3 Hz), 2.05 (m, 2H), 1.97 (m, 1H), 1.41 (m. 1H), 1.23 (m, 1H), 0.83 (m, 6H). $^{13}$C ($D_2O$, 125 MHz) δ ppm 169.29, 64.51, 53.55, 48.14, 46.52, 36.07, 25.92, 21.34, 13.76, 11.09. $[\alpha]_D$=+22.6° (c=0.0023 in water), ES-MS 266 (M−1).

Preparation of 3-{[(1S)-1-(oxycarbonyl)-3-methylbutyl]amino}-1-propanesulfonic acid (Compound HA)

L-Isoleucine methylester hydrochloride (5.0 g, 27.5 mmol) was treated with a saturated solution of $K_2CO_3$ (100 mL). The mixture was extracted with EtOAc (3×100 mL). The organic layers were separated, combined, dried with $Na_2SO_4$, filtered and evaporated under reduced pressure.

To a solution of L-Isoleucine methlylester (3.43 g, 23.6 mmol) in acetone (30 mL) was added 1,3-propane sultone (2.62 g, 21.5 mmol). The solution was stirred at reflux for 2 hours. The reaction mixture was cooled to room temperature. The solid was filtered and washed with acetone (2×20 mL). The filtrate was evaporated under reduced pressure. The residue was suspended in acetone (50 mL). The solid was filtered. The solid materials were combined and dissolved in water (100 mL). Dowex Marathon C ion exchange resin (strongly acidic) was added to the solution. The suspension was stirred for 15 minutes before the resin was removed by filtration. The filtrate was evaporated under reduced pressure. The solid product was suspended in acetone (100 mL), filtered and dried in vacuo (3.23 g, 56%).

The solid (1.0 g, 3.7 mmol) was dissolved in 2M NaOH (30 mL). The reaction mixture was stirred at room temperature overnight. Dowex Marathon C ion exchange resin (strongly acidic, 15 g) was added to the solution. The suspension was stirred for 15 minutes before the resin was removed by filtration. The filtrate was co-evaporated with EtOH and lyophilized, affording the title compound (740 mg, 83%). $^1$H NMR ($D_2O$, 500 MHz) δ ppm 4.00 (m, 1H), 3.59 (m, 3H), 3.07 (t, 2H, J=7.3 Hz), 2.86 (m, 2H), 2.02 (m, 2H), 1.84 (m, 1H), 1.39 (m. 1H), 1.19 (m, 1H), 0.81 (m, 6H). $^{13}$C ($D_2O$, 125 MHz) δ ppm 169.29, 64.51, 53.55, 48.14, 46.52, 36.07, 25.92, 21.34, 13.76, 11.09. $[\alpha]_D$=+30.4° (c=0.0031 in water), ES-MS 252 (M−1).

Preparation of 3-{[(1S)-1-carbamoyl-2-phenylethyl]amino}-1-propanesulfonic acid (Compound HB)

L-Phenylalaninamide hydrochloride (5.0 g, 24.9 mmol) was treated with a saturated solution of $K_2CO_3$ (75 mL). The mixture was extracted with EtOAc (3×75 mL). The organic layers were separated, combined, dried with $Na_2SO_4$, filtered and evaporated under reduced pressure.

To a solution of L-Phenylalaninamide (3.93 g, 23.9 mmol) in acetonitrile (25 mL) was added 1,3-propane sultone (2.70 g, 21.8 mmol). The solution was stirred at reflux for 2 hours. The reaction mixture was cooled to room temperature. The solid was filtered and washed with acetonitrile (2×25 mL). The solid product was suspended in EtOH (100 mL). The suspension was stirred at reflux for 1 hour. The solid material was filtered and dried in vacuo, affording the title compound (5.18 g, 83%). $^1$H NMR ($D_2O$, 500 MHz) δ ppm 7.24 (m, 3H), 7.16 (m, 2H), 4.02 (m, 1H), 3.15 (m, 1H), 3.01 (m, 3H), 2.83 (m, 2H), 2.02 (m, 2H), 1.98 (m, 2H). $^{13}$C ($D_2O$, 125 MHz)$_6$ ppm 170.48, 133.72, 129.58, 129.21, 128.11, 61.55, 47.95, 45.52, 36.21, 21.44. $[\alpha]_D$=+23.1° (c=0.0021 in water), ES-MS 285 (M−1).

Preparation of 3-{[(1R)-1-(methoxycarbonyl)-3-methylbutyl]amino}-1-propanesulfonic acid (Compound HC)

D-Leucine methylester hydrochloride (2.63 g, 14.5 mmol) was treated with a saturated solution of $K_2CO_3$ (50 mL). The aqueous mixture was extracted with EtOAc (3×50 mL). The organic layers were separated, combined, dried with $Na_2SO_4$, filtered and evaporated under reduced pressure.

To a solution of D-Leucine methylester (1.58 g, 10.9 mmol) in acetonitrile (35 mL) was added 1,3-propanesultone (1.21 g, 9.9 mmol). The solution was stirred at reflux for 2 hours. The reaction mixture was cooled to room temperature. The solid material was collected by filtration, recrystallized from EtOH and dried in vacuo, affording the title compound (1.59 g, 60%). $^1$H NMR ($D_2O$, 500 MHz) δ ppm 3.98 (m, 1H), 3.70 (s, 3H), 3.11 (m, 2H), 2.85 (m, 2H), 2.00 (m, 2H), 1.72 (m, 1H), 1.60 (m, 2H), 0.81 (m, 6H). $^{13}$C ($D_2O$, 125 MHz) δ ppm 170.51, 58.78, 53.69, 47.97, 45.36, 38.09, 24.34, 22.07, 21.51, 20.82. $[\alpha]_D$=+13.1° (c=0.0019 in water), ES-MS 266 (M−1).

Preparation of 3-{[(1R)-1-(aminocarbonyl)-2-methylpropyl]amino}-1-propanesulfonic acid (Compound HD)

D-Valinamide hydrochloride (2.49 g, 14.7 mmol) was treated with a solution of $K_2CO_3$ (50 mL). The organic mixture was extracted with EtOAc (3×50 mL). The organic extracts were separated, combined, dried with $Na_2SO_4$, filtered, evaporated under reduced pressure and dried in vacuo.

To a solution of D-valinamide (1.76 g, 14.7 mmol) in acetonitrile (30 mL) was slowly added 1,3-propanesultone (1.75 g, 14.4 mmol). The solution was stirred at reflux for 2 hours. The reaction mixture was cooled to room temperature. The solid was collected by filtration, washed with acetonitrile (2×25 mL). The solid product was dissolved in water (75 mL). Dowex Marathon C resin (strongly acidic) was added to the solution. The suspension was stirred for 15 minutes before the resin was removed by filtration. The filtrate was evaporated under reduced pressure. The solid material was suspended in acetone (50 mL), filtered and dried in vacuo, affording the title compound (1.57 g, 51%). $^1$H NMR (D$_2$O, 500 MHz) δ ppm 3.80 (m, 1H), 3.19 (m, 2H), 3.00 (m, 2H), 2.25 (m, 1H), 2.16 (m, 2H), 1.08 (d, 3H, J=6.8 Hz), 1.02 (d, 3H, J=6.8 Hz). $^{13}$C (D$_2$O, 125 MHz) δ ppm 169.94, 65.86, 48.10, 46.27, 29.54, 21.23, 17.99, 17.02. [α]$_D$=−12.4° (c=0.0037 in water), ES-MS 237 (M−1).

Preparation of 3-{[(1R)-1-carbamoyl-2-phenylethyl]amino}-1-propanesulfonic acid (Compound HE)

D-Phenylalaninamide hydrochloride (2.53 g, 12.6 mmol) was treated with a saturated solution of K$_2$CO$_3$ (50 mL). The mixture was extracted with EtOAc (3×50 mL). The organic layers were separated, combined, dried with Na$_2$SO$_4$, filtered and evaporated under reduced pressure.

To a solution of D-Phenylalaninamide (1.83 g, 11.1 mmol) in acetonitrile (20 mL) was added 1,3-propane sultone (1.29 g, 10.6 mmol). The solution was stirred at reflux for 2.5 hours. The reaction mixture was cooled to room temperature. The solid was filtered and washed with acetonitrile (2×20 mL). The solid product was suspended in EtOH (75 mL). The suspension was stirred at reflux for 1 hours. The solid material was filtered, washed with acetone (1×25 mL) and dried in vacuo, affording the title compound (2.62 g, 89%). $^1$H NMR (D$_2$O, 500 MHz) δ ppm 7.28 (m, 3H), 7.19 (m, 2H), 4.05 (m, 1H), 3.19 (dd, 1H, J=5.3 Hz, 14.2 Hz), 3.04 (m, 3H), 2.86 (t, 2H, J=5.8 Hz), 2.03 (m, 2H). $^{13}$C (D$_2$O, 125 MHz) δ ppm 170.39, 133.73, 129.62, 129.26, 128.15, 61.57, 47.99, 45.57, 36.21, 21.45. [α]$_D$=−20.7° (c=0.0038 in water), ES-MS 285 (M−1).

Preparation of 3-({(1S)-1-[(benzyloxy)carbonyl]-2-methylbutyl}amino)-1-propanesulfonic acid (Compound HF)

L-Isoleucine benzylester p-tosylate (2.50 g, 6.4 mmol) was treated with a saturated solution of K$_2$CO$_3$ (30 mL). The mixture was extracted with EtOAc (3×30 mL). The organic extracts were separated, combined, dried with Na$_2$SO$_4$, filtered and evaporated under reduced pressure.

To a solution of L-isoleucine benzylester (1.41 g, 6.4 mmol) in acetonitrile (12 mL) was added 1,3-propane sultone (706 mg, 5.8 mmol). The solution was stirred at reflux for 2 hours. The reaction mixture was cooled to room temperature. The solid was filtered and washed with acetone (2×20 mL). The solid material was dissolved in 50% EtOH/water (50 mL). Dowex Marathon C ion exchange resin (strongly acidic, 10 g) was added to the solution. The suspension was stirred for 15 minutes before the resin was removed by filtration. The filtrate was evaporated under reduced pressure and lyophilized affording the title compound (778 mg, 39%). $^1$H NMR (D$_2$O, 500 MHz) δ ppm 7.49 (m, 5H), 5.42 (d, 1H, J=11.7 Hz), 5.31 (d, 1H, J=11.7 Hz), 3.24 (m, 2H), 2.98 (m, 2H), 2.13 (m, 3H), 1.46 (m, 1H), 1.34 (m, 1H), 0.93 (m, 6H). $^{13}$C (D$_2$O, 125 MHz) δ ppm 168.53, 134.69, 129.28, 129.22, 129.06, 68.86, 64.45, 48.12, 46.56, 36.21, 25.97, 21.31, 13.73, 11.05. [α]$_D$=−1.5° (c=0.0031 in water), ES-MS 342 (M−1).

Preparation of 3-{[(1R)-1-(aminocarbonyl)-3-methylbutyl]amino}-1-propanesulfonic acid (Compound HG)

D-Leucinamide hydrochloride (1.0 g, 6.0 mmol) was treated with a saturated solution of K$_2$CO$_3$ (30 mL). The aqueous mixture was extracted with EtOAc (3×30 mL). The organic extracts were separated, combined, dried with Na$_2$SO$_4$, filtered and evaporated under reduced pressure.

To a solution of D-Leucinamide (6.0 mmol) in acetonitrile (35 mL) was added 1,3-propanesultone (666 mg, 5.5 mmol). The solution was stirred at reflux for 2 hours. The reaction mixture was cooled to room temperature. The solid was filtered and washed with MeCN (2×20 mL). The solid was suspended in EtOH (50 mL). The suspension was stirred at reflux for 1 hour. The mixture was cooled to room temperature. The solid material was filtered, washed with acetone (1×20 mL) and dried in a vacuum oven (50° C.), affording the title compound (1.03 g, 74%): $^1$H NMR (D$_2$O, 500 MHz) δ ppm 3.81 (m, 1H), 3.07 (m, 2H), 2.85 (t, 2H, J=7.3 Hz), 2.03 (m, 2H), 1.68 (t, 1H, J=7.8 Hz), 1.58 (m, 2H), 0.83 (m, 6H). $^{13}$C (D$_2$O, 125 MHz) δ ppm 171.45, 59.39, 48.01, 45.41, 39.02, 24.24, 22.21, 21.47, 21.13. [α]$_D$=−13.7° (c=0.0019 in water), ES-MS 251 (M−1).

3-[(1-methylcyclopentyl)amino]-1-propanesulfonic acid (Compound FQ)

For the Ritter reaction, the flask was closed with a septum and connected to a 20% NaOH scrubber. Sodium cyanide (powdered, 5.5 g, 112 mmol) was added to acetic acid (30 mL) in one portion. The mixture was stirred for 10 minutes at room temperature. A solution of sulfuric acid (16 mL) in acetic acid (15 mL) was added dropwise over a 20 minute period. Then, a solution of 1-methyl-1-cyclopentanol (10 g, 99.8 mmol) in acetic acid (5 mL) was added dropwise over a 5 minute period. The mixture was stirred at room temperature for 22 hours then poured over ice (approx. 100 g). The pH of the solution was adjusted to 9 with the addition of 50% NaOH (about 135 g). The layers were separated and the aqueous layer was extracted with ether (1×40 mL). The combined organic layers were washed with saturated sodium carbonate (1×10 mL) then dried over sodium sulfate. The ether was evaporated under reduced pressure to afford light brown oil (12.04 g, 94.7 mmol, 95%). The oil showed to be a mixture of cis and trans formamide but what otherwise pure enough to be used as such. $^1$H NMR (500 MHz, CDCl$_3$) δ [1.40 and 1.45 (s, 3H)], 1.68-1.76 (m, 7H), 1.97-1.98 (m, 1H), [5.42 and 6.24 (br s, 1H)], [8.05 (s) and 8.24 (d, J=12.2 Hz) for 1H]; $^{13}$C NMR (125 MHz, CDCl$_3$) δ 23.1, 23.6, 25.5, 28.2, 39.5, 40.7, 60.7, 61.3, 160.7, 163.9

A solution of NaOH (25%, 80 mL) was added to the crude 1-methyl-1-cyclopentylformamide (12.00 g, 94.7 mmol). The mixture was heated to reflux for 2.5 hours then cooled at room temperature. Some sodium chloride (20 g) was added to facilitate the phase separation. The layers were separated and the aqueous layer was extracted with toluene (1×15 mL). The combined organic layers were agitated. The addition of isopropyl ether (2.5 mL, chloroform (1 g) and cyclohexane (6.5 g) did not improved the seperation of the solution. The combined organic layers were washed with brine (1×10 mL) then dried over sodium sulfate and filtered. The filtrate was used as such in the next step. $^1$H NMR (500 MHz, CDCl$_3$) δ 1.22 (s, 3H), 1.47-1.75 (4 m, 9H): $^{13}$C NMR (125 MHz, CDCl$_3$) δ 24.1, 29.6, 42.2, 58.4

A solution of 1,3-propanesultone (9.4 g, 75 mmol) in 2-butanone (35 mL) was added dropwise to a the crude solution of 1-methyl-1-cyclopentylamine (mixture of solvent from previous step).

The mixture was heated to reflux for 20 hours then was cooled to room temperature. The solid was collected by suction-filtration and rinsed with acetone (2×10 mL). The solid was dried overnight at 45° C. in the vacuum oven. The title compound was obtained as a fine white solid (16.26 g, 73.47 mmol, 74% overall yield). $^1$H NMR (500 MHz, $D_2O$) δ 1.31 (s, 3H), 1.591.6-1-85 (m, 8H), 2.03-2.06 (m, 2H), 2.96 (t, J=6.8 Hz, 2H), 3.15 (t, J=7.6 Hz, 2H); $^{13}$C NRM (125 MHz, $D_2O$) δ 22.1, 22.5, 23.6, 36.5, 41.4, 48.1, 66.8.1; ES-MS 220 (M−H)

3-[(1-methylcyclohexyl)amino]-1-propanesulfonic acid (Compound FR)

For the Ritter reaction, the flask was closed with a septum and connected to a 20% NaOH scrubber. Potassium cyanide (powdered, 3.3 g, 50 mmol) was added in portions to acetic acid (13 mL). The mixture was stirred for 10 minutes at room temperature. A solution of sulfuric acid (7 mL) in acetic acid (7 mL) was added drop-wise over a 10 minute period. Then, a solution of 1-methyl-1-cyclohexanol (5 g, 43.8 mmol) in acetic acid (4 mL) was added dropwise over a 5 minute period. The mixture was stirred at room temperature for 22 hours then poured over ice (approx. 50 g). The pH of the solution was adjusted to 9 with the addition of 50% NaOH (about 70 g). The layers were separated and the aqueous layer was extracted with ether (2×20 mL). The combined organic layers were washed with saturated sodium carbonate (1×10 mL) then dried over sodium sulfate. The ether was evaporated under reduced pressure to afford a clear yellow oil (6.56 g, quantitative). The oil showed to be a mixture of cis and trans formamide but what otherwise pure enough to be used as such. $^1$H NMR (500 MHz, $CDCl_3$) δ 1.33-1.53 (3 m, 11H), 1.67 (br s, 1H), 1.99 (m, 1H), [5.16 and 6.09 (br s, 1H)], [8.11 (s) and 8.25 (d, J=12.2 Hz) for 1H]; $^{13}$C NMR (125 MHz, $CDCl_3$) δ 23.1, 23.6, 25.5, 28.2, 39.5, 40.7, 60.7, 61.3, 160.7, 163.9

A solution of NaOH (20%, 40 mL) was added to the crude 1-methyl-1-cyclohexylformamide (43.8 mmol). The mixture was heated to reflux for 3 hours then cooled at room temperature. Some sodium chloride (7.5 g) was added to facilitate the phase separation. The layers were separated and the aqueous layer was extracted with MTBK (1×10 mL). The combined organic layers were washed with brine (1×5 mL) the dried over sodium sulfate and filtered. The filtrate was used as such in the next step. $^1$H NMR (500 MHz, $CDCl_3$) δ 1.08 (s, 3H), 1.33-1.51 (m, 10H); $^{13}$C NMR (125 MHz, $CDCl_3$) δ 22.8, 25.8, 29.6, 40.8, 48.6

A solution of 1,3-propanesultone (5.00 g, 40 mmol) in toluene (10 mL) was added dropwise to a the crude solution of 1-methyl-1-cyclohexylamine in MTBK (total volume 30 mL). The mixture was heated to reflux for 18 hours then cooled to room temperature. The solid was collected by suction filtration, rinsed with acetone (2×8 mL). The solid was dried overnight at 45° C. in the vacuum oven. The title compound was obtained as a fine white solid (9.22 g). However, the proton NMR and the ES-MS were not clean. The solid was suspended in methanol (45 mL) and the suspension was warmed to reflux. Water (12 mL) was added dropwise until a clear yellow solution was obtained. The mixture was slowly cool to room temperature with stirring. The solid was collected by suction-filtration, rinsed with methanol (2×5 mL). Another crop was collected from the filtrate. Both crops were dried overnight at 45° C. in the vacuum oven. The title compound was obtained as a fine white solid (6.82 g, 29.0 mmol, 66% overall yield). Both crops were identical and were mixed for submitting the compound. $^1$H NMR (500 MHz, $D_2O$) δ 1.04-1.11 (m, 1H), 1.19 (s, 3H), 1.31 (q, J=12.2 Hz, 2H), 1.40 (qt, J=12.2 Hz, 2H), 1.46-1.62 (m, 2H), 1.63 (br d, J=11.7 Hz, 2H), 1.94 (q, J=7.3 Hz, 2H), 2.86 (t, J=7.1 Hz, 2H), 3.03 (t, J=7.6 Hz, 2H); $^{13}$C NMR (125 MHz, $D_2O$) δ 19.1, 21.5, 22.0, 24.6, 34.1, 39.1, 48.2, 60.2; ES-MS 236 (M+H)

3-[(1-methylcycloheptyl)amino]-1-propanesulfonic acid (Compound FS)

For the Ritter reaction, the flask was closed with a septum and connected to a 20% NaOH scrubber. Potassium cyanide (powdered, 2.8 g, 43 mmol) was added in portions to acetic acid (10 mL). The mixture was stirred for 10 minutes at room temperature. A solution of sulfuric acid (7 mL) in acetic acid (7 mL) was added drop-wise over a 20 minute period. Then, the 1-methyl-1-cycloheptanol (5 g, 39.0 mmol) was added drop-wise over 5 minutes. The mixture was stirred at room temperature for 22 h then cooled to 0° C. with a ice/water bath. The pH of the solution was adjusted to 9 with the addition of 50% NaOH (about 70 g). The layers were separated and the aqueous layer was extracted with ether (1×20 mL). The combined organic layers were washed with saturated sodium carbonate (1×5 mL) then dried over sodium sulfate. The ether was evaporated under reduced pressure to afford a clear yellow oil (5.71 g, 94%). The oil showed to be a mixture of cis and trans formamide but what otherwise pure enough to be used as such. $^1$H NMR (500 MHz, $CDCl_3$) δ 1.34 (s, 1.5H), 1.43 (s, 1.5H), 1.49-1.60 (m, 8H), 1.96-2.00 (m, 1H), [5.28 and 5.95 (br s, 1H)], [8.06 (s) and 8.28 (d, J=12.2 Hz) for 1H]; $^{13}$C NMR (125 MHz, $CDCl_3$) δ 22.2, 22.4, 27.7, 29.3, 29.4, 30.7, 40.5, 42.5, 56.0, 57.4, 160.5, 163.3

A solution of NaOH (25%, 40 mL) was added to the crude 1-methyl-1-cycloheptylformamide (5.7 g). The mixture was heated to reflux for 3 hours then cooled at room temperature. Some sodium chloride (7.5 g) was added to facilitate the phase separation. The layers were separated and the aqueous layer was extracted with MTBK (1×10 mL). The combined organic layers were washed with brine (1×5 mL) the dried over sodium sulfate and filtered. The filtrate was used as such in the next step. $^1$H NMR (500 MHz, $CD_3OD$) δ 1.10 (s, 3H), 1.40-1.48 (m, 2H), 1.5-1.65 (m, 10H); $^{13}$C NMR (125 MHz, $CD_3OD$) δ 24.0, 31.2, 31.4, 44.4, 53.6.

A solution of 1,3-propanesultone (4.3 g, 35 mmol) in toluene (10 mL) was added dropwise to a the crude solution of 1-methyl-1-cycloheptylamine in MTBK (total volume 30 mL). The mixture was heated to reflux for 18 hours then was cooled to room temperature. The solid was collected by suction filtration, rinsed with acetone (2×5 mL). The solid was dried overnight at 45° C. in the vacuum oven. The title compound was obtained as a fine white solid (7.77 g, 31.2 mmol, 80% overall yield). $^1$H NMR (500 MHz, $D_2O$) δ 1.27 (s, 3H), 1.40-1.60 (m, 8H), 1.71-1.81 (m, 4H), 2.00-2.06 (m, 2H), 2.95 (t, J=6.3 Hz, 2H), 3.13 (t, J=7.1 Hz, 2H); $^{13}$C NMR (125 MHz, $D_2O$) δ 22.0, 22.1, 23.3, 29.5, 37.1, 40.0, 48.3, 64.0; ES-MS 250(M+H)

Preparation of 3-{[(1R)-1-(benzyloxycarbonyl)-3-methylbutyl]amino}-1-propanesulfonic acid (Compound HI)

D-Leucine benzylester p-tosylate (2.5 g, 6.3 mmol) was treated with an aqueous solution of $K_2CO_3$ (30 mL). The mixture was extracted with EtOAc (3×30 mL). The organic extracts were separated, combined, dried with $Na_2SO_4$, filtered, evaporated under reduced pressure and dried in vacuo.

To a solution of D-Leucine benzylester (6.3 mmol) in acetonitrile (9 mL) and MeOH (3 mL) was added 1,3-propane sultone (691 mg, 5.7 mmol). The solution was stirred at reflux for 2.5 hours. The reaction mixture was cooled to room temperature. The solid material was filtered and washed with aconitrile (2×20 mL). The solid was dissolved in 20% water/EtOH (75 mL). Dowex Marathon C ion exchange resin (strongly acidic) was added to the solution. The suspension was stirred for 15 minutes before the resin was removed by filtration. The filtrate was evaporated under reduced pressure and dried in vacuo, affording the title compound (960 mg, 49%). $^1$H NMR ($D_2O$, 500 MHz) δ ppm 7.52 (m, 5H), 5.41 (d, 1H, J=12.2 Hz), 5.35 (d, 1H, J=12.2 Hz), 4.16 (m, 1H), 3.22 (m, 2H), 2.97 (t, 2H, J=6.8 Hz), 2.16 (m, 2H), 1.88 (m, 1H), 1.79 (m, 1H), 1.76 (m, 1H), 0.94 (d, 6H, J=3.9 Hz). $^{13}$C (DMSO, 125 MHz) δ ppm 169.60, 135.62, 129.24, 129.21, 129.11, 68.08, 58.09, 49.87, 46.48, 24.77, 23.50, 22.50, 22.04. $[α]_D$=−2.1° (c=0.00095 in water), ES-MS 344 (M+1).

Preparation of 3-[(5-hydroxy-1,5-dimethylhexyl)amino]-1-propanesulfonic acid (Compound HJ)

To a solution of 6-amino-2-methyl-2-heptanol (2.5 g, 17.2 mmol) in acetonitrile (22 mL) was added 1,3-propane sultone (2.0 g, 16.4 mmol). The solution was stirred at reflux for 2 hours. The reaction mixture was cooled to room temperature. The solid material was filtered and washed with acetonitrile (2×20 mL). The solid was dissolved in 20% MeOH (75 mL). Dowex Marathon C ion exchange resin (strongly acidic) was added to the solution. The suspension was stirred for 15 minutes before the resin was removed by filtration. The filtrate was evaporated under reduced pressure. The solid was suspended in acetone (150 mL), and then the solid material was filtered and dried in vacuo, affording the title compound (3.08 g, 70%). $^1$H NMR ($D_2O$, 500 MHz) δ ppm 3.19 (m, 1H), 3.08 (m, 2H), 2.88 (t, 2H, J=7.3 Hz), 1.99 (m, 2H), 1.60 (m, 2H), 1.36 (m, 4H), 1.18 (d, 3H, J=6.8 Hz), 1.07 (s, 6H). $^{13}$C ($D_2O$, 125 MHz) δ ppm 71.63, 54.73, 48.08, 43.46, 42.27, 32.97, 27.78, 27.73, 21.64, 19.67, 15.43. ES-MS 268 (M+1).

Preparation of 3-{[(1R)-2-methoxy-1-methyl-2-oxoethyl]amino}-1-propanesulfonic acid (Compound HK)

D-Alanine methylester hydrochloride (3.0 g, 21.5 mmol) was treated with a aqueous solution of $K_2CO_3$ (50 mL). The mixture was extracted with EtOAc (3×50 mL). The organic extracts were separated, combined, dried with $Na_2SO_4$, filtered and evaporated under reduced pressure.

To a solution of D-Alanine methylester (1.33 g, 12.9 mmol) in acetonitrile (15 mL was added 1,3-propane sultone (1.42 g, 11.7 mmol). The solution was stirred at reflux for 2 hours. The reaction mixture was cooled to room temperature. The solid material was filtered and washed with acetonitrile (2×15 mL). The solid was dissolved in water (30 mL). Dowex Marathon C ion exchange resin (strongly acidic) was added to the solution. The suspension was stirred for 15 minutes before the resin was removed by filtration. The filtrate was evaporated under reduced pressure and dried in vacuo, affording the title compound (1.52 g, 42%). $^1$H NMR ($D_2O$, 500 MHz) δ ppm 4.07 (m, 1H), 3.72 (s, 3H), 3.14 (m, 2H), 2.89 (t, 2H, J=7.3 Hz), 2.03 (m, 2H), 1.46 (dd, 3H, J=1.95 Hz, 7.3 Hz). $^{13}$C (DMSO, 125 MHz) δ ppm 170.74, 55.62, 53.82, 47.96, 44.76, 21.53, 14.03. $[α]_D$=+1.4° (c=0.0088 in water), ES-MS 224 (M−1).

Preparation of 4-(1,2,3,4-tetrahydro-1-naphthylamino)-2-butanesulfonic acid (Compound JF)

To a solution of 1,2,3,4-tetrahydro-1-naphthylamine (2.01 g, 13.6 mmol) in 2-butanone (15 mL) was added 2,4-butane sultone (1.95 g, 14.3 mmol). The solution was stirred at for 2 hours. The reaction was cooled to room temperature. The solid was collected by filtration, washed with acetone (2×25 mL) and dried in vacuo. $^1$H NMR (DMSO, 500 MHz) δ ppm 8.56 (s, broad), 1H), 7.49 (dd, 1H, J=8.0 Hz, 11.9 Hz), 7.29 (m, 1H), 7.26 (m, 1H), 7.19 (d, 1H, J=8.0 Hz), 4.40 (d, 1H, J=13.7 Hz), 3.14 (m, 2H), 2.75 (m, 3H), 1.96 (m, 5H), 1.40 (m, 1H), 1.23 (m, 3H). $^{13}$C (DMSO, 125 MHz) δ ppm 138.81, 131.81, 130.40, 130.28, 130.16, 129.41, 126.76, 126.73, 54.97, 54.58, 54.08, 44.18, 43.23, 29.50, 28.84, 24.84, 24.76, 18.23, 18.20, 17.79, 17.01. ES-MS 284 (M+1).

Preparation of 4-(octylamino)-2-butanesulfonic acid (Compound JG)

To a solution of octylamine (2.00 g, 15.5 mmol) in 2-butanone (17 mL) was added 2,4-butane sultone (2.21 g, 16.2 mmol). The solution was stirred at reflux for 2 hours. The reaction was cooled to room temperature. The solid was collected by filtration, washed with acetone (2×25 mL) and dried in vacuo. It was suspended in a solution of 25% EtOH/acetone (50 mL). The suspension was stirred for 5 minutes. The solid was collected by filtration, washed with acetone (2×25 mL) and dried in vacuo. $^1$H NMR (DMSO, 500 MHz) δ ppm 8.45 (s (broad), 1H), 3.01 (m, 1H), 2.84 (m, 2H), 2.58 (m, 1H), 1.92 (m, 1H), 1.75 (m, 1H), 1.51 (m, 2H), 1.10 (d, 1H, J=6.8 Hz), 0.85 (t, 3H, J=6.8 Hz). $^{13}$C (DMSO, 125 MHz) δ ppm 53.05, 47.27, 46.15, 31.83, 29.42, 29.13, 26.51, 26.27, 22.75, 17.19, 14.64. ES-MS 266 (M+1).

Preparation of 4-(adamantyl)amino-2-butanesulfonic acid (Compound JH)

1-adamantaneamine hydrochloride (2.51 g, 13.3 mmol) was treated with 1N NaOH (20 mL) and $CH_2Cl_2$ (3×20 mL). The organic extracts were combined, dried with $Na_2SO_4$, filtered, evaporated under reduced pressure and dried in vacuo.

To a solution of 2-adamantanamine (1.99 g, 13.1 mmol) in acetonitrile (15 mL) was added 2,4-butane sultone (1.87 g, 13.8 mmol). The solution was stirred at reflux for 2 hours. The reaction was cooled to room temperature. The solid was collected by filtration, washed with acetonitrile (3×25 mL) and dried in vacuo. $^1$H NMR (DMSO, 500 MHz) δ ppm 8.53 (s (broad), 1H), 3.33 (m, 2H), 2.61 (m, 1H), 2.10 (s, 3H), 1.93 (m, 1H), 1.77 (m, 7H), 1.61 (m, 6H), 1.12 (d, 1H, J=6.8 Hz). $^{13}$C (DMSO, 125 MHz) δ ppm 56.20, 53.34, 35.85, 29.75, 29.04, 17.206. ES-MS 288 (M+1).

Preparation of 4-(2-adamantyl)amino-2-butanesulfonic acid (Compound JI)

The 2-adamantanamine hydrochloride (2.50 g, 13.3 mmol) was treated with 1N NaOH (20 mL) and $CH_2Cl_2$ (3×20 mL). The organic extracts were combined, dried with $Na_2SO_4$, filtered, evaporated under reduced pressure and dried in vacuo.

To a solution of 1-adamantanamine (1.99 g, 13.1 mmol) in acetonitrile (15 mL) was added 2,4-butane sultone (1.87 g, 13.8 mmol). The solution was stirred at reflux for 2 hours. The reaction was cooled to room temperature. The solid was collected by filtration, washed with acetonitrile (2×25 mL) and dried in vacuo. $^1$H NMR (DMSO, 500 MHz) δ ppm 3.20 (m, 1H), 3.05 (m, 2H), 2.67 (m, 1H), 2.07 (m, 2H), 2.00 (m, 1H), 1.95 (m, 4H), 1.82 (m, 4H), 1.69 (m, 4H), 1.55 (m, 4H), 1.12 (d, 1H, J=8.0 Hz). $^{13}$C (DMSO, 125 MHz) δ ppm 62.27, 53.91, 44.33, 37.30, 36.82, 36.77, 30.30, 30.20, 29.57, 29.50, 28.95, 17.12, 26.85, 17.44. ES-MS 288 (M+1).

Preparation of 4-(bicyclo[2.2.1]hept-2-ylamino)-2-butanesulfonic acid (Compound JJ)

To a solution of exo-2-aminonorbornane (1.0 g, 9.0 mmol) in tetrahydrofuran (THF, 10 mL) was added 2,4-butane sultone (1.28 g, 9.3 mmol). The solution was stirred at reflux for 3 hours. The reaction was cooled to room temperature. The solid was collected by filtration, washed with THF (2×20 mL) and dried in vacuo. $^1$H NMR (DMSO, 500 MHz) δ ppm 8.43 (s (broad), 1H), 2.96 (m, 3H), 2.62 (m, 1H), 2.38 (m, 1H), 2.28, (m, 1H), 1.91 (m, 1H), 1.82 (m, 1H), 1.61 (m, 1H), 1.54 (m, 2H), 1.42 (m, 2H), 1.12 (m, 6H). $^{13}$C (DMSO, 125 MHz) δ ppm 60.92, 60.79, 53.61, 53.21, 44.55, 44.36, 39.80, 39.55, 36.27, 36.15, 36.11, 35.98, 35.19, 35.13, 29.62, 29.43, 28.07, 26.88, 17.56, 14.11. ES-MS 248 (M+1).

Preparation of 4-(azoniabicyclo[2.2.2]oct-2-ylamino)-2-butanesulfonate (Compound JK)

Quinuclidine hydrochloride (2.50 g, 16.9 mmol) was treated with 1N NaOH (20 mL) and $CH_2Cl_2$ (4×20 mL). The organic extracts were combined, dried with $Na_2SO_4$, filtered, evaporated under reduced pressure and dried in vacuo.
To a solution of quinuclidine (900 g, 8.2 mmol) in tetrahydrofuran (THF, 18 mL) and MeOH (0.5 mL) was added 2,4-butane sultone (1.16 g, 8.6 mmol). The solution was stirred at reflux overnight. The reaction was cooled to room temperature. The solid was collected by filtration, washed with THF (2×25 mL) and dried in vacuo. $^1$H NMR (DMSO, 500 MHz) δ ppm 3.40 (m, 7H), 3.20 (td, 1H, J=3.9 Hz, 12.7 Hz), 2.38 (m, 1H), 2.01 (m, 2H), 1.83, (m, 6H), 1.70 (m, 1H), 1.10 (d, 3H, J=12.7 Hz). $^{13}$C (DMSO, 125 MHz) δ ppm 62.63, 54.23, 52.18, 25.67, 24.07, 19.78, 17.04. ES-MS 208 (M+1).

Preparation of 4-[(dl)-1-hydroxy-2-pentyl]amino-2-butane sulfonic acid (Compound JL)

To a solution of DL-2-aminopentanol (1.0 g, 9.7 mmol) in tetrahydrofuran (11 mL) was added 2,4-butane sultone (1.45 g, 10.2 mmol). The solution was stirred at reflux for 4 hours. The reaction was cooled to room temperature. The supernatant was removed and the solid was dried in vacuo. The product was suspended in 2-propanol (100 mL) and the mixture was stirred for 5 minutes. The white solid was filtered, washed with 2-propanol and dried in vacuo. $^1$H NMR ($D_2O$, 500 MHz) δ ppm 3.74 (d, 1H, J=12.7 Hz,), 3.59 (dd, 1H, J=5.4 Hz, 12.9 Hz), 3.13 (m, 3H), 2.89 (m, 1H), 2.07 (m, 1H), 1.82, (m, 1H), 1.52 (m, 2H), 1.28 (m, 2H), 1.18 (d, 3H, J=6.8 Hz). $^{13}$C ($D_2O$, 125 MHz) δ ppm 59.43, 58.80, 53.47, 42.88, 29.30, 28.43, 18.40, 14.99, 13.23. ES-MS 240 (M+1).

Preparation of 4-(nonylamino)-2-butanesulfonic acid (Compound JN)

To a solution of nonylamine (2.00 g, 14.0 mmol) in tetrahydrofuran (THF, 15 mL) was added 2,4-butane sultone (2.08 g, 14.7 mmol). The solution stirred at reflux for 5 hours. The reaction was cooled to room temperature. The solid was collected by filtration, washed with THF (2×25 mL) and dried in vacuo.
The product (1.10 g, 3.9 mmol) was dissolved with heating in a solution of EtOH (20 mL), water (600 uL) and NaOH (163 mg, 4.1 mmol). After a few minutes a white solid precipitated. The solid was collected by filtration, washed with acetone (2×25 mL) and dried in vacuo. $^1$H NMR ($D_2O$, 500 MHz) δ ppm 2.70 (m, 1H), 2.52 (m, 2H), 2.37 (m, 1H), 1.95 (m, 1H), 1.46 (m, 1H), 1.34 (m, 1H), 1.14 (m, 17H), 0.70 (t, 3H, J=6.8 Hz). $^{13}$C ($D_2O$, 125 MHz) δ ppm 54.31, 52.90, 50.44, 31.31, 28.80, 28.74, 28.57, 27.31, 26.95, 22.20, 14.60, 13.57. ES-MS 302 (M+1).

Preparation of 4-(dimethylamino)-2-butanesulfonic acid (Compound JO)

2,4-butanesultone (1.27 g, 8.9 mmol) was added to an ice-chilled solution of dimethylamine (40% w/w in water). The solution was stirred at 0° C. for 4 hours. The solvent was evaporated in vacuo until complete dryness. The solid was washed with acetone (50 mL), collected by filtration and dried in vacuo. $^1$H NMR ($D_2O$, 500 MHz) δ ppm 3.18 (t, 2H, J=8.1 Hz), 2.85 (m, 1H), 2.76 (s, 6H), 2.09 (m, 1H), 1.81 (m, 1H), 1.17 (d, 3H, J=7.3 Hz). $^{13}$C ($D_2O$, 125 MHz) δ ppm 55.65, 53.05, 42.88, 26.72, 14.81. ES-MS 182 a (M+1).

Preparation of 4-(benzylamino)-2-butanesulfonic acid, sodium salt (Compound JP)

To a solution of benzylamine (1.50 g, 14.0 mmol) in tetrahydrofuran (THF, 18 mL) was added 2,4-butane sultone (1.98 g, 14.6 mmol). The solution was stirred at reflux for 2 hours. The reaction was cooled to room temperature. The solid was collected by filtration, washed with THF (2×25 mL) and dried in vacuo.
The product (2.55 g, 10.5 mmol) was dissolved with heating in a solution of EtOH (25 mL), water (1.6 mL) and NaOH (440 mg, 11.0 mmol). Diethyl ether (150 mL) was added to the filtrate. The solid was filtered and dried in vacuo. Yield: 27%. $^1$H NMR (DMSO, 500 MHz) δ ppm 7.29 (m, 4H), 7.20 (m, 1H), 3.67 (m, 2H), 2.56 (m, 1H), 2.45 (m, 2H), 1.98 (m, 1H), 1.36 (m, 1H), 1.04 (d, 3H, J=6.8 Hz). $^{13}$C (DMSO, 125 MHz) δ ppm 141.49, 128.73, 128.61, 127.16, 53.49, 52.88, 47.31, 32.67, 16.53. ES-MS 266 (M+1).

Preparation of 4-(ethylamino)-2-butanesulfonic acid, sodium salt (Compound JQ)

A solution of 2,4-butanesultone (1.33 g, 9.3 mmol) in tetrahydrofuran (THF, 3.0 mL) was added via syringe pump over a 2 h period to ethylamine (70% w/w in water, 12.0 mL, 186.0 mmol) at 5° C. The solution was stirred at 5° C. for an additional 2 hours. The solvent was co-evaporated with EtOH (3×25 mL). The solid was suspended in acetone (25 mL). The suspension was stirred for 5 minutes the solid was filtered, washed with acetone (2×25 mL) and dried in vacuo. Yield: 70%. $^1$H NMR ($D_2O$, 500 MHz) δ ppm 3.06 (t, 2H, J=8.1 Hz), 2.97 (m, 2H), 2.87 (m, 2H), 2.06 (m, 1H), 1.77 (m, 1H), 1.18 (d, 3H, J=7.3 Hz), 1.14 (t, 3H, J=7.3 Hz). $^{13}$C ($D_2O$, 125 MHz) δ ppm 53.16, 44.91, 43.03, 28.20, 14.76, 10.66. ES-MS 182 (M+1).

Preparation of 4-(tert-butylamino)-1-butanesulfonic acid (Compound LD)

To a solution of tert-butylamine (1.0 mL, 9.5 mmol) in tetrahydrofuran (4 mL) was added 1,4-butane sultone (1.36 g, 10.0 mmol) at room temperature. The solution was stirred at reflux for 2 hours. The reaction was cooled to room temperature. The solid was collected by filtration, washed with acetone (2×20 mL) and dried in vacuo. Yield: 690 mg (34%). $^1$H NMR ($D_2O$, 500 MHz) δ ppm 2.92 (t, 2H, J=7.1 Hz), 2.82

(t, 2H, J=7.1 Hz), 1.68 (m, 4H), 1.22 (s, 9H). $^{13}$C (D$_2$O, 125 MHz) δ ppm 57.07, 50.30, 40.95, 25.28, 24.96, 21.62. ES-MS 210 (M−1).

Preparation of 4-amino-2-butanesulfonic acid (Compound JR)

A solution of 2,4-butanesultone (1.0 g, 7 mmol) in tetrahydrofuran (THF, 4.0 mL) was added via syringe pump over a 4 h period to ammonium hydroxide (28-30% NH$_3$, 43 mL, 350 mmol) at 5° C. The solution was stirred at 5° C. for an additional 30 minutes. The solvent was co-evaporated with EtOH (3×25 mL). The solid was dried in vacuo. Yield: 94%. $^1$H NMR (D$_2$O, 500 MHz) δ ppm 3.05 (m, 2H), 2.90 (m, 1H), 2.05 (m, 1H), 2.06 (m, 1H), 1.77 (m, 1H), 1.18 (d, 3H, J=6.8 Hz), 1.14 (t, 3H, J=7.3 Hz). $^{13}$C (DMSO, 125 MHz) δ ppm 52.75, 38.20, 30.87, 17.27. ES-MS 154 (M+1).

Preparation of 4-piperidin-1-yl-2-butanesulfonic acid (Compound JS)

To a solution of piperidine (1.50 g, 17.6 mmol) in tetrahydrofuran (THF, 20 mL) was added 2,4-butanesultone (2.50 g, 18.5 mmol). The solution was stirred at reflux for 3 hours. The reaction was cooled to room temperature. The solid was collected by filtration, washed with THF (2×20 mL) and dried in vacuo.

The product (3.53 g, 15.9 mmol) was dissolved with heating in a solution of EtOH (30 mL), water (1.3 mL) and NaOH (670 mg, 16.7 mmol). The solution was poured in a large excess of Et$_2$O (500 mL). The solid was filtered, washed with Et$_2$O (1×25 mL) and acetone (1×20 mL) and dried in vacuo. Yield: 64%. $^1$H NMR (D$_2$O, 500 MHz) δ ppm 2.72 (m, 1H), 2.33 (m, 6H), 1.97 (m, 1H), 1.48 (m, 1H), 1.43 (m, 4H), 1.31 (m, 1H), 1.13 (d, 3H, J=6.8 Hz). $^{13}$C (D$_2$O, 125 MHz) δ ppm 55.78, 54.42, 53.61, 27.73, 24.92, 23.59, 14.61. ES-MS 244 (M+1).

Preparation of 4-(ethylamino)-1-butanesulfonic acid (Compound LE)

A solution of 1,4-butanesultone (2.66 g, 18.6 mmol) in tetrahydrofuran (total volume: 4 mL) was added via syringe pump over a 4 hour period to ethylamine (70% w/w in water, 24 mL, 372 mmol) at 5° C. The solution was stirred at 5° C. for an additional 3 hours before it was warm up to room temperature. The reaction was stirred in these conditions overnight. The solvent was co-evaporated with EtOH (1×25 mL). The solid was suspended in 50% acetone/EtOH (50 mL). The suspension was stirred for 5 minutes, the solid was filtered and dried in vacuo. Yield: 75%. $^1$H NMR (D$_2$O, 500 MHz) δ ppm 2.95 (m, 4H), 2.82 (m, 2H), 1.68 (m, 4H), 1.13 (t, 3H, J=7.3 Hz), 1.14 (t, 3H, J=7.3 Hz). $^{13}$C (D$_2$O, 125 MHz) δ ppm 50.27, 46.68, 42.99, 24.66, 21.48, 10.64. ES-MS 182 (M+1).

Preparation of 4-(azoniabicyclo[2.2.2]oct-2-ylamino)-1-butanesulfonate (Compound LF)

To a solution of quinuclidine (1.5 g, 13.5 mmol) in tetrahydrofuran (THF, 15 mL) was added 1,4-butanesultone (2.0 g, 14.4 mmol) at room temperature. The solution was stirred at reflux for 2 hours. The reaction was cooled to room temperature. The solid was collected by filtration, washed with THF (2×25 mL) and dried in vacuo. $^1$H NMR (D$_2$O, 500 MHz) δ ppm 3.26 (m, 6H), 3.02 (m, 2H), 2.82 (t, 2H, J=17.3 Hz), 2.04 (m, 1H), 1.84, (m, 6H), 1.75 (m, 2H), 1.64 (m, 2H). $^{13}$C (D$_2$O, 125 MHz) δ ppm 63.68, 54.81, 50.14, 23.51, 21.45, 20.58, 19.19. ES-MS 248 (M+1).

Preparation of 3-(dimethylamino)-2-hydroxy-1-propane sulfonic acid, sodium salt (Compound JT)

A solution of 3-chloro-2-hydroxy-1-propanesulfonic acid, sodium salt (10 g, 48.3 mmol) in water (40 mL total volume) was added via a syringe pump over 4 hours to a cold (2.8-3.1° C.) solution of dimethylamine (40% wt in water, 300 mL) with stirring. The mixture was slowly warmed to room temperature overnight. The mixture was then co-evaporated with absolute ethanol (20 mL) and concentrated to dryness. The solid was dried overnight at 60° C. in the vacuum oven. The solid was suspended in ethanol (40 mL) stirred at reflux for 2 hours. The suspension was cooled to 5° C. and the solid was collected by suction-filtration, aspirator-dried 5 minutes, then dried for the weekend at 60° C. in the vacuum oven (wet cake: 13.74 g). The desired material was obtained as an off-white solid (11.65 g, quantitative).

Preparation of 4-Dimethylamino-1-butanesulfonic acid (Compound LH)

A solution of 1,4-butane sultone (7.5 mL, 73.6 mmol) in 1,4-dioxane (total volume: 10 mL) was added over 4 hours via a syringe pump to a cold (4.3° C.) solution of dimethylamine (40% wt in water, 275 mL). The mixture was stirred for 3 hours at 4° C. after the end of the addition, then overnight at room temperature. The mixture was concentrated to dryness. The solid was suspended in absolute ethanol (50 mL) and the mixture was heated to reflux for 90 minutes. The suspension was cooled to 5° C. and the solid was collected by suction-filtration, rinsed with ethanol (2×10 mL). The solid was dried for 18 h at 60° C. in the vacuum oven. The desired material was obtained as a fine white powder 13.21 g, 72.9 mmol, 99% yield. The $^1$H and $^{13}$C NMR and MS were consistent with the structure.

Preparation of 3-(ethylamino)-2-hydroxy-1-propanesulfonic acid (Compound JU)

A solution of 3-chloro-2-hydroxy-1-propanesulfonic acid sodium salt (10 g, 50.9 mmol) in water (total volume: 40 mL) was added over 5 hours, via a syringe pump, to a cold (4.7° C.) solutionsolution of ethyl amine in water. The mixture was stirred for an additional 2 hours at 4.7° C. then for 18 hours at room temperature. NMR: quantitative yield. The mixture was concentrated. A solid could not be obtained: the sodium salt was too hygroscopic. The solution was treated with Amberlite IR-120 Plus, acid form, ion-exchange resin to give the free acid. It was still too hygroscopic to be obtained as a solid form. Submitted as a solution: d=1.314 g/mL, 62.5% w/w of the free acid in water. The $^1$H and $^{13}$C NMR and MS were consistent with the structure.

Preparation of 3-(tert-butylamino)-2-hydroxy-1-propanesulfonic acid (Compound JV)

A solution of 3-chloro-2-hydroxy-1-propanesulfonic acid, sodium salt (15 g, 25 mmol) in water (12 mL total volume) was added over 5 minutes to a mixture of tert-butylamine (12.5 mL), water (6 mL) and methanol (3 mL). The mixture was heated at 35° C. for 1 h, 40° C. for 1 h, 45° C. for 1.5 hours. The mixture was the concentrated to a thick oil. The crude reaction mixture was passed over a column of Dowex 50×8 (125 g). The fractions containing the product were concentrated to dryness. The solid was dried overnight at 60° C. in the vacuum oven. The solid was recrystallized in a mixture of methanol (25 mL) and water (7 mL). The mixture was cooled slowly to room temperature, then to 5° C. The solid was collected by suction-filtration, rinsed with ethanol (1×10 mL). The solid was then dried for 18 hours at 60° C. in the vacuum oven. The desired material was obtained as an off-white solid (3.11 g, 14.7 mmol, 59%). The $^1$H and $^{13}$C NMR and MS were consistent with the structure.

Preparation of
1-(N-octylamino)-2-hydroxy-1-propanesulfonic acid
(Compound JW)

A solution of 3-chloro-2-hydroxy-1-propanesulfonic acid, sodium salt (4 g, 20 mmol) in water (17.5 mL total volume) was added over 2 hours to a mixture of octylamine (8 mL), water (20 mL) and 1,4-dioxane (11 mL) at 70-75° C. The mixture was stirred at this temperature for another 2 hours after the end of the addition. The 1,4-dioxane was removed under reduced pressure and the mixture was diluted with water (10 mL). The mixture was extracted with 40% ethyl acetate/hexane (3×40 mL). The aqueous layer was concentrated then the mixture was passed over a column of Dowex 50×8 (125 g). The fractions containing the pure product were concentrated to a thick oil then freeze-dried. The desired material was obtained as a white fluffy solid (150 mg, 0.56 mmol, 3%). The $^1$H and $^{13}$C NMR and MS were consistent with the structure.

Preparation of 1-(3-sulfo-2-hydroxypropyl)
quinuclidinium, inner salt (Compound JX)

A solution of 3-chloro-2-hydroxy-1-propanesulfonic acid, sodium salt (2 g, 10 mmol) in water (12 mL total volume) was added over 1 hour to a mixture of quinuclidine (1.63 g, 4.7 mmol), water (10 mL) and 1,4-dioxane (10 mL) at 80° C. The mixture was stirred at this temperature for another 2 hours after the end of the addition. The reaction mixture was concentrated then the mixture was passed over a column of Dowex 50×8 (125 g). The fractions containing the pure product were concentrated to a white solid. The solid was dried for 18 hours at 60° C. in the vacuum oven. The desired material was obtained as a white solid (1.92 g, 7.7 mmol, 77%). The $^1$H and $^{13}$C NMR and MS were consistent with the structure.

Preparation of
1-(N-benzylamino)-2-hydroxy-1-propanesulfonic
acid, sodium salt (Compound JY)

A solution of 3-chloro-2-hydroxy-1-propanesulfonic acid, sodium salt (4 g, 20 mmol) in water (12.5 mL total volume) was added over 2 hours to a mixture of benzylamine (4.28 g, 40 mmol), water (10 mL) and 1,4-dioxane (5 mL) at 80° C. The mixture was stirred at this temperature for another 2.5 hours after the end of the addition. The reaction mixture was extracted with chloroform (2×40 mL). It was then concentrated to dryness. The crude solid was recrystallized in a mixture of ethanol (30 mL) and water (4 mL). The mixture was left to cool to room temperature for the night. The solid was collected by suction-filtration, rinsed with ethanol (10 mL) and dried in the vacuum oven at 60° C. The desired material was obtained as a white solid (2.67 g, 10 mmol, 50%). The $^1$H and $^{13}$C NMR and MS were consistent with the structure.

Preparation of 2-hydroxy-3-(1,2,3,4-tetrahydronaph-
thalen-1-ylamino)propane-1-sulfonic acid (Com-
pound JZ)

A solution of 3-chloro-2-hydroxy-1-propanesulfonic acid, sodium salt (2 g, 10 mmol) in water (9.75 mL total volume) was added over 8 hours to a mixture of 1,2,3,4-tetrahydro-1-nahtylamine (2 g, 13.6 mmol), water (10 mL) and 1,4-dioxane (4 mL) at 40° C. The mixture was stirred at this temperature for another 18 hours after the end of the addition. The reaction was not completed. The mixture was heated for 2 hours at reflux. The mixture was diluted with water (10 mL) and 50% w/w NaOH (0.25 mL) was added. The reaction mixture was extracted with chloroform (2×25 mL). It was then concentrated to a thick oil. The solution was applied on a Dowex 50 W 8 column (100 g). The fractions containing the product were concentrated, treated with activated charcoal (no effect) and freeze-dried. The desired material was obtained as a glassy solid (0.85 g, 3 mmol, 30%). The $^1$H and $^{13}$C NMR and MS were consistent with the structure.

Preparation of
2-hydroxy-3-piperidin-1-ylpropane-1-sulfonic acid
(Compound KA)

A solution of 3-chloro-2-hydroxy-1-propanesulfonic acid, sodium salt (4 g, 20 mmol) in water (13.35 mL total volume) was added over 5 hours to a solution of piperidine (8 mL g, 80 mmol), in water (15 mL) at 70° C. The mixture was stirred at 80° C. for 2 hours. The reaction was completed. The mixture was stirred at room temperature for the night. The mixture was diluted with water (10 mL) and was extracted with chloroform (3×30 mL). It was then concentrated to a thick oil. The solution was applied on a Dowex 50 W 8 column (100 g). The fractions containing the product were concentrated to dryness then recrystallized in a mixture of ethanol (30 mL) and water (2.1 mL). The mixture was cooled slowly at room temperature. The solid was collected by suction filtration, rinsed with ethanol (2×5 mL) air dried 5 minutes, then 18 hours at 60° C. in the vacuum oven. The desired material was obtained as a fine white solid (3.06 g, 13.7 mmol, 68%). The $^1$H and $^{13}$C NMR and MS were consistent with the structure.

Preparation of 4-(adamantyl)amino-1-butanesulfonic
acid (Compound LI)

1-adamantaneamine hydrochloride (2.67 g, 13.3 mmol) was treated with 1N NaOH (20 mL) and $CH_2Cl_2$ (3×20 mL). The biphasic solution was shaken. The organic extracts were combined, dried with $Na_2SO_4$, filtered, evaporated under reduced pressure and dried in vacuo.
To a solution of 2-adamantanamine (1.87 g, 12.4 mmol) in tetrahydrofuran (THF, 15 mL) was added 1,4-butane sultone (1.76 g, 13.0 mmol). The solution was stirred at reflux overnight. The reaction was cooled to room temperature. The solid was collected by filtration, washed with THF (1×15 mL) and dried in vacuo. A suspension of the solid in EtOH (25 mL) was stirred at reflux for 1 hour. The warm mixture was filtered. The solid was dried in vacuo. $^1$H NMR ($D_2O$, 500 MHz) δ ppm 2.92 (m, 2H), 2.82 (m, 1H), 2.05 (s, 3H), 1.75 (s, 6H), 1.63 (m, 6H), 1.52 (m, 3H). $^{13}$C ($D_2O$, 125 MHz) δ ppm 57.62, 50.30, 39.03, 38.14, 35.09, 28.98, 25.25, 21.63. ES-MS 288 (M+1).

Preparation of 4-(octylamino)-1-butanesulfonic acid (Compound LJ)

To a solution of octylamine (2.20 g, 17.0 mmol) in tetrahydrofuran (11 mL) was added 1,4-butane sultone (2.30 g, 16.2 mmol). The solution was heated to reflux for 5 hours. The reaction was cooled to room temperature. The product formed a gel. A few drops of EtOH were added to dissolve the product. The solution was poured in a large excess of acetone (25 mL). After 5 minutes, a white solid precipitated. The solid was collected by filtration and dried in vacuo. The product was dissolved in EtOH and Dowex 50×8 resin (pre-washed, 6 g) was added to the solution. The suspension was stirred for 15 minutes and the resin was filtered. The filtrate was evaporated under educed pressure and the product was dried in vacuo. Yield: 31%. $^1$H NMR (DMSO, 500 MHz) δ ppm 8.24 (s (broad), 1H), 2.85 (m, 4H), 2.45 (m, 2H), 1.64 (m, 4H), 1.61 (m, 2H), 1.25 (m, 10H), (m, 2H), 0.85 (t, 3H, J=6.8 Hz). $^{13}$C (DMSO, 125 MHz) δ ppm 51.22, 47.54, 47.38, 31.82, 29.14, 26.59, 26.13, 25.51, 22.95, 22.75, 14.64. ES-MS 266 (M+1).

Preparation of 4-(cyclohexylamino)-2-butanesulfonic acid (Compound KM)

To a solution of cyclohexylamine (1.50 g, 15.1 mmol) in tetrahydrofuran (15 mL) was added 2,4-butane sultone (2.04 g, 14.4 mmol). The solution stirred at reflux for 2 hours. The reaction was cooled to room temperature. The solid was collected by filtration and dried in vacuo. Yield: 59%. $^1$H NMR (DMSO, 500 MHz) δ ppm 8.50 (s (broad), 1H), 3.02 (m, 2H), 2.93 (m, 1H), 2.60 (m, 1H), 1.93 (m, 3H), 1.75 (m, 3H), 1.57 (m, 1H), 1.21 (m, 4H), 1.11 (m, 4H). $^{13}$C (DMSO, 125 MHz) δ ppm 56.23, 53.20, 43.09, 29.54, 29.41, 29.39, 25.40, 24.42, 17.23. ES-MS 234 (M−1).

Preparation of 4-[(dl)-1-hydroxy-2-pentyl]amino-1-butanesulfonic acid (Compound LL)

To a solution of DL-2-aminopentanol (1.0 g, 9.7 mmol) in tetrahydrofuran (6 mL) was added 1,4-butane sultone (1.31 g, 9.2 mmol) at room temperature. The solution was stirred at reflux for 5 hours. The reaction was cooled to room temperature. The supernatant was removed and the solid was dried in vacuo. The white solid was filtered, washed with acetone (2×25 mL) and dried in vacuo. Yield: 45%. $^1$H NMR (DMSO, 500 MHz) δ ppm 8.20 (s (broad), 1H), 5.23 (m, 1H), 3.66 (m, 1H), 3.49 (m, 1H), 3.02 (m, 1H), 2.91 (m, 2H), 2.46 (t, 2H, J=7.3 Hz), 1.65, (m, 4H), 1.54 (m, 2H), 1.38 (m, 2H), 0.88 (t, 3H, J=7.3 Hz). $^{13}$C (DMSO, 125 MHz) δ ppm 58.83, 58.54, 51.23, 44.77, 29.91, 25.56, 23.06, 18.95, 14.48. ES-MS 238 (M−1).

Preparation of 3-[(3,4-dimethoxybenzyl)amino]-1-butanesulfonic acid (Compound LM)

To a solution of veratrylamine (1.50 g, 9.0 mmol) in 1,4-dioxane (8 mL) was added 1,4-butane sultone (1.21 g, 8.5 mmol) at room temperature. The mixture was then heated at reflux for 2 hours. The reaction was cooled to room temperature. The solid was collected by filtration, washed with acetone (2×25 mL) and dried on pump. Yield: 18%. $^1$H NMR (D$_2$O, 500 MHz) δ 6.96 (m, 3H), 4.04 (s, 2H), 3.74 (m, 6H), 2.95 (t, 2H, J=6.8 Hz), 2.80 (t, 2H, J=7.3 Hz), 1.68, (m, 4H). $^{13}$C (D$_2$O, 125 MHz) δ ppm 149.19, 148.50, 123.82, 123.36, 113.25, 112.17, 55.91, 50.88, 50.24, 46.41, 24.55, 21.50. ES-MS 302 (M−1).

Preparation of 4-(adamantan-1-ylamino)-2-hydroxy-1-propanesulfonic acid (Compound KB)

1-adamantaneamine hydrochloride (2.67 g, 14.2 mmol) was treated with 1N NaOH (20 mL) and CH$_2$Cl$_2$ (3×20 mL). The organic extracts were combined, dried with Na$_2$SO$_4$, filtered, evaporated under reduced pressure and dried in vacuo.

To an 80° C. solution of 1-adamantanamine (2.15 g, 14.2 mmol) in 1,4-dioxane (10 mL) and water (5 mL) was added via syringe pump (1 h addition) a solution of 3-chloro-2-hydroxy-propanesulfonic acid, sodium salt (1.93 g, 9.7 mmol) in 1,4-dioxane (0.5 mL) and water (10 mL). The solution was stirred at reflux overnight. The reaction was cooled to room temperature. The solvent was evaporated under reduced pressure. The solid was suspended in 25% acetone/EtOH. The mixture was heated to reflux for 1 minute. The solid was collected by filtration. The pure product crystallized in the filtrate. The product was filtered, washed with EtOH (2×10 mL), dissolved in water and lyophilized. Yield: 15%. $^1$H NMR (D$_2$O, 500 MHz) δ ppm 4.18 (m, 1H), 3.22 (m, 1H), 3.01 (m, 2H), 2.94 (m, 1H), 2.06 (s, 3H), 1.77 (m, 7H), 1.61 (d, 3H), 1.53 (m, 3H). $^{13}$C (D$_2$O, 125 MHz) δ ppm 64.23, 57.99, 55.05, 44.10, 38.10, 35.07, 29.03. ES-MS 288 (M−Na (23)).

Preparation of 4-(2-adamantyl)amino-1-butanesulfonic acid (Compound LN)

2-adamantanamine hydrochloride (2.50 g, 13.3 mmol) was treated with 1N NaOH (20 mL) and CH$_2$Cl$_2$ (3×20 mL). The organic extracts were combined, dried with Na$_2$SO$_4$, filtered, evaporated under reduced pressure and dried in vacuo.

To a solution of 2-adamantanamine (1.06 g, 7.0 mmol) in 1,4-dioxane (6 mL) was added 1,4-butane sultone (955 mg, 6.7 mmol). The solution was stirred at reflux for 5 hours. The reaction was cooled to room temperature. The solid was collected by filtration. It was suspended in EtOH (25 mL) and the mixture was heated to reflux for 1 minute before the solid was filtered. It was washed with EtOH (1×15 mL) and dried in vacuo. Yield: 55%. $^1$H NMR (D$_2$O, 500 MHz) δ ppm 3.29 (m, 1H), 2.97 (m, 2H), 2.83 (m, 2H), 2.02 (m, 2H), 1.83 (m, 2H), 1.68 (m, 14H). $^{13}$C NMR (D20, 125 MHz) δ ppm 63.07, 50.25, 45.03, 36.55, 36.31, 29.85, 29.05, 26.68, 26.41, 24.47, 21.61. ES-MS 286 (M−1).

Preparation of 3-(2-adamantylamino)-2-hydroxy-1-propanesulfonic acid (Compound KJ)

To an 80° C. solution of 2-adamantanamine hydrochloride (2.50 g, 13.3 mmol) and sodium hydroxide (586 mg, 14.6 mmol) in 1,4-dioxane (7 mL) and water (7 mL) was added via syringe pump (1 hour addition) a solution of 3-chloro-2-hydroxy-propane sulfonic acid, sodium salt (1.76 g, 8.9 mmol) in 1,4-dioxane (1 mL) and water (9 mL). The solution was stirred at 80° C. for an additional 4 hours. The reaction was cooled to room temperature. The solvent was evaporated under reduced pressure. The solid was suspended in EtOH (25 mL). The mixture was heated to reflux for 1 minute. The solid was removed by filtration. The pure product crystallized in the filtrate. The product was filtered, washed with EtOH (1×10 mL) and dried in vacuo. Yield: 30%. $^1$H NMR (D$_2$O, 500 MHz) δ ppm 4.30 (m, 1H), 3.35 (m, 2H), 3.03 (m, 3H), 2.07 (m, 2H), 1.84 (m, 2H), 1.75 (m, 4H), 1.65 (d, 6H). $^{13}$C (D$_2$O, 125 MHz) δ ppm 63.31, 55.03, 49.51, 36.51, 36.33, 36.26, 29.78, 29.23, 28.81, 26.63, 26.38. ES-MS 289 (M+1).

Preparation of 3-(bicyclo[2.2.1]hept-2-ylamino)-2-hydroxy-1-propanesulfonic acid (Compound KI)

To an 80° C. solution of exo-2-aminonorbornane (910 mg, 8.2 mmol) and sodium hydroxide (242 mg, 6.1 mmol) in 1,4-dioxane (4 mL) and water (4 mL) was added via syringe pump (1 hour addition) a solution of 3-chloro-2-hydroxy-propane sulfonic acid, sodium salt (1.09 g, 5.5 mmol) in 1,4-dioxane (0.5 mL) and water (5.5 mL). The solution was stirred at 80° C. for an additional 5 hours. The reaction was cooled to room temperature. The solvent was evaporated under reduced pressure. The solid was suspended in EtOH (25 mL). The mixture was heated to reflux for 1 minute. The solid was recovered by filtration and it was passed through an ion exchange column (Dowex 50×8, 100 g, solvent: water). The product was recrystallized in EtOH/water (99/1). Yield: 17%. $^1$H NMR (D$_2$O, 500 MHz) δ ppm 4.25 (m, 1H), 3.25 (m, 2H), 3.01 (m, 4H), 2.39 (m, 1H), 2.27 (m, 1H), 1.69 (m, 1H), 1.51 (m, 1H), 1.38 (m, 3H), 1.19 (m, 1H), 1.07 (m, 2H). $^{13}$C (D$_2$O, 125 MHz) δ ppm 63.66, 63.50, 62.21, 61.98, 54.94, 50.11, 50.04, 39.26, 39.21, 36.02, 35.97, 35.91, 35.80, 34.70, 34.61, 27.11, 27.08, 26.50, 26.45. ES-MS 250 (M−1).

Preparation of 4-[(3-methylbutyl)amino]-2-butanesulfonic acid (Compound KH)

To a hot solution of isoamylamine (2.0 g, 22.9 mmol) in tetrahydrofuran (THF, 11 mL) was added via syringe pump (2 hour addition) a solution of 2,4-butane sultone (3.1 g, 21.8 mmol in THF (total of 5 mL)). The solution was stirred at reflux for an additional 2 hours. The reaction was cooled to room temperature. The solid was recovered by filtration and it was washed with THF (25 mL) and acetone (25 mL). The solid was dissolved in water (20 mL) and Dowex 50×8 (10 g) was suspended in the solution. The mixture was stirred for 15 minutes and the resin was filtered. The solvent was evaporated under reduced pressure. Yield: 28%. $^1$H NMR (H$_2$O, 500 MHz) δ ppm 3.07 (t, 2H, J=7.8 Hz), 2.92 (t, 2H, J=7.8 Hz), 2.87 (m, 1H), 2.06 (m, 1H), 1.77 (m, 1H), 1.51 (m, 1H), 1.42 (m, 2H), 1.18 (d, 3H, J=6.8 Hz), 0.78 (d, 3H, J=6.3 Hz). $^{13}$C (H$_2$O, 125 MHz) δ ppm 53.21, 46.32, 45.37, 34.36, 28.16, 25.35, 21.51, 14.79. ES-MS 224 (M+1).

Preparation of 2-hydroxy-3-[(3-methylbutyl)amino]-1-propane sulfonic acid (Compound KK)

To a 80° C. solution of isoamylamine (2.0 g, 22.9 mmol) in 1,4-dioxane (9 mL) and water (3 mL) was added via syringe pump (1 h addition) a solution of 3-chloro-2-hydroxy-propane sulfonic acid, sodium salt (3.04 g, 15.3 mmol) in 1,4-dioxane (9.5 mL) and water (0.5 mL). The solution was stirred overnight at 80° C. The solvent was evaporated. The product was passed through an ion exchange column (Dowex 50×8, 100 g, solvent: water). It was recrystallized in absolute EtOH and lyophilized. Yield: 27%. $^1$H NMR (H$_2$O, 500 MHz) δ ppm 4.24 (m, 1H), 3.22 (m, 1H), 3.02 (m, 5H), 1.49 (m, 3H), 0.79 (d, 3H, J=6.3 Hz). $^{13}$C (H$_2$O, 125 MHz) δ ppm 63.54, 54.89, 51.53, 46.48, 34.12, 25.46, 21.56, 21.46. ES-MS 226 (M+1).

Preparation of 3-[(dl)-1-Hydroxy-2-pentyl]amino-1-propane sulfonic acid (Compound KL)

To a 80° C. solution of DL-2-amino-1-pentanol (1.0 g, 9.7 mmol) in 1,4-dioxane (5 mL) and water (3 mL) was added via syringe pump (1 hour addition) a solution of 3-chloro-2-hydroxy-propane sulfonic acid, sodium salt (1.84 g, 9.2 mmol) in 1,4-dioxane (6 mL) and water (0.5 mL). The solution was stirred overnight at 80° C. The solvent was evaporated. The product was passed through an ion exchange column (Dowex 50×8, 100 g, solvent: water). The product was dissolved. It was recrystallized in absolute EtOH and lyophilized. Yield: 27%. $^1$H NMR (H$_2$O, 500 MHz) δ ppm 4.26 (m, 1H), 3.77 (m, 1H), 3.32 (m, 1H), 3.24 (m, 1H), 3.03 (m, 3H), 1.54 (m, 2H), 1.29 (m, 2H), 0.81 (t, 3H, J=7.3 Hz). $^{13}$C (H$_2$O, 125 MHz) δ ppm 63.69, 63.60, 59.49, 59.38, 58.81, 58.36, 54.98, 48.68, 48.27, 29.32, 28.85, 18.40, 18.38, 13.12. ES-MS 242 (M+1).

Preparation of 4-(cyclohexylamino)-1-butanesulfonic acid (Compound LK)

To a solution of cyclohexylamine (2.0 g, 20.2 mmol) in 1,4-dioxane (13 mL) was added 1,4-butane sultone (2.61 g, 19.2 mmol). The solution was heated to reflux for 2 hours. The reaction was cooled to room temperature. The solid was collected by filtration, washed with acetone (2×20 mL) and dried in vacuo. Yield: 52%. $^1$H NMR (D$_2$O, 500 MHz) δ ppm 2.95 (m, 3H), 2.81 (m, 2H), 1.92 (m, 2H), 1.67 (m, 6H), 1.52 (m, 1H), 1.18 (m, 4H), 1.02 (m, 1H). $^{13}$C (D2O, 125 MHz) δ ppm 57.32, 50.31, 44.01, 29.02, 24.84, 24.68, 24.07, 24.55. ES-MS 236 (M+1).

Preparation of 3-[(1-ethyl-1-methylpropyl)amino]-1-propanesulfonic acid (Compound FP)

The flask was closed with a septum and connected to a 20% NaOH scrubber for the Ritter Reaction. Potassium cyanide (3.25 g, 50 mmol) was added to acetic acid (13 mL) and the mixture was stirred for 10 min at room temperature. A solution of sulfuric acid (7 mL) in acetic acid (6 mL) was added and the resulting suspension was stirred 10 minutes at room temperature. The 3-methyl-3-pentanol (5 g, 48.9 mmol) was added drop-wise over a 5 minute period. The mixture was stirred at room temperature for 4 hours, at which time some chunks of potassium cyanide were still visible.

Another portion of potassium cyanide (0.6 g, powdered) was added and the mixture was stirred for 18 hours at room temperature. The mixture was purged with nitrogen for 1 h then poured over ice (approx. 50 g). The pH of the solution was adjusted to 9 with the addition of 20% NaOH (use 50% next time to reduce the volume). The layers were separated and the aqueous layer was extracted with ether (1×20 mL). The combined organic layers were washed with saturated potassium carbonate (1×5 mL) then dried over magnesium sulfate. The ether was evaporated under reduced pressure to afford a yellow oil (4.11 g, 31.8 mmol, 64%). The oil showed to be a mixture of cis and trans formamide but what otherwise pure enough to be used as such. $^1$H NMR (500 MHz, DMSO-d6) δ 0.75-0.80 (m, 6H), 1.11-1.12 (m, 3H), 1.40-1.54 (m, 2H), 1.66-1.73 (m, 2H), 7.35-7.45 (br s and br d, 1H), [7.88 (s) and 8.08 (d, J=11.7 Hz) for 1H); $^{13}$C NMR (125 MHz, DMSO-d6) δ 7.7, 7.9, 23.4, 24.2, 30.6, 33.8, 55.6, 160.3, 163.3

The 1-ethyl-1-methyl-propylformamide (4.00 g, 31.1 mmol) was added to 20% NaOH (40 mL). The mixture was heated to reflux for 4 hours then was left overnight at room temperature. Toluene (10 mL) was added and the layers were separated. The organic layer was dried over sodium sulfate then filtered. The final volume of the filtrate was about 30 mL. It was used as such in the next step.

A solution of 1,3-propanesultone (2.5 g, 20 mmol) in 2-butanone (10 mL) was added to a solution of 3-methyl-3-ethyl-3-propylamine in toluene (total volume: 30 mL). The mixture was heated to reflux for 5 hours then was cooled to room temperature. The solid was collected by suction-filtration and rinsed with acetone (2×5 mL). The solid was dried overnight at 45° C. in the vacuum oven. The title compound was obtained as a fine white solid (3.63 g, 16.3 mmol, 33% overall yield). $^1$H NMR (500 MHz, DMSO-d6) δ 0.79 (t, J=7.3 Hz, 6H), 1.15 (s, 3H), 1.53-1.59 (m, 4H), 1.97-2.00 (m, 2H), 2.89 (t, J=7.1 Hz, 2H), 3.03 (t, J=7.6 Hz, 2H); $^{13}$C NMR (125 MHz, DMSO-d6) δ 6.8, 20.2, 21.9, 27.7, 39.7, 48.2, 63.3 ES-MS 224; (M+H)

Preparation of 3-({2-hydroxy-1,1-dimethyl-2-(3-methoxyphenyl)ethyl]amino)-1-propanesulfonic acid (Compound NG)

To a cooled solution of sodium methoxide (0.5 M in MeOH, 25 mLl) was added via syringe over a 10 minutes period 2-nitropropane (5.0 g, 56 mmol). The reaction mixture was stirred at room temperature for 30 minutes and recooled before m-anisaldehyde (6.8 mL, 56 mmol) was added. The reaction mixture was stirred at room temperature overnight. The mixture was neutralized with Amberlite IR-120 (strongly acidic). The resin was removed by filtration and washed with MeOH (2×20 mL). The filtrate was evaporated. The resulting oil was purified by flash chromatography: 98% Hexanes/EtOAc to 90% Hexanes/EtOAc, affording the desired nitro compound (5.70 g, 45%).

To a solution of the nitro compound (5.70 g, 25.3 mmol)) in MeOH (25 mL) was added 6M HCl (25 mL). After cooling to 5° C., zinc powder (8.2 g, 125 mmol) was added. The suspension was stirred at 0-5° C. and at room temperature overnight. The mixture was filtered on a celite pad. The filter cake was washed with MeOH (2×20 mL). The combined filtrates were evaporated under reduced pressure. The residue was dissolved in EtOAc (40 mL). The mixture was exctracted with 5% NaOH (1×40 mL). The aqueous phase was exctracted with EtOAc (2×40 mL). The combined organic extracts were dried with Na$_2$SO$_4$, filtered, evaporated and dried in vacuo to afford the corresponding amine. The amine (2.15 g, 44%) was used without further purification.

To a solution of amine (2.15 g, 11.0 mmol) in Pinacolone (6 mL) and toluene (6 mL) was added 1,3-propane sultone (1.28 g, 10.5 mmol). The solution was stirred at reflux overnight. The reaction mixture was cooled to room temperature. The solid material was collected by filtration, was washed with acetone (2×20 mL). The solid was suspended in EtOH (30 mL). The suspension was stirred at reflux for 1 hour. The mixture was cooled to room temperature. The white solid was filtered, washed with acetone (2×15 mL) and dried in a vacuum oven at 50° C., affording the title compound, 2.26 g (66%). $^1$H NMR (DMSO, 500 MHz) δ ppm 8.45 (s (broad), 1H), 7.26 (t, 1H, J=7.9 Hz), 6.89 (m, 3H), 6.30 (d, 1H, J=3.2 Hz), 4.69 (d, 1H, J=3.8 Hz), 3.74 (s, 3H), 3.10 (m, 2H), 2.62 (t, 2H, J=6.7 Hz), 2.00 (m, 2H), 1.07 (m, 6H). $^{13}$C (DMSO, 125 MHz) δ ppm 159.24, 142.09, 129.45, 120.80, 114.30, 113.76, 74.16, 62.48, 55.92, 50.10, 41.57, 23.30, 21.18, 19.37. ES-MS 316 (M−1).

Preparation of 3-{[1-(4-methylbenzyl)cyclohexyl]amino}-1-propane-1-sulfonic acid (Compound NH)

NaOMe (0.5M, 40 mL) was added to nitrocyclohexane (2.58 g, 20 mmol) and the solution was stirred for 30 minutes then concentrated to afford a white solid. To this solid was added 4-methylbenzylpyrridinium (6.6 g, 13 mmol) and DMSO (20 mL). The mixture was heated at 100° C. for 15 hours then cooled to rt and diluted with HCl (1M) and EtOAc. After separation of the two phases, the organic layer was washed twice with HCl (1M) then concentrated to obtain an oily crude. Methanol was added to precipitate the pyridinium byproduct which was filtered off, and the filtrate was concentrated and purified by column using Hex:EtOAc 90:10 to obtain the desired nitro (still contaminated with the pyridinium salt). 2 g, 66% yield.

To a stirred solution of the nitro (2.0 g, 8.58 mmol) in methanol (20 mL) was added a spatula of Raney-Ni in water. The suspension was hydrogenated under atmospheric pressure of hydrogen for 15 hours (TLC indicates complete consumption of the starting material) then filtered on celite and concentrated under reduced pressure. The crude was purified by column using CH$_2$Cl$_2$:MeOH 80:10 to afford 1.2 g of the corresponding amine.

To a stirred solution of the amine (800 mg, 3.93 mmol) in THF (8 mL) was added 1,3-propane sultone (480 mg, 3.93 mmol). The reaction mixture was stirred at reflux for 15 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1.1 g (86%). $^1$H NMR (500 MHz, DMSO-d$_6$) δ 1.18-1.78 (m, 10H), 2.00 (m, 2H), 2.29 (s, 3H), 2.65 (m, 2H), 2.92 (s, 2H), 3.12 (m, 2H), 7.10-7.16 (m, 2H), 8.39 (bs, 2H). $^{13}$NMR (125 MHz, DMSO-d$_6$) δ 20.74, 21.35, 22.80, 25.05, 31.60, 41.04, 50.24, 61.63, 129.71, 131.38, 132.44, 136.80. ES-MS 324 (M−1).

Preparation of 3-{[2-(4-methoxyphenyl)-1,1-dimethylethyl]amino}-1-propanesulfonic acid (Compound NI)

To a stirred solution of the phenol (233 mg, 1 mmol) in DMF/THF (2.5 mL/2.5 mL) was added MeI (93 uL, 1.5 mmol) followed by K$_2$CO$_3$ (276 mg, 2 mmol). The suspension was heated at reflux for 15 hours then diluted with HCl (1M) and with EtOAc. The organic layer was washed with HCl (1M) then concentrated under high vacuum. The crude was purified by column using Hex:EtOAc 90:10 to obtain 215 mg of the methoxy (87% yield).

To a stirred solution of the nitro (300 mg, 1.2 mmol) in methanol (5 mL) was added a small spatula of Raney-Ni in water. The suspension was hydrogenated under atmospheric pressure of hydrogen for 3 hours (TLC indicates complete consumption of the starting material) then filtered on pre-washed celite and concentrated under reduced pressure. The crude amine was used as such in the next step.

To the crude amine (240 mg, 1.34 mmol) in solution in THF (3 mL) was added 1,3-sultone (181 mg, 1.48 mmol) and the mixture was heated at reflux of THF for 12 hours. The suspension of was cooled down and filtered. The solid was dried to afford 270 mg of the homotaurin as a white solid (67% yield). $^1$H NMR (500 MHz, D$_2$O) δ 1.11 (s, 6H), 2.00 (m, 2H), 2.67 (m, 2H), 2.80 (m, 2H), 3.12 (m, 2H), 3.74 (s, 3H), 6.90 (m, 2H), 7.14 (m, 2H), 8.61 (bs, 2H). ES-MS 272 (M−1). ES-MS 300 (M−1).

Preparation of 3-{[2-hydroxy-1,1-dimethyl-2-(4-methylphenyl)ethyl]amino}-1-propanesulfonic acid (Compound NJ)

To a solution of 2-nitropropane (3.0 g, 34 mmol), p-tolualdehyde (4.0 mL, 34 mmol) and Tetrahydrofuran (30 mL)

was added Amberlyst A-21 (7 g). The reaction mixture was stirred at room temperature for 40 hours. The resin was removed by filtration and washed with THF (2×20 mL). The filtrate was evaporated. The resulting oil was purified by flash chromatography: 98% Hexanes/EtOAc to 90% Hexanes/EtOAc, affording the desired nitro compound (820 mg, 12%).

A suspension of Pd/C and the nitro compound (820 mg, 3.9 mmol) in EtOAc (10 mL) was stirred under $H_2$ (1 atm) overnight. The mixture was filtered on a celite pad. The celite was washed with EtOAc (2×15 mL). The combined filtrates were evaporated under reduced pressure to afford the corresponding amine. The amine (470 mg, 67%) was used without further purification.

To a solution of amine (470 mg, 2.6 mmol) in pinacolone (5 mL) and Toluene (5 mL) was added 1,3-propane sultone (310 mg, 2.5 mmol). The solution was stirred at reflux for 4 hours. The reaction mixture was cooled to room temperature. The solid was collected by filtration, was washed with acetone (2×10 mL) and dried in vacuo, affording the title compound, 196 mg (26%). $^1$H NMR (DMSO, 500 MHz) δ ppm 8.46 (s (broad), 1H), 7.24 (d, 2H, J=7.8 Hz), 7.16 (d, 2H, J=8.3 Hz), 6.23 (d, 1H, J=3.9 Hz), 4.68 (d, 1H, J=3.9 Hz), 3.11 (m, 2H), 2.63 (t, 2H, J=6.8 Hz), 2.29 (s, 3H), 2.00 (m, 2H), 1.04 (s, 6H). $^{13}$C (DMSO, 125 MHz) δ ppm 137.69, 137.56, 129.03, 128.45, 74.07, 62.38, 49.91, 41.35, 22.99, 21.39, 20.81, 18.76. ES-MS 300 (M−1).

Preparation of 3-{[1,1-dimethyl-2-(4-methylphenyl)ethyl]amino}-1-propanesulfonic acid (Compound NK)

NaOMe (0.5M, 20 mL) was added to 2-nitropropane (890 mg, 10 mmol) and the solution was stirred for 30 minutes then concentrated to afford a white solid. To this solid was added 4-methylbenzylpyrridinium (3.3 g, 15 mmol) and DMSO (15 mL). The mixture was heated at 100° C. for 15 hours then cooled to room temperature and diluted with HCl (1M) and EtOAc. After separation of the two phases, the organic layer was washed twice with HCl (1M) then concentrated to obtain an oily crude product. Methanol was added to precipitate the pyridinium byproduct which was filtered off, and the filtrate was concentrated and purified by column using Hex:EtOAc 90:10 to obtain the desired nitro but still contaminated with the pyridinium salt. 1.32 g, 66% yield.

To a stirred solution of the nitro (700 mg, 3.62 mmol) in methanol (10 mL) was added a small spatula of Raney-Ni in water. The suspension was hydrogenated under atmospheric pressure of hydrogen for 15 hours (TLC indicates complete consumption of the starting material) then filtered on celite and concentrated under reduced pressure. The crude amine was used as such in the next step.

To a stirred solution of the amine (550 mg, 3.39 mmol) in THF (8 mL) was added 1,3-propane sultone (414 mg, 3.39 mmol). The reaction mixture was stirred at reflux for 6 hours then cooled to room temperature. The solid was collected by filtration and was washed with THF. The solid was suspended in EtOH (5 mL) and stirred at reflux for 1 hour. The suspension was then cooled to room temperature. The solid was collected by filtration, washed with ethanol and dried under high vacuum to afford the title compound, 210 mg (22%). $^1$H NMR (500 MHz, DMSO-$d_6$) δ 1.13 (s, 6H), 2.00 (m, 2H), 2.66 (dd, J=7.0 & 7.0 Hz, 2H), 2.75 (s, 2H), 3.10 (dd, J=7.0 & 7.0 Hz, 2H), 6.72 (d, J=8.3 Hz, 2H), 7.00 (d, J=8.3 Hz, 2H), 8.60 (bs, 2H), 9.36 (s, 1H). $^{13}$NMR (125 MHz, DMSO-$d_6$) 623.1, 41.2, 43.2, 49.8, 59.4, 115.7, 125.8, 132.3, 157.1. ES-MS 284 (M−1).

Preparation of 4-(bicyclo[2.2.1]hept-2-ylamino)-1-butanesulfonic acid (Compound MX)

To a solution of exo-2-aminonorbornane (800 mg, 7.2 mmol) in 1,4-dioxane (5 mL) was added 1,4-butanesultone (1.00 g, 7.0 mmol) at room temperature. The solution was stirred at reflux for 5 hours. The reaction was cooled to room temperature. The solid was collected by filtration, washed with 1,4-dioxane (2×20 mL) and dried in vacuo. The solid was suspended in EtOH (20 mL). The mixture stirred at reflux for 5 minutes before the solid was filtered and it was dried in vacuo. Yield: 51%. $^1$H NMR ($D_2O$, 500 MHz) δ ppm, 3.00 (m, 1H), 2.95 (m, 2H), 2.81 (m, 2H), 2.34 (m, 1H), 2.26 (m, 1H), 1.68 (m, 5H), 1.48 (m, 1H), 1.37 (m, 3H), 1.18 (d, 1H, J=10.7 Hz), 1.06 (m, 2H). $^{13}$C ($D_2O$, 125 MHz) δ ppm. 61.82, 50.26, 45.44, 39.37, 35.93, 35.78, 34.67, 27.11, 26.40, 24.63, 21.56. ES-MS 248 (M+1).

Preparation of 4-(1H-benzimidazol-2-ylthio)-2-butanesulfonic acid (Compound NE)

To a hot solution of 2-mercaptobenzimidazole (2.0 g, 13.3 mmol) in 1,4-dioxane (12 mL) and water (3 mL) was added via syringe pump (1 hour addition) a solution of 2,4-butane sultone (1.80 g, 12.7 mmol in 1,4-dioxane (total of 3 mL)). The solution was stirred at reflux for an additional 3 hours. The solid was collected by filtration. It was washed with acetone (2×20 mL) and dried in vacuo. Yield: 86%. $^1$H NMR (DMSO, 500 MHz) δ ppm 7.64 (m, 2H), 7.44 (m, 2H), 3.63 (t, 2H, J=7.3 Hz), 2.68 (m, 1H), 2.10 (m, 1H), 1.90 (m, 1H), 1.15 (d, 3H, J=6.8 Hz). $^{13}$C (DMSO, 125 MHz) δ ppm 152.64, 133.32, 125.66, 113.67, 53, 10, 39.72, 33.48, 30.14, 16.85. ES-MS 287 (M+1).

Preparation of 3-[(1,1-diethylpropyl)amino]-1-propanesulfonic acid (Compound NM)

For the Ritter reaction, the flask was closed with a septum and connected to a 20% NaOH scrubber. Potassium cyanide (powdered, 6.19 g, 95 mmol) was added to acetic acid (28 mL) in portions over a 2 minute period. The mixture was stirred for 10 minutes at room temperature. A solution of sulfuric acid (14 mL) in acetic acid (11 mL) was added over a 2 minute period and the resulting suspension was stirred 10 minutes at room temperature. The 3-ethyl-3-pentanol (10 g, 86 mmol) was added dropwise over a 12 minute period. The mixture was stirred at room temperature for 22 hours and then poured over ice (approx. 100 g). The pH of the solution was adjusted to 9 with the addition of 50% NaOH (about 120 g). The layers were separated and the aqueous layer was extracted with ether (1×50 mL). The combined organic layers were washed with saturated sodium carbonate (1×5 mL) then dried over sodium sulfate. The ether was evaporated under reduced pressure to afford a beige waxy solid (12.31 g, 84.76 mmol, 99%). The solid showed to be a mixture of cis and trans formamide but what otherwise pure enough to be used as such. $^1$H NMR (500 MHz, $CDCl_3$) δ [0.81 (t, J=7.3 Hz) and 0.86 (t, J=7.3 Hz) for 9H], [1.55 (q, J=7.3 Hz) and 1.70 (q, J=7.3 Hz) for 9H], [4.83 and 5.65 (br s, 1H)], [8.09 (s) and 8.16 (d, J=12.7 Hz) for 1H]; $^{13}$C NMR (125 MHz, $CDCl_3$) δ 7.2, 26.7, 29.5, 58.3, 60.0, 160.2, 163.4

A solution of NaOH (20%, 80 mL) was added to a solution of the 1,1-diethyl-1-propylformamide (12.31 g, 84.8 mmol) in toluene (10 mL). The hydrolysis was not completed after 4 hours at reflux. A catalytic amount of Triton X-100 and 1,4-dioxane (2 mL) were added. The mixture was heated to reflux for 48 hours then the mixture was cooled at room temperature. Some sodium chloride (10 g) was added to facilitate the phase separation. The layers were separated and the aqueous layer was extracted with toluene (1×20 mL). The combined organic layers were washed with brine (1×10 mL) then dried over sodium sulfate and filtered. The final volume of the filtrate was about 40 mL. It was used as such in the next step.

A solution of 1,3-propanesultone (8.4 g, 68 mmol) in 2-butanone (20 mL) was added dropwise over a 10 minute period to a solution of 1,1-diethyl-3-propylamine in toluene (40 mL total). The mixture was heated to reflux for 5 hours then was cooled to room temperature. The solid was collected by suction-filtration and rinsed with acetone (2×5 mL). The solid was dried overnight at 45° C. in the vacuum oven. The title compound was obtained as a fine white solid (13.33 g, 56.16 mmol, 65% overall yield). $^1$H NMR (500 MHz, D$_2$O) δ 0.81 (m, 9H), 1.59 (m, 6H), 2.04 (m, 2H), 2.94 (m, 2H), 3.05 (m, 2H); $^{13}$C NMR (125 MHz, D$_2$O) δ 6.5, 21.9, 25.1, 39.6, 48.3, 66.1; ES-MS 238 (M+H)

Preparation of
3-[(1-ethylcyclopentyl)amino]-1-propanesulfonic
acid (Compound NN)

For the Ritter reaction, the flask was closed with a septum and connected to a 20% NaOH scrubber. Sodium cyanide (powdered, 1.07 g, 22 mmol) was added in one portion to acetic acid (5 mL). The mixture was stirred for 5 minutes at room temperature. A solution of sulfuric acid (3 mL) in acetic acid (3 mL) was added dropwise over a 2 minute period. The suspension was stirred 10 minutes at room temperature then a solution of 1-ethyl-1-cyclopentanol (2 g, 17.5 mmol) in acetic acid (1 mL) was added dropwise over a 2 minute period. The mixture was stirred at room temperature for 22 hours then poured on ice (about 50 g). The pH of the solution was adjusted to 9 with the addition of 50% NaOH (about 24 g). The layers were separated and the aqueous layer was extracted with ether (2×10 mL). The combined organic layers were washed with saturated sodium carbonate (1×5 mL) then dried over magnesium sulfate. The ether was evaporated under reduced pressure to afford a clear yellow oil (2.35 g, 16.6 mmol, 95%). The oil showed to be a mixture of cis and trans formamide but what otherwise pure enough to be used as such. $^1$H NMR (300 MHz, CDCl$_3$) δ 0.85-0.96 (m, 3H), 1.61-1.97 (m, 10H), [5.23 and 5.77 (br s, 1H)], [8.06 (s) and 8.17 (d, J=12.3 Hz) for 1H]; $^{13}$C NMR (75 MHz, CDCl$_3$) δ 9.0, 9.3, 23.0, 23.8, 30.1, 34.0, 37.8, 38.6, 160.3, 163.4

A solution of NaOH (20%, 20 mL) was added to a mixture of the crude 1-ethyl-1-cyclopentylformamide (2.3 g), Triton X-100 (2 drops) and tetrabutylammonium bromide (45 mg). The mixture was heated to reflux for 3 days then cooled at room temperature. Some sodium chloride (5 g) was added to facilitate the phase separation. The layers were separated and the aqueous layer was extracted with MTBK (2×10 mL) and toluene (1×2 mL). The combined organic layers were washed with brine (1×5 mL) then dried over sodium sulfate and filtered. The filtrate was used as such in the next step. $^1$H NMR (500 MHz, CD$_3$OD) δ 0.95 (t, J=7.3 Hz, 3H) 1.15-1.65 (m, 8H), 1.76-1.80 (m, 2H); $^{13}$C NMR (125 MHz, CD$_3$OD) δ 9.3, 25.2, 36.7, 40.6, 62.4

A solution of 1,3-propane sultone (1.9 g, 15 mmol) in toluene (2 mL) was added to the crude solution of 1-ethyl-1-cyclopentylamine in MTBK/toluene (total volume 30 mL). The mixture was heated to reflux for 20 hours then cooled to room temperature. The solid was collected by suction filtration, rinsed with acetone (2×5 mL). There were specs in the dry crude solid (3.15 g). The solid was recrystallized in hot 90% ethanol. The solid was dried overnight at 60° C. in the vacuum oven. The title compound was obtained as a fine white solid (2.35 g, 10 mmol, 57% overall yield). $^1$H NMR (500 MHz, D$_2$O) δ 0.81 (t, J=7.3 Hz, 3H), 1.53-1.67 (m, 8H), 1.71-1.77 (m, 2H), 1.98 (q, J=7.6 Hz, 2H), 2.88 (t, J=7.8 Hz, 2H), 3.04 (t, J=7.3 Hz, 2H); $^{13}$C NMR (125 MHz, D$_2$O) 7.3, 22.0, 24.3, 29.3, 34.6, 41.1, 48.2, 70.4; ES-MS 234 (M–H)

Preparation of
3-[(1-ethylcycloheptyl)amino]-1-propanesulfonic
acid (Compound NO)

A solution of cycloheptanone (5.69 mL, 50 mmol) was added dropwise to a cold (0° C.) solution of 1M ethyl magnesium bromide in THF (50 mL). The mixture was strirred 1.5 hours at room temperature then for 1 hour at reflux. The reaction mixture was cooled with an ice-water bath and the reaction was quenched with the addition of saturated ammonium chloride (20 mL). The layers were separated and the aqueous phase was extracted once with ether (1×20 mL). The combined organic layers were dried over magnesium sulfate and the ether was removed under reduced pressure. The crude oil (6.34 g) was distilled to afford a clear oil (3.81 g) that contained some cycloheptanone. The product was placed under high vacuum until the cycloheptanone contains was less than 5 mol % (2.81 g, 19.8 mmol, 39%). $^1$H NMR (300 MHz, CDCl$_3$) δ 0.91 (t, J=12.3 Hz, 3H), 1.19 (br s, 1H), 1.36-1.68 (m, 14H); $^{13}$C NMR (75 MHz, CDCl$_3$) δ 7.9, 22.6, 30.0, 35.9, 40.8, 75.5

For the Ritter reaction, the flask was closed with a septum and connected to a 20% NaOH scrubber. Sodium cyanide (powdered, 1.20 g, 24 mmol) was added in one portion to acetic acid (5 mL). The mixture was stirred for 5 minutes at room temperature. A solution of sulfuric acid (3.5 mL) in acetic acid (4 mL) was added dropwise over a 5 minute period. The suspension was stirred 10 minutes at room temperature then a solution of 1-ethyl-1-cycloheptanol (2 g, 17.5 mmol) in acetic acid 31 mL) was added dropwise over a 5 minute period. The mixture was stirred at room temperature for 22 hours then poured on ice (about 50 g). The pH of the solution was adjusted to 9 with the addition of 50% NaOH (about 24 g). The layers were separated and the aqueous layer was extracted with ether (2×10 mL). The combined organic layers were washed with saturated sodium carbonate (1×5 mL) then dried over magnesium sulfate. The ether was evaporated under reduced pressure to afford a clear yellow oil (3.18 g, 18.8 mmol, 95%). A trace the cycloheptanone was still present has indicated by the proton NMR. The oil showed to be a mixture of cis and trans formamide but what otherwise pure enough to be used as such. $^1$H NMR (300 MHz, CDCl$_3$) δ 0.80-0.91 (m, 3H), 1.49-1.96 (m, 14H), [5.07 and 5.70 (br s, 1H)], [8.07 (d, J=2.1 Hz) and 8.17 (d, J=12.3 Hz) for 1H]; $^{13}$C NMR (75 MHz, CDCl$_3$) δ 7.9, 8.2, 22.3, 22.5, 29.6, 29.7, 31.2, 35.7, 38.3, 39.9, 58.7, 60.4, 160.1, 163.3

A solution of NaOH (20%, 20 mL) was added to a mixture of the crude 1-ethyl-1-cycloheptylformamide (3.18 g), Triton X-100 (2 drops) and tetrabutylammonium bromide (45 mg). The mixture was heated to reflux for 4 days then cooled at room temperature. The layers were separated and the aqueous layer was extracted with ether (2×5 mL). The ethereal solution was dried over magnesium sulfate and filtered. Then, a solution of 2N HCl was added and the mixture was concentrated to a thick oil. The oil was diluted with 1N HCl and washed with ether (2×10 mL). The pH of the aqueous layer was adjusted to 10 with the addition of 50% NaOH. The organic layer was eparated and the aqueous phase was extracted with MTBK (2×4 mL). The combined organic layers were washed with brine (1×5 mL) then dried over sodium sulfate and filtered. The filtrate was used as such in the next step. A trace of cycloheptanone and 1-ethyl-1-cycloheptyl-formamide were still visible on the proton NMR. $^1$H NMR (500 MHz, CD$_3$OD) δ 0.90 (t, J=7.2 Hz, 3H) 1.42-1.64 (m, 14H); $^{13}$C NMR (125 MHz, CD$_3$OD) δ 8.1, 23.9, 31.6, 36.6, 42.1, 55.7

A solution of 1,3-propane sultone (1.0 g, 8 mmol) in toluene (3 mL) was added to the crude solution of 1-ethyl-1-cycloheptylamine in MTBK/toluene (total volume 20 mL). The mixture was heated to reflux for 1 hour, for the night at room temperature then another hour at reflux. The mixture was cooled to room temperature. The solid was collected by suction filtration, rinsed with acetone (2×5 mL) then ethanol (1×5 mL). The solid was dried 5 hours at 60° C. in the vacuum oven. The title compound was obtained as a fine white solid (1.35 g, 5.12 mmol, 10% overall yield). $^1$H NMR (500 MHz, DMSO-d$_6$) δ 0.87 (t, J=7.6 Hz, 3H), 1.37-1.41 (m, 2H), 1.49 (br s, 4H), 1.58-1.77 (m, 8H), 2.00 (q, J=6.2 Hz, 2H), 2.68 (t, J=6.3 Hz, 2H), 2.99 (br s, 2H), 8.42 (br s, 2H); $^{13}$C NMR (125 MHz, DMSO-d$_6$) 7.1, 21.6, 21.9, 28.6, 29.7, 34.8, 40.8, 49.9, 64.1; ES-MS 262 (M−H)

Preparation of
3-[(1,3-dimethylbutyl)amino]-1-propanesulfonic
acid (Compound NP)

A solution of 1,3-propanesultone (6.1 g, 50 mmol) in a mixture of MTBK/toluene (60:40, 15 mL) was added in one portion to a solution of 1,3-dimethylbutylamine (5 g, 49 mmol) in mixture of MTBK/toluene (60:40, 25 mL). The mixture was heated under reflux for 3 hours then at room temperature for the night. Ethanol (5 mL) was added and the mixture was heated at reflux for 1 hours then it was cooled to 4° C. The solid was collected by suction filtration, rinsed with acetone (3×10 mL). The solid was dried overnight at 60° C. in the vacuum oven. The title compound was obtained as a fine white solid (9.33 g, 41.8 mmol, 85% overall yield). $^1$H NMR (500 MHz, D$_2$O) δ 0.75 (d, J=6.8 Hz, 3H), 0.81 (d, J=6.8 Hz, 3H), 1.17 (d, J=6.3 Hz, 3H), 1.55-1.60 (m, 1H), 1.95-2.02 (m, 2H), 2.88 (t, J=7.3 Hz, 2H), 3.03-3.11 (m, 2H), 3.21-3.25 (m, 1H); $^{13}$C NMR (125 MHz, D$_2$O) 15.7, 50.6, 21.7, 22.7, 24.3, 41.7, 43.3, 48.1, 53.4; ES-MS 222 (M−H)

Preparation of 3-{[(1S)-1,2,2-trimethylpropyl]
amino}-1-propanesulfonic acid (Compound NQ)

A solution of 1,3-propane sultone (6.6 g, 54 mmol) in toluene (20 mL) was added in one portion to a solution of (S)-3,3-Dimethyl-2-butylamine (5 g, 49 mmol) in MTBK (20 mL). The mixture was heated to reflux. Within 1 hour, it had turned to a lump. More solvent (10 mL of MTBK, 5 mL of toluene then 4 mL of ethanol) were added to restore the stirring. The mixture was then heated at reflux for 18 hours and then it was cooled to 3° C. The solid was collected by suction filtration, rinsed with acetone (2×10 mL). The solid was dried overnight at 60° C. in the vacuum oven. The title compound was obtained as a fine white solid (9.79 g, 43.8 mmol, 89% overall yield). $^1$H NMR (300 MHz, D$_2$O) δ 0.88 (s, 9H), 1.15 (d, J=6.7 Hz, 3H), 1.94-2.14 (m, 2H), 2.87-3.10 (m, 4H), 3.18-3.28 (m, 1H); $^{13}$C NMR (125 MHz, D$_2$O) 11.2, 21.2, 25.2, 33.2, 45.5, 48.3, 64.1; ES-MS 222 (M−H)

Preparation of
3-[(1-ethylcyclohexyl)amino]-1-propanesulfonic
acid (Compound NR)

For the Ritter reaction, the flask was closed with a septum and connected to a 20% NaOH scrubber. Potassium cyanide (powdered, 3.0 g, 46 mmol) was added in portions to acetic acid (10 mL). The mixture was stirred for 10 minutes at room temperature. A solution of sulfuric acid (6 mL) in acetic acid (5 mL) was added dropwise over a 10 minute period. The suspension was stirred for 10 minutes at room temperature then the 1-methyl-1-cycloheptanol (5 g, 39.0 mmol) was added dropwise. The mixture was stirred at room temperature for 22 hours then poured on ice (about 50 g). The pH of the solution was adjusted to 9 with the addition of 50% NaOH (about 70 g). The layers were separated and the aqueous layer was extracted with ether (2×20 mL). The combined organic layers were washed with saturated sodium carbonate (1×5 mL) then dried over sodium sulfate. The ether was evaporated under reduced pressure to afford a clear yellow oil (5.44 g, 90%). The oil showed to be a mixture of cis and trans formamide but what otherwise pure enough to be used as such. $^1$H NMR (400 MHz, CDCl$_3$) δ 0.81-0.90 (m, 3H), 1.19-1.60 (m, 9H), 1.68-1.71 (m, 1H), 1.78-1.84 (m, 1H), 2.02-2.06 (m, 1H), [5.03 and 5.65 (br s, 1H)], [8.15 (s) and 8.18 (d, J=12.4 Hz) for 1H]; $^{13}$C NMR (100 MHz, CDCl$_3$) δ 7.2, 7.6, 21.5, 21.9, 25.8, 25.9, 31.0, 34.7, 35.1, 36.4, 55.0, 56.9, 160.7, 163.8

A solution of NaOH (20%, 40 mL) was added to the crude 1-ethyl-1-cyclohexylformamide (5.44 g). The mixture was heated to reflux for 3 hours. The reaction was not completed by proton NMR. It was heated to reflux overnight. The reaction was still not completed. A catalytic amount of tetrabutylammonium bromide (200 mg) was added. The mixture was heated to reflux for 3 more days then cooled at room temperature. The layers were separated and the aqueous layer was extracted with MTBK (2×10 mL). The combined organic layers were washed with brine (1×5 mL), then dried over sodium sulfate and filtered. The filtrate was used as such in the next step. $^1$H NMR (400 MHz, CD$_3$OD) δ 0.84-0.88 (m, 3H), 1.30-1.55 (m, 12H); $^{13}$C NMR (100 MHz, CD$_3$OD) δ 6.2, 22.0, 25.8, 37.4, 50.3, 66.9

A solution of 1,3-propane sultone (3.2 g, 26 mmol) in toluene (6 mL) was added to the crude solution of 1-ethyl-1-cyclohexylamine in MTBK (total volume: 30 mL). The mixture was heated to reflux for 18 hours. Another portion of 1,3-propane sultone (0.7 g) in toluene (6 mL) was added. The mixture was heated to reflux for another 4 hours then it was cooled to room temperature. The solid was collected by suction filtration, rinsed with acetone (2×5 mL). The solid was dried overnight at 60° C. in the vacuum oven. The title compound was obtained as a fine white solid (3.55 g, 14.2 mmol, 36% overall yield). $^1$H NMR (500 MHz, D$_2$O) δ 0.84 (t, J=7.3 Hz, 3H), 1.18-1.24 (m, 1H), 1.39-1.49 (m, 4H), 1.54-1.60 (m, 3H), 1.73-1.81 (m, 4H), 2.06 (q, J=7.6 Hz, 2H), 2.96 (t, J=7.8 Hz, 2H), 3.10 (t, J=7.3 Hz, 2H)); $^{13}$C NMR (100 MHz, D$_2$O) 6.1, 21.2, 22.0, 23.7, 24.6, 32.0, 39.1, 48.3, 62.9; ES-MS 248 (M−H)

Preparation of 3-{[1-(4-hydroxyphenyl)-2-methyl]-
2-propylamine}-1-propanesulfonic acid (Compound
NS)

Benzyl alcohol (1.2 g, 10 mmol), the tetrabutylammonium fluoride (5 mL, 5 mmol) and 2-nitropropane (1.78 g, 20 mmol) were placed in a sealed tube and heated at 130° C. for 15 hours. The reaction was cooled and diluted with EtOAc. The resulting solution was washed with water, dried and concentrated to yield a dark oil. Chromatography over silica eluting with Hex:EA 70:30 gave a yellowish solid 1.42 g, 73%.

To a stirred solution of the nitro (800 mg, 4.12 mmol) in methanol (20 mL) was added a small spatula of Raney-Ni in water. The suspension was hydrogenated under atmospheric pressure of hydrogen for 15 hours (TLC indicates complete consumption of the starting material) then filtered on celite and concentrated under reduced pressure. The corresponding amine was used as such in the next step.

To a stirred solution of the amine (750 mg, 4.57 mmol) in THF (9 mL) was added 1,3-propane sultone (614 mg, 5.02 mmol). The reaction mixture was stirred at reflux for 4 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1.1 g (85%). $^1$H NMR (500 MHz, DMSO-$d_6$) δ 1.21 (s, 6H), 1.42-1.48 (m, 2H), 1.55-1.50 (m, 2H), 1.90-2.00 (m, 2H), 2.68 (dd, J=7.0 & 7.0 Hz, 2H), 3.00 (dd, J=7.0 & 7.0 Hz, 2H), 3.40 (dd, J=6.2 Hz, 2H). $^{13}$C NMR (125 MHz, DMSO-$d_6$) δ 23.0, 23.6, 27.1, 35.1, 41.1, 50.0, 58.8, 61.3. ES-MS 286 (M−1).

Preparation of 3-[(5-hydroxy-1,1-dimethylbutyl) amino]-1-propanesulfonic acid (Compound NT)

A mixture of the acrylate (2.7 mL, 30 mmol), nitropropane (5.4 mL, 60 mmol) and NaOMe (0.5 M, 12 mL) was stirred for 15 hours. The reaction mixture was quenched with HCl (1M) and extracted with EtOAc. The organic layer was dried and concentrated under reduced pressure. The crude was purified by column using Hex:EtOAc 80:20 to afford the desired product. 4.5 g (85% yield)

To a stirred solution of the nitro-ester (1.7 g, 10 mmol) in MeOH/THF 50 mL/5 mL was added at −10° C. in one portion LiBH$_4$ (436 mg, 20 mmol). The reaction was stirred for 2 h then another portion of LiBH$_4$ (436 mg, 20 mmol) was added. The cooling bath was removed allowing the reaction to reach the room temperature and the stirring was continued for 6 hours. The reaction was acidified with HCl (1M) and concentrated under reduced pressure to remove methanol. The reaction was extracted with EtOAc (3×100 mL). The combined organic layers were dried over Na$_2$SO$_4$ and concentrated. The crude was was purified by column on silica using Hex:EA 80:20 to 50:50 to afford the desired product (1 g, 70%) along with starting material (340 mg, 20%).

To a stirred solution of the nitro (1.47 g, 10 mmol) in methanol (20 mL) was added a spatula of Raney-Ni in water. The suspension was hydrogenated under atmospheric pressure of hydrogen for 3 hours (TLC indicates complete consumption of the starting material) then filtered on celite and concentrated under reduced pressure. The corresponding amine was used as such in the next step.

To a stirred solution of the amine (600 mg, 5.12 mmol) in THF (10 mL) was added 1,3-propane sultone (626 mg, 5.12 mmol). The reaction mixture was stirred at reflux for 4 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 770 mg (87%). $^1$H NMR (500 MHz, DMSO-$d_6$) δ 1.13 (s, 6H), 2.00 (m, 2H), 2.66 (dd, J=7.0 & 7.0 Hz, 2H), 2.75 (s, 2H), 3.10 (dd, J=7.0 & 7.0 Hz, 2H), 6.72 (d, J=8.3 Hz, 2H), 7.00 (d, J=8.3 Hz, 2H), 8.60 (bs, 2H), 9.36 (s, 1H). $^{13}$NMR (125 MHz, DMSO-$d_6$) δ 23.1, 41.2, 43.2, 49.8, 59.4, 115.7, 125.8, 132.3, 157.1. ES-MS 238 (M−1).

Preparation of 3-{[(1S)-1-(4-chlorophenyl)ethyl] amino}-1-propanesulfonic acid (Compound NU)

To a solution of (1S)-(−)-1-(4-chlorophenyl)ethylamine (5.0 g, 32.1 mmol) in Pinacolone (20 mL) and toluene (20 mL) was added 1,3-propane sultone (3.7 g, 30.6 mmol). The solution was stirred at reflux for 4 hours. The reaction mixture was cooled to room temperature. The solid was collected by filtration and was washed with acetone (2×25 mL). The solid was suspended in EtOH (60 mL). The suspension was stirred at reflux for 1 hour. The mixture was cooled to room temperature, the solid was collected by filtration, washed with acetone (2×25 mL) and dried in a vacuum oven at 50° C., affording the title compound, 7.14 g (84%). $^1$H NMR (D$_2$O, 500 MHz) δ ppm 7.39 (dd, 2H, J=2.4 Hz, 6.6 Hz), 7.32 (dd, 2H, J=2.4 Hz, 6.6 Hz), 4.30 (q, 11H, J=6.8 Hz), 3.00 (m, 1H), 2.84 (m, 1H), 2.79 (t, 2H, J=7.3 Hz), 1.94 (m, 2H), 1.53 (d, 3H, J=6.8 Hz). $^{13}$C (D$_2$O, 125 MHz) δ ppm 135.16, 134.43, 129.56, 129.36, 57.93, 48.03, 44.45, 21.50, 18.12. [α]$_D$=−22.8° (c=0.0029 in water), ES-MS 276 (M−1).

Preparation of 3-{[(1R)-1-(4-chlorophenyl)ethyl] amino}-1-propanesulfonic acid (Compound NV)

To a solution of (1R)-(−)-1-(4-chlorophenyl)ethylamine (5.07 g, 32.6 mmol) in pinacolone (20 mL) and toluene (20 mL) was added 1,3-propane sultone (3.79 g, 31.0 mmol). The solution was stirred at reflux for 4 hours. The reaction mixture was cooled to room temperature. The solid was collected by filtration and was washed with acetone (2×25 mL). The solid was suspended in EtOH (60 mL). The suspension was stirred at reflux for 1 hour. The mixture was cooled to room temperature, the solid was collected by filtration, washed with acetone (2×25 mL) and dried in a vacuum oven at 50° C., affording the title compound, 6.84 g (79%). $^1$H NMR (D$_2$O, 500 MHz) δ ppm 7.39 (dd, 2H, J=2.4 Hz, 6.8 Hz), 7.32 (dd, 2H, J=2.4 Hz, 6.3 Hz), 4.31 (q, 1H, J=6.8 Hz), 3.00 (m, 1H), 2.84 (m, 1H), 2.79 (t, 2H, J=7.3 Hz), 1.94 (m, 2H), 1.53 (d, 3H, J=6.8 Hz). $^{13}$C (D$_2$O, 125 MHz) δ ppm 135.16, 134.41, 129.57, 129.36, 57.93, 48.02, 44.44, 21.49, 18.11. [α]$_D$=+20.3° (c=0.0018 in water), ES-MS 276 (M−1).

Preparation of 3-({1-[hydroxy(4-methylphenyl)methyl]cyclohexyl}amino)-1-propanesulfonic acid (Compound NW)

To a cooled solution of sodium methoxide (0.5 M in MeOH, 80 mL, 40 mmol), nitrocyclohexane (5.0 g, 38.7 mmol) was added via syringe over a 10 minute period. The reaction mixture was stirred at room temperature for 30 minutes and recooled before p-tolualdehyde (4.6 mL, 38.7 mmol) was added. The reaction mixture was stirred at room temperature overnight. The mixture was neutralized with Amberlite IR-120 (strongly acidic). The resin was removed by filtration and washed with MeOH (2×20 mL). The filtrate was evaporated. The resulting oil was purified by flash chromatography: 98% Hexanes/EtOAc to 95% Hexanes/EtOAc, affording the desired nitro compound (1.2 g).

To a solution of the nitro compound (1.26 g, 5.0 mmol)) in MeOH was added 6M HCl (5 mL). After cooling to 5° C., zinc powder (1.63 g, 25.0 mmol) was added. The suspension was stirred at room temperature overnight. The mixture was filtered on a celite pad. The filter cake was washed with MeOH (2×20 mL). The combined filtrates were evaporated under reduced pressure to afford the corresponding amine. The amine (1.03 g, 67%) was used without further purification.

To a solution of amine (1.03 g, 4.7 mmol) in Pinacolone (9 mL) and Toluene (9 mL) was added 1,3-propane sultone (558 mg, 4.5 mmol). The solution was stirred at reflux overnight. The reaction mixture was cooled to room temperature. The solid was collected by filtration, was washed with acetone (2×15 mL) and dried in vacuo, affording the title compound, 930 mg (62%). $^1$H NMR (DMSO, 500 MHz) δ ppm 8.26 (s (broad), 1H), 8.13 (s (broad), 1H), 7.24 (d, 2H, J=8.3 Hz), 7.16 (d, 2H, J=7.8 Hz), 6.19 (s, 1H), 4.74 (s, 1H), 3.22 (m, 1H), 3.11 (m, 1H), 2.72 (m, 1H), 2.64 (m, 1H), 2.30 (s, 3H), 2.07 (m, 2H), 1.86 (m, 2H), 1.56 (m, 2H), 1.41 (m, 3H), 1.21 (m, 2H), 0.88 (m, 1H). $^{13}$C (DMSO, 125 MHz) δ ppm 148.33, 137.67, 129.07, 128.82, 73.18, 64.57, 50.11, 41.45, 28.13, 27.65, 25.23, 23.46, 22.70, 21.42, 19.85, 19.58. ES-MS 340 (M−1).

Preparation of 3-{[(1S)-1-(4-methylphenyl)ethyl]amino}propane-1-sulfonic acid (Compound NX)

To a solution of (1S)-(−)-1-(4-methylphenyl)ethylamine (5.00 g, 37.0 mmol) in Pinacolone (24 mL) and Toluene (24 mL) was added 1,3-propane sultone (4.30 g, 35.2 mmol). The solution was stirred at reflux for 4 hours. The reaction mixture was cooled to room temperature. The solid was collected by filtration and was washed with acetone (2×25 mL). The solid was suspended in EtOH (60 mL). The suspension was stirred at reflux for 1 hour. The mixture was cooled to room temperature, the solid material was collected by filtration, washed with acetone (2×25 mL) and dried in a vacuum oven at 50° C., affording the title compound, 7.72 g (85%). $^1$H NMR (D$_2$O, 500 MHz) δ ppm 7.22 (m, 4H), 4.26 (q, 1H, J=6.8 Hz), 2.97 (m, 1H), 2.80 (m, 3H), 2.22 (s, 3H), 1.92 (m, 2H), 1.53 (d, 3H, J=6.8 Hz). $^{13}$C (D$_2$O, 125 MHz) δ ppm 140.38, 132.79, 130.09, 127.71, 58.34, 48.06, 44.34, 21.50, 20.41, 18.31. [α]$_D$=−26.4° (c=0.0019 in water), ES-MS 256 (M−1).

Preparation of 3-{[(1R)-1-(4-methylphenyl)ethyl]amino}propane-1-sulfonic acid (Compound NY)

To a solution of (1R)-(+)-1-(4-methylphenyl)ethylamine (5.30 g, 39.1 mmol) in pinacolone (25 mL) and toluene (25 mL) was added 1,3-propane sultone (4.55 g, 37.3 mmol). The solution was stirred at reflux for 4 hours. The reaction mixture was cooled to room temperature. The solid was collected by filtration and was washed with acetone (2×25 mL). The solid was suspended in EtOH (60 mL). The suspension was stirred at reflux for 1 hour. The mixture was cooled to room temperature, the solid material was collected by filtration, washed with acetone (2×25 mL) and dried in a vacuum oven at 50° C., affording the title compound, 7.65 g (80%). $^1$H NMR (D$_2$O, 500 MHz) δ ppm 7.21 (m, 4H), 4.25 (q, 1H, J=6.8 Hz), 2.96 (m, 1H), 2.79 (m, 3H), 2.22 (s, 3H), 1.92 (m, 2H), 1.52 (d, 3H, J=6.8 Hz). $^{13}$C (D$_2$O, 125 MHz) δ ppm 140.40, 132.79, 130.10, 127.72, 58.34, 48.05, 44.34, 21.49, 20.39, 18.30. [α]$_D$=+28.8° (c=0.0025 in water), ES-MS 256 (M−1).

Preparation of 3-[(cyclopropylmethyl)amino]-1-propanesulfonic acid (Compound NZ)

To a solution of cyclopropanemethylamine (5.12 g, 72.0 mmol) in Pinacolone (40 mL) and Toluene (40 mL) was added 1,3-propane sultone (8.36 g, 68.7 mmol). The solution was stirred at reflux for 4 hours. The product formed a sticky paste in the bottom of the flask. The reaction mixture was cooled to room temperature. The supernatant was removed. The residue was dissolved in a minimum of MeOH with heating. The solution was poured in acetone (300 mL) to precipitate the product. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×15 mL) and dried in a vacuum oven at 50° C., affording the title compound, 3.48 g (27%). $^1$H NMR (D$_2$O, 500 MHz) δ ppm 3.04 (t, 2H, J=7.8 Hz), 2.81 (m, 4H), 1.96 (m, 2H), 0.90 (m, 1H), 0.51 (m, 2H), 0.18 (m, 2H). $^{13}$C (D$_2$O, 125 MHz) δ ppm 52.82, 48.21, 46.01, 21.75, 7.09, 3.83. ES-MS 192 (M−1).

Preparation of 3-{[(1R)-1-(3-methoxyphenyl)ethyl]amino}propane-1-sulfonic acid (Compound OA)

To a solution of (1S)-(−)-1-(3-methoxyphenyl)ethylamine (5.00 g, 33.1 mmol) in pinacolone (20 mL) and toluene (20 mL) was added 1,3-propane sultone (3.84 g, 31.5 mmol). The solution was stirred at reflux for 4 hours. The product formed a sticky paste in the bottom of the flask. The reaction mixture was cooled to room temperature. The supernatant was removed. The residue was dissolved in MeOH with heating. Acetone (3×50 mL) was added to precipitate the product. The solid material was collected by filtration and washed with acetone (2×20 mL). The solid was suspended in EtOH (60 mL). The suspension was stirred at reflux for 1 hour. The mixture was cooled to room temperature, the solid material was collected by filtration, washed with acetone (2×25 mL) and dried in a vacuum oven at 50° C., affording the title compound, 3.49 g (41%). $^1$H NMR (D$_2$O, 500 MHz) δ ppm 7.27 (t, 1H, J=8.0 Hz), 6.90 (m, 3H), 4.22 (q, 1H, J=6.7 Hz), 3.68 (s, 3H), 2.93 (m, 1H), 2.77 (m, 3H), 1.90 (m, 2H), 1.49 (d, 3H, J=6.7 Hz). $^{13}$C (D$_2$O, 125 MHz) δ ppm 159.41, 137.34, 130.81, 120.10, 115.24, 113.27, 58.65, 55.72, 48.18, 44.62, 21.76, 18.65. [α]$_D$=−23.0° (c=0.0019 in water), ES-MS 272 (M−1).

Preparation of 3-{[(1S)-1-phenylpropyl]amino}-1-propanesulfonic acid (Compound OB)

To a solution of (S)-(−)-1-phenylpropylamine (10.0 g, 74.1 mmol) in pinacolone (40 mL) and toluene (40 mL) was added 1,3-propane sultone (8.60 g, 70.6 mmol). The solution was stirred at reflux for 4 hours. The reaction mixture was cooled to room temperature. The solid material was collected by filtration and washed with acetone (2×25 mL). The solid was suspended in EtOH (80 mL). The suspension was stirred at reflux for 1 hour. The mixture was cooled to room temperature, the solid material was collected by filtration, washed with acetone (2×25 mL) and dried in a vacuum oven at 50° C., affording the title compound, 14.38 g (79%). $^1$H NMR (D$_2$O, 500 MHz) δ ppm 7.32 (m, 5H), 4.00 (dd, 1H, J=4.4 Hz, 10.7 Hz), 2.91 (m, 1H), 2.74 (m, 3H), 1.90 (m, 4H), 0.62 (t, 3H, J=7.3 Hz). $^{13}$C (D$_2$O, 125 MHz) δ ppm 133.85, 129.89, 129.56, 128.41, 64.46, 48.01, 44.48, 25.77, 21.40, 9.46. [α]$_D$=−15.6° (c=0.00077 in water), ES-MS 256 (M−1).

Preparation of 3-{[(1R)-(1-naphthyl)ethyl]amino}-1-propanesulfonic acid (Compound OD)

To a solution of (R)-(+)-1-(naphthyl)ethylamine (5.02 g, 29.3 mmol) in pinacolone (15 mL) and toluene (15 mL) was added 1,3-propane sultone (3.40 g, 27.9 mmol). The solution was stirred at reflux for 4 hours. The reaction mixture was cooled to room temperature. The solid material was collected by filtration and washed with acetone (2×25 mL). The solid was suspended in EtOH (40 mL). The suspension was stirred at reflux for 1 hour. The mixture was cooled to room temperature, the solid material was collected by filtration, washed with acetone (2×25 mL) and dried in a vacuum oven at 50° C., affording the title compound, 6.46 g (79%). $^1$H NMR (DMSO, 500 MHz) δ ppm 8.21 (d, 1H, J=8.3 Hz), 7.98 (m, 2H), 7.73 (d, 1H, J=7.3 Hz), 7.59 (m, 3H), 5.27 (m, 1H), 3.15 (m, 1H), 2.95 (m, 1H), 2.55 (m, 2H), 1.96 (m, 2H), 1.59 (d, 3H, J=6.8 Hz). $^{13}$C (DMSO, 125 MHz) δ ppm 134.86, 134.05, 130.84, 129.67, 129.57, 127.62, 126.92, 126.25, 124.34, 123.35, 52.55, 49.96, 46.21, 22.64, 20.38. $[\alpha]_D$=−45.5° (c=0.0010 in water), ES-MS 292 (M−1).

Preparation of 3-{[(1S)-(1-naphthyl)ethyl]amino}-1-propanesulfonic acid (Compound OE)

To a solution of (S)-(−)-1-(naphthyl)ethylamine (5.00 g, 29.2 mmol) in pinacolone (15 mL) and toluene (15 mL) was added 1,3-propane sultone (3.39 g, 27.8 mmol). The solution was stirred at reflux for 4 hours. The reaction mixture was cooled to room temperature. The solid material was collected by filtration and washed with acetone (2×25 mL). The solid was suspended in EtOH (40 mL). The suspension was stirred at reflux for 1 hour. The mixture was cooled to room temperature, the solid material was collected by filtration, washed with acetone (2×25 mL) and dried in a vacuum oven at 50° C., affording the title compound, 6.34 g (78%). $^1$H NMR (DMSO, 500 MHz) δ ppm 8.21 (d, 1H, J=8.3 Hz), 7.97 (m, 2H), 7.72 (d, 1H, J=7.3 Hz), 7.59 (m, 3H), 5.27 (m, 1H), 3.15 (m, 1H), 2.95 (m, 1H), 2.61 (m, 2H), 1.96 (m, 2H), 1.59 (d, 3H, J=6.8 Hz). $^{13}$C (DMSO, 125 MHz) δ ppm 134.85, 134.06, 130.86, 129.68, 129.58, 127.64, 126.92, 126.26, 124.35, 123.36, 52.55, 49.92, 46.20, 22.63, 20.36. $[\alpha]_D$=+47.3° (c=0.00047 in water), ES-MS 292 (M−1).

Preparation of 3-{[4-methoxy-1,1-dimethylbutyl]amino}-1-propanesulfonic acid (Compound OF)

To a stirred solution of the alcohol (500 mg, 3.40 mmol) in DMF (6 mL) was added iodomethane (423 μL, 6.80 mmol) followed by NaH (163 mg, 6.80 mmol). The reaction mixture was stirred for 15 hours then diluted with HCl (1M) and with EtOAc. The organic layer was washed with HCl (1M) then concentrated under high vacuum. The crude was purified by column using Hex:EtOAc 80:20 to obtain 450 mg of the desired product (82% yield).

To a stirred solution of the nitro (400 mg, 2.45 mmol) in methanol (5 mL) was added a small spatula of Raney-Ni in water. The suspension was hydrogenated under atmospheric pressure of hydrogen for 3 hours (TLC indicates complete consumption of the starting material) then filtered on pre-washed celite and concentrated under reduced pressure. The crude amine was used as such in the next step.

To the crude amine (300 mg, 2.29 mmol) in solution in THF (5 mL) was added 1,3-sultone (300 mg, 2.52 mmol) and the mixture was heated at reflux for 15 hours. The suspension was cooled down and filtered. The solid was dried under high vacuum to afford 400 mg of the corresponding homotaurin as a white solid (69% yield). $^1$H NMR (500 MHz, DMSO-d$_6$) δ ppm 1.21 (s, 6H), 1.56 (m, 4H), 1.95 (m, 2H), 2.65 (m, 2H), 3.00 (m, 2H), 3.23 (s, 3H), 3.32 (m, 2H), 8.53 (bs, 2H). $^{13}$C NMR (125 MHz, DMSO-d$_6$) δ ppm 22.93, 23.43, 23.85, 35.23, 41.16, 50.10, 58.52, 58.75, 72.28. ES-MS 328 (M−1).

Preparation of 3-[(1,1-dimethyl-3-oxobutyl)amino]-1-propanesulfonic acid (Compound OG)

A mixture of mesityl oxide (4 g, 40 mmol) and aq. NH$_3$ was stirred for 15 hours then diluted with EtOAc. Nitrogen was blown through the solution to remove the excess of ammonia. Water was added and the two phases were separated. The aqueous phase was extracted with CH$_2$Cl$_2$ and the two phases were combined, dried (Na$_2$SO$_4$) and concentrated under rotavap and pump vacuum.

The crude amine was dissolved in THF (20 mL) to which was added 1,3-propane sultone (2.2 g, 13.13 mmol). The reaction mixture was stirred at reflux for 6 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1 g (10%, the low yield is due to partial solubility of the final product in EtOH and Et$_2$O). $^1$H NMR (500 MHz, D$_2$O) δ 1.27 (s, 6H), 1.99 (m, 2H), 2.12 (s, 3H), 2.88 (m, 2H), 2.92 (s, 2H), 3.03 (m, 2H), 4.65 (s, 2H). $^{13}$NMR (125 MHz, D$_2$O) δ 21.99, 22.58, 23.61, 30.72, 40.30, 47.33, 47.98, 58.02, 110.00. ES-MS 236 (M−1).

Preparation of 3-{[4-(benzyloxy)-1,1-dimethylbutyl]amino}-1-propanesulfonic acid (Compound OH)

To a stirred solution of the alcohol (500 mg, 3.40 mmol) in DMF (5 mL) was added benzyl bromide (456 uL, 3.74 mmol) followed by NaH (106 mg, 4.42 mmol). The reaction mixture was stirred for 15 hours then diluted with HCl (1M) and EtOAc. The organic layer was washed with HCl (1M) then concentrated under high vacuum. The crude product was purified by column using Hex:EtOAc 90:10 to obtain 605 mg of the desired product (74% yield).

To a stirred solution of the nitro (237 mg, 1.2 mmol) in ethanol (8 mL) was added HCl (6N) (2 mL) followed by Zn-dust. The suspension was stirred for 10 minutes, then filtered and concentrated. The crude reaction mixture was diluted with EtOAc and neutralized with saturated K$_2$CO$_3$. The organic layer was washed with water, dried over Na$_2$SO$_4$ and concentrated. The crude amine was used as such in the next step.

To the crude amine (500 mg, 2.41 mmol) in solution in THF (5 mL) was added 1,3-sultone (234 mg, 2.65 mmol) and the mixture was heated at reflux of THF for 15 hours. The suspension was cooled down and filtered. The solid was dried to afford 300 mg of the homotaurine as a white solid (38% yield). $^1$H NMR (500 MHz, DMSO-d$_6$) δ 1.21 (s, 6H), 1.60 (m, 4H), 1.95 (m, 2H), 2.65 (m, 2H), 3.00 (m, 2H), 3.42 (m, 2H), 4.46 (s, 2H), 7.25-7.38 (m, 5H), 8.48 (bs, 2H). $^{13}$C NMR (125 MHz, DMSO-d$_6$) δ 22.93, 23.43, 24.04, 35.29, 41.18, 50.08, 58.79, 70.07, 72.56, 128.09, 128.19, 128.96, 139.23. ES-MS 328 (M−1).

Preparation of 3-piperidinylmethanesulfonic acid (Compound OI)

A solution of 3-hydroxymethylpiperidine (15 g, 129 mmol) in anhydrous CHCl$_3$ (120 mL) was saturated with HCl(g) and then treated dropwise at reflux with SOCl$_2$ (24 mL). The resulting mixture was refluxed for 1 hour and concentrated to yield a white solid, which was collected by filtration and washed with Et$_2$O. It was then dissolved in EtOH and then recrystallized in EtOH/Et$_2$O to obtain 22 g of the desired chloride (96% yield).

A solution of the chloride (21.5 g, 121 mmol) in water (30 mL) was added dropwise to a refluxed solution of N$_2$SO$_3$ (30.41 g, 242 mmol) in water (120 mL). After the end of the addition, the reaction was stirred at reflux for 60 minutes then cooled down and concentrated under reduced pressure. 75 mL of HCl (conc) were added to dissolve the aminosulfonic acid and precipitate the inorganic salts which were removed by filtration. The filtrate was concentrated, then ethanol was added to cause amino sulfonic acid to appear as white solid which was collected by filtration. It was washed with EtOH and Et$_2$O, then dried under high vacuum to obtain 18 g of a white solid (88% yield). $^1$H NMR (500 MHz, D$_2$O) δ 1.25 (ddd, J=12.0, 9.0 and 3.0 Hz, 1H), 1.55-1.65 (m, 1H), 1.82 (m, 1H), 1.90 (m, 1H), 2.10-2.20 (m, 1H), 2.68 (m, 1H), 2.72-2.86 (m, 3H), 3.25 (dd, J=12.0 and 3.0 Hz, 1H), 3.50 (dd, J=12.0 & 3.0 Hz, 1H), 4.69 (s, 2H). $^{13}$NMR (125 MHz, D$_2$O) δ 21.78, 28.08, 30.67, 44.05, 47.75, 54.07. ES-MS 178 (M–1).

Preparation of 3-[3-(hydroxymethyl)piperidin-1-yl]-1-propanesulfonic acid (Compound OJ)

To a stirred solution of the 3-piperidinemethanol (1.15 g, 10 mmol) in THF (20 mL) was added 1,3-propane sultone (1.2 g, 10 mmol). The reaction mixture was stirred at reflux for 15 hours then cooled to room temperature. The solid was collected by filtration and was washed with THF. The solid was suspended in EtOH (20 mL) and stirred at reflux for 1 hour. The suspension was then cooled to room temperature. The solid was collected by filtration, washed with ethanol and dried under high vacuum to afford the title compound, 2.12 g (90%). $^1$H NMR (500 MHz, DMSO-d$_6$) δ 1.12 (m, 1H), 1.50-1.85 (m, 5H), 1.55-1.75 (m, 2H), 1.80-1.95 (m, 2H), 1.992-2.10 (m, 2H), 2.60 (m, 1H), 2.70-2.80 (m, 1H), 2.85 (t, J=9.0 Hz, 2H), 3.15 (t, J=9.0 Hz, 2H), 3.35-3.50 (m, 2H), 4.65 (s, 1H). $^{13}$NMR (125 MHz, DMSO-d$_6$) δ 19.58, 22.43, 24.34, 36.84, 48.01, 53.18, 55.10, 56.06, 63.37. ES-MS 236 (M–1).

Preparation of 3-[2-(2-hydroxyethyl)piperidin-1-yl]-1-propanesulfonic acid (Compound OK)

To a stirred solution of the 2-piperidinethanol (1.3 g, 10 mmol) in THF (20 mL) was added 1,3-propane sultone (1.2 g, 10 mmol). The reaction mixture was stirred at reflux for 15 hours then cooled to room temperature. The solid was collected by filtration and was washed with THF. The solid was suspended in EtOH (20 mL) and stirred at reflux for 1 hour. The suspension was then cooled to room temperature. The solid was collected by filtration, washed with ethanol and dried under high vacuum to afford the title compound, 2.10 g (84%). $^1$H NMR (500 MHz, DMSO-d$_6$) δ 1.42 (m, 2H), 1.50-1.85 (m, 5H), 1.90-2.10 (m, 3H), 2.95 (m, 1H), 3.10-3.22 (m, 3H), 3.30-3.70 (m, 3H), 4.63 (s, 11H). $^{13}$NMR (125 MHz, DMSO-d$_6$) δ 19.03, 20.80, 22.37, 27.66, 32.20, 49.35, 51.49, 52.38, 57.76, 61.16. ES-MS 250 (M–1).

Preparation of (S)-3-[1-(4-bromophenyl)ethylamino]-1-propanesulfonic acid (Compound OL)

A solution of 1,3-propane sultone (1M, 5 mL) in toluene was added to a solution of (S)-(–)-1-(4-bromophenyl)ethylamine (1 g, 5.00 mmol) in MTBK (5 mL). The mixture was heated to reflux for 4 hours then cooled to room temperature. The solid was collected by suction filtration, rinsed with acetone (2×5 mL). The solid was dried 18 hours at 60° C. in the vacuum oven. The title compound was obtained as a fine white solid (1.12 g, 3.48 mmol, 70%). $^1$H NMR (500 MHz, DMSO-d$_6$) δ 1.50 (d, J=6.8 Hz, 3H), 1.93 (qt, J=6.6 Hz, 2H), 2.61 (t, J=6.6 Hz, 2H), 2.79 (qt, J=6.3 Hz, 2H), 3.01 (qt, J=6.3 Hz, 2H), 4.38 (q, J=6.7 Hz, 1H), 7.45 (d, J=8.8 Hz, 1H), 7.67 (d, J=8.8 Hz, 2H), 9.06 (br s, 11H), 9.20 (br s, 1H); $^{13}$C NMR (125 MHz, DMSO-d$_6$) 19.0, 21.9, 45.1, 49.1, 56.1, 122.3, 129.9, 131.9, 136.6; ES-MS 320-322 (M–H); [α]$_D$=–34° (c=0.00401, 0.1 N NaOH).

Preparation of (S)-3-[1-(4-nitrophenyl)ethylamino]-1-propanesulfonic acid (Compound OM)

A solution of 1,3-propane sultone (1M, 5.40 mL) in toluene was added to a solution of (S)-(–)-1-(4-nitrophenyl)ethylamine (0.895 g, 5.39 mmol) in MTBK (5 mL). The mixture was heated to reflux for 4 hours then cooled to room temperature. The solid was collected by suction filtration, rinsed with acetone (2×5 mL). The solid was dried 18 hours at 60° C. in the vacuum oven. The title compound was obtained as a fine white solid (0.73 g, 2.53 mmol, 47%). $^1$H NMR (500 MHz, DMSO-d$_6$) δ 1.55 (d, J=6.8 Hz, 3H), 1.95 (qt, J=6.6 Hz, 2H), 2.63 (t, J=6.6 Hz, 2H), 2.84 (qt, J=6.3 Hz, 2H), 3.07 (qt, J=6.2 Hz, 2H), 4.58 (q, J=6.4 Hz, 1H), 7.78 (d, J=8.8 Hz, 1H), 8.33 (d, J=8.8 Hz, 2H), 9.23 (br s, 1H), 9.38 (br s, 1H); $^{13}$C NMR (125 MHz, DMSO-d$_6$) 18.9, 21.9, 45.3, 49.1, 56.0, 124.1, 129.1, 144.5, 147.8; ES-MS 287 (M–H); [α]$_D$=–37°, c=0.0043, 0.1 N NaOH Preparation of 3-(1-Carbamoyl-cyclohexylamino)-1-propanesulfonic acid (Compound ON)

To a 250 mL 1 neck flask containing 30% NH$_4$OH (120 mL) was added NaCN (15.34 g, 0.31 mol) and NH$_4$Cl (19.75 g, 0.37 mol) with vigorous stirring. The corresponding ketone was added dropwise within 20 minutes at room temperature. The mixture was stirred for 3 days at room temperature follwed by extraction with dichloromehtnae (50 mL). The organic layer was separated and dried over anhydrous sodium sulfate for 2 hours. The sodium sulfate was removed by filtration, the solvent was removed under reduced pressure to yield the crude aminonitrile. The desired material was obtained as a light brown oil (90% crude yield). $^1$H NMR (500 MHz, CD$_3$OD-d6) δ 1.23-1.28 (m, 1H), 1.43-1.49 (m, 2H), 1.51-1.60 (m, 2H), 1.69-1.73 (m, 1H), 1.78-1.83 (m, 2H), 2.02 (br s, 1H), 2.05 (br s, 1H); $^{13}$C NMR (125 MHz, CD$_3$OD-d6) 24.2, 25.9, 38.9, 52.9, 124.9; FT-IR 2221 cm$^{-1}$ (CN).

To 10 g of concentrated sulfuric acid stirred in an ice cooled water bath was added dropwise a solution of the aminonitrille (41 mmol) in 30 mL CH$_2$Cl$_2$, maintaining the internal temperature at 15° C. Then, the bath was removed and the mixture heated to 40° C. for 1 hour. The mixture was cooled in ac ice bath and poured onto 200 g of crushed ice. The mixture was made pH 7-8 with 28% aqueous NH$_3$ and extracted with EtOAc (3×100 mL). The extracts were collected, dried (MgSO$_4$), and evaporated to dryness". The crude solid was recrystallized in EtOAc/Hex. The desired material was obtained as a white foamy solid 0.89 g, 6.26 mmol, 43%. $^1$H NMR (500 MHz, DMSO-d$_6$) δ 1.12-1.23 (m, 1H), 1.27 (br s, 1H), 1.30 (br s, 1H), 1.40-1.45 (m, 2H), 1.49-1.27(m, 3H), 1.67-1.72 (m, 4H), 7.34 (br s, 1H), 6.82 (br s, 1H); $^{13}$C NMR (125 MHz, DMSO-d$_6$) 21.0, 25.4, 34.7, 56.4, 180.3.

A solution of 1,3-propane sultone (1M, 6.20 mL) in toluene was added to a solution of 1-aminocyclohexanecarboxamide (0.880 g, 6.19 mmol) in MTBK (5 mL). The mixture was heated to reflux for 4 hours then cooled to room temperature. The solid was collected by suction filtration, rinsed with acetone (2×5 mL). The solid was dried 18 hours at 60° C. in the vacuum oven (0.79 g). The solid was recrystallized in ethanol (5 mL) and water (5 mL). After drying, the title compound was obtained as a fine white solid (0.4477 g, 1.69 mmol, 27%). $^1$H NMR (500 MHz, DMSO-d$_6$) δ 1.42 (br s, 4H), 1.63 (br s, 2H), 1.67-1.72 (m, 2H), 1.99 (qt, J=6.6 Hz, 2H), 2.06-2.10 (m, 2H), 2.63 (t, J=6.6 Hz, 2H), 2.93 (br s, 2H), 7.69 (s, 1H), 7.80 (s, 1H), 8.77 (br s, 2H); $^{13}$C NMR (125 MHz, DMSO-d$_6$) 20.7, 22.1, 24.1, 29.9, 42.5, 49.0, 64.4, 170.5; ES-MS 263 (M−H).

Preparation of 3-{[(1R)-1-(2-naphthyl)ethyl]amino}-1-propanesulfonic acid (Compound OO)

To a solution of (R)-(+)-1-(2-naphthyl)ethylamine (5.00 g, 29.2 mmol) in pinacolone (20 mL) and toluene (15 mL) was added 1,3-propane sultone (3.39 g, 27.8 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 7.36 g (90%). $^1$H NMR (DMSO, 500 MHz) δ ppm 9.15 (s (broad), 1H), 8.01 (m, 2H), 7.93 (m, 2H), 7.62 (d, 1H, J=8.3 Hz), 7.56 (m, 2H), 4.52 (m, 1H), 3.03 (m, 1H), 2.81 (m, 1H), 2.60 (m, 2H), 1.94 (m, 2H), 1.60 (d, 3H, J=6.8 Hz). $^{13}$C (DMSO, 125 MHz) δ ppm 135.30, 133.60, 133.34, 129.51, 128.67, 128.37, 127.91, 127.45, 125.22, 57.67, 49.92, 45.91, 22.56, 19.87. $[\alpha]_D$=+15.2° (c=0.00084 in water), ES-MS 292 (M−1).

Preparation of 3-{[(1SR)-1-(2-naphthyl)ethyl]amino}-1-propanesulfonic acid (Compound OP)

To a solution of (S)-(−)-1-(2-naphthyl)ethylamine (5.00 g, 29.2 mmol) in pinacolone (20 mL) and toluene (15 mL) was added 1,3-propane sultone (3.39 g, 27.8 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 7.62 g (93%). $^1$H NMR (DMSO, 500 MHz) δ ppm 9.20 (s (broad), 1H), 8.01 (m, 2H), 7.95 (m, 2H), 7.62 (d, 1H, J=8.3 Hz), 7.56 (m, 2H), 4.52 (m, 1H), 3.04 (m, 1H), 2.81 (m, 1H), 2.61 (m, 2H), 1.93 (m, 2H), 1.60 (d, 3H, J=6.8 Hz). $^{13}$C (DMSO, 125 MHz) δ ppm 135.30, 133.60, 133.32, 129.51, 128.65, 128.37, 127.90, 127.46, 125.20, 57.64, 49.95, 45.94, 22.55, 19.85. $[\alpha]_D$=−17.3° (c=0.00052 in water), ES-MS 292 (M−1).

Preparation of (R)-(−)-3-(1-methylpropylamino)-1-propanesulfonic acid (Compound OQ)

A solution of 1,3-propane sultone (1.83 g, 15.0 mmol) in toluene (15 mL) was added to a solution of (R)-(−)-2-butylamine (1 g, 13.7 mmol) in acetone (10 mL). The mixture was heated to reflux for 24 hours. The mixture was cooled to room temperature, and the solid was collected by suction filtration, rinsed with acetone (2×5 mL) and dried under vacuum (2.59 g). The solid was suspended in ethanol (17 mL) and the suspension was heated to reflux. Water (0.1 mL) was then added to afford a clear solution. The mixture was slowly cooled to room teperature and the solid was collected by suction filtration, rinsed with acetone (2×5 mL) and dried 2 hours at 60° C. in the vacuum oven. The title compound was obtained as a fine white solid (2.39 g, 12.2 mmol, 89%). $^1$H NMR (500 MHz, D$_2$O) δ 0.82 (t, J=7.6 Hz, 3H), 1.14 (d, J=6.3 Hz, 3H), 1.39-1.46 (m, 1H), 1.59-1.66 (m, 1H), 1.96 (q, J=7.7 Hz, 2H), 2.86 (t, J=7.3 Hz, 2H), 3.00-3.12 (m, 3H); $^{13}$C NMR (125 MHz, D$_2$O) δ 8.8, 15.0, 21.6, 25.7, 43.5, 48.1, 56.0; ES-MS 194 (M−H); $[\alpha]_D$=−1.2 (c=0.0157, H$_2$O)

Preparation of 3-{[(1R)-1-phenylpropyl]amino}-1-propanesulfonic acid (Compound OR)

To a solution of (R)-(+)-1-phenylpropylamine (10.0 g, 74.1 mmol) in pinacolone (40 mL) and toluene (40 mL) was added 1,3-propane sultone (8.60 g, 70.4 mmol). The solution was stirred at reflux for 4 hours. The reaction mixture was cooled to room temperature. The solid material was collected by filtration and washed with acetone (2×25 mL). The solid was suspended in EtOH (80 mL). The suspension was stirred at reflux for 1 hour. The mixture was cooled to room temperature, the solid material was collected by filtration, washed with acetone (2×25 mL) and dried in a vacuum oven at 50° C., affording the title compound, 13.11 g (72%). $^1$H NMR (D$_2$O, 500 MHz) δ ppm 7.31 (m, 5H), 4.00 (dd, 1H, J=4.7 Hz, 10.5 Hz), 2.89 (m, 1H), 2.74 (m, 3H), 1.89 (m, 4H), 0.62 (t, 3H, J=7.3 Hz). $^{13}$C (D$_2$O, 125 MHz) δ ppm 133.73, 129.80, 129.47, 128.32, 64.60, 48.21, 44.70, 26.07, 21.72, 9.83. $[\alpha]_D$=+15.4° (c=0.00081 in water), ES-MS 256 (M−1).

Preparation of 3-(1-Carbamoyl-1-methylamino)-1-propanesulfonic acid (Compound OS)

To a 250 mL 1 neck flask containing 30% NH$_4$OH (120 mL) was added NaCN (15.34 g, 0.31 mol) and NH$_4$Cl (19.75 g, 0.37 mol) with vigorous stirring. The corresponding ketone was added dropwise within 20 minutes at room temperature. The mixture was stirred for 3 days at room temperature follwed by extraction with dichloromehtnae (50 mL). The organic layer was separated and dried over anhydrous sodium sulfate for 2 hours. The sodium sulfate was removed by filtration, the solvent was removed under reduced pressure to yield the crude aminonitrile. The desired material was obtained as an light brown oil (clear oil, 80% crude yield). Used as such. $^1$H NMR (500 MHz, DMSO-d$_6$) δ 1.35 (s, 6H), 2.56 (s, 2H); $^{13}$C NMR (125 MHz, DMSO-d$_6$) 28.94, 45.7, 125.9

To 10 g of concentrated sulfuric acid stirred in an ice cooled water bath was added dropwise a solution of the aminonitrille (41 mmol) in 30 mL CH$_2$Cl$_2$, maintaining the internal temperature at 15° C. Then the bath was removed and the mixture heated to 40° C. for 1 hour. The mixture was cooled in an ice bath and poured onto 200 g of crushed ice. The mixture was made pH 7-8 with 28% aqueous NH$_3$ and extracted with EtOAc (3×100 mL). The extracts were collected, dried (MgSO$_4$), and evaporated to dryness. The crude solid was recrystallized in EtOAc/Hex. The desired material was obtained as a white foamy solid 0.4462 g, 4.37 mmol, 4%. $^1$H NMR (500 MHz, DMSO-d$_6$) δ 1.15 (s, 6H), 1.82 (br s, 2H), 6.84 (br s, 1H), 7.26 (br s, 1H); $^{13}$C NMR (125 MHz, DMSO-d$_6$) 28.7, 54.1, 108.1

A solution of 1,3-propane sultone (1M, 4.30 mL) in toluene was added to a solution of 2-amino-2-methylpropaneamide (0.4350 g, 4.26 mmol) in MTBK (6 mL) and ethanol (0.5 mL). The mixture was heated to reflux for 4 hours then cooled to room temperature. The solid was collected by suction filtration, rinsed with acetone (2×5 mL). The solid was dried 18 hours at 60° C. in the vacuum oven (0.56 g). The solid was recrystallizeed in ethanol (5 mL) and water (5 mL). After drying, the title compound was obtained as a fine white solid (0.3500 g, 1.56 mmol, 37%). $^1$H NMR (500 MHz, D$_2$O) δ

1.47 (s, 6H), 1.99 (qt, J=7.6 Hz, 2H), 2.87 (t, J=7.3 Hz, 2H), 3.01 (t, J=7.8 Hz, 2H); $^{13}$C NMR (125 MHz, D$_2$O) 21.7, 21.9, 42.0, 48.0, 62.5, 174.6; ES-MS 223 (M–H)

Preparation of 3-(1-Carbamoyl-1-cyclopentylamino)-1-propanesulfonic acid (Compound OT)

To a 250 mL 1 neck flask containing 30% NH$_4$OH (120 mL) was added NaCN (15.34 g, 0.31 mol) and NH$_4$Cl (19.75 g, 0.37 mol) with vigorous stirring. The corresponding ketone was added dropwise within 20 minutes at room temperature. The mixture was stirred for 3 days at room temperature follwed by extraction with dichloromehtnae (50 mL). The organic layer was separated and dried over anhydrous sodium sulfate for 2 hours. The sodium sulfate was removed by filtration, the solvent was removed under reduced pressure to yield the crude aminonitrile. The desired material was obtained as colorless oil after distillation under reduced pressure (14.03 g, 127 mmol, 51% yield). Used as such. $^1$H NMR (500 MHz, DMSO-d$_6$) δ 1.61-1.71 (m, 2H), 1.72-1.83(m, 4H), 1.8-1.94 (m, 2H), 2.42 (s, 2H); $^{13}$C NMR (125 MHz, DMSO-d$_6$) 23.0, 40.0, 54.2, 125.7

To 10 g of concentrated sulfuric acid stirred in an ice cooled water bath was added dropwise a solution of the aminonitrile (41 mmol) in 30 mL CH$_2$Cl$_2$, maintaining the internal temperature at 15° C. Then the bath was removed and the mixture heated to 40° C. for 1 hour. The mixture was cooled in ac ice bath and poured onto 200 g of crushed ice. The mixture was made pH 7-8 with 28% aqueous NH$_3$ and extracted with EtOAc (3×100 mL). The extracts were collected, dried (MgSO$_4$), and evaporated to dryness. The crude solid was recrystallized in EtOAc/Hex. The desired material was obtained as a white solid 1.36 g, 10.6 mmol, 27%. $^1$H NMR (500 MHz, DMSO-d$_6$) δ 1.37-1.41 (m, 2H), 1.57-1.63 (m, 2H), 1.68-1.76 (m, 2H), 1.78 (br s, 2H), 1.88-1.94 (m, 2H), 6.91 (br s, 1H), 7.40 (br s, 1H); $^{13}$C NMR (125 MHz, DMSO-d$_6$) 24.2, 39.3, 64.7, 180.0.

A solution of 1,3-propane sultone (1M, 6.30 mL) in toluene was added to a solution of 2-amino-2-methylpropaneamide (0.4350 g, 4.26 mmol) in MTBK (7 mL) and ethanol (0.5 mL). The mixture was heated to reflux for 4 hours then cooled to room temperature. The solid was collected by suction filtration, rinsed with acetone (2×5 mL). The solid was dried 18 hours at 60° C. in the vacuum oven (0.74 g). The solid was recrystallized in ethanol (5 mL) and water (5 mL). After drying, the title compound was obtained as a fine white solid (0.39 g, 2.80 mmol, 45%). $^1$H NMR (500 MHz, D$_2$O) δ 1.72-1.76 (m, 4H), 1.91-2.02 (m, 4H), 2.08-2.14- (m, 2H), 2.86 (t, J=7.3 Hz, 2H), 3.00 (t, J=7.6 Hz, 2H); $^{13}$C NMR (125 MHz, D$_2$O) 22.0, 24.6, 34.8, 43.3, 48.0, 72.4, 174.8; ES-MS 249 (M–H)

Preparation of 3-(1-Carbamoyl-cycloheptylamino)-1-propanesulfonic acid (Compound OU)

To a 250 mL 1 neck flask containing 30% NH$_4$OH (120 mL) was added NaCN (15.34 g, 0.31 mol) and NH$_4$Cl (19.75 g, 0.37 mol) with vigorous stirring. The corresponding ketone was added dropwise within 20 minutes at room temperature. The mixture was stirred for 3 days at room temperature follwed by extraction with dichloromehtnae (50 mL). The organic layer was separated and dried over anhydrous sodium sulfate for 2 hours. The sodium sulfate was removed by filtration, the solvent was removed under reduced pressure to yield the crude aminonitrile. The desired material was obtained as light yellow oil (33.09 g, 239 mmol, 96% crude yield). An attempt to purify it further by distillation under reduced pressure was not effective. The material obtained after the distillation was less pure than the crude product by was used as such in the nest step. $^1$H NMR (500 MHz, DMSO-d$_6$) δ 1.41-67 (m, 10H), 1.91-95 (m, 2H), 2.47 (s, 2H); $^{13}$C NMR (125 MHz, DMSO-d$_6$) 21.8, 27.4, 40.1, 53.8, 125.8

To 10 g of concentrated sulfuric acid stirred in an ice cooled water bath was added dropwise a solution of the aminonitrille (41 mmol) in 30 mL CH$_2$Cl$_2$, maintaining the internal temperature at 15° C. Then the bath was removed and the mixture heated to 40° C. for 1 hour. The mixture was cooled in ac ice bath and poured onto 200 g of crushed ice. The mixture was made pH 7-8 with 28% aqueous NH$_3$ and extracted with EtOAc (3×100 mL). The extracts were collected, dried (MgSO$_4$), and evaporated to dryness. The crude solid was recrystallized in EtOAc/Hex. The desired material was obtained as a white solid 2.15 g, 13.8 mmol, 31%. $^1$H NMR (500 MHz, DMSO-d$_6$) δ 1.34-1.38 (m, 2H), 1.49 (br s, 8H), 1.74 (s, 2H), 1.88-1.93 (m, 2H), 6.76 (br s, 1H), 7.27 (br s, 1H); $^{13}$C NMR (125 MHz, DMSO-d$_6$) 22.4, 29.6, 39.1, 59.6, 181.1

A solution of 1,3-propane sultone (1M, 5.20 mL) in toluene was added to a solution of 2-amino-2-methylpropaneamide (0.4350 g, 4.26 mmol) in MTBK (5 mL) and ethanol (0.5 mL). The mixture was heated to reflux for 4 hours then cooled to room temperature. The solid was collected by suction filtration, rinsed with acetone (2×5 mL). The solid was dried 18 hours at 60° C. in the vacuum oven (0.62 g). The solid was recrystallized in ethanol (5 mL) and water (5 mL). After drying, the title compound was obtained as a fine white solid (0.39 g, 1.40 mmol, 27%). $^1$H NMR (500 MHz, DMSO-d$_6$) δ 1.53 (br s, 6H), 1.65-1.69 (m, 2H), 1.83-1.88- (m, 2H), 1.97 (qt, J=6.7 Hz, 2H), 2.06-2.11 (m, 2H), 2.61 (t, J=6.6 Hz, 2H), 2.91 (br s, 2H), 7.57 (s, 1H0, 7.79 (s, 1H), 8.75 (br s, 2H); $^{13}$C NMR (125 MHz, DMSO-d$_6$) 21.8, 22.2, 29.1, 33.1, 43.0, 49.1, 68.3, 172.0; ES-MS 277 (M–H)

Preparation of 3-(1,4-dimethyl-pentylamino)-1-propanesulfonic acid (Compound OV)

At reflux, a solution of 1,3-propane sultone (10.90 g, 89 mmol) in toluene (75 mL) was added dropwise over a 20 minute period to a solution of to a solution of 2-amino-5-methylhexane (10.00 g, 88.6 mmol) in acetone (80 mL). The mixture was heated to reflux for 7 hours then left at room temperature for the night. The solid was collected by suction filtration, rinsed with acetone (2×25 mL). The solid was dried 1 hour at 60° C. in the vacuum oven (15.20 g). The solid was recrystallized in methanol (90 mL) and water (5 mL). The mixture was left to cool to room temperature with stirring. The solid was collected by suction filtration, rinsed with methanol (2×15 mL). The solid was dried 18 hours at 60° C. in the vacuum oven. The title compound was obtained as a fine white solid (12.67 g, 53.38 mmol, 60%). $^1$H NMR (500 MHz, D$_2$O) δ ppm 0.88 (dd, J=6.6, 2.2 Hz, 6H), 1.22-1.27 (m, 2H), 1.29 (d, J=6.3 Hz, 3H), 1.51-1.60 (m, 2H), 1.71-1.78 (m, 1H), 2.08-2.14 (m, 2H), 3.00 (t, J=7.3 Hz, 2H), 3.15-3.24 (m, 2H), 3.25-3.31 (m, 1H); $^{13}$C NMR (125 MHz, D$_2$O) δ ppm 15.5, 21.5, 21.6, 21.9, 27.3, 30.4, 33.5, 43.4, 48.1, 55.1; ES-MS 236 (M–H)

Preparation of 3-(1,5-dimethyl-hexylamino)-1-propanesulfonic acid (Compound OW)

At reflux, a solution of 1,3-propane sultone (9.80 g, 80 mmol) in toluene (70 mL) was added dropwise over a 30 minute period to a solution of to a solution of 2-amino-6-methylheptane (10.00 g, 78 mmol) in acetone (75 mL). The mixture was heated to reflux for 7 hours then it was left at room temperature for the night. The solid was collected by suction filtration, rinsed with acetone (2×20 mL). The solid was dried 1 hour at 60° C. in the vacuum oven (15.20 g). The solid was recrystallized in methanol (45 mL). The mixture was left to cool to room temperature without stirring. The lump was crushed and diluted with acetone. The solid was collected by suction filtration, rinsed with acetone (2×25 mL). The solid was dried 18 hours at 60° C. in the vacuum oven. The title compound was obtained as a white solid (14.10 g, 56.10 mmol, 72%). $^1$H NMR (500 MHz, D$_2$O) δ 0.86 (dd, J=6.6, 2.0 Hz, 6H), 1.20 (q, J=7.3 Hz, 2H), 1.30 (d, J=6.8 Hz, 3H), 1.32-1.45 (m, 2H), 1.49-1.58 (m, 2H), 1.68-1.75 (m, 1H), 2.07-2.16 (m, 2H), 3.01 (t, J=7.3 Hz, 2H), 3.15-3.25 (m, 2H), 3.27-3.34 (m, 1H); $^{13}$C NMR (125 MHz, D$_2$O) 15.5, 21.6, 21.8, 22.0, 22.4, 27.2, 32.7, 37.9, 43.4, 48.1, 54.9; ES-MS 250 (M−H)

Preparation of
3-(1-methyl-butylamino)-1-propanesulfonic acid
(Compound OX)

At reflux, a solution of 1,3-propane sultone (10.05 g, 115 mmol) in toluene (100 mL) was added dropwise over a 30 minutes period to a solution of to a solution of 2-aminopentane (10.00 g, 115 mmol) in acetone (100 mL). The mixture was heated to reflux for 24 hours then was cooled to 0° C. with an ice/water bath. The solid was collected by suction filtration, rinsed with acetone (2×20 mL). The solid was dried 1 hours at 60° C. in the vacuum oven (19.42 g). The solid was recrystallized in methanol (45 mL). The mixture was left to cool to room temperature without stirring. The lump was crushed and diluted with acetone. The solid was collected by suction filtration, rinsed with ethanol (2×20 mL). The solid was dried 3 days at 60° C. in the vacuum oven. The title compound was obtained as a white solid (15.53 g, 74.20 mmol, 65%). $^1$H NMR (500 MHz, D$_2$O) δ 0.92 (t, J=7.3 Hz, 3H), 1.29 (d, J=6.3 Hz, 3H), 1.31-1.47 (m, 2H), 1.50-1.57 (m, 1H), 1.67-1.74 (m, 1H), 2.06-2.16 (m, 2H), 3.01 (t, J=7.3 Hz, 2H), 3.15-3.26 (m, 2H), 3.28-3.34 (m, 1H); $^{13}$C NMR (125 MHz, D$_2$O) 13.1, 15.4, 18.1, 21.6, 34.7, 43.4, 48.1, 54.6; ES-MS 208 (M−H)

Preparation of (R)-(+)-3-(1-methyl-octylamino)-1-propanesulfonic acid (Compound OY)

At reflux, a solution of 1,3-propane sultone (7.46 g, 39.0 mmol) in toluene (30 mL) was added to a solution of to a solution of (R)-(−)-2-aminononane (5.49 g, 38.3 mmol) in acetone (30 mL). The mixture was heated under reflux for 8 hours then at room temperature for the weekend. Ether (20 mL) was added then the solid was collected by suction filtration, rinsed with acetone (2×10 mL). The solid was dried 1 hours at 60° C. in the vacuum oven (7.97 g). The solid was suspended in ethanol (40 mL) and heated to reflux for 90 minutes. The mixture was then cooled to 0° C. The solid was collected by suction filtration, rinsed with ethanol (2×10 mL). The solid was dried 18 hours at 60° C. in the vacuum oven. The title compound was obtained as a fine white solid (7.82 g, 29.5 mmol, 77%). $^1$H NMR (500 MHz, DMSO-d$_6$) δ 0.87 (t, J=6.8 Hz, 3H), 1.16 (d, J=6.8 Hz, 3H), 1.26-1.40 (m, 11H), 1.60-1.65 (m, 1H), 1.93 (qt, J=6.6 Hz, 2H), 2.64 (t, J=6.6 Hz, 2H), 3.04-3.11 (m, 3H), 8.47 (br s, 2H); $^{13}$C NMR (125 MHz, DMSO-d$_6$) δ 13.9, 15.7, 21.9, 22.1, 24.5, 28.5, 28.7, 31.2, 32.5, 44.0, 49.2, 53.1; ES-MS 264 (M−H); [α]$_D$=1.34±0.14 (c=0.008753 in 0.1N NaOH)

Preparation of 3-{[1-(3,5-dimethoxy)cyclohexyl]amino}-1-propanesulfonic acid (Compound OZ)

NaOMe (0.5M, 40 mL) was added to nitrocyclohexane (2.58 g, 20 mmol) and the solution was stirred for 30 minutes then concentrated to afford a white solid. To this solid was added 3,5-dimethoxybenzylpyrridinium (5.45 g, 10 mmol) and DMSO (20 mL). The mixture was heated at 100° C. for 15 hours then cooled to room temperature and diluted with HCl (1M) and EtOAc. After separation of the two phases, the organic layer was washed twice with HCl (1M) then concentrated to obtain an oily crude, mixed with some solid. Methanol was added to precipitate the pyridinium byproduct which was filtered off, and the filtrate was concentrated under high vacuum. The crude was submitted to hydrogenation without further purification.

To a stirred solution of the crude nitro in methanol (20 mL) was added a spatula of Raney-Ni in water. The suspension was hydrogenated under atmospheric pressure of hydrogen for 15 hours (TLC indicates complete consumption of the starting material) then filtered on celite and concentrated under reduced pressure. The crude was purified by column using CH$_2$Cl$_2$:MeOH 80:10 to afford 1.2 g of the corresponding amine.

To a stirred solution of the amine (800 mg, 3.20 mmol) in THF (10 mL) was added 1,3-propane sultone (390 mg, 3.20 mmol). The reaction mixture was stirred at reflux for 15 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1.1 g (86%). $^1$H NMR (500 MHz, DMSO-d$_6$) δ 1.31 (m, 2H), 1.54-1.68 (m, 8H), 1.96 (m, 2H), 2.62 (m, 2H), 2.89 (s, 2H), 3.08 (m, 2H), 6.32 (m, 2H), 6.42 (s, 1H), 8.39 (bs, 2H). $^{13}$NMR (125 MHz, DMSO-d$_6$) δ 20.92, 22.81, 25.07, 31.84, 41.04, 50.09, 55.82, 61.64, 109.47, 161.01. ES-MS 370 (M−1).

Preparation of 3-{[1-(3,5-dimethoxy)cyclohexyl]amino}-1-propanesulfonic acid (Compound PA)

NaOMe (0.5M, 40 mL) was added to nitrocyclohexane (2.58 g, 20 mmol) and the solution was stirred for 30 minutes then concentrated to afford a white solid. To this solid was added 3,5-dimethoxybenzylpyrridinium (5.45 g, 10 mmol) and DMSO (20 mL). The mixture was heated at 100° C. for 15 hours then cooled to room temperature and diluted with HCl (1M) and EtOAc. After separation of the two phases, the organic layer was washed twice with HCl (1M) then concentrated to obtain an oily crude, mixed with some solid. Methanol was added to precipitate the pyridinium byproduct which was filtered off, and the filtrate was concentrated under high vacuum. The crude was submitted to hydrogenation without further purification.

To a stirred solution of the crude nitro in methanol (20 mL) was added a spatula of Raney-Ni in water. The suspension was hydrogenated under atmospheric pressure of hydrogen for 15 hours and then was filtered on celite and concentrated under reduced pressure. The crude was purified by column using CH$_2$Cl$_2$:MeOH 80:10 to afford 1.2 g of the corresponding amine.

To a stirred solution of the amine (800 mg, 3.20 mmol) in THF (10 mL) was added 1,3-propane sultone (390 mg, 3.20 mmol). The reaction mixture was stirred at reflux for 15 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1.1 g (86%). $^1$H NMR (500 MHz, DMSO-$d_6$) δ 1.31 (m, 2H), 1.54-1.68 (m, 8H), 1.96 (m, 2H), 2.62 (m, 2H), 2.89 (s, 2H), 3.08 (m, 2H), 6.32 (m, 2H), 6.42 (s, 1H), 8.39 (bs, 2H). $^{13}$NMR (125 MHz, DMSO-$d_6$) δ 20.92, 22.81, 25.07, 31.84, 41.04, 50.09, 55.82, 61.64, 109.47, 161.01. ES-MS 370 (M−1).

Preparation of 3-{[2-(3,5-dimethoxyphenyl)-1,1-dimethylethyl]amino}-1-propanesulfonic acid (Compound PB)

NaOMe (0.5M, 40 mL) was added to 2-nitropropane (1.78 g, 20 mmol) and the solution was stirred for 30 minutes then concentrated to afford a white solid. To this solid was added 3,5-dimethoxybenzylpyrridinium (5.45 g, 10 mmol) and DMSO (20 mL). The mixture was heated at 100° C. for 15 hours then cooled to room temperature and diluted with HCl (1M) and EtOAc. After separation of the two phases, the organic layer was washed twice with HCl (1M) then concentrated to obtain an oily crude, mixed with some solid. Methanol was added to precipitate the pyridinium byproduct which was filtered off, and the filtrate was concentrated under high vacuum. The crude was submitted to hydrogenation without further purification.

To a stirred solution of the crude nitro in methanol (20 mL) was added a spatula of Raney-Ni in water. The suspension was hydrogenated under atmospheric pressure of hydrogen for 15 hours (TLC indicates complete consumption of the starting material) then filtered on celite and concentrated under reduced pressure. The crude was purified by column using $CH_2Cl_2$:MeOH 80:10 to afford 1.2 g (57%) of the corresponding amine.

To a stirred solution of the amine (1.1 g, 5.25 mmol) in pinacolone/toluene (8 mL/2 mL) was added 1,3-propane sultone (642 mg, 5.25 mmol). The reaction mixture was stirred at reflux for 15 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1.4 g (80%). $^1$H NMR (500 MHz, DMSO-$d_6$) δ 1.19 (s, 6H), 1.98 (m, 2H), 2.67 (m, 2H), 2.82 (s, 2H), 3.11 (m, 2H), 3.74 (s, 6H), 6.38 (s, 2H), 6.42 (s, 1H), 8.60 (bs, 2H). $^{13}$NMR (125 MHz, DMSO-$d_6$) δ 23.07, 23.53, 41.37, 44.20, 49.86, 55.83, 59.28, 99.49, 109.49, 137.83, 160.91. ES-MS 330 (M−1).

Preparation of 3-{[2-(2,4-dichlorophenyl)-1,1-dimethylethyl]amino}-1-propanesulfonic acid (Compound PD)

NaOMe (0.5M, 40 mL) was added to 2-nitropropane (1.78 g, 20 mmol) and the solution was stirred for 30 minutes then concentrated to afford a white solid. To this solid was added 2,4-dichlorobenzylpyrridinium (5.5 g, 10 mmol) and DMSO (20 mL). The mixture was heated at 100° C. for 15 hours then cooled to room temperature and diluted with HCl (1M) and EtOAc. After separation of the two phases, the organic layer was washed twice with HCl (1M) then concentrated to obtain an oily crude, mixed with some solid. Methanol was added to precipitate the pyridinium byproduct which was filtered off, and the filtrate was concentrated under high vacuum. The crude was submitted to hydrogenation without further purification.

To a stirred solution of the crude nitro in methanol (20 mL) was added a spatula of Raney-Ni in water. The suspension was hydrogenated under atmospheric pressure of hydrogen for 15 hours (TLC indicates complete consumption of the starting material) then filtered on celite and concentrated under reduced pressure. The crude was purified by column using $CH_2Cl_2$:MeOH 80:10 to afford 980 mg (45%) of the corresponding amine.

To a stirred solution of the amine (960 mg, 4.40 mmol) in pinacolone/toluene (8 mL/2 mL) was added 1,3-propane sultone (537 mg, 4.40 mmol). The reaction mixture was stirred at reflux for 15 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1.4 g (80%). $^1$H NMR (500 MHz, DMSO-$d_6$) 61.20 (s, 6H), 2.00 (m, 2H), 2.70 (m, 2H), 3.10 (s, 2H), 3.20 (m, 2H), 3.7.40 (s, 2H), 7.65 (s, 1H). $^{13}$NMR (125 MHz, DMSO-$d_6$) δ 23.08, 23.18, 41.37, 49.83, 60.13, 128.04, 129.85, 132.88, 133.49, 135.14, 135.90. ES-MS 340 & 338 (M−1).

Preparation of 3-{[2-(2,4-dichlorophenyl)-1,1-dimethylethyl]amino}-1-propanesulfonic acid (Compound PE)

NaOMe (0.5M, 40 mL) was added to 2-nitropropane (1.78 g, 20 mmol) and the solution was stirred for 30 minutes then concentrated to afford a white solid. To this solid was added 2,4-dichlorobenzylpyrridinium (5.5 g, 10 mmol) and DMSO (20 mL). The mixture was heated at 100° C. for 15 hours then cooled to room temperature and diluted with HCl (1M) and EtOAc. After separation of the two phases, the organic layer was washed twice with HCl (1M) then concentrated to obtain an oily crude, mixed with some solid. Methanol was added to precipitate the pyridinium byproduct which was filtered off, and the filtrate was concentrated under high vacuum. The crude was submitted to hydrogenation without further purification.

To a stirred solution of the crude nitro in methanol (20 mL) was added a spatula of Raney-Ni in water. The suspension was hydrogenated under atmospheric pressure of hydrogen for 15 hours (TLC indicates complete consumption of the starting material) then filtered on celite and concentrated under reduced pressure. The crude was purified by column using $CH_2Cl_2$:MeOH 80:10 to afford 980 mg (45%) of the corresponding amine.

To a stirred solution of the amine (960 mg, 4.40 mmol) in pinacolone/toluene (8 mL/2 mL) was added 1,3-propane sultone (537 mg, 4.40 mmol). The reaction mixture was stirred at reflux for 15 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 1.4 g (80%). $^1$H NMR (500 MHz, DMSO-$d_6$) 1.20 (s, 6H), 2.00 (m, 2H), 2.70 (m, 2H), 3.10 (s, 2H), 3.20 (m, 2H), 3.7.40 (s, 2H), 7.65 (s, 1H). $^{13}$NMR (125 MHz, DMSO-$d_6$) 23.08, 23.18, 41.37, 49.83, 60.13, 128.04, 129.85, 132.88, 133.49, 135.14, 135.90. ES-MS 340 & 338 (M−1).

Preparation of 3-{[1,1-dimethyl-2-(4-propoxyphenyl)ethyl]amino}-1-propanesulfonic acid (Compound PF)

To a stirred solution of the phenol (195 mg, 1 mmol) in DMF (10 mL) was added NaH (48 mg, 2 mmol) followed by AllBr (170/L, 2 mmol). The suspension was heated at reflux for 15 hours then diluted with HCl (1M) and with EtOAc. The organic layer was washed with HCl (1M) then concentrated under high vacuum to afford 200 mg of the desired product (97% yield).

To a stirred solution of the crude nitro in methanol (5 mL) was added a small spatula of Raney-Ni in water. The suspension was hydrogenated under atmospheric pressure of hydrogen for 15 hours (TLC indicates complete consumption of the starting material) then filtered on pre-washed celite and concentrated under reduced pressure. The crude amine was used as such in the next step.

To the crude amine (207 mg, 1 mmol) in solution in pinacolone (3 mL) was added 1,3-propane sultone (122 mg, 1 mmol) and the mixture was heated at reflux for 12 hours. The suspension of was cooled down and filtered. The solid was dried to afford 270 mg of the homotaurine as a white solid (79% yield). $^1$H NMR (500 MHz, DMSO-$d_6$) δ 0.97 (t, J=7.5 Hz, 3H), 1.14 (s, 6H), 1.70 (m, 2H), 1.99 (m, 2H), 2.67 (m, 2H), 2.81 (s, 2H), 3.12 (m, 2H), 3.90 (t, J=6.4 Hz, 2H), 6.88 (d, J=7.5 Hz, 2H), 7.12 (d, J=7.5 Hz, 2H), 8.59 (bs, 2H). $^{13}$NMR (125 MHz, DMSO-$d_6$) δ 11.13, 22.75, 23.11, 41.24, 43.06, 49.82, 59.44, 69.50, 114.86, 127.38, 132.37, 158.43. ES-MS 328 (M−1).

Preparation of 2-piperidinylethanesulfonic acid (Compound PG)

A solution of 2-piperidineethanol (containing 10% of impurity) (6 g, 46.44 mmol) in anhydrous CHCl$_3$ was saturated with HCl(g) and then treated drop wise at reflux with SOCl$_2$. The resulting mixture was refluxed for 1 hour and concentrated to yield a brown solid. The solid was dissolved in EtOH and then recrystallized in EtOH/Et$_2$O to obtain 6.4 g of the desired chloride (76% yield).

A solution of the chloride (3.7 g, 20 mmol) in water (4 mL) was added drop wise to a refluxed solution of N$_2$SO$_3$ (5.04 g, 40 mmol) in water (18 mL). After the end of the addition, the reaction was stirred at reflux for 40 minutes then cooled down and concentrated under reduced pressure. 12 mL of HCl (conc) were added to dissolve the aminosulfonic acid and precipitate the inorganic salts which were removed by filtration. The filtrate was concentrated then ethanol was added to cause amino sulfonic acid to appear as white solid which was collected by filtration. It was washed with EtOH and Et$_2$O, then dried under high vacuum to obtain 2.84 g of a white solid (73% yield). $^1$H NMR (500 MHz, D$_2$O) δ 1.33-1.53 (m, 3H), 1.75 (m, 2H), 1.82-1.92 (m, 2H), 1.93-2.00 (m, 1H), 2.80-2.92 (m, 3H), 3.13 (m, 1H), 3.30 (m, 1H), 4.65 (s, 2H). $^{13}$NMR (125 MHz, D$_2$O) δ 21.59, 21.94, 27.97, 28.60, 45.02, 46.79, 55.79. ES-MS 178 (M−1).

Preparation of 3-(1,1-Dimethyl-prop-2-ynylamino)-1-propanesulfonic acid (Compound PH)

The 1,3-propane sultone (1.22 g, 10 mmol) was added to a solution of 1,1,-dimethylpropargylamine (0.8300 g, 10.00 mmol) in MeCN (15 mL). The mixture was heated to 75° C. for 4.5 hours then cooled to room temperature. The solid was collected by suction filtration, rinsed with acetone (2×5 mL). The solid was dried 18 hours at 60° C. in the vacuum oven. The title compound was obtained as a fine white solid (1.46 g, 7.11 mmol, 71%). $^1$H NMR (500 MHz, D$_2$O) δ 1.65 (s, 6H), 2.13 (qt, J=7.7 Hz, 2H), 3.03 (t, J=7.6 Hz, 2H), 3.12 (s, 1H), 3.37 (t, J=7.8 Hz, 2H); $^{13}$C NMR (125 MHz, D$_2$O) 621.8, 25.6, 41.7, 48.0, 54.1, 76.8, 50.5; ES-MS 204 (M−H).

Preparation of (R)-(+)-3-[1-(4-bromophenyl)ethylamino]-1-propanesulfonic acid (Compound PI)

The 1,3-propane sultone (0.6110 g, 5 mmol) was added to a solution of (R)-(+)-1-(4-bromophenyl)ethylamine (1 g, 5.00 mmol) in MeCN (10 mL). The mixture was heated to 75° C. for 4.5 hours then cooled to room temperature. The solid was collected by suction filtration, rinsed with acetone (2×5 mL). The solid was dried 18 hours at 60° C. in the vacuum oven. The title compound was obtained as a fine white solid (1.63 g, 5.06 mmol, 100%). $^1$H NMR (500 MHz, DMSO-$d_6$) δ 1.50 (d, J=6.8 Hz, 3H), 1.93 (qt, J=6.6 Hz, 2H), 2.61 (t, J=6.6 Hz, 2H), 2.79 (qt, J=6.3 Hz, 2H), 3.01 (qt, J=6.3 Hz, 2H), 4.38 (q, J=6.7 Hz, 1H), 7.45 (d, J=8.8 Hz, 1H), 7.67 (d, J=8.8 Hz, 2H), 9.05 (br s, 1H), 9.21 (br s, 1H); $^{13}$C NMR (125 MHz, DMSO-$d_6$) 19.0, 21.8, 45.1, 49.2, 56.1, 122.3, 129.9, 131.9, 136.6; ES-MS 320-322 (M−H); $[α]_D$=+34.2±0.2° (c=0.003345 in 0.1 N NaOH)

Preparation of (S)-(+)-3-(1-methylpropylamino)-1-propanesulfonic acid (Compound PJ)

The 1,3-propane sultone (1.67 g, 13.7 mmol) was added to a solution of (S)-(+)-2-butylamine (1 g, 13.7 mmol) in a mixture of acetone (7 mL) and toluene (7 mL). The mixture was heated to reflux for 6 hours. The mixture was cooled to room temperature, and the solid was collected by suction filtration, rinsed with acetone (2×5 mL) and dried under vacuum. The title compound was obtained as a fine white solid (1.90 g, 9.73 mmol, 71%). $^1$H NMR (500 MHz, D$_2$O) δ 0.96 (t, J=7.6 Hz, 3H), 1.29 (d, J=6.3 Hz, 3H), 1.54-1.60 (m, 1H), 1.76-1.81 (m, 1H), 2.12 (q, J=7.7 Hz, 2H), 3.01 (t, J=7.3 Hz, 2H), 3.15-3.27 (m, 3H); $^{13}$C NMR (125 MHz, D$_2$O) δ 8.8, 14.9, 21.6, 25.7, 43.5, 48.1, 56.0; ES-MS 194 (M−H); $[α]_D$=1.10±0.04° (c=0.01364 in water)

Preparation of (−)-3-[(1R,2S,5R)-2-Isopropyl-5-methyl-cyclohexylamino]-1-propanesulfonic acid (Compound PK)

The 1,3-propane sultone (0.3940 g, 3.22 mmol) was added to a solution of L-menthylamine (0.500 g, 3.22 mmol) in a mixture of acetone (3 mL) and toluene (4 mL). The mixture was heated to reflux for 6 hours. The mixture was cooled to room temperature, and the solid was collected by suction filtration, rinsed with acetone (2×5 mL) and dried 2 hours in the vacuum oven at 60° C. (0.68 g). The solid was recrystallized in ethanol (7 mL). The mixture was cooled to room temperature, and the solid was collected by suction filtration, rinsed with acetone (2×5 mL) and dried 18 hours in the vacuum oven at 60° C. The title compound was obtained as a fine white solid (0.3200 g, 1.15 mmol, 36%). $^1$H NMR (500 MHz, DMSO-$d_6$) δ 0.75 (d, J=6.8 Hz, 3H), 0.78-1.07 (m, 3H), 0.91 (d, J=6.3 Hz, 6H), 1.31-1.35 (m, 1H0, 1.40-1.42 (m, 1H), 1.95-2.03 (m, 4H), 2.63-2.70 (m, 2H), 2.95-3.05 (m, 2H), 3.10-3.20 (m, 1H), 8.40 (br s, 1H), 8.65 (br s, 1H); $^{13}$C NMR (125 MHz, DMSO-$d_6$) δ 15.4, 21.0, 21.8, 22.0, 22.4, 24.5, 30.8, 33.3, 36.1, 43.4, 44.4, 49.6, 56.8; ES-MS 276 (M−H); $[\alpha]_D$=−46.2±0.3° (c=0.0568 in water).

Preparation of 3-{[(1S)-1-methylpentyl]amino}-1-propanesulfonic acid (Compound PL)

To a solution of (S)-2-aminohexane (5.10 g, 50.4 mmol) in acetone (20 mL) and toluene (20 mL) was added 1,3-propane sultone (5.85 g, 48.0 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 7.86 g (73%). $^1$H NMR (D$_2$O, 500 MHz) δ ppm 3.06 (m, 3H), 2.83 (t, 2H, J=7.3 Hz), 1.93 (quintet, 2H, J=7.4 Hz), 1.56 (m, 1H), 1.37 (m, 1H), 1.16 (m, 7H), 0.71 (m, 3H). $^{13}$C (D$_2$O, 125 MHz) δ ppm 54.96, 48.26, 43.57, 32.46, 26.97, 22.16, 21.91, 15.79, 13.54. $[\alpha]_D$=−6.3° (c=0.0051 in water), ES-MS 222 (M−1).

Preparation of 3-{[(1SR)-1-methylpentyl]amino}-1-propanesulfonic acid (Compound PM)

To a solution of (R)-2-aminohexane (5.12 g, 50.6 mmol) in acetone (20 mL) and toluene (20 mL) was added 1,3-propane sultone (5.87 g, 48.2 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 7.66 g (71%). $^1$H NMR (D$_2$O, 500 MHz) δ ppm 3.01 (m, 3H), 2.86 (t, 2H, J=7.3 Hz), 1.97 (m, 2H), 1.59 (m, 1H), 1.40 (m, 1H), 1.19 (m, 7H), 0.74 (t, 3H, J=6.8 Hz). $^{13}$C (D$_2$O, 125 MHz) δ ppm 54.83, 48.08, 43.38, 32.22, 26.70, 21.87, 21.64, 15.50, 13.21. $[\alpha]_D$=+6.4° (c=0.0025 in water), ES-MS 222 (M−1).

Preparation of 3-{[(1S)-1,2-dimethylpropyl]amino}-1-propanesulfonic acid (Compound PN)

To a solution of (S)-(+)-3-methyl-2-butylamine (5.00 g, 57.4 mmol) in acetone (35 mL) and toluene (35 mL) was added 1,3-propane sultone (6.68 g, 54.7 mmol). The solution was stirred at reflux for 4 hours. The reaction mixture was cooled to room temperature. The solid material was collected by filtration and washed with acetone (2×25 mL). The solid was suspended in EtOH (40 mL). The suspension was stirred at reflux for 1 hour. The mixture was cooled to room temperature, the solid material was collected by filtration, washed with acetone (2×25 mL) and dried in a vacuum oven at 50° C., affording the title compound, 4.95 g (43%). $^1$H NMR (D$_2$O, 500 MHz) δ ppm 3.07 (m, 3H), 2.87 (td, 2H, J=1.2 Hz, 7.3 Hz), 1.95 (m, 3H), 1.07 (d, 3H, J=6.8 Hz), 0.83 (d, 3H, J=6.8 Hz), 0.78 (t, 3H, J=6.8 Hz). $^{13}$C (D$_2$O, 125 MHz) δ ppm 59.76, 48.16, 44.15, 29.71, 21.49, 18.42, 14.99, 10.66. $[\alpha]_D$=+2.3° (c=0.0015 in water), ES-MS 208 (M−1).

Preparation of 3-{[(1R)-1,2,2-trimethylpropyl]amino}-1-propanesulfonic acid (Compound PO)

To a solution of (R)-3,3-dimethyl-2-butylamine (10.0 g, 98.8 mmol) in acetone (40 mL) and toluene (40 mL) was added 1,3-propane sultone (11.5 g, 94.1 mmol). The solution was stirred at reflux for 4 hours. The reaction mixture was cooled to room temperature. The solid material was collected by filtration and washed with acetone (2×25 mL). The solid was recrystallized in EtOH. After the crystals were filtered and washed with acetone (2×25 mL), the product was dried in a vacuum oven at 50° C., affording the title compound, 11.94 g (57%). $^1$H NMR (D$_2$O, 500 MHz) δ ppm 3.20 (m, 1H), 3.05 (m, 1H), 2.95 (quartet, 1H, J=6.8 Hz), 2.89 (t, 2H, J=6.8 Hz), 2.02 (m, 2H), 1.13 (d, 3H, J=6.8 Hz), 0.86 (s, 9H). $^{13}$C (D$_2$O, 125 MHz) δ ppm 64.03, 48.30, 45.42, 33.20, 25.11, 21.15, 11.15. $[\alpha]_D$=−28.6° (c=0.0026 in water), ES-MS 222 (M−1).

Preparation of 3-{[(1R)-1,2-dimethylpropyl]amino}-1-propanesulfonic acid (Compound PP)

To a solution of (R)-(−)-3-methyl-2-butylamine (10.0 g, 115 mmol) in acetone (70 mL) and toluene (70 mL) was added 1,3-propane sultone (13.4 g, 110 mmol). The solution was stirred at reflux for 4 hours. The reaction mixture was cooled to room temperature. The solid material was collected by filtration and washed with acetone (2×25 mL). The solid was suspended in EtOH (40 mL). The suspension was stirred at reflux for 1 hour. The mixture was cooled to room temperature, the solid material was collected by filtration, washed with acetone (2×25 mL) and dried in a vacuum oven at 50° C., affording the title compound, 11.36 g (49%). $^1$H NMR (D$_2$O, 500 MHz) δ ppm 3.07 (m, 3H), 2.86 (td, 2H, J=1.2 Hz, 7.3 Hz), 1.95 (m, 3H), 1.07 (d, 3H, J=6.8 Hz), 0.83 (d, 3H, J=6.8 Hz), 0.78 (t, 3H, J=6.8 Hz). $^{13}$C (D$_2$O, 125 MHz) δ ppm 59.77, 48.17, 44.16, 29.72, 21.50, 18.43, 15.00, 10.67. $[\alpha]_D$=−2.9° (c=0.0026 in water), ES-MS 208 (M−1).

Preparation of 3-(1-Methyl-3-phenylpropylamino)-1-propanesulfonic acid (Compound PQ)

A solution of 1,3-propane sultone (8.60 g, 70.40 mmol) in toluene (35 mL) was added to a solution of 3-amino-1-phenylbutane (10.50 g, 70.36 mmol) in acetone (35 mL). The mixture was heated to reflux for 4 hours. The mixture was cooled to room temperature, and the solid was collected by suction filtration, rinsed with acetone (2×20 mL) and dried 1 hour in the vacuum oven at 60° C. (14.02 g). The solid was suspended in ethanol (90 mL) and the mixture was heated 1 hours at reflux. The mixture was cooled to room temperature, and the solid was collected by suction filtration, rinsed with ethanol (2×15 mL) and dried 18 hours in the vacuum oven at 60° C. The title compound was obtained as a fine white solid (13.95 g, 51.40 mmol, 73%). $^1$H NMR (500 MHz, DMSO-d$_6$) δ 1.25 (d, J=6.8 Hz, 3H), 1.67-1.74 (m, 1H), 1.92-2.01 (m, 3H), 2.57-2.72 (m, 4H), 3.04-3.18 (m, 3H), 7.19-7.25 (m, 3H), 7.29-7.32 (m, 2H), 8.56 (br s, 2H); $^{13}$C NMR (125 MHz, DMSO-d$_6$) δ 15.7, 22.0, 30.7, 34.3, 43.9, 49.1, 52.9, 126.1, 128.3, 128.5, 140.8; ES-MS 270 (M−H)

Preparation of 3-({1-[hydroxy(3-methoxyphenyl)methyl]cyclopentyl}amino)-1-propanesulfonic acid (Compound PR)

To a cooled solution of sodium methoxide (0.5 M in MeOH, 20 mL) was added via syringe over a 10 minutes period 2-nitrocyclopentane (3.00 g, 26 mmol). The reaction mixture was stirred at room temperature for 30 minutes and recooled before m-anisaldehyde (3.2 mL, 26 mmol) was added. The reaction mixture was stirred at room temperature overnight. The mixture was neutralized with Amberlite IR-120 (strongly acidic). The resin was removed by filtration and washed with MeOH (2×15 mL). The filtrate was evaporated. The resulting oil was purified by flash chromatography: 100% Hexanes to 90% Hexanes/EtOAc, affording the desired nitro compound (1.6 g, 22%).

To a solution of the nitro compound (1.6 g, 5.6 mmol) in MeOH (12 mL) was added 6M HCl (7 mL). After cooling to 5° C., zinc powder (1.85 g, 28.2 mmol) was added. The suspension was stirred at 0-5° C. for 30 minutes and at room temperature for 6 h. The mixture was filtered on a celite pad. The filter cake was washed with MeOH (2×15 mL). The combined filtrates were evaporated under reduced pressure. The residue was dissolved in EtOAc (40 mL). The mixture was exctracted with 5% NaOH (1×40 mL). The aqueous phase was exctracted with EtOAc (2×40 mL). The combined organic extracts were dried with $Na_2SO_4$, filtered, evaporated and dried in vacuo to afford the corresponding amine. The amine (0.920 g, 66%) was used without further purification.

To a solution of amine (1.31 g, 6.3 mmol) in acetone (5 mL) and toluene (5 mL) was added 1,3-propane sultone (0.422 g, 3.4 mmol). The solution was stirred at reflux overnight. The reaction mixture was cooled to room temperature. The solid material was collected by filtration, was washed with acetone (2×15 mL). The solid was suspended in EtOH (15 mL). The suspension was stirred at reflux for 1 hour. The mixture was cooled to room temperature. The white solid was filtered, washed with acetone (2×15 mL) and dried in a vacuum oven at 50° C., affording the title compound, 0.637 g (51%). $^1$H NMR (DMSO, 300 MHz) δ ppm 8.51 (s (broad), 2H), 7.26 (t, 1H, J=8.1 Hz), 7.01 (m, 2H), 6.87 (dd, 1H, J=1.9 Hz, 7.3 Hz), 6.29 (d, 1H, J=3.5 Hz), 4.84 (d, 1H, J=3.2 Hz), 3.74 (s, 3H), 3.16 (m, 2H), 2.63 (t, 2H, J=6.8 Hz), 2.13 (m, 1H), 2.01 (m, 2H), 1.80 (m, 2H), 1.51 (m, 3H), 0.92 (m, 1H), 0.71 (m, 1H). $^{13}$C (DMSO, 75 MHz)$_6$ ppm 159.37, 142.03, 129.62, 120.97, 114.51, 113.76, 72.89, 72.54, 55.96, 50.10, 42.78, 31.96, 31.56, 25.35, 25.20, 23.29. ES-MS 342 (M−1).

Preparation of 3-{[(1S)-1-methylhexyl]amino}-1-propanesulfonic acid (Compound PS)

To a solution of (S)-(+)-2-aminoheptane (5.19 g, 45.0 mmol) in Acetone (25 mL) and Toluene (25 mL) was added 1,3-propane sultone (5.23 g, 42.9 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 6.77 g (63%). $^1$H NMR (D$_2$O, 300 MHz) δ ppm 3.08 (m, 3H), 2.84 (t, 2H, J=7.3 Hz), 1.94 (m, 2H), 1.55 (m, 1H), 1.38 (m, 1H), 1.18 (m, 9H), 0.70 (m, 3H). $^{13}$C (D$_2$O, 75 MHz) δ ppm 55.00, 48.27, 43.59, 32.70, 31.06, 24.48, 22.17, 21.93, 15.79, 13.70. [α]$_D$=−6.4° (c=0.0020 in water), ES-MS 236 (M−1).

Preparation of 3-{[(1S)-1-methylheptyl]amino}-1-propanesulfonic acid (Compound PT)

To a solution of (S)-(+)-2-aminooctane (5.50 g, 42.5 mmol) in Acetone (25 mL) and Toluene (25 mL) was added 1,3-propane sultone (4.95 g, 40.5 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 6.11 g (57%). $^1$H NMR (D$_2$O, 300 MHz) δ ppm 3.08 (m, 3H), 2.84 (t, 2H, J=7.3 Hz), 1.94 (m, 2H), 1.56 (m, 1H), 1.39 (m, 1H), 1.16 (m, 11H), 0.70 (m, 3H). $^{13}$C (D$_2$O, 75 MHz) δ ppm 55.00, 48.27, 43.59, 32.74, 31.19, 28.49, 24.75, 22.33, 21.93, 15.80, 13.79. [α]$_D$=−6.5° (c=0.0031 in water), ES-MS 250 (M−1).

Preparation of 3-(1-propylamino)-1-propanesulfonic acid (Compound PU)

A mixture of propylamine (1.20 g, 20 mmo), 1,3-propane sultone (9.5 mL of 2.0 M in acetone) and toluene (7 mL) was heated to 50° C. for 3 h. The solid from the brownish suspension was collected by filtration, rinsed with acetone (2×5 mL) and dried 1 hour in vacuo (1.59 g). The solid was suspended in ethanol (10 mL) and the suspension was heated to reflux. Water (0.7 mL) was added and the mixture turned to a clear solution. The mixture was then cooled with an ice/water bath. The solid was collected by filtration, rinsed with acetone (2×5 mL) and dried 3 days at 60° C. in the vacuum oven. The title compound was obtained as a fine white powder 1.36 g, 7.56 mmol, 39%; $^1$H NMR (500 MHz, D$_2$O) δ 0.97 (t, J=7.6 Hz, 3H), 1.69 (hex, J=7.5 Hz, 2H), 2.12 (qt, J=7.6 Hz, 2H), 3.01 (qt, J=7.3 Hz, 4H), 3.19 (t, J=7.8 Hz, 2H); $^{13}$C NMR (125 MHz, D$_2$O) δ 10.3, 19.3, 21.4, 46.2, 48.0, 49.4; ES-MS 180 (M−H)

Preparation of 3-{[(1R)-1-methylheptyl]amino}-1-propanesulfonic acid (Compound PV)

To a solution of (R)-(−)-2-aminooctane (5.00 g, 38.7 mmol) in acetone (25 mL) and toluene (25 mL) was added 1,3-propane sultone (4.50 g, 36.8 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 5.72 g (56%). $^1$H NMR (D$_2$O, 300 MHz) δ ppm 3.09 (m, 3H), 2.84 (t, 2H, J=7.3 Hz), 1.95 (m, 2H), 1.56 (m, 1H), 1.38 (m, 1H), 1.15 (m, 11H), 0.70 (m, 3H). $^{13}$C (D$_2$O, 75 MHz) δ ppm 55.00, 48.26, 43.59, 32.74, 31.19, 28.48, 24.74, 22.31, 21.91, 15.79, 13.78. [α]$_D$=+6.8° (c=0.0024 in water), ES-MS 250 (M−1).

Preparation of (R)-3-{[1-methylhexyl]amino}-1-propanesulfonic acid (Compound PW)

To a solution of (R)-(−)-2-aminoheptane (5.0 g, 43.4 mmol) in acetone (25 mL) and toluene (25 mL) was added 1,3-propane sultone (5.04 g, 41.3 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 6.77 g (63%). $^1$H NMR (D$_2$O, 300 MHz) δ ppm 3.15 (m, 1H), 3.04 (m, 2H), 2.85 (t, 2H, J=7.3 Hz), 1.96 (m, 2H), 1.57 (m, 1H), 1.39 (m, 1H), 1.19 (m, 9H), 0.72 (m, 3H). $^{13}$C (D$_2$O, 75 MHz) δ ppm 54.84, 48.08, 43.38, 32.45, 30.80, 24.18, 21.88, 21.63, 15.49, 13.35. [α]$_D$=+6.4° (c=0.0023 in water), ES-MS 236 (M−1).

Preparation of 3-[(3-oxocyclohex-1-en-1-yl)amino]-1-propanesulfonic acid (Compound PX)

A solution of 1,3-propane sultone (1.0 M in MeCN, 5.00 mL) was added to a solution of 3-amino-2-cyclohexenone (0.5558 g, 5.00 mmol) in a mixture of MeCN (5 mL) and DMF (1.0 mL). The mixture was heated to 85° C. for 3 hours on the Radley caroussel. The suspension was cooled to room temperature. The solid was collected by suction filtration, rinsed with acetone (2×5 mL). The solid was dried 18 hours at 60° C. in the vacuum oven. The title compound was obtained as a fine white solid (0.64 g, 2.74 mmol, 55%). $^1$H NMR (500 MHz, DMSO-d$_6$) δ 2.01 (qt, J=6.5 Hz, 2H), 2.22 (qt, J=6.8 Hz, 2H), 2.57 (t, J=6.3 Hz, 2H), 2.74 (t, J=6.6 Hz, 2H), 3.05 (t, J=7.6 Hz, 2H), 4.28 (t, J=6.3 Hz, 2H), 5.85 (s, 1H); $^{13}$C NMR (125 MHz, DMSO-d$_6$) δ 20.2, 23.7, 28.8, 28.9, 47.5, 68.7, 95.2, 183.4, 186.2; ES-MS 340, 232 (M−H).

Preparation of 3-(1-butylamino)-1-propanesulfonic acid (Compound PY)

At reflux, a solution of 1,3-propane sultone (2.45 g, 20 mmol) in toluene (20 mL) was added dropwise over a 10 minutes period to a solution of to a solution of butylamine (1.46 g, 20 mmol) in acetone (20 mL). The mixture was heated to reflux for 2 hours then was cooled to room temperature. The solid was collected by suction filtration, rinsed with acetone (2×5 mL). The solid was dried 1 hour at 60° C. in the vacuum oven (1.96 g). The solid was recrystallized in ethanol (20 mL). The mixture was left to cool to room temperature without stirring. The solid was collected by suction filtration, rinsed with acetone (2×5 mL). The solid was dried 18 hours at 60° C. in the vacuum oven. The title compound was obtained as a white solid (1.55 g, 7.94 mmol, 40%). $^1$H NMR (500 MHz, D$_2$O) δ 0.92 (t, J=7.3 Hz, 3H), 1.38 (hex, J=7.5 Hz, 2H), 1.65 (qt, J=7.7 Hz, 2H), 2.12 (qt, J=7.6 Hz, 4H), 3.00 (t, J=7.3 Hz, 2H), 3.05 (t, J=7.6 Hz, 2H), 3.18 (t, J=7.8 Hz, 2H); $^{13}$C NMR (125 MHz, D$_2$O) δ 12.9, 19.3, 21.5, 27.7, 46.3, 47.6, 48.1; ES-MS 194 (M−H).

Preparation of 3-[benzyl(tert-butyl)amino]-1-propanesulfonic acid (Compoun PZ)

A mixture of 1,3-propane sultone (12.30 g, 100 mmol), toluene (20 mL) N-benzyl-N-tert-butylamine (16.33 g, 100 mmol) in cyclohexanenone (100 mL) was heated to reflux for 2 hours, diluted with toluene then cooled to room temperature. The mixture was stirred overnight at room temperature then diluted with acetone (100 mL). The solid was collected by suction filtration, rinsed with acetone (2×50 mL). The solid was dried 6 hours at 60° C. in the vacuum oven (23 g). The solid was recrystallized in methanol (150 mL) and water (38 mL). The mixture was left to cool to room temperature. The solid was collected by suction filtration, rinsed with methanol (2×5 mL). The solid was dried 18 hours at 60° C. in the vacuum oven. The title compound was obtained as a white solid 12.75 g in the first crop. The mother liquor was concentrated to a thick paste and refluxed with ethanol (80 mL) for 30 minutes. The solid was collected by filtration, rinsed with ethanol (2×20 mL) and was dried 18 hours at 60° C. in the vacuum oven to afford a second crop of 6.42 g for a total yield: 19.17 g, 67.17 mmol, 67%. $^1$H NMR (500 MHz, D$_2$O) δ 0.99 (m, 1H), 1.54 (s, 9H), 1.80 (m, 1H), 2.53 (m, 1H), 2.64 (m, 1H), 3.21 (m, 1H), 3.59 (m, 1H), 4.08 (br d, J=12.7 Hz, 3H), 4.71 (br d, J=12.7 Hz, 3H), 7.50-7.58 (m, 5H); $^{13}$C NMR (125 MHz, D$_2$O) 622.8, 24.3, 47.8, 49.3, 66.3, 129.7, 130.1, 130.4, 131.3; ES-MS 284 (M−H).

Preparation of (R)-3-{[1-(3-methoxyphenyl)ethyl]amino}-1-propanesulfonic acid (Compound QA)

To a solution of (1R)-(−)-1-(3-methoxyphenyl)ethylamine (5.0 g, 33.1 mmol) in acetonitrile (30 mL) and toluene (10 mL) was added 1,3-propane sultone (3.85 g, 31.5 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 7.98 g (91%). $^1$H NMR (D$_2$O, 500 MHz) δ ppm 7.298 (td, 1H, J=1.0 Hz, 7.8 Hz), 6.92 (m, 3H), 4.23 (q, 1H, J=6.8 Hz), 3.69 (s, 3H), 2.95 (m, 1H), 2.78 (m, 3H), 1.92 (m, 2H), 1.50 (d, 3H, J=6.8 Hz). $^{13}$C (D$_2$O, 125 MHz) δ ppm 159.69, 137.59, 130.99, 120.23, 115.36, 113.38, 58.53, 55.64, 48.08, 44.50, 21.52, 18.42. [α]$_D$=+23.7° (c=0.0036 in water), ES-MS 272 (M−1).

Preparation of 3-[(1,1-dimethylbut-3-enyl)amino]-1-propanesulfonic acid (Compound QB)

A 100-mL., three-necked, round-bottomed flask equipped with stir-bar, dropping funnel, and low-temperature thermometer is charged with 2.03 g. (15.8 mmole) of 2,2-dimethylpentenoic acid and 15 mL of acetone. The mixture is stirred, and 2.45 mL. (17.4 mmole) of triethylamine is added over 5 minutes. The solution is chilled to −5 to 0° in an ice-salt bath, and 1.67 mL. (17.4 mmole) of ethyl chlorocarbonate in 5 mL of acetone is added slowly (25 minutes), maintaining the temperature between −5 to 00. After the addition is complete, the cold mixture is stirred for an additional 15 minutes. A solution of 2.05 g. (31.6 mmole) of sodium azide in 8 mL of water is added over a 25-minute period while the temperature is kept at −5 to 0°. The mixture is stirred for 30 minutes longer at this temperature, poured into 75 ml. of ice water, and shaken with four 25-ml. portions of toluene. The combined toluene extracts are dried over anhydrous magnesium sulfate and transferred to a 250 mL, three-necked, round-bottomed flask equipped with a two-necked, Claisen-type adapter, stirrer, and reflux condenser. The stirred solution is heated cautiously under reflux for 1 hour (nitrogen evolution is observed initially). The amine hydrochloride solution was concentrated to dryness. The amine hydrochloride was dissolved in a minimum of hot methanol (4 mL) and was poured into ether (20 mL). The amine was collected by filtration and dried in vacuo. Proton NMR indicated a purity of about 97% (trace of triethylamine hydrochloride) (1.27 g, 9. mmol, 59%). The amine was dissolved in water and the solution was made to pH 12 with a saturated potassium carbonate solution. The amine was extracted with MTBK (4×5 mL), dried over sodium sulfate, rinsed with toluene (5 mL). The solution obtained was used as such in the next step. $^1$H NMR (500 MHz, D$_2$O) δ 1.34 (s, 6H), 1.38 (hex, J=7.5 Hz, 2H), 2.39 (d, J=7.3 Hz, 2H), 5.23-5.29 (m, 2H), 5.84-5.92 (m, 1H); $^{13}$C NMR (125 MHz, D$_2$O) δ 24.7, 44.0, 54.1, 121.2, 131.3

To the solution of 1,1-dimethylbut-3-enylamine (9 mmol) in MTBK (20 mL)/toluene (5 mL) was added 1,3-propane sultone (0.8 mL, 9 mmol). The mixture was heated to gentle reflux for 5 hours then was cooled to room temperature. The solid was collected by suction filtration, rinsed with acetone (2×5 mL). The solid was dried 60 hours at 60° C. in the vacuum oven. The title compound was obtained as a beige solid (0.83 g, 3.75 mmol, 42% from the amine hydrochloride, 24% overall). $^1$H NMR (500 MHz, D$_2$O) δ 1.34 (s 6H), 2.08 (qt, J=7.6 Hz, 2H), 2.44 (d, J=7.3 Hz, 4H), 3.00 (t, J=7.3 Hz, 2H), 3.19 (t, J=7.8 Hz, 2H), 5.28-5.31 (m, 2H), 5.82-5.90 (m. 2H); $^{13}$C NMR (125 MHz, D$_2$O) δ 12.9, 19.3, 21.5, 27.7, 46.3, 47.6, 48.1; ES-MS 194 (M−H)

Preparation of
3-[(4-methylbenzyl)amino]-1-propanesulfonic acid
(Compound QC)

To a solution of 4-methylbenzylamine (5.0 g, 41.3 mmol) in acetonitrile (35 mL) and toluene (15 mL) was added 1,3-propane sultone (4.80 g, 39.3 mmol). The solution was stirred at reflux for 4 hours. The reaction mixture was cooled to room temperature. The solid material was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×20 mL) and dried in a vacuum oven at 50° C., affording the title compound, 8.62 g (90%). $^1$H NMR (D$_2$O, 500 MHz) δ ppm 7.20 (d, 2H, J=7.8 Hz), 7.17 (d, 2H, J=7.8 Hz), 4.04 (s, 2H), 3.05 (t, 2H, J=7.8 Hz), 2.82 (t, 2H, J=7.3 Hz), 2.20 (s, 3H), 1.97 (m, 2H). $^{13}$C (D$_2$O, 125 MHz) δ ppm 140.37, 129.99, 127.77, 51.00, 48.09, 45.78, 21.43, 20.48. ES-MS 242 (M−1).

Preparation of 3-{[2-(4-methoxyphenyl)-2-oxoethyl]amino}-1-propanesulfonic acid (Compound QD)

2-Amino-4-methoxyacetophenone hydrochloride (2.5 g, 12.4 mmol) was treated with a saturated solution of K$_2$CO$_3$ (65 mL) and EtOAc (3×65 mL) was added. The organic extracts were combined, dried with Na$_2$SO$_4$, filtered, evaporated under reduced pressure and dried in vacuo.

To a solution of 2-amino-4-methoxyacetophenone (12.4 mmol) in 25% Toluene/Acetonitrile (15 mL) was added 1,3-propane sultone solution (1.34 g, 11.0 mmol). The solution was stirred at reflux for 4 hours. The reaction mixture was cooled to room temperature. The solid material was collected by filtration and washed with acetone (2×20 mL). The beige solid was dissolved with heating in 50% MeOH/Water (200 mL) before Dowex Marathon C ion exchange resin (strongly acidic) was added. The suspension was stirred at room temperature for 15 minutes. The resin was filtered and washed with 50% MeOH/Water (2×15 mL). The filtrate was evaporated. The solid was suspended in acetone before it was collected by filtration, washed with acetone (2×20 mL) and dried in a vacuum oven (50° C.), affording the title compound, 1.84 g (58%). $^1$H NMR (DMSO, 500 MHz) δ ppm 9.06 (s (broad), 1H)), 7.98 (d, 2H, J=8.8 Hz), 7.12 (d, 2H, J=8.8 Hz), 4.72 (m, 2H), 3.87 (s, 3H), 3.13 (m, 2H), 2.62 (t, 2H, J=6.6 Hz), 2.02 (m, 2H). $^{13}$C (D$_2$O, 75 MHz) δ ppm 191.04, 164.69, 131.24, 127.09, 114.97, 56.64, 52.82, 49.95, 47.80, 22.63. ES-MS 286 (M−1).

Preparation of 3-[(1,1-dimethylprop-2-enyl)amino]-1-propanesulfonic acid (Compound QE)

A dry, 250-ml., three-necked flask is equipped with a magnetic stirring bar, a pressure-equalizing dropping funnel, a thermometer, and a nitrogen inlet tube. The apparatus was flushed with nitrogen and charged with 410 mg. (0.0103 mole) of sodium hydride dispersed in mineral oil and 15 mL of hexane. The suspension was stirred, and the hydride was allowed to settle. The hexane was removed with a long dropping pipette, 60 mL of anhydrous diethyl ether was added, and a solution of 8.55 g. (0.0993 mole) of 3-methyl-2-butenol in 15 mL of anhydrous ether was added over 5 minutes. After the evolution of hydrogen ceases, the reaction mixture was stirred for an additional 15 minutes. The clear solution was then cooled to between −10 and 0° in an ice-salt bath. Trichloroacetonitrile (10.0 ml., 14.4 g., 0.0996 mole) was added dropwise to the stirred solution, while the reaction temperature was maintained below 0°. The addition was completed within 15 minutes, and the reaction mixture was allowed to warm to room temperature. The light amber mixture was poured into a 250-ml., round-bottomed flask, and the ether was removed with a rotary evaporator. Hexane [150 ml., containing 0.4 ml. (0.01 mole) of methanol] was added, the mixture was shaken vigorously for 1 minute, and a small amount of dark, insoluble material is removed by gravity filtration. The residue was washed two times with hexane (50 ml. total), and the combined filtrate was concentrated with a rotary evaporator A 500-ml., round-bottomed flask was charged with imidate and 300 mL of xylene. The solution was refluxed for 8 hours. After cooling to room temperature the dark xylene solution was filtered through a short column packed with silica gel and toluene. The column was eluted with an additional 250 mL of toluene, and the combined light yellow eluant is concentrated with a rotary evaporator.

A 500-mL round-bottomed was charged with 9.0 g. (0.030 mole) of the crude amide, 160 mL of ethanol, and 150 mL of aqueous 6 N sodium hydroxide. The air was replaced with nitrogen, and the solution was stirred at room temperature for 40 hours. Ether (300 mL) was added, the organic layer was separated, and the aqueous layer was washed twice with 50 mL of ether.

After extraction in ether (5×100 mL), the crude amine was back extracted in 6N HCl (2×20 mL). The combined organic extract were washed with ether (1×100 mL). The acid solution was adjusted to pH 12 with 50% NaOH. The basic aqueous layer was extracted with ether (2×50 mL). A solution of 2M HCl in ether (100 mL) was added and the amine hydrochloride solution was concentrated to dryness. The amine hydrochloride was dissolved in a minimum of hot methanol (10 mL) and was poured into ether (100 mL). The amine was collected by filtration and dried in vacuo. The pure aminde hydrochloride was obtained in two crops (6.92 g, 56.9. mmol, 57%). The amine was dissolved in water and the solution was made to pH 12 with 50% NaOH. The amine was extracted with toluene (3×13 mL0 then MTBK (1×10 mL), dried over potassium carbonate (20 minutes), rinsed with acetone (5 mL). $^1$H NMR (500 MHz, D$_2$O) δ 1.34 (s 6H), 5.30 (d, J=10.7 Hz, 1H), 5.31 (d, J=17.6 Hz, 1H), 5.98 (dd, J=17.6 and 11.2 Hz, 1H); $^{13}$C NMR (125 MHz, D$_2$O) 25.1, 54.9, 115.5, 139.3

Preparation of 3-[(1-Carbamoyl-1-ethyl)propylamino]-1-propanesulfonic acid (Compound QF)

To a 250 mL I neck flask containing 30% NH$_4$OH (120 mL) was added NaCN (15.34 g, 0.31 mol) and NH$_4$Cl (19.75 g, 0.37 mol) with vigorous stirring. The corresponding ketone was added dropwise within 20 minutes at room temperature. The mixture was stirred for 3 days at room temperature follwed by extraction with dichloromethane (50 mL). The organic layer was separated and dried over anhydrous sodium sulfate for 2 hours. The sodium sulfate was removed by filtration, the solvent was removed under reduced pressure to yield the crude aminonitrile. The desired material was obtained as an light brown oil (colorless oil, 89% crude yield). $^1$H NMR (500 MHz, DMSO-d$_6$) δ 0.95 (t, J=7.6 Hz, 6H), 1.52 (hex, J=7.2 Hz, 2H), 1.61 (hex, J=7.3 Hz, 2H), 2.39 (br s, 2H); $^{13}$C NMR (125 MHz, DMSO-d$_6$) δ 8.3, 31.9, 54.6, 124.2

To 10 g of concentrated sulfuric acid stirred in an ice cooled water bath was added dropwise a solution of the aminonitrille (41 mmol) in 30 mL CH$_2$Cl$_2$, maintaining the internal temperature at 15° C. Then the bath was removed and the mixture heated to 40° C. for 1 hour. The mixture was cooled in ac ice bath and poured onto 200 g of crushed ice. The mixture was made pH 7-8 with 28% aqueous NH$_3$ and extracted with EtOAc (3×100 mL). The extracts were collected, dried (MgSO$_4$), and evaporated to dryness. The crude solid was recrystallized in EtOAc/Hex. The desired material was obtained as a white foamy solid 0.941 g, 7.23 mmol, 6%. $^1$H NMR (500 MHz, DMSO-d$_6$) δ 0.77 (t, J=7.6 Hz, 6H), 1.29-1.36(m, 2H), 1.57-1.65 (m, 2H), 6.95 (br s, 1H), 7.23 (br s, 1H); $^{13}$C NMR (125 MHz, DMSO-d$_6$) δ 8.2, 32.5, 60.6, 178.2

One equivalent of 1,3-propane was added to a solution of 2-amino-2-ethylpropaneamide (0.941 g, 7.23 mmol). A paste was obtained after the reaction. The paste was dissolved in water and washed with ethyl acetate. The sodium salt was prepared with 1N NaOH and the solution was concentrated to dryness. The crude product was purified by preparative RP-HPLC (Delta Prep pack cartridge C18, 215 nm, 50 mL/min, 0% to 30% MeCN in water containing 0.01% TFA). After freeze-drying, the title compound was obtained as a fine white solid (0.3700 g, 1.47 mmol, 20%). $^1$H NMR (300 MHz, D$_2$O) δ 0.89 (t, J=7.5 Hz, 6H), 1.83 (q, J=7.3 Hz, 4H), 2.05 (qt, J=7.4 Hz, 4H), 2.84-2.86 (m, 2H), 2.99 (t, J=7.3 Hz, 2H); $^{13}$C NMR (75 MHz, D$_2$O) δ 7.4, 23.5, 26.0, 41.5, 48.9, 68.3, 176.9; ES-MS 251 (M−H).

Preparation of 3-[(4-tert-butylbenzyl)amino]-1-propanesulfonic acid (Compound QG)

To a solution of 4-tert-butylbenzylamine (5.0 g, 30.6 mmol) in 25% Toluene/Acetonitrile (30 mL) was added 1,3-propane sultone solution (3.56 g, 29.1 mmol). The solution was stirred at reflux for 4 hours. The reaction mixture was cooled to room temperature. The solid material was collected by filtration and washed with acetone (2×20 mL). The solid was suspended in EtOH (50 mL). The suspension was stirred at reflux for 1 hour. The mixture was cooled to room temperature, the solid material was collected by filtration, washed with acetone (2×20 mL) and dried in a vacuum oven (50° C.), affording the title compound, 7.58 g (91%). $^1$H NMR (DMSO, 500 MHz) δ ppm 8.95 (s (broad), 1H), 7.44 (d, 2H, J=8.3 Hz), 7.38 (d, 2H, J=8.3 Hz), 4.07 (s, 2H), 3.08 (t, 2H, J=6.3 Hz), 2.63 (t, 2H, J=6.5 Hz), 1.96 (m, 2H), 1.27 (s, 9H). $^{13}$C (DMSO, 75 MHz) δ ppm 154.21, 132.32, 132.05, 128.31, 52.77, 52.32, 49.89, 34.17, 24.81. ES-MS 284 (M−1).

Preparation of 3-{[1-(3-methoxyphenyl)propyl]amino}-1-propanesulfonic acid (Compound QH)

To a 0° C. solution of m-Anisaldehyde (27 mL, 22 mmol) in anhydrous tetrahydrofuran (THF, 5 mL) was added dropwise lithium bis(trimethylsilyl)amide (1M solution in THF, 26 mL, 26 mmol). The solution was stirred at 0° C. for 20 minutes before ethylmagnesium bromide (1M solution in THF, 28 mL, 28 mmol) was added via syringe. The reaction mixture was stirred at reflux for 24 hours. After cooling to room temperature, the reaction mixture was poured into a saturated solution of NH$_4$Cl (50 mL). The mixture was extracted with EtOAc (3×75 mL). The organic extracts were combined and concentrated under reduced pressure. The residue was stirred with 3M HCl (40 mL) for 30 minutes. The resulting mixture was extracted with EtOAc (3×40 mL). The combined organic extracts were dried with Na$_2$SO$_4$, filtered, evaporated and dried in vacuo, affording 1-(3-methoxyphenyl)-1-propanamine (2.47 g, 67%).

To a solution of 1-(3-methoxyphenyl)-1-propanamine (2.45 g, 14.8 mmol) in 25% toluene/acetonitrile (15 mL) was added 1,3-propane sultone solution (1.72 g, 14.1 mmol). The solution was stirred at reflux for 4 hours. The reaction mixture was cooled to room temperature. The solid material was collected by filtration and washed with acetone (2×20 mL). The solid was suspended in EtOH (20 mL). The suspension was stirred at reflux for 1 hour. The mixture was cooled to room temperature, the solid material was collected by filtration, washed with acetone (2×20 mL) and dried in a vacuum oven (50° C.), affording the title compound, 3.16 g (78%). $^1$H NMR (D$_2$O, 500 MHz) δ ppm, 7.28 (t, 1H, J=7.9 Hz), 6.90 (m, 3H), 3.98 (m, 1H), 3.69 (m, 3H), 2.89 (m, 1H), 2.74 (m, 3H), 1.89 (m, 4H), 0.63 (t, 2H, J=7.3 Hz). $^{13}$C (D$_2$O, 75 MHz) δ ppm 159.47, 135.45, 130.81, 120.84, 115.32, 113.87, 64.50, 55.72, 48.23, 44.73, 26.14, 21.72, 9.80. ES-MS 286 (M−1).

Preparation of 3-{[2-(2-hydroxyphenyl)-1,1-dimethylethyl]amino}propane-1-sulfonic acid (Compound QI)

The benzyl alcohol (1.2 g, 10 mmol), the tetrabutylammonium fluoride (5 mL, 5 mmol) and the nitro compound (1.78 g, 20 mmol) were placed in a sealed tube and heated at 130° C. for 15 hours. The reaction was cooled and diluted with EtOAc. The resulting solution was washed with water, dried and concentrated to yield a dark oil. Chromatography over silica eluting with Hex:EA 80:20 gave a yellowish solid 0.48 g, 25% yield.

To a stirred solution of the nitro (800 mg, 4.12 mmol) in methanol (20 mL) was added a small spatula of Raney-Ni in water. The suspension was hydrogenated under atmospheric pressure of hydrogen for 15 hours (TLC indicates complete consumption of the starting material) then filtered on celite and concentrated under reduced pressure. The corresponding amine was used as such in the next step.

To a stirred solution of the amine (420 mg, 2.58 mmol) in THF (5 mL) was added 1,3-propane sultone (614 mg, 5.02 mmol). The reaction mixture was stirred at reflux for 15 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 75 mg (10% yield). $^1$H NMR (500 MHz, DMSO-d$_6$) δ 1.17 (s, 6H), 2.00 (m, 2H), 2.64 (m, 2H), 2.85 (s, 2H), 3.12 (m, 2H), 6.70-6.82 (m, 2H), 7.10 (m, 2H), 8.49 (bs, 2H), 9.64 (s, 1H, OH). $^{13}$C NMR (125 MHz, DMSO-d$_6$) δ 23.42, 23.73, 37.98, 41.51, 49.89, 60.54, 115.99, 119.44, 122.09, 128.87, 133.14, 156.30. ES-MS 286 (M−1).

Preparation of 3-[(1-methyl-1-thien-2-ylethyl)amino]-1-propanesulfonic acid (Compound QJ)

CeCl$_3$·7H$_2$O was dried at 140° C.-150° C. for 15 hours. To this solid was added THF (80 mL), and after stirring for 30 minutes the suspension was cooled to −78° C. and to it was added MeLi. After stirring for 30 minutes, 2-thiophencarbonotrile was added dropwise, and the reaction was stirred at −78° C. to −35° C. for 3 hours. Concentrated aqueous $NH_3$ was added (25 mL) and the mixture was warmed to room temperature and filtered through celite. The filtrate was extracted with EtOAc dried (Na2SO4) and concentrated. Column using $CH_2Cl_2MeOH$ (95/05) allowed the isolation of the desired product, 600 mg (23% yield).

To a stirred solution of the amine (500 mg, 3.5 mmol) in pinacolone (7 mL) was added 1,3-propane sultone (427 mg, 3.5 mmol). The reaction mixture was stirred at reflux for 4 hours then cooled to room temperature. The solid was collected by filtration and was washed with THF. The solid was suspended in EtOH (10 mL) and stirred at reflux for 1 hour. The suspension was then cooled to room temperature. The solid was collected by filtration, washed with ethanol and dried under high vacuum to afford the title compound, 800 mg (87%). $^1H$ NMR (500 MHz, $D_2O$) δ 1.70 (s, 6H), 1.85 (m, 2H), 2.75 (t, J=7.0 Hz, 2H), 2.84 (t, J=7.0 Hz, 2H), 7.00 (m, 1H), 7.16 (m, 1H), 7.40 (m, 1H) $^{13}C$ NMR (125 MHz, DMSO-$d_6$) δ 21.75, 25.82, 41.07, 48.07, 59.52, 127.67, 127.90, 127.95. ES-MS 262 (M−1).

Preparation of 3-{[4-(methylsulfonyl)benzyl]amino}-1-propanesulfonic acid (Compound QK)

4-methylsulfonylbenzylamine hydrochloride (2.5 g, 11.8 mmol) was treated with a saturated solution of $K_2CO_3$ (40 mL) and EtOAc (3×40 mL) was added. The organic extracts were combined, dried with $Na_2SO_4$, filtered, evaporated under reduced pressure and dried in vacuo.

To a solution of 4-methylsulfonylbenzylamine (2.11 g, 11.4 mmol) in 25% Toluene/Acetonitrile (15 mL) was added 1,3-propane sultone solution (1.35 g, 10.8 mmol). The solution was stirred at reflux for 4 hours. The reaction mixture was cooled to room temperature. The solid material was collected by filtration and washed with acetone (2×20 mL). The solid was suspended in EtOH (20 mL). The suspension was stirred at reflux for 1 hour. The mixture was cooled to room temperature, the solid material was collected by filtration, washed with acetone (2×20 mL) and dried in a vacuum oven (50° C.), affording the title compound, 3.10 g (91%). $^1H$ NMR ($D_2O$, 300 MHz) δ ppm 7.87 (dd, 2H, J=1.9 Hz, 6.6 Hz), 7.57 (dd, 2H, J=1.9 Hz, 6.6 Hz), 4.22 (s, 2H), 3.12 (m, 3H), 2.84 (t, 2H, J=7.3 Hz), 2.00 (m, 2H). $^{13}C$ ($D_2O$, 75 MHz) δ ppm 139.83, 137.22, 130.92, 128.02, 50.59, 48.17, 46.50, 43.48, 21.69. ES-MS 306 (M−1).

Preparation of (R)-(+)-3-[1-(4-nitrophenyl)ethylamino]-1-propanesulfonic acid (Compound QL)

A solution of 1,3-propane sultone (1M, 5.0 mL) in acetonitrille was added to a solution of (R)-(+)-1-(4-nitrophenyl)ethylamine (0.8185 g, 4.93 mmol) in toluene (10 mL). The mixture was heated to reflux for 24 hours then cooled to 0° C. The solid was collected by suction filtration, rinsed with acetone (2×5 mL). The solid was dried 4 hours at 60° C. in the vacuum oven. The title compound was obtained as a fine white solid (1.14 g, 3.95 mmol, 80%). $^1H$ NMR (300 MHz, DMSO-$d_6$) δ 1.55 (d, J=6.7 Hz, 3H), 1.97 (qt, J=6.5 Hz, 2H), 2.62 (t, J=6.4 Hz, 2H), 2.84 (br s, 1H), 3.05 (br s, 2H), 4.58 (br s, 1H), 7.77 (d, J=8.8 Hz, 1H), 8.31 (d, J=8.8 Hz, 2H), 9.21 (br s, 1H), 9.37 (br s, 1H); $^{13}C$ NMR (75 MHz, DMSO-d6) 19.0, 22.0, 45.2, 49.0, 56.0, 123.8, 128.8, 147.4, 147.4; ES-MS 287 (M-H); $[\alpha]_D$=+37.1°±0.1, c=0.005512, 0.1 N NaOH Preparation of 3-[(1,1-diethylprop-2-enyl)amino]-1-propanesulfonic acid (Compound QM)

A solution of triethyl phosphonoacetate (11.4 g, 50.8 mmol) in ether (50 mL) was added dropwise to a suspension of sodium hydride (60% in oil, 2.20 g, 55 mmol) in ether (100 mL) at 0° C. The mixture was stirred 1 hour at room temperature. The clear solution was cooled again to 0° C. and a solution of 3-pentanone (5.85 mL, 55 mmol) in ether (20 mL) was added dropwise over 20 minutes. The mixture was then heated overnight at reflux. The liquid from the flask was decanted to leave the phosphate sodium salt behind. The solid was rinsed with ether (3×20 mL). The combined organic phase was rinsed with water (1×20 m), 1N NaOH (1×20 mL) and brine (1×20 mL). The organic layers was dried over sodium sulfate and the solution was concentrated to an oil under reduced pressure. The crude residue was flash chromatographied on a 70 g silica gel cartridge on a Biotage system to afford the desire material as a clear oil (5.37 g, 34.4 mmol, 68% yield, about 90% pure: some phosphonate). $^1H$ NMR (500 MHz, $CDCl_3$) δ 1.069 (t, J=7.3 Hz, 3H), 1.073 (t, J=7.6 Hz, 3H), 2.190 (q, J=7.5 Hz, 1H), 2.192 (q, J=7.5 Hz, 1H), 2.62 (q, J=7.6 Hz, 2H), 4.15 (qt, J=7.2 Hz, 2H), 5.60 (s, 1H); $^{13}C$ NMR (75 MHz, $CDCl_3$) δ 12.2, 13.2, 14.5, 25.6, 30.9, 59.5, 113.5, 166.3, 167.0.

A solution of 3-Ethyl-2-pentenoic acid ethyl ester (5.30 g, 34 mmol) in ether (40 mL) was added dropwise over 20 minutes to an ico-cold suspension of LAH (1.5 g) in ether (150 g). The mixture was stirred for 5 minutes at 0° C. The mixture was quenched with methanol then a saturated sodium tartrate solution was added. The layers were separated and the organic layer was dried over sodium sulfate, concentrated to dryness. The crude alcohol obtained was flashed on a 70 g silica gel cartridge (Bioatge) using 20 to 30% ether in hexane. The desired product was obtained as a clear oil, 1.55 g, 14.5 g, 43%. $^1H$ NMR (500 MHz, $CDCl_3$) δ 0.96-1.03 (m, 6H), 1.36 (m, 1H), 2.07-2.12 (m, 4H), 4.17 (d, J=6.8 Hz, 2H), 5.36 (t, J=7.1 Hz, 1H); $^{13}C$ NMR (75 MHz, $CDCl_3$) δ 12.6, 13.9, 23.7, 29.2, 59.1, 121.3, 147.1.

A dry, 50-mL, three-necked flask was equipped with a magnetic stirring bar, a pressure-equalizing dropping funnel, a thermometer, and a nitrogen inlet tube. The apparatus was flushed with nitrogen and charged with 55 mg of sodium hydride dispersed in mineral oil and 3 mL of hexane. The suspension was stirred, and the hydride was allowed to settle. The hexane was removed with a long dropping pipette, 8 mL of anhydrous diethyl ether was added, and a solution of 8.55 g. (0.0993 mole) of 3-ethyl-2-pentenol in 3 mL of anhydrous ether was added over 5 minutes. After the evolution of hydrogen ceased, the reaction mixture was stirred for an additional 15 minutes. The clear solution was cooled to −10° C. in an ice-salt bath. Trichloroacetonitrile (1.35 ml, 13.4 mmole) was added dropwise to the stirred solution, while the reaction temperature was maintained below 00. Addition was completed within 15 minutes, and the reaction mixture was allowed to warm to room temperature. The light amber mixture was poured into a 100 mL, round-bottomed flask, and the ether was removed with a rotary evaporator. Hexane [20 mL, containing a drop of methanol] was added, the mixture was shaken vigorously for 1 minute, and a small amount of dark, insoluble material was removed by gravity filtration. The residue is washed two times with hexane (10 mL total), and the combined filtrate is concentrated with a rotary evaporator.

A 100-mL, round-bottomed flask was charged with the imidate and 40 mL of xylene. The solution is refluxed for 8 hours. After cooling to room temperature the dark xylene solution was filtered through a short column packed with silica gel (20 g) and toluene. The column was eluted with an additional 40 mL of toluene, and the combined light yellow eluant was concentrated with a rotary evaporator.

To the crude product was added 60 ml. of ethanol and 60 ml. of aqueous 6 N sodium hydroxide. The air was replaced with nitrogen, and the solution was stirred at room temperature for 40 hours. Ether (300 mL) is added, the organic layer is separated, and the aqueous layer is washed twice with 50 mL of ether.

After extraction in ether (5×20 mL), the crude amine was back extracted in 6N HCl (2×20 mL). The combined organic extract were washed with ether (1×100 mL). The acid solution was adjusted to pH 12 with 50% NaOH. The basic aqueous layer was extracted with ether (2×50 mL). A solution of 2M HCl in ether (100 mL) was added and the amine hydrochloride solution was concentrated to dryness. The amine hydrochloride was dissolved in a minimum of hot methanol (4 mL) and was poured into ether (50 mL). The amine was collected by filtration and dried in vacuo. The pure amide hydrochloride was obtained in two crops (0.67 g, 4.48 mmol, 34%). The amine was dissolved in water and the solution was made to pH 12 with 50% NaOH. The amine was extracted with toluene (1×5 mL) then MTBK (2×5 mL), dried over potassium carbonate (20 minutes). NMR data on the amine hydrochloride: $^1$H NMR (500 MHz, $D_2O$) δ 0.91 (t, J=7.6 Hz, 6H), 1.74-1.79 (m, 4H), 5.22 (d, J=17.6 Hz, 1H), 5.40 (d, J=11.2 Hz, 1H), 5.85 (dd, J=18.1 and 11.2 Hz, 1H); $^{13}$C NMR (75 MHz, $D_2O$) δ 12.6, 13.9, 23.7, 29.2, 59.1, 121.3, 147.1

The 1,3-propane sultone (0.40 mL, 4.5 mmol) was added to a solution of to a solution of 1,1-diethylprop-2-enylamine (4.48 mmol) in 20% MTBK/toluene (15 mL). The mixture was heated to reflux for 20 hours then was cooled to 0° C. The solid was collected by suction filtration, rinsed with acetone (2×5 mL). The solid was dried 6 hours at 60° C. in the vacuum oven. The title compound was obtained as a white solid (0.58 g, 2.46 mmol mmol, 55%, 5% overall). $^1$H NMR (300 MHz, DMSO-$d_6$) δ 0.82 (t, J=7.5 Hz, 6H), 1.69 (non, J=7.3 Hz, 4H), 1.99 (qt, J=6.4 Hz, 2H), 2.65 (t, J=6.4 Hz, 2H), 2.87-2.90 (m, 2H), 5.35 (d, J=17.6 Hz, 1H), 5.48 (d, J=11.1 Hz, 1H), 5.75 (dd, J=17.6 and 11.1 Hz, 1H), 8.71 (br s, 2H); $^{13}$C NMR (75 MHz, DMSO-$d_6$) 67.1, 22.1, 24.2, 41.2, 64.5, 119.7, 136.0; ES-MS 234 (M–H).

Preparation of
4-(tert-butylamino)-1-phenyl-2-butanesulfonic acid
(Compound QN)

To a –78° C. solution of 1,3-propane sultone (1 eq) in anhydrous tetrahydrofuran (THF, 1.8 M) was added butyl lithium (2.5 M in hexanes, 1.5 eq). The solution was stirred at –78° C. for 0.5 hours before benzyl bromide (1 eq diluted with THF) was added via syringe pump over 0.5 hours period. The reaction mixture was stirred at –78° C. for 2 hours. The reaction mixture was warmed up to 0° C. before water (100 mL) was slowly added. The organic layer was recovered and diluted with EtOAc (20 mL). The solution was dried with $Na_2SO_4$, filtered and evaporated under reduced pressure. The product was purified on a silica gel pad (90% Hex/EtOAc to 60% Hex/EtOAc) affording the resulting 1-Benzyl-1,3-propane sultone.

To a solution of 1-Benzyl-1,3-propane sultone (1 eq) in 25% Toluene/Acetonitrile (0.8 M) was added Tert-Butylamine (1.05 eq). The solution was stirred at reflux for 4 hours. The reaction mixture was cooled to room temperature. The solid material was collected by filtration and washed with acetone (2×20 mL). The solid material was suspended in EtOH. The suspension was stirred at reflux for 1 hour. The mixture was cooled to room temperature, the solid material was collected by filtration, washed with acetone (2×20 mL) and dried in a vacuum oven (50° C.), affording the title compound. $^1$H NMR ($D_2O$, 500 MHz) δ ppm 7.23 (m, 5H), 3.28 (dd, 1H, J=3.7 Hz, 13.9 Hz), 3.06 (m, 1H), 2.87 (m, 1H), 2.58 (m, 2H), 1.90 (m, 1H), 1.76 (m, 1H), 1.06 (s. 9H). $^{13}$C ($D_2O$, 125 MHz) δ ppm 138.09, 129.45, 129.13, 127.25, 59.41, 57.09, 39.49, 36.11, 26.40, 24.90. ES-MS 284 (M–1).

Preparation of
1-(tert-butylamino)hex-5-ene-3-sulfonic acid
(Compound QO)

To a –48° C. solution of 1,3-propane sultone (5.0 g, 41 mmol) in anhydrous tetrahydrofuran (THF, 150 mL) was added butyl lithium (2.5 M in hexanes, 18 mL, 45 mmol). The solution was stirred at –78° C. for 30 minutes before benzyl bromide (3.5 mL, 41 mmol) was added via syringe pump over a 30 minute period. The reaction mixture was stirred at –48° C. for 2 hours. The reaction mixture was warmed up to 0° C. before water (100 mL) was slowly added. The organic layer was recovered and diluted with EtOAc (20 mL). The solution was dried with $Na_2SO_4$, filtered and evaporated under reduced pressure. The product was purified on a silica gel column (90% Hex/EtOAc to 70% Hex/EtOAc) affording the corresponding 1-allyl-1,3-propane sultone (3.03 g, 46%).

To a solution of Tert-Butylamine (1.43 g, 19.6 mmol) in 25% Acetonitrile/Toluene (20 mL) was added 1-allyl-1,3-propane sultone (3.03 g, 18.6 mmol) in 25% Acetonitrile/Toluene (5 mL). The solution was stirred at reflux for 4 hours. The solution was stirred at reflux for 4 hours. The reaction mixture was cooled to room temperature. The solid material was collected by filtration and washed with acetone (2×15 mL). The solid material was suspended in EtOH (25 mL). The suspension was stirred at reflux for 1 hour. The mixture was cooled to room temperature, the solid material was collected by filtration, washed with acetone (2×15 mL) and dried in a vacuum oven (50° C.), affording the title compound, 3.97 g (90%). $^1$H NMR ($D_2O$, 500 MHz) δ ppm 5.71 (m, 1H), 5.04 (m, 2H), 3.05 (m, 2H), 2.85 (m, 1H), 2.53 (m, 1H), 2.20 (m, 1H), 1.90 (m, 2H), 1.20 (s. 9H). $^{13}$C ($D_2O$, 125 MHz) δ ppm 132.26, 116.10, 55.15, 55.02, 37.15, 31.97, 24.08, 22.82. ES-MS 234 (M–1).

Preparation of 4-amino-1-phenyl-2-butanesulfonic acid (Compound QQ)

To a –78° C. solution of 1,3-propane sultone (1 eq) in anhydrous tetrahydrofuran (THF, 1.8M) was added butyl lithium (2.5 M in hexanes, 1.5 eq). The solution was stirred at –78° C. for 30 minutes before benzyl bromide (1 eq diluted with THF) was added via syringe pump over a 30 minute period. The reaction mixture was stirred at –78° C. for 2 hours. The reaction mixture was warmed up to 0° C. before water (100 mL) was slowly added. The organic layer was recovered and diluted with EtOAc (20 mL). The solution was dried with $Na_2SO_4$, filtered and evaporated under reduced pressure. The product was purified on a silica gel pad (90% Hex/EtOAc to 60% Hex/EtOAc) affording the corresponding 1-Benzyl-1,3-propane sultone.

To 0° C. ammonium hydroxide (28-30% $NH_3$, 50 eq) was added via syringe pump over a 4 hours period a solution of 1-Benzyl-1,3-propane sultone (1 eq) in tetrahydrofuran (0.8 M). The solution was stirred at 0° C. for an additional 30 minutes. The solvent was co-evaporated with EtOH. The solid was suspended in EtOH. The mixture was stirred at reflux for 1 hour. After cooling to room temperature, the solid material was collected by filtration, washed with EtOH (2×20 mL) and dried in a vacuum oven (50° C.), affording the title compound (57%). $^1$H NMR (500 MHz, $D_2O$) δ (ppm) 1.77 (m, 1H), 1.89 (m, 1H), 2.57 (t, 1H, J=10.5 Hz), 2.76 (m, 1H), 2.94 (m, 1H), 3.05 (m, 1H), 3.23 (dd, 1H, J=4.1 Hz, 13.9 Hz), 7.22 (m, 5H); $^{13}$C NMR (125 MHz, D$_2$O) δ (ppm) 26.89, 36.05, 37.79, 59.42, 127.12, 129.03, 129.48, 138.16; ES-MS 230 (M+H).

Preparation of 1-aminohex-5-ene-3-sulfonic acid (Compound QR)

To a −78° C. solution of 1,3-propane sultone (5.0 g, 41 mmol) in anhydrous tetrahydrofuran (THF, 150 mL) was added butyl lithium (2.5 M in hexanes, 18 mL, 45 mmol). The solution was stirred at −78° C. for 30 minutes before Allyl bromide (3.5 mL, 41 mmol) was added via syringe pump over a 30 minute period. The reaction mixture was stirred at −48° C. for 2 hours. The reaction mixture was warmed up to 0° C. before water (100 mL) was slowly added. The organic layer was recovered and diluted with EtOAc (20 mL). The solution was dried with Na$_2$SO$_4$, filtered and evaporated under reduced pressure. The product was purified on a silica gel column (100% Hexanes to 80% Hex/EtOAc) affording the corresponding 1-allyl-1,3-propane sultone (5.76 g, 43%).

To 0° C. ammonium hydroxide (28-30% NH$_3$, 230 mL, 1.8 mol), a solution of 1-allyl-1,3-propane sultone (6.66 g, 0.041 mol) in tetrahydrofuran (25 mL) was added via syringe pump over a 4 hour period. The solution was stirred at 0° C. for an additional 30 minutes. The solvent was co-evaporated with EtOH. The solid was suspended in acetone, collected by filtration and dried in a vacuum oven (50° C.), affording the title compound, 4.96 g (68%). $^1$H NMR (D$_2$O, 500 MHz) δ ppm 5.73 (m, 1H), 5.01 (m, 2H), 3.06 (m, 2H), 2.85 (m, 1H), 2.54 (m, 1H), 2.20 (m, 1H), 1.93 (m, 2H). $^{13}$C (D$_2$O, 125 MHz) δ ppm 134.42, 118.26, 57.24, 37.63, 34.20, 26.95. ES-MS 180 (M+1).

Preparation of (R)-(−)-3-(1-methylpropylamino)-1-propanesulfonic acid (Compound QS)

A solution of 1,3-propane sultone (9.35 g, 75 mmol, Avocado A11923 lot D14N12) in toluene (50 mL, Fisher T290-4, lot 041983) was added to a solution of (R)-(−)-2-butylamine (5.45 g, 74 mmol, Lancaster 3889 lot FA018393) in acetone (25 mL, EMD AX0115-1, lot 44215432). The mixture was heated to reflux for 24 hours. The mixture was cooled to 0° C., and the solid was collected by suction filtration, rinsed with acetone (2×10 mL) and dried under vacuum (13.28 g). The solid was suspended in ethanol (60 mL, ADSQ-7, lot 5730) and the suspension was heated to reflux. Water (0.1 mL) was then added to afford a clear solution. The mixture was slowly cooled to 0° C. and the solid was collected by suction filtration, rinsed with ethanol (2×10 mL) and dried 20 hours at 60° C. in the vacuum oven. The title compound was obtained as a fine white solid (10.51 g, 53.82 mmol, 73%). $^1$H NMR (300 MHz, D$_2$O) δ 0.92 (t, J=7.6 Hz, 3H), 1.28 (d, J=6.3 Hz, 3H), 1.48-1.63 (m, 1H), 1.71-1.85 (m, 1H), 2.10 (q, J=7.7 Hz, 2H), 3.00 (t, J=7.3 Hz, 2H), 3.11-3.29 (m, 3H); $^{13}$C NMR (75 MHz, D$_2$O) δ 9.2, 15.3, 21.9, 26.0, 43.6, 48.2, 56.2; ES-MS 194 (M−H); [α]$_D$=−1.2±0.1 (c=0.0157, H$_2$O).

Preparation of (1E,3S)-3-amino-4-phenylbut-1-ene-1-sulfonic acid (Compound QT)

n-BuLi ((24 mL, 60 mmol, 2.5M in THF) was added at −78° C. to a solution of methanesulfonate (4.17 mL, 40.3 mmol). The mixture was stirred for 15 minutes then chlorophosphonate was added dropwise. The reaction was allowed to slowly warm to room temperature overnight. NH$_4$Cl solution was added and the reaction was extracted with EtOAc. The organic layer was washed with brine, dried (Na$_2$SO$_4$) and concentrated. The crude was purified by column using Hex: EtOAc 50/50 to obtain 2.5 g (50% yield) of the desired product. $^1$H NMR (CDCl$_3$, 500 MHz) δ 1.37 (t, J=7.0 Hz, 6H), 1.44 (t, J=7.0 Hz, 3H), 3.71 (d, J=17.0 Hz, 2H), 4.23 (m, 4H), 4.43 (q, J=2H).

Dibal (39 mL, 1M solution in cyclohexane) was added slowly within two hours to a cold (−78° C.) solution of ester (7.2 g, 25.77 mmol) in CH$_2$Cl$_2$ (60 mL). After the end of the addition, the reaction was left stirring at −78° C. for one additional hour before it was quenched carefully with MeOH at −78° C. To the resulting white emulsion was added HCl (1M) (170 mL) and the mixture was stirred for 15 minutes and the aqueous mixture was extracted with CH$_2$Cl$_2$. The combined organic layers were dried over Na$_2$SO$_4$, filtered and concentrated. The crude product was purified by column using Hexanes:EtOAc 70:30 to afford the aldehyde as a white solid 5 g (78% yield).

To a suspension of NaH (173 mg, 7.23 mmol) in THF (5 mL) was added dropwise a solution of phosphonate (2.55 g, 9.46 mmol) in THF (40 mL) at 0° C. After the end of the addition the reaction was stirred for 15 minutes then the aldehyde (1.2 g, 4.82 mmol) was added in one portion. The reaction mixture was stirred at room temperature for 30 minutes before being quenched with H$_2$O and EtOAc. The organic layer was dried over Na$_2$SO$_4$, filtered and concentrated. The crude product was purified by column using Hex: EtOAc 90:10 - - - 70:30 to afford 1.6 g (93%) of the desired product. $^1$H NMR (CDCl$_3$, 500 MHz) δ 1.1.32 (m, 12H0, 3.00 (m, 2H), 4.05 (m, 2H), 4.60 (m, 1H), 4.70 (bs, 1H), 6.12 (m, 1H), 6.85 (m, 1H), 7.15-7.40 (m, 5H).

A solution of the sulfonate (800 mg, 2.25 mol) in a mixture of formic acid/water (5 mL/0.2 mL) was heated at reflux for 48 hours then concentrated under reduced pressure. EtOH (15 mL) was added under vigorous stirring with heating at reflux for 30 minutes. The suspension was cooled then diluted with acetone (5 mL) and filtered. The white solid was washed with EtOH and Et$_2$O then dried under high vacuum to obtain 420 mg (82% yield). $^1$H NMR (D$_2$O, 500 MHz) δ 2.94 (d, J=7.3 Hz, 2H), 4.10 (m, 1H), 6.33 (m, 2H), 7.10-7.32 (m, 5H). $^{13}$C (D$_2$O, 125 MHz) δ 38.53, 52.82, 127.77, 129.10, 129.71, 132.70, 134.50. ES-MS 226 (M−1).

Preparation (3S)-3-amino-4-phenylbutane-1-sulfonic acid (Compound QU)

To a stirred solution of the sulfonate (1.4 g, 3.94 mmol) in MeOH was added Pd/C (300 mg). The suspension was stirred under H$_2$ pressure for 3 hours then filtered on celite and the filtrate was concentrated to afford a white solid 1.2 g, 86% yield. $^1$H NMR (CDCl$_3$, 500 MHz) δ 1.34 (t, J=7 Hz, 3H), 1.39 (s, 9H), 1.83 (m, 1H), 2.10 (m, 1H), 2.80 (m, 2H), 3.15 (m, 2H), 3.90 (m, 1H), 4.23 (q, J=7.0 hz, 2H), 4.40 (bd, NH), 7.14-7.30 (m, 5H).

A solution of the sulfonate (1.3 g, 3.63 mol) in a mixture of formic acid/water (8 mL/0.4 mL) was heated for 3 days then concentrated under reduced pressure. EtOH (15 mL) was added under vigorous stirring with heating at reflux for 30 minutes. The suspension was cooled then diluted with acetone (5 mL) and filtered. The white solid was washed with EtOH and Et$_2$O then dried under high vacuum to obtain 700 mg (84% yield). $^1$H NMR (D$_2$O, 500 MHz) δ 2.00 (m, 2H), 2.70 and 2.95 (ABX, J=15.0 and 8.0 Hz, 2H), 2.88 (m, 2H), 3.55 (m, 1H), 7.14-7.30 (m, 5H). $^{13}$C (D$_2$O, 125 MHz) δ 27.82, 38.18, 47.29, 52.25, 127.70, 129.22, 129.48, 135.33. ES-MS 228 (M−1).

Preparation of 3-{[1-(3-fluorophenyl)propyl]amino}-1-propanesulfonic acid (Compound QV)

Borane solution (120 mL 1M in THF) was added dropwise to a solution of amino-acid (5 g, 48.54 mmol) in THF (100 mL) and the reaction mixture was heated at reflux for 15 hours. The reaction was quenched carefully with MeOH then concentrated under reduced pressure. It was rediluted with MeOH and concentrated HCl then heated at reflux for one hour and concentrated under reduced pressure. The residue (~6 g) was dried under pump vacuum to afford an oil. $^1$H NMR (300 MHz, $D_2O$) δ 0.81 (d, J=7.0 Hz, 3H), 1.88 (m, 1H), 2.75 & 2.92 (ABX, J=14.0 & 7.0 Hz, 2H), 3.53 &3.45 (ABX, J=14.0 and 7.0 Hz, 2H).

A solution of the crude amino-alcohol (6 g, 48 mmol) in anhydrous $CHCl_3$ was saturated with HCl(g) and then treated dropwise at reflux with $SOCl_2$. After the addition was completed, precipitation of a white solid occurred. After refluxing for 1 hour, the reaction mixture became clear. The reaction was concentrated to yield a colorless syrup which did not precipitate by trying different solvent systems. $^1$H, $^{13}$C NMR and MS showed a mixture of at least two products including the desired chloride.

A solution of the crude chloride in water (5 mL) was added dropwise to a refluxed solution of $N_2SO_3$ (8 g, 63.5 mmol) in water (25 mL). After the end of the addition, the reaction was stirred at reflux for 20 minutes then cooled down and concentrated under reduced pressure. 16 mL of HCl (conc) were added to dissolve the aminosulfonic acid and precipitate the inorganic salts which were removed by filtration. The filtrate was concentrated, then ethanol was added to cause amino sulfonic acid to appear as white solid which was collected by filtration. It was washed with EtOH and $Et_2O$, then dried under high vacuum to obtain 1.9 g of a white solid (25% yield over three steps). $^1$H NMR (500 MHz, $D_2O$) δ 1.05 (d, J=7.0 Hz, 3H), 2.27 (m, 1H), 2.84 & 2.88 (ABX J=15.0 and 7.0 Hz, 2H), 2.86 & 3.10 (ABX, J=15.0 and 7.0 Hz, 2H). $^{13}$NMR (125 MHz, $D_2O$) 617.26, 28.90, 44.49, 54.99. ES-MS 152 (M–1).

Preparation of 4-(2-aminoethyl)hepta-1,6-diene-4-sulfonic acid (Compound N2)

To a –48° C. solution of 1,3-propane sultone (5.0 g, 41 mmol) in anhydrous THF (150 mL) was added butyl lithium (2.5 M in hexanes, 18 mL, 45 mmol). The solution was stirred at –78° C. for 0.5 hours before allyl bromide (3.5 mL, 41 mmol) was added via syringe pump over 0.5 hour period. The reaction mixture was stirred at –48° C. for 2 hours. The reaction mixture was warmed to 0° C. before water (100 mL) was slowly added. The organic layer was recovered. The aqueous layer was extracted with EtOAc (3×100 mL). The organic extracts were combined, dried over $Na_2SO_4$, filtered and evaporated under reduced pressure. The product was purified on a silica gel column (90% Hexanes/EtOAc to 70% Hexanes/EtOAc), affording the corresponding 1,1-diallyl-1,3-propane sultone (0.73 g).

To an aqueous solution of ammonium hydroxide (28-30% $NH_3$, 21 mL, 180 mmol) at 0° C. was added a solution of 1,1-diallyl-1,3-propane sultone (0.73 g, 3.6 mmol) in THF (5 mL) via syringe pump over a 4 hour period. The solution was stirred at 0° C. for an additional 0.5 hours. The solvent was co-evaporated with EtOH. The residue was dissolved in water (15 mL) before the solution was extracted with EtOAc (3×15 mL). The aqueous phase was recovered and evaporated to dryness and lyophilized, affording the title compound (493 mg, 63%). $^1$H NMR (500 MHz, $D_2O$) δ ppm 5.81 (m, 2H), 5.04 (m, 4H), 3.08 (m, 2H), 2.37 (t, 4H, J=8.3 Hz), 1.86 (m, 2H); $^{13}$C ($D_2O$, 125 MHz) δ ppm 133.40, 119.81, 62.21, 38.38, 35.86, 31.97; ES-MS 217 (M–1).

Preparation of 3-(1,1-dimethyl-2-methoxy-2-oxoethyl)amino-1-propanesulfonic acid (Compound N3)

Methyl α-aminoisobutyrate hydrochloride (10.0 g, 65.1 mmol) was treated with a saturated aqueous solution of $K_2CO_3$ (50 mL) and EtOAc (3×50 mL). The organic extracts were combined, dried over $Na_2SO_4$, evaporated under reduced pressure and dried in vacuo to give methyl α-aminoisobutyrate.

To a solution of methyl α-aminoisobutyrate (3.58 g, 30.6 mmol, from step 1) in a solvent mixture of toluene and acetonitrile (40 mL, v/v=1:3) was added 1,3-propane sultone (3.56 g, 29.1 mmol). The solution was stirred at reflux overnight. The reaction mixture was cooled to room temperature. The solid was collected by filtration, washed with acetone (2×25 mL) and dried in a vacuum oven (50° C.), affording the title compound (6.35 g, 87%); $^1$H NMR ($D_2O$, 500 MHz) δ ppm 3.87 (s, 3H), 3.24 (t, 2H, J=7.3 Hz), 3.03 (t, 2H, J=7.3 Hz), 2.17 (m, 2H), 1.62 (s, 6H); $^{13}$C ($D_2O$, 125 MHz) δ ppm 172.44, 62.64, 54.21, 48.12, 42.16, 22.01, 21.47; ES-MS 238 (M–1).

Preparation of 3-amino-2-benzyl-1-propanesulfonic acid (Compound N4)

To a cold (–78° C.) solution of 3-hydroxypropionitrile (1 g, 14.06 mmol) in THF (30 mL), was added a solution of lithium bis(trimethylsilyl)amide (1 M in THF, 28 mL). After the reaction mixture was stirred for 1 h at –78° C., benzyl bromide (1.67 mL, 14.06 mmol) was added dropwise and the reaction mixture was warmed to reach 0° C. at which temperature the mixture was stirred overnight. The reaction was quenched with 1N HCl and extracted with EtOAc. The organic layer was washed with 1N HCl, dried over $Na_2SO_4$ and concentrated. The residue was applied on silica gel column (eluant:Hexanes:EtOAc 70:30 to 50:50) to afford 1.3 g (69%) of the 2-benzyl-3-hydroxypropionitrile. $^1$H NMR (300 MHz, $CDCl_3$) δ 2.80 (bs, 1H), 2.95 (m, 3H), 3.77 (m, 2H), 7.20-7.35 (m, 5H); $^{13}$C NMR (125 MHz, $CDCl_3$) δ 34.71, 37.03, 61.98, 120.78, 127.58, 129.06, 129.25, 136.71. The dialkylated product was isolated in 8.5% yield.

To a solution of 2-benzyl-3-hydroxypropionitrile (obtained in step 1, 3 g, 24.75 mmol) in EtOH (60 mL) was added an aqueous solution of $NH_4OH$ (30%, 20 mL), followed by Ra—Ni (3 g). The suspension was stirred under atmosphere $H_2$ pressure for 15 hours and then filtered. The filtrate was concentrated under high vacuum; and the residual product (3-1mino-2-benzyl-1-propanol) was used in the next step without purification.

A solution of the crude 3-amino-2-benzyl-1-propanol (4.5 g, 27.23 mmol) in anhydrous $CHCl_3$ (24 mL) was saturated with HCl (g), and then $SOCl_2$ (5.2 mL, 71.0 mmol) was added dropwise at reflux. The reaction was maintained under reflux for an additional 2 hours. The reaction was then concentrated to yield a syrupy product. The crude 3-chloro-2-benzyl-1-propylamine thus obtained was used in the next step without further purification.

A solution of the crude 3-chloro-2-benzyl-1-propylamine (obtained in step 3) in water (10 mL) was added dropwise to a solution of $Na_2SO_3$ (6.8 g, 54.46 mmol) in water (25 mL) under reflux. After the end of the addition, the reaction was stirred at reflux for 1 hour, then cooled down and concentrated under reduced pressure. HCl (conc. 16 mL) were added to dissolve the aminosulfonic acid and precipitate the inorganic salts which were removed by filtration. The filtrate was concentrated; and ethanol was added. The title amino sulfonic acid was precipitated as white solid which was collected by filtration, washed with EtOH and Et$_2$O, then dried under high vacuum to give a white solid (1.87 g, 30% yield over three steps). $^1$H NMR (500 MHz, D$_2$O) δ 2.52 (m, 1H), 2.8 (m, 2H), 2.94 (m, 2H), 3.08 & 3.18 (ABX, J=13.0 & 7.0 Hz, 2H), 7.25-7.37 (m, 5H). $^{13}$C NMR (125 MHz, D$_2$O) δ 35.47, 37.78, 42.67, 52.55, 127.15, 129.09, 129.54, 138.32. ES-MS 228 (M−1).

Preparation of 1-aminopentane-3-sulfonic acid
(Compound N5)

To a −78° C. solution of 1,3-propane sultone (5.0 g, 41.0 mmol) in anhydrous THF (150 mL) was added butyl lithium (2.5 M in hexanes, 18 mL, 45 mmol). The solution was stirred at −78° C. for 0.5 h before iodoethane (3.3 mL, 41 mmol) was added via syringe pump over 0.5 hour period. The reaction mixture was stirred at −78° C. for 4 hours. The reaction mixture was warmed up to 0° C. before water (100 mL) was slowly added. The organic layer was recovered. The aqueous layer was extracted with EtOAc (3×100 mL). The organic extracts were combines, dried over Na$_2$SO$_4$, and evaporated under reduced pressure. The residual material was purified on a silica gel column (Hexanes/EtOAc from v/v=9:1 to v/v=8:2), affording the 1-ethyl-1,3-propane sultone (3.19 g, 52%).

To a 0° C. aqueous solution of ammonium hydroxide (28-30%, 153 mL, 1.31 mol) was added via syringe pump over a 4 hour period a solution of 1-ethyl-1,3-propane sultone (3.19 g, 26.4 mmol) in THF (26 mL). The solution was stirred at 0° C. for 3 hours and at room temperature overnight. The solvent was co-evaporated with EtOH. The solid material was treated acetone (150 mL), collected by filtration, and dried in a vacuum oven (50° C.), affording the title compound (2.96 g, 67%); $^1$H NMR (D$_2$O, 500 MHz) δ ppm 3.21 (m, 2H), 2.83 (m, 1H), 2.09 (m, 2H), 1.93 (m, 1H), 1.63 (m, 1H), 1.03 (t, 3H, J=7.3 Hz); $^{13}$C (D$_2$O, 125 MHz) δ ppm 59.39, 37.75, 26.90, 22.87, 10.69; ES-MS 166 (M−1).

General Procedure for the Synthesis of Compounds Starting from β-Amino Acids.

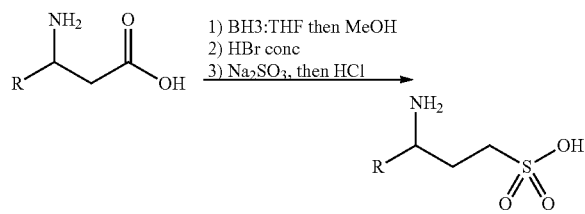

A solution of borane:tetrahydrofurane complex (1M, 3-4 mL per mmol=3-11 equiv. of β-amino acid) was added dropwise over a period of 1 hour to a cold (0° C.) suspension of beta amino acid (1 equiv.) in THF (1 mL per mmol). The mixture was stirred 20 minutes at room temperature at the end of the addition. It was then heated at reflux for 22 hours. The mixture was then cooled to 0° C.; and methanol (2 mL per mmol) was added over a period of 30 minutes. The mixture was then heated at reflux for 20 minutes and concentrated to a thick oil. The oil was co-evaporated with methanol (3×200 mL). The solid obtained was dried in vacuo to afford the coresponding 3-substituted 3-amino-1-propanol derivative as a white waxy solid (quantitative yield).

An aqueous solution of HBr (48%, 2 mL per equiv. of the alcohol) was added slowly to a flask containing a 3-substituted 3-amino-1-propanol (1 equilv.). The mixture was heated at reflux for 6 hours, and then concentrated to dryness. The crude material was used directly in the next step.

The 1-substituted 3-bromo-1-propylamine hydrobromide (obtained in step 2) was added to a solution of sodium sulfite (1.0 equiv. of the 1-substituted 3-bromo-1-propylamine) in water and 1,4-dioxane. The mixture was heated under reflux for 6 h then concentrated to dryness. The residual material was treated with concentrated HCl. The inorganic material was removed by filtration; and the filtrate was treated ethanol, causing precipitation of the corresponding sulfonic acid. The crude sulfonic acid was suspended in ethanol and the mixture was heated at reflux for 1 hour. After cooling to room temperature, the solid material was collected by filtration, rinsed with ethanol and dried overnight in the vacuum oven at 60° C., giving the corresponding 3-substituted 3-amino-1-propanesulfonic acid as a fine white crystalline solid.

3-amino-1-butanesulfonic acid, (Compound N6)

Overall yield 5.4% (0.29 g); NMR (500 MHz, D$_2$O) δ 1.22 (d, J=6.8 Hz, 3H), 1.85-1.93 (m, 1H), 1.99-2.06 (m, 1H), 2.86-2.96 (m, 2H), 3.04-3.44 (m, 1H); $^{13}$C (125 MHz, D$_2$O) δ 17.6, 29.5, 46.9, 47.3; ES-MS 152 (M−1)

3-amino-3-cyclohexyl-1-propanesulfonic acid,
(Compound N10)

Overall yield 60% (14.5 g); $^1$H NMR (500 MHz, D$_2$O) δ 0.87-1.04 (m, 3H), 1.07-1.17 (m, 2H), 1.47-1.65 (m, 6H), 1.84-1.92 (m, 1H), 1.99-2.06 (m, 1H), 2.81-2.91 (m, 2H), 3.11-3.15 (m, 1H); $^{13}$C (125 MHz, D$_2$O) 625.0, 25.5, 25.6, 25.7, 27.4, 28.2, 39.1, 47.2, 55.5; ES-MS: 220 (M−1)

3-amino-1-heptanesulfonic acid, (Compound N16)

Overall yield 48% (3.1 g); $^1$H NMR (500 MHz, D$_2$O) δ 0.73 (t, J=5.9 Hz, 3H), 1.20 (very br s, 4H), 1.46-1.57 (m, 2H), 1.87-1.99 (m, 2H), 2.86 (t, J=7.8 Hz, 2H), 3.26-3.31 (m, 1H); $^{13}$C (125 MHz, D$_2$O) δ 14.1, 21.8, 26.4, 27.4, 31.3, 47.0, 50.8; ES-MS (M−1)

3-amino-5-methyl-1-hexanesulfonic acid,
(Compound N17)

$^1$H NMR (500 MHz, D$_2$O) δ 0.76-0.77 (m, 6H), 1.37 (oct, J=7.4 Hz, 2H), 1.54 (hep, J=6.8 Hz, 1H), 1.92 (dec, J=7.3 Hz, 2H), 2.84-2.90 (m, 2H), 3.56 (qt, J=6.7 Hz, 1H); $^{13}$C (125 MHz, D$_2$O) δ 21.3, 31.8, 23.9, 27.9, 41.0, 46.9, 49.1; ES-MS 194 (M−1)

Preparation of 3-cycloheptylmethyl-1-propansulfonic acid
(Compound N7)

A solution of 1,3-propane sultone (1.20 g, 9.5 mmol) in toluene (6 mL) was added to a solution of cycloheptanemethylamine (1.19 g, 9.35 mmol) in acetone (6 mL). The mixture was stirred at reflux for 4 hours. Ethanol (10 mL) was added and the mixture was cooled to room temperature. The solid was collected by suction-filtration, rinsed with ethanol (2×5 mL), and dried overnight at 60° C. in the vacuum oven, giving the title compound as a white solid (1.83 g, 79%); $^1$H NMR (500 MHz, DMSO-d$_6$) δ 1.18-1.20 (m, 2H), 1.41-1.79 (m, 11H), 1.95 (br s, 2H), 2.64 (br s, 2H), 2.74-2.76 (m, 2H), 3.04 (br s, 2H), 5.51 (br s, 2H); $^{13}$C (125 MHz, DMSO-d$_6$) δ 21.6, 25.3, 27.8, 31.1, 36.1, 47.6, 49.4, 53.0; ES-MS 248 (M−1)

Preparation of 3-[(R)-(3-benzylthio-1-hydroxy-2-propyl)amino]-1-propansulfonic acid (Compound N8)

A solution of S-benzyl-L-cysteol (1 g, 4.9 mmol) in acetone (6 mL) was filtered on paper. To the solution was added a solution of 1,3-propane sultone (0.70 g, 5.5 mmol) in toluene (6 mL). The mixture was stirred at reflux for 4 hours. Ethanol (5 mL) was added and the mixture was cooled to room temperature. The solid was collected by filtration, rinsed with ethanol (2×2.5 mL) then dried overnight at 60° C. in a vacuum oven, giving the title compound as a white solid (0.85 g, 54%); $^1$H NMR (500 MHz, DMSO-d$_6$) δ 1.94 (qt, J=6.7 Hz, 2H), 2.59-2.74 (m, 4H), 3.08 (m, 2H), 3.22 (m, 1H), 3.34 (s, 1H), 3.82 (t, J=3.7 Hz, 1H), 5.37 (T, J=4.7 Hz, 1H), 7.22-7.36 (m, 5H), 8.64 (BR S, 2H); $^{13}$C (125 MHz, DMSO-d6) δ 21.9, 28.2, 35.3, 44.8, 49.1, 57.3, 57.5, 126.7, 128.2, 128.7, 137.8; ES-MS 318 (M−1); [α]$_D$ −13.5±0.1 (c=0.0103 in water).

Preparation of 1-amino-5-methyl-3-hexanesulfonic acid (Compound N9)

To a −78° C. solution of 1,3-propane sultone (10 g, 82 mmol) in anhydrous THF (300 mL) was added butyl lithium (2.5 M in hexanes, 36 mL, 90 mmol). The solution was stirred at −78° C. for 0.5 hours before 1-iodo2-methylpropane (9.5 mL, 82 mmol) was added via syringe pump over 0.5 hour period. The reaction mixture was stirred at −78° C. for 4 hours. The reaction mixture was warmed up to 0° C. before water (200 mL) was slowly added. The organic layer was recovered. The aqueous layer was extracted with EtOAc (3×100 mL). The organic extracts were combined, dried over Na$_2$SO$_4$, and evaporated under reduced pressure. The residual material was purified on a silica gel column (100% Hexanes to 80% Hexanes/EtOAc), affording 1-isobutyl-1,3-propane sultone (0.3 g, 2%).

Step 2: To an aqueous solution of ammonium hydroxide (28-30%, 10 mL, 85 mmol) at 0° C. was added via syringe pump over a 4-h period a solution of 1-isobutyl-1,3-propane sultone (0.3 g, 1.7 mmol) in THF (5 mL). The solution was stirred at 0° C. for 1 hour and at room temperature overnight. The solvent was co-evaporated with EtOH. The solid was dried in a vacuum oven (50° C.), affording the title compound (0.258 g, 78.7%). $^1$H NMR (D$_2$O, 500 MHz) δ ppm 3.21 (m, 2H), 2.95 (m, 1H), 2.06 (m, 2H), 1.71 (m, 2H), 1.45 (m, 1H), 0.94 (d, 3H, J=6.3 Hz), 0.94 (d, 3H, J=6.3 Hz), 0.90 (d, 3H, J=6.3 Hz); $^{13}$C (D$_2$O, 125 MHz) δ ppm 56.19, 38.69, 37.58, 27.77, 25.19, 22.55, 20.97; ES-MS 196 (M+1).

Preparation of 6-(aminomethyl)-3,4-dimethylcyclohex-3-ene-1-sulfonic acid (Compound N1)

To a cold (−40° C.) solution of allyl alcohol (20 ml, 300 mmol) and NEt$_3$ (26 mL, 186 mmol) in THF (150 mL) was added dropwise 2-chloroethanesulfonyl chloride (10.4 mL, 100 mmol). The reaction was stirred at −40 to −20° C. for 5 hours, quenched with HCl (1M) and extracted with EtOAc. The organic layer was washed with water and dried over Na$_2$SO$_4$. The product was purified by column chromatography using Hexanes/EtOAc 80/20 as eluant to afford allyl vinylsulfonate as a yellowish oil (7 g, 47%). $^1$H NMR (500 MHz, CDCl$_3$) δ 4.55 (m, 2H), 5.34 (m, 2H), 5.85 (m, 1H), 6.06 (d, J=6.0 Hz, 1H), 6.35 (d, J=17.0 Hz, 1H), 6.50 (dd, J=17 & 9.5 Hz, 1H).

To a degassed (by Nitrogen bubbling) solution of allyl vinylsulfonate (3 g, 20.24 mmol) in CH$_2$Cl$_2$ (1 L) was added Grubbs Catalyst (170 mg, 0.2 mmol). The reaction was heated at reflux for 2 h then concentrated. The residual material was applied on silica gel column using Hexanes/EtOAc 80/20 to 50/50 as eluant to afford 1,3-prop-1-ene sultone 2.2 g (92%). $^1$H NMR (500 MHz, CDCl$_3$) δ 5.11 (dd, J=2.2 & 2.2 Hz, 2H), 6.80 (dt, J=6.6 & 2.2 Hz, 1H), 7.00 (dt, J=6.6 & 2.0 Hz, 1H); $^{13}$C NMR (125 MHz, CDCl$_3$) δ 72.54, 124.76, 137.04.

A mixture of 1,3-propene sultone (1.44 g, 12 mmol), 2,3-dimethyl-1,3-butanediene (9.5 mL, 84 mmol) in 30 mL of toluene was placed in a sealed tube and heated at 150° C. for 15 hours. The solvent was removed and the residual material was applied on silica gel column using Hexanes/EtOAc 80:20 to 70:30 as eluant to afford 700 mg (86%) of the Diels-Alder adduct. $^1$H NMR (500 MHz, CDCl$_3$) δ 1.62 (s, 3H), 1.66 (s, 3H), 1.88-1.92 (m, 1H), 2.28-2.42 (m, 3H), 3.12-3.18 (m, 1H), 3.48 (q, J=7.6 Hz, 1H), 3.96 (t, J=8.5 Hz, 1H), 4.40 (dd, J=8.50 & 7.25 Hz, 1H). $^{13}$C NMR (125 MHz, CDCl$_3$) δ 19.13, 19.25, 27.20, 30.79, 34.18, 53.04, 72.61, 122.70, 123.44.

To an ice-cooled solution of NH$_4$OH (28% in water, 22 mL, 168 mmol) in a co-solvent of THF and EtOH (20 mL, v/v=1:1) was added slowly via a syringe pump a solution of the Diels-Alder adduct from step 3 (680 mg, 3.36 mmol). After the addition (2 h), the reaction was stirred for two more hours until TLC indicated complete consumption of the starting material. The solvent was evaporated and the resulting solid was suspended in mixed solvents of EtOH, acetone and ether, heated for 15 minutes and cooled. The solid was collected by filtration, washed with ether and dried, to give the title compound (450 mg, 61%). $^1$H NMR (500 MHz, D$_2$O) δ 1.49 (s, 3H), 1.52 (s, 3H), 1.86-1.92 (m, 1H), 2.14-2.28 (m, 3H), 2.44-2.49 (m, 1H), 2.80 (dd, J=13.0 & 6.0 Hz, 1H), 3.10-3.16 (m, 1H), 3.27 (dd, J=14.0 & 6.0 Hz, 1H); $^{13}$C NMR (125 MHz, D$_2$O) δ 18.02, 18.28, 28.93, 32.36, 34.69, 38.79, 57.85, 123.09, 123.72. ES-MS 218 (M−1).

Preparation of 6-[(tert-butylamino)methyl]-3,4-dimethylcyclohex-3-ene-1-sulfonic acid (Compound N13)

To a solution of the Diels-Alder adduct from step 3 in the synthesis of Compound N11 (607 mg, 3 mmol) in pinacolone (6 mL) was added t-butylamine (381 μL, 3.6 mmol). The mixture was stirred at reflux for 3 hours then another 381/L of amine was added. The reaction was stirred at reflux for 2 more hours then concentrated. The solid was suspended in EtOH and heated for 15 minutes and then cooled. The solid was collected by filtration, giving the title compound (720 mg, 87%); $^1$H NMR (500 MHz, DMSO-d$_6$) δ 1.22 (s, 9H), 1.57 (s, 3H), 1.60 (s, 3H), 1.84-1.90 (m, 1H), 2.03 (m, 2H), 2.36-2.42 (m, 1H), 2.58 (m, 1H), 2.64 (m, 1H), 2.82 (m, 1H), 3.00 (m, 1H); $^{13}$C NMR (125 MHz, DMSO-d$_6$) δ 19.33, 19.48, 25.81, 29.67, 31.78, 38.40, 41.38, 56.10, 57.64, 123.30, 124.02. ES-MS 274 (M−1).

Preparation of 6-(2-adamantylamino)methyl-3,4-dimethylcyclohex-3-ene-1-sulfonic acid (Compound N14)

To a solution of the Diels-Alder adduct from step 3 in the synthesis of Compound N11(607 mg, 3 mmol) in pinacolone (6 mL) was added 2-adamantaneamine (544 mg, 3.6 mmol). The reaction was stirred at reflux for 5 hours then concentrated. The solid was suspended in MeOH and heated for 15 min and then cooled. The solid was collected by filtration, affording the title compound (260 mg, 24%). $^1$H NMR (500 MHz, DMSO-$d_6$) δ 1.25-1.69 (m, 9H), 1.70 (m, 5H), 1.80 (s, 3H), 1.64 (s, 3H), 2.00 (m, 1H), 2.08 (m, 2H), 2.23 (m, 2H), 2.41 (m, 1H), 2.50 (s, 1H), 2.73 (m, 2H), 2.82 (m, 1H), 3.02 (m, 1H), 3.20 (m, 1H), 8.49 (bs, 1H), 9.31 (bs, 1H); $^{13}$C NMR (125 MHz, DMSO-$d_6$) δ 19.30, 19.46, 26.82, 27.12, 28.15, 29.64, 30.03, 30.25, 30.47, 31.59, 36.69, 36.89, 37.29, 38.89, 46.14, 57.43, 62.73, 123.23, 124.04. ES-MS 352 (M−1).

Preparation of
1-amino-4-hydroxy-4-methyl-3-pentanesulfonic acid
(Compound N15)

To a −78° C. solution of 1,3-propane sultone (5.0 g, 41 mmol) in anhydrous THF (150 mL) was added butyl lithium (2.5 M in hexanes, 18 mL, 45 mmol). The solution was stirred at −78° C. for 0.5 hours before acetone (3.0 mL, 41 mmol) was added via syringe pump over a 0.5-h period. The reaction mixture was stirred at −78° C. for 4 hours. The mixture was warmed up to 0° C. before water (100 mL) was slowly added. The organic layer was separateded. The aqueous layer was extracted with EtOAc (3×100 mL) and combined with the organic layer. The combined organic extracts were dried over $Na_2SO_4$ and evaporated under reduced pressure. The residue was separated on a silica gel column (100% Hexanes to 80% Hexanes/EtOAc), affording the corresponding sultone derivative (4.36 g, 60%).

To an aqueous solution of ammonium hydroxide (28-30%, 140 mL, 12.1 mol) at 0° C. was added via syringe pump over a 4 hour period a solution of sultone derivative from step 1 (4.36 g, 24.2 mmol) in THF (25 mL). The mixture was stirred at 0° C. for 1 hour and at room temperature overnight. The solvent was co-evaporated with EtOH. The solid was dried in a vacuum oven (50° C.), affording the title compound (4.37 g, 92%). $^1$H NMR ($D_2O$, 500 MHz) δ ppm 3.10 (m, 1H), 3.05 (m, 1H), 2.80 (m, 1H), 1.26 (d, 3H, J=8.8 Hz), 1.19 (d, 3H, J=8.8 Hz); $^{13}$C ($D_2O$, 125 MHz) δ ppm 72.26, 67.22, 39.38, 26.80, 26.10, 25.55; ES-MS 198 (M+1).

Preparation of
3-(2-benzylthio-1-ethylamino)-1-propansulfonic acid
(Compound N18)

S-Benzylcystamine hydrochloride (2.40 g, 11.8 mmol) was dissolved in water and the pH was adjusted to basic with potassium carbonate. The aqueous mixture was extracted with ethyl acetate (3×15 mL). The combined organic layers were washed with brine, dried over anhydrous sodium sulfate; and the solvent was removed under reduced pressure. The residue, a mixture of yellowish oil and white solid, was taken in acetonitrile (10 mL); and the mixture was filtered through filter paper and the residue on the paper was rinsed with toluene (10 mL). To the homogenous organic solution was added 1,3-propane sultone (1.00 mL, containing 11 mmol 1,3-propane sultone). The mixture was stirred at reflux for 20 hours, and then cooled to room temperature. The solid was collected by suction-filtration, rinsed with acetone (2×5 mL) then dried under vacuum for 1 hour. The solid was suspended in ethanol (10 mL) and the mixture was heated under reflux for 1 hour and then cooled to room temperature. The solid was collected by suction-filtration, washed with ethanol (2×3 mL), dried at 60° C. for 4 hours, providing the title compound as a white solid (1.60, 47%); $^1$H NMR (500 MHz, DMSO-$d_6$) δ 1.93 (qt, J=6.7 Hz, 2H), 2.60-2.64 (m, 4H), 3.08 (v br d, 4H), 3.81 (s, 2H), 7.26 (t, J=7.6 Hz, 1H), 7.32-7.39 (m, 4H), 8.62 (br s, 2H); $^{13}$C (125 MHz, DMSO-$d_6$) δ 21.7, 26.2, 34.5, 45.4, 46.7, 48.9, 127.0, 128.5, 129.0, 138.1; ES-MS 288 (M−1).

Preparation of 6-(1-adamantylamino)methyl-3,4-
dimethylcyclohex-3-ene-1-sulfonic acid (Compound
N19)

To a solution of the Diels-Alder adduct from step 3 in the preparation of Compound N11 (607 mg, 3 mmol) in pinacolone (6 mL) was added 1-adamantaneamine (544 mg, 3.6 mmol). The reaction mixture was stirred at reflux for 5 hours, and then concentrated to dryness. The solid residue was suspended in MeOH, heated for 15 minutes, cooled to room temperature, and collected by filtration, giving the title compound (260 mg, 24%); $^1$H NMR (500 MHz, DMSO-$d_6$) δ 1.54-1.66 (m, 11H), 1.75 (s, 3H), 1.77 (s, 3H), 1.84 (m, 1H), 2.10 (s, 4H), 2.22 (m, 2H), 2.40 (m, 1H), 2.58 (m, 1H), 2.64 (m, 1H), 2.84 (m, 1H), 3.00 (m, 1H), 8.30 (bs, 1H), 9.40 (bs, 1H); $^{13}$C NMR (125 MHz, DMSO-$d_6$) δ 19.34, 19.48, 29.05, 29.36, 31.63, 35.84, 38.42, 38.55, 39.54, 56.23, 57.71, 123.33, 124.01. ES-MS 352 (M−1).

Preparation of (Z)-3-(tert-butylamino)prop-1-ene-1-
sulfonic acid (Compound N20)

To a boiling solution of allyl bromide (21.6 mL, 250 mmol) in a solvent mixture of EtOH and $H_2O$ (200 mL, v/v=3:1) was added dropwise a solution of sodium sulfite (15.75 g, 125 mmol) in water (60 mL). The reaction mixture was heated under reflux for 3 hours, and concentrated to dryness under reduced pressure. The obtained white solid was suspended in EtOH in water (130 mL, 90%), heated for 30 minutes, cooled to room temperature, and collected by filtration, giving sodium prop-2-ene-1-sulfonate (14 g, 76%); $^1$H NMR (500 MHz, $D_2O$) δ 3.55 (d, J=7.3 Hz, 2H), 5.35-5.41 (m, 2H), 5.85-6.00 (m, 1H).

To a stirred solution of sulfonate obtained from step 1 (12.0 g, 84 mmol) in water (48 mL) was added bromine (about 4.5 mL) dropwise with stirring until the solution turned pale brown. The solution was stirred at room temperature for 3 hours. A small amount of $Na_2SO_3$ was added to destroy the excess bromine. The solvent was then removed in vacuo and a white solid was obtained. Without further purification, the 2,3-dibromo-1-propanesulfonate was treated with concentrated HCl (50 mL) by stirring at room temperature for 1 day. The precipitate (inorganic salt) was removed by filtration. The filtrate was concentrated to yellow syrup. Without further purification, the syrup residue was subjected to vacuum distillation at 140-150° C. to give 2-bromo-1,3-propane sultone (6.5 g, 32%); $^1$H NMR (500 MHz, CDCl$_3$) δ 3.52 (dd, J=14.0 & 7.0 Hz, 1H), 3.88 (dd, J=14.0 & 7.0 Hz, 1H), 4.50-4.60 (m, 1H), 4.70-4.82 (m, 2H).

To a solution of 2-bromo-1,3-propane sultone (obtained in Step 2, 8.0 g, 39.80 mmol) in toluene (200 mL) was added NEt$_3$ (9 mL, 65 mmol). The reaction mixture was stirred for 3 h (or until complete consumption of the starting material), diluted with an aqueous solution of HCl (1 M), and extracted twice with EtOAc. The organic layer was dried over $Na_2SO_4$ and concentrated to give 1,3-prop-1-ene sultone (4.5 g, 94%) as a white solid; $^1$H NMR (500 MHz, CDCl$_3$) δ 5.11 (dd, J=2.2 & 2.2 Hz, 2H), 6.80 (dt, J=6.6 & 2.2 Hz, 1H), 7.00 (dt, J=6.6 & 2.0 Hz, 1H); $^{13}$C NMR (125 MHz, CDCl$_3$) δ 72.54, 124.76, 137.04.

To a solution of 1,3-prop-1-ene sultone (obtained in step 3, 36 mg, 3 mmol) in THF (5 mL) was added tert-butylamine (316 µL, 3 mmol). The reaction mixture was refluxed for 4 h, and then concentrated to dryness. The residual solid material was suspended in a solvent mixture of EtOH, acetone and ether, heated for 15 minutes, and cooled to room temperature. The solid was collected by filtration, washed with ether then dried, providing the title compound (130 mg, 22%); $^1$H NMR (500 MHz, D$_2$O) δ 1.24 (s, 9H), 4.00 (d, J=7.0 Hz, 2H), 5.94 (m, 1H), 6.50 (d, J=11.0 Hz, 1H). $^{13}$C NMR (125 MHz, D$_2$O) δ 25.08, 37.84, 57.63, 127.81, 136.08. ES-MS 192 (M−1).

Preparation of (1Z)-(3-(1-adamantylamino)prop-1-ene-1-sulfonic acid (Compound N21)

To a solution of 1,3-prop-1-ene sultone (obtained in step 3 in the preparation of Compound N20, 360 mg, 3 mmol) in THF (5 mL) was added 1-adamantylamine (545 mg, 3.6 mmol). The reaction mixture was refluxed for 6 h, and then concentrated to dryness. The residual solid was suspended in a solvent mixture of EtOH and ether (2.5 mL/2.5 mL), heated under reflux for 15 minutes, and cooled to room temperature. The solid material was collected by filtration, washed with ether, and dried; providing the title compound (130 mg, 22%); $^1$H NMR (500 MHz, D$_2$O) δ 1.40-1.70 (m, 12H), 2.00 (m, 3H), 3.7 (d, J=7.0 Hz, 2H), 5.90 (m, 1H), 6.30 (d, J=11.0 Hz, 1H). $^{13}$C NMR (125 MHz, D$_2$O) δ 28.95, 29.23, 35.05, 35.68, 36.67, 40.05, 40.75, 128.00, 132.98. ES-MS 270 (M−1).

Preparation of (1Z)-3-aminoprop-1-ene-1-sulfonic acid (Compound N22)

A solution of 1,3-prop-1-ene sultone (obtained in step 3 for the preparation Compound N20, 360 mg, 3 mmol) in a solvent mixture of THF and EtOH (10 mL, v/v=1:1) was added slowly to an aqueous solution of ammonium hydroxide (28%, 26 mL, 200 mmol). The reaction mixture was stirred at room temperature for 4 hours and then concentrated to dryness. The resulting solid was suspended in EtOH, heated at reflux for 15 min, and cooled. The solid was collected by filtration, washed with ether, and dried, giving the title compound (500 mg, 91%); $^1$H NMR (500 MHz, D$_2$O) δ 3.95 (d, J=6.3 Hz, 2H), 5.96 (m, 1H), 6.44 (d, J=11.5 Hz, 1H). $^{13}$C NMR (125 MHz, D$_2$O) δ 36.25, 129.10, 135.10. ES-MS 136 (M−1).

Preparation of anti-4-amino-1-hydroxy-1-phenyl-2-butanesulfonic acid, trifluoroacetic acid salt (Compound N23), syn-4-amino-1-hydroxy-1-phenyl-2-butanesulfonic acid, trifluoroacetic acid salt (Compound N24) and 4-amino-1-hydroxy-1-phenyl-2-butanesulfonic acid, trifluoroacetic acid salt (Compound N25)

To a −78° C. solution of 1,3-propane sultone (5.0 g, 41 mmol) in anhydrous THF (150 mL) was added butyl lithium (2.5 M in hexanes, 18 mL, 45 mmol). The mixture was stirred at −78° C. for 0.5 hours before benzaldehyde (4.2 mL, 41 mmol) was added via syringe pump over 0.5 hour period. The reaction mixture was stirred at −78° C. for 4 hours, and then warmed up to 0° C. before water (100 mL) was slowly added. The organic layer was separated; and the aqueous layer was extracted with EtOAc (3×100 mL). The organic phase and extracts were combined, dried over Na$_2$SO$_4$, and evaporated under reduced pressure. The residue was separated on a silica gel column (100% Hexanes to 70% Hex/EtOAc), affording the corresponding sultone derivative (3.04 g, 33%).

To an aqueous solution of ammonium hydroxide (28-30%, 78 mL, 665 mmol) at 0° C. was added via syringe pump, over a 4 hour period, a solution of the sultone derivative (obtained in step 1, 3.04 g, 13.3 mmol) in THF (15 mL). The mixture was stirred at 0° C. for 1 hour and then at room temperature overnight. The solvent was co-evaporated with EtOH. The mixture of diastereoisomers was separated by preparative HPLC; and the corresponding fractions were lyophilized, affording the following three compounds:

anti-4-amino-1-hydroxy-1-phenyl-2-butanesulfonic acid, trifluoroacetic acid salt (Compound N23): mixture of enantiomers (204 mg). $^1$H NMR (D$_2$O, 500 MHz) δ ppm 7.30 (m, 5H), 4.87 (d, 1H, J=8.0 Hz), 3.17 (m, 1H), 2.86 (m, 1H), 2.66 (m, 1H), 1.74 (m, 1H), 1.65 (m, 1H); $^{13}$C (D$_2$O, 125 MHz) δ ppm 139.51, 128.93, 127.65, 73.82, 63.14, 37.96, 25.40; ES-MS 244 (M−1).

syn-4-amino-1-hydroxy-1-phenyl-2-butanesulfonic acid, trifluoroacetic acid salt (Compound N24): mixture of enantiomers (131 mg); $^1$H NMR (D$_2$O, 500 MHz) δ ppm 7.30 (m, 4H), 7.26 (m, 1H), 5.30 (d, 1H, J=2.8 Hz), 3.05 (m, 1H), 2.94 (m, 1H), 2.66 (m, 1H), 1.96 (m, 1H); $^{13}$C (D$_2$O, 125 MHz) δ ppm 141.35, 128.84, 128.05, 125.91, 71.54, 63.65, 38.44, 22.22; $^{19}$F NMR δ ppm-76.31; ES-MS 244 (M−1).

4-amino-1-hydroxy-1-phenyl-2-butanesulfonic acid, trifluoroacetic acid salt (Compound N25): mixture of diastereoisomers (165 mg). $^1$H NMR (D$_2$O, 500 MHz) δ ppm 7.30 (m, 5H), 5.30 (d, 0.5H, J=2.8 Hz), 4.87 (d, 0.5H, J=8.0 Hz), 3.17 (m, 0.5H), 3.05 (m, 0.5H), 2.94 (m, 0.5H), 2.86 (m, 0.5H), 2.66 (m, 1H), 1.96 (m, 1H), 1.74 (m, 0.5H), 1.65 (m, 0.5H); $^{13}$C (D$_2$O, 125 MHz) δ ppm 141.35, 128.84, 128.05, 125.91, 71.54, 63.65, 38.44, 22.22; ES-MS 244 (M−1).

Preparation of 3-amino-1-phenyl-1-butanesulfonic acid, trifluoroacetic acid salt: Compound N26)

To a 0° C. solution of α-toluenesulfonyl chloride (5 g, 26 mmol) in anhydrous dichloromethane (100 mL) was added ethanol (3 mL, 52 mmol) and triethylamine (5.5 mL, 39 mmol). The reaction mixture was stirred at 0° C. for 1 h before water was added (100 mL). The organic layer was separated and extracted with 2N HCl (1×100 mL) and Brine (1×100 mL). The organic phase was dried over Na$_2$SO$_4$, evaporated under reduced pressure, and dried in vacuo, affording ethyl phenylmethanesulfonate (4.76 g, 91%).

To a −78° C. solution of ethyl phenylmethanesulfonate (4.76 g, 23.8 mmol) in anhydrous THF (100 mL) was added butyl lithium (2.5 M in hexanes, 10 mL, 25 mmol). The mixture was stirred at −78° C. for 1 h before allyl bromide (3.1 mL, 35.7 mmol) was added via syringe pump over a 0.5 hour period. The reaction mixture was stirred at −78° C. for 5 h, and then warmed up to 0° C. before water (60 mL) was slowly added. The organic layer was separated; and the aqueous layer was extracted with EtOAc (3×60 mL). The combined organic layer and extracts were dried over Na$_2$SO$_4$, and evaporated to dryness under reduced pressure, affording the corresponding sultone (4.83 g, 80%).

To an aqueous solution of ammonium hydroxide (28-30%, 87 mL, 750 mmol) at 0° C. was added a solution of sultone (3.19 g, 15.0 mmol) in THF (25 mL) and EtOH (20 mL). The solution was stirred at 70° C. overnight. The solvent was co-evaporated with EtOH. The solid residue was purified by preparative HPLC and the corresponding fractions were combined and lyophilized, affording the title compound in a mixture of diastereoisomers (170 mg). $^1$H NMR (D$_2$O, 500 MHz) δ ppm 7.28 (m, 5H), 4.02 (m, 0.8H), 3.92 (m, 0.2H), 3.52 (m, 0.2H), 3.27 (m, 0.3H), 2.94 (m, 0.5H), 2.44 (m, 1H), 2.21 (m, 1H), 1.12 (d, 1.5H, J=6.3 Hz), 1.08 (d, 0.9H, J=6.3 Hz), 1.00

(d, 0.6H, J=6.3 Hz); $^{13}$C (D$_2$O, 125 MHz) δ ppm 135.15, 133.87, 129.37, 129.35, 129.09, 129.00, 128.91, 128.81, 128.79, 128.40, 65.84, 63.60, 63.02, 62.66, 46.67, 45.61, 39.18, 35.84, 34.85, 21.15, 18.56, 16.64; ES-MS 228 (M−1).

Preparation of
4-amino-4-methyl-1-phenyl-1-pentanesulfonic acid,
trifluoroacetic acid salt: (Compound N27)

To a 0° C. solution of α-toluenesulfonyl chloride (10 g, 52 mmol) in anhydrous dichloromethane (200 mL) was added ethanol (6 mL, 104 mmol) and triethylamine (11 mL, 78 mmol). The reaction mixture was stirred at 0° C. for 1 hour before water (200 mL) was added. The organic layer was separated and extracted with 2N HCl (1×200 mL) and brine (1×200 mL). The organic phase was dried over Na$_2$SO$_4$, evaporated under reduced pressure, and dried in vacuo, affording the corresponding ethyl phenylmethanesulfonate (9.79 g, 93%).

To a −78° C. solution of ethyl phenylmethanesulfonate (4.59 g, 22.9 mmol) in anhydrous THF (100 mL) was added butyl lithium (2.5 M in hexanes, 10 mL, 25 mmol). The mixture was stirred at −78° C. for 1 hour before 1-bromo-3-methyl-2-butene (2.9 mL, 25.0 mmol) was added via syringe pump over a 0.5 hour period. The reaction mixture was stirred at −78° C. for 4 hour, and then was warmed up to 0° C. before water (60 mL) was slowly added. The organic layer was separated. The aqueous layer was extracted with EtOAc (3×60 mL). The organic layer and extracts were combined, dried over Na$_2$SO$_4$, and evaporated under reduced pressure, affording ethyl 4-methyl-1-phenylpent-3-ene-1-sulfonate (3.93 g, 64%).

A solution of ethyl 4-methyl-1-phenylpent-3-ene-1-sulfonate (3.01 g, 11.2 mmol) in 2% TFA/CH$_2$Cl$_2$ (20 mL) was stirred at reflux for 24 hours. The solvent was evaporated under reduced pressure. The crude oil was dissolved in 20% TFA/CH$_2$Cl$_2$ (20 mL). The solution was stirred at reflux for 24 hours. After cooling to room temperature, water (20 mL) was added. The organic phase was separated and extracted with a saturated solution of NaHCO$_3$ (1×20 mL). The organic phase was dried over Na$_2$SO$_4$, evaporated, and dried in vacuo, affording the corresponding sultone derivative (2.42 g, 90%).

To an aqueous solution of ammonium hydroxide (28-30%, 78 mL, 665 mmol) at 0° C. to ammonium hydroxide (28-30% NH$_3$, 30 mL) was added a solution of the sultone derivative obtained from step 3 (2.42 g, 10.1 mmol) in THF (25 mL) and EtOH (20 mL). The solution was stirred at 70° C. overnight. The solvent was co-evaporated with EtOH. The residual solid was purified by preparative HPLC and the corresponding fractions were combined and lyophilized, affording the title compound (222 mg). $^1$H NMR (D$_2$O, 500 MHz) δ ppm 7.27 (m, 5H), 3.82 (dd, 1H, J=3.2 Hz, 11.5 Hz), 2.14 (m, 1H), 1.98 (m, 1H), 1.32 (m, 1H), 1.10 (m, 1H), 1.02 (s, 6H); $^{13}$C (D$_2$O, 125 MHz) δ ppm 135.70, 129.50, 128.92, 128.77, 128.34, 71.34, 40.13, 27.74, 27.54, 25.24; ES-MS 256 (M−1).

Preparation of 3-amino-1-phenyl-1-pentanesulfonic
acid, trifluoroacetic acid salt: (Compound N30)

To a 0° C. solution of α-toluenesulfonyl chloride (10 g, 52 mmol) in anhydrous dichloromethane (200 mL) was added ethanol (6 mL, 104 mmol) and triethylamine (11 mL, 78 mmol). The reaction mixture was stirred at 0° C. for 1 hour before water (100 mL) was added. The organic layer was separated and extracted with 2N HCl (1×100 mL) and Brine (1×100 mL). The organic phase was dried over Na$_2$SO$_4$, evaporated under reduced pressure, and dried in vacuo, affording ethyl phenylmethanesulfonate (10.47 g, 99%).

To a −78° C. solution of ethyl phenylmethanesulfonate (4.70 g, 23.5 mmol) in anhydrous THF (100 mL) was added butyl lithium (2.5 M in hexanes, 10 mL, 25 mmol). The solution was stirred at −78° C. for 1 hour before crotyl bromide (2.4 mL, 23.5 mmol) was added via syringe pump over a 0.5-h period. The reaction mixture was stirred at −78° C. for 5 hours. The mixture was warmed up to 0° C. before water (60 mL) was slowly added. The organic layer was separated; and the aqueous layer was extracted with EtOAc (3×60 mL). The organic layer and the extracts were combined, dried over Na$_2$SO$_4$, and evaporated under reduced pressure, affording ethyl 1-phenylbut-3-ene-1-sulfonate (4.06 g, 70%).

A solution of ethyl 1-phenylbut-3-ene-1-sulfonate (4.06 g, 11.2 mmol) in 2% TFA/CH$_2$Cl$_2$ (30 mL) was stirred at reflux for 30 hours. The solvent was evaporated under reduced pressure. The residual oil was dissolved in 20% TFA/CH$_2$Cl$_2$ (30 mL) The solution was stirred at reflux for 36 hours. After cooling to room temperature, water (30 mL) was added. The organic phase was separated and extracted with a saturated solution of NaHCO$_3$ (1×30 mL). The organic phase was dried over Na$_2$SO$_4$, evaporated to dryness, and further dried in vacuo. The residual material was purified by flash chromatography (100% Hexanes to 80% Hexanes/Ethyl acetate), affording a mixture of sultone derivatives (1.36 g)

To ammonium hydroxide (28-30% NH$_3$, 30 mL, 260 mmol) was added a solution of sultone (1.38 g, 6.1 mmol) in 1,4-dioxane (20 mL). The solution was stirred at room temperature for 60 hours. The solvent was co-evaporated with EtOH. The residue was dissolved in water (30 mL), and the aqueous solution was extracted with ethyl acetate (30 mL). The aqueous phase was separated, and evaporated to dryness. The solid residue was purified by preparative HPLC; and the corresponding fractions were combined and lyophilized, affording the title compound (72 mg). $^1$H NMR (D$_2$O, 500 MHz) δ ppm 7.29 (m, 5H), 4.07 (m, 1H), 2.99 (m, 1H), 2.35 (m, 2H), 1.49 (m, 1H), 0.75 (t, 3H, J=7.3 Hz); $^{13}$C (D$_2$O, 125 MHz) δ ppm 134.80, 129.41, 129.03, 128.84, 62.90, 51.68, 33.37, 25.91, 8.66; ES-MS 242 (M−1).

Preparation of 4-amino-1-phenyl-1-pentanesulfonic
acid, trifluoroacetic acid salt: (Compound N31)

To a 0° C. solution of α-toluenesulfonyl chloride (10 g, 52 mmol) in anhydrous dichloromethane (200 mL) was added ethanol (6 mL, 104 mmol) and triethylamine (11 mL, 78 mmol). The reaction mixture was stirred at 0° C. for 1 hour before water (100 mL) was added. The organic layer was separated, and extracted with 2N HCl (1×100 mL) and Brine (1×100 mL). The organic phase and extracts were combined, dried over Na$_2$SO$_4$, evaporated under reduced pressure, and dried in vacuo, affording ethyl phenylmethanesulfonate (10.47 g, 99%).

To a −78° C. solution of ethyl phenylmethanesulfonate (4.70 g, 23.5 mmol) in anhydrous THF (100 mL) was added butyl lithium (2.5 M in hexanes, 10 mL, 25 mmol). The mixture was stirred at −78° C. for 1 h before crotyl bromide (2.4 mL, 23.5 mmol) was added via syringe pump over a 0.5 hour period. The reaction mixture was stirred at −78° C. for 5 hours, and then was warmed up to 0° C. before water (60 mL) was slowly added. The organic layer was separated; and the aqueous layer was extracted with EtOAc (3×60 mL). The organic layer and extracts were combined, dried over Na$_2$SO$_4$, and evaporated under reduced pressure, affording ethyl 1-phenylbut-3-ene-1-sulfonate (4.06 g, 70%).

A solution of ethyl 1-phenylbut-3-ene-1-sulfonate (4.06 g, 11.2 mmol) in 2% TFA/CH$_2$Cl$_2$ (30 mL) was stirred at reflux for 30 hours. The solvent was evaporated under reduced pressure. The residual oil was dissolved in 20% TFA/CH$_2$Cl$_2$ (30 mL). The solution was stirred at reflux for 36 hours, and then cooled to room temperature, followed by addition of water (30 mL). The organic phase was separated and extracted with a saturated solution of NaHCO$_3$ (1×30 mL). The organic phase was dried over Na$_2$SO$_4$, evaporated to dryness, and further dried in vacuo. The residual material was purified by flash chromatography. (100% hexanes to 80% hexanes/Ethyl acetate), affording a mixture of sultone derivatives (1.36 g)

To ammonium hydroxide (28-30% NH$_3$, 30 mL, 260 mmol) was added a solution of sultone (1.38 g, 6.1 mmol) in 1,4-dioxane (20 mL). The solution was stirred at room temperature for 60 hours. The solvent was co-evaporated with EtOH. The residue was dissolved in water (30 mL). The solution was extracted with ethyl acetate (30 mL). The organic phase was recovered, dried over NaSO$_4$, filtered, evaporated and dried in vacuo, affording the butanesultone (0.777 g).

To ammonium hydroxide (28-30% NH$_3$, 15 mL, 130 mmol) was added a solution of the sultone derivatives obtained from step 4 (0.777 g, 3.4 mmol) in 1,4-dioxane (20 mL). The solution was stirred at 85° C. for 48 hours. The solvent was co-evaporated with EtOH; and the residual solid was purified by preparative HPLC. The corresponding fractions were combined and lyophilized, affording the title compound (213 mg) as a pair of enantiomers of the title compound; $^1$H NMR (D$_2$O, 500 MHz) δ ppm 7.26 (m, 5H), 3.87 (dd, 1H, J=3.6 Hz, 11.4 Hz), 3.66 (m, 1H), 2.07 (m, 2H), 1.25 (m, 1H), 1.11 (m, 1H), 0.94 (d, 3H, J=6.3 Hz); $^{13}$C (D$_2$O, 125 MHz) δ ppm 135.61, 129.52, 128.77, 128.34, 67.31, 66.37, 35.47, 26.32, 21.97; ES-MS 243 (M−1).

Preparation of
3-(aminomethyl)bicyclo[2.2.2]oct-5-ene-2-sulfonic
acid (Compound N32)

A mixture of 1,3-prop-1-ene sultone (obtained in step 3 for the prepareation of Compound N20, 720 mg, 6 mmol) and 2,3-cyclohexadiene (4.0 mL, 42 mmol) in toluene (20 mL) was placed in a sealed tube and heated at 150° C. for 30 hours. The solvent was removed and the residue was applied on silica gel column using hexanes/EtOAc 80/20 to 70/30 as eluant to afford the corresponding Diels-Alder adduct (1.1 g, 92%); $^1$H NMR (500 MHz, CDCl$_3$) δ 1.30-1.62 (m, 4H), 2.76 (m, 1H), 3.00 (m, 1H), 3.18 (, 1H), 3.48 (dd, J=1.0.0 & 2.0 Hz, 1H), 3.94 (dd, J=10.0 & 3.5 Hz, 1H), 4.30 (t, J=8.5 Hz, 1H), 6.30 (t, J=8.5 Hz, 1H), 6.41 (t, J=8.5 Hz, 1H).

A solution of the Diels-Alder adduct obtained from step1 (1.1 g, 5.49 mmol) in a solvent mixture of THF and EtOH (20 mL, v/v=1:1) was added slowly to an aqueous solution of ammonium hydroxide (28%, 32 mL, 253 mmol). The reaction mixture was stirred at room temperature for 7 hours and concentrated under reduced pressure. The resultant solid was suspended in EtOH, heated at reflux for 15 minutes, and cooled to room temperature. The solid was collected by filtration, washed with ether, and then dried, affording the title compound (700 mg, 59%); $^1$H NMR (500 MHz, D$_2$O) δ 1.10-1.28 (m, 2H), 1.40-1.58 (m, 2H), 2.40 (m, 1H), 2.56 (m, 1H), 2.87-2.95 (m, 2H), 3.30 (m, 1H), 6.12 (t, J=8.0 Hz, 1H), 6.30 (t, J=8.0 Hz, 1H); $^{13}$C NMR (125 MHz, D$_2$O) δ 22.82, 25.70, 32.43, 34.28, 40.72, 40.82, 62.64, 130.72, 134.49; ES-MS 216 (M−1).

Preparation of
3-(aminomethyl)bicyclo[2.2.2]octane-2-sulfonic acid
(Compound N33)

Pd/C (100 mg) was added to a solution of the Diels-Alder adduct obtained in step 1 for the preparation of 3-(aminomethyl)bicyclo[2.2.2]oct-5-ene-2-sulfonic acid (Compound N32) (300 mg, 1.5 mmol) in a cosolvent of EtOAc and methanol (15 mL, v/v=2:1). The suspension was stirred under atmosphere pressure of H$_2$ for 6 h and filtered. The filtrate was concentrated to give 300 mg of the reduced product. $^1$H NMR (500 MHz, CDCl$_3$) δ 1.40-1.85 (m, 8H), 2.10-2.20 (m, 2H), 2.88-2.92 (m, 1H), 3.38 (m, 1H), 4.28 (dd, J=10.0 & 2.0 Hz, 1H), 4.41 (dd, J=10.0 & 8.0 Hz, 1H).

A solution of the reduced product prepared as described in step 1 (607 mg, 3 mmol) in a solvent mixture of THF and EtOH (10 mL, v/v=1/1) was added slowly to an aqueous solution of ammonium hydroxide (28%, 32 mL, 253 mmol). The reaction mixture was stirred at room temperature for 6 hours and then concentrated. The residual solid was suspended in EtOH; the mixture was heated at reflux for 15 minutes and then cooled to room temperature. The solid was collected by filtration, washed with ether, and then dried, yielding the title compound (520 mg, 79%); $^1$H NMR (500 MHz, D$_2$O) δ 1.30-1.60 (m, 8H), 1.80-1.90 (m, 1H), 1.98 (m, 1H), 2.22-2.29 (m, 1H), 3.10 (dd, J=13.0 & 7.0 Hz, 1H), 3.20 (d, J=10.5 Hz, 1H), 3.64 (dd, J=13.0 & 7.0 Hz, 1H); $^{13}$C NMR (125 MHz, D$_2$O) δ 18.96, 19.93, 25.06, 25.91, 26.94, 27.97, 36.12, 40.20, 59.69. ES-MS 218 (M−1).

Preparation of 3-amino-3-methyl-1-butanesulfonic
acid (Compound N34)

To a cold (0° C.) solution of chloroethanesulfonyl chloride in MeOH (10 mL) was added slowly NaOMe (25%, 4.3 g, 20 mmol). NaCl precipitated during the addition of NaOMe. The mixture was stirred at 0° C. for 1 h; and the cooling bath was removed. To the mixture was added 2-nitropropane. pH indicated 1-2 value, and NaOMe was added until basic pH. The reaction mixture was stirred for 3 hours, and then filtered. The filtrate was concentrated, diluted with aqueous HCl (1 M), and then extracted twice with EtOAc. The combined organic layers were dried over Na$_2$SO$_4$, and concentrated. The resultant residue was purified by column chromatography using hexanes/EtOAc 80:20 to 50:50 as eluant to provide 500 mg (23%) of the desired intermediate; $^1$H NMR (500 MHz, CDCl$_3$) δ 1.65 (s, 6H), 2.42 (m, 2H), 3.17 (m, 2H), 3.92 (s, 3H); $^{13}$C NMR (125 MHz, CDCl$_3$) δ 50.01, 56.17, 59.13, 66.11.

Ra—Ni (100 mg) was added to a stirred solution of the nitro intermediate (obtained from step 1, 400 mg, 1.89 mmol). The suspension was stirred under atmospheric pressure of H$_2$ for 5 hours. TLC indicated complete consumption of the starting material. The mixture was filtered and the filtrate was concentrated to a residue. NMR of the residue showed the desired product but contaminated probably with a sultame of cyclization. The crude product was dissolved in HCl (12N). The solution was heated at reflux for 2 hours, and then concentrated under reduced pressure to afford greenish foam. The crude was dissolved in MeOH and precipitated by addition of Et$_2$O. The product was isolated by filtration, washed with MeOH and ether, to afford the title compound (140 mg, 42% overall for two steps); $^1$H NMR (500 MHz, D$_2$O) δ 1.24 (s, 6H), 1.92-1.98 (m, 2H), 2.82-2.89 (m, 2H); $^{13}$C NMR (125 MHz, D$_2$O) δ 24.36, 34.68, 46.04, 53.81. ES-MS 166 (M−1).

Preparation of 2-(1-aminocycohexyl)-1-ethanesulfonic acid (Compound N35)

To a cold (0° C.) solution of 2-chloroethanesulfonyl chloride (2.14 mL, 20 mmol) in MeOH (10 mL) was added slowly NaOMe (25%, 4.3 g, 20 mmol). NaCl precipitated during the addition of NaOMe. The mixture was stirred at 0° C. for 1 hour; and the cooling bath was removed, followed by addition of nitrocyclohexane (2.58 g, 20 mmol). pH indicated 1-2 value, and NaOMe was added until the mixture was basic. The reaction mixture was stirred for 3 hours then filtered. The filtrate was concentrated and diluted with aqueous HCl (1 M), and then extracted twice with EtOAc. The combined organic layers were dried over $NaSO_4$, and concentrated to dryness. The resultant residue was purified by column chromatography using hexanes/EtOAc 80:20 to 50:50 as eluant. The corresponding fractions were collected and evaporated to dryness, providing the corresponding intermediate (500 mg, 23%); $^1$H NMR (500 MHz, $CDCl_3$) δ 1.35-1.70 (m, 8H), 2.35 (m, 2H), 2.38-2.45 (m, 2H), 3.08 (m, 2H), 3.90 (s, 3H). $^{13}$C NMR (125 MHz, $CDCl_3$) δ 22.36, 24.75, 34.17, 44.57, 89.88.

Ra—Ni (300 mg) was added to a stirred solution of the nitro intermediate (obtained in step 1, 1 g, 3.58 mmol). The suspension was stirred under atmospheric pressure of $H_2$ for 3 hours. TLC indicated complete consumption of the starting material. The reaction was filtered and the filtrate was concentrated. NMR of the residual material showed the desired product but contaminated probably with the sultame of cyclization. The crude product was dissolved in aqueous HCl (6 N, 5 mL) and the solution was heated at reflux for 2 hours, concentrated under reduced pressure to afford a foamy residue. The foamy residue was dissolved in MeOH and the desired product was precipitated by addition of $Et_2O$. The product was isolated by filtration then washed with MeOH and ether to afford the title compound (422 mg, 42% overall in two steps); $^1$H NMR (500 MHz, $D_2O$) δ 1.20-1.32 (m, 2H), 1.32-1.56 (m, 6H), 1.60-1.74 (m, 2H), 2.24 (m, 2H), 2.86 (m, 2H); $^{13}$C NMR (125 MHz, $D_2O$) δ 20.82, 24.21, 31.52, 33.34, 45.06, 56.20. ES-MS 206 (M−1).

Preparation of 3-(aminomethyl)-4,5-dimethyl-1-cycloheanesulfonic acid (Compound N36)

Pd/C (100 mg) was added to a solution of 6-(aminomethyl)-3,4-dimethylcyclohex-3-ene-1-sulfonic acid (420 mg, 1.92 mmol) in EtOH (60% in water, 50 mL). The suspension was stirred under $H_2$ pressure for 6 hours, filtered and concentrated to obtain 380 mg of the reduced product as a 1:1 mixture of cis/trans diastereoisomers. $^1$H NMR (500 MHz, $H_2O$) δ 0.70 (d, J=5.5 Hz, 1.5H), 0.73 (d, J=5.5 Hz, 1.5H), 0.76 (d, J=5.5 Hz, 1.5H), 0.79 (d, J=5.5 Hz, 1.5H), 1.03 (m, 1H), 1.23 (m, 1H), 1.40 (m, 0.5H), 1.60 (1.78 (m, 3H), 1.85 (m, 0.5H), 2.32-2.43 (m, 1H), 2.91-3.02 (m, 2H), 3.30-3.38 (m, 1H). $^{13}$C NMR (125 MHz, $D_2O$) δ 14.12, 18.51, 18.90, 19.19, 25.50, 30.57, 31.18, 31.98, 33.56, 33.77, 34.31, 36.87, 37.13, 38.10, 38.16, 41.01, 60.75, 60.91. ES-MS 220 (M−1).

Preparation of 3-{[(2S)-2-hydroxy-2-phenylethyl]amino}-2-propanesulfonic acid: (Compound N37)

To a solution of (S)-(+)-2-amino-1-phenylethanol (5.0 g, 36.4 mmol) in 25% toluene/acetonitrile (35 mL) was added 1,3-propane sultone (4.2 g, 34.7 mmol). The solution was stirred at reflux for 3 hours. The reaction mixture was cooled to room temperature. The solid was collected by filtration and washed with acetone (2×20 mL). The solid was suspended in EtOH (40 mL). The suspension was stirred at reflux for 1 hour. The mixture was cooled to room temperature, the solid material was collected by filtration, washed with acetone (2×10 mL), and dried in a vacuum oven (50° C.), affording the title compound (7.77 g, 86%); $^1$H NMR ($D_2O$, 300 MHz) δ ppm 7.31 (m, 5H), 4.91 (dd, 1H, J=3.9 Hz, 9.3 Hz), 3.18 (m, 2H), 3.12 (t, 2H, J=6.8 Hz), 2.87 (t, 2H, J=7.3 Hz), 2.02 (m, 2H); $^{13}$C NMR ($D_2O$, 75 MHz) δ ppm 139.58, 129.16, 128.97, 126.31, 69.05, 53.21, 48.07, 46.60, 21.29; ES-MS 258 (M−1).

Preparation of 3-{[(2R)-2-hydroxy-2-phenylethyl]amino}-2-propanesulfonic acid: (Compound N39)

To a solution of (R)-(−)-2-amino-1-phenylethanol (5.0 g, 36.4 mmol) in 25% toluene/acetonitrile (40 mL) was added 1,3-propane sultone (4.2 g, 34.7 mmol). The solution was stirred at reflux for 4 hours. The reaction mixture was cooled to room temperature. The solid was collected by filtration and washed with acetone (2×20 mL). The solid was suspended in EtOH (50 mL). The suspension was stirred at reflux for 1 hour. The mixture was cooled to room temperature, the solid material was collected by filtration, washed with acetone (2×10 mL), and dried in a vacuum oven (50° C.), affording the title compound (8.10 g, 90%); $^1$H NMR ($D_2O$, 300 MHz) δ ppm 7.46 (m, 5H), 5.06 (dd, 1H, J=4.1 Hz, 9.0 Hz), 3.36 (m, 2H), 3.29 (m, 2H), 3.02 (t, 2H, J=7.3 Hz), 2.18 (m, 2H); $^{13}$C NMR ($D_2O$, 75 MHz) δ ppm 139.56, 129.16, 128.97, 126.12, 69.03, 53.20, 48.06, 46.59, 21.27; $[α]_D$=−36.9° (c=0.0116 in water); ES-MS 260 (M+1).

Preparation of 3-[(thiophen-2-methyl)amino]-1-propanesulfonic acid (Compound N43)

To a 0° C. solution of 2-thiophene methylamine (1.0 g, 8.8 mmol) in 40% toluene/acetonitrile (15 mL) was added via syringe pump 1,3-propanesultone (1.0 g, 8.4 mmol) in 40% toluene/acetonitrile (3 mL) over a 3 hour period. When the slow addition was completed, the reaction mixture was allowed to warm up to room temperature and the product started to precipitate. The mixture was stirred under these conditions for 60 hours. The solid material was collected by filtration and washed with acetone (2×10 mL). The solid was suspended in EtOH (15 mL). The suspension was stirred at reflux for 1 hour. The mixture was cooled to room temperature; and the solid material was collected by filtration, washed with acetone (2×10 mL), and dried in a vacuum oven (50° C.), affording the title compound (1.24 g, 63%). $^1$H NMR ($D_2O$, 500 MHz) δ ppm 1.99 (m, 2H), 2.85 (t, 2H, J=7.3 Hz), 3.10 (t, 2H, J=7.3 Hz), 4.35 (s, 2H), 6.99 (t, 1H, J=4.4 Hz), 7.14 (d, 1H, J=2.4 Hz); $^{13}$C NMR ($D_2O$, 125 MHz) δ ppm 21.39, 45.03, 45.47, 48.01, 128.00, 128.85, 131.07, 131.55; ES-MS 234 (M−1).

Preparation of 3-[1-(2-thienyl)-cyclohexylamino]-1-propanesulfonic acid (Compound N45)

To a vigorously stirred suspension of magnesium (dried, 5 g, 205 m mmol) in THF (anhydrous, 60 mL) was added slowly 2-bromothiophene (5.7 g, 35 mmol) (note: exothermic reaction). The mixture was stirred for 2 hours at room temperature, followed by dropwise addition of cyclohexanone (3 g, 31 mmol) in THF (10 mL). The reaction mixture was stirred for 1 hour, quenched carefully by adding HCl (2.5N, 10 mL) and diluted with $Et_2O$ (100 mL). The liquid part was transferred to a separator funnel to which was added HCl (1 M, 50 mL). The organic layer was isolated, dried ($MgSO_4$), and concentrated. The residual material was used in the next step without purification.

The residual material from step 1 was diluted in $CH_2Cl_2$ (60 mL). To the obtained solution was added $NaN_3$ (4.7 g, 73 mmol) followed by TFA (6 mL). The reaction mixture was stirred for 1 hour, quenched with water, and diluted with ether. The organic layer was washed with water and 1N $NH_4OH$ in sequence, dried over $Na_2SO_4$, and carefully concentrated. The resultant azide derivative was used in the next step without purification.

LAH (1 g, 26 mmol) was added portion-wise to a solution of the azide derivative (obtained from step 2) in ether (80 mL). The reaction mixture was stirred for 3 hours before being quenched with NaOH (1N). The quenched mixture was extracted twice with $Et_2O$. The combined organic layers were dried ($Na_2SO_4$), and concentrated to a residue, which was purified by column chromatography using $CH_2Cl_2$/MeOH 95:05 to 90:10 as eluant, affording the desired amine intermediate (2 g).

To a stirred solution of the amine intermediate (obtained in step 3, 1.5 g, 8.27 mmol) in $CH_3CN$ (25 mL) was added 1,3-propane sultone (1.01 g, 8.27 mmol). The reaction mixture was stirred at room temperature over the week-end. The solid was collected by filtration, suspended in EtOH (40 mL). The suspension was stirred at reflux for 1 hour, cooled to room temperature; and the solid material was collected by filtration, washed with ethanol, and dried under high vacuum to afford the title compound (1.3 g, 78%); $^1$H NMR (500 MHz, $D_2O$+a drop of NaOD) δ 1.10-1.28 (m, 4H), 1.40 (m, 2H), 2.52 (m, 4H), 1.95 (m, 2H), 2.13 (t, J=8.0 Hz, 2H), 2.57 (t, J=8.0 Hz, 2H), 6.82 (m, 2H), 7.16 (m, 1H). $^{13}$C NMR (125 MHz, $D_2O$+a drop of NaOD) δ 22.20, 24.77, 25.40, 37.10, 40.32, 49.27, 57.44, 124.46, 124.63, 125.39, 126.86. ES-MS 302 (M−1).

Preparation of
3-[(2-furylmethyl)amino]-1-propanesulfonic acid
(Compound N48)

A solution of 1,3-propane sultone (1.5 g, 12.28 mmol) in $CH_3CN$ (10 mL) was added slowly within 4 hours via a syringe pump to a boiling solution of (2-furylmethyl)amine (6 g; 61.78 mmol) in $CH_3CN$ (120 mL). The reaction was stirred for an hour before being concentrated under reduced pressure. The residue was diluted with water and EtOAc. The organic layer was discarded and the aqueous phase was washed twice with EtOAc, concentrated under high vacuum to afford the title compound as a white solid (2.6 g, 96%); $^1$H NMR (500 MHz, $D_2O$) δ 1.94 (m, 2H), 2.83 (m, 2H), 3.03 (m, 2H), 4.12 (s, 2H), 6.35 (m, 1H), 6.46 (m, 1H), 7.44 (m, 1H). $^{13}$C NMR (125 MHz, $D_2O$) δ 21.60, 43.30, 45.54, 48.08, 11.11, 112.43, 144.79, 154.27. ES-MS 218 (M−1).

Preparation of 3-[(tetrahydrofuran-2-ylmethyl)amino]-1-propanesulfonic acid (Compound N47)

A solution of 1,3-propane sultone (1.5 g, 12.58 mmol) in $CH_3CN$ (10 mL) was added slowly within 4 h via a syringe pump to a boiling solution of tetrahydrofurfurylamine (6 g, 59.91 mmol) in $CH_3CN$ (120 mL). The reaction was stirred for an hour before being concentrated under reduced pressure. The residual material was diluted with water and EtOAc. The organic layer was discarded; and the aqueous phase was washed twice with EtOAc, concentrated under high vacuum to afford the desired product as a complex with tetrahydrofurfurylamine. $^1$H NMR (500 MHz, $D_2O$) δ 1.40-1.52 (m, 1H), 1.75-2.00 (m, 5H), 2.71-2.88 (m, 5H), 3.62-3.75 (m, 2H), 4.00 (m, 1H). $^{13}$C NMR (125 MHz, $D_2O$) δ 22.61, 25.10, 25.18, 28.38, 28.89, 43.43, 47.03, 48.59, 51.69, 28.25, 28.31, 76.11, 76.89.

To the solution of product obtained in step 1 in water (20 mL) was added one equivalent of NaOH, followed by $CH_2Cl_2$ (30 mL) and the mixture was stirred vigorously. The organic layer was discarded and the aqueous phase was washed twice with $CH_2Cl_2$, concentrated under reduced pressure to afford the title compound (1.8 g, 96%); $^1$H NMR (500 MHz, $D_2O$) δ 1.42 (m, 1H), 1.78 (m, 4H), 1.90 (m, 1H), 2.55 (m, 4H), 2.80 (m, 2H), 3.63 (m, 1H), 3.70 (m, 1H), 3.90 (m, 1H); $^{13}$C NMR (125 MHz, $D_2O$) δ 24.05, 25.19, 29.12, 47.52, 49.14, 52.49, 67.96, 78.25. ES-MS 246 (M+1).

Preparation of 3-[2-(furan-2-yl)-2-propylamino]-1-propanesulfonic acid (Compound N46)

$CeCl_3$-$7H_2O$ (8.00 g, 21.48 mmol) was dried at 140° C.-150° C. for 15 h. The dry solid was palced in THF (100 mL). The mixture was stirred vigorously for 1 hour, cooled to −78° C., and followed by addition of MeLi (13.42 mL, 21.48 mmol). The suspension was stirred for 2 hours, followed by the dropwise addition of 2-furanecarbonitrile (1 g, 10.74 mmol). The reaction mixture was stirred at −78° C. for 6 hours, followed by addition of concentrated aqueous $NH_4OH$ (70 mL). The mixture was warmed to room temperature and filtered through celite. The filtrate was extracted with EtOAc. The organic layer was dried ($Na_2SO_4$) and concentrated. The residual material was subjected to column chromatography ($CH_2Cl_2$/MeOH 95:5 as the eluant) to give the desired amine intermediate (500 mg, 36%); $^1$H NMR (500 MHz, $CDCl_3$) δ 1.45 (s, 6H), 5.60 (bs, $NH_2$), 6.05 (m, 1H), 6.26 (m, 1H), 7.31 (m, 1H). $^{13}$C NMR (125 MHz, $CDCl_3$) δ 29.74, 49.79, 102.28, 110.08, 141.18, 163.17.

To a stirred solution of the amine intermediate (obtained in step 1, 200 mg, 1.55 mmol) in $CH_3CN$ (10 mL) was added 1,3-propane sultone (2.16 g, 17.7 mmol). The reaction mixture was stirred overnight at reflux then cooled to room temperature. The solid was collected by filtration, suspended in EtOH (40 mL). The ethanol suspension was stirred at reflux for 1 hour, and then cooled to room temperature. The solid was collected by filtration, washed with ethanol, and dried under high vacuum, providing the title compound (120 mg, 31%); $^1$H NMR (500 MHz, $D_2O$) δ 1.59 (m, 6H), 1.87 (m, 2H), 2.75-2.83 (m, 4H), 6.36 (m, 1H), 6.46 (m, 1H), 7.45 (m, 1H). $^{13}$C NMR (125 MHz, $D_2O$) δ 21.72, 22.80, 41.18, 48.08, 57.95, 110.17, 110.91, 144.36, 151.12. ES-MS 246 (M−1).

Preparation of
3-(5-indanylamino)-1-propanesulfonic acid
(Compound N49)

A solution 1,3-propane sultone (8.67 g, 71 mmol) in toluene (30 mL) was added to a solution of 5-aminoindan (10 g, 71 mmol) in MeCN (70 mL). The mixture was heated under reflux. After 20 minutes, the mixture turned into a lump. Ethanol (50 mL) was added to restore stirring and the suspension was heated at reflux for another 2 hours. The mixture was cooled to 5° C. with an ice bath. The solid was collected by suction filtration and rinsed with ethanol (2×20 mL). The wet cake was aspirator dried for 10 minutes. The solid was dried overnight in a vacuum oven at 60° C. The resulting solid (13.57 g) was recrystallized in a mixture of ethanol (80 mL) and water (20 mL). The suspension was cooled to 1.0° C. The solid was collected by suction filtration, rinsed with ethanol (2×20 mL), aspirator dried for 15 min., and further dried overnight in a vacuum oven at 60° C., finishing as the title compound as a fine white powder (12.23 g, 67%); $^1$H NMR (500 MHz, D$_2$O) δ 1.94 (m, 2H), 2.01 (m, 2H), 2.79 (m, 4H), 2.85 (m, 2H), 3.41 (m, 2H), 7.07 (m, 1H), 7.19 (m, 1H), 7.27 (m, 1H); $^{13}$C (125 MHz, D$_2$O) δ 21.07, 25.45, 32.13, 32.51, 47.91, 50.53, 118.41, 120.13, 125.89, 132.66, 146.81, 147.47; ES-MS 254(M−1)

Preparation of
3-(4-indanylamino)-1-propanesulfonic acid
(Compound N50)

To a 0° C. solution of 4-aminoindan (5.0 g, 37.5 mmol) in 25% toluene/acetonitrile (50 mL) was added 1,3-propane sultone (4.37 g, 35.8 mmol). The mixture was stirred at reflux overnight, and then cooled to room temperature. The solid material was collected by filtration, and washed with acetone (2×25 mL). The resultant solid was suspended in EtOH (60 mL). The suspension was stirred at reflux for 1 hour, and then cooled to room temperature. The solid material was collected by filtration, washed with acetone (2×25 mL) and dried in a vacuum oven (50° C.), affording the title compound (7.75 g, 85%). $^1$H NMR (D$_2$O, 500 MHz) δ ppm 2.01 (m, 4H), 2.84 (m, 6H), 3.42 (t, 2H, J=7.8 Hz), 7.05 (d 1H, J=7.8 Hz), 7.18 (t, 1H, J=7.6 Hz), 7.26 (d, 1H, J=7.3 Hz); $^{13}$C NMR (D$_2$O, 125 MHz) δ ppm 21.16, 25.25, 29.87, 32.60, 47.94, 49.10, 119.84, 125.81, 128.39, 137.50, 148.73; ES-MS 254 (M−1).

Preparation of 3-{[2-(2-benzothiophenyl)-2-propyl]amino}-1-propanesulfonic acid (Compound N52)

A solution of benzothiophene-2-carboxaldehyde (1.5 g, 9.2 mmol), hydroxylamine hydrochloride (760 mg, 11.0 mmol) in N-methyl-2-pyrrolidinone (NMP, 15 mL) was stirred at 115° C. for 4 hours. After the reaction mixture was cooled to room temperature, and it was poured into water (50 mL). The resultant mixture was extracted with diethyl ether (2×20 mL). The organic extracts were combined, dried over Na$_2$SO$_4$, evaporated to dryness, and further dried in vacuo. The residual material was purified by flash chromatography (R$_f$=0.45, 10% EtOAc/hexanes), affording 1-benzothiophene-2-carbonitrile (0.850 g, 58%).

Cerium chloride heptahydrate (7.5 g, 20.2 mmol) was dried in vacuo at 150° C. overnight, and then palced in anhydrous THF (40 mL). The suspension was stirred at room temperature and sonicated for 15 minutes. The mixture was cooled to −50° C. before methyl lithium (1.6 M in Et2O, 12.6 mL, 20.2 mmol) was slowly added. The mixture was stirred at −50° C. for 1 h, followed by addition of 1-benzothiophene-2-carbonitrile (from step 1, 0.850 g, 5.3 mmol) via syringe. The reaction mixture was stirred at −50° C. for 2 hours, and then quenched with concentrated NH$_4$OH (15 mL). The mixture was warmed up to 0° C. before the solid material was removed by filtration. The organic phase was separated and the solvent was evaporated. The residue was dissolved in diethyl ether (25 mL). The solution was extracted with Brine (2×25 mL). The organic phase was dried over Na$_2$SO$_4$. After removal of the solvent by evaporation, the residue was dried in vacuo, purified by flash chromatography (R$_f$=0.33, 5% MeOH/CH$_2$Cl$_2$, affording 2-(2-benzothiophenyl)-2-propylamine (0.620 g, 61%).

To a solution of 2-(2-benzothienyl)-2-propylamine (0.620 g, 3.2 mmol) in 25% toluene/acetonitrile (15 mL) was added 1,3-propane sultone (0.377 g, 3.1 mmol). The reaction mixture was stirred at reflux overnight. The solid material was collected by filtration and washed with acetone (2×10 mL). The solid was recrystallized in EtOH (10 mL) and water (2 mL). The resultant light-blue crystals were dissolved in a hot solvent mixture (15% water/EtOH); and the solution was treated with activated charcoal. The hot suspension was filtered on celite. The filtrate was evaporated to dryness. The resulting solid was suspended in acetone (20 mL), collected by filtration and dried in a vacuum oven (50° C.), affording the title compound (0.514 g, 51%). $^1$H NMR (DMSO, 500 MHz) δ ppm 1.77 (s, 6H), 1.92 (m, 2H), 2.59 (t, 2H, J=6.3 Hz), 2.90 (m, 2H), 7.40 (m, 2H), 7.59 (s, 1H), 7.85 (m, 1H), 7.95 (m, 1H), 9.38 (s (br), 2H); $^{13}$C NMR (DMSO, 125 MHz) δ ppm 144.66, 139.60, 139.55, 125.97, 125.58, 124.89, 123.26, 59.04, 50.07, 42.73, 26.62, 22.78; ES-MS 312 (M−1).

Preparation of
3-(4-chlorophenyl-2-propylamino)-1-propanesulfonic acid (Compound N54)

CeCl$_3$-7H$_2$O (20.15 g, 59.1 mmol) was dried at 150° C. for 15 hours. The dry solid was placed in THF (200 mL). The mixture was stirred vigorously for 1.5 hours, and cooled to −78° C. To the suspension was added MeLi (1.6 M, 37 mL, 59.2 mmol). The suspension was warmed to −50° C., stirred for 1 hour, and then cooled to −78° C., followed by the dropwise addition of a solution of 4-chlorothiobenzamide (2.0 g, 11.6 mmol) in THF (15 mL). The mixture was warmed slowly to 0° C. in 2.5 hours, and then was cooled to −50° C., followed by addition of concentrated aqueous NH$_4$OH (50 mL). The mixture was warmed to room temperature and filtered through celite. The filtrate was extracted with EtOAc; the organic layer was dried (Na$_2$SO$_4$) and concentrated to dryness. The desired amine derivative (0.80 g, 41%) was obtained after purification using column chromatography on silica gel (CH$_2$Cl$_2$/MeOH as the eluant).

To a stirred solution of the amine derivative (obtained in step 1, 0.8 g, 4.7 mmol) in a solvent mixture of CH$_3$CN (10 mL) and toluene (3 mL) was added 1,3-propane sultone (600 mg, 5 mmol). The reaction mixture was stirred overnight at reflux and then cooled to room temperature. The solid material was collected by filtration, suspended in EtOH (10 mL), and stirred at reflux for 1 hour. The suspension was then cooled to room temperature;e and the solid was collected by filtration, washed with ethanol, and dried under high vacuum to afford the title compound (1.11 g, 81%); $^1$H NMR (500 MHz, DMSO-d$_6$) δ 1.66 (s, 6H), 1.91-1.95 (m, 2H), 2.61 (t, J=6.3 Hz, 2H), 2.75 (br s, 2H), 7.54 (d, J=8.8 Hz, 2H), 7.60 (d, J=8.8 Hz, 2H), 9.21 (br s, 2H); $^{13}$C (125 MHz, DMSO-d$_6$) δ 22.13, 25.09, 41.86, 49.31, 59.73, 128.23, 128.82, 133.37, 138.56; ES-MS 290 (M−1)

Preparation of
3-[(1-thien-2-ylethyl)amino]-1-propanesulfonic acid
(Compound N55)

To a solution of 1-thiophene-2-yl ethylamine (0.500 g, 3.9 mmol) in 25% toluene/acetonitrile (15 mL) was added 1,3-propane sultone (0.457 g, 3.7 mmol). The reaction mixture was stirred at reflux for 3 hours. After cooling to room temperature, the solid material was collected by filtration and washed with acetone (2×10 mL). The solid product was suspended in EtOH (20 mL). The mixture was stirred at reflux for 1 hour. After cooling to room temperature, the solid material was collected by filtration, washed with acetone (2×10 mL) and dried in a vacuum oven (50° C.), affording the title compound (0.556 g, 60%). $^1$H NMR (DMSO, 500 MHz) δ ppm 1.57 (d, 3H, J=6.8 Hz), 1.91 (m, 2H), 2.59 (t, 2H, J=6.8 Hz), 2.86 (m, 1H), 3.15 (m, 1H), 4.71 (m, 1H), 7.09 (t, 1H, J=3.9 Hz), 7.26 (d, 1H, J=2.9 Hz), 7.62 (d, 1H, J=4.9 Hz), 9.11 (s (br), 2H); $^{13}$C NMR (DMSO, 125 MHz) δ ppm 20.24, 22.43, 45.39, 49.91, 52.32, 128.00, 128.94, 139.80; ES-MS 248 (M−1).

Preparation of 3-(4-fluorophenyl-2-propylamino)-1-propanesulfonic acid (Compound N57)

CeCl$_3$·7H$_2$O (21.5 g, 57.7 mmol) was dried at 150° C. for 15 hours. To the solid was added THF (250 mL). The mixture was stirred vigorously for 1.5 hours, cooled to −78° C. To the suspension was added MeLi (1.6 M, 38 mL, 60.8 mmol). The suspension was warmed to −50° C., stirred for 1 hour and then cooled to −78° C., followed by the dropwise addition of 4-fluorothiobenzamide (2.2 g, 14 mmol). The mixture was warmed slowly to 0° C. in 2.25 hours, and then was cooled to at −50° C., followed by addition of concentrated aqueous NH$_4$OH (40 mL). The mixture was warmed to room temperature and filtered through celite. The filtrate was extracted with EtOAc; and the organic layer was dried (Na$_2$SO$_4$) and concentrated. The resultant residue was separated using column chromatography (CH$_2$Cl$_2$/MeOH as the eluant), yielding the corresponding amine derivative (0.78 g, 36%).

To a stirred solution of the amine derivative (obtained in step 1, 780 mg, 5.09 mmol) in mixed solvents of CH$_3$CN (7 mL) and toluene (3 mL) was added 1,3-propane sultone (650 mg, 5.10 mmol). The reaction mixture was stirred overnight at reflux then cooled to room temperature. The solid was collected by filtration, suspended in EtOH (7 mL) and stirred at reflux for 1 hour. The suspension was then cooled to room temperature; and the solid was collected by filtration, washed with ethanol and dried under high vacuum to afford the title compound (1.16 g, 83%); $^1$H NMR (500 MHz, DMSO-d$_6$) δ 1.65 (s, 6H), 1.91 (qt, J=6.3 Hz, 2H), 2.60 (t, J=6.3 Hz, 2H), 2.75 (br s, 2H), 7.30-7.33 (m, 2H), 7.60-7.63 (m, 2H), 9.21 (br s, 2H); $^{13}$C (125 MHz, DMSO-d$_6$) δ 22.05, 25.22, 41.89, 49.46, 59.60, 115.63 (d, J=21.1 Hz), 128.56 (d, J=8.6 Hz), 135.83, 161.91 (d, J=245 Hz); $^{19}$F (282 MHz, DMSO-d6) δ−114.0 to −114.1 (m); ES-MS 274 (M−1).

Preparation of 3-{[1-methyl-1-(5-methylthien-2-yl) ethyl]amino}-1-propanesulfonic acid: (Compound N60)

A solution of 5-methyl-2-thiophenecarboxaldehyde (3.0 g, 23.8 mmol), hydroxylamine hydrochloride (2.0 g, 28.7 mmol) in N-methyl-2-pyrrolidinone (NMP, 40 mL) was stirred at 115° C. for 4 hours. After cooling to room temperature, the solution was poured in water (50 mL) and extracted with diethyl ether (3×40 mL). The organic extracts were combined, dried over Na$_2$SO$_4$. Solvent was evaporated; and the residue was dried in vacuo, and purified by flash chromatography (R$_f$=0.41, 10% EtOAc/hexanes), affording the pure 5-methylthiophene-2-carbonitrile (1.30 g, 44%).

Cerium chloride heptahydrate (10 g, 26.9 mmol) was dried in vacuo at 150° C. overnight. To this solid was added anhydrous THF (100 mL). The suspension was stirred at room temperature for 30 minutes. The reaction mixture was cooled to −50° C. before methyl lithium (1.6 M in Et$_2$O, 26.9 mL, 26.9 mmol) was slowly added. The mixture was stirred at −50° C. for 1 hour, and then cooled to −78° C., followed by addition of 5-methylthiophene-2-carbonitrile obtained from step 1 (1.3 g, 10.6 mmol) via syringe. The reaction mixture was stirred at −50° C. for 2 hours, and then quenched with concentrated NH$_4$OH (30 mL). The mixture was warmed up to 0° C., and the solid material was removed by filtration. The organic phase was evaporated to dryness. The residue was dissolved in diethyl ether (30 mL). The solution was extracted with brine (2×30 mL). The combined organic phase was dried over Na$_2$SO$_4$ and the solvent was evaporated. The residue was dried in vacuo, and purified by flash chromatography (R$_f$=0.48, 5% MeOH/CH$_2$Cl$_2$), affording 1-methyl-1-(5-methylthien-2-yl)ethylamine (920 mg, 61%).

To a solution of 1-methyl-1-(5-methylthien-2-yl)ethylamine (920 mg, 6.5 mmol) in 25% toluene/acetonitrile (15 mL) was added 1,3-propane sultone (758 mg, 6.2 mmol). The reaction mixture was stirred at reflux overnight, and cooled to room temperature. The solid material was collected by filtration, washed with acetone (2×15 mL), and suspended in EtOH (20 mL). The suspension was stirred at reflux for 1 hour, and then cooled to room temperature. The solid material was collected by filtration, washed with acetone (2×10 mL) and dried in a vacuum oven (50° C.), affording the title compound (1.26 g, 74%). $^1$H NMR (D$_2$O, 500 MHz) δ ppm 1.82 (s, 6H), 1.92 (m, 2H), 2.48 (s, 3H), 2.90 (t, 2H, J=7.3 Hz), 3.00 (t, 2H, J=7.8 Hz), 6.87 (m, 1H), 7.09 (d, 1H, J=3.4 Hz); $^{13}$C NMR (D$_2$O, 125 MHz) δ ppm 14.48, 21.77, 25.66, 41.03, 48.10, 59.71, 125.81, 128.02, 139.53, 142.84; ES-MS 276 (M−1).

Preparation of 4-amino-1-hydroxy-1-(5-methylthien-2-yl)-2-butanesulfonic acid (Compound N63)

To a −78° C. solution of 1,3-propane sultone (2.5 g, 20.5 mmol) in anhydrous THF (100 mL) was added butyl lithium (2.5 M in hexanes, 9 mL, 22.5 mmol). The solution was stirred at −78° C. for 0.5 hours, followed by addition of 5-methyl-2-thiophenecarboxaldehyde (2.2 mL, 20.5 mmol) via syringe pump over a 0.5 hour period. The reaction mixture was stirred at −78° C. for 3 hours, and then warmed up to 0° C., followed by a slow addition of water (50 mL). The organic layer was separated; and the aqueous layer was extracted with Et$_2$O (2×50 mL). The organic phase and extracts were combined and dried over Na$_2$SO$_4$. Solvent was removed under reduced pressure. The residue was purified on a flash chromatography (R$_f$=0.26, 70% Hex/EtOAc), affording the corresponding sultone derivative (2.08 g, 41%).

To 0° C. concentrated ammonium hydroxide (28-30% NH$_3$, 50 mL) was added a solution of sultone (3.04 g, 13.3 mmol) in THF (15 mL) via syringe pump over a 4 hour period. The solution was stirred at 0° C. for 1 h and at room temperature overnight. The solvent was co-evaporated with EtOH. The solid was suspended in EtOH (15 mL). The mixture was stirred at reflux for 1 hour. After cooling to room temperature, the solid was filtered, washed with acetone (2×10 mL), and dried in a vacuum oven (50° C.), affording the title compound as a mixture of diastereoisomers (0.785 g, 35%). $^1$H NMR (D$_2$O, 500 MHz) δ ppm 6.80 (d, 0.2H, J=3.4 Hz), 6.72 (d, 0.8H, J=2.9 Hz), 6.65 (m, 1H), 5.43 (d, 0.8H, J=2.4 Hz), 5.12 (d, 0.2H, J=7.3 Hz), 3.08 (m, 1.6H), 2.97 (m, 0.4H), 2.85 (m, 1H), 2.31 (m, 3H), 2.04 (m, 1.6H), 1.84 (m, 0.4H); $^{13}$C (D$_2$O, 125 MHz) δ ppm 14.44, 22.85, 38.54, 63.80, 68.70, 124.18, 125.36, 140.26, 142.98; ES-MS 264 (M−1).

Preparation of 3-(4-trifluoromethylphenyl-2-propylamino)-1-propanesulfonic acid (Compound N64)

CeCl$_3$·7H$_2$O (21.0 g, 56.4 mmol) was dried at 150° C. for 15 hours. To the solid was added THF (250 mL). The mixture was stirred vigorously for 1.5 hours, cooled to −78° C. To the suspension was added MeLi (1.6 M, 38 mL, 60.8 mmol). The suspension was warmed to −50° C., stirred for 1 hour and then cooled to −78° C., followed by dropwise-addition of a solution of 4-trifluoromethylthiobenzamide (2.46 g, 12 mmol) in THF (20 mL). The mixture was warmed slowly to 0° C. in 2.5 h, and then was cooled to −50° C. followed by addition of concentrated aqueous $NH_4OH$ (70 mL). The mixture was warmed to room temperature and filtered through celite. The filtrate was extracted with EtOAc; and the organic layer was dried ($Na_2SO_4$) and concentrated. The residue was separated using column chromatography ($CH_2Cl_2$/MeOH as the eluant), affording the corresponding amine (1.69 g, 69%).

To a stirred solution of the amine (obtained in step 1, 1.69 g, 8.3 mmol) in mixed solvents of $CH_3CN$ (10 mL) and toluene (3 mL) was added 1,3-propane sultone (0.75 mL, 8.5 mmol). The reaction mixture was stirred overnight at reflux and then cooled to room temperature. The solid was collected by filtration and suspended in EtOH (10 mL). The suspension was stirred at reflux for 1 hour, and then cooled to room temperature. The solid material was collected by filtration, washed with ethanol and dried under high vacuum to give the title compound, 2.39 g (89%); $^1H$ NMR (300 MHz, DMSO-$d_6$) δ 1.69 (s, 6H), 1.94 (qt, J=6.4 Hz, 2H), 2.60 (t, J=6.4 Hz, 2H), 2.79 (br s, 2H), 7.82 (q, J=8.5 Hz, 4H), 9.32 (br s, 2H); $^{13}C$ (75 MHz, DMSO-$d_6$) δ 22.25, 25.15, 41.97, 49.26, 59.93, 123.70 (q, J=271 Hz), 125.52 (d, J=3.5 Hz), 126.89, 128.71 (q, J=31.9 Hz), 143.84; $^{19}F$ (282 MHz, DMSO-d6) δ−61.87 (s); ES-MS 324 (M−1)

Preparation of
3-(2-phenyl-2-butylamino)-1-propanesulfonic acid
(Compound N65)

The flask was closed with a septum and connected to a 20% NaOH scrubber.

Sodium cyanide (powdered, 2.6 g) was added in portions to acetic acid (10 mL). The mixture was stirred for 10 minutes at room temperature. A solution of sulfuric acid (8 mL) in acetic acid (10 mL) was added dropwise over a 20 minute period. Then, the 2-phenyl-2-butanol (5 g, 33.3 mmol) was added dropwise over 5 min. The mixture was stirred at room temperature for 22 hours then cooled to 0° C. with an ice-water bath. The pH of the solution was adjusted to 9 with addition of ammonium hydroxide (460 mL). The organic phase was separated and the aqueous layer was extracted with ether (3×30 mL). The organic phase and extracts were combined, washed with saturated potassium carbonate (1×5 mL), and dried over sodium sulfate. The solvent was evaporated under reduced pressure. The residue was purified by flash chromatography on silica gel (MeOH/$CH_4Cl_2$ as eluant), affording clear yellow oil (3.84 g, 65%).

A solution of NaOH (20%, 30 mL) was added to the crude product from step 1 (3.84 g). The mixture was heated at reflux for 2 h, and then cooled to room temperature. Sodium chloride (7.5 g) was added to facilitate the phase separation. The organic layer were separated and the aqueous layer was extracted with mixed solvent of toluene and MTBK (3×5 mL, v/v=1:3). The combined organic layers were washed with brine (1×5 mL), dried over sodium sulfate and filtered. The filtrate was used in the next step without purification.

A solution of 1,3-propane sultone (400 mg, 3.3 mmol) and 2-phenyl-2-aminobutane (425 mg, 2.85 mmol, from step 2) in mixed solvents of toluene and $CH_3CN$ (5 mL, v/v=3:7) was heated under reflux for 22 h and then cooled to room temperature. The product had formed a gum. It was triturated with ether/ethanol to provide a brownish solid. The solid was collected by suction filtration. The crude solid was purified by reverse phase preparative HPLC (299 mg, 39%); $^1H$ NMR (500 MHz, $D_2O$) δ 0.77 (t, J=7.3 Hz, 3H), 1.77 (s, 3H), 1.99-2.11 (m, 3H), 2.20-2.27 9 m, 1H), 2.66-2.71 (m, 1H), 2.79-2.89 (m, 2H), 3.06-3.11 (m, 1H), 7.42-7.45 (m, 1H), 7.49-7.55 (m, 4H); $^{13}C$ (125 MHz, $D_2O$) δ 8.62, 19.90, 23.37, 34.22, 43.15, 50.29, 66.31, 127.93, 130.38, 130.60, 138.16; ES-MS 270 (M−1):

Preparation of 3-(4-methoxyphenyl-2-propylamino)-
1-propanesulfonic acid (Compound N66)

$CeCl_3·7H_2O$ (21.5 g, 57.7 mmol) was dried at 150° C. for 15 hours. To the solid was added THF (250 mL). The mixture was stirred vigorously for 1.5 hours, and then cooled to −78° C. To the suspension was added MeLi (1.6 M, 38 mL, 60.8 mmol). The suspension was warmed to −50° C., stirred for 1 hour and then cooled to −78° C., followed by dropwise-addition of a solution of 4-trifluoromethylthiobenzamide (2.00 g, 12 mmol) in THF (20 mL). The mixture was warmed slowly to −50° C. in 4 hours. Concentrated aqueous $NH_4OH$ (70 mL) was added and the mixture was warmed to room temperature and filtered through celite. The filtrate was extracted with EtOAc, the organic layer dried ($Na_2SO_4$) and concentrated. The residue was separated using column chromatography ($CH_2Cl_2$/MeOH as the eluant), yielding the corresponding amine (0.60 g, 30%).

To a stirred solution of the amine (obtained in step 1, 0.60 mg, 3.6 mmol) in mixed solvents of $CH_3CN$ (10 mL) and toluene (2 mL) was added 1,3-propane sultone (0.34 mL, 3.8 mmol). The reaction mixture was stirred overnight at reflux then cooled to room temperature. The solid was collected by filtration, suspended in EtOH (10 mL). The suspension was stirred at reflux for 1 hour, and then cooled to room temperature. The solid was collected by filtration, washed with ethanol and dried under high vacuum to afford the title compound, 0.97 g (94%); $^1H$ NMR (300 MHz, DMSO-$d_6$) δ 1.64 (s, 6H), 1.91 (qt, J=6.5 Hz, 2H), 2.58 (t, J=6.3 Hz, 2H), 2.71 (br s, 2H), 3.77 (s, 3H), 6.99-7.02 (m, 2H), 7.47-7.50(m, 2H), 9.06 (br s, 2H); $^{13}C$ NMR (75 MHz, DMSO-$d_6$) δ 22.09, 25.27, 41.77, 49.40, 55.20, 59.67, 114.04, 127.54, 131.34, 159.21; ES-MS 286 (M−1).

Preparation of
3-(3-chlorophenyl-2-propylamino)-1-propanesulfonic
acid (Compound N67)

$CeCl_3·7H_2O$ (21.5 g, 57.7 mmol) was dried at 150° C. for 15 hours. To the solid was added THF (250 mL). The mixture was stirred vigorously for 1.5 hours, cooled to −78° C., and to the suspension was added MeLi (1.6 M, 40 mL, 64 mmol). The suspension was warmed to −50° C., stirred for 1 hour and then cooled to −78° C., followed by dropwise-addition of a solution of 3-chlorobenzonitrile (2.5 g, 18 mmol) in THF (20 mL). The mixture was warmed slowly to 0° C. in 2.5 hours, and then was cooled to at −50° C. Concentrated aqueous $NH_4OH$ (45 mL) was added and the mixture was warmed to room temperature and filtered through celite. The filtrate was extracted with EtOAc, the organic layer dried ($Na_2SO_4$) and concentrated. The residue was separated using column chromatography ($CH_2Cl_2$/MeOH as the eluant) to yield the corresponding amine (2.1 g, 69%).

To a stirred solution of the amine (obtained in step 1, 2.1 g, 12.4 mmol) in mixed solvents of $CH_3CN$ (12 mL) and toluene (3 mL) was added 1,3-propane sultone (1.6 g, 13 mmol). The reaction mixture was stirred overnight at reflux then cooled to room temperature. The solid was collected by filtration, suspended in EtOH (20 mL). The suspension was stirred at reflux for 1 hour, and then cooled to room temperature. The solid was collected by filtration, washed with ethanol and dried under high vacuum to afford the title compound (3.1 g, 86%); $^1$H NMR (500 MHz, DMSO-$d_6$) δ 1.66 (s, 6H), 1.93 (qt, J=6.5 Hz, 2H), 2.64 (t, J=6.6 Hz, 2H), 2.78 (br s, 2H), 7.48-7.57 (m, 3H), 7.63 (s, 1H), 9.25 (br s, 2H); $^{13}$C (100 MHz, DMSO-$d_6$) δ 22.13, 25.02, 41.95, 49.34, 59.86, 124.90, 126.31, 128.63, 130.79, 133.69, 142.10; ES-MS 290, 292 (M−1).

Preparation of
4-[(1R)-indan-1-ylamino]-2-butanesulfonic acid: (Compound N69)

To a solution of (R)-(−)-1-aminoindan (2.0 g, 15.0 mmol) in 25% toluene/acetonitrile (15 mL) was added 2,4-butane sultone (1.95 g, 14.3 mmol). The reaction mixture was stirred at reflux for 3 hours, and then cooled to room temperature. The solid material was collected by filtration and washed with acetone (2×15 mL). The solid was suspended in EtOH (20 mL). The suspension was stirred at reflux for 1 hour, and then cooled to room temperature. The solid material was collected by filtration, washed with acetone (2×10 mL) and dried in a vacuum oven (50° C.), affording the title compound (3.04 g, 79%). $^1$H NMR (D$_2$O, 500 MHz) δ ppm 1.14 (d, 1.5H, J=2.9 Hz), 1.16 (d, 1.5H, J=2.9 Hz), 1.78 (m, 1H), 2.09 (m, 2H), 2.40 (m, 1H), 2.92 (m, 2H), 3.00 (m, 1H), 3.12 (t, 2H, J=8.0 Hz), 4.67 (m, 1H), 7.21 (m, 1H), 7.28 (m, 2H), 7.38 (d, 1H, J=7.8 Hz); $^{13}$C NMR (D$_2$O, 125 MHz) δ ppm 14.74, 14.82, 28.29, 28.37, 28.64, 28.65, 29.83, 43.03, 43.09, 53.28, 53.31, 62.91, 62.95, 125.52, 125.71, 127.19, 130.28, 136.44, 145.34; $[α]_D$=−0.5° (c=0.0083 in water); ES-MS 268 (M−1).

Preparation of
4-[(1S)-indan-1-ylamino]-2-butanesulfonic acid: (Compound N70)

To a solution of (S)-(+)-1-aminoindan (2.0 g, 15.0 mmol) in 25% toluene/acetonitrile (15 mL) was added 2,4-butane sultone (1.95 g, 14.3 mmol). The reaction mixture was stirred at reflux for 3 h, and then cooled to room temperature. The solid material was collected by filtration, washed with acetone (2×15 mL), and then was suspended in EtOH (20 mL). The suspension was stirred at reflux for 1 hour, and cooled to room temperature. The solid material was collected by filtration, washed with acetone (2×10 mL) and dried in a vacuum oven (50° C.), affording the title compound (3.32 g, 86%). $^1$H NMR (D$_2$O, 500 MHz) δ ppm 1.16 (m, 3H), 1.78 (m, 1H), 2.10 (m, 2H), 2.42 (m, 1H), 2.86 (m, 2H), 3.01 (m, 1H), 3.13 (t, 2H, J=7.8 Hz), 4.68 (m, 1H), 7.22 (m, 1H), 7.29 (m, 2H), 7.39 (d, 1H, J=7.8 Hz); $^{13}$C NMR (D$_2$O, 125 MHz) δ ppm 14.74, 14.82, 28.29, 28.37, 28.64, 28.65, 29.83, 43.03, 43.09, 53.28, 53.31, 62.91, 62.95, 125.51, 125.70, 127.19, 130.28, 136.43, 145.34; $[α]_D$=+0.8° (c=0.0126 in water); ES-MS 268 (M−1).

Preparation of 4-amino-1-(1-benzothien-2-yl)-2-butanesulfonic acid (Compound N71)

Sodium borohydride (250 mg, 6.5 mmol) was added in two portions to a 0° C. solution of benzo[b]thiophene-2-carboxaldehyde (2.0 g, 12.3 mmol) in ethanol (15 mL). The reaction mixture was stirred at room temperature for 2 hours. The volume of solvent was reduced to ⅓ by evaporation. Diethyl ether (20 mL) and water (20 mL) were added. The organic layer was separated and the aqueous phase was extracted with diethyl ether (2×20 mL). The organic layer and extracts were combined and dried over Na$_2$SO$_4$. Solvent was evaporated under reduced pressure, affording 1-benzothien-2-ylmethanol (2.02 g, 99%).

To a 0° C. solution of 1-benzothien-2-ylmethanol (2.02 g, 12.3 mmol) in anhydrous CH$_2$Cl$_2$ (25 mL) was added phosphorus tribromide (1.7 mL, 18.4 mmol). The reaction mixture was stirred at room temperature for 1 hour. After the mixture was cooled to 0° C., water (20 mL) was slowly added. The organic phase was separated and the aqueous phase was extracted with CH$_2$Cl$_2$ (2×20 mL). The extracts were combined with the organic phase and dried over Na$_2$SO$_4$. Solvent was evaporated under reduced pressure, affording 2-(bromomethyl)-1-benzothiophene (2.57 g, 92%).

To a −78° C. solution of 1,3-propane sultone (1.38 g, 11.3 mmol) in anhydrous THF (100 mL) was added butyl lithium (2.5 M in hexanes, 5.0 mL, 12.5 mmol). The solution was stirred at −78° C. for 0.5 hours, followed by addition of 2-(bromomethyl)-1-benzothiophene (2.57 g, 11.3 mmol, from step 2) via syringe pump over a 0.5-h period. The reaction mixture was stirred at −78° C. for 3 hours and then warmed up to 0° C. before water (100 mL) was slowly added. The organic layer was separated and the aqueous layer was extracted with Et$_2$O (2×100 mL). The organic layer and extracts were combined, dried over Na$_2$SO$_4$, and evaporated under reduced pressure. The residue was purified by a flash chromatography (Rf=0.15, 70% Hex/EtOAc), affording the corresponding sultone (970 mg, 32%).

To a 0° C. aqueous solution of ammonium hydroxide (28-30%, 50 mL) in acetone (10 mL) was added via syringe pump over a 4 hour period a solution of the sultone (3.04 g, 13.3 mmol, from step 3) in acetone (15 mL). The solution was stirred at 0° C. for 1 hour and at room temperature for 3 hours. The solvent was co-evaporated with EtOH. The solid was suspended in acetone (20 mL), and then collected by filtration, washed with acetone (1×10 mL), and dried in a vacuum oven (50° C.), affording the title compound (0.390 g, 38%); $^1$H NMR (DMSO, 500 MHz) δ ppm 1.81 (m, 2H), 2.81 (m, 1H), 2.90 (m, 2H), 3.00 (m, 1H), 3.48 (m, 1H), 7.28 (m, 3H), 7.61 (s (broad), 2H), 7.71 (d, 1H, J=7.8 Hz), 7.88 (d, 1H, J=7.8 Hz); $^{13}$C NMR (DMSO, 125 MHz) δ ppm 27.90, 32.81, 38.38, 59.05, 122.95, 123.23, 123.60, 124.46, 125.00, 139.58, 140.54, 144.08; ES-MS 284 (M−1).

Preparation of 3-{[3-(methoxycarbonyl)thien-2-yl]amino}-1-propanesulfonic acid: (Compound N72)

To a solution of methyl 2-amino-3-thiophenecarboxylate (3.0 g, 19.1 mmol) in 25% toluene/acetonitrile (20 mL) was added 1,3-propane sultone (2.22 g, 18.2 mmol). The reaction mixture was stirred at reflux for 5 hours, and then cooled to room temperature. The reaction mixture was concentrated under reduced pressure. The oil residue was extracted with diethyl ether (1×30 mL) and water (1×30 mL). The residual material from aqueous phase was purified by preparative HPLC, affording the title compound (0.55 g, 10%). $^1$H NMR (D$_2$O, 500 MHz) δ ppm 1.91 (m, 2H), 2.82 (t, 2H, J=7.6 Hz), 3.36 (t, 2H, J=7.1 Hz), 3.70 (s, 3H), 6.84 (m, 1H), 7.56 (d, 1H, J=5.4 Hz); $^{13}$C NMR (D$_2$O, 125 MHz) δ ppm 23.76, 45.55, 48.26, 52.25, 119.36, 134.48, 149.98, 165.46; ES-MS 278 (M−1).

Preparation of 4-amino-1-dibenzyl-2-butanesulfonic acid (Compound N75)

To a −78° C. solution of 1,3-propane sultone (5.0 g, 41 mmol) in anhydrous THF (150 mL) was added butyl lithium (2.5 M in hexanes, 18 mL, 45 mmol). The solution was stirred at −78° C. for 0.5 h before benzyl bromide (4.9 mL, 41 mmol) was added via syringe pump over a 0.5-h period. The reaction mixture was stirred at −78° C. for 2 hours. The reaction mixture was warmed up to 0° C. before water (100 mL) was slowly added. The organic layer was collected. The aqueous phase was extracted EtOAc (2×25 mL). The organic layer and the extracts were combined, dried over $Na_2SO_4$, and evaporated under reduced pressure. The residue was purified by flash chromatography ($R_f$=0.25, 80% Hex/EtOAc), affording 1,1-dibenzyl-1,3-propane sultone (0.637 g).

To a 0° C. solution of aqueous solution of ammonium hydroxide (28-30%, 10 mL) in acetone (5 mL) was added via syringe pump over a 4 hour period a solution of 1,1-dibenzyl-1,3-propane sultone (0.636 g, 2.1 mmol) in acetone (10 mL). The solution was stirred at room temperature overnight. The solvent was co-evaporated with EtOH. The resultant solid was suspended in acetone (20 mL), collected by filtration, and dried in a vacuum oven (50° C.), affording the title compound (0.420 g, 63%). $^1$H NMR (500 MHz, DMSO) δ (ppm) 1.67 (t, 2H, J=6.8 Hz), 2.69 (d, 2H, J=14.2 Hz), 3.15 (m, 4H), 7.18 (m, 10H), 7.61 (s (br), 2H); $^{13}$C NMR (125 MHz, DMSO) δ (ppm) 30.39, 35.61, 40.57, 60.89, 125.95, 127.46, 131.36, 137.71; ES-MS 318 (M−1).

Preparation of 3-amino-2-(thien-2-ylmethyl)propane-1-sulfonic acid (two methods) (Compound N83)

Method 1:

To a cold (−78° C.) solution of 3-hydroxypropionitrile (2 g, 28.12 mmol) in THF (60 mL) was added a solution of lithium bis(trimethylsilyl)amide (1 M in THF, 56 mL). After the reaction mixture was stirred for 1 h at this temperature, 2-thieylmethyl bromide (4.98 g, 28.12 mml) was added dropwise. The reaction mixture was left warming to reach 0° C. at which temperature the mixture was stirred for 2 hours. The reaction was quenched with 1N HCl and extracted with EtOAc. The organic layer was washed with 1N HCl, dried over $Na_2SO_4$ and concentrated. The residue was applied on silica gel column (eluant: hexane:EtOAc 70:30 to 50:50) to afford 3-hydroxy-2-(2-thieylmethyl)-1-propionitrile (2.0 g, 42%); $^1$H NMR (500 MHz, CDCl$_3$) δ 2.60 (bs, 1H), 3.00 (m, 1H), 3.20 (m, 2H), 3.80 (m, 2H). 6.97 (m, 2H), 7.22 (m, 1H); The dialkylated product was isolated in 23% yield (1.7 g).

To a stirred solution of 3-hydroxy-2-(2-thieylmethyl)-1-propionitrile (obtained in step 1, 1 g, 6 mmol) in THF (60 mL) was added portion-wise LAH (450 mg, 12 mmol). The reaction was stirred for 2 h, quenched with NaOH (1 M) and left stirred vigorously for 1 hour before the addition of $Boc_2O$ (1.6 g, 7.2 mmol). The reaction mixture was stirred for 2 hours and then diluted with $Et_2O$. The two phases were separated and the organic layer was dried and concentrated. The residual material was purified by column chromatography (Hexanes/EtOAc 70:30 as eluant) to afford the corresponding alcohol product (1.43 g, 88% yield).

To a cold (0° C.) solution of the alcohol product of step 2 (630 mg, 2.32 mmol) in $CH_2Cl_2$ (30 mL) was added $NEt_3$ (646 μL, 4.64 mmol) followed by MsCl (200 μL, 2.55 mmol). The reaction mixture was stirred for 1 hour, diluted with $H_2O$. The organic layer was isolated and concentrated to give the corresponding mesylate which was used in the next step without further purification.

The solution of mesylate (obtained in step 3) in EtOH (5 mL) was added dropwise to a refluxed solution of $Na_2SO_3$ (440 mg, 3.48 mmol). After 15 minutes, the starting material was completely consumed. The reaction mixture was diluted with water and EtOAc. The organic layer was isolated and concentrated. The residue was separated by column chromatography (hexanes/EtOAc, 50:50) to afford the N-Boc protected title compound (300 mg); $^1$H NMR (500 MHz, CD$_3$OD) δ 1.43 (s, 9H), 2.40 (m, 1H), 2.82 (m, 2H), 3.02 (m, 2H), 3.20 & 3.28 (ABX, J=15 and 8 Hz, 2H), 6.91 (m, 2H), 7.20 (m, 1H); $^{13}$C NMR (125 MHz, D$_2$O) δ 27.77, 31.62, 38.39, 42.81, 52.34, 79.23, 123.70. The aqueous layer was concentrated and the residue was purified by column chromatography (CH$_2$Cl$_2$/MeOH 80/20) to afford a small amount of the title compound (40 mg, 3%).

The N-Boc protected title compound (100 mg) in $CH_2Cl_2$ (2 mL) was treated with TFA (1 mL). The reaction mixture was stirred for 30 minutes, concentrated and suspended in EtOH. The white solid was collected by filtration to give the title compound (65 mg, 93%); $^1$H NMR (500 MHz, D$_2$O) δ 2.43 (m, 1H), 2.83 (dd, J=7.8 & 15 Hz, 1H), 2.85 (m, 1H), 2.92 (m, 2H), 3.03 & 3.10 (ABX, J=13 and 7 Hz, 2H), 6.83 (m, 1H), 6.88 (m, 1H), 7.20 (m, 1H); $^{13}$C NMR (125 MHz, D$_2$O) δ 31.68, 35.81, 42.44, 52.32, 125.18, 127.04, 127.54, 140.31; ES-MS 234 (M−1).

Method 2:

Steps 1 to 3 are the same as those in Method 1.

To a solution of the mesylate (obtained in step 3) in $CH_2Cl_2$ (2 mL) was added TFA (1 mL). The reaction was stirred for 1 hour, concentrated to afford the corresponding amine TFA salt; $^1$H NMR (500 MHz, D$_2$O) δ 2.39 (m, 1H), 2.85-3.08 (m, 4H), 3.03 (s, 3H), 4.13 (m, 1H), 4.22 (m, 1H), 6.83 (m, 1H), 6.88 (m, 1H), 7.18 (m, 1H).

A solution of the amine TFA salt (from step 4) in H$_2$O (5 mL) was added slowly to a refluxed solution of $Na_2SO_3$ (1.17 g, 9.28 mmol). The reaction mixture was stirred for 3 hours, and the solvent was removed. Concentrated HCl (5 mL) was added to precipitate the inorganic salt which was removed by filtration. The filtrate was concentrated; and the resultant residue was purified by column chromatography using CH$_2$Cl$_2$/MeOH 90:10 to 80:20 as eluant to afford the title compound in 37% yield; NMR and MS spectra are identical to those from method 1.

Preparation of 4-amino-1-(2-thienyl)-2-butanesulfonic acid (Compound N84)

To a solution of 2-thienylmethanol (5 g, 43.80 mmol) in dry ether (80 mL) was added a solution of PBr$_3$ (17.7 g, 65.51 mmol) in ether (20 mL). The reaction mixture was stirred at room temperature for 30 minutes, quenched carefully by adding H$_2$O. The organic layer was isolated, washed with brine and dried over Na$_2$SO$_4$. The solvent was removed carefully and the residual material was purified rapidly by flash chromatography (hexanes/Et$_2$O 90:10 as eluant) to give 2-thienylmethyl bromide (6.2 g, 80%).

To a cold (−50° C.) solution of 1,3-propane sultone (1.6 g, 13 mmol) in THF (70 mL) was added a solution of BuLi (2 M in THF, 6.5 mL, 13 mmol). After stirring for 30 min, 2-thienylmethyl bromide (obtained in step 1, 2.3 g, 13 mmol) was added and the reaction mixture was stirred for 2 hours, and during this period the temperature was controlled between −50° C. and −20° C. The reaction mixture was cooled to −78° C., quenched with 1N HCl, and diluted with EtOAc. The organic phase was separated, washed with 1N HCl and concentrated. The residue was diluted with toluene (10 mL) and separated by column chromatography (hexanes/EtOAc 70:30 as eluant) to give 1-(2-thienyl)-2,4-butane sultone (800 mg, 35%); $^1$H NMR (500 MHz, CDCl$_3$) δ 2.40 (m, 1H), 2.60 (m, 1H), 3.15 (m, 1H), 3.55 (m, 2H), 4.38 (m 1H), 4.43 (m, 1H), 6.94 (m, 2H), 7.22 (m, 1H). $^{13}$C NMR (125 MHz, CDCl$_3$) δ 29.31, 29.54, 56.76, 67.00, 125.29, 126.95, 127.60, 137.92. 1,1-bis(2-thienylmethyl)-1,3-propane sultone was isolated in 9% yield (380 mg).

A solution of 1-(2-thienyl)-2,4-butane sultone (obtained in step 2, 218 mg, 1 mmol) in a cosolvent of THF and EtOH (20 mL, v/v=1:1) was added slowly to ammonium hydroxide (28%-30%, 10 mL, 80 mmol). The reaction mixture was stirred at room temperature for 4 hours, and then concentrated. The resulting solid was suspended in EtOH, heated at reflux for 15 minutes and cooled to room temperature. The solid material was collected by filtration, washed with ether and dried, finishing the title compound (170 mg, 71%); $^1$H NMR (500 MHz, D$_2$O) δ 1.84-2.00 (m, 2H), 2.80-3.10 (m, 4H), 3.38 (m, 1H), 6.88 (m, 2H), 7.20 (m, 1H); $^{13}$C NMR (125 MHz, D$_2$O) δ 27.05, 30.28, 37.78, 59.55, 125.16, 126.96, 127.54; ES-MS 234 (M−1).

Preparation of 4-amino-1-(2-thienyl)-2-(2-thienylmethyl)-2-butanesulfonic acid (Compound N85)

To a solution of 1,1-bis(2-thienylmethyl)-1,3-propane sultone (obtained in step 2 in the preparation of Compound N84, 150 mg, 0.48 mmol) in a cosolvent of THF and EtOH (10 mL, v/v=1:1) was added slowly an aqueous solution of ammonium hydroxide (28%, 5 mL, 38 mmol). The reaction mixture was stirred at room temperature for 8 hours, and then concentrated. The resulting solid was suspended in EtOH, heated at reflux for 15 minutes and cooled to room temperature. The solid was collected by filtration, washed with ether then dried, providing the title compound (140 mg, 88%); $^1$H NMR (500 MHz, DMSO-d$_6$) δ 1.78 (t, J=7.0 Hz, 2H), 3.07-3.10 (m, 4H), 3.28 (s, 2H), 6.87 (m, 2H), 6.92 (m, 2H), 7.30 (m, 2H), 7.60 (bs, 2H); $^{13}$C NMR (125 MHz, DMSO-d$_6$) δ 31.88, 34.96, 36.31, 60.74, 125.34, 127.37, 128.88, 139.60; ES-MS 330 (M−1).

Preparation of 4-(tert-butylamino)-1-(thien-2-yl)butane-2-sulfonic acid (Compound N86)

To a solution of 1-(2-thienylmethyl)-1,3-propane sultone (obtained in step 2 from the preparation of Compound N84, 218 mg, 1 mmol) in THF (5 mL) was added t-butylamine (1 mL). The reaction was stirred at room temperature for 15 hours, and then concentrated. The resulting solid was suspended in EtOH (10 mL), heated at reflux for 1 hour and cooled to room temperature. The solid was collected by filtration, washed with ether then dried, giving the title compound (142 mg, 63%); $^1$H NMR (500 MHz, D$_2$O) δ 1.12 (s, 9H), 1.82 (m, 1H), 1.95 (m, 1H), 2.70 (m, 1H), 2.96 (m, 2H), 3.07 (m, 1H), 3.40 (m, 1H), 6.90 (m, 2H), 7.21 (m, 1H). $^{13}$C NMR (125 MHz, D$_2$O) δ 24.92, 26.50, 30.25, 39.46, 57.16, 59.56, 125.27, 126.99, 127.63; ES-MS 290 (M−1).

Preparation of 4-[2-(2-thien-2-ylpropyl)amino]-2-butanesulfonic acid (Compound N87)

To a stirred solution of 2-(2-thienyl)-2-propylamine (400 mg, 2.84 mmol) in THF (9 mL) was added 2,4-butane sultone (386 mg, 2.84 mmol). The reaction mixture was stirred at reflux for 15 h, and then cooled to room temperature. The solid was collected by filtration, suspended in EtOH (5 mL) and stirred at reflux for 1 hour. The suspension was then cooled to room temperature. The solid was collected by filtration, washed with ethanol and dried under high vacuum to afford the title compound (450 mg, 57%); $^1$H NMR (500 MHz, DMSO-d$_6$) δ 1.06 (d, J=6.8 Hz, 3H), 1.62 (m, 1H), 1.71 (s, 6H), 1.95 (m, 1H), 2.75 (m, 1H), 2.85 (t, J=8.0 Hz, 2H), 6.99 (m, 1H), 7.18 (m, 1H), 7.42 (m, 1H); $^{13}$C NMR (125 MHz, DMSO-d$_6$) δ 14.65, 25.83, 25.87, 28.41, 40.20, 53.28, 59.50, 127.68, 127.95, 142.27; ES-MS 276 (M−1).

Preparation of 4-[2-(2-thien-2-ylpropyl)amino]-1-(2-thienyl)-2-butanesulfonic acid (Compound N88)

To a stirred solution of 2-(2-thien-2-ylpropyl)amine (110 mg, 1.3 mmol) in pinacolne (9 mL) was added 1-(thien-2-ylmethyl)-1,3-propane sultone (obtained from step 2 in the preparation of Compound N84, 218 mg, 1.0 mmol). The reaction mixture was stirred at reflux for 24 hours then cooled to room temperature. The solid was collected by filtration, suspended in EtOH (5 mL) and stirred at reflux for 1 hour. The suspension was then cooled to room temperature. The solid was collected by filtration, washed with ethanol and dried under high vacuum to afford the title compound (280 mg, 78%); $^1$H NMR (500 MHz, DMSO-d$_6$) δ 1.68 (s, 6H), 1.82 (m, 2H), 2.50-2.88 (m, 4H), 6.82 (m, 1H), 6.92 (m, 1H), 7.12 (m, 1H), 7.26 (m, 1H), 7.34 (m, 1H), 7.65 (m, 1H), 9.00 (bs, 1H), 9.26 (bs, 1H). $^{13}$C NMR (125 MHz, DMSO-d$_6$) δ 26.31, 26.56, 26.85, 31.24, 58.41, 60.14, 125.06, 126.64, 127.74, 127.80, 127.92, 128.24, 142.11, 144.00; ES-MS 358 (M−1).

Preparation of 3-(1-adamantyl)-3-aminopropane-1-sulfonic acid (Compound QX)

A solution of 1-adamantanemethanol (10 g, 60 mmol) in dichloromethane (90 mL) was added to a suspension of pyridinium chlorochromate (18.5 g, 86 mmol) in dichloromethane (120 mL) at room temperature over 15 minutes. The reaction mixture was stirred at room temperature for 90 minutes, followed by addition of heptane (450 mL). The mixture was filtered and the filtrate was concentrated. The residue was dissolved in pentane (100 mL) and the mixture was washed with NaOH (0.2N, 3×50 mL) and with water, dried over MgSO$_4$ and concentrated to give adamantane-1-carbaldehyde as a white solid (7.2 g, 73%); $^1$H NMR (CDCl$_3$, 500 MHz) δ ppm 9.32 (s, 1H), 2.08-2.03 (m, 3H), 1.92-1.91 (m, 3H), 1.80-1.75 (m, 3H), 1.73-1.68 (m, 6H).

Malonic acid (4.6 g, 43.8 mmol), ammonium acetate (7.0 g, 91 mmol) and adamantane-1-carbaldehyde from step 1 (7.2 g, 43.8 mmol) were refluxed in ethanol (11 mL) for 4 hours. The reaction mixture was cooled and filtered. The solution was concentrated and the residue was distributed between dichloromethane and water. A precipitate, formed at this point, was collected by filtration. The water phase was freeze-dried; and the solid material was combined with the solid obtained by filtration, giving 3-(1-adamantyl)-3-aminopropanoic acid as a white solid (6.82 g, 70%); $^1$H NMR (CD$_3$OD, 500 MHz) δ ppm 2.96 (dd, 1H, J=2.9 and 11.2 Hz), 2.48 (dd, 1H, J=2.9 and 16.6 Hz), 2.23 (dd, 1H, J=11.7 and 16.6 Hz), 2.04 (bs, 3H), 1.80-1.69 (m, 6H), 1.61 (m, 6H).

Borane (1 M solution in THF, 80.4 mL, 80.4 mmol) was added to a solution of 3-(1-adamantyl)-3-aminopropanoic acid (from step 2, 5.98 g, 26.8 mmol) in dry THF (25 mL). The reaction mixture was heated at reflux and stirred overnight. The reaction was quenched with a few drops of methanol then co-evaporated twice with methanol. The residue was treated with methanol (5 mL) and conc. HCl (5 mL) at reflux for 30 minutes. The solvent was evaporated and the residual material was dissolved in a minimum amount of methanol then precipitated with ether, collected by filtration and dried under vacuum, to give 3-(1-adamantyl)-3-aminopropan-1-ol as a white solid (4.77 g, 72%); $^1$H NMR (CD$_3$OD, 500 MHz) δ ppm 3.86-3.82 (m, 1H), 3.75-3.71 (m, 1H), 2.91 (d, 1H, J=10.7 Hz), 2.04 (bs, 3H), 1.98-1.94 (m, 1H), 1.80-1.78 (m, 3H), 1.72-1.70 (m, 3H), 1.67-1.58 (m, 7H).

The alcohol from step 3 (4.77 g, 19.4 mmol) was refluxed in hydrobromic acid (47%, 45 mL) overnight. Solvent was removed under reduced pressure and the solid was dried under vacuum, providing 1-(1-adamantyl)-3-bromopropan-1-amine as a white solid (6.04 g, 88%); $^1$H NMR (CD$_3$OD, 500 MHz) δ ppm 3.70-3.66 (m, 1H), 3.55-3.49 (m, 1H), 2.93 (dd, 1H, J=2.4 and 9.5 Hz), 2.39-2.32 (m, 1H), 2.06 (bs, 3H), 2.00-1.93 (m, 1H), 1.81-1.78 (m, 3H), 1.73-1.70 (m, 3H), 1.62 (m, 6H).

1-(1-Adamantyl)-3-bromopropan-1-amine from step 4 (6.04 g, 17.1 mmol) and sodium sulfite (3.23 g, 25.7 mmol) were stirred in water at reflux overnight. The solid was collected by filtration and dried. It was then treated with concentrated HCl (15 mL) and warmed. After 15 minutes, the solution was cooled to room temperature and the solid was collected by filtration, washed with a minimum amount of water, washed with ether and dried under vacuum, giving the title compound as a white solid (2.75 g, 59%); $^1$H NMR (DMSO, 500 MHz) δ ppm 7.83 (bs, 3H), 2.81-2.78 (m, 1H), 2.72-2.70 (m, 1H), 2.06-2.02 (m, 1H), 2.01-1.97 (m, 3H), 1.68-1.49 (m, 13H); $^{13}$C NMR (DMSO, 500 MHz) δ ppm 107.0, 61.0, 50.1, 37.7, 36.8, 35.3, 28.1, 23.7; ES-MS 272 (M−1).

Preparation of
2-(2-adamantyl)-3-aminopropane-1-sulfonic acid
(Compound SX)

To a solution of diisopropylamine (5.0 mL, 0.036 mol) in THF (30 mL) was added at −78° C. n-BuLi (21 mL, 1.6 M, 0.035 mol). The solution was stirred at −78° C. for 30 minutes, then warmed to 0° C. and stirred for an additional 30 minutes. The solution was then cooled to −78° C. and treated with a solution of 2-adamantaneacetonitrile (4.5 g, 0.015 mol) in THF (10 mL). The mixture was stirred at −78° C. for 30 minutes, and warmed to room temperature for 30 minutes. The mixture was then cooled to −78° C. and treated with diethylcarbonate (2.0 mL, 0.016 mol). The reaction mixture was stirred at −78° C. for 3 hours. The mixture was quenched with a saturated aqueous solution of NH$_4$Cl (10 mL), followed by addition of water. The aqueous phase was extracted with ether and the combined organic phase was washed with 5% HCl, and dried over MgSO$_4$. Hexane was added and the mixture was filtered. The filtrate was purified by Biotage (5% EtOAc in hexanes) to furnish ethyl α-cyano-adamantane-2-acetate (2.74 g, 74%) containing about 20% of starting material. The material was used in the following reaction without further purification.

To a solution of crude ethyl ester (from step 1, 1.29 g, 5.22 mmol) in THF (4 mL) was added LAH 2.0 M (8.0 mL, 16 mmol) slowly. The mixture was heated at reflux overnight, quenched with a minimum amount of 20% KOH in water. The mixture was filtered through Celite™. The filtrate was evaporated under vacuum; and the residue was dissolved in dichloromethane (15 mL). To this dichloromethane solution was added (BOC)$_2$O (1.5 g) and the mixture was stirred overnight. Solvent was removed by evaporation and the resulting residue was purified on Biotage, affording 2-(2-adamantyl)-N-Boc-3-amino-1-propanol (425 mg, 26%).

2-(2-Adamantyl)-N-Boc-3-amino-1-propanol (425 mg from step 2, 1.38 mmol) was treated with aqueous HBr 48% (20 mL) and heated at reflux overnight. Water was evaporated and solid was triturated with ether to afford 2-(2-adamantyl)-3-bromo-1-propylamine HBr salt (486 mg, 100%) as beige solid. 2-(2-Adamantyl)-3-bromo-1-propylamine HBr salt (486 mg from step 3, 1.38 mmol) and sodium sulfite (260 mg, 2.06 mmol) in degassed water (3 mL) were heated at reflux overnight. The solid was filtered and washed with water (20 mL). The solid was transferred in methanol (20 mL), and the mixture was refluxed for 1 hour. The solid material was collected by filtration, providing the title compound (105 mg, 28%); $^1$H NMR (500 MHz, DMSO-d$_6$) δ 3.06 (dd, J=1.9 Hz, J=12.7 Hz, 1H), 2.73 (m, 2H), 2.60 (m, 1H), 2.31 (m, 1H), 1.84-1.79 (m, 8H), 1.68-1.62 (m, 4H), 1.45 (m, 3H); ES-MS 272 (M−1).

Preparation of
3-(2-adamantyl)-3-aminopropane-1-sulfonic acid
(Compound SY)

A mixture of adamantane-2-carbaldehyde (9.6 g, 0.058 mol), ammonium acetate (9.4 g, 0.12 mol) and malonic acid (6.0 g, 0.058 mol) in ethanol (30 mL) was heated at reflux overnight. The mixture was cooled to room temperature; and the solid was removed by filtration. The filtrate was poured into a mixture of dichloromethane/water (150 mL/150 mL). The solid thus formed was collected by filtration and dried under vacuum, giving 3-amino-3-(2-adamantyl)propanoic acid (4.6 g, 35%)

To a solution of the above obtained acid (2.0 g, 0.0090 mol) in dry THF (10 mL) was added BH$_3$-THF 1 M (27 mL, 0.0027 mol). The mixture was heated at reflux overnight. The reaction mixture was cooled to room temperature, and quenched carefully with methanol (1 mL). Evaporation of the solvent left a residue which was then treated with methanol (20 mL) and concentrated HCl (20 mL) at reflux for 30 minutes. All volatiles were evaporated and the solid residue was dissolved in methanol (100 mL) and precipitated with ether (150 mL). The solid was collected by filtration, providing the 3-amino-3-(2-adamantyl)-1-propanol as a hydrochloride salt (1.6 g, 74%).

A suspension of the amino alcohol (820 mg from step 2, 3.34 mmol) in aqueous HBr solution (48%, 25 mL) was heated at reflux overnight. An additional amount of aqueous HBr (48%, 25 mL) was added and the mixture was refluxed for additional 24 hours. Evaporation of the solvent gave 3-bromo-1-(2-adamantyl)-propylamine as HBr salt (1.27 g, 100%).

The product of step 3 (1.27 g, 3.59 mmol) and Na$_2$SO$_3$ (680 mg, 5.40 mmol) in degassed water (10 mL) was heated at reflux overnight. The mixture was cooled to room temperature; and the solid was collected by filtration and washed with a small amount of water (5-10 mL). The resulting solid was treated with ethanol (10 mL) at reflux for 30 minutes. The solid was collected by filtration and dried in vacuo, giving the title compound (658 mg, 67%) as a white solid; $^1$H NMR (500 MHz, CD$_3$OD), δ 3.69 (m, 1H), 2.87 (t, 2H, J=6.3 Hz), 2.22 (m, 1H), 1.93-1.73 (m, 14H), 1.57 (m, 2H); ES-MS 272 (M−1).

Preparation of
2-(1-adamantyl)-3-aminopropane-1-sulfonic acid
(Compound SZ)

A solution of ethyl methanesulfonate (1.21 mL, 11.7 mmol) in THF (10 mL) was cooled to −78° C. To this cold solution was added LiHMDS 1M solution in THF (12.5 mL, 12.5 mmol) dropwise. The yellow solution was stirred for 30 minutes, and then transferred via cannula to a second flask containing a solution of adamantyl bromomethyl ketone (2.00 g, 7.80 mmol) in THF (40 mL) at −78° C. The mixture was stirred at −78° C. for 1.5 hours, warmed slowly to −45°

C., and further stirred for 2.5 hours. The reaction was quenched by adding a saturated aqueous solution of NH₄Cl (100 mL). The mixture was extracted with AcOEt (3×100 mL), washed with brine, dried over MgSO₄, and concentrated under reduced pressure to give 2-(1-admantyl)-1,3-prop-1-ene sultone as a yellow solid (1.93 g, 97%).

Palladium on activated carbon (10%, 0.198 g) was added to a solution of the above obtained sultone (0.66 g, 2.59 mmol) in MeOH (60 mL) in a Pyrex™ high pressure bottle, and hydrogenated at 40 psi for 48 hours. The reaction mixture was filtered through Celite™ and the filtrate was concentrated to dryness, providing 2-(1-adamantyl)-1,3-propane sultone as a white solid (0.65 g, 98%). 2-(1-adamantyl)-1,3-propane sultone (0.620 g from step 2, 2.42 mmol) was dissolved in DMF (10 mL). NaN₃ (0.188 g, 2.90 mmol) was added and the solution was heated at 130° C. overnight. Solvent was evaporated and a beige solid was obtained. The solid was dissolved in methanol, and the solution was passed through Amberlite™ IR-120 (plus) ion-exchange resin (10 g, pre-washed with water and then MeOH). Evaporation of the solvent gave a yellow viscous liquid which became beige solid under vacuum (0.43 g, 76%).

Palladium on activated carbon (10%, 0.150 g) was added to a solution of the sulfonic acid derivative from step 3 (0.4176 g, 1.79 mmol) in a solvent mixture of methanol (36 mL) and acetic acid (4 mL) in a Pyrex™ high pressure bottle. The mixture was hydrogenated at 30 psi overnight. The reaction mixture was filtered through Celite™ and the filtrate was concentrated to dryness, giving the title compound as a white solid (0.210 g, 57%); $^1$H NMR (DMSO, 500 MHz) δ ppm 7.81 (large s, 3H), 3.11 (d, 1H, J=12.7 Hz), 2.90 (d, 1H, J=13.7 Hz), 2.70 (dd, 1H, J=10.1 Hz, J=12.4 Hz), 1.9 (large s, 3H), 1.67-1.59 (m, 7H), 1.49-1.31 (m, 6H). 1H is partially hidden with DMSO signal.

Preparation of 2-[(benzylamino)methyl]-3,3-dimethylbutane-1-sulfonic acid (Compound N42)

To a solution of 4-tert-butyl-1,2-oxathiolane 2,2-dioxide (167 mg, 0.94 mmol) in dimethylformamide (2 mL) was added benzylamine (0.153 mL). The solution was stirred at 130° C. for 24 hours. The reaction mixture was cooled to room temperature and triturated with ethanol. The solid material was collected by filtration and washed successively with ethanol (2×20 mL) and with acetone (2×20 mL), giving the title compound (205 mg, 77%); $^1$H NMR (CD₃OD, 500 MHz) δ ppm 7.24 (m, 5H), 4.21 (q, 2H, J=13 & 12.5 Hz), 3.43 (d, 1H, J=13 Hz), 3.23 (d, 1H, J=14 Hz), 3.09 (m, 1H), 2.87 (dd, 1H, J=9.5, J=10 Hz), 2.05 (br t, 1H, J=9.5 Hz), 1.02 (s, 9H); ES-MS 284 (M−1).

Preparation of 3-(9H-fluoren-9-ylamino)propane-1-sulfonic acid (Compound N44)

9-Aminofluorene hydrochloride (1.02 g, 4.69 mmol) was treated with a saturated solution of K₂CO₃ (100 mL) and the mixture was extracted with EtOAc (3×75 mL). The organic extracts were combined, dried over Na₂SO₄, concentrated to furnish a residue, which was azeotroped with toluene to yield 9-aminofluorene (0.831 g, 4.59 mmol). The free amine was dissolved in 25% toluene/acetonitrile (10 mL). To the resulting solution was added 1,3-propane sultone (532 mg, 4.36 mmol). The reaction mixture was stirred at reflux for 4 h, and cooled to room temperature. The solid material was collected by filtration, washed with acetone, and then treated with ethanol at reflux for 1 hours. After the mixture was cooled to room temperature, the solid was collected by filtration, washed with acetone, and dried in vacuo, providing the title compound (808 mg, 74%); $^1$H NMR (DMSO, 500 MHz) δ ppm 9.96 (large s, 2H), 7.96 (d, 2H, J=7.3 Hz), 7.88 (d, 2H, J=7.8 Hz), 7.56 (t, 2H, J=7.3 Hz), 7.45 (t, 2H, J=7.3 Hz), 5.66 (s, 1H), 2.98 (s, 1H), 2.64 (t, 2H, J=5.9 Hz), 1.96 (t, 2H, J=5.9 Hz). $^{13}$C NMR (CD₃OD, 125 MHz) δ ppm 141.02, 137.63, 130.10, 128.12, 126.15, 120.80, 59.44, 49.64, 43.43, 21.82.

3-[(4,7-dimethoxyindan-1-yl)amino]propane-1-sulfonic acid (Compound N51)

To a stirred solution of 4,7-dimethoxy-1-indanone (515 mg, 2.67 mmol) in ethanol (10 mL) was added a suspension of hydroxylamine hydrochloride (447 mg, 6.43 mmol) in ethanol/water (1 mL/1 mL), followed by addition of a suspension of sodium acetate (527 mg, 6.43 mmol) in ethanol/water (1 mL/1 mL). The reaction mixture was heated at reflux for 3.5 hours. Water was added and the white solid thus formed was collected by filtration, furnishing 4,7-dimethoxyindan-1-one oxime (463 mg, 84%).

Palladium on activated carbon (10%, 100 mg) was added to a degassed solution of the 4,7-dimethoxyindan-1-one oxime obtained from step 1 (463 mg, 2.23 mmol) in a mixture of methanol (45 mL) and acetic acid (5 mL). The reaction mixture was stirred under hydrogen atmosphere (1 Atm) overnight. The reaction mixture was flushed with nitrogen and filtered through Celite™. The filtrate was concentrated and the residual material was azeotroped twice with toluene to yield 1-amino-4,7-dimethoxyindan (quantitative).

To a solution of 1-amino-4,7-dimethoxyindan (2.23 mmol) in a 25% acetonitrile/toluene solution (20 mL) was added 1,3-propane sultone (259 mg, 2.12 mmol). The reaction mixture was heated at reflux for 4 hours, and then cooled to room temperature. The mixture was concentrated to a beige solid; and the solid material was dissolved in ethanol by heating. The hot mixture was cooled to room temperature and left standing overnight. The crystalline solid thus formed was collected by filtration and dried in vacuo, providing the title compound as a white solid (223 mg, 32%.); $^1$H NMR (DMSO, 500 MHz) δ ppm 8.86 (bs, 1H), 8.66 (bs, 1H), 6.95 (d, 1H, J=8.8 Hz), 6.85 (d, 1H, J=8.8 Hz), 4.73 (m, 1H), 3.78 (s, 3H), 3.75 (s, 3H), 3.05 (m, 2H), 3.00-2.94 (m, 1H), 2.79-2.74 (m, 1H), 2.62-2.60 (m, 2H), 2.39-2.34 (m, 1H), 2.19-2.15 (m, 1H), 1.98 (m, 2H); ES-MS 314 (M−1).

Preparation of 3-[(5,6-dimethoxyindan-1-yl)amino]propane-1-sulfonic acid (Compound N53)

To a stirred solution of 5,6-dimethoxy-1-indanone (565 mg, 2.94 mmol) in ethanol (10 mL) was added a suspension of hydroxylamine hydrochloride (490 mg, 7.05 mmol) in ethanol/water (1 mL/1 mL), followed by addition of a suspension of sodium acetate (578 mg, 7.05 mmol) in ethanol/water (1 mL/1 mL). The reaction mixture was heated at reflux for 3.5 hours. Water was then added and the white solid was collected by filtration and dried in vacuo to provide 5,6-dimethoxy-1-indanone oxime (488 mg, 80%).

Palladium on activated carbon (10%, 80 mg) was added to a solution of the oxime obtained from step 1 (285 mg, 1.37 mmol) in methanol (36 mL) and acetic acid (4 mL). The reaction mixture was stirred under hydrogen atmosphere (1 Atm) overnight. The reaction mixture was flushed with nitrogen and filtered through Celite™. The filtrate was concentrated and the residue was azeotroped twice with toluene to yield 1-amino-5,6-dimethoxy-1-indan as a light yellow solid (quantitative), containing a small amount of solvent.

To a solution of 1-amino-5,6-dimethoxy-1-indan (1.37 mmol) in a 25% toluene/acetonitrile solution (10 mL) was added 1,3-propane sultone (159 mg, 1.30 mmol). The reaction mixture was stirred at reflux for 4 hours. The white solid formed was collected by filtration, washed with acetone, and then treated in ethanol at refluxed for 1 hour. The ethanolic mixture was cooled to room temperature; and the solid material was collected by filtration, washed with acetone and dried in vacuo to furnish the title compound (191 mg, 44%); $^1$H NMR (DMSO, 500 MHz) δ ppm 8.87 (large s, 2H), 7.17 (s, 1H), 6.94 (s, 1H), 4.65-4.64 (m, 1H), 3.76 (s, 6H), 3.14-2.98 (m, 3H), 2.83-2.77 (m, 1H), 2.68-2.65 (m, 2H), 2.44-2.37 (m, 1H), 2.15-2.11 (m, 2H); ES-MS: 314 (M−1).

Preparation of
3-[(5-methoxyindan-1-yl)amino]propane-1-sulfonic acid (Compound N56)

To a stirred solution of 5-methoxy-1-indanone (1.06 g, 6.5 mmol) in ethanol (20 mL) was added a suspension of hydroxylamine hydrochloride (1.08 g, 15.6 mmol) in ethanol/water (2 mL/2 mL), followed by the addition of a suspension of sodium acetate (1.28 g, 15.6 mmol) in ethanol/water (2 mL/2 mL). The reaction mixture was heated at reflux for 3.5 hours. Water was added and the beige solid was collected by filtration, giving 5-methoxyindan-1-one oxime (1 g, 87%).

Palladium on activated carbon (10%, 100 mg) was added to a solution of 5-methoxyindan-1-one oxime from step 1 (1 g, 5.64 mmol) in methanol (90 mL) and acetic acid (10 mL). The reaction mixture was stirred under an hydrogen atmosphere overnight, then was flushed with nitrogen and filtered through Celite™. The filtrate was concentrated and the residual material was azeotroped twice with toluene to give 1-amino-5-methoxyindan (quantitative).

To a solution of 1-amino-5-methoxy-1-indan (5.64 mmol) in a 25% acetonitrile/toluene solution (50 mL) was added 1,3-propane sultone (654 mg, 5.36 mmol). The reaction mixture was stirred at reflux for 4 hours. The white solid formed was collected by filtration, transferred in ethanol and heated at reflux for 1 hour. After cooling to room temperature, the solid was collected by filtration and dried in vacuo to provide the title compound as a white solid (985 mg, 64%); $^1$H NMR (DMSO, 500 MHz) δ ppm 9.05 (bs, 1H), 8.86 (bs, 1H), 7.46 (d, 1H, J=8.8 Hz), 6.92 (d, 1H, J=2 Hz), 6.86 (dd, 1H, J=2.4 and 8.5 Hz), 4.65-4.63 (m, 1H), 3.76 (s, 3H), 3.11 (t, 2H, J=6.8 Hz), 3.08-3.03 (m, 1H), 2.87-2.81 (m, 1H), 2.69-2.64 (m, 2H), 2.44-2.37 (m, 1H), 2.17-2.11 (m, 1H), 2.00-1.95 (m, 2H); $^{13}$C NMR (DMSO, 500 MHz) δ ppm 161.3, 147.3, 130.2, 127.2, 113.8, 110.6, 61.7, 56.0, 50.0, 45.4, 30.7, 29.1, 22.5; ES-MS 284 (M−1).

Preparation of
3-[(5-fluoroindan-1-yl)amino]propane-1-sulfonic acid (Compound N58)

To a stirred solution of 5-fluoro-1-indanone (1 g, 6.7 mmol) in ethanol (20 mL) was added a suspension of hydroxylamine hydrochloride (1.11 g, 16 mmol) in ethanol/water (2 mL/2 mL), followed by the addition of a suspension of sodium acetate (1.31 g, 16 mmol) in ethanol/water (2 mL/2 mL). The reaction mixture was heated at reflux for 3.5 h. Water was added and the white solid was collected by filtration, giving 5-fluoroindan-1-one oxime (1.1 g, 99%).

Palladium on activated carbon (10%, 200 mg) was added to a solution flushed with nitrogen of the 5-fluoroindan-1-one oxime obtained in step 1 (1.1 g, 6.6 mmol) in methanol (90 mL) and acetic acid (10 mL). The reaction mixture was and stirred under an hydrogen atmosphere overnight. The reaction mixture was flushed with nitrogen and filtered through Celite™. The filtrate was concentrated and residual material was azeotroped twice with toluene to yield 1-amino-5-fluoroindan (quantitative).

To a solution of 1-amino-5-fluoroindan (6.6 mmol) in a 25% acetonitrile/toluene solution (50 mL) was added 1,3-propane sultone (766 mg, 6.3 mmol). The mixture was heated at reflux for 4 hours. The white solid material thus formed was collected by filtration, transferred in ethanol and heated at reflux for 1 hour. After cooling to room temperature, the solid was collected by filtration and dried in vacuo to furnish the title compound as a white solid (1.16 g, 68%); $^1$H NMR (DMSO, 500 MHz) δ ppm 9.16 (bs, 1H), 8.96 (bs, 1H), 7.60 (dd, 1H, J=8.3 and 5.4 Hz), 7.21 (dd, 1H, J=2 and 9 Hz), 7.17-7.13 (m, 1H), 4.73-4.70 (m, 1H), 3.18-3.13 (m, 2H), 3.11-3.06 (m, 1H), 2.92-2.86 (m, 1H), 2.71-2.65 (m, 2H), 2.47-2.41 (m, 1H), 2.21-2.14 (m, 1H), 2.03-1.96 (m, 2H); ES-MS 272 (M−1).

Preparation of
3-[(2-methylindan-1-yl)amino]propane-1-sulfonic acid (Compound N59)

To a stirred solution of 2-methyl-1-indanone (1 g, 6.8 mmol) in ethanol (20 mL) was added a suspension of hydroxylamine hydrochloride (1.14 g, 16 mmol) in ethanol/water (2 mL/2 mL), followed by addition of a suspension of sodium acetate (1.34 g, 16 mmol) in ethanol/water (2 mL/2 mL). The reaction mixture was heated at reflux for 5 h, cooled to room temperature, and poured into water. The mixture was extracted twice with AcOEt. The extracts were combined, washed with brine, dried over sodium sulfate, and concentrated to dryness, giving 2-methylindan-1-one oxime as colorless oil (quantitative).

Palladium on activated carbon (10%, 200 mg) was added to a solution of 2-methylindan-1-one oxime obtained from step 1 (1.1 g, 6.6 mmol) in methanol (90 mL) and acetic acid (10 mL). The reaction mixture was stirred under hydrogen atmosphere overnight, then flushed with nitrogen and filtered through Celite™. The filtrate was concentrated and the residue was azeotroped twice with toluene, providing 1-amino-2-methylindan (quantitative).

To a solution of 1-amino-2-methylindan (6.8 mmol) in a 25% acetonitrile/toluene solution (50 mL) was added 1,3-propane sultone (794 mg, 6.5 mmol). The reaction mixture was stirred at reflux for 4 hours, and then cooled to room temperature. The white solid was collected by filtration, transferred in ethanol and heated at reflux for 30 min. After the mixture was cooled to room temperature, and the solid formed was collected by filtration and dried in vacuo to give the title compound as a mixture of isomers (267 mg, 15%); $^1$H NMR of the major isomer (DMSO, 500 MHz) δ ppm 8.95 (bs, 2H), 7.51 (d, 1H, J=7.3 Hz), 7.38-7.33 (m, 2H), 7.29-7.26 (m, 1H), 4.54-4.53 (m, 1H), 3.18-3.17 (m, 1H), 3.10-3.08 (m, 1H), 2.99-2.95 (m, 1H), 2.82-2.75 (m, 2H), 2.70-2.67 (m, 2H), 2.04-1.99 (m, 2H), 1.17 (d, 3H, J=6.8 Hz); ES-MS 268 (M−1).

Preparation of 3-[(4-methoxy-2,3-dihydro-1H-inden-1-yl)amino]propane-1-sulfonic acid (Compound N61)

To a stirred solution of 4-methoxy-1-indanone (1 g, 6.5 mmol) in ethanol (20 mL) was added a suspension of hydroxylamine hydrochloride (1.08 g, 16 mmol) in ethanol/water (2 mL/2 mL), followed by the addition of a suspension of sodium acetate (1.28 g, 16 mmol) in ethanol/water (2 mL/2 mL). The reaction mixture was heated at reflux for 4 hours, cooled to room temperature, followed by addition of water. The solid material was collected by filtration, affording 4-methoxy-1-indanone oxime (1.1 g, quantitative).

Palladium on activated carbon (10%, 200 mg) was added to a solution of the 4-methoxyindan-1-one oxime obtained from step 1 (1.1 g, 6.5 mmol) in methanol (90 mL) and acetic acid (10 mL). The reaction mixture was stirred under hydrogen atmosphere overnight. The reaction mixture was flushed with nitrogen and filtered through Celite™. The filtrate was concentrated and the residue was azeotroped twice with toluene to yield 4-methoxyindan-1-amine (quantitative).

To a solution of 4-methoxyindan-1-amine (6.5 mmol) in a 25% acetonitrile/toluene solution (50 mL) was added 1,3-propane sultone (754 mg, 6.2 mmol). The reaction mixture was stirred at reflux for 4 hours. The white solid was collected by filtration, transferred in ethanol and heated at reflux for 30 minutes. After cooling to room temperature, the solid material was collected by filtration and dried in vacuo, furnishing the title compound as a white solid (1.08 g, 59%); $^1$H NMR (DMSO, 500 MHz) δ ppm 9.20 (bs, 1H), 8.94 (bs, 1H), 7.31 (t, 1H, J=8.3 Hz), 7.15 (d, 1H, J=7.3 Hz), 6.99 (d, 1H, J=8.3 Hz), 4.75-4.73 (m, 1H), 3.81 (s, 3H), 3.12-3.11 (m, 2H), 2.98-2.92 (m, 1H), 2.81-2.75 (m, 1H), 2.68-2.66 (m, 2H), 2.45-2.37 (m, 1H), 2.16-2.10 (m, 1H), 2.00-1.95 (m, 2H). $^{13}$C NMR (DMSO, 500 MHz) δ ppm 156.5, 139.9, 132.6, 129.4, 118.0, 111.8, 62.4, 55.9, 50.0, 45.5, 28.4, 27.5, 22.5; ES-MS 284 (M−1).

Preparation of
3-[(6-methoxyinden-1-yl)amino]propane-1-sulfonic acid (Compound N62)

To a stirred solution of 6-methoxyindan-1-one 1 (1.00 g, 6.16 mmol) in ethanol (20 mL) was added a suspension of hydroxylamine hydrochloride (1.03 g, 14.8 mmol) in ethanol/water (2 mL/2 mL), followed by the addition of a suspension of sodium acetate (1.28 g, 15.6 mmol) in ethanol/water (4 mL/4 mL). The reaction mixture was heated at reflux for 3 hours. Water was added to the reaction mixture; and the white solid thus formed was collected by filtration, giving 6-methoxyindan-1-one oxime (0.81 g, 74%).

Palladium on activated carbon (10%, 180 mg) was added to a solution of the oxime (obtained from step 1, 0.810 g, 4.57 mmol) in methanol (54 mL) and acetic acid (6 mL). The reaction mixture was stirred under an hydrogen atmosphere overnight, and then flushed with nitrogen and filtered through Celite™. The filtrate was concentrated and the residue was azeotroped twice with toluene to yield 6-methoxyindan-1-amine (quantitative) as beige solid, containing a small amount of solvent which was used in next step without purification.

To a solution of 6-methoxyindan-1-amine (4.57 mmol) in a 25% toluene/acetonitrile solution (20 mL) was added 1,3-propane sultone (714 mg, 5.85 mmol). The reaction mixture was heated at reflux for 4 hours. The white solid thus formed was collected by filtration, washed with acetone, transferred in ethanol and heated at reflux for 1 hour, and then cooled to room temperature. The solid was collected by filtration, washed with acetone and dried in vacuo, providing the title compound as a white solid (568 mg, 44%); $^1$H NMR (CD$_3$OD, 500 MHz) δ ppm 7.25 (d, 1H, J=8.3 Hz), 7.15 (d, 1H, J=2.0 Hz), 6.95 (dd, 1H, J=2.4 Hz, J=8.8 Hz), 4.75 (dd, 1H, J=4.4 Hz, J=7.8 Hz), 3.81 (s, 3H), 3.30-3.24 (m, 2H), 3.13-3.07 (m, 1H), 2.97-2.88 (m, 3H), 2.61-2.53 (m, 1H), 2.27-2.21 (m, 1H), 2.19-2.14 (m, 2H) $^{13}$C NMR (CD$_3$OD, 125 MHz) δ ppm 161.00, 139.50, 137.73, 127.29, 117.89, 111.22, 64.37, 56.20, 50.07, 46.24, 30.37, 30.35, 23.24; ES-MS 284 (M−1).

3-[(4-methylindan-1-yl)amino]propane-1-sulfonic acid (Compound N68)

To a stirred solution of 4-methyl-1-indanone (1 g, 6.8 mmol) in ethanol (20 mL) was added a suspension of hydroxylamine hydrochloride (1.14 g, 16 mmol) in ethanol/water (2 mL/2 mL), followed by the addition of a suspension of sodium acetate (1.35 g, 16 mmol) in ethanol/water (2 mL/2 mL). The reaction mixture was heated at reflux for 4 hours. Water was added to the reaction mixture; and the white solid thus formed was collected by filtration, giving 4-methyl-1-indanone oxime (1.1 g, quantitative).

Palladium on activated carbon (10%, 200 mg) was added to a nitrogen-flushed solution of the 4-methoxyindan-1-one oxime (1.1 g, 6.8 mmol) in methanol (90 mL) and acetic acid (10 mL). The reaction mixture was stirred under hydrogen atmosphere overnight, flushed with nitrogen and filtered through Celite™. The filtrate was concentrated and the residual material was azeotroped twice with toluene to yield 4-methoxyindan-1-amine (quantitative).

To a solution of 4-methoxyindan-1-amine (6.8 mmol) in a 25% acetonitrile/toluene solution (50 mL) was added 1,3-propane sultone (794 mg, 6.5 mmol). The reaction mixture was stirred at reflux for 4 hours. The white solid obtained was collected by filtration, transferred in ethanol and heated at reflux for 30 minutes, and then cooled to room temperature. The solid was collected by filtration and dried in vacuo to furnish the title compound as a white solid (395 mg, 25%); $^1$H NMR (DMSO, 500 MHz) δ ppm 9.19 (bs, 1H), 8.92 (bs, 1H), 7.39 (d, 1H, J=7.3 Hz), 7.24-7.19 (m, 2H), 4.74 (m, 1H), 3.14 (m, 2H), 3.02-2.96 (m, 1H), 2.84-2.78 (m, 1H), 2.68-2.66 (m, 2H), 2.44-2.38 (m, 1H), 2.25 (s, 3H), 2.16-2.10 (m, 1H), 2.01-1.97 (m, 2H); ES-MS 268 (M−1).

(3R)-3-amino-5-methylhexane-1-sulfonic acid (Compound N73)

Di t-butyldicarbonate (9 g, 41 mmol) was added to a solution of leucine methyl ester hydrochloride salt (5 g, 28 mmol) and triethylamine (7.7 mL, 55 mmol) in dichloromethane (200 mL). The reaction mixture was stirred at room temperature overnight, washed with citric acid (10%), saturated NaHCO$_3$, and brine subsequently, and dried over sodium sulfate. The solution was concentrated to give an oil residue. The residue was purified by flash chromatography using EtOAc/hexane 30%, giving Boc-Leu-OMe as colorless oil (quantitative).

In a dry 3-neck 500 mL flask equipped with a low temperature thermometer was added the above-obtained ester (27.5 mmol) and toluene (70 mL). The solution was cooled to −78° C. then Diisobutyl aluminum hydride 1M solution in toluene (38.5 mL 38.5 mmol) was added dropwise using an addition funnel so that the internal temperature was kept under −65° C. (over 2 h). The reaction mixture was stirred at −78° C. for an additional 2 hours then it was quenched by slowly adding 10 mL of cold methanol (−78° C.) also keeping the internal temperature below −65° C. The reaction mixture was slowly poured into 100 mL of ice-cold HCl 1N solution with stirring over 15 minutes. The aqueous mixture was extracted with EtOAc (3×500 mL). The organic layers were combined, washed with brine, dried over sodium sulfate, and concentrated to give the corresponding aldehyde as colorless oil (quantitative).

Ethyl(diethoxyphosphoryl)methanesulfonate (4.8 g, 18.6 mmol) was added to a suspension of sodium hydride (334 mg, 14 mmol) in dry THF (100 mL) at 0° C. The reaction mixture was stirred at 0° C. for 15 minutes, then the aldehyde (2 g, 9.3 mmol) was added in one portion. The reaction mixture was stirred at 0° C. for 2 h, then at room temperature for 1 hour. The mixture was poured into water, extracted with EtOAc. The combined extracts were washed with brine, dried over sodium sulfate, and concentrated to give colorless oil. Purification of the oil residue by Biotage chromatography using EtOAc/hexane 50% gave ethyl(1E,3R)-3-[(tert-butoxycarbonyl)amino]-5-methylhex-1-ene-1-sulfonate as colorless oil which crystallized on the pump (2.43 g, 81%).

Palladium on activated charcoal (10%, 200 mg) was added to a solution of the product from step 3 (1.89 g, 5.87 mmol) in ethanol (50 mL) under $N_2$ atmosphere. The reaction mixture was stirred under hydrogen atmosphere for 1.5 hours. The mixture was flushed with nitrogen, passed through Celite™ pad and washed with ethanol several times. Solvent was removed to give ethyl(3R)-3-[(tert-butoxycarbonyl)amino]-5-methylhexane-1-sulfonate as colorless oil which solidified on standing in vacuo. (1.72 g, 91%)

The reaction product from step 4 (1.72 g, 5.3 mmol) in formic acid (15 mL) and water (0.6 mL) was heated at 50° C. for 24 hours. The reaction mixture was concentrated and dried in vacuo. The gum-like material thus obtained was dissolved in a minimum amount of methanol and precipitated with ether. The solid was collected by filtration. The precipitation step was done twice to yield the title compound as a white solid (0.571 g, 55%); $^1$H NMR ($D_2O$, 500 MHz) δ ppm 3.39-3.36 (m, 1H), 2.89 (t, 2H, J=7.3 Hz), 1.98-1.91 (m, 2H), 1.57-1.55 (m, 1H), 1.41-1.36 (m, 2H), 0.78 (dd, 6H, J=3.4 and 7.2 Hz) $^{13}$C NMR ($D_2O$, 500 MHz) δ ppm 49.1, 46.9, 41.0, 27.9, 23.9, 21.8, 21.3; ES-MS 194 (M−1).

Preparation of (1E,3R)-3-amino-5-methylhex-1-ene-1-sulfonic acid (Compound N74)

Ethyl(1E,3R)-3-[(tert-butoxycarbonyl)amino]-5-methylhex-1-ene-1-sulfonate (see step 3 in the preparation of NRM8588) (532 mg, 1.7 mmol) in formic acid (5 mL) and water (0.2 mL) was heated at 50° C. for 24 hours. The reaction mixture was concentrated and dried in vacuo. The gum-like material thus obtained was dissolved in a minimum amount of methanol and precipitated with ether. The solid was collected by filtration. The precipitation step was done twice to yield the title compound as a white solid (0.082 g, 26%); $^1$H NMR ($D_2O$, 500 MHz) δ ppm 6.57 (d, 1H, J=15 Hz), 6.30 (dd, 1H, J=8.2 and 15 Hz), 3.90-3.87 (m, 1H), 1.55-1.46 (m, 3H), 0.80-0.77 (m, 6H). ES-MS 192 (M−1).

Preparation of 2-{[(1R)-2,3-dihydro-1H-inden-1-ylamino]methyl}-3,3-dimethylbutane-1-sulfonic acid (Compound N76)

To a solution of 4-tert-butyl-1,2-oxathiolane 2,2-dioxide (225 mg, 1.26 mmol) in dimethylformamide (5 mL) was added excess of (R)-indanamine (410 mg). The solution was stirred at 130° C. for 48 hours. The reaction mixture was cooled to room temperature and the solvent was evaporated under reduced pressure. The residue was triturated with ethanol. The solid material was collected by filtration and washed with acetone (2×20 mL) to give the title compound (295 mg, 75% yield); $^1$H NMR ($CD_3OD$, 500 MHz) δ ppm 7.43 (m, 1H), 7.16 (m, 3H), 4.25 (m, 1H), 3.14 (m, 1H), 2.00 (m, 2H), 2.72 (m, 2H), 2.69 (m, 1H), 2.23 (m, 1H), 1.88 (m, 2H), 1.00 (s, 9H); ES-MS 310 (M−1).

Preparation of 3-[(4,5-dimethoxyinadan-1-yl)amino)propane-1-sulfonic acid (Compound N77)

A mixture of 4,5-dimethoxy-1-indanone (1.06 g, 5.5 mmol), hydroxylamine hydrochloride (0.92 g), and sodium acetate (1.08 g) was heated at reflux in a mixture of EtOH (100 mL) and water (10 mL) for 4 hours. After cooling to room temperature the precipitate was collected by filtration, washed with water (2×50 mL), and dried under vacuum to give 4,5-dimethoxy-1-indanone oxime (0.80 g, 72%).

To a degassed solution of the crude oxime (from step 1, 0.80 g, 3.80 mmol) in EtOH/AcOH (9/1, 50 mL) was added Pd—C (10%, 100 mg). The mixture was hydrogenated under an atmospheric hydrogen pressure overnight, and then filtrated through Celite™. The filtrate was concentrated and the residual material was azeotroped twice with toluene to yield 4,5-dimethoxyindan-1-amine as the acetate salt, employed in the next step without further purification.

A mixture of the 4,5-dimethoxyindan-1-amine acetic acid (0.93 g, 3.67 mmol) and the sultone (0.49 g, 3.67 mmol) in mixture of acetonitrile/toluene (15 mL/5 mL) was heated at reflux for 5 hours. After cooling to room temperature the solid formed was collected by filtration, and then suspended in EtOH (40 mL). The suspension was heated at reflux for 1 hour. The mixture was cooled to room temperature; the solid material was collected by filtration, washed with acetone (2×20 mL) and dried in vacuo to afford the title compound (0.75 g, 65%); $^1$H NMR ($CD_3OD$, 500 MHz) δ ppm 7.09 (d, 1H, J=8.5 Hz), 6.87 (d, 1H, J=8.0 Hz), 4.18 (t, 1H, J=6.5 Hz), 3.32 (s, 3H), 3.31 (s, 3H), 3.04 (m, 1H), 2.88 (m, 1H), 2.78 (m, 3H), 2.34 (m, 1H), 2H), 2.02 (m, 2H), 1.91 (m, 1H); ES-MS 314 (M−1).

Preparation of 2-(aminomethyl)-3,3-dimethylbutane-1-sulfonic acid: (Compound N78)

To a solution of 4-tert-butyl-1,2-oxathiolane 2,2-dioxide (468 mg, 26.3 mmol) in dimethylformamide (4 mL) was added sodium azide (187 mg). The solution was heated at 130° C. for 36 hours. The reaction mixture was cooled to room temperature and the solvent was evaporated under vacuum. The residue was triturated with ethanol; and the solid material was collected by filtration and washed with acetone (2×20 mL) to give the corresponding azido derivative (420 mg, 72%).

To a degassed solution of the above obtained azido derivative (400 mg) in EtOH (75 mL) was added Pd—C (10%, 80 mg). The mixture was hydrogenated under an atmospheric hydrogen pressure for 24 hours, and then filtrated through Celite™ to give sodium salt of the title compound quantitatively. The salt was dissolved in MeOH (20 mL); and the methanolic solution was treated with Amberlite® IR-120 (plus) ion exchange resin (4 g, pre-washed with methanol and water). The mixture was stirred at room temperature for 30 minutes, and the insoluble materials was removed by filtration. Evaporation of the solvent gave the the title compound as a white solid (400 mg, 98%); $^1$H NMR ($CD_3OD$, 500 MHz) δ ppm 3.08 (m, H), 2.95 (m, 1H), 2.74 (m, 1H), 2.63 (m, 1H), 1.76 (br t, 1H, J=9.5 Hz), 0.95 (s, 9H); ES-MS 194 (M−1).

Preparation of (1E,3S)-3-amino-5-methylhex-1-ene-1-sulfonic acid (Compound N79)

In a dry 500-mL three necked round-bottomed flask equipped with magnetic stirring bar, additional funnel and a thermometer, was added N-Boc.Leu.OMe (6.0 g, 23.4 mmol)

under nitrogen. Dry toluene was added and the solution was cooled to −78° C. DIBAL-H 1M solution in toluene (36 mL, 36 mmol) was added dropwise to the reaction mixture over 1 hour. The rate of addition was adjusted so that the internal temperature was maintained below −65° C. The reaction mixture was then stirred for an additional 2 h at −78° C. under nitrogen. The reaction was quenched by adding slowly 5 mL of cold MeOH (−78° C.). Again the internal temperature was kept below −65° C. The reaction mixture was then carefully poured into a cold solution of HCl 1N (100 mL) with stirring over 15 minutes. The aqueous mixture was then extracted with EtOAc (3×150 mL). The organic layers were combined, washed with brine (3×100 mL), and dried over $MgSO_4$. The solvent was removed by evaporation under reduced pressure to give of the corresponding aldehyde quantitatively, which was used in the next step without purification.

Ethyl(diethoxyphosphoryl)methanesulfonate (5.05, 19.4 mmol) was added to a suspension of sodium hydride (400 mg, 16.7 mmol) in dry THF (100 mL) at 0° C. The reaction mixture was stirred at 0° C. for 15 minutes, followed by addition of the aldehyde pepared in step 1 (4.8 g, 22 mmol). The reaction mixture was stirred at 0° C. for 2 hours, and then at room temperature for 30 minutes. The reaction mixture was poured into water, extracted with EtOAc (3×100 mL). The extracts were combined, washed with brine, dried over $MgSO_4$, and concentrated to dryness. The oily residue was purified by Biotage chromatography using EtOAc/hexane (1:1), providing the corresponding unsaturated sulfonic acid ethyl ester as a colorless oil which crystallized on a standing in vacuo. (5.43 g, 77% yield).

The ester product from step 2 (1.0 g, 4.6 mmol) was dissolved in formic acid (10 mL) and water (0.5 mL). The mixture was heated at 50° C. for 24 hours, cooled to room temperature, and concentrated under reduced pressure. The resultant residue was dried in vacuo. The gum-like material was triturated in ethanol and turned into solid. The solid was collected by filtration, washed with ethanol to give the title compound (0.495 g, 82%); $^1$H NMR ($CD_3OD$, 500 MHz) δ ppm 6.66 (d, 1H, J=15 Hz), 6.32 (dd, 1H, J=8.3 & 7.3 Hz), 3.88-3.93 (m, 1H), 1.52-1.65 (m, 3H), 0.97 (dd, 6H, J=6 and 7.0 Hz); ES-MS 192 (M−1).

Preparation of 3-[(6-methylindan-1-yl)amino)propane-1-sulfonic acid (Compound N81)

A mixture of 6-methyl-1-indanone (0.97 g, 6.64 mmol), hydroxylamine hydrochloride (1.11 g) and sodium acetate (1.31 g,) was heated at reflux in ethanol/water (50 mL/1.5 mL) for 5 hours. After cooling to room temperature the resulting precipitate was filtered and washed with water (2×50 mL) and dried in vacuo to give 6-methyl-1-indanone oxime (0.98, 91%) oxime which was used in the next step without purification.

To a degassed a solution of the crude oxime (from step 1, 1 g, 6.2 mmol) in EtOH/AcOH (9/1, 50 mL) was added Pd—C (10%, 200 mg). The mixture was hydrogenated under an atmospheric hydrogen pressure overnight, and then filtrated through Celite™. The filtrate was concentrated and the residue was azeotroped twice with toluene to yield 6-methylindan-1-amine as the acetate salt (1.24 g, quantitative), which was employed in the next step without purification.

The a mixture of the 6-methylindan-1-amine acetic acid (1.2 g, 6.15 mmol) and 1,3-propane sultone (0.75 g, 5.5 mmol) in acetonitrile/toluene mixture (15 mL/5 mL) was refluxed for 5 hours. After cooling to room temperature the white solid obtained was collected by filtration, and was suspended in EtOH (40 mL). The suspension was stirred at reflux for 1 hour. The mixture was cooled to room temperature; the solid material was collected by filtration, washed with acetone (2×20 mL) and dried in vacuo to afford the title compound (0.85 g, 53% yield); $^1$H NMR ($CD_3OD$, 500 MHz) δ ppm 7.20 (s, 1H), 7.08 (d, 1H, J=7.5 Hz) 7.00 (d, 1H, J=5.3 Hz), 4.20 (t, 1H, J=7.0 Hz), 2.87 (m, 1H), 2.78 (m, 3H), 2.36 (m, 1H), 2.31 (s, 3H), 2H), 2.02 (m, 2H), 1.84 (m, 1H). ES-MS 268 (M−1).

Preparation of (3S)-3-amino-5-methylhexane-1-sulfonic acid (Compound N82)

To a degassed a solution of 3-(t-butyloxycarbamido)-5-methylhex-1-ene-1-sulfonic acid ethyl ester (1.0 g, 2 mmol) in EtOH/AcOH (9/1, 50 mL) was added Pd—C (10%, 100 mg). The mixture was hydrogenated under an atmospheric hydrogen pressure for 1.5 hours, and then it was flushed with nitrogen and filtrated through Celite™. The celite pad was washed with ethanol several times. The filtrate and the washings were combined; and the solvent was removed by evaporation, providing 3-(t-butyloxycarbamido)-5-methylhexane-1-sulfonic acid ethyl ester (0.99 g, 98%) which was used in the next step without purification. 3-(t-Butyloxycarbamido)-5-methylhexane-1-sulfonic acid ethyl ester (1.0 g, 3.0 mmol) was treated in formic acid (10 mL) and water (0.5 mL) at 50° C. for 24 hours. The reaction mixture was concentrated and dried in vacuo. The gum-like material was triturated in ethanol. The solid was collected by filtration, washed with ethanol to give the title compound (0.430 g, 72%); $^1$H NMR ($CD_3OD$, 500 MHz) δ ppm 3.39-3.36 (m, 1H), 3.45-3.41 (m, 1H), 2.95-2.91 (m, 2H) 2.04-1.98 (m, 1H), 1.74-1.70 (m, 1H), 1.56-1.41 (m, 2H), 0.98 (dd, 6H, J=3.4 and 7.2 Hz); ES-MS 194 (M−1).

Preparation of Compounds N38, N40, and N41

These three compounds were prepared from a common starting material, namely 2-(t-butyl)-1,3-propane sultone, which was prepared as the following: To a stirred solution of lithium bis(trimethylsilyl)amide 1.0M solution in THF (42 mL, 42 mmol) at −78° C. was added dropwise a solution of ethyl methanesulfonate (4.30 mL, 10 mmol) in dry THF (5 mL). The mixture was stirred at −78° C. for 30 minutes then bromopinacolone (5 g, 27.9 mmol) in dry THF (10 mL) was added dropwise. The mixture was then stirred at −78° C. for 2 hours, and at −50° C. for 2 hours, and finally quenched with a saturated solution of ammonium chloride (100 mL). The mixture was extracted with EtOAc (3×100 mL). The organic layers were combined, washed with water (2×50 mL), brine (100 mL), dried over $MgSO_4$, and concentrated under reduced pressure. The residual material was purified by Biotage using Hexane:EtOAc (9:1) to give 2-(t-butyl)-1,3-prop-1-ene sultone (3.78 g, 75%). To a degassed a solution of 2-(t-butyl)-1,3-prop-1-ene sultone (1 g, 5.67 mmol) in MeOH (50 mL) was added 10% Pd—C (10%, 150 mg). The mixture was hydrogenated under 40 Psi hydrogen pressure for 48 h. The mixture was filtered through Celite™ and the filtrate was concentrated to give 2-(t-butyl)-1,3-propane sultone (0.90 g, 89%).

2-[(t-Butylamino)methyl]-3,3-dimethylbutane-1-sulfonic acid (Compound N38)

To a solution of 2-(t-butyl)-1,3-propane sultone (83 mg, 0.466 mmol) in dimethylformamide (2 mL) was added t-butylamine (2 mL). The solution was stirred at 130° C. for 48 hours. The reaction mixture was cooled to room temperature and the solvent was removed under reduced pressure. The residue was triturated with ethanol; and the solid material was collected by filtration, washed successively with ethanol (2×20 mL) and with acetone (2×20 mL), and dried under high vacuum to afford the title compound (56 mg, 62%); $^1$H NMR (CD$_3$OD, 500 MHz) δ ppm 3.29 (m, 2H), 2.98 (m, 1H), 2.82 (m, 1H), 1.98 (br t, 1H, J=9.5 Hz), 1.36 (s, 9H), 1.05 (s, 9H); ES-MS 250 (M−1).

2-[(1-Adamantylamino)methyl]-3,3-dimethylbutane-1-sulfonic acid (Compound N40)

To a solution of 2-(t-butyl)-1,3-propane sultone (240 mg, 1.34 mmol) in dimethylformamide (10 mL) was added 1-adamanthanamine (204 mg, 1.34 mmol). The solution was heated at 130° C. for 24 hours. The reaction mixture was cooled to room temperature and was triturated with ethanol. The solid was collected by filtration, washed successively with ethanol (2×20 mL) and acetone (2×20 mL), and purified by LC-MS to provide the title compound (25 mg, 5%); $^1$H NMR (CD$_3$OD, 500 MHz) δ ppm 3.00 (m, 2H), 2.98 (m, 1H), 2.81 (m, 1H), 2.21 (br s, 3H), 1.94 (br t, 1H, J=9.5 Hz), 1.92 (m, 6H), 1.75 (m, 6H), 1.02 (s, 9H); ES-MS 328 (M−1).

3,3-Dimethyl-2-[(methylamino)methyl]butane-1-sulfonic acid: (Compound N41)

A mixture of 2-(t-butyl)-1,3-propane sultone (70 mg, 0.39 mmol) and excess of methylamine 1M in THF (5 mL) was heated in a metal cylinder at 130-° C. for 72 hours. The reaction mixture was cooled to room temperature and the solid material was collected by filtration and washed with acetone (2×20 mL) to give the title compound (50 mg, 62%); $^1$H NMR (CD$_3$OD, 500 MHz) δ ppm $^1$H NMR (CD$_3$OD, 500 MHz) δ ppm 3.13 (m, 1H), 2.79 (m, 1H), 2.70 (m, 1H), 2.53 (m, 1H), 2.35 (s, 3H), 1.86 (m, 1H), 0.98 (s, 9H); ES-MS 208 (M−1).

Preparation of (3S)-3-amino-5-methylhexane-1-sulfonic acid: (Compound N89)

To a 1.0 M stirred solution of lithium bis(trimethylsilyl) amide in THF (9 mL, 9 mmol) at −78° C. was added dropwise a solution of ethyl(3S)-3-[(tert-butoxycarbonyl)amino]-5-methylhexane-1-sulfonate (1.96 g, 6.0 mmol) in dry THF (50 mL). The mixture was stirred at −78° C. for 30 minutes followed by dropwise addition of methyl iodide (0.47 mL, 7.6 mmol) in dry THF (10 mL). The mixture was stirred at −78° C. for 4 hours, and then quenched with a saturated solution of ammonium chloride (10 mL). The mixture was extracted with EtOAc (3×50 mL). The combined organic phase was washed with water (2×50 mL), brine (100 mL), dried over MgSO$_4$ and concentrated in vacuo to give colorless oil. The resultant oil was purified by Biotage chromatography using EtOAc/Hexane 1/5, to giving the corresponding α-methylated intermediate (0.85 g, 42%). The methylated intermediate (0.85 g, 2.5 mmol) was treated with formic acid (5 mL) and water (0.25 mL) at 50° C. for 24 hours. The reaction mixture was concentrated and dried in vacuo. The gum-like material thus obtained was triturated in ethanol. The solid material was collected by filtration and washed with ethanol, providing the title compound (0.273 g, 54%); $^1$H NMR (CD$_3$OD, 500 MHz) δ ppm 3.47-3.45 (1 m, 1H), 3.45-3.41 (m, 1H), 2.99-2.91 (m, 1H), 2.24-2.18 (m, 1H), 2.09-2.03 (m, 1H), 1.86-1.80 (m, 2H), 1.78-1.69 (m, 2H), 1.32 (d, 3H, J=4.3), 0.98 (dd, 6H, J=3.9 and 4.2 Hz); ES-MS 208 (M−1).

Preparation of 2-(1-adamantyl)-3-(tert-butylamino)propane-1-sulfonic acid (Compound N90) and 2-(1-adamantyl)-3-(methylamino)propane-1-sulfonic acid (Compound N91)

A solution of ethylmethane sulfonate (1.21 mL, 11.7 mmol) in THF (10 mL) was cooled to −78° C. To the cold solution was added dropwise LiHMDS 1M solution in THF (12.5 mL, 12.5 mmol). The mixture was stirred for 30 minutes, and then transferred via cannula to a second flask containing a solution of adamanthyl bromomethyl ketone (2.00 g, 7.80 mmol) in THF (40 mL) at −78° C. under N$_2$ atmosphere. The resultant mixture was stirred at −78° C. for 1.5 hours and then warmed slowly to −45° C., and stirred for 2.5 hours at this temperature. The reaction was quenched by adding a saturated solution of NH$_4$Cl (100 mL). The mixture was extracted with EtOAc (3×100 mL) and washed with brine, dried over MgSO$_4$ and concentrated under reduced pressure to obtain a yellow solid (1.93 g, 97%). The solid (0.66 g, 2.59 mmol) was hydrogenated in the presence of palladium on activated charcoal (10%, 0.198 g) in MeOH (60 mL), in a Pyrex™ high pressure bottle and hydrogenated at 40 psi for 48 h. The reaction mixture was filtered through Celite™ and concentrated to give 2-(1-admantyl)-1,3-propane sultone as a white solid (0.65 g, 98%).

2-(1-Adamantyl)-3-(tert-butylamino)propane-1-sulfonic acid (Compound N90)

The above-derived 2-(1-adamantyl)-1,3-propane sultone (0.12 g, 0.466 mmol) was dissolved in DMF, followed by addition of t-butylamine (0.074 mL, 0.699 mmol). The mixture was heated at 130° C. Additional t-butylamine (0.07 mL, 0.663 mmol) was added to the reaction mixture. The next day, reaction mixture was cooled to room temperature and more t-butylamine (1.0 mL) was added and the resulting mixture was heated again 130° C. After being stirred for 8 hours, some more t-butylamine (3 mL) was added and the reaction mixture was heated for 3 more days at 130° C. The reaction mixture was concentrated by evaporation, causing a white solid to precipitate. The mixture was diluted with MeOH (1 mL); and the white solid was collected by filtration, washed with Et$_2$O, and dried in vacuo, providing the title compound (0.062 g, 51%); $^1$H NMR (CD$_3$OD, 500 MHz) δ ppm 3.36-3.32 (m, 2H), 2.93 (dd, 1H, J=9.8 Hz, J=12.7), 2.75 (dd, 1H, J=9.3 Hz, J=14.6 Hz), 2.02 (large s, 3H), 1.78-1.50 (m, 13H), 1.37 (s, 9H). $^{13}$C NMR (CD$_3$OD, 125 MHz) δ ppm 56.70, 51.71, 48.43, 43.53, 43.31, 38.87, 36.58, 35.52, 28.75, 24.67. ES-MS: 328 (M−1).

2-(1-Adamantyl)-3-(methylamino)propane-1-sulfonic acid (Compound N91)

2-(1-Adamantyl)-1,3-propane sultone (0.104 g, 0.405 mmol) was introduced into a Pyrex™ high pressure bottle and a solution of 2 M methylamine in THF (8 mL) was added. The bottle was closed and heated at 110° C. overnight, and then cooled to room temperature. The white precipitate was collected by filtration, washed with Et$_2$O, and dried in vacuo, giving the title compound (0.0681 g, 59%); ¹H NMR (CD₃OD, 500 MHz) δ ppm 4.39-4.36 (m, 1H), 3.27-3.24 (m, 1H), 3.0 (dd, 1H, J=9.3 Hz, J=12.7 Hz), 2.78 (dd, 1H, J=9.8 Hz, J=14.2 Hz), 2.71 (s, 3H), 2.02 (large s, 3H), 1.80-1.57 (m, 13H); ES-MS: 286 (M−1).

Example 2

Binding and Antifibrillogenic Assays

A representative number of compounds according to the invention were synthesized and screened by mass spectrometry ("MS") assays, except for selected compounds which were purchased from a commercial source. The MS assay gives data on the ability of selected compounds to bind to proteins, in this example, to Aβ40.

Samples were prepared as aqueous solutions (adding 20% ethanol if necessary to solubilize in water). For those compounds selected from Table 2A, the binding experiment was done with 200 μM of a test compound and 20 μM of solubilized Aβ40, or 400 μM of a test compound and 40 μM of solubilized Aβ40. For those compounds selected from Table 3A and Table 3B, the binding experiment was done with 150 μM of a test compound and 30 μM of solubilized Aβ40. The pH value of each sample was adjusted to 7.4 (±0.2) by addition of 0.1% aqueous sodium hydroxide. The solutions were then analyzed by electrospray ionization mass spectrometry using a Waters ZQ 4000™ mass spectrometer. Samples were introduced by direct infusion at a flow-rate of 25 μL/min within 2 hours after sample preparation. The source temperature was kept at 70° C. and the cone voltage was 20 V for all the analysis. Data were processed using Masslynx 3.5™ software. The MS assay gives data on the ability of compounds to bind to soluble Aβ, whereas the ThT, EM and CD assays give data on inhibition of fibrillogenesis. The results from the assay for binding to Aβ for compounds selected from Table 2A are summarized in Table 4 and the results from the assay for binding to Aβ for compounds selected from Tables 3A and 3B are summarized in Table 5.

TABLE 4

Relative Binding Affinities of Selected Compounds Shown in Table 2A

| Aβ binding (%) | Compound ID |
| --- | --- |
| 90-100% @ 400 μM; | AY; BB; BV; BW; BX; BY; BZ; CE; CG; CH; CI; CJ; CK; |
| 60-100% @ 200 μM | CV; CY; DC; DD; DK; DO; DU; DV; DX; DY; DZ; EB; ED; EE; EG; EH; EK; ES; ET; EY; EZ; FA; FS; FX; FY; NJ; |
| 70-89% @ 400 μM; | AG; AK; AL; AW; AX; AZ; BA; CC; CD; DH; DM; DN; |
| 30-69% @ 200 μM | DW; EA; EJ; EL; ER; FP; FR; FU; GD; GJ; GL; I; NG; |
| 45-59% @ 400 μM; | AC; AD; AE; AF; AH; AM; B; BC; C; D; DG; DL; DP; DQ; |
| 20-44% @ 200 μM | DR; DS; DT; E; EF; EN; EO; EP; EQ; F; FQ; FZ; G; GB; GH; GI; GK; GS; GU; H; HC; HG; J; L; NH; NI; NK; |
| 20-39% @ 400 μM and 200 μM | DE; DF; DI; DJ; EI; FH; FO; FT; FV; FW; GA; GC; GM; GN; GO; GP; GQ; GR; GT; GZ; HA; HB; HD; HE; HF; HJ; HK; K; M; N; P; Q |

TABLE 5

Relative Binding Affinities of Selected Compounds Shown in Tables 3A and 3B

| Aβ binding (%) | Compound ID |
| --- | --- |
| ≧70% | OE; OM; OV; OW; OY; PD; PI; PK; PT; PW; QG; QT; QU; QW; SX; SY; SZ; N1; N4; N10; N11; N12; N16; N17; N24; N25; N30; N33; N36; N42; N44; N52; N53; N54; N56; N57; N58; N61; N64; N65; N66; N73; N74; N78; N79 |
| 40-69% | NN; NM; NO; NP; NR; NU; NV; NZ; OA; OB; OC; OD; OI; OL; ON; OO; OP; OQ; OR; OU; OX; OZ; PA; PE; PF; PG; PH; PJ; PL; PQ; PR; PS; PV; PY; QB; QC; QD; QE; QF; QH; QI; QJ; QL; QM; QN; QP; QQ; QR; QS; QV; QX; N2; N5; N7; N8; N9; N13; N14; N18; N19; N20; N23; N26; N31; N32; N34; N35; N37; N38; N39; N40; N41; N43; N47; N48; N49; N50; N51; N55; N59; N60; N62; N63; N69; N70; N71; N72; N77; N82; N84; N85; N87; |
| 15-39% | NQ; NS; NT; NW; NX; NY; OF; OG; OH; OJ; OK; OS; OT; PB; PM; PN; PO; PP; PU; PX; PZ; QA; QK; QO; N3; N6; N15; N21; N22; N27; |

Example 3

Effects of Short Term Treatment in Adult Transgenic CRND8 Mice Overexpressing βAPP Transgenic mice, TgCRND8, expressing the human amyloid precursor protein (hAPP) develop a pathology resembling Alzheimer's disease. In particular, high levels of Aβ40 and Aβ42 have been documented in the plasma and the brain of these animals at 8-9 weeks of age, followed by early accumulation of amyloid plaques similar to the senile plaques observed in AD patients. These animals also display progressive cognitive deficits that parallel the appearance of degenerative changes. See, e.g., (Chishti, et al., J. Biol. Chem. 276, 21562-70 (2001).

The short term therapeutic effect of 19 compounds of the invention was studied. These compounds were administered over a 14 or 28 day period at the end of which the levels of Aβ peptides in the plasma and brain of TgCRND8 animals were determined.

Methods

Male and female transgenic mice from the $3^{rd}$ and $4^{th}$ B6C3F1 generations were used in this example and given daily subcutaneous or oral administrations of one of a series of compounds for 14 or 28 days. The following abbreviations are used to designate these animals from the $3^{rd}$ and 4th generation backcross in the present protocol: TgCRND8-2.B6C3F1($N_3$); TgCRND8-2.B6C3F1 (N4).

Baseline animals (Group 1) consisted of naive TgCRND8-2. B6C3F1($N_3$) at 11±1 weeks of age. These mice were used to determine the Aβ levels in the plasma and brain of naive transgenic animals at the initiation of treatment.

Starting at 11 weeks of age (±1 week) animals received daily administration of their respective treatment for a period of 14 or 28 days (groups 2-21), at a dose of 250 mg/kg at 10 ml/kg or of vehicle only (water; group 2) or 1% methyl cellulose only (group 21). The route of administration was subcutaneous for water-soluble compounds and oral for compounds solubilized in methylcellulose 1%. (MC 1%). At the end of the treatment periods, plasma and perfused brains were collected for quantification of Aβ levels.

The mice used in this study were derived from a breeding colony at Institut Armand Frappier, and were well-acclimated to the animal facility environment prior to initiation of the study. Animals were assigned, according to age and gender, into the following experimental groups:

TABLE 6

Groups of Mice

| Group No. | Treatment | Daily Dose (mg/kg) | Duration of Treatment (days) |
|---|---|---|---|
| 1 | Baseline | NA | NA |
| 2 | Water | NA | 14 & 28 |
| 4 | BY | 250 | 14 & 28 |
| 6 | CV | 250 | 14 & 28 |
| 12 | CY | NA | 14 & 28 |
| 15 | BW | 250 | 14 & 28 |
| 16 | BZ | 250 | 14 & 28 |
| 18 | BX | 250 | 14 & 28 |
| 20 | DC | 250 | 14 & 28 |
| 21 | Methylcellulose 1% | 100 | 14 & 28 |
| 22 | DD | 250 | 14 & 28 |
| 23 | DH | 250 | 14 & 28 |
| 24 | DM | 250 | 14 & 28 |
| 25 | DX | 250 | 14 & 28 |
| 26 | DY | 250 | 14 & 28 |
| 27 | DZ | 250 | 14 & 28 |
| 28 | ED | 250 | 14 & 28 |
| 29 | EG | 250 | 14 & 28 |

Animal Health Monitoring

All animals were examined daily for signs of ill health when handled in the morning for their daily treatment and twice a day for mortality checks (once daily during weekends and holidays). Detailed examinations were performed on the treatment initiation, weekly during the study, and once before terminal procedures. More frequent observations were undertaken when considered appropriate. Death and all individual clinical signs were individually recorded. Individual body weights were recorded at randomization, once weekly during the study, and once before terminal procedures.

Sample Collection

At 11±1 weeks of age for the Baseline group, and at the end of the treatment period (14 or 28 days) for Groups 2 to 21, at 24 hours after the last compound administration animals were sacrificed and samples collected. An approximate blood volume of 500 µl was collected from the orbital sinus and kept on ice until centrifugation at 4° C. at a minimum speed of 3,000 rpm for 10 minutes. Plasma samples were immediately frozen and stored at −80° C. pending analysis. The brains were removed, frozen, and stored at −80° C. awaiting analysis.

Measurements of Aβ Levels

Brains were weighted frozen and homogenized with 4 volumes of ice cold 50 mM Tris-Cl pH 8.0 buffer with protease inhibitor cocktail (4 mL of buffer for 1 g of wet brain). Samples were spun at 15000 g for 20 minutes and the supernatants were transferred to fresh tubes. One hundred fifty (150) µl from each supernatant were mixed with 250 µl of 8M guanidine-HCL/50 mM Tris-HCL pH 8.0 (ratio of 0.6 vol supernatant:1 vol 8M guanidium/Tris-HCL 50 mM pH8.0) and 400 µL 5 M guanidium/Tris-HCL 50 mM pH8.0 were added. The tubes were vortexed for 30 seconds and frozen at −80° C. In parallel, pellets were treated with 7 volumes of 5 M guanidine-HCL/50 mM Tris-HCL pH 8.0 (7 mL of guanidine for 1 g of wet brain), vortexed for 30 seconds and frozen at −80° C. Samples were thawed at room temperature, sonicated at 80° C. for 15 minutes and frozen again. This cycle was repeated 3 times to ensure homogeneity and samples were returned to −80° C. pending analysis.

Aβ levels were evaluated in plasma and brain samples by ELISA using Human Aβ40 and Aβ42 Fluorometric ELISA kits from Biosource (Cat. No. 89-344 and 89-348) according to manufacturer's recommended procedures. In short, samples were thawed at room temperature, sonicated for 5 minutes at 80° C. (sonication for brain homogenates; no sonication for plasma samples) and kept on ice. Aβ peptides were captured using 100 µl of the diluted samples to the plate and incubated without shaking at 4° C. overnight. The samples were aspirated and the wells were rinsed 4 times with wash buffer obtained from the Biosource ELISA kit. The anti-Aβ40 or anti-Aβ42 rabbit polyclonal antiserum (specific for the Aβ40 or Aβ42 peptide) was added (100 µl) and the plate was incubated at room temperature for 2 hours with shaking. The wells were aspirated and washed 4 times before adding 100 µl of the alkaline phosphatase labeled anti-rabbit antibody and incubating at room temperature for 2 hours with shaking. The plates were then rinsed 5 times and the fluorescent substrate (100 μl) was added to the plate. The plate was incubated for 35 minutes at room temperature and the plate was read using a titer plate reader at an excitation wavelength of 460 nm and emission at 560 nm.

Compounds were scored based on their ability to modulate levels of Aβ peptides in the plasma and the cerebral soluble/insoluble levels in the brain. Levels of Aβ observed in the plasma and brain of treated animals were normalized using values from vehicle-treated (water) or methylcellulose-treated control groups and ranked according to the strength of the pharmacological effect. Results are shown in Tables 3 to 11. Increases in the levels of Aβ peptides are indicated using "+" symbols, while decreases in the levels of Aβ peptides are indicated using "−" symbols. The strongest effects are recorded as "+++" or "---" while the weakest are shown as "+" or "−".

Specifically, increases in the levels of Aβ (relative to untreated control) of 20 to 39% are scored as "+"; increases of 40 to 69% are scored as "++"; and increases of 70% or higher are scored as "+++". Decreases in the levels of Aβ of 5 to 19% are scored as "−"; decreases of 20 to 38% are scored as "−−"; and decreases of 39% or more are scored as "---".

The data are presented in Tables 6-11. Treatment with these compounds after 14 and/or 28 days resulted in a significant change in the cerebral levels of Aβ640 and/or A042 (Tables 8-11). Furthermore, treatment with these compounds, for instance, Compound BX (3-(t-butyl)amino-1-propanesulfonic acid), resulted after 14 and 28 days (Tables 6-7) in a significant increase in the levels of Aβ peptides in the plasma. This suggests that some of these compounds may act by a peripheral sink effect, sequestering Aβ peptides in the plasma and thereby facilitating their clearance from the CNS as previously suggested for treatment by passive immunization using anti-Aβ monoclonal antibody m266 (DeMattos et al., Science 295(5563):2264-7).

The tables show levels of Aβ peptides in the plasma and brain of TgCRND8 mice treated for 14 and 28 days with compounds of the invention.

Tables 6A and 6C show the data from Day 14 and Day 28 for the Plasma Vehicle group, respectively. Tables 6B and 7 show the data for the Plasma Methylcellulose group on Days 14 and 28, respectively. Tables 8 and 10 show the data on Days 14 and 28 for the Brain homogenate vehicle group, respectively. Tables 9 and 11 show the data for brain homogenate for the Methylcellulose group on Days 14 and 28, respectively.

TABLE 6A

Plasma Vehicle Group, Day 14

| Treatment | Aβ40 Change | Aβ42 Change |
|---|---|---|
| BY | + | + |
| CV | + | ++ |
| DC | ++ | ++ |
| BX | +++ | ++ |

TABLE 6B

Plasma Methylcellulose Group, Day 14

| Treatment | Aβ40 Change | Aβ42 Change |
|---|---|---|
| BZ | + | |
| BW | | |
| CY | | |

TABLE 6C

Plasma Vehicle Group, Day 28

| Treatment | Aβ40 Change | Aβ42 Change |
|---|---|---|
| BY | | |
| CV | ++ | ++ |
| DC | ++ | |
| BX | +++ | |

TABLE 7

Plasma Methylcellulose Group, Day 28

| Treatment | Aβ40 Change | Aβ42 Change |
|---|---|---|
| BZ | ++ | ++ |
| BW | | + |
| CY | | + |

TABLE 8

Brain Homogenate Vehicle Group, Day 14

| Treatment | Aβ40 Change Soluble | Aβ40 Change Insoluble | Aβ42 Change Soluble | Aβ42 Change Insoluble |
|---|---|---|---|---|
| BY | +++ | +++ | +++ | |
| CV** | | | | − |
| DC | | −− | + | −− |
| BX | − | --- | −− | --- |
| DD | | − | | |
| DX | | −− | | − |
| DY | | −− | | −− |
| DZ | | | | −− |
| EG | − | −− | −− | −− |
| DH | | −− | --- | --- |
| DM | | + | − | − |
| ED | − | + | | |

**The effect of this compound in the brain has only been tested on its ability to modulate the total levels of Aβ40 and Aβ42 peptides rather than measuring soluble and insoluble levels independently.

TABLE 9

Brain Homogenate Methylcellulose Group, Day 14

| Treatment | Aβ40 Change Soluble | Aβ40 Change Insoluble | Aβ42 Change Soluble | Aβ42 Change Insoluble |
|---|---|---|---|---|
| BZ | | --- | | −− |
| BW | | --- | −− | --- |
| CY | − | | +++ | ++ |

TABLE 10

Brain Homogenate Vehicle Group, Day 28

| Treatment | Aβ40 Change | | Aβ42 Change | |
| --- | --- | --- | --- | --- |
| | Soluble | Insoluble | Soluble | Insoluble |
| BY | + | +++ | | +++ |
| CV** | | ++ | | +++ |
| DC | − | + | ++ | +++ |
| BX | −−− | −−− | −− | − |
| DD | | − | | |
| DX | | −− | − | −− |
| DY | | −−− | − | −− |
| DZ | − | −− | −− | −− |
| EG | | −− | | −− |
| DH | | − | | − |
| DM | − | −− | −− | −− |
| ED | − | −− | − | − |

**The effect of this compound in the brain has only been tested on its ability to modulate the total levels of Aβ40 and 42 peptides rather than measuring soluble and insoluble levels independently.

TABLE 11

Brain Homogenate Methylcellulose Group, Day 28

| Treatment | Aβ40 Change | | Aβ42 Change | |
| --- | --- | --- | --- | --- |
| | Soluble | Insoluble | Soluble | Insoluble |
| BZ | −− | −− | | −− |
| BW | − | − | − | −− |
| CY | ++ | +++ | +++ | + |

Example 4

Effects of Long Term Treatment in Adult Transgenic CRND8 Mice Overexpressing βAPP Transgenic mice, TgCRND8, as those used in the short term treatment, overexpress a human APP gene with the Swedish and Indiana mutations leading to the production of high levels of the amyloid peptides and to the development of an early-onset, aggressive development of brain amyloidosis. The high levels of Aβ peptides and the relative overabundance of $A\beta_{42}$ compared to $A\beta_{40}$ are believed to be associated with the severe and early degenerative pathology observed. The pattern of amyloid deposition, presence of dystrophic neuritis, and cognitive deficit has been well documented in this transgenic mouse line. The levels of Aβ peptides in the brain of these mice increase dramatically as the animals age. While the total amyloid peptide levels increase from ~$1.6 \times 10^5$ pg/g of brain to ~$3.8 \times 10^6$ between 9 and 17 weeks of age.

While the early deposition of amyloid in this model allows the rapid testing of compounds in a relatively short time frame, the aggressivity of this model and the high levels of Aβ peptides renders therapeutic assessment in the longer term a more difficult task.

The long-term therapeutic effects of compounds of the present invention on cerebral amyloid deposition and β-amyloid (Aβ) levels in the plasma and in the brains of transgenic mice, TgCRND8, expressing the human amyloid precursor protein (hAPP) was studied. These compounds were administered over an 8 or 16 week period at the end of which the levels of Aβ peptides in the plasma and brain of TgCRND8 animals were determined. The goal of this study was to evaluate the efficacy of the compounds at modulating the progression of the amyloidogenic process in the brain and in the plasma of a transgenic mouse model of Alzheimer's disease (AD)

Methods

The mice used in the study consisted of animals bearing one copy of the hAPP gene (+/−) from the $2^{nd}$ and $3^{rd}$ generation progenies (N2 and N3) derived from backcrosses from TgCRND8.FVB(N2)AJ(N3) with B6AF1/J hybrid animals.

N1=TgCRND8.FVB(N2)AJ(N3)×B6AF1/J
N2=TgCRND8.FVB(N2)AJ(N3).B6AF1/J(N1)×B6AF1/J
N3=TgCRND8.FVB(N2)AJ(N3).B6AF1/J(N2)×B6AF1/J

The following abbreviations are used to designate these animals in the present study: TgCRND8.B6AF1/J(N2); TgCRND8.B6AF1/J(N3). Male and female transgenic mice were given daily subcutaneous (compound BX) or oral (compounds BW and BZ) administrations of the appropriate compounds for 8 or 16 weeks.

Baseline animals consisted of 9±1 week old naive TgCRND8.B6AF1/J animals from the $2^{nd}$ and $3^{rd}$ generations. These mice were used to determine the extent of cerebral amyloid deposits and Aβ levels in the plasma and brain of naive transgenic animals at the initiation of treatment.

Starting at 9 weeks of age (+1 week) animals received daily administration of their respective treatment for a period of 8 or 16 weeks, at a dose of 30 or 100 mg/kg at 10 ml/kg. The route of administration was subcutaneous for water-soluble compounds (Compound BX) and oral for compounds solubilized in methylcellulose 1% (MC 1%) (Compounds BW and BZ). At the end of the treatment periods, plasma and perfused brains were collected for quantification of Aβ levels.

Animal health was monitored, samples were collected and Aβ levels were measured as described above in the short term treatment study. Compounds were scored based on their ability to modulate levels of Aβ peptides in the plasma and the cerebral soluble/insoluble levels in the brain. Levels of Aβ observed in the plasma and brain of treated animals were compared to that of vehicle-treated (water) or methylcellulose-treated control groups and ranked according to the strength of the pharmacological effect. Results are shown in Table 12. Increases in the levels of Aβ peptides are indicated using "+" symbols, while decreases in the levels of Aβ peptides are indicated using "−" symbols. The strongest effects are recorded as "+++" or "−−−" while the weakest are shown as "+" or "−".

Specifically, increases in the levels of Aβ (relative to vehicle treated control) of 5 to 14% are scored as "+"; increases of 15 to 29% are scored as "++"; and increases of 30% or higher are scored as "+++". Decreases in the levels of Aβ of 5 to 14% are scored as "−"; decreases of 15 to 29% are scored as "−−"; and decreases of 30% or more are scored as "−−−". Additionally, changes of 4% or less in either direction are scored as "0".

Table 12 shows levels of Aβ peptides in the plasma and brain of TgCRND8 mice treated for 8 and 16 weeks with compounds of the invention. Treatment with these compounds after 8 and/or 16 weeks in many cases resulted in a change in the levels of $A\beta_{40}$ and/or $A\beta_{42}$ in the plasma and/or brain. For example, administration of compound BX generally resulted in a dramatic decrease in the amount of Aβ in the brain at both 8 and 16 weeks. Compound BW also resulted in a dramatic decrease in brain and plasma levels of Aβ at 8 weeks and plasma levels at 16 weeks.

For the ThioS studies, the plaques in the brains of the mice were quantified as follows. Mice were transcardially perfused with saline solution. Brains were dissected out and separated in 2 hemispheres. The left hemisphere was immersed in freshly-prepared 4% paraformaldehyde for 3 hrs at 4° C., then transfered into 30% sucrose at 4° C. When cryoprotection was achieved (24-48 hours), brains were frozen in isopentane at −45° C. and subsequently stored at −80° C. until sectioning.

Coronal 40 μm-thick sections were performed, and stained with thioflavin S (1% solution in water) for 8 min. After differentiation of the thioflavin S staining, sections were counterstained with hematoxylin for 5 minutes. Two sets of pictures were captured simultaneously. A first set of pictures was captured under brightfield illumination to obtain morphological details of the section; a second set of pictures was captured under a green, specific, fluorescent filter (fluorescein filter, Ex 495 nm, Em 525 nm). Image analysis to quantify the number of plaques and the area occupied by these plaques was performed using Image Pro Plus software (Media Cybernetics, MD, USA).

The data from the histological ThioS studies is summarized in Table 13. Increases in the areas and numbers of plaques are indicated using "+" symbols, while decreases in the areas and numbers of the plaques are indicated using "−" symbols. Preliminary histochemical experiments using ThioS staining of brain sections indicated that both the number of plaques and the area occupied by the plaques were decreased in mice treated with 30 mg/kg of compound BX.

Specifically, increases in the areas and numbers of plaques (relative to vehicle treated control) of 10 to 19.99% are scored as "+". Decreases in the areas and numbers of plaques of 10 to 19.99% are scored as "−". Additionally, changes of 9.99% or less in either direction are scored as "0".

most abundantly in the amygdala (Hamilton. 2000. Brain Pathol, 10:378; Mukaetova-Ladinska, et al. 2000. J Neuropathol Exp Neurol 59:408). Interestingly, the highly hydrophobic non-amyloid component (NAC) region of α-synuclein has also been described as the second most abundant component of amyloid plaques in the brain of AD patients, after. Alpha-synuclein has been shown to form fibrils in vitro. Futhermore it binds to Aβ and promotes its aggregation (Yoshimoto, et al. 1995. Proc Natl Acad Sci USA 92:9141). It was in fact originally identified as the precursor of the non-amyloid beta (Aβ) component (NAD) of AD plaques (Ueda, et al. 1993. Proc Natl Acad Sci USA 90:11282; Iwai. 2000. Biochem Biophys Acta 1502:95; Masliah, et al. 1996. Am J Pathol 148:201). NAC is a 35 amino acid long peptide with highly hydrophobic stretches which can self-aggregate and form fibrils in vitro. Moreover, these fibrils can efficiently seed the formation of Aβ fibrils in vitro (Han, et al. 1995. Chem Biol. 2: 163-169; Iwai, et al. 1995. Biochemistry 34:10139). It is in fact through its NAC domain that alpha-synuclein retains its fibrillogenic properties. Modulating the properties of NAC or targeting NAC with the compounds of the invention could therefore be a valid therapeutic avenue to inhibit the formation of protein aggregates and inclusions associated with alpha-synucleopathies, as well as the formation of aggregates between the beta-amyloid peptide and NAC of alpha-synuclein.

TABLE 12

Effects of Compounds BX, BW and BZ on levels of Aβ in plasma and brain

| Compound | Dose (mg/kg) | Timepoint (weeks) | Plasma | | Brain | | | |
| --- | --- | --- | --- | --- | --- | --- | --- | --- |
| | | | | | Abeta40 | | Abeta42 | |
| | | | Abeta40 | Abeta42 | soluble | insoluble | soluble | insoluble |
| BX | 30 | 8 wks | + | + | --- | --- | --- | -- |
| BX | 100 | 8 wks | ++ | +++ | + | ++ | + | 0 |
| BX | 30 | 16 wks | − | − | -- | --- | 0 | − |
| BX | 100 | 16 wks | − | 0 | − | --- | 0 | -- |
| BW | 30 | 8 wks | --- | --- | − | -- | -- | 0 |
| BW | 100 | 8 wks | − | − | --- | --- | -- | --- |
| BW | 30 | 16 wks | -- | -- | + | ++ | − | + |
| BW | 100 | 16 wks | − | − | ++ | + | + | ++ |
| BZ | 30 | 8 wks | 0 | 0 | 0 | -- | 0 | --- |
| BZ | 100 | 8 wks | ++ | +++ | ++ | 0 | 0 | − |
| BZ | 30 | 16 wks | 0 | + | 0 | + | + | 0 |
| BZ | 100 | 16 wks | ++ | ++ | -- | 0 | − | + |

TABLE 13

Histological effects of compounds BW and BX on numbers of plaques and areas occupied by plaques

| Compound | Dose (mg/kg) | Timepoint (weeks) | Analyzed Surface Area (μm²) | ThioS Sites | |
| --- | --- | --- | --- | --- | --- |
| | | | | Change in Plaque Number | Change in Plaque Area |
| BX | 30 | 16 wks | 7,773,230 | − | − |
| BX | 100 | 16 wks | 7,803,230 | 0 | + |
| BW | 30 | 16 wks | 7,563,737 | 0 | 0 |
| BW | 100 | 16 wks | 7,812,844 | − | 0 |

Example 5

Evaluation of CompoundS Binding to NAC Peptide by Mass Spectrometry

Recent findings have demonstrated that a high percentage of Alzheimer Disease (AD) patients also form Lewy bodies, The ability of the compounds of the present invention to bind to NAC peptide in aqueous solution was evaluated. The binding ability correlates to the intensities of the peptide-compound complex peaks observed by the Electrospray Mass Spectrum. Millipore distilled deionized water was used to prepare all aqueous solutions. For pH determination a Beckman Φ36 pH meter fitted with a Corning Semi-Micro Combination pH Electrode was employed.

NAC (MW 3260.6 Da) at 20 μM was first analyzed at pH 7.40 and the usual sodium clusters was observed at +2, +3 and +4 at m/z 1335.5, 1116.7 and 843.4 respectively. The optimal cone voltage was determined to be 20V.

Mass spectrometry—Mass spectrometric analysis was performed using a Waters ZQ 4000 mass spectrometer equipped with a Waters 2795 sample manager. MassLynx 4.0 (earlier by MassLynx 3.5) was used for data processing and analysis. Test compounds were mixed with disaggregated peptides in aqueous media (6.6% EtOH) at a 5:1 ratio (20 μM NAC:100 μM of test compound or 40 μM NAC:200 μM of test compound). The pH of the mixture was adjusted to 7.4 (+0.2) using 0.1% NaOH (3-5 μL). Periodically, NAC peptide solution at 20 μM or 40 μM was also prepared in the same fashion and run as control. The spectra were obtained by introducing the solutions to the electrospray source by direct infusion using a syringe pump at a flow rate of 25 μl/min, and scanning from 100 to 2100 Da in the positive mode. The scan time was 0.9 sec per scan with an inter-scan delay of 0.1 sec and the run time was 5 min for each sample. All the mass spectra were sum of 300 scans. The desolvation and source temperature was 70° C. and the cone and capillary voltage were maintained at 20 V and 3.2 kV respectively.

The total area under the peaks for the bound NAC-compound complex divided by total area under the peaks for unbound NAC was determined for each compound tested. The results are summarized in Table 14 below.

TABLE 14

NAC Peptide Binding Data

| Structure | Binding Strength* |
|---|---|
| $NaO_3SCH_2(CH_2)_2CH_2SO_3Na$ | − |
| $NaO_3SOCH_2CH_2CH_2OSO_3Na$ | − |
| $NH_2CH_2CH_2OSO_3H$ | − |
| $H_2NCH_2CH_2CH_2OSO_3Na$ | ++ |
| $H_2NCH_2CH_2SO_3H$ | + |
| [structure: t-butyl N-propylsulfonic acid] | ++ |
| [structure: adamantyl-NH-propyl-SO3H] | ++ |
| [structure: H2N-butyl-SO3H] | + |
| [structure: cyclohexyl-NH-CH2-CH(OH)-CH2-SO3H] | +++ |
| [structure: adamantyl stereo-NH-CH2CH2CH(CH3)-SO3H] |  |

*+++ = Strong; when the total binding is 120% and higher
++ = Moderate; when the total binding is between 120% and 70%
+ = Weak; when the total binding is between 70% and 30%
− = None; when the total binding is between 30% and 0%

Example 6

Maintenance of Neuroblastoma SH-SY5Y, Treatments and Hoechst Staining

A representative subset of coumpunds shown hereinbefore in Tables 2 and 3 were tested for neuroprotective activity. Briefly, SH-SY5Y cells were cultured according to American Type Culture Collection (ATCC) recommendations. Briefly, cells were grown in a culture medium containing 10% fetal bovine serum (Gibco), 1× non-essential amino acids in a 1:1 mixture of Eagle's minimum essential medium (Sigma) and Ham's F12 medium (Gibco).

Synthetic $A\beta_{42}$ (American Peptide) was resuspended in 1,1,1,3,3,3-Hexafluoro-2-propanol (HFIP), sonicated, and stored at −80° C. Preparations were thawed, dried under nitrogen gas, and dissolved in 0.04 M Tris, 0.3 M NaCl (pH 7.4) at 120 μM. SH-SY5Y cells were seeded on glass coverslips in a 24-well plate at a density of $3 \times 10^5$ cells/well. Treatments were performed the next day. Cells were incubated for 24 hours with 12 μM $A\beta_{1-42}$, diluted in the culture medium from the 120 μM stock in the presence or absence of 240 μM NRM compounds (1:20 Aβ:drug ratio).

Cell death was assessed using the DNA-binding dye Hoechst (33342) (Molecular Probes) to detect condensed or fragmented chromatin. The coverslips containing SH-SY5Y cells were stained with Hoechst 33342 (2 μg/ml) for 10 min, fixed in 4% paraformaldehyde (Electron Microscopy Science) for 30 minutes at room temperature, washed in Phosphate Buffered Saline (Gibco) and mounted onto glass slides using prolong anti-fade reagent (Molecular Probes). The nuclei were visualized using a fluorescence microscope at 200× magnification. Live cells and cells considered morphologically apoptotic were counted. Apoptotic nuclei appear condensed and occasionally fragmented. Five random fields were captured for each condition in a blinded fashion. Apoptotic and normal nuclei in each field were quantified by manual examination. The results are summarized in Table 15 below.

TABLE 15

Neuroprotective activity of selected compounds according to the invention

| Inhibition of Aβ-induced toxicity (%) | Compound ID |
|---|---|
| <20% | NM; NP; OQ; PJ; QD; QJ; QQ; N5; N9; N10; N11; N33; N47; N48; N49; N50; N53; N54; N55; N57; N58; N60; N61; N62; N63; N64; N65; N66; N67; N68; N70; N71; N72; N73; N74; N77; N79; N84; |
| 20%-40% | N14; N16; N37; N43; N44; N52; N75; N78; N80; N81; N83; N85; N86; N87; |
| >40% | N56; N59; N69; N82; |

It is understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A compound of the formula (XII):

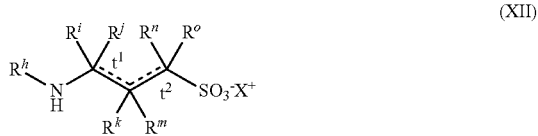

(XII)

wherein:
R^h is hydrogen or unsubstituted alkyl;
R^i is unsubstituted $C_2$-$C_7$ alkyl;
R^j, R^k, R^m, R^n, and R^o are each independently hydrogen or unsubstituted alkyl;
X^+ is hydrogen, a cationic group, or an ester-forming group; and
t^1 and t^2 are each a single bond or a pharmaceutically acceptable salt, ester, or prodrug thereof.

2. A compound selected from the group consisting of:

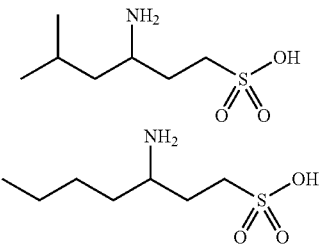

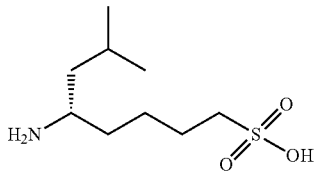

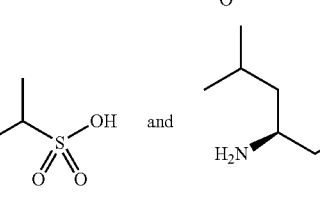

or a pharmaceutically acceptable salt or ester, thereof.

3. A pharmaceutical composition comprising a compound according to claim 1.

4. A pharmaceutical composition comprising a compound selected from the group consisting of:

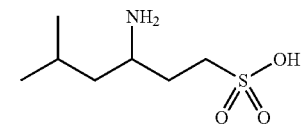

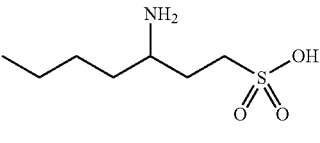

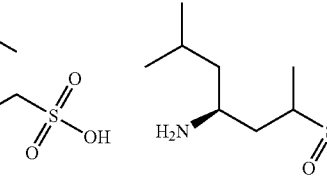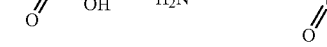 and

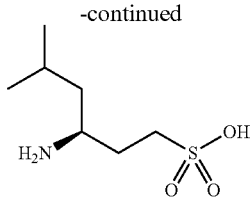

and a pharmaceutically acceptable carrier.

5. The compound of claim 1, wherein R^h is hydrogen.

6. The compound of claim 5, wherein R^j, R^m, and R^o are each hydrogen.

7. The compound of claim 5, wherein R^j, R^k, R^m, R^n and R^o are each hydrogen.

8. The compound of claim 7, wherein R^i is ethyl, propyl, butyl, pentyl, hexyl or heptyl.

9. The compound of claim 1, wherein said compound has the structure:

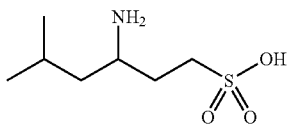

or a pharmaceutically acceptable salt thereof.

10. The compound of claim 9, wherein said compound has the structure:

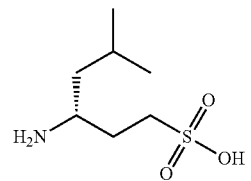

or a pharmaceutically acceptable salt thereof.

11. The compound of claim 9, wherein said compound has the structure:

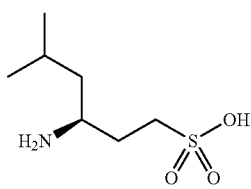

or a pharmaceutically acceptable salt thereof.

* * * * *

UNITED STATES PATENT AND TRADEMARK OFFICE
CERTIFICATE OF CORRECTION

PATENT NO. : 8,044,100 B2
APPLICATION NO. : 11/316693
DATED : October 25, 2011
INVENTOR(S) : Kong et al.

It is certified that error appears in the above-identified patent and that said Letters Patent is hereby corrected as shown below:

Column 377, Line 25 the structure 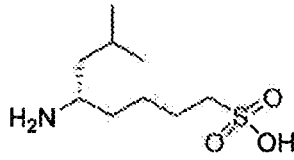 should be replaced with the structure 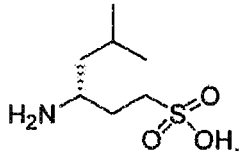.

Signed and Sealed this
Tenth Day of January, 2012

David J. Kappos
*Director of the United States Patent and Trademark Office*